(12) United States Patent
Giuliano et al.

(10) Patent No.: US 10,501,479 B2
(45) Date of Patent: Dec. 10, 2019

(54) BENZENESULFONYL-ASYMMETRIC UREAS AND MEDICAL USES THEREOF

(71) Applicant: HELSINN HEALTHCARE SA, Lugano/Pazzallo (CH)

(72) Inventors: Claudio Giuliano, Como (IT); Antoine Daina, Lausanne (CH); Claudio Pietra, Como (IT)

(73) Assignee: Helsinn Healthcare SA, Lugano/Pazzallo (CH)

(*) Notice: Subject to any disclaimer, the term of this patent is extended or adjusted under 35 U.S.C. 154(b) by 0 days.

(21) Appl. No.: 15/464,430

(22) Filed: Mar. 21, 2017

(65) Prior Publication Data

US 2017/0275301 A1 Sep. 28, 2017

Related U.S. Application Data

(60) Provisional application No. 62/311,573, filed on Mar. 22, 2016.

(51) Int. Cl.
| | |
|---|---|
| *C07D 487/04* | (2006.01) |
| *C07D 471/04* | (2006.01) |
| *C07D 513/04* | (2006.01) |
| *C07C 311/47* | (2006.01) |
| *C07C 317/42* | (2006.01) |
| *C07D 209/08* | (2006.01) |
| *C07D 209/44* | (2006.01) |
| *C07D 213/34* | (2006.01) |
| *C07D 213/76* | (2006.01) |
| *C07D 215/06* | (2006.01) |
| *C07D 215/08* | (2006.01) |
| *C07D 215/10* | (2006.01) |
| *C07D 215/58* | (2006.01) |
| *C07D 217/04* | (2006.01) |
| *C07D 217/10* | (2006.01) |
| *C07D 223/16* | (2006.01) |
| *C07D 231/56* | (2006.01) |
| *C07D 233/64* | (2006.01) |
| *C07D 235/14* | (2006.01) |
| *C07D 237/20* | (2006.01) |
| *C07D 239/48* | (2006.01) |
| *C07D 241/04* | (2006.01) |
| *C07D 241/12* | (2006.01) |
| *C07D 295/088* | (2006.01) |
| *C07D 307/87* | (2006.01) |
| *C07D 311/76* | (2006.01) |
| *C07D 317/34* | (2006.01) |
| *C07D 401/12* | (2006.01) |
| *C07D 403/12* | (2006.01) |
| *C07D 405/04* | (2006.01) |
| *C07D 405/06* | (2006.01) |
| *C07D 405/12* | (2006.01) |
| *C07D 409/12* | (2006.01) |

(Continued)

(52) U.S. Cl.
CPC .......... *C07D 513/04* (2013.01); *C07C 311/47* (2013.01); *C07C 317/14* (2013.01); *C07C 317/26* (2013.01); *C07C 317/42* (2013.01); *C07C 317/44* (2013.01); *C07D 209/04* (2013.01); *C07D 209/08* (2013.01); *C07D 209/44* (2013.01); *C07D 213/34* (2013.01); *C07D 213/76* (2013.01); *C07D 215/06* (2013.01); *C07D 215/08* (2013.01); *C07D 215/10* (2013.01); *C07D 215/58* (2013.01); *C07D 217/04* (2013.01); *C07D 217/10* (2013.01); *C07D 223/16* (2013.01); *C07D 231/56* (2013.01); *C07D 233/64* (2013.01); *C07D 235/14* (2013.01); *C07D 237/20* (2013.01); *C07D 239/26* (2013.01); *C07D 239/48* (2013.01); *C07D 241/04* (2013.01); *C07D 241/12* (2013.01); *C07D 295/088* (2013.01); *C07D 307/87* (2013.01); *C07D 311/76* (2013.01); *C07D 317/34* (2013.01); *C07D 401/12* (2013.01); *C07D 403/12* (2013.01); *C07D 405/04* (2013.01); *C07D 405/06* (2013.01); *C07D 405/12* (2013.01); *C07D 409/12* (2013.01); *C07D 413/12* (2013.01); *C07D 417/10* (2013.01); *C07D 417/12* (2013.01); *C07D 471/04* (2013.01); *C07D 471/08* (2013.01); *C07D 487/04* (2013.01); *C07D 495/04* (2013.01); *C07C 2601/02* (2017.05)

(58) Field of Classification Search
None
See application file for complete search history.

(56) References Cited

U.S. PATENT DOCUMENTS

| 6,399,619 B1 | 6/2002 | Berk |
| 7,534,893 B2 | 5/2009 | Alvaro et al. |

(Continued)

FOREIGN PATENT DOCUMENTS

| JP | 52085174 | 7/1977 |
| JP | 2003533510 A | 11/2003 |

(Continued)

OTHER PUBLICATIONS

Supuran, Claudiu. Eur. J. Med. Chem. 33(1998) 821-830.*

(Continued)

*Primary Examiner* — Emily A Bernhardt
*Assistant Examiner* — Laura M Daniel
(74) *Attorney, Agent, or Firm* — Clark G. Sullivan

(57) ABSTRACT

Benzenesulfonyl-asymmetric ureas are provided for the treatment of conditions modulated by the ghrelin receptor.

51 Claims, No Drawings

(51) Int. Cl.
| | |
|---|---|
| C07D 413/12 | (2006.01) |
| C07D 417/10 | (2006.01) |
| C07D 417/12 | (2006.01) |
| C07D 471/08 | (2006.01) |
| C07D 495/04 | (2006.01) |
| C07C 317/14 | (2006.01) |
| C07D 239/26 | (2006.01) |
| C07C 317/26 | (2006.01) |
| C07C 317/44 | (2006.01) |
| C07D 209/04 | (2006.01) |

(56) References Cited

U.S. PATENT DOCUMENTS

| | | |
|---|---|---|
| 7,669,477 B2 | 3/2010 | Georgeson |
| 7,829,589 B2 | 11/2010 | Saunders et al. |
| 7,841,252 B2 | 11/2010 | Remmler |
| 8,658,797 B2 | 2/2014 | Rubio et al. |
| 2004/0006081 A1 | 1/2004 | Burrows et al. |
| 2005/0014794 A1 | 1/2005 | Liu et al. |
| 2006/0040906 A1 | 2/2006 | Bakshi et al. |
| 2006/0161006 A1 | 7/2006 | Takemoto |
| 2007/0149512 A1 | 6/2007 | Antel et al. |
| 2008/0064706 A1 | 3/2008 | Folmer et al. |
| 2008/0148853 A1 | 6/2008 | Kim |
| 2008/0227780 A1 | 9/2008 | Gless |
| 2008/0280886 A1 | 11/2008 | Gant et al. |
| 2008/0300251 A1 | 12/2008 | Sattigeri et al. |
| 2008/0306055 A1 | 12/2008 | Egner et al. |
| 2009/0186870 A1 | 7/2009 | Allen et al. |
| 2009/0239841 A1 | 9/2009 | Hutchison et al. |
| 2009/0253673 A1 | 10/2009 | Ge et al. |

FOREIGN PATENT DOCUMENTS

| | | | |
|---|---|---|---|
| JP | 2004517890 A | 6/2004 | |
| JP | 2009514818 A | 4/2009 | |
| JP | 2010540454 A | 12/2010 | |
| WO | 1995/06635 A1 | 3/1995 | |
| WO | 1998/06709 A1 | 2/1998 | |
| WO | 2001-066521 A1 | 9/2001 | |
| WO | 2002/070479 A1 | 9/2002 | |
| WO | 2002/076948 A1 | 10/2002 | |
| WO | 2003/042205 A1 | 5/2003 | |
| WO | 2003/080574 A1 | 10/2003 | |
| WO | 2004064738 A2 | 5/2004 | |
| WO | 2004/046110 A1 | 6/2004 | |
| WO | 2005/077914 A1 | 8/2005 | |
| WO | 2005112927 A1 | 12/2005 | |
| WO | 2006/001751 A1 | 1/2006 | |
| WO | 2006020959 A2 | 2/2006 | |
| WO | 2006014136 A1 | 9/2006 | |
| WO | 2009/020960 A1 | 2/2009 | |
| WO | 2009039460 A2 | 3/2009 | |
| WO | 2009039461 A2 | 3/2009 | |
| WO | 2009/089659 A1 | 7/2009 | |
| WO | 2009/092293 A1 | 7/2009 | |
| WO | 2010032856 A1 | 3/2010 | |
| WO | 2010111353 A1 | 9/2010 | |
| WO | 2011060397 A1 | 5/2011 | |
| WO | WO-2011109441 A1 * | 9/2011 | ........... C07C 275/28 |
| WO | 2001087839 | 11/2011 | |
| WO | WO-2012031196 A1 * | 3/2012 | ........... C07C 317/42 |
| WO | 2012113103 A1 | 8/2012 | |

OTHER PUBLICATIONS

Hasegawa, Masaichi. J. Med. Chem. (2007) 50, 4453-4470.*
Kojima et al., Nature, 402, 656-660, 1999.
Cummings et al., Diabetes, 50, 1714-1719, 2001.
Tschop et al., Nature, 407, 908-913, 2000.
Tschop et al., Diabetes, 50, 707-709, 2001.
Wren et al., J. Clin. Endocrinology and Metabolism, 86, 5992, 2001.
Esler et al., Endocrinology 148 (11):5175-5185), (2007).
Bioorg. & Med. Chem. Lett., 2004, 14, 5873-5876.
J Pharm Sci, 88 (10), 955-958, by Finnin and Morgan (Oct. 1999).
Wren et al., Endocrinology, 141, 4325-4328, 2000.
Berlin, et al, "Reduction of hERG inhibitory activity in the 4-piperidinyl urea series of H3 antagonists", Bioorganic & Medicinal Chemistry Letters, vol. 20, No. 7, pp. 2359-2364.
Li, et al., "Studies on the structure-activity relationship of 1,3,3,4-tetra-substituted pyrrolidine embodied CCR5 receptor antagonists. Part 2: Discovery of highly potent anti-HIV agents", Bioorganic & Medicinal Chemistry Letters, vol. 20, No. 17, pp. 5334-5336.
International Search Report and Written Opinion dated Dec. 5, 2015 issued in corresponding PCT Patent Application No. PCT/US2015/019112.
Carpino "Recent development . . . " Exp. Op in. ther. Patents 12(11)1599-1618 (2002).
Haehling et al. "Cachexia as a . . . " J. Cachexia Sarcopenia Muscle v.1, p. 1-5 (2010).
STN Registry No. 1210246-85-7 (Mar. 16, 2017).
De Boer "Ghrelin and cachexia . . . " Mol. Cell. Endcrin. 340:970105 (2011).
Rudolph et al. "Quinazolinone deri . . . " J. Med. Chem. 50:5202-16 (2007).
Silverman "The organic Chem . . . " p. 65-73 (2993).
Solomou and Korbonits. The role of ghrelin in weight-regulation disorders: Implications in clinical practice. Hormones 2014, 13(4):458-475.
Vengeliene. The role of ghrelin in drug and natural reward. Addict. Biol., Nov. 2013: 18(6):897-900.
Kilian et al. Rational design of dual peptides targeting ghrelin and Y2 receptors to regulate food intake and body weight J. Med. Chem., May 28, 2015;58(10):4180-93.
Kishimoto, et al. Ghrelin and cardiovascular diseases. Journal of Cardiology, 2012, 59: 8-13.
Charoenthongtrakul, et al. Enhanced gastrointestinal motility with orally active ghrelin receptor agonists. The Journal of Pharmacology and Experimental Therapeutics, 2009, 329(3):1178-1186.
Garcia, et al. Anamorelin for patients with cancer cachexia: an integrated analysis of two phase 2, randomised placebo-controlled, double-blind trials. Lancet Oncol. 2015, 16(1):108-16.
Costantino et al. "Ghrelin receptor . . . " Expert Op in Ther Patents 24(9) 1007-1019 (2014).
International Search Report, dated Jun. 8, 2012, which issued during the prosecution of International Patent Application No. PCT/US12/26315, which corresponds to the present application.
Written Opinion, dated Jun. 8, 2012, which issued during the prosecution of International Patent Application No. PCT/US12/26315, which corresponds to the present application.
International Preliminary Report on Patentability, dated Mar. 27, 2014, which issued during the prosecution of International Patent Application No. PCT/US12/26315, which corresponds to the present application.
Burrows et al. Bioorganic and Medicinal Chemistry Letters 2005, 15, 25-28.
Definition of the term adduct- dictionary.com (2012).
CAS RN 355401-28-4 (Entered into CAS STN system Sep. 10, 2001).
CAS RN 1290954-39-0 (Entered into CAS STN system May 6, 2011).
CAS RN 1259089-82-1 (Entered into CAS STN system Jan. 12, 2011).
CAS RN 1259199-34-2 (Entered into CAS STN system Jan. 12, 2011).

* cited by examiner

BENZENESULFONYL-ASYMMETRIC UREAS AND MEDICAL USES THEREOF

FIELD OF THE INVENTION

The present invention relates to novel asymmetric urea compounds, medical uses thereof, particularly in the treatment of medical conditions modulated by the ghrelin receptor.

BACKGROUND

The growth hormone secretagogue receptor (GHS-R) regulates a number of physiological processes, including growth hormone (GH) release, metabolism, and appetite. Ghrelin, a circulating hormone produced predominantly by endocrine cells in the stomach, is its endogenous ligand. Ghrelin is a 28 amino acid peptide with an acyl side chain required for biological activity (Kojima et al., Nature, 402, 656-660, 1999). Ghrelin has been shown to stimulate growth hormone (GH) release and to increase food intake when administered both centrally and peripherally (Wren et al., Endocrinology, 141, 4325-4328, 2000).

Endogenous levels of ghrelin rise on fasting and fall on re-feeding in humans (Cummings et al., Diabetes, 50, 1714-1719, 2001). Ghrelin also appears to play a role in maintaining long term energy balance and appetite regulation. Chronic administration of ghrelin in rodents leads to hyperphagia and weight gain that are independent of growth hormone secretion (Tschop et al., Nature, 407, 908-913, 2000). Circulating ghrelin levels decrease in response to chronic overfeeding and increase in response to chronic negative energy balance associated with anorexia or exercise. Obese people generally have low plasma ghrelin levels (Tschop et al., Diabetes, 50, 707-709, 2001) according to the physiological response of the body in reducing calories intake. Intravenous ghrelin is effective in stimulating food intake in humans. A recent study showed a 28% food intake increase from a buffet meal with a ghrelin infusion compared with saline control (Wren et al., J. Clin. Endocrinology and Metabolism, 86, 5992, 2001).

In view of the above experimental evidence, compounds that modulate ghrelin receptor activity have been proposed for preventing and/or treating disorders associated with ghrelin receptor physiology. For example, antagonists at ghrelin receptor might one day be developed to reduce appetite, reduce food intake, induce weight loss and treat obesity without affecting or reducing the circulating growth hormone levels. On the other hand, agonists at ghrelin receptor might also be developed for stimulating food intake and thus be useful in treating eating disorders, for example anorexia nervosa, or in treating cachexia resulting from cancer, AIDS or Chronic Obstructive Pulmonary Disease (COPD). Ghrelin agonists may also be useful as gastroprokinetic agents which can enhance gastrointestinal motility by increasing the frequency of contractions in the small intestine or making them stronger, but without disrupting their rhythm. Gastroprokinetic agents are used to relieve gastrointestinal symptoms such as abdominal discomfort, bloating, constipation, heart burn, nausea, and vomiting, and are used to treat a number of gastrointestinal disorders, including but not limiting to, irritable bowel syndrome, gastritis, acid reflux disease, gastroparesis, and functional dyspepsia. Furthermore, compounds that modulate ghrelin receptor activity might also be used to prevent or treat diseases related to substance abuse, for example, alcohol or drug (e.g., amphetamines, barbiturates, benzodiazepines, cocaine, methaqualone, and opioids) abuse, which refers to a maladaptive pattern of use of a substance that is not considered dependent.

Ghrelin receptor possesses a naturally high constitutive activity representing 50% of its maximal activity. Given the role that ghrelin and its receptor play in food intake and appetite control, a ghrelin receptor inverse agonist may be used as anti-obesity drug. An inverse agonist would decrease the receptor's activity to below the basal or constitutive level.

A number of compounds acting on the ghrelin receptor have been reported in the literature. YIL-781, for example, is a small molecule ghrelin receptor antagonist from Bayer that reportedly improves glucose tolerance, suppresses appetite and promotes weigh loss (Esler et al., Endocrinology 148 (11):5175-5185); LY444711 is an orally active ghrelin receptor agonist from Lilly that reportedly induces adiposity by stimulating food consumption and sparing fat utilization (Bioorg. & Med. Chem. Lett., 2004, 14, 5873-5876); anamorelin is an orally available ghrelin receptor small molecule agonist from Helsinn Therapeutics that is in clinical trials for the treatment of anorexia and cachexia in cancer patients. Ghrelin receptor agonists and antagonists based on asymmetric ureas are disclosed in US 2012/0220629, which is incorporated herein by reference in its entirety. Other small molecule ghrelin receptor modulators can be found in WO 2008/092681, US 2009/0253673, WO 2008/148853, WO 2008/148856, US 2007/0270473 and US 2009/0186870.

In view of the above, it is desirable to find new compounds which modulate ghrelin receptor activity.

SUMMARY

The present inventors have, through intensive research and experimentation, unexpectedly discovered a novel series of compounds having inverse agonist activity against the ghrelin receptors.

The present invention provides compounds of Formulae I-IV:

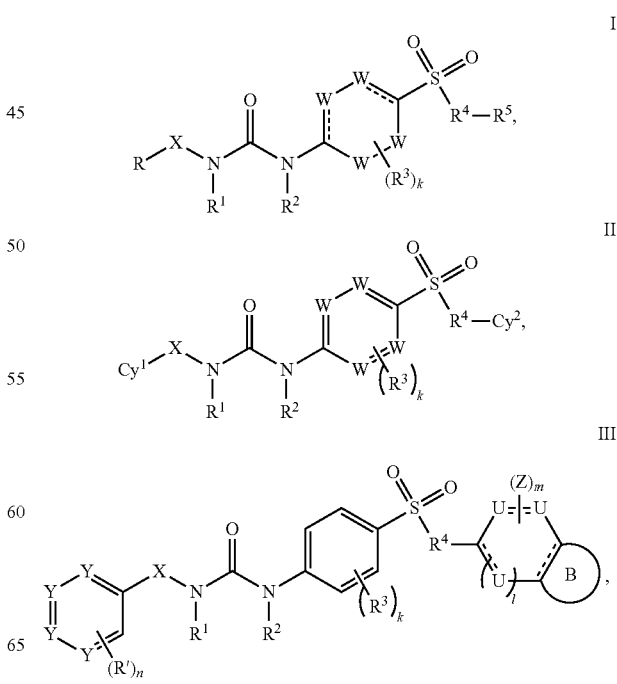

-continued

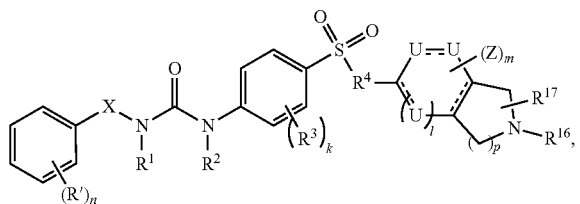

IV with U, W, X, Y, Z, $Cy^1$, $Cy^2$, R, R', $R^1$-$R^5$, $R^{16}$, $R^{17}$, k, l, m, n, and p as defined herein, and pharmaceutically acceptable salts thereof.

Compounds of Formulae I-IV, also referred to herein as sulfonyl-asymmetric ureas, are particularly useful for preventing and/or treating diseases that are pathophysiologically related to the ghrelin receptor in a subject. Accordingly, in another embodiment the invention provides a method of treating a disease that is mediated by the ghrelin receptor, comprising administering to said subject a therapeutically effective amount of a compound of Formula I-IV, or a pharmaceutically acceptable salt thereof.

Also disclosed are pharmaceutical compositions for preventing and/or treating diseases which are pathophysiologically related to ghrelin receptor in a subject, comprising a therapeutically effective amount of a compound of Formulae I-IV, or a pharmaceutically acceptable salt thereof, and one or more pharmaceutically acceptable excipients.

DETAILED DESCRIPTION

Before the present compounds, compositions, articles, devices, and/or methods are disclosed and described, it is to be understood that they are not limited to specific synthetic methods or specific treatment methods unless otherwise specified, or to particular reagents unless otherwise specified, as such may, of course, vary. It is also to be understood that the terminology used herein is for the purpose of describing particular embodiments only and is not intended to be limiting.

In a first principal embodiment, the present invention provides compounds of Formula I:

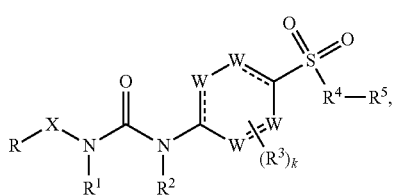

I or a pharmaceutically acceptable salt thereof, wherein:
a dashed line indicates an optional bond;
W is C, N, or O;
X is a bond, CO, or $CR^7R^8$;
k is 0-2;
R is $C_{1-6}$ alkyl or $Cy^1$ wherein said $C_{1-6}$ alkyl or $Cy^1$ is optionally substituted with 1-3 substituents selected from halo, heteroaryl, $C_{1-6}$ alkoxy, $C_{1-6}$ alkyl, heterocycloalkyl, $CO_2(C_{1-6}$ alkyl), and $CO(C_{1-6}$ alkyl);
$R^1$ and $R^2$ are each, independently, H, $C_{1-3}$ alkyl, methoxy, halo, or OH;

or $R^1$ and $R^2$ taken together with the atoms to which they are attached form a 5-6 membered ring;

or $R^1$ and X taken together with the atoms to which they are attached form a 5-6 membered ring;

or $R^1$, X and R taken together with the atoms to which they are attached form a bicyclic structure;

$R^3$ is H, $C_{1-3}$ alkyl, methoxy, halo, or —OH, —$COOR^{12}$, —$CR^{13}R^{14}OH$, —$CONHR^{15}$, cycloalkyl, heteroaryl;

$R^4$ is a bond, $NR^6$ or $CR^9R^{10}$;

or $R^3$ and $R^4$ taken together with the atoms to which they are attached form a 3-6-membered ring;

$R^5$ is $Cy^2$, $CO(C_{1-6}$ alkyl), $C_{1-6}$ alkyl, cycloalkyl, or heterocycloalkyl, wherein said $Cy^2$, $CO(C_{1-6}$ alkyl), $C_{1-6}$ alkyl, cycloalkyl, or heterocycloalkyl is optionally substituted with 1-3 substituents selected from halo, $C_{1-6}$ alkylamine, $COR^{11}$, $SO_2R^{11}$, heterocycloalkyl, $CO_2R^{11}$, $C_{1-6}$ hydroxyalkyl, heteroaryl, $CH_2CO_2R^{11}$, $C_{1-6}$ alkoxy, OH, CN, $R^{11}$, $CH_2OSO_3H$, benzyl, $CH_2SO_3H$, $CH_2CN$, and $NHCH_2$ cycloalkyl;

$R^6$ is a bond, H, or $CH_3$;

$R^7$ and $R^8$ are each, independently, H, $C_{1-3}$ alkyl, or $CONH_2$, wherein said $C_{1-3}$ alkyl is optionally substituted with halo;

$R^9$ and $R^{10}$ are each, independently, H or $C_{1-3}$ alkyl, wherein said $C_{1-3}$ alkyl is optionally substituted with halo;

$R^{11}$ is H, $NH_2$, or optionally substituted $C_{1-6}$ alkyl;

$R^{12}$ is H or $C_{1-3}$ alkyl;

$R^{13}$ and $R^{14}$ are each independently H or $C_{1-3}$ alkyl; and $R^{15}$ is H or $C_{1-3}$ alkyl.

In a second principal embodiment, the present invention provides compounds of Formula II:

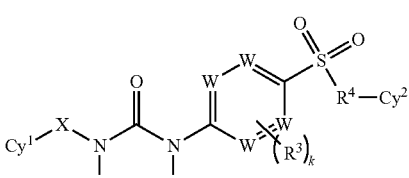

II or a pharmaceutically acceptable salt thereof, wherein:
X, W, $R^1$-$R^4$, and k are as defined above;
$Cy^1$ is a cyclic moiety selected from the group consisting of aryl, heteroaryl, cycloalkyl, and heterocycloalkyl, wherein said cyclic moiety is optionally substituted with 1-3 substituents selected from halo, heteroaryl, $C_{1-6}$ alkoxy, $C_{1-6}$ alkyl, heterocycloalkyl, $CO_2(C_{1-6}$ alkyl), and $CO(C_{1-6}$ alkyl); and $Cy^2$ is a cyclic moiety selected from the group consisting of aryl, heteroaryl, cycloalkyl, and heterocycloalkyl, wherein said cyclic moiety is optionally substituted with 1-3 substituents selected from halo, $C_{1-6}$ alkylamine, $COR^{11}$, $SO_2R^{11}$, heterocycloalkyl, $CO_2R^{11}$, $C_{1-6}$ hydroxyalkyl, heteroaryl, $CH_2CO_2R^{11}$, $C_{1-6}$ alkoxy, OH, CN, $R^{11}$, $CH_2OSO_3H$, benzyl, $CH_2SO_3H$, $CH_2CN$, and $NHCH_2$ cycloalkyl.

In a third principal embodiment, the compounds have the structure of Formula III:

[Formula III structure]

or a pharmaceutically acceptable salt thereof, wherein:
X, $R^1$-$R^4$, and k are as defined above;
a dashed line indicates an optional bond;
U is C, N, S, or O
B is 5-7-membered ring or a bicyclic structure, wherein said 5-7-membered ring or a bicyclic structure is optionally substituted with $COR^{11}$, $SO_2R^{11}$, heterocycloalkyl, $CO_2R^{11}$, $C_{1-6}$ hydroxyalkyl, heteroaryl, $CH_2CO_2R^{11}$, $C_{1-6}$ alkoxy, OH, CN, $R^{11}$, $CH_2OSO_3H$, benzyl, $CH_2SO_3H$, or $CH_2CN$;
Y is each, independently, a C or N;
Z is halo, methoxy, or $C_{1-3}$ alkyl optionally substituted with halo;
R' is a halo, heteroaryl, $C_{1-6}$ alkoxy, $C_{1-6}$ alkyl, heterocycloalkyl, CN cycloalkyl, $CO_2(C_{1-6}$ alkyl), or $CO(C_{1-6}$ alkyl);
or two R' taken together with the atoms to which they are attached form a 5-6-membered ring;
l is 0-3;
m is 0-3; and
n is 0-3.

In a fourth principal embodiment, the compounds have the structure of Formula IV:

[Formula IV structure]

or a pharmaceutically acceptable salt thereof, wherein X, $R^1$-$R^4$, k, U, Z, R', k, l, m, and n are defined as above; $R^{16}$ is H, $C_{1-3}$ alkyl; $R^{17}$ is H, halo or $C_{1-3}$ alkyl; and p is 1-3.

In the first, second, third and fourth principal embodiments, in one subembodiment, X is CO.

In the first, second, third and fourth principal embodiments, in one subembodiment, X is a bond.

In the first, second, third and fourth principal embodiments, in one subembodiment, X is $C_{1-3}$ alkyl.

In the first principal embodiment, as well as the second, third and fourth principal embodiments discussed below, in one subembodiment X is $CHCH_3$.

In some embodiments, X is not $CHCH_3$.

In the first, second, third and fourth principal embodiments, in one subembodiment, X is $CH_2$.

In some embodiments, X is not $CH_2$.

In the first, second, third and fourth principal embodiments, in one subembodiment, X is $C(CH_3)_2$.

In the first, second, third and fourth principal embodiments, in one subembodiment, X is $CHCF_3$.

In the first, second, third and fourth principal embodiments, in one subembodiment, X is $CH(CH_2CH_3)$.

In the first principal embodiment, in one subembodiment, R is $Cy^1$.

In the first and second principal embodiments, in one subembodiment, $Cy^1$ is aryl, heteroaryl, cycloalkyl, or heterocycloalkyl.

In the first and second principal embodiments, in one subembodiment, $Cy^1$ is substituted and unsubstituted.

In the first and second principal embodiments, in one subembodiment, said $Cy^1$ is

[Structures of various Cy¹ groups]

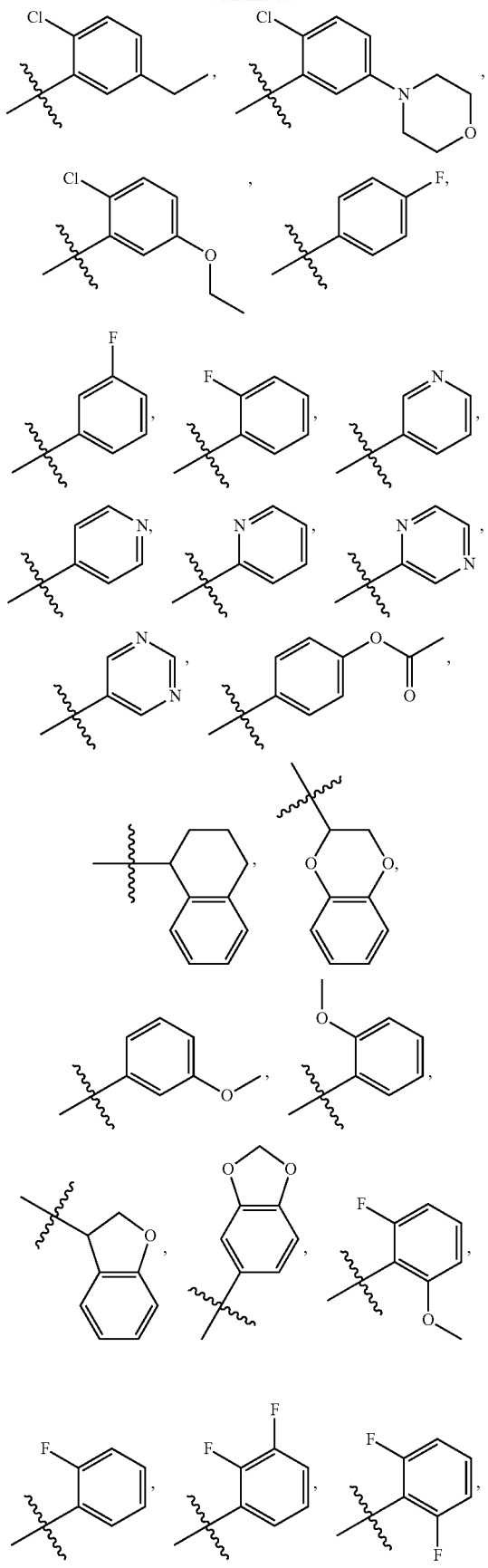
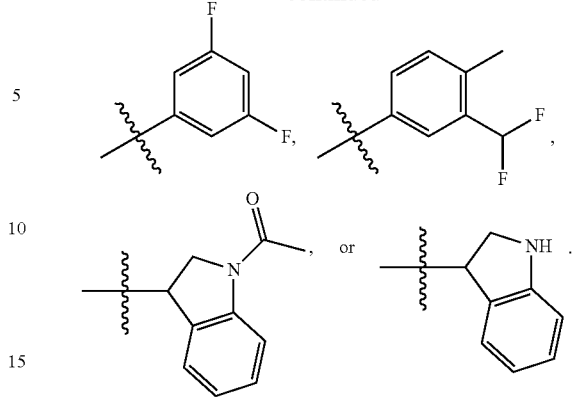

In the first and second principal embodiments, in one subembodiment, said Cy$^1$ is phenyl.

In some embodiments, R is not naphthalene.

In the first embodiment, in one subembodiment, R is $C_{1-6}$ alkyl.

In the first principal embodiment, in one subembodiment, R is $CH_3$, $C(CH_3)_3$, or $CH(CH_3)_2$.

In the first principal embodiment, in one subembodiment, R is cycloalkane.

In the first principal embodiment, in one subembodiment, R is cyclopropane.

In the first, second, third, and fourth principal embodiments, in one subembodiment, $R^1$ is H, OH, or $CH_3$.

In the first, second, third, and fourth principal embodiments, in one subembodiment, $R^1$ is H.

In some embodiments, $R^1$ is not H.

In the first, second, third, and fourth principal embodiments, in one subembodiment, $R^1$ is OH.

In the first, second, third, and fourth principal embodiments, in one subembodiment, $R^1$ is $CH_3$.

In the first, second, third, and fourth principal embodiments, in one subembodiment, $R^1$ and X come together to form a 5-6 membered ring.

In the first, second, third, and fourth principal embodiments, in one subembodiment, $R^1$, X and R come together to form a bicyclic structure.

In the first, second, third, and fourth principal embodiments, in one embodiment, $R^2$ is H, OH or $CH_3$.

In the first, second, third, and fourth principal embodiments, in one subembodiment, $R^2$ is H.

In some embodiments $R_2$ is not H.

In the first, second, third, and fourth principal embodiments, in one subembodiment, $R^2$ is $CH_3$.

In the first, second, third, and fourth principal embodiments, in one subembodiment, $R^2$ and $R^1$ come together to form a 5-6 membered ring.

In the first, second, third, and fourth principal embodiments, in one subembodiment, $R^3$ is H, $C_{1-3}$ alkyl, methoxy, halo, or —OH, —COOR$^{12}$, —CR$^{13}$R$^{14}$OH, —CONHR$^{15}$, cycloalkyl, heteroaryl.

In the first, second, third, and fourth principal embodiments, in one subembodiment, $R^3$ is H.

In some embodiments, $R_3$ is not H.

In the first, second, third, and fourth principal embodiments, in one subembodiment, $R^3$ is halo.

In the first, second, third, and fourth principal embodiments, in one subembodiment, $R^3$ is F.

In the first, second, third, and fourth principal embodiments, in one subembodiment, $R^3$ is Cl.

In the first, second, third, and fourth principal embodiments, in one subembodiment, $R^3$ is methoxy.

In the first, second, third, and fourth principal embodiments, in one subembodiment, $R^3$ is $C_{1-3}$ alkyl.

In the first, second, third, and fourth principal embodiments, in one subembodiment, $R^3$ is methyl.

In the first, second, third, and fourth principal embodiments, in one subembodiment, $R^3$ is $COOR^{12}$.

In the first, second, third, and fourth principal embodiments, in one subembodiment, $R^3$ is COOH.

In the first, second, third, and fourth principal embodiments, in one subembodiment, $R^3$ is $COOCH_3$.

In the first, second, third, and fourth principal embodiments, in one subembodiment, $R^3$ is $CONHR^{15}$.

In the first, second, third, and fourth principal embodiments, in one subembodiment, $R^3$ is $CONH_2$.

In the first, second, third, and fourth principal embodiments, in one subembodiment, $R^3$ is cycloalkyl.

In the first, second, third, and fourth principal embodiments, in one subembodiment, $R^3$ is cyclopropane.

In the first, second, third, and fourth principal embodiments, in one subembodiment, $R^3$ is heteroaryl.

In the first, second, third, and fourth principal embodiments, in one subembodiment, $R^3$ is heteroaryl, optionally substituted with $C_{1-3}$ alkyl.

In the first, second, third, and fourth principal embodiments, in one subembodiment, $R^4$ is a bond.

In the first, second, third, and fourth principal embodiments, in one subembodiment, $R^4$ is $CH_2$.

In the first, second, third, and fourth principal embodiments, in one subembodiment, $R^4$ is $CHCH_3$.

In the first, second, third, and fourth principal embodiments, in one subembodiment, $R^4$ is $C(CH_3)_2$.

In the first, second, third, and fourth principal embodiments, in one subembodiment, $R^4$ is NH.

In some embodiments, $R^4$ is not NH.

In the first, second, third, and fourth principal embodiments, in one subembodiment, $R^4$ is $NCH_3$.

In the first, second, third, and fourth principal embodiments, in one subembodiment, $R^4$ and $R^3$ come together to form a 5-membered heterocyclic ring.

In the first principal embodiment, in one subembodiment, $R^5$ is $Cy^2$.

In the first, and second principal embodiments, in one subembodiment, said $Cy^2$ is aryl, heteroaryl, cycloalkyl, or heterocycloalkly.

In the first and second principal embodiments, in one subembodiment, said $Cy^2$ is isoindoline.

In the first and second principal embodiments, in one subembodiment, said isoindoline is optionally substituted with 1-3 substituents selected from the group consisting of $CH_3$,

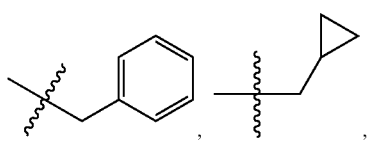 [SMILES: *Cc1ccccc1 ; *CC1CC1]

$CH_2CH_3$,

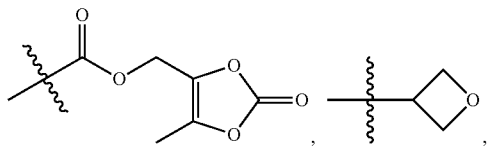 [SMILES: *C(=O)OCc1oc(=O)oc1C ; *C1COC1]

$CH_2CH_2OCH_3$, $CH_2CN$,

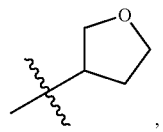

and fluoro.

In the first and second principal embodiments, in one subembodiment, said $Cy^2$ is tetrahydroisoquinoline.

In the first, second and third principal embodiments, in one subembodiment, said tetrahydroisoquinoline is optionally substituted with 1-3 substituents selected from the group consisting of $CH_3$, $CH_2CH_3$, $COCH_3$, $SO_2CH_3$, $CO_2CH_2CH_3$,

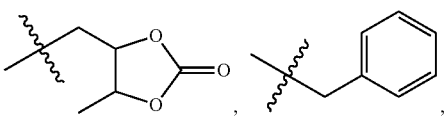

F, and methoxy.

In the first principal embodiment, in one subembodiment, $R^5$ is phenyl, wherein said phenyl is optionally substituted with 1-3 substituents from the group consisting of

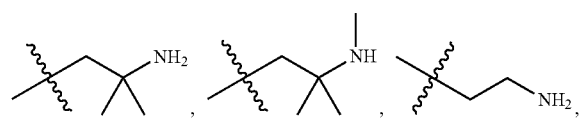

$CH_3$,

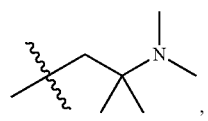 [SMILES: *CC(C)(C)N(C)C]

$CH_2NH_2$, $CO_2CH_3$, $CO_2H$, $CH_2OH$,

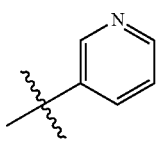

CONH$_2$, C(CH$_3$)$_2$NH$_2$, CH$_2$CO$_2$CH$_3$,
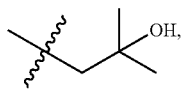 [SMILES: *CC(C)(C)O]
methoxy, OH, CH$_2$OCH$_3$, CH$_2$CH$_2$OH, CN,
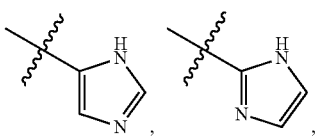 [SMILES: *c1cnc[nH]1 ; *c1ncc[nH]1]
CH$_2$OSO$_3$H,
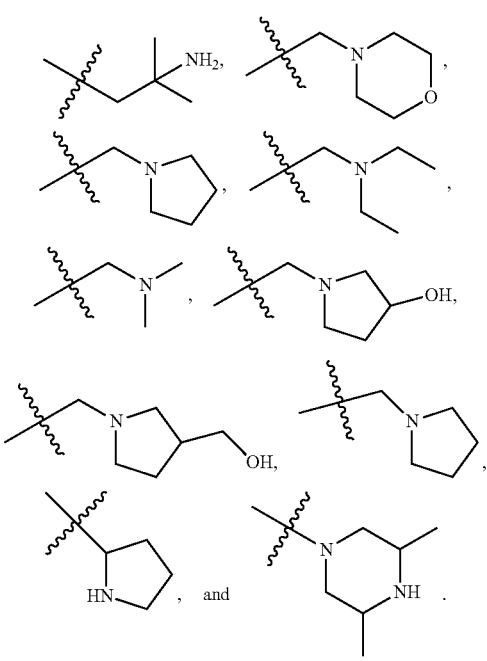
In some embodiments, R$^5$ is not phenyl substituted with
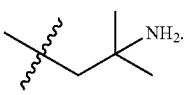 [SMILES: *CC(C)(C)N]
In the first principal embodiment, in one subembodiment, R$^5$ is
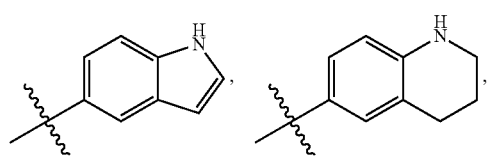
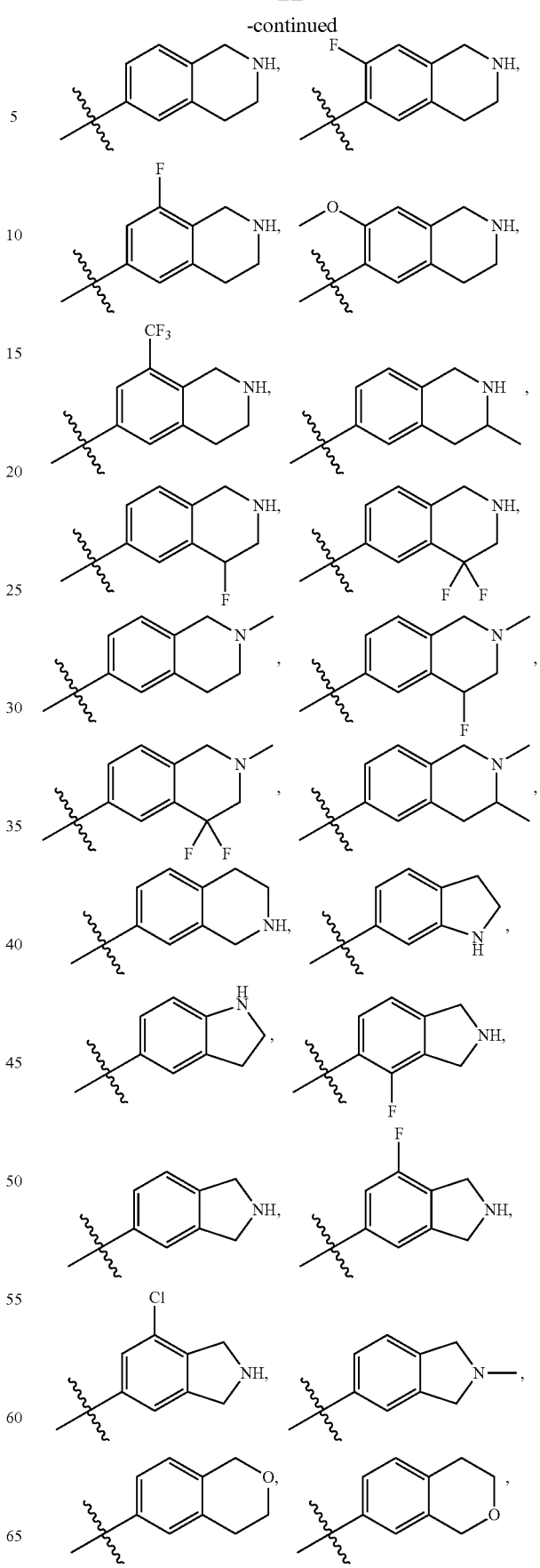

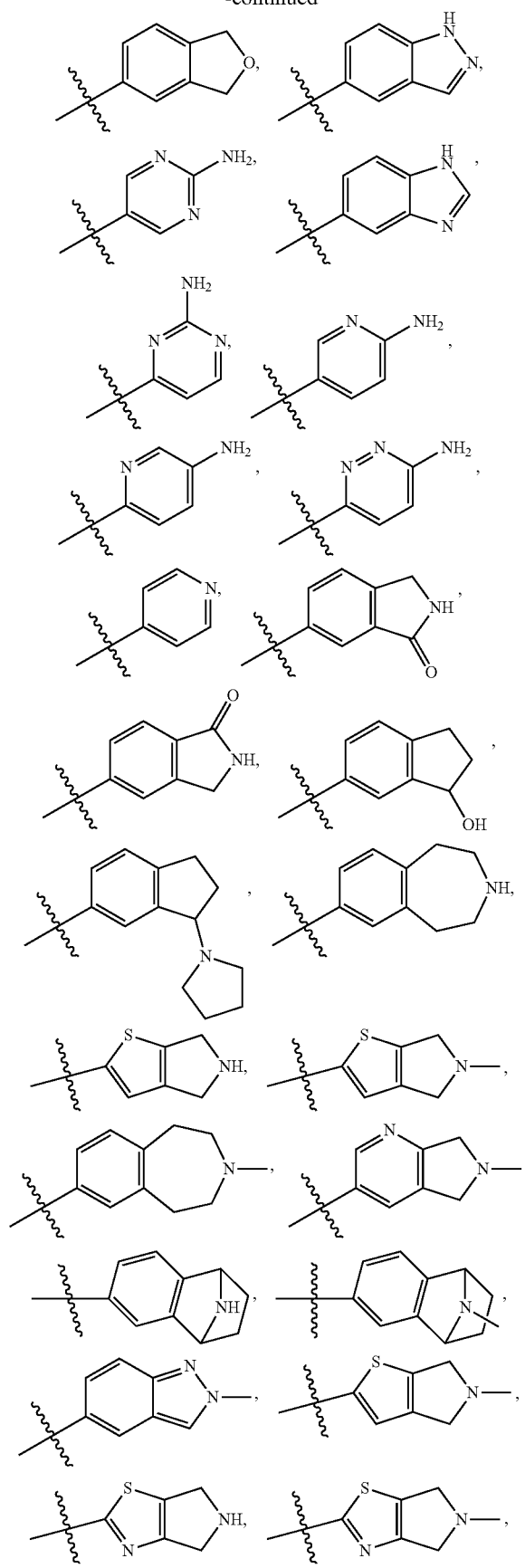
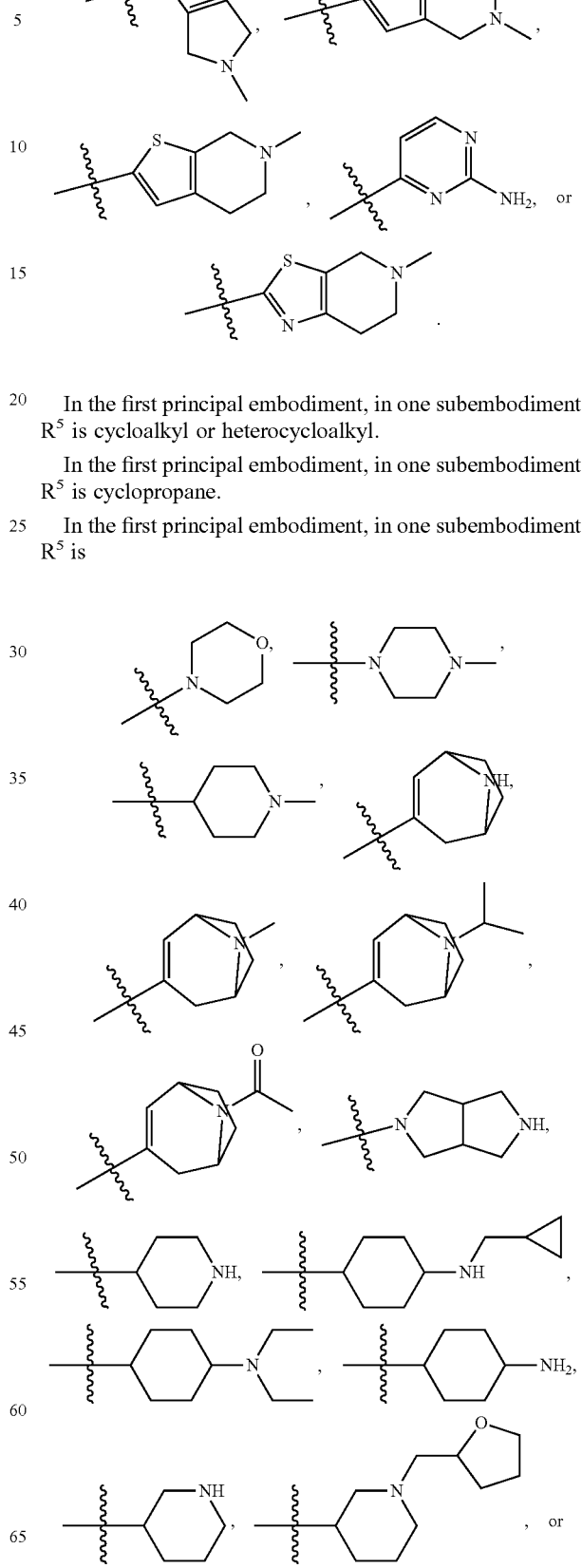
In the first principal embodiment, in one subembodiment, $R^5$ is cycloalkyl or heterocycloalkyl.
In the first principal embodiment, in one subembodiment, $R^5$ is cyclopropane.
In the first principal embodiment, in one subembodiment, $R^5$ is

15

-continued

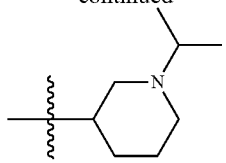

In the first principal embodiment, in one subembodiment, R⁵ is CO(C$_{1-6}$ alkyl).

In the first principal embodiment, in one subembodiment, R⁵ is COCH$_3$.

In the first principal embodiment, in one subembodiment, R⁵ is C$_{1-6}$ alkyl.

16

In the first principal embodiment, in one subembodiment, R⁵ is

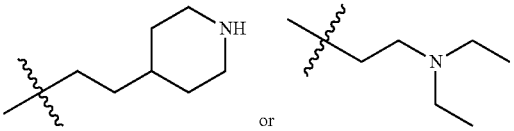

In some forms, the compounds as presently disclosed are compounds of Formula I, or pharmaceutically acceptable salts thereof, wherein the compound of Formula I is a compound selected from the group consisting of:

| | Chemical Structure | Chemical Name |
|---|---|---|
| H0906 | 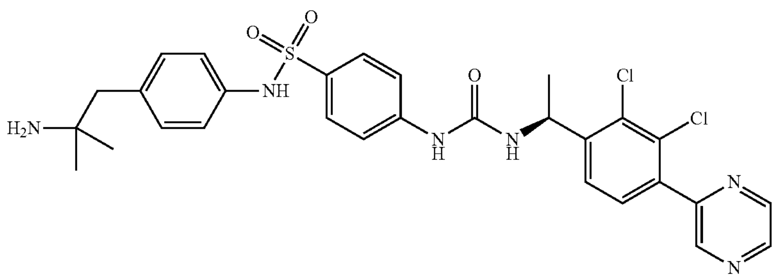 [SMILES: C[C@H](NC(=O)Nc1ccc(S(=O)(=O)Nc2ccc(CC(C)(C)N)cc2)cc1)c1ccc(-c2cnccn2)c(Cl)c1Cl] | (S)-N-(4-(2-amino-2-methylpropyl)phenyl)-4-(3-(1-(2,3-dichloro-4-(pyrazin-2-yl)phenyl)ethyl)ureido)benzenesulfonamide |
| H0907 | 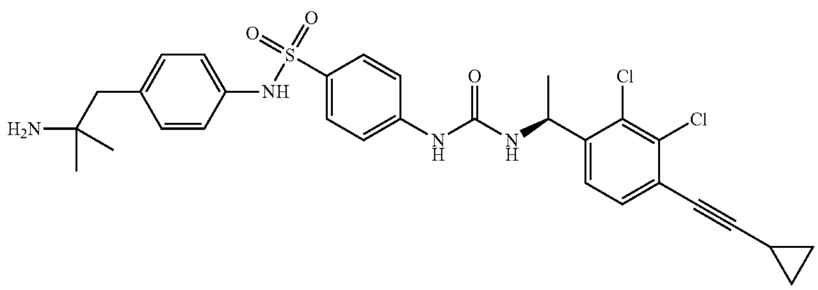 [SMILES: C[C@H](NC(=O)Nc1ccc(S(=O)(=O)Nc2ccc(CC(C)(C)N)cc2)cc1)c1ccc(C#CC2CC2)c(Cl)c1Cl] | (S)-N-(4-(2-amino-2-methylpropyl)phenyl)-4-(3-(1-(2,3-dichloro-4-(cyclopropylethynyl)phenyl)ethyl)ureido)benzenesulfonamide |
| H0937 | 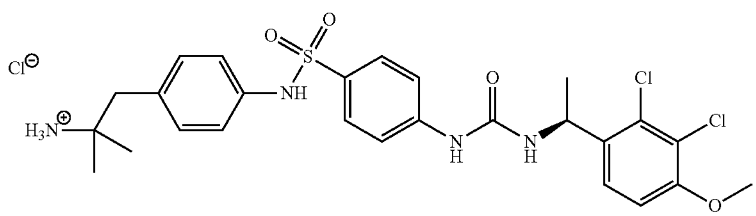 [SMILES: [Cl-] ; COc1ccc([C@H](C)NC(=O)Nc2ccc(S(=O)(=O)Nc3ccc(CC(C)(C)[NH3+])cc3)cc2)c(Cl)c1Cl] | (S)-N-(4-(2-amino-2-methylpropyl)phenyl)-4-(3-(1-(2,3-dichloro-4-methoxyphenyl)ethyl)ureido)benzenesulfonamide |
| H0941 | 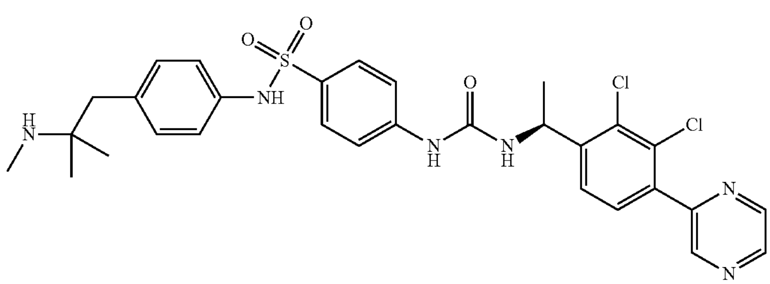 [SMILES: CNC(C)(C)Cc1ccc(NS(=O)(=O)c2ccc(NC(=O)N[C@@H](C)c3ccc(-c4cnccn4)c(Cl)c3Cl)cc2)cc1] | (S)-4-(3-(1-(2,3-dichloro-4-(pyrazin-2-yl)phenyl)ethyl)ureido)-N-(4-(2-methyl-2-(methylamino)propyl)phenyl)benzenesulfonamide |

-continued

| | Chemical Structure | Chemical Name |
|---|---|---|
| H0942 | 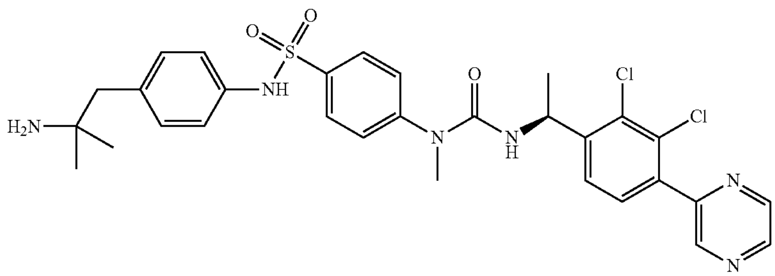 [SMILES: C[C@H](NC(=O)N(C)c1ccc(S(=O)(=O)Nc2ccc(CC(C)(C)N)cc2)cc1)c1ccc(-c2cnccn2)c(Cl)c1Cl] | (S)-N-(4-(2-amino-2-methylpropyl)phenyl)-4-(3-(1-(2,3-dichloro-4-(pyrazin-2-yl)phenyl)ethyl)-1-methylureido)benzenesulfonamide |
| H0943 | 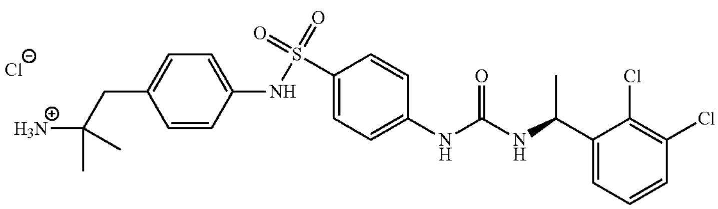 [SMILES: [Cl-] ; C[C@H](NC(=O)Nc1ccc(S(=O)(=O)Nc2ccc(CC(C)(C)[NH3+])cc2)cc1)c1cccc(Cl)c1Cl] | (S)-N-(4-(2-amino-2-methylpropyl)phenyl)-4-(3-(1-(2,3-dichlorophenyl)ethyl)ureido)benzenesulfonamide |
| H0944 | 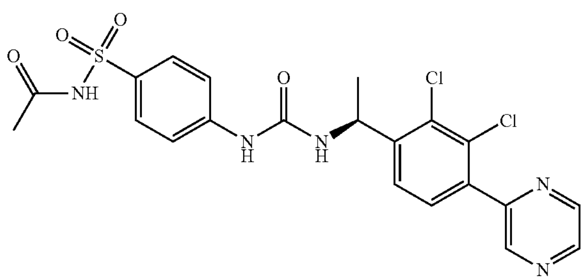 [SMILES: CC(=O)NS(=O)(=O)c1ccc(NC(=O)N[C@@H](C)c2ccc(-c3cnccn3)c(Cl)c2Cl)cc1] | (S)-N-((4-(3-(1-(2,3-dichloro-4-(pyrazin-2-yl)phenyl)ethyl)ureido)phenyl)sulfonyl)acetamide |
| H0950 | 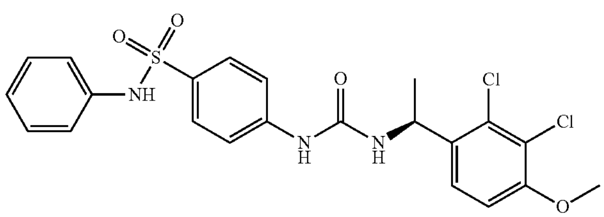 [SMILES: COc1ccc([C@H](C)NC(=O)Nc2ccc(S(=O)(=O)Nc3ccccc3)cc2)c(Cl)c1Cl] | (S)-4-(3-(1-(2,3-dichloro-4-methoxyphenyl)ethyl)ureido)-N-phenylbenzenesulfonamide |
| H0951 | 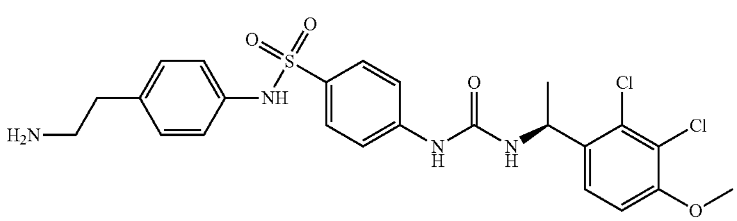 [SMILES: COc1ccc([C@H](C)NC(=O)Nc2ccc(S(=O)(=O)Nc3ccc(CCN)cc3)cc2)c(Cl)c1Cl] | (S)-N-(4-(2-aminoethyl)phenyl)-4-(3-(1-(2,3-dichloro-4-methoxyphenyl)ethyl)ureido)benzenesulfonamide |
| H0953 | 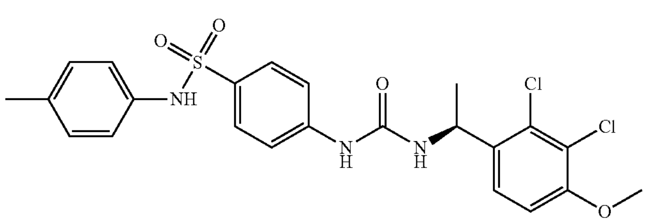 | (S)-4-(3-(1-(2,3-dichloro-4-methoxyphenyl)ethyl)ureido)-N-(p-tolyl)benzenesulfonamide |

-continued

| | Chemical Structure | Chemical Name |
|---|---|---|
| H0954 | 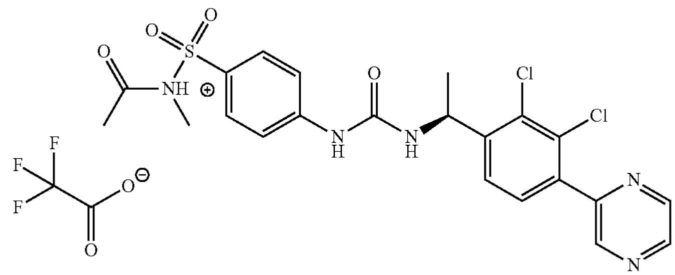 [SMILES: O=C([O-])C(F)(F)F ; CC(=O)[NH+](C)S(=O)(=O)c1ccc(NC(=O)N[C@@H](C)c2ccc(-c3cnccn3)c(Cl)c2Cl)cc1] | (S)-N-((4-(3-(1-(2,3-dichloro-4-(pyrazin-2-yl)phenyl)ethyl)ureido)phenyl)sulfonyl)-N-methylacetamide |
| H0963 | 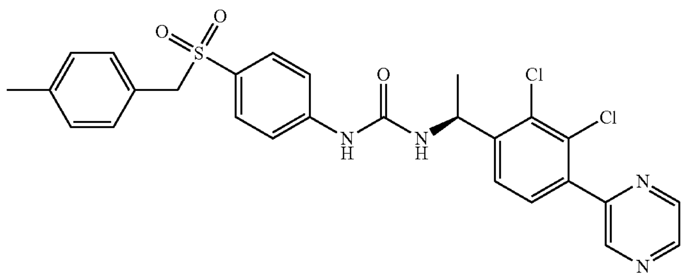 [SMILES: Cc1ccc(CS(=O)(=O)c2ccc(NC(=O)N[C@@H](C)c3ccc(-c4cnccn4)c(Cl)c3Cl)cc2)cc1] | (S)-1-(1-(2,3-dichloro-4-(pyrazin-2-yl)phenyl)ethyl)-3-(4-((4-methylbenzyl)sulfonyl)phenyl)urea |
| H0964 | 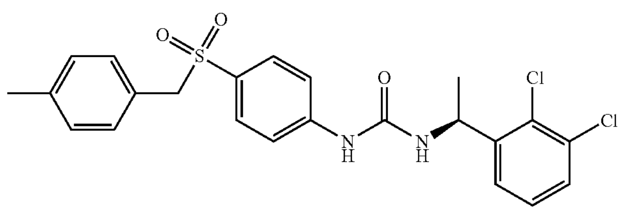 [SMILES: Cc1ccc(CS(=O)(=O)c2ccc(NC(=O)N[C@@H](C)c3cccc(Cl)c3Cl)cc2)cc1] | (S)-1-(1-(2,3-dichlorophenyl)ethyl)-3-(4-((4-methylbenzyl)sulfonyl)phenyl)urea |
| H0965 | 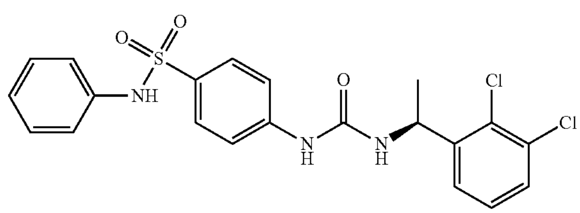 [SMILES: C[C@H](NC(=O)Nc1ccc(S(=O)(=O)Nc2ccccc2)cc1)c1cccc(Cl)c1Cl] | (S)-4-(3-(1-(2,3-dichlorophenyl)ethyl)ureido)-N-phenylbenzenesulfonamide |
| H0966 | 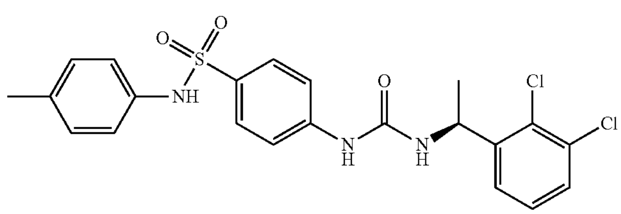 [SMILES: Cc1ccc(NS(=O)(=O)c2ccc(NC(=O)N[C@@H](C)c3cccc(Cl)c3Cl)cc2)cc1] | (S)-4-(3-(1-(2,3-dichlorophenyl)ethyl)ureido)-N-(p-tolyl)benzenesulfonamide |
| H0967 | 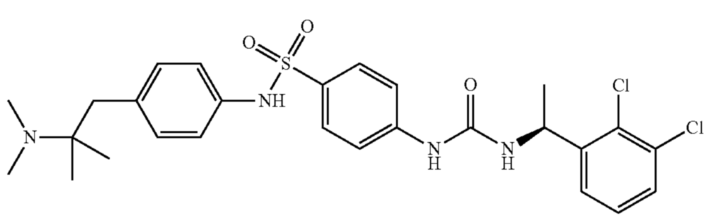 | (S)-4-(3-(1-(2,3-dichlorophenyl)ethyl)ureido)-N-(4-(2-(dimethylamino)-2-methylpropyl)phenyl)benzenesulfonamide |

-continued

| | Chemical Structure | Chemical Name |
|---|---|---|
| H0968 | 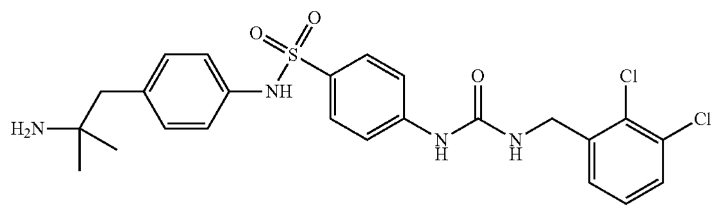 [SMILES: CC(C)(N)Cc1ccc(NS(=O)(=O)c2ccc(NC(=O)NCc3cccc(Cl)c3Cl)cc2)cc1] | N-(4-(2-amino-2-methylpropyl)phenyl)-4-(3-(2,3-dichlorobenzyl)ureido)benzenesulfonamide |
| H0969 | 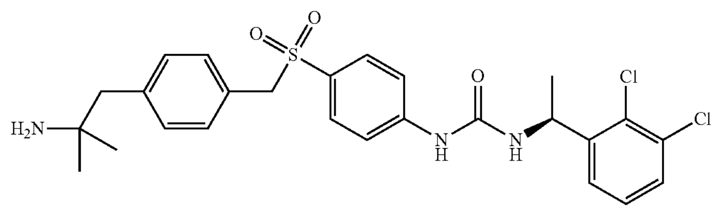 [SMILES: C[C@H](NC(=O)Nc1ccc(S(=O)(=O)Cc2ccc(CC(C)(C)N)cc2)cc1)c1cccc(Cl)c1Cl] | (S)-1-(4-((4-(2-amino-2-methylpropyl)benzyl)sulfonyl)phenyl)-3-(1-(2,3-dichlorophenyl)ethyl)urea |
| H0971 | 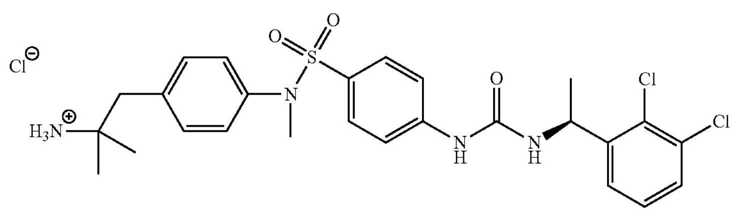 [SMILES: [Cl-] ; C[C@H](NC(=O)Nc1ccc(S(=O)(=O)N(C)c2ccc(CC(C)(C)[NH3+])cc2)cc1)c1cccc(Cl)c1Cl] | (S)-N-(4-(2-amino-2-methylpropyl)phenyl)-4-(3-(1-(2,3-dichlorophenyl)ethyl)ureido)-N-methylbenzenesulfonamide |
| H0975 | 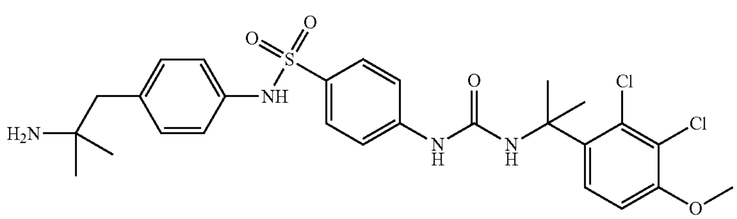 [SMILES: COc1ccc(C(C)(C)NC(=O)Nc2ccc(S(=O)(=O)Nc3ccc(CC(C)(C)N)cc3)cc2)c(Cl)c1Cl] | N-(4-(2-amino-2-methylpropyl)phenyl)-4-(3-(2-(2,3-dichloro-4-methoxyphenyl)propan-2-yl)ureido)benzenesulfonamide |
| H0981 | 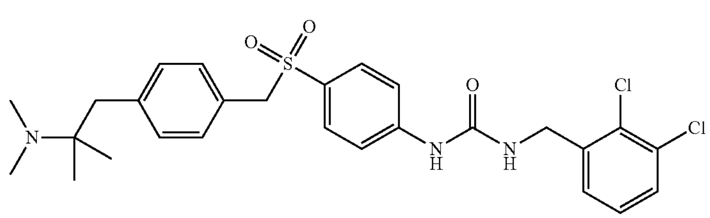 [SMILES: CN(C)C(C)(C)Cc1ccc(CS(=O)(=O)c2ccc(NC(=O)NCc3cccc(Cl)c3Cl)cc2)cc1] | 1-(2,3-dichlorobenzyl)-3-(4-((4-(2-(dimethylamino)-2-methylpropyl)benzyl)sulfonyl)phenyl)urea |
| H0990 | 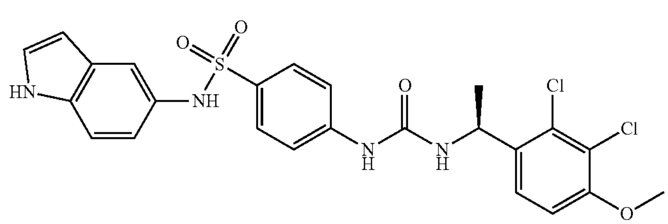 [SMILES: COc1ccc([C@H](C)NC(=O)Nc2ccc(S(=O)(=O)Nc3ccc4[nH]ccc4c3)cc2)c(Cl)c1Cl] | (S)-4-(3-(1-(2,3-dichloro-4-methoxyphenyl)ethyl)ureido)-N-(1H-indol-5-yl)benzenesulfonamide |
| H0991 | 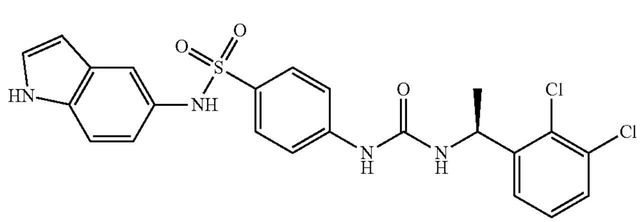 [SMILES: C[C@H](NC(=O)Nc1ccc(S(=O)(=O)Nc2ccc3[nH]ccc3c2)cc1)c1cccc(Cl)c1Cl] | (S)-4-(3-(1-(2,3-dichlorophenyl)ethyl)ureido)-N-(1H-indol-5-yl)benzenesulfonamide |

| | Chemical Structure | Chemical Name |
|---|---|---|
| H0993 | 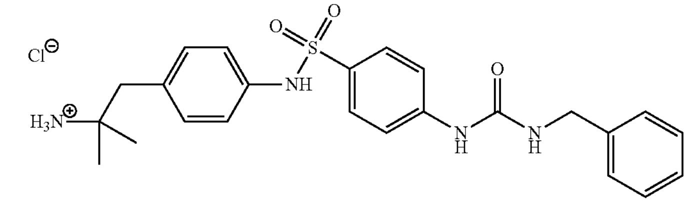 [SMILES: [Cl-] ; CC(C)([NH3+])Cc1ccc(NS(=O)(=O)c2ccc(NC(=O)NCc3ccccc3)cc2)cc1] | N-(4-(2-amino-2-methylpropyl)phenyl)-4-(3-benzylureido)benzenesulfonamide |
| H0994 | 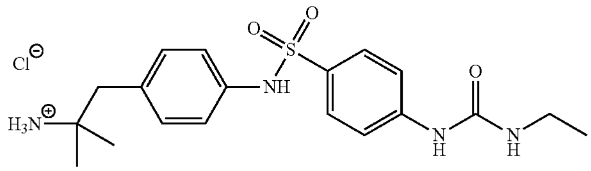 [SMILES: [Cl-] ; CCNC(=O)Nc1ccc(S(=O)(=O)Nc2ccc(CC(C)(C)[NH3+])cc2)cc1] | N-(4-(2-amino-2-methylpropyl)phenyl)-4-(3-ethylureido)benzenesulfonamide |
| H0995 | 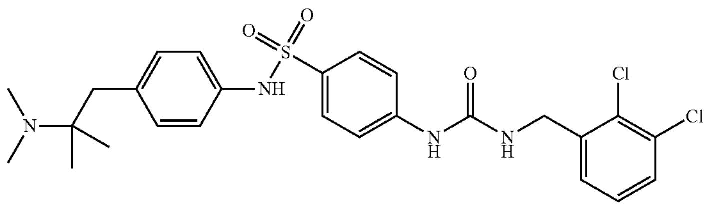 [SMILES: CN(C)C(C)(C)Cc1ccc(NS(=O)(=O)c2ccc(NC(=O)NCc3cccc(Cl)c3Cl)cc2)cc1] | 4-(3-(2,3-dichlorobenzyl)ureido)-N-(4-(2-(dimethylamino)-2-methylpropyl)phenyl)benzenesulfonamide |
| H0996 | 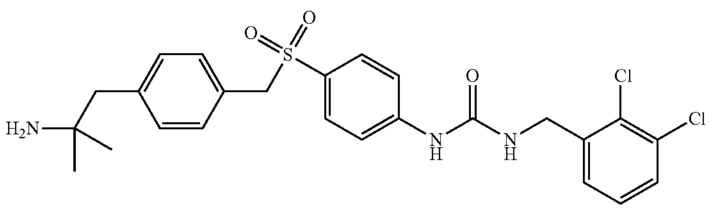 [SMILES: CC(C)(N)Cc1ccc(CS(=O)(=O)c2ccc(NC(=O)NCc3cccc(Cl)c3Cl)cc2)cc1] | 1-(4-((4-(2-amino-2-methylpropyl)benzyl)sulfonyl)phenyl)-3-(2,3-dichlorobenzyl)urea |
| H0997 | 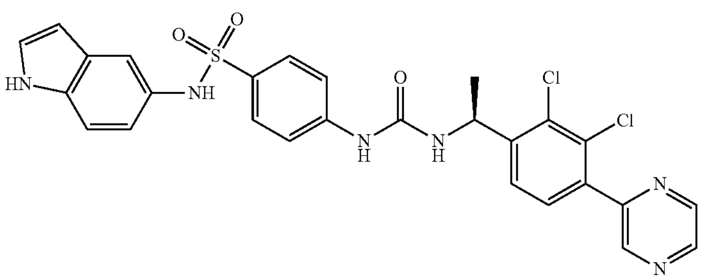 [SMILES: C[C@H](NC(=O)Nc1ccc(S(=O)(=O)Nc2ccc3[nH]ccc3c2)cc1)c1ccc(-c2cnccn2)c(Cl)c1Cl] | (S)-4-(3-(1-(2,3-dichloro-4-(pyrazin-2-yl)phenyl)ethyl)ureido)-N-(1H-indol-5-yl)benzenesulfonamide |
| H1003 | 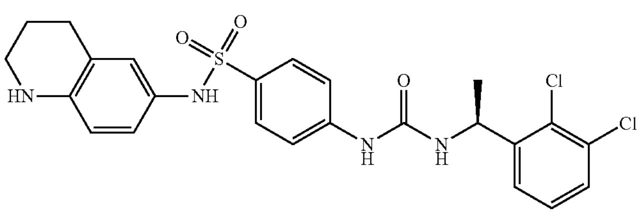 [SMILES: C[C@H](NC(=O)Nc1ccc(S(=O)(=O)Nc2ccc3c(c2)CCCN3)cc1)c1cccc(Cl)c1Cl] | (S)-4-(3-(1-(2,3-dichlorophenyl)ethyl)ureido)-N-(1,2,3,4-tetrahydroquinolin-6-yl)benzenesulfonamide |
| H1004 | 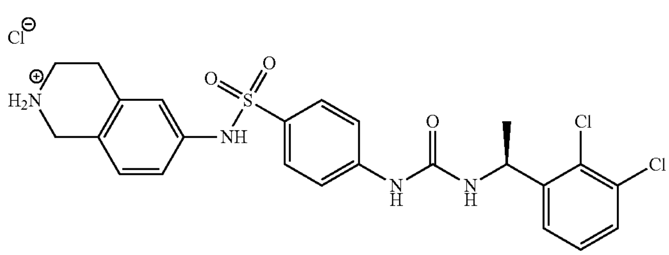 [SMILES: [Cl-] ; C[C@H](NC(=O)Nc1ccc(S(=O)(=O)Nc2ccc3c(c2)CC[NH2+]C3)cc1)c1cccc(Cl)c1Cl] | (S)-4-(3-(1-(2,3-dichlorophenyl)ethyl)ureido)-N-(1,2,3,4-tetrahydroisoquinolin-6-yl)benzenesulfonamide |

| | Chemical Structure | Chemical Name |
|---|---|---|
| H1005 | 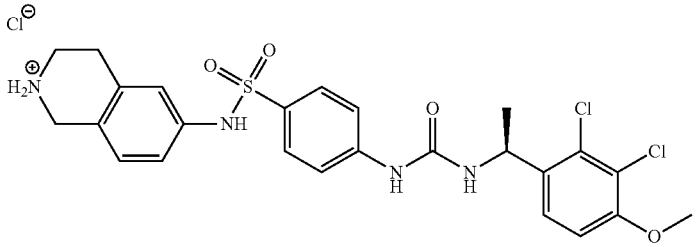 [SMILES: [Cl-] ; COc1ccc([C@H](C)NC(=O)Nc2ccc(S(=O)(=O)Nc3ccc4c(c3)CC[NH2+]C4)cc2)c(Cl)c1Cl] | (S)-4-(3-(1-(2,3-dichloro-4-methoxyphenyl)ethyl)ureido)-N-(1,2,3,4-tetrahydroisoquinolin-6-yl)benzenesulfonamide |
| H1006 | 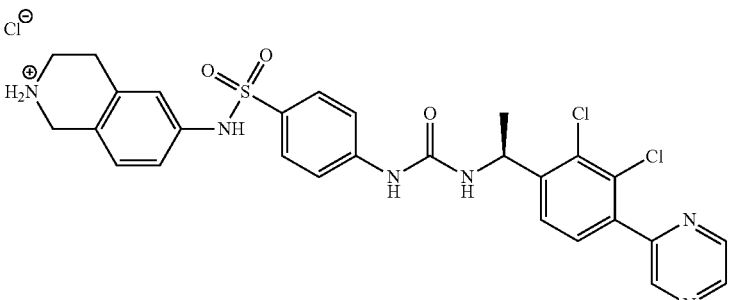 | (S)-4-(3-(1-(2,3-dichloro-4-(pyrazin-2-yl)phenyl)ethyl)ureido)-N-(1,2,3,4-tetrahydroisoquinolin-6-yl)benzenesulfonamide |
| H1008 | 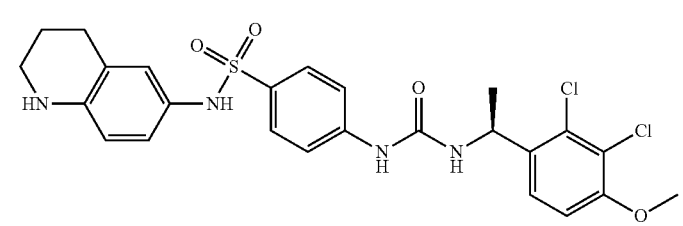 [SMILES: COc1ccc([C@H](C)NC(=O)Nc2ccc(S(=O)(=O)Nc3ccc4c(c3)CCCN4)cc2)c(Cl)c1Cl] | (S)-4-(3-(1-(2,3-dichloro-4-methoxyphenyl)ethyl)ureido)-N-(1,2,3,4-tetrahydroquinolin-6-yl)benzenesulfonamide |
| H1009 | 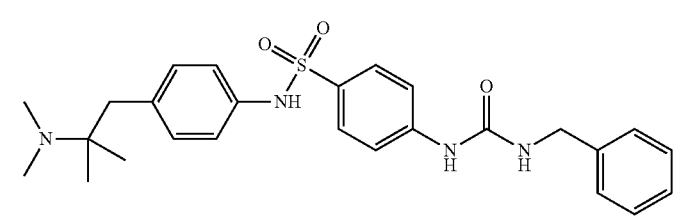 [SMILES: CN(C)C(C)(C)Cc1ccc(NS(=O)(=O)c2ccc(NC(=O)NCc3ccccc3)cc2)cc1] | 4-(3-benzylureido)-N-(4-(2-(dimethylamino)-2-methylpropyl)phenyl)benzenesulfonamide |
| H1010 | 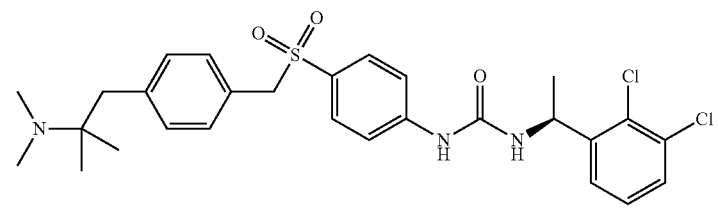 [SMILES: C[C@H](NC(=O)Nc1ccc(S(=O)(=O)Cc2ccc(CC(C)(C)N(C)C)cc2)cc1)c1cccc(Cl)c1Cl] | (S)-1-(1-(2,3-dichlorophenyl)ethyl)-3-(4-((4-(2-(dimethylamino)-2-methylpropyl)benzyl)sulfonyl)phenyl)urea |
| H1017 | 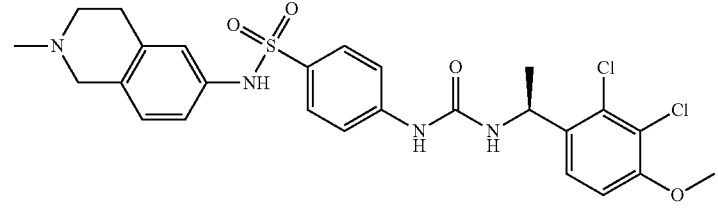 | (S)-4-(3-(1-(2,3-dichloro-4-methoxyphenyl)ethyl)ureido)methyl-1,2,3,4-tetrahydroisoquinolin-6-yl)benzenesulfonamide |

-continued

| | Chemical Structure | Chemical Name |
|---|---|---|
| H1018 | 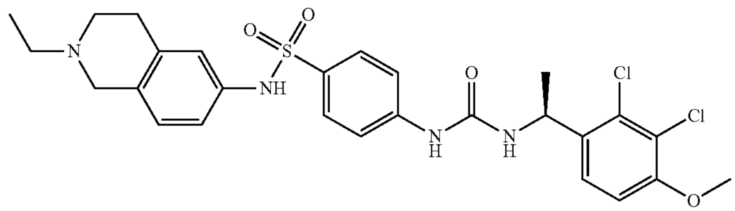 [SMILES: CCN1CCc2cc(NS(=O)(=O)c3ccc(NC(=O)N[C@@H](C)c4ccc(OC)c(Cl)c4Cl)cc3)ccc2C1] | (S)-4-(3-(1-(2,3-dichloro-4-methoxyphenyl)ethyl)ureido)-N-(2-ethyl-1,2,3,4-tetrahydroisoquinolin-6-yl)benzenesulfonamide |
| H1024 | 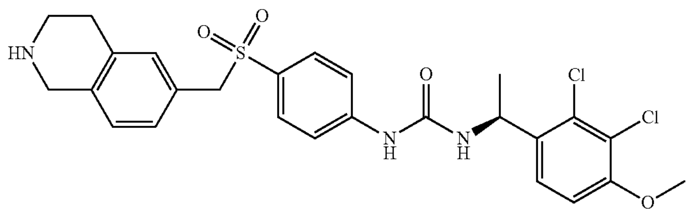 [SMILES: COc1ccc([C@H](C)NC(=O)Nc2ccc(S(=O)(=O)Cc3ccc4c(c3)CCNC4)cc2)c(Cl)c1Cl] | (S)-1-(1-(2,3-dichloro-4-methoxyphenyl)ethyl)-3-(4-(((1,2,3,4-tetrahydroisoquinolin-6-yl)methyl)sulfonyl)phenyl)urea |
| H1025 | 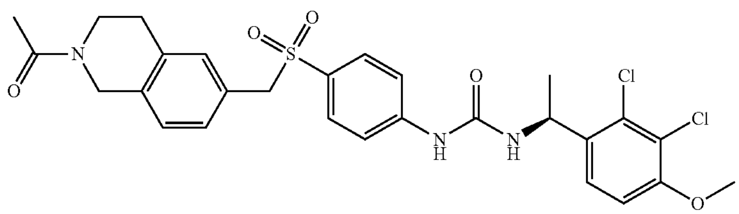 [SMILES: COc1ccc([C@H](C)NC(=O)Nc2ccc(S(=O)(=O)Cc3ccc4c(c3)CCN(C(C)=O)C4)cc2)c(Cl)c1Cl] | (S)-1-(4-(((2-acetyl-1,2,3,4-tetrahydroisoquinolin-6-yl)methyl)sulfonyl)phenyl)-3-(1-(2,3-dichloro-4-methoxyphenyl)ethyl)urea |
| H1026 | 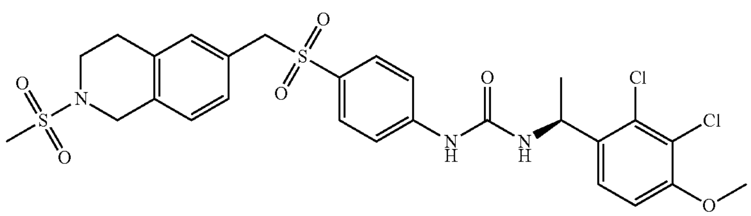 | (S)-1-(1-(2,3-dichloro-4-methoxyphenyl)ethyl)-3-(4-(((2-(methylsulfonyl)-1,2,3,4-tetrahydroisoquinolin-6-yl)methyl)sulfonyl)phenyl)urea |
| H1027 | 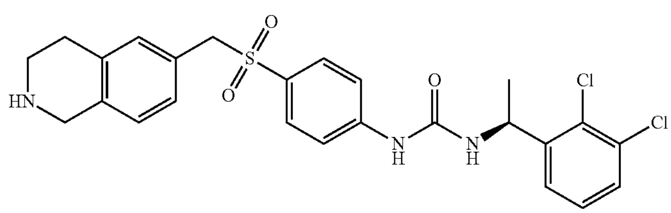 [SMILES: C[C@H](NC(=O)Nc1ccc(S(=O)(=O)Cc2ccc3c(c2)CCNC3)cc1)c1cccc(Cl)c1Cl] | (S)-1-(1-(2,3-dichlorophenyl)ethyl)-3-(4-(((1,2,3,4-tetrahydroisoquinolin-6-yl)methyl)sulfonyl)phenyl)urea |
| H1028 | 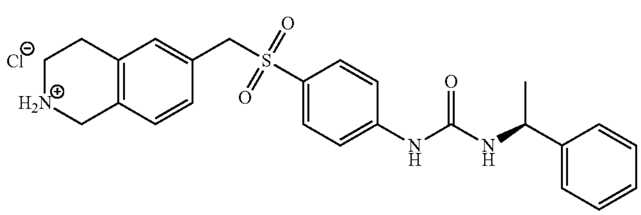 [SMILES: [Cl-] ; C[C@H](NC(=O)Nc1ccc(S(=O)(=O)Cc2ccc3c(c2)CC[NH2+]C3)cc1)c1ccccc1] | (S)-1-(1-phenylethyl)-3-(4-(((1,2,3,4-tetrahydroisoquinolin-6-yl)methyl)sulfonyl)phenyl)urea |
| H1029 | 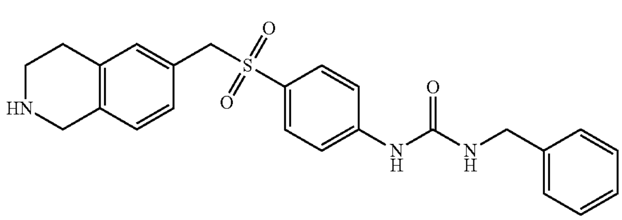 [SMILES: O=C(NCc1ccccc1)Nc1ccc(S(=O)(=O)Cc2ccc3c(c2)CCNC3)cc1] | 1-benzyl-3-(4-(((1,2,3,4-tetrahydroisoquinolin-6-yl)methyl)sulfonyl)phenyl)urea |

| | Chemical Structure | Chemical Name |
|---|---|---|
| H1033 | 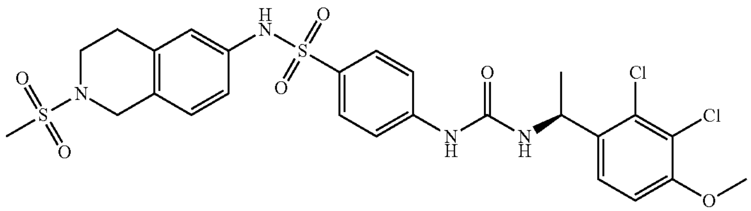 | (S)-4-(3-(1-(2,3-dichloro-4-methoxyphenyl)ethyl)ureido)-N-(2-(methylsulfonyl)-1,2,3,4-tetrahydroisoquinolin-6-yl)benzenesulfonamide |
| H1034 | 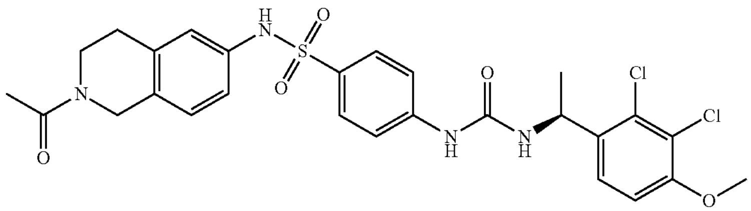 [SMILES: COc1ccc([C@H](C)NC(=O)Nc2ccc(S(=O)(=O)Nc3ccc4c(c3)CCN(C(C)=O)C4)cc2)c(Cl)c1Cl] | (S)-N-(2-acetyl-1,2,3,4-tetrahydroisoquinolin-6-yl)-4-(3-(1-(2,3-dichloro-4-methoxyphenyl)ethyl)ureido)benzenesulfonamide |
| H1038 | 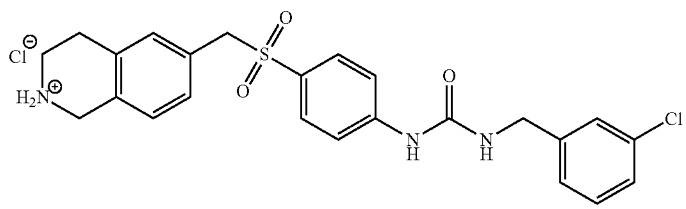 [SMILES: [Cl-] ; O=C(NCc1cccc(Cl)c1)Nc1ccc(S(=O)(=O)Cc2ccc3c(c2)CC[NH2+]C3)cc1] | 1-(3-chlorobenzyl)-3-(4-(((1,2,3,4-tetrahydroisoquinolin-6-yl)methyl)sulfonyl)phenyl)urea |
| H1039 | 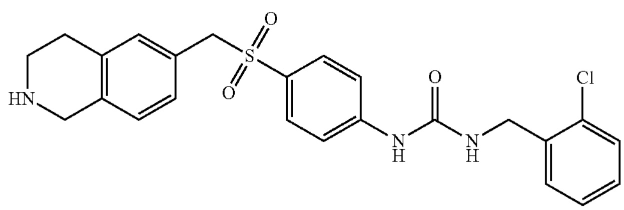 [SMILES: O=C(NCc1ccccc1Cl)Nc1ccc(S(=O)(=O)Cc2ccc3c(c2)CCNC3)cc1] | 1-(2-chlorobenzyl)-3-(4-(((1,2,3,4-tetrahydroisoquinolin-6-yl)methyl)sulfonyl)phenyl)urea |
| H1040 | 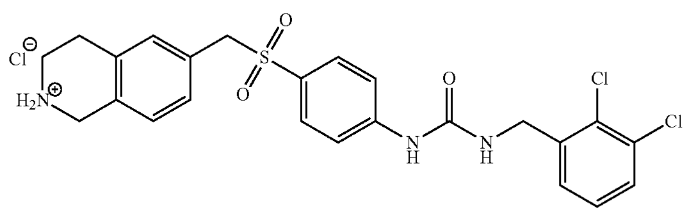 [SMILES: [Cl-] ; O=C(NCc1cccc(Cl)c1Cl)Nc1ccc(S(=O)(=O)Cc2ccc3c(c2)CC[NH2+]C3)cc1] | 1-(2,3-dichlorobenzyl)-3-(4-(((1,2,3,4-tetrahydroisoquinolin-6-yl)methyl)sulfonyl)phenyl)urea |
| H1041 | 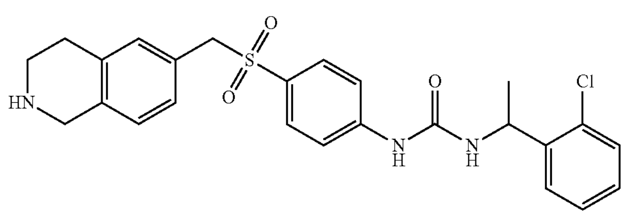 [SMILES: CC(NC(=O)Nc1ccc(S(=O)(=O)Cc2ccc3c(c2)CCNC3)cc1)c1ccccc1Cl] | 1-(1-(2-chlorophenyl)ethyl)-3-(4-(((1,2,3,4-tetrahydroisoquinolin-6-yl)methyl)sulfonyl)phenyl)urea |
| H1042 | 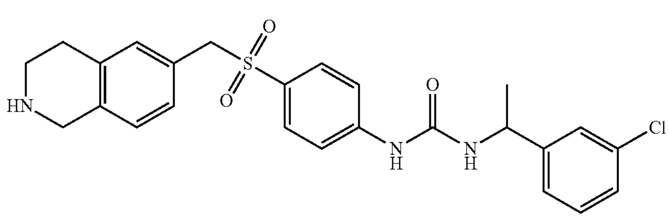 [SMILES: CC(NC(=O)Nc1ccc(S(=O)(=O)Cc2ccc3c(c2)CCNC3)cc1)c1cccc(Cl)c1] | 1-(1-(3-chlorophenyl)ethyl)-3-(4-(((1,2,3,4-tetrahydroisoquinolin-6-yl)methyl)sulfonyl)phenyl)urea |

| | Chemical Structure | Chemical Name |
|---|---|---|
| H1043 | 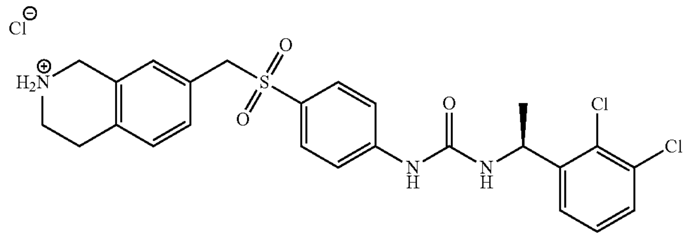 [SMILES: [Cl-] ; C[C@H](NC(=O)Nc1ccc(S(=O)(=O)Cc2ccc3c(c2)C[NH2+]CC3)cc1)c1cccc(Cl)c1Cl] | (S)-1-(1-(2,3-dichlorophenyl)ethyl)-3-(4-(((1,2,3,4-tetrahydroisoquinolin-7-yl)methyl)sulfonyl)phenyl)urea |
| H1044 | 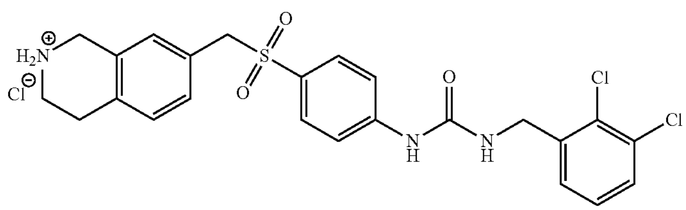 [SMILES: [Cl-] ; O=C(NCc1cccc(Cl)c1Cl)Nc1ccc(S(=O)(=O)Cc2ccc3c(c2)C[NH2+]CC3)cc1] | 1-(2,3-dichlorobenzyl)-3-(4-(((1,2,3,4-tetrahydroisoquinolin-7-yl)methyl)sulfonyl)phenyl)urea |
| H1045 | 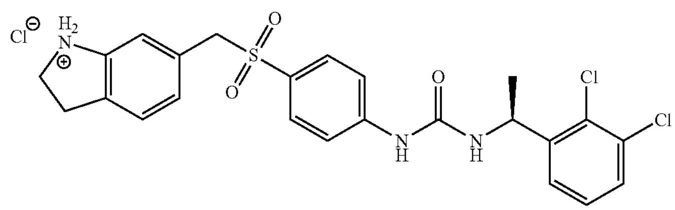 | (S)-1-(1-(2,3-dichlorophenyl)ethyl)-3-(4-((indolin-6-ylmethyl)sulfonyl)phenyl)urea |
| H1046 | 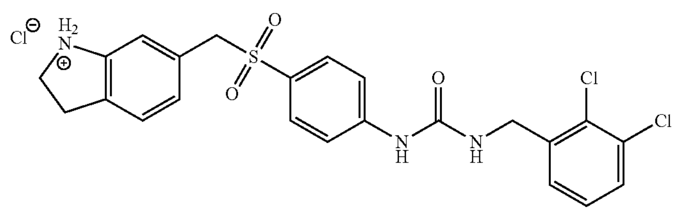 | 1-(2,3-dichlorobenzyl)-3-(4-((indolin-6-ylmethyl)sulfonyl)phenyl)urea |
| H1047 | 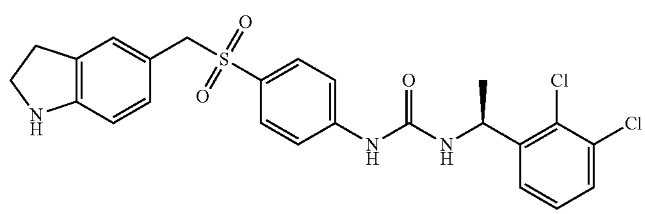 [SMILES: C[C@H](NC(=O)Nc1ccc(S(=O)(=O)Cc2ccc3c(c2)CCN3)cc1)c1cccc(Cl)c1Cl] | (S)-1-(1-(2,3-dichlorophenyl)ethyl)-3-(4-((indolin-5-ylmethyl)sulfonyl)phenyl)urea |
| H1048 | 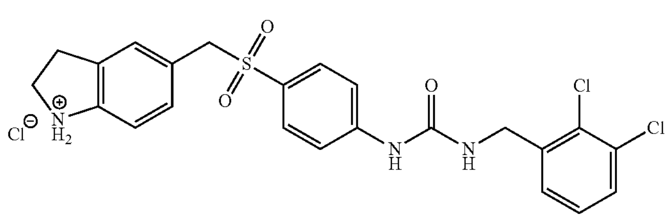 [SMILES: [Cl-] ; O=C(NCc1cccc(Cl)c1Cl)Nc1ccc(S(=O)(=O)Cc2ccc3c(c2)CC[NH2+]3)cc1] | 1-(2,3-dichlorobenzyl)-3-(4-((indolin-5-ylmethyl)sulfonyl)phenyl)urea |
| H1049 | 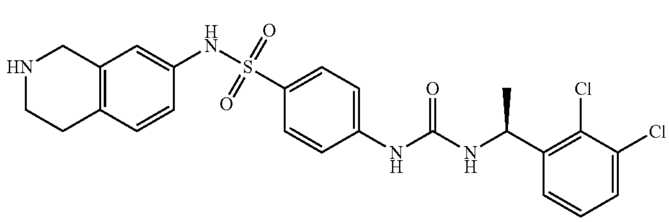 [SMILES: C[C@H](NC(=O)Nc1ccc(S(=O)(=O)Nc2ccc3c(c2)CNCC3)cc1)c1cccc(Cl)c1Cl] | (S)-4-(3-(1-(2,3-dichlorophenyl)ethyl)ureido)-N-(1,2,3,4-tetrahydroisoquinolin-7-yl)benzenesulfonamide |

-continued

| | Chemical Structure | Chemical Name |
|---|---|---|
| H1050 | 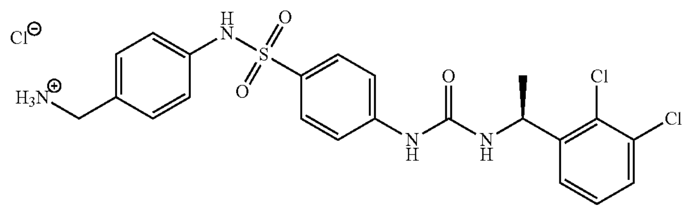 [SMILES: [Cl-] ; C[C@H](NC(=O)Nc1ccc(S(=O)(=O)Nc2ccc(C[NH3+])cc2)cc1)c1cccc(Cl)c1Cl] | (S)-N-(4-(aminomethyl)phenyl)-4-(3-(1-(2,3-dichlorophenyl)ethyl)ureido)benzenesulfonamide |
| H1051 | 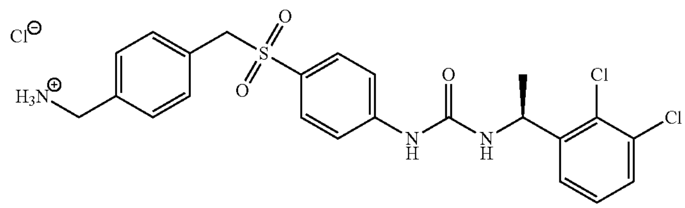 [SMILES: [Cl-] ; C[C@H](NC(=O)Nc1ccc(S(=O)(=O)Cc2ccc(C[NH3+])cc2)cc1)c1cccc(Cl)c1Cl] | (S)-1-(4-((4-(aminomethyl)benzyl)sulfonyl)phenyl)-3-(1-(2,3-dichlorophenyl)ethyl)urea |
| H1052 | 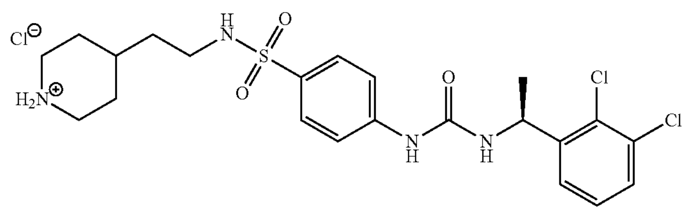 [SMILES: [Cl-] ; C[C@H](NC(=O)Nc1ccc(S(=O)(=O)NCCC2CC[NH2+]CC2)cc1)c1cccc(Cl)c1Cl] | (S)-4-(3-(1-(2,3-dichlorophenyl)ethyl)ureido)-N-(2-(piperidin-4-yl)ethyl)benzenesulfonamide |
| H1054 | 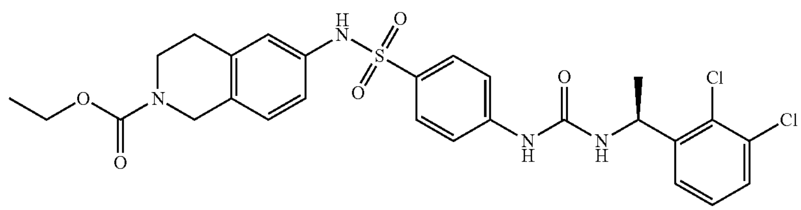 [SMILES: CCOC(=O)N1CCc2cc(NS(=O)(=O)c3ccc(NC(=O)N[C@@H](C)c4cccc(Cl)c4Cl)cc3)ccc2C1] | ethyl (S)-6-((4-(3-(1-(2,3-dichlorophenyl)ethyl)ureido)phenyl)sulfonamido)-3,4-dihydroisoquinoline-2(1H)-carboxylate |
| H1055 | 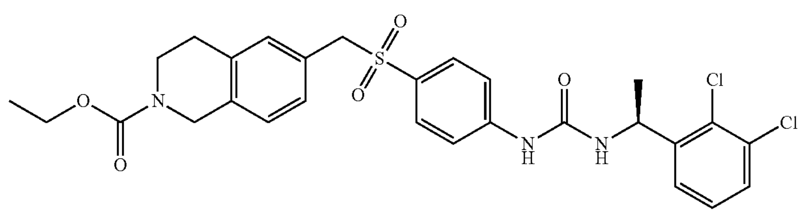 [SMILES: CCOC(=O)N1CCc2cc(CS(=O)(=O)c3ccc(NC(=O)N[C@@H](C)c4cccc(Cl)c4Cl)cc3)ccc2C1] | ethyl (S)-6-(((4-(3-(1-(2,3-dichlorophenyl)ethyl)ureido)phenyl)sulfonyl)methyl)-3,4-dihydroisoquinoline-2(1H)-carboxylate |
| H1056 | 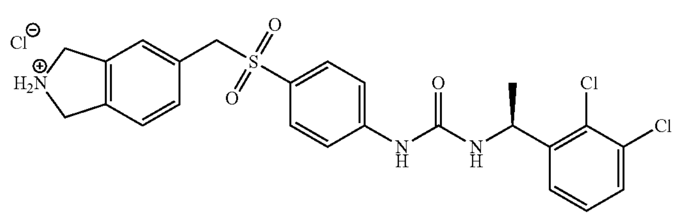 [SMILES: [Cl-] ; C[C@H](NC(=O)Nc1ccc(S(=O)(=O)Cc2ccc3c(c2)C[NH2+]C3)cc1)c1cccc(Cl)c1Cl] | (S)-1-(1-(2,3-dichlorophenyl)ethyl)-3-(4-((isoindolin-5-ylmethyl)sulfonyl)phenyl)urea |
| H1057 | 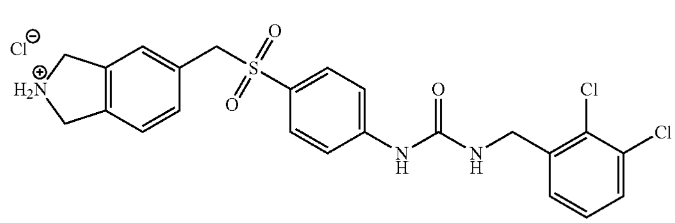 [SMILES: [Cl-] ; O=C(NCc1cccc(Cl)c1Cl)Nc1ccc(S(=O)(=O)Cc2ccc3c(c2)C[NH2+]C3)cc1] | 1-(2,3-dichlorobenzyl)-3-(4-((isoindolin-5-ylmethyl)sulfonyl)phenyl)urea |

-continued

| | Chemical Structure | Chemical Name |
|---|---|---|
| H1058 | 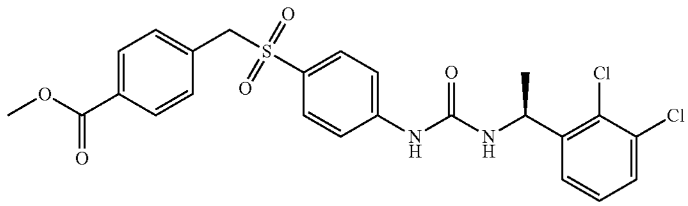 [SMILES: COC(=O)c1ccc(CS(=O)(=O)c2ccc(NC(=O)N[C@@H](C)c3cccc(Cl)c3Cl)cc2)cc1] | methyl (S)-4-(((4-(3-(1-(2,3-dichlorophenyl)ethyl)ureido)phenyl)sulfonyl)methyl)benzoate |
| H1059 | 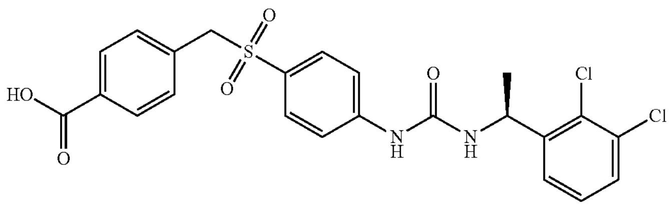 [SMILES: C[C@H](NC(=O)Nc1ccc(S(=O)(=O)Cc2ccc(C(=O)O)cc2)cc1)c1cccc(Cl)c1Cl] | (S)-4-(((4-(3-(1-(2,3-dichlorophenyl)ethyl)ureido)phensulfonyl)methyl)benzoic acid |
| H1060 | 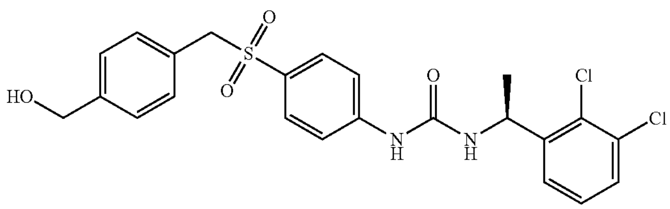 [SMILES: C[C@H](NC(=O)Nc1ccc(S(=O)(=O)Cc2ccc(CO)cc2)cc1)c1cccc(Cl)c1Cl] | (S)-1-(1-(2,3-dichlorophenyl)ethyl)-3-(4-((4-(hydroxymethyl)benzyl)sulfonyl)phenyl)urea |
| H1061 | 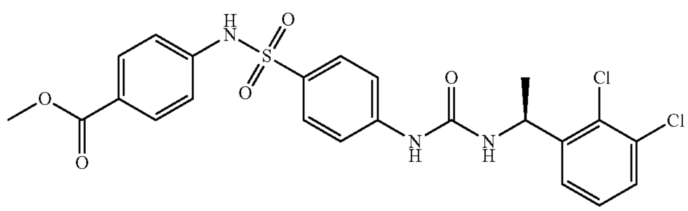 [SMILES: COC(=O)c1ccc(NS(=O)(=O)c2ccc(NC(=O)N[C@@H](C)c3cccc(Cl)c3Cl)cc2)cc1] | methyl (S)-4-((4-(3-(1-(2,3-dichlorophenyl)ethyl)ureido)phenyl)sulfonamido)benzoate |
| H1062 | 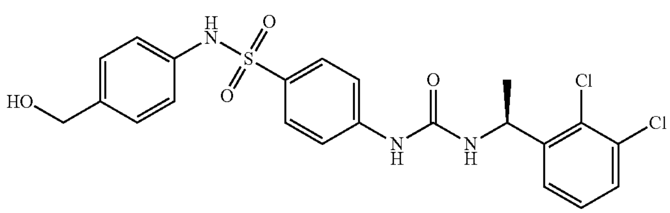 [SMILES: C[C@H](NC(=O)Nc1ccc(S(=O)(=O)Nc2ccc(CO)cc2)cc1)c1cccc(Cl)c1Cl] | (S)-4-(3-(1-(2,3-dichlorophenyl)ethyl)ureido)-N-(4-(hydroxymethyl)phenyl)benzenesulfonamide |
| H1067 | 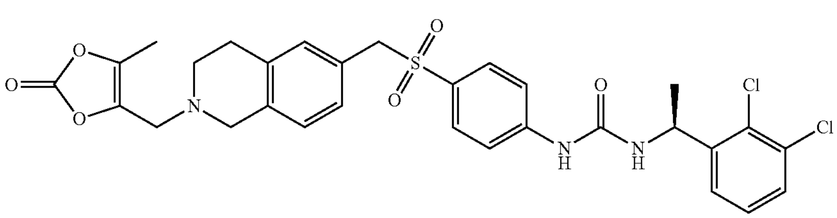 [SMILES: Cc1oc(=O)oc1CN1CCc2cc(CS(=O)(=O)c3ccc(NC(=O)N[C@@H](C)c4cccc(Cl)c4Cl)cc3)ccc2C1] | (S)-1-(1-(2,3-dichlorophenyl)ethyl)-3-(4-(((2-((5-methyl-2-oxo-1,3-dioxol-4-yl)methyl)-1,2,3,4-tetrahydroisoquinolin-6-yl)methyl)sulfonyl)phenyl)urea |
| H1068 | 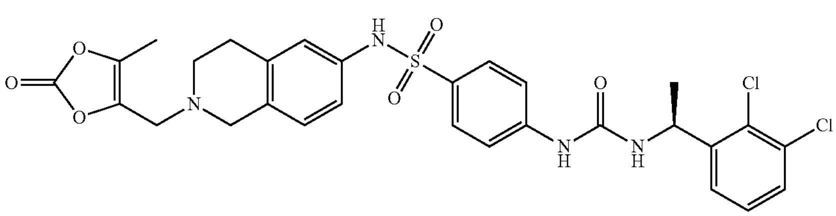 [SMILES: Cc1oc(=O)oc1CN1CCc2cc(NS(=O)(=O)c3ccc(NC(=O)N[C@@H](C)c4cccc(Cl)c4Cl)cc3)ccc2C1] | (S)-4-(3-(1-(2,3-dichlorophenyl)ethyl)ureido)-N-(2-((5-methyl-2-oxo-1,3-dioxol-4-yl)methyl)-1,2,3,4-tetrahydroisoquinolin-6-yl)benzenesulfonamide |

-continued

| | Chemical Structure | Chemical Name |
|---|---|---|
| H1070 | 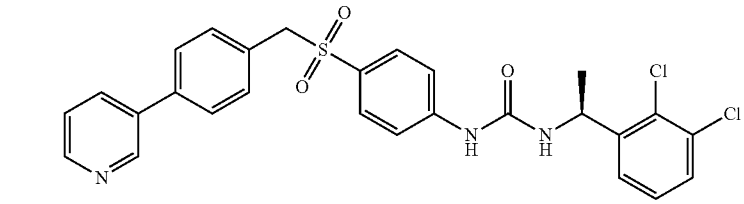 [SMILES: C[C@H](NC(=O)Nc1ccc(S(=O)(=O)Cc2ccc(-c3cccnc3)cc2)cc1)c1cccc(Cl)c1Cl] | (S)-1-(1-(2,3-dichlorophenyl)ethyl)-3-(4-((4-(pyridin-3-yl)benzyl)sulfonyl)phenyl)urea |
| H1071 | 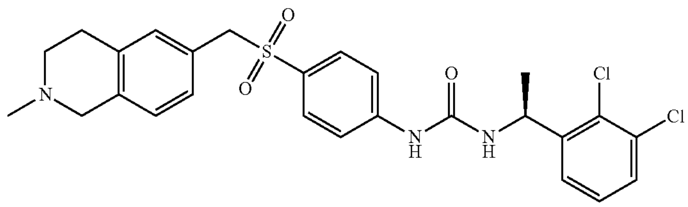 [SMILES: C[C@H](NC(=O)Nc1ccc(S(=O)(=O)Cc2ccc3c(c2)CCN(C)C3)cc1)c1cccc(Cl)c1Cl] | (S)-1-(1-(2,3-dichlorophenyl)ethyl)-3-(4-(((2-methyl-1,2,3,4-tetrahydroisoquinolin-6-yl)methyl)sulfonyl)phenyl)urea |
| H1072 | 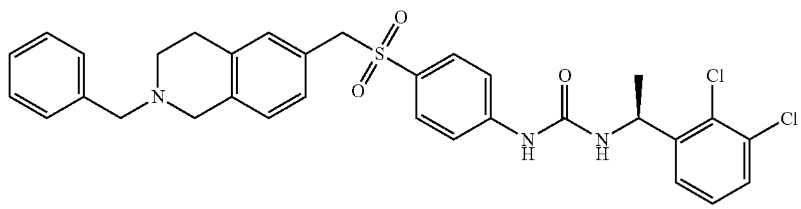 [SMILES: C[C@H](NC(=O)Nc1ccc(S(=O)(=O)Cc2ccc3c(c2)CCN(Cc2ccccc2)C3)cc1)c1cccc(Cl)c1Cl] | (S)-1-(4-(((2-benzyl-1,2,3,4-tetrahydroisoquinolin-6-yl)methyl)sulfonyl)phenyl)-3-(1-(2,3-dichlorophenyl)ethyl)urea |
| H1073 | 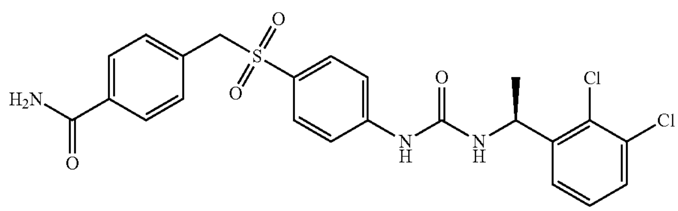 [SMILES: C[C@H](NC(=O)Nc1ccc(S(=O)(=O)Cc2ccc(C(N)=O)cc2)cc1)c1cccc(Cl)c1Cl] | (S)-4-(((4-(3-(1-(2,3-dichlorophenyl)ethyl)ureido)phenyl)sulfonyl)methyl)benzamide |
| H1074 | 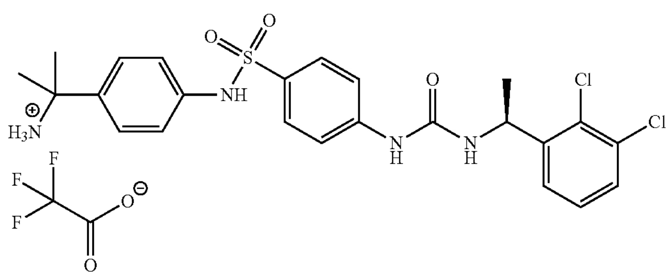 [SMILES: O=C([O-])C(F)(F)F ; C[C@H](NC(=O)Nc1ccc(S(=O)(=O)Nc2ccc(C(C)(C)[NH3+])cc2)cc1)c1cccc(Cl)c1Cl] | (S)-N-(4-(2-aminopropan-2-yl)phenyl)-4-(3-(1-(2,3-dichlorophenyl)ethyl)ureido)benzenesulfonamide |
| H1075 | 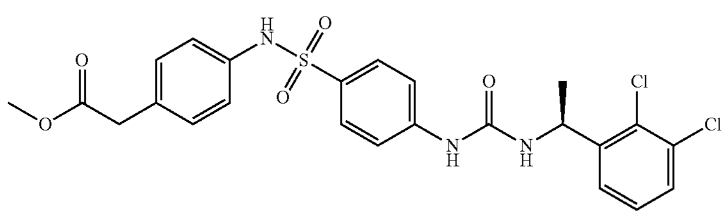 [SMILES: COC(=O)Cc1ccc(NS(=O)(=O)c2ccc(NC(=O)N[C@@H](C)c3cccc(Cl)c3Cl)cc2)cc1] | methyl (S)-2-(4-((4-(3-(1-(2,3-dichlorophenyl)ethyl)ureido)phenyl)sulfonamido)phenyl)acetate |
| H1076 | 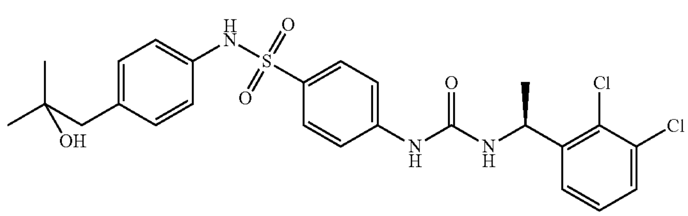 [SMILES: C[C@H](NC(=O)Nc1ccc(S(=O)(=O)Nc2ccc(CC(C)(C)O)cc2)cc1)c1cccc(Cl)c1Cl] | (S)-4-(3-(1-(2,3-dichlorophenyl)ethyl)ureido)-N-(4-(2-hydroxy-2-methylpropyl)phenyl)benzenesulfonamide |

| | Chemical Structure | Chemical Name |
|---|---|---|
| H1078 | 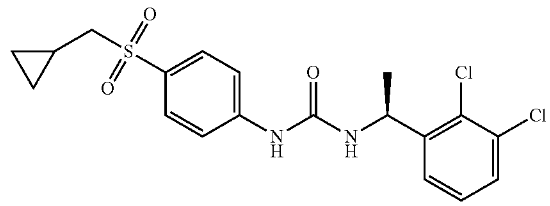 [SMILES: C[C@H](NC(=O)Nc1ccc(S(=O)(=O)CC2CC2)cc1)c1cccc(Cl)c1Cl] | (S)-1-(4-((cyclopropylmethyl)sulfonyl)phenyl)-3-(1-(2,3-dichlorophenyl)ethyl)urea |
| H1080 | 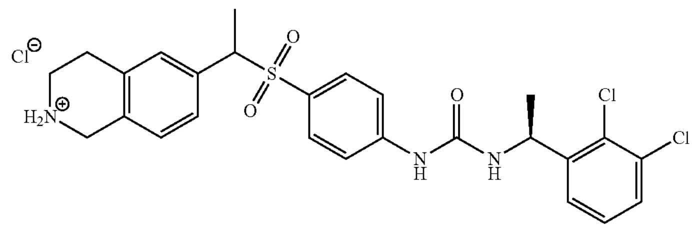 [SMILES: [Cl-] ; CC(c1ccc2c(c1)CC[NH2+]C2)S(=O)(=O)c1ccc(NC(=O)N[C@@H](C)c2cccc(Cl)c2Cl)cc1] | 1-((S)-1-(2,3-dichlorophenyl)ethyl)-3-(4-((1-(1,2,3,4-tetrahydroisoquinolin-6-yl)ethyl)sulfonyl)phenyl)urea |
| H1081 | 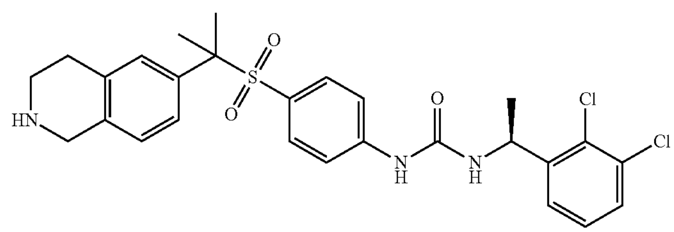 [SMILES: C[C@H](NC(=O)Nc1ccc(S(=O)(=O)C(C)(C)c2ccc3c(c2)CCNC3)cc1)c1cccc(Cl)c1Cl] | (S)-1-(1-(2,3-dichlorophenyl)ethyl)-3-(4-((2-(1,2,3,4-tetrahydroisoquinolin-6-yl)propan-2-yl)sulfonyl)phenyl)urea |
| H1082 | 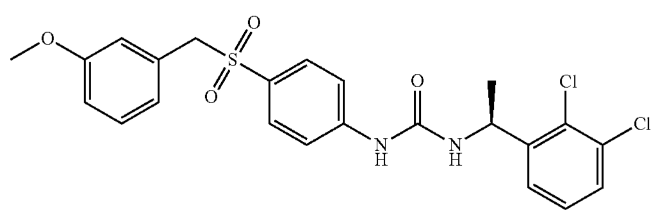 [SMILES: COc1cccc(CS(=O)(=O)c2ccc(NC(=O)N[C@@H](C)c3cccc(Cl)c3Cl)cc2)c1] | (S)-1-(1-(2,3-dichlorophenyl)ethyl)-3-(4-((3-methoxybenzyl)sulfonyl)phenyl)urea |
| H1083 | 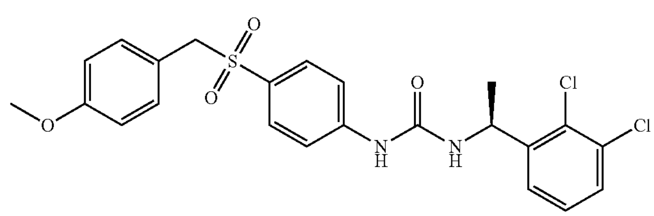 [SMILES: COc1ccc(CS(=O)(=O)c2ccc(NC(=O)N[C@@H](C)c3cccc(Cl)c3Cl)cc2)cc1] | (S)-1-(1-(2,3-dichlorophenyl)ethyl)-3-(4-((4-methoxybenzyl)sulfonyl)phenyl)urea |
| H1084 | 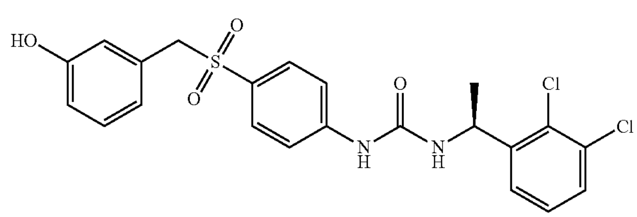 [SMILES: C[C@H](NC(=O)Nc1ccc(S(=O)(=O)Cc2cccc(O)c2)cc1)c1cccc(Cl)c1Cl] | (S)-1-(1-(2,3-dichlorophenyl)ethyl)-3-(4-((3-hydroxybenzyl)sulfonyl)phenyl)urea |
| H1087 | 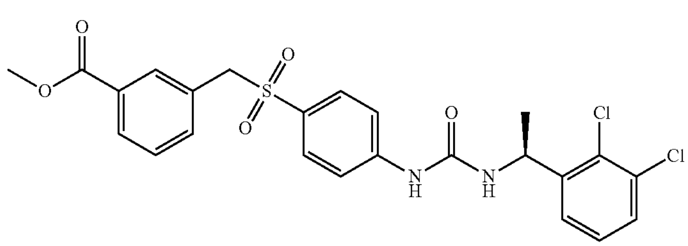 [SMILES: COC(=O)c1cccc(CS(=O)(=O)c2ccc(NC(=O)N[C@@H](C)c3cccc(Cl)c3Cl)cc2)c1] | methyl (S)-3-(((4-(3-(1-(2,3-dichlorophenyl)ethyl)ureido)phenyl)sulfonyl)methyl)benzoate |

| | Chemical Structure | Chemical Name |
|---|---|---|
| H1088 | 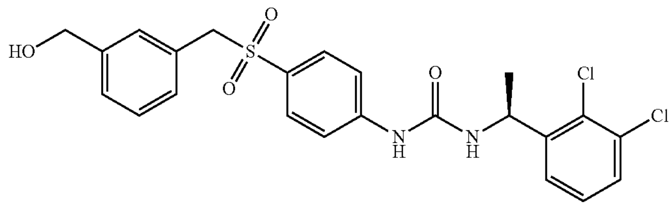 [SMILES: C[C@H](NC(=O)Nc1ccc(S(=O)(=O)Cc2cccc(CO)c2)cc1)c1cccc(Cl)c1Cl] | (S)-1-(1-(2,3-dichlorophenyl)ethyl)-3-(4-((3-(hydroxymethyl)benzyl)sulfonyl)phenyl)urea |
| H1092 | 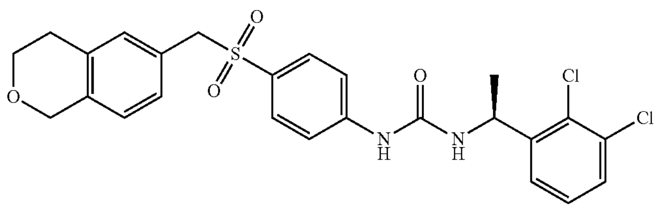 [SMILES: C[C@H](NC(=O)Nc1ccc(S(=O)(=O)Cc2ccc3c(c2)CCOC3)cc1)c1cccc(Cl)c1Cl] | (S)-1-(1-(2,3-dichlorophenyl)ethyl)-3-(4-((isochroman-6-ylmethyl)sulfonyl)phenyl)urea |
| H1093 | 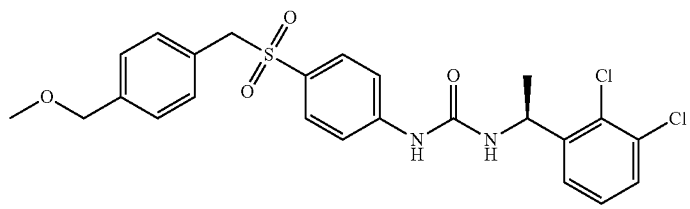 [SMILES: COCc1ccc(CS(=O)(=O)c2ccc(NC(=O)N[C@@H](C)c3cccc(Cl)c3Cl)cc2)cc1] | (S)-1-(1-(2,3-dichlorophenyl)ethyl)-3-(4-((4-(methoxymethyl)benzyl)sulfonyl)phenyl)urea |
| H1094 | 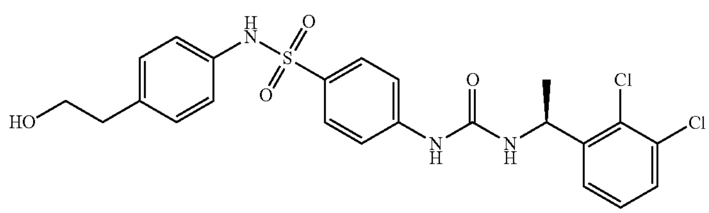 [SMILES: C[C@H](NC(=O)Nc1ccc(S(=O)(=O)Nc2ccc(CCO)cc2)cc1)c1cccc(Cl)c1Cl] | (S)-4-(3-(1-(2,3-dichlorophenyl)ethyl)ureido)-N-(4-(2-hydroxyethyl)phenyl)benzenesulfonamide |
| H1095 | 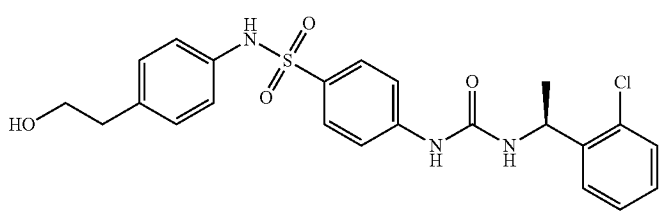 [SMILES: C[C@H](NC(=O)Nc1ccc(S(=O)(=O)Nc2ccc(CCO)cc2)cc1)c1ccccc1Cl] | (S)-4-(3-(1-(2-chlorophenyl)ethyl)ureido)-N-(4-(2-hydroxyethyl)phenyl)benzenesulfonamide |
| H1096 | 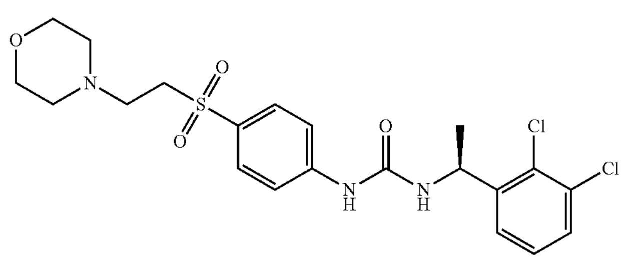 [SMILES: C[C@H](NC(=O)Nc1ccc(S(=O)(=O)CCN2CCOCC2)cc1)c1cccc(Cl)c1Cl] | (S)-1-(1-(2,3-dichlorophenyl)ethyl)-3-(4-((2-morpholinoethyl)sulfonyl)phenyl)urea |
| H1097 | 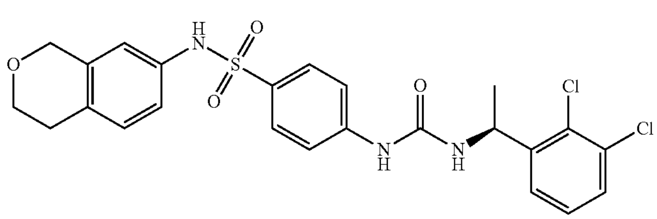 [SMILES: C[C@H](NC(=O)Nc1ccc(S(=O)(=O)Nc2ccc3c(c2)COCC3)cc1)c1cccc(Cl)c1Cl] | (S)-1-(1-(2,3-dichlorophenyl)ethyl)-3-(4-((isochroman-7-ylmethyl)sulfonyl)phenyl)urea |

-continued

| | Chemical Structure | Chemical Name |
|---|---|---|
| H1098 | 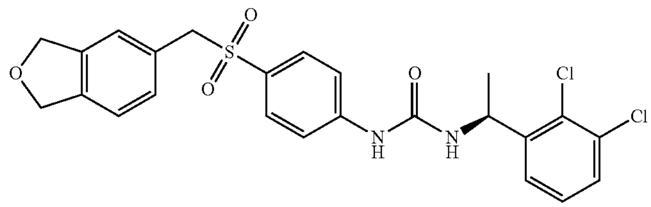 [SMILES: C[C@H](NC(=O)Nc1ccc(S(=O)(=O)Cc2ccc3c(c2)COC3)cc1)c1cccc(Cl)c1Cl] | (S)-1-(1-(2,3-dichlorophenyl)ethyl)-3-(4-(((1,3-dihydroisobenzofuran-5-yl)methyl)sulfonyl)phenyl)urea |
| H1099 | 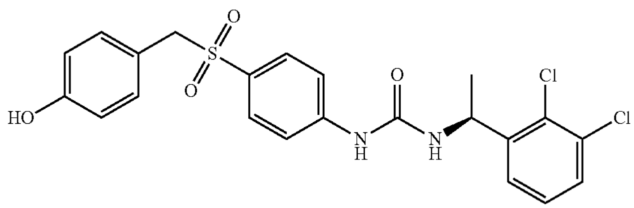 [SMILES: C[C@H](NC(=O)Nc1ccc(S(=O)(=O)Cc2ccc(O)cc2)cc1)c1cccc(Cl)c1Cl] | (S)-1-(1-(2,3-dichlorophenyl)ethyl)-3-(4-((4-hydroxybenzyl)sulfonyl)phenyl)urea |
| H1101 | 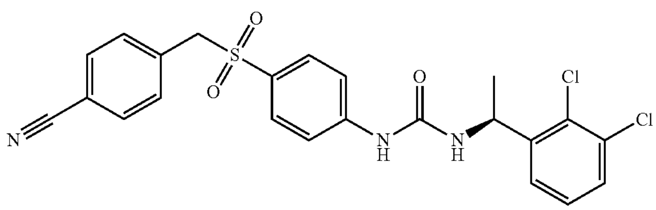 [SMILES: C[C@H](NC(=O)Nc1ccc(S(=O)(=O)Cc2ccc(C#N)cc2)cc1)c1cccc(Cl)c1Cl] | (S)-1-(4-((4-cyanobenzyl)sulfonyl)phenyl)-3-(1-(2,3-dichlorophenyl)ethyl)urea |
| H1102 | 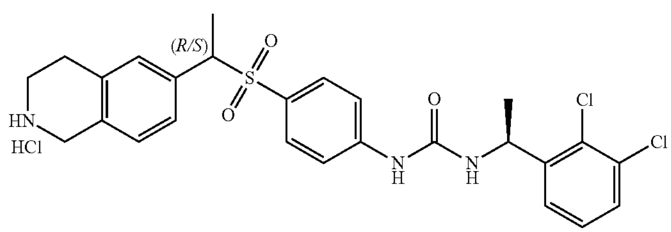 [SMILES: Cl ; CC(c1ccc2c(c1)CCNC2)S(=O)(=O)c1ccc(NC(=O)N[C@@H](C)c2cccc(Cl)c2Cl)cc1] | 1-((S)-1-(2,3-dichlorophenyl)ethyl)-3-(4-((1-(1,2,3,4-tetrahydroisoquinolin-6-yl)ethyl)sulfonyl)phenyl)urea hydrochloride |
| H1103 | 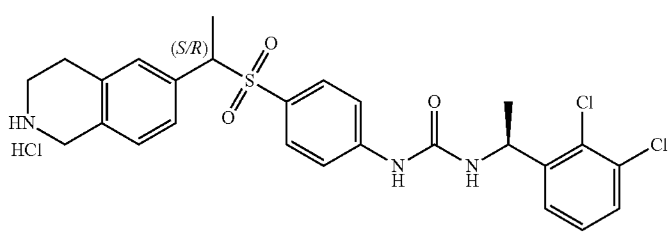 [SMILES: Cl ; CC(c1ccc2c(c1)CCNC2)S(=O)(=O)c1ccc(NC(=O)N[C@@H](C)c2cccc(Cl)c2Cl)cc1] | 1-((S)-1-(2,3-dichlorophenyl)ethyl)-3-(4-((1-(1,2,3,4-tetrahydroisoquinolin-6-yl)ethyl)sulfonyl)phenyl)urea hydrochloride |
| H1106 | 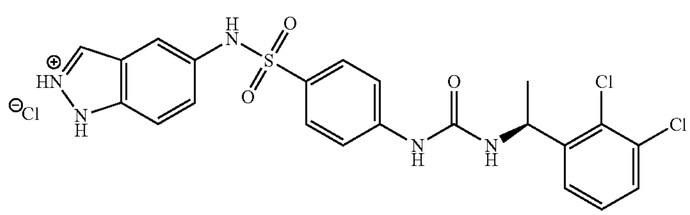 [SMILES: [Cl-] ; C[C@H](NC(=O)Nc1ccc(S(=O)(=O)Nc2ccc3[nH][nH+]cc3c2)cc1)c1cccc(Cl)c1Cl] | (S)-4-(3-(1-(2,3-dichlorophenyl)ethyl)ureido)-N-(1H-indazol-5-yl)benzenesulfonamide |
| H1108 | 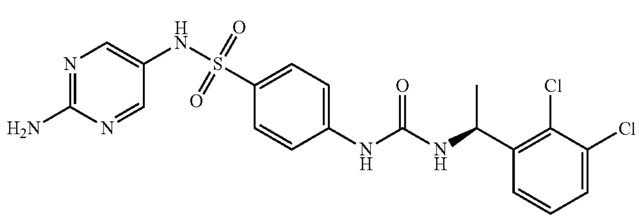 | ((S)-N-(2-aminopyrimidin-5-yl)-4-(3-(1-(2,3-dichlorophenyl)ethyl)ureido)benzenesulfonamide |

-continued

| | Chemical Structure | Chemical Name |
|---|---|---|
| H1109 | 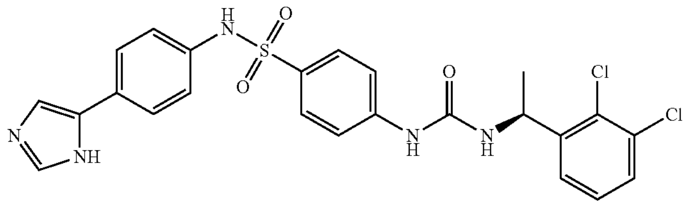 [SMILES: C[C@H](NC(=O)Nc1ccc(S(=O)(=O)Nc2ccc(-c3cnc[nH]3)cc2)cc1)c1cccc(Cl)c1Cl] | (S)-N-(4-(1H-imidazol-5-yl)phenyl)-4-(3-(1-(2,3-dichlorophenyl)ethyl)ureido)benzenesulfonamide |
| H1110 | 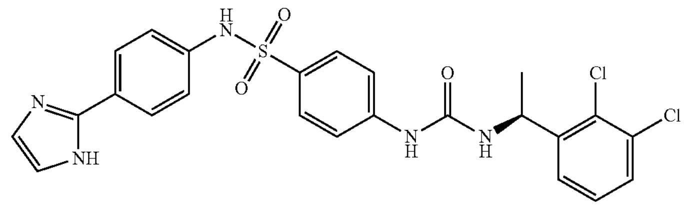 [SMILES: C[C@H](NC(=O)Nc1ccc(S(=O)(=O)Nc2ccc(-c3ncc[nH]3)cc2)cc1)c1cccc(Cl)c1Cl] | (S)-N-(4-(1H-imidazol-2-yl)phenyl)-4-(3-(1-(2,3-dichlorophenyl)ethyl)ureido)benzenesulfonamide |
| H1111 | 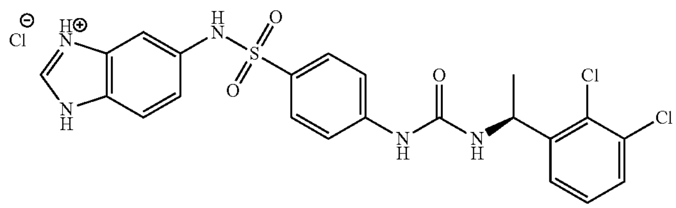 | (S)-N-(1H-benzo[d]imidazol-5-yl)-4-(3-(1-(2,3-dichlorophenyl)ethyl)ureido)benzenesulfonamide |
| H1125 | 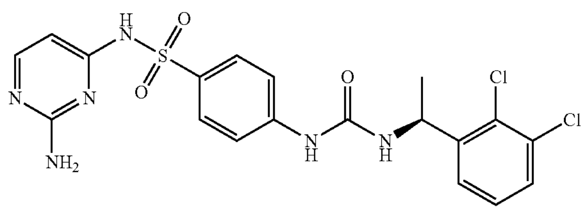 [SMILES: C[C@H](NC(=O)Nc1ccc(S(=O)(=O)Nc2ccnc(N)n2)cc1)c1cccc(Cl)c1Cl] | (S)-N-(2-aminopyrimidin-4-yl)-4-(3-(1-(2,3-dichlorophenyl)ethyl)ureido)benzenesulfonamide |
| H1126 | 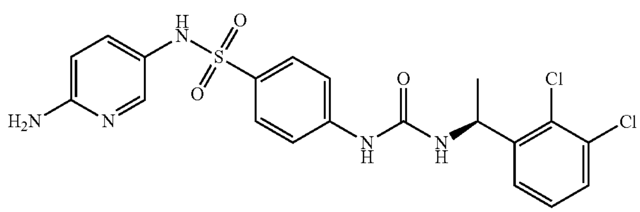 [SMILES: C[C@H](NC(=O)Nc1ccc(S(=O)(=O)Nc2ccc(N)nc2)cc1)c1cccc(Cl)c1Cl] | (S)-N-(6-aminopyridin-3-yl)-4-(3-(1-(2,3-dichlorophenyl)ethyl)ureido)benzenesulfonamide |
| H1127 | 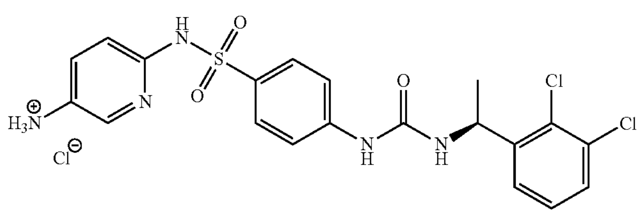 [SMILES: C[C@H](NC(=O)Nc1ccc(S(=O)(=O)Nc2ccc([NH3+])cn2)cc1)c1cccc(Cl)c1Cl ; [Cl-]] | (S)-N-(5-aminopyridin-2-yl)-4-(3-(1-(2,3-dichlorophenyl)ethyl)ureido)benzenesulfonamide |
| H1129 | 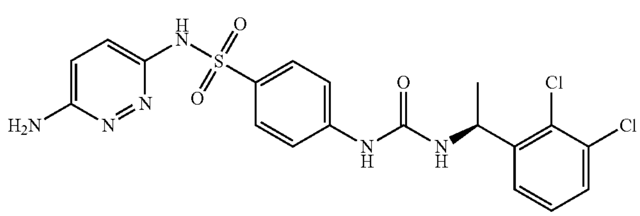 [SMILES: C[C@H](NC(=O)Nc1ccc(S(=O)(=O)Nc2ccc(N)nn2)cc1)c1cccc(Cl)c1Cl] | (S)-N-(6-aminopyridazin-3-yl)-4-(3-(1-(2,3-dichlorophenyl)ethyl)ureido)benzenesulfonamide |

-continued

| | Chemical Structure | Chemical Name |
|---|---|---|
| H1130 | 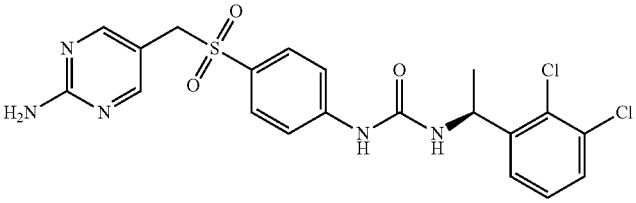 [SMILES: C[C@H](NC(=O)Nc1ccc(S(=O)(=O)Cc2cnc(N)nc2)cc1)c1cccc(Cl)c1Cl] | (S)-1-(4-(((2-aminopyrimidin-5-yl)methyl)sulfonyl)phenyl)-3-(1-(2,3-dichlorophenyl)ethyl)urea |
| H1131 | 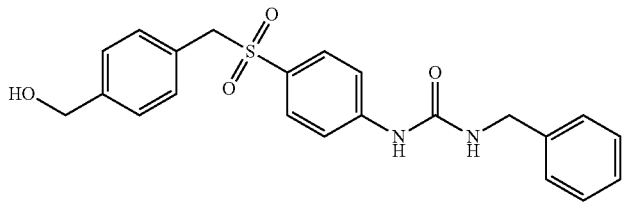 [SMILES: O=C(NCc1ccccc1)Nc1ccc(S(=O)(=O)Cc2ccc(CO)cc2)cc1] | 1-benzyl-3-(4-((4-(hydroxymethyl)benzyl)sulfonyl)phenyl)urea |
| H1132 | 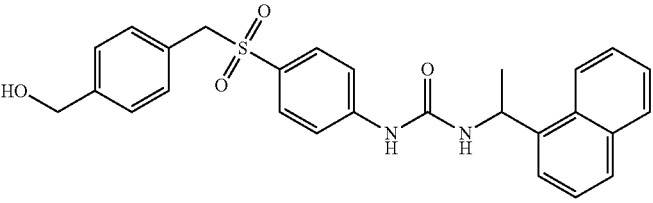 [SMILES: CC(NC(=O)Nc1ccc(S(=O)(=O)Cc2ccc(CO)cc2)cc1)c1cccc2ccccc12] | 1-(4-((4-(hydroxymethyl)benzyl)sulfonyl)phenyl)-3-(1-(naphthalen-1-yl)ethyl)urea |
| H1133 | 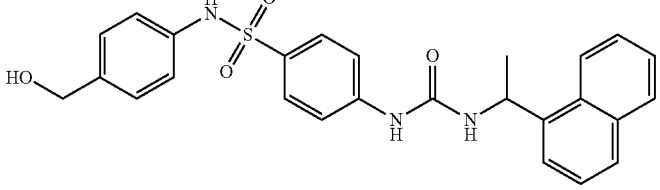 | N-(4-(hydroxymethyl)phenyl)-4-(3-(1-(naphthalen-1-yl)ethyl)ureido)benzenesulfonamide |
| H1140 | 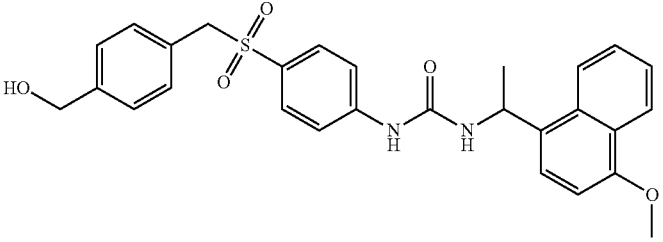 [SMILES: COc1ccc(C(C)NC(=O)Nc2ccc(S(=O)(=O)Cc3ccc(CO)cc3)cc2)c2ccccc12] | 1-(4-((4-(hydroxymethyl)benzyl)sulfonyl)phenyl)-3-(1-(4-methoxynaphthalen-1-yl)ethyl)urea |
| H1141 | 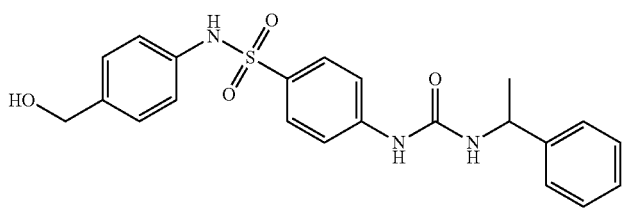 [SMILES: CC(NC(=O)Nc1ccc(S(=O)(=O)Nc2ccc(CO)cc2)cc1)c1ccccc1] | N-(4-(hydroxymethyl)phenyl)-4-(3-(1-phenylethyl)ureido)benzenesulfonamide |
| H1142 | 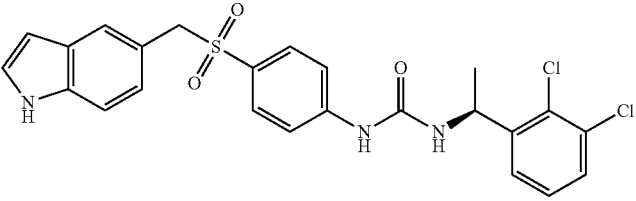 [SMILES: C[C@H](NC(=O)Nc1ccc(S(=O)(=O)Cc2ccc3[nH]ccc3c2)cc1)c1cccc(Cl)c1Cl] | (S)-1-(4-(((1H-indol-5-yl)methyl)sulfonyl)phenyl)-3-(1-(2,3-dichlorophenyl)ethyl)urea |

-continued

| | Chemical Structure | Chemical Name |
|---|---|---|
| H1145 | 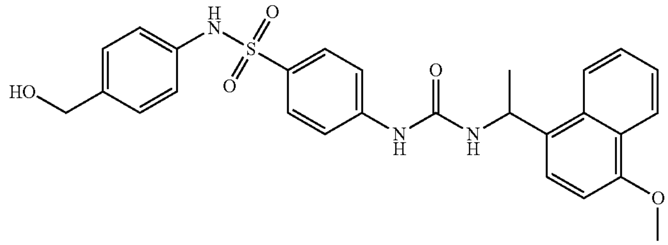 [SMILES: COc1ccc(C(C)NC(=O)Nc2ccc(S(=O)(=O)Nc3ccc(CO)cc3)cc2)c2ccccc12] | N-(4-(hydroxymethyl)phenyl)-4-(3-(1-(4-methoxynaphthalen-1-yl)ethyl)ureido)benzenesulfonamide |
| H1148 | 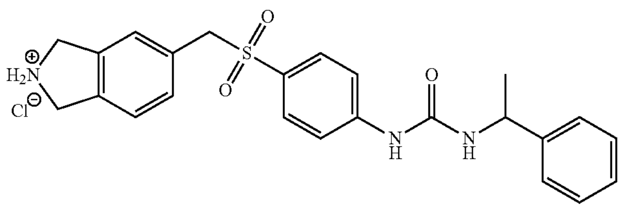 [SMILES: [Cl-] ; CC(NC(=O)Nc1ccc(S(=O)(=O)Cc2ccc3c(c2)C[NH2+]C3)cc1)c1ccccc1] | 1-(4-((isoindolin-5-ylmethyl)sulfonyl)phenyl)-3-(1-phenylethyl)urea |
| H1149 | 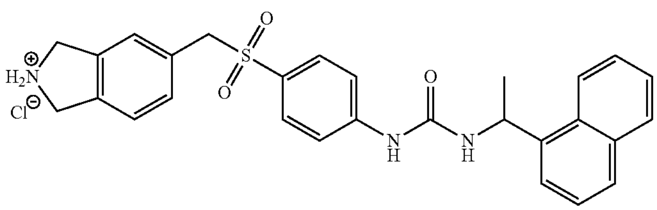 [SMILES: [Cl-] ; CC(NC(=O)Nc1ccc(S(=O)(=O)Cc2ccc3c(c2)C[NH2+]C3)cc1)c1cccc2ccccc12] | 1-(4-((isoindolin-5-ylmethyl)sulfonyl)phenyl)-3-(1-(naphthalen-1-yl)ethyl)urea |
| H1154 | 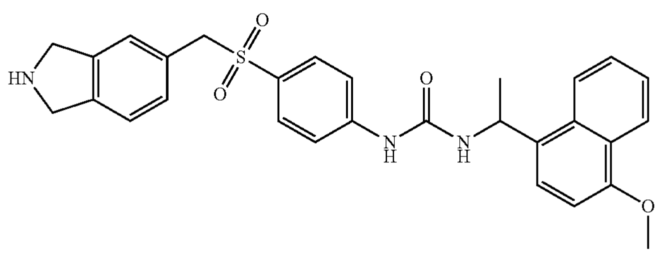 [SMILES: COc1ccc(C(C)NC(=O)Nc2ccc(S(=O)(=O)Cc3ccc4c(c3)CNC4)cc2)c2ccccc12] | 1-(4-((isoindolin-5-ylmethyl)sulfonyl)phenyl)-3-(1-(4-methoxynaphthalen-1-yl)ethyl)urea |
| H1155 | 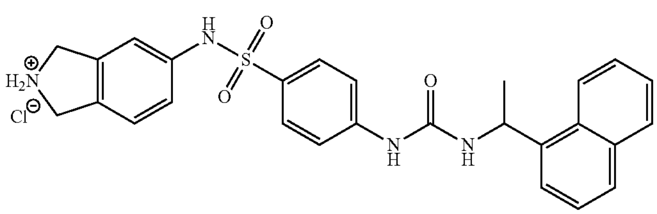 [SMILES: [Cl-] ; CC(NC(=O)Nc1ccc(S(=O)(=O)Nc2ccc3c(c2)C[NH2+]C3)cc1)c1cccc2ccccc12] | N-(isoindolin-5-yl)-4-(3-(1-(naphthalen-1-yl)ethyl)ureido)benzenesulfonamide |
| H1156 | 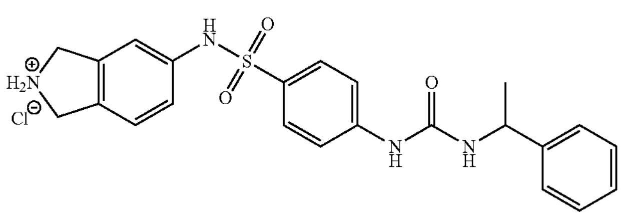 [SMILES: [Cl-] ; CC(NC(=O)Nc1ccc(S(=O)(=O)Nc2ccc3c(c2)C[NH2+]C3)cc1)c1ccccc1] | N-(isoindolin-5-yl)-4-(3-(1-phenylethyl)ureido)benzenesulfonamide |
| H1166 | 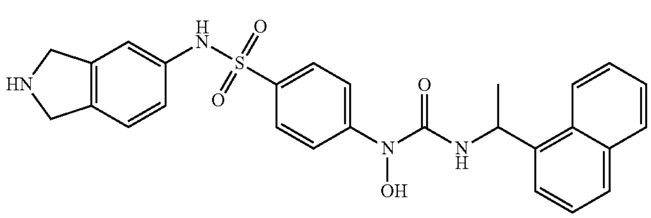 [SMILES: CC(NC(=O)N(O)c1ccc(S(=O)(=O)Nc2ccc3c(c2)CNC3)cc1)c1cccc2ccccc12] | 4-(1-hydroxy-3-(1-(naphthalen-1-yl)ethyl)ureido)-N-(isoindolin-5-yl)benzenesulfonamide |

-continued

| | Chemical Structure | Chemical Name |
|---|---|---|
| H1178 | 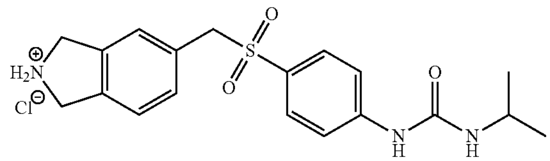 [SMILES: [Cl-] ; CC(C)NC(=O)Nc1ccc(S(=O)(=O)Cc2ccc3c(c2)C[NH2+]C3)cc1] | 1-(4-((isoindolin-5-ylmethyl)sulfonyl)phenyl)-3-isopropylurea |
| H1179 | 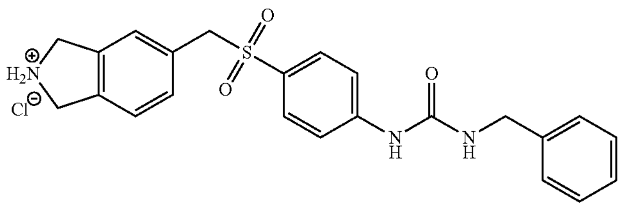 [SMILES: [Cl-] ; O=C(NCc1ccccc1)Nc1ccc(S(=O)(=O)Cc2ccc3c(c2)C[NH2+]C3)cc1] | 1-benzyl-3-(4-((isoindolin-5-ylmethyl)sulfonyl)phenyl)urea |
| H1180 | 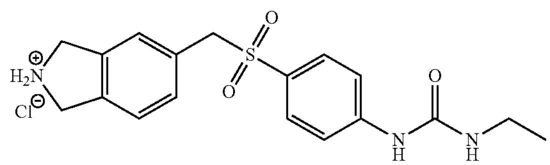 [SMILES: [Cl-] ; CCNC(=O)Nc1ccc(S(=O)(=O)Cc2ccc3c(c2)C[NH2+]C3)cc1] | 1-ethyl-3-(4-((isoindolin-5-ylmethyl)sulfonyl)phenyl)urea |
| H1181 | 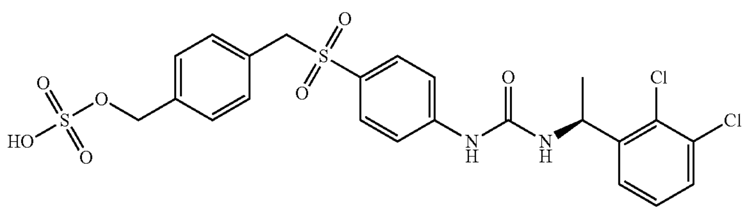 [SMILES: C[C@H](NC(=O)Nc1ccc(S(=O)(=O)Cc2ccc(COS(=O)(=O)O)cc2)cc1)c1cccc(Cl)c1Cl] | (S)-4-(((4-(3-(1-(2,3-dichlorophenyl)ethyl)ureido)phenyl)sulfonyl)methyl)benzyl hydrogen sulfate |
| H1188 | 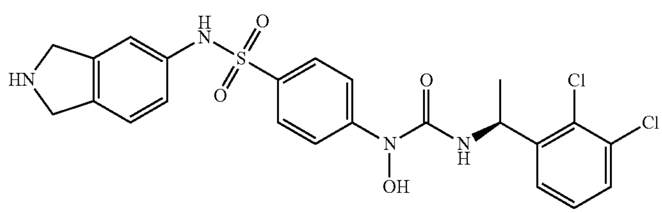 [SMILES: C[C@H](NC(=O)N(O)c1ccc(S(=O)(=O)Nc2ccc3c(c2)CNC3)cc1)c1cccc(Cl)c1Cl] | (S)-4-(3-(1-(2,3-dichlorophenyl)ethyl)-1-hydroxyureido)-N-(isoindolin-5-yl)benzenesulfonamide |
| H1190 | 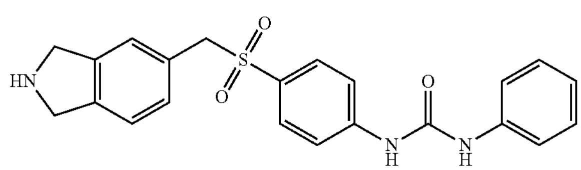 [SMILES: O=C(Nc1ccccc1)Nc1ccc(S(=O)(=O)Cc2ccc3c(c2)CNC3)cc1] | 1-(4-((isoindolin-5-ylmethyl)sulfonyl)phenyl)-3-phenylurea |
| H1193 | 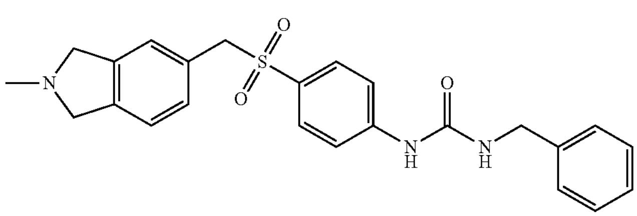 [SMILES: CN1Cc2ccc(CS(=O)(=O)c3ccc(NC(=O)NCc4ccccc4)cc3)cc2C1] | 1-benzyl-3-(4-(((2-methylisoindolin-5-yl)methyl)sulfonyl)phenyl)urea |
| H1194 | 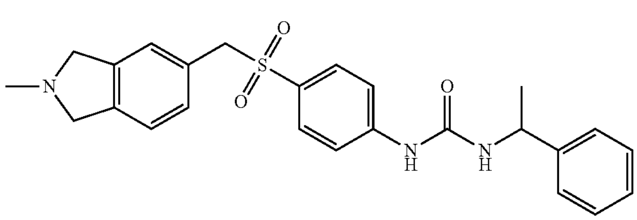 [SMILES: CC(NC(=O)Nc1ccc(S(=O)(=O)Cc2ccc3c(c2)CN(C)C3)cc1)c1ccccc1] | 1-(4-(((2-methylisoindolin-5-yl)methyl)sulfonyl)phenyl)-3-(1-phenylethyl)urea |

| | Chemical Structure | Chemical Name |
|---|---|---|
| H1199 | 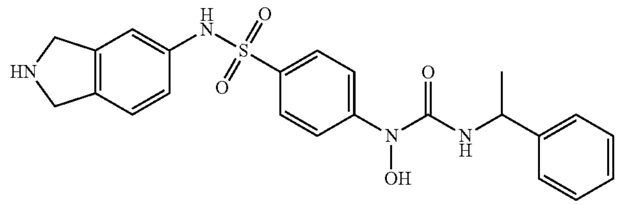 [SMILES: CC(NC(=O)N(O)c1ccc(S(=O)(=O)Nc2ccc3c(c2)CNC3)cc1)c1ccccc1] | 4-(1-hydroxy-3-(1-phenylethyl)ureido)-N-(isoindolin-5-yl)benzenesulfonamide |
| H1203 | 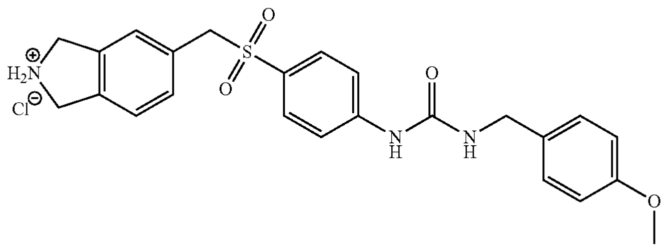 [SMILES: [Cl-] ; COc1ccc(CNC(=O)Nc2ccc(S(=O)(=O)Cc3ccc4c(c3)C[NH2+]C4)cc2)cc1] | 1-(4-((isoindolin-5-ylmethyl)sulfonyl)phenyl)-3-(4-methoxybenzyl)urea |
| H1204 | 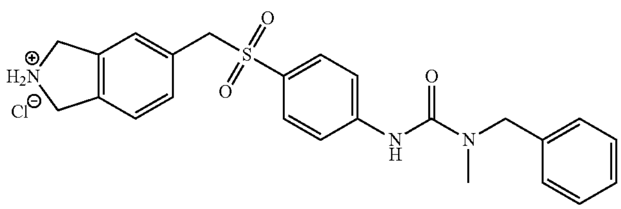 [SMILES: [Cl-] ; CN(Cc1ccccc1)C(=O)Nc1ccc(S(=O)(=O)Cc2ccc3c(c2)C[NH2+]C3)cc1] | 1-benzyl-3-(4-((isoindolin-5-ylmethyl)sulfonyl)phenyl)-1-methylurea |
| H1205 | 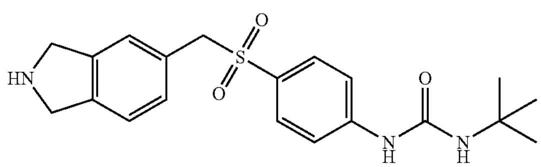 [SMILES: CC(C)(C)NC(=O)Nc1ccc(S(=O)(=O)Cc2ccc3c(c2)CNC3)cc1] | 1-(tert-butyl)-3-(4-((isoindolin-5-ylmethyl)sulfonyl)phenyl)urea |
| H1206 | 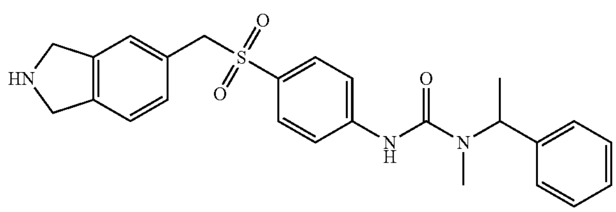 [SMILES: CC(c1ccccc1)N(C)C(=O)Nc1ccc(S(=O)(=O)Cc2ccc3c(c2)CNC3)cc1] | 3-(4-((isoindolin-5-ylmethyl)sulfonyl)phenyl)-1-methyl-1-(1-phenylethyl)urea |
| H1208 | 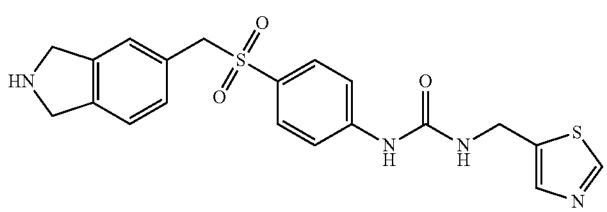 [SMILES: O=C(NCc1cncs1)Nc1ccc(S(=O)(=O)Cc2ccc3c(c2)CNC3)cc1] | 1-(4-((isoindolin-5-ylmethyl)sulfonyl)phenyl)-3-(thiazol-5-ylmethyl)urea |
| H1212 | 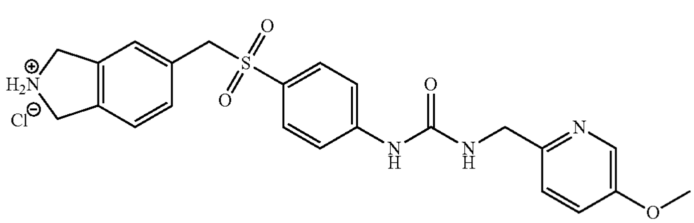 [SMILES: [Cl-] ; COc1ccc(CNC(=O)Nc2ccc(S(=O)(=O)Cc3ccc4c(c3)C[NH2+]C4)cc2)nc1] | 1-(4-((isoindolin-5-ylmethyl)sulfonyl)phenyl)-3-((5-methoxypyridin-2-yl)methyl)urea |

| | Chemical Structure | Chemical Name |
|---|---|---|
| H1213 | 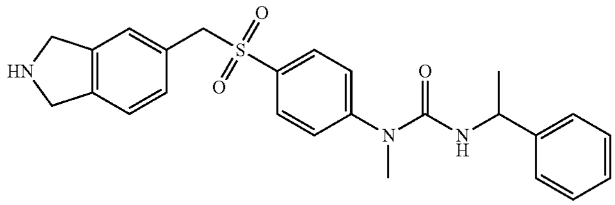 [SMILES: CC(NC(=O)N(C)c1ccc(S(=O)(=O)Cc2ccc3c(c2)CNC3)cc1)c1ccccc1] | 1-(4-((isoindolin-5-ylmethyl)sulfonyl)phenyl)-1-methyl-3-(1-phenylethyl)urea |
| H1214 | 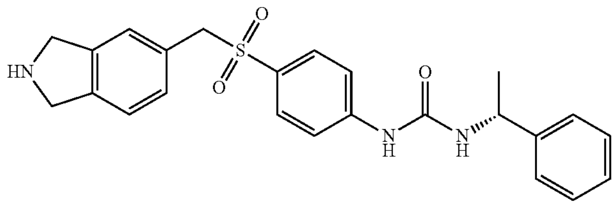 [SMILES: C[C@@H](NC(=O)Nc1ccc(S(=O)(=O)Cc2ccc3c(c2)CNC3)cc1)c1ccccc1] | (R)-1-(4-((isoindolin-5-ylmethyl)sulfonyl)phenyl)-3-(1-phenylethyl)urea |
| H1215 | 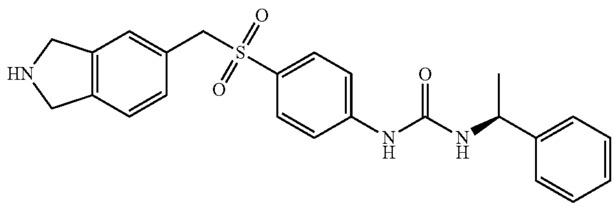 [SMILES: C[C@H](NC(=O)Nc1ccc(S(=O)(=O)Cc2ccc3c(c2)CNC3)cc1)c1ccccc1] | (S)-1-(4-((isoindolin-5-ylmethyl)sulfonyl)phenyl)-3-(1-phenylethyl)urea |
| H1216 | 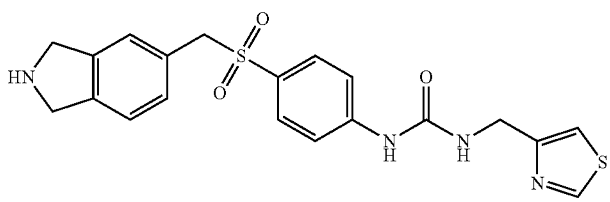 [SMILES: O=C(NCc1cscn1)Nc1ccc(S(=O)(=O)Cc2ccc3c(c2)CNC3)cc1] | 1-(4-((isoindolin-5-ylmethyl)sulfonyl)phenyl)-3-(thiazol-4-ylmethyl)urea |
| H1217 | 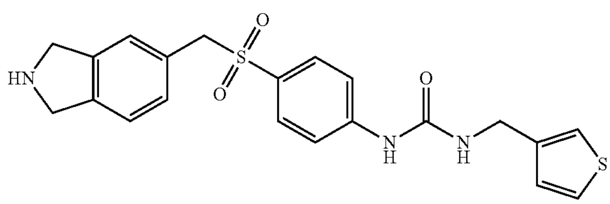 [SMILES: O=C(NCc1ccsc1)Nc1ccc(S(=O)(=O)Cc2ccc3c(c2)CNC3)cc1] | 1-(4-((isoindolin-5-ylmethyl)sulfonyl)phenyl)-3-(thiophen-3-ylmethyl)urea |
| H1219 | 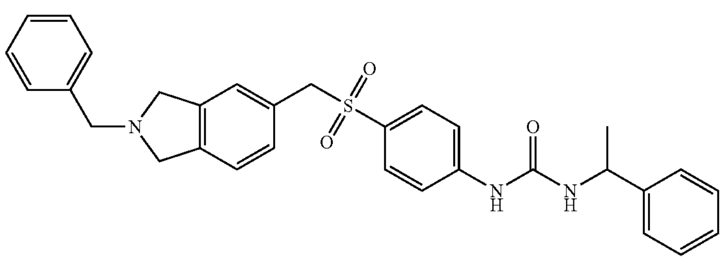 [SMILES: CC(NC(=O)Nc1ccc(S(=O)(=O)Cc2ccc3c(c2)CN(Cc2ccccc2)C3)cc1)c1ccccc1] | 1-(4-(((2-benzylisoindolin-5-yl)methyl)sulfonyl)phenyl)-3-(1-phenylethyl)urea |
| H1220 | 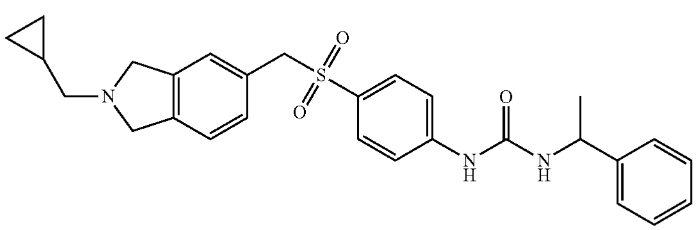 [SMILES: CC(NC(=O)Nc1ccc(S(=O)(=O)Cc2ccc3c(c2)CN(CC2CC2)C3)cc1)c1ccccc1] | 1-(4-(((2-(cyclopropylmethyl)isoindolin-5-yl)methyl)sulfonyl)phenyl)-3-(1-phenylethyl)urea |

| | Chemical Structure | Chemical Name |
|---|---|---|
| H1221 | 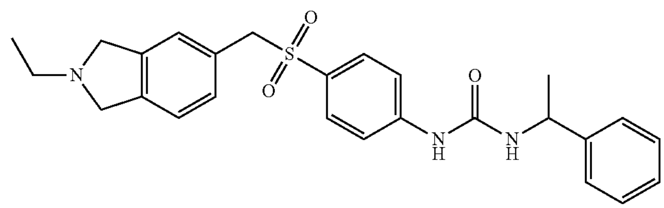 [SMILES: CCN1Cc2ccc(CS(=O)(=O)c3ccc(NC(=O)NC(C)c4ccccc4)cc3)cc2C1] | 1-(4-(((2-ethylisoindolin-5-yl)methyl)sulfonyl)phenyl)-3-(1-phenylethyl)urea |
| H1222 | 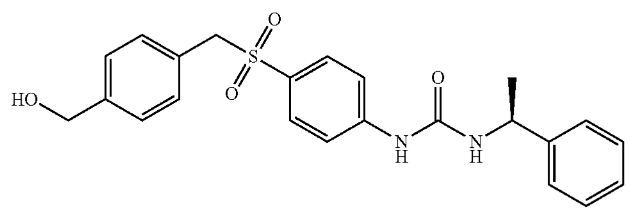 [SMILES: C[C@H](NC(=O)Nc1ccc(S(=O)(=O)Cc2ccc(CO)cc2)cc1)c1ccccc1] | (S)-1-(4-((4-(hydroxymethyl)benzyl)sulfonyl)phenyl)-3-(1-phenylethyl)urea |
| H1225 | 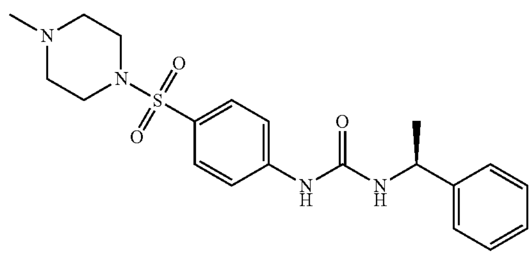 | (S)-1-(4-((4-methylpiperazin-1-yl)sulfonyl)phenyl)-3-(1-phenylethyl)urea |
| H1227 | 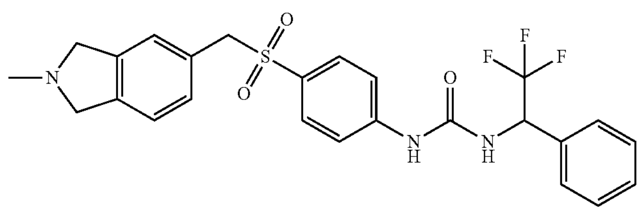 [SMILES: CN1Cc2ccc(CS(=O)(=O)c3ccc(NC(=O)NC(c4ccccc4)C(F)(F)F)cc3)cc2C1] | 1-(4-(((2-methylisoindolin-5-yl)methyl)sulfonyl)phenyl)-3-(2,2,2-trifluoro-1-phenylethyl)urea |
| H1228 | 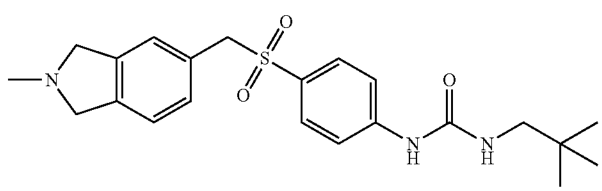 [SMILES: CN1Cc2ccc(CS(=O)(=O)c3ccc(NC(=O)NCC(C)(C)C)cc3)cc2C1] | 1-(4-(((2-methylisoindolin-5-yl)methyl)sulfonyl)phenyl)-3-neopentylurea |
| H1229 | 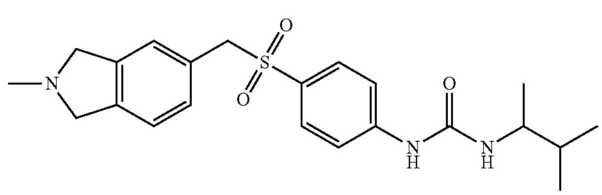 [SMILES: CC(C)C(C)NC(=O)Nc1ccc(S(=O)(=O)Cc2ccc3c(c2)CN(C)C3)cc1] | 1-(3-methylbutan-2-yl)-3-(4-(((2-methylisoindolin-5-yl)methyl)sulfonyl)phenyl)urea |
| H1230 | 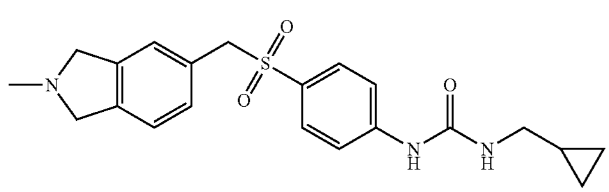 [SMILES: CN1Cc2ccc(CS(=O)(=O)c3ccc(NC(=O)NCC4CC4)cc3)cc2C1] | 1-(cyclopropylmethyl)-3-(4-(((2-methylisoindolin-5-yl)methyl)sulfonyl)phenyl)urea |

| | Chemical Structure | Chemical Name |
|---|---|---|
| H1231 | 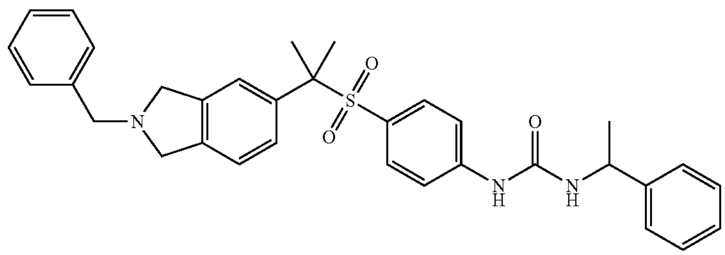 [SMILES: CC(NC(=O)Nc1ccc(S(=O)(=O)C(C)(C)c2ccc3c(c2)CN(Cc2ccccc2)C3)cc1)c1ccccc1] | 1-(4-((2-(2-benzylisoindolin-5-yl)propan-2-yl)sulfonyl)phenyl)-3-(1-phenylethyl)urea |
| H1232 | 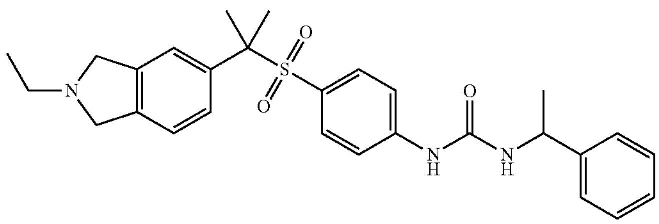 [SMILES: CCN1Cc2ccc(C(C)(C)S(=O)(=O)c3ccc(NC(=O)NC(C)c4ccccc4)cc3)cc2C1] | 1-(4-((2-(2-ethylisoindolin-5-yl)propan-2-yl)sulfonyl)phenyl)-3-(1-phenylethyl)urea |
| H1233 | 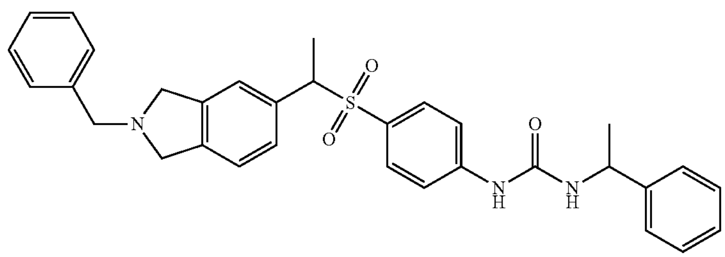 [SMILES: CC(NC(=O)Nc1ccc(S(=O)(=O)C(C)c2ccc3c(c2)CN(Cc2ccccc2)C3)cc1)c1ccccc1] | 1-(4-((1-(2-benzylisoindolin-5-yl)ethyl)sulfonyl)phenyl)-3-(1-phenylethyl)urea |
| H1234 | 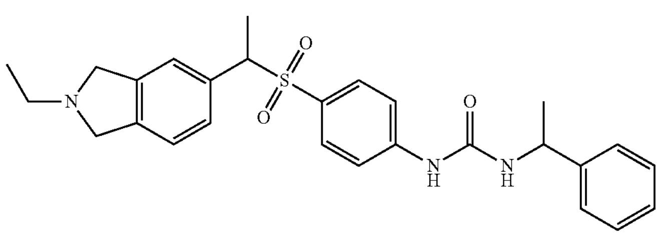 [SMILES: CCN1Cc2ccc(C(C)S(=O)(=O)c3ccc(NC(=O)NC(C)c4ccccc4)cc3)cc2C1] | 1-(4-((1-(2-ethylisoindolin-5-yl)ethyl)sulfonyl)phenyl)-3-(1-phenylethyl)urea |
| H1235 | 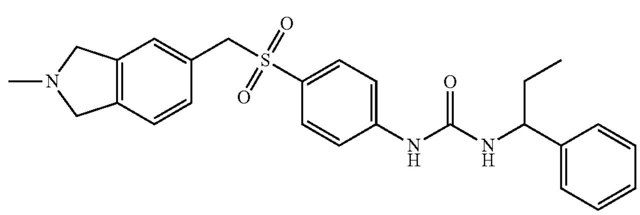 [SMILES: CCC(NC(=O)Nc1ccc(S(=O)(=O)Cc2ccc3c(c2)CN(C)C3)cc1)c1ccccc1] | 1-(4-(((2-methylisoindolin-5-yl)methyl)sulfonyl)phenyl)-3-(1-phenylpropyl)urea |
| H1236 | 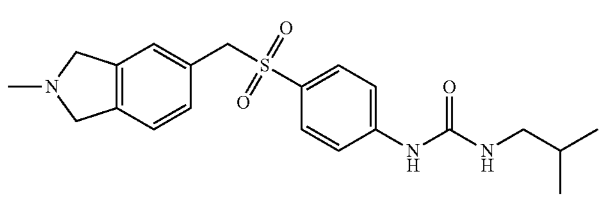 [SMILES: CC(C)CNC(=O)Nc1ccc(S(=O)(=O)Cc2ccc3c(c2)CN(C)C3)cc1] | 1-isobutyl-3-(4-(((2-methylisoindolin-5-yl)methyl)sulfonyl)phenyl)urea |

-continued

| | Chemical Structure | Chemical Name |
|---|---|---|
| H1237 | 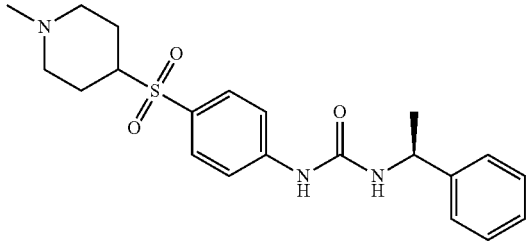 [SMILES: C[C@H](NC(=O)Nc1ccc(S(=O)(=O)C2CCN(C)CC2)cc1)c1ccccc1] | (S)-1-(4-((1-methylpiperidin-4-yl)sulfonyl)phenyl)-3-(1-phenylethyl)urea |
| H1238 | 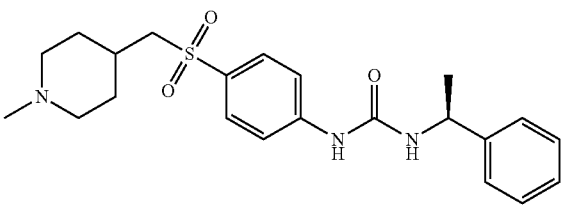 [SMILES: C[C@H](NC(=O)Nc1ccc(S(=O)(=O)CC2CCN(C)CC2)cc1)c1ccccc1] | (S)-1-(4-(((1-methylpiperidin-4-yl)methyl)sulfonyl)phenyl)-3-(1-phenylethyl)urea |
| H1239 | 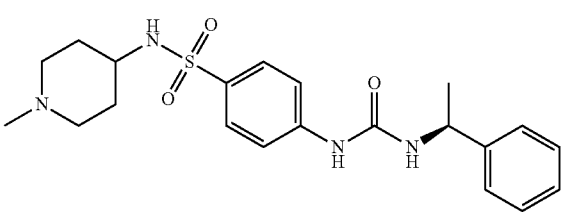 [SMILES: C[C@H](NC(=O)Nc1ccc(S(=O)(=O)NC2CCN(C)CC2)cc1)c1ccccc1] | (S)-N-(1-methylpiperidin-4-yl)-4-(3-(1-phenylethyl)ureido)benzenesulfonamide |
| H1244 | 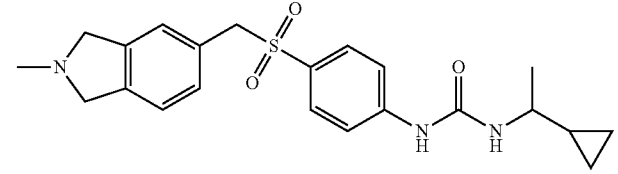 | 1-(1-cyclopropylethyl)-3-(4-(((2-methylisoindolin-5-yl)methyl)sulfonyl)phenyl)urea |
| H1248 | 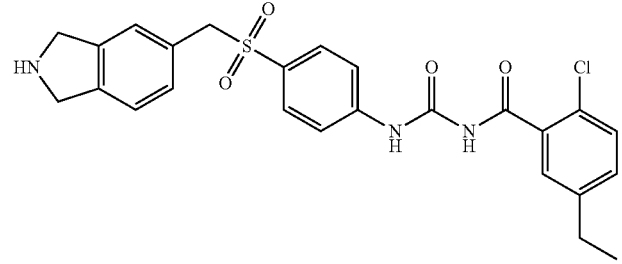 [SMILES: CCc1ccc(Cl)c(C(=O)NC(=O)Nc2ccc(S(=O)(=O)Cc3ccc4c(c3)CNC4)cc2)c1] | 2-chloro-5-ethyl-N-((4-((isoindolin-5-ylmethyl)sulfonyl)phenyl)carbamoyl)benzamide |
| H1249 | 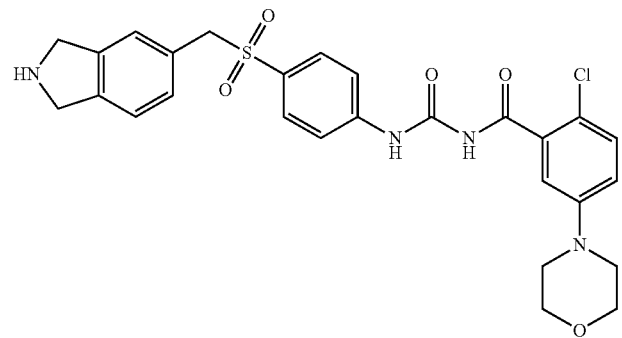 [SMILES: O=C(NC(=O)c1cc(N2CCOCC2)ccc1Cl)Nc1ccc(S(=O)(=O)Cc2ccc3c(c2)CNC3)cc1] | 2-chloro-N-((4-((isoindolin-5-ylmethyl)sulfonyl)phenyl)carbamoyl)-5-morpholinobenzamide |

-continued

| | Chemical Structure | Chemical Name |
|---|---|---|
| H1250 | 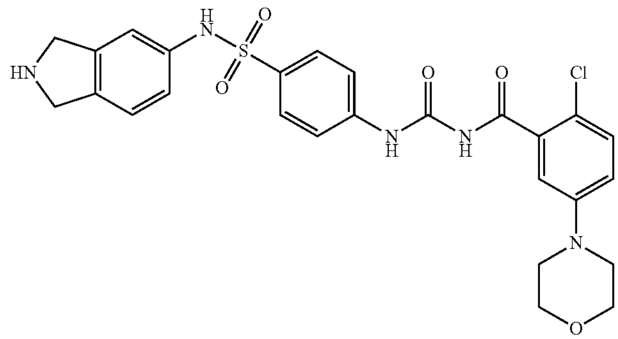 | 2-chloro-N-((4-((isoindolin-5-yl)sulfamoyl)phenyl)carbamoyl)-5-morpholinobenzamide |
| H1251 | 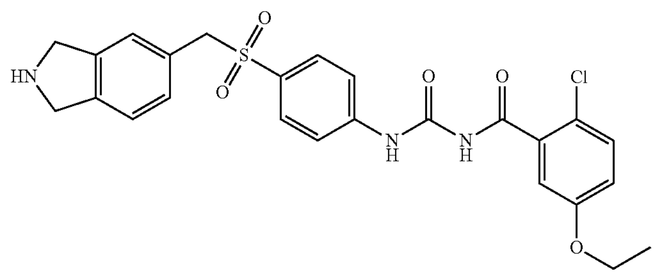 | 2-chloro-5-ethoxy-N-((4-((isoindolin-5-ylmethyl)sulfonyl)phenyl)carbamoyl)benzamide |
| H1252 | 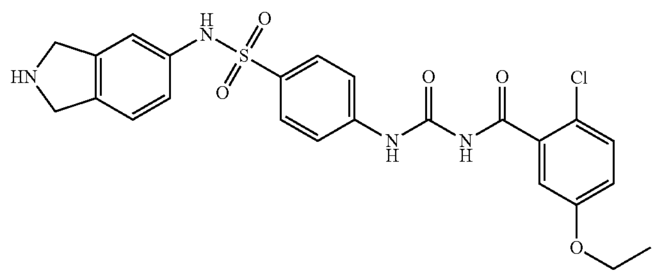 [SMILES: CCOc1ccc(Cl)c(C(=O)NC(=O)Nc2ccc(S(=O)(=O)Nc3ccc4c(c3)CNC4)cc2)c1] | 2-chloro-5-ethoxy-N-((4-(N-(isoindolin-5-yl)sulfamoyl)phenyl)carbamoyl)benzamide |
| H1253 | 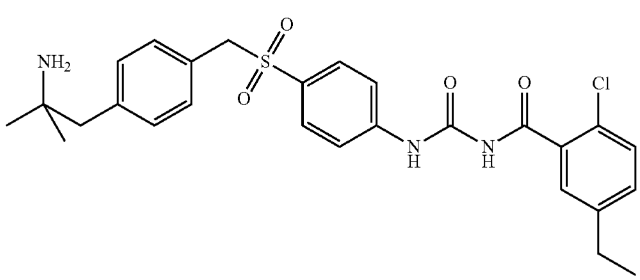 [SMILES: CCc1ccc(Cl)c(C(=O)NC(=O)Nc2ccc(S(=O)(=O)Cc3ccc(CC(C)(C)N)cc3)cc2)c1] | N-((4-((4-(2-amino-2-methylpropyl)benzyl)sulfonyl)phenyl)carbamoyl)-2-chloro-5-ethylbenzamide |
| H1254 | 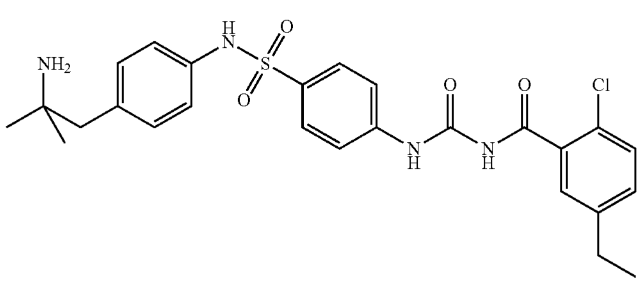 [SMILES: CCc1ccc(Cl)c(C(=O)NC(=O)Nc2ccc(S(=O)(=O)Nc3ccc(CC(C)(C)N)cc3)cc2)c1] | N-((4-(N-(4-(2-amino-2-methylpropyl)phenyl)sulfamoyl)phenyl)carbamoyl)-2-chloro-5-ethylbenzamide |

-continued

| | Chemical Structure | Chemical Name |
|---|---|---|
| H1255 | 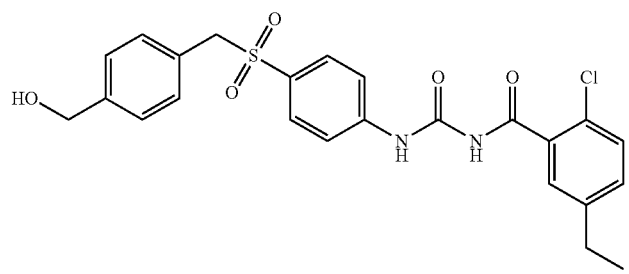 [SMILES: CCc1ccc(Cl)c(C(=O)NC(=O)Nc2ccc(S(=O)(=O)Cc3ccc(CO)cc3)cc2)c1] | 2-chloro-5-ethyl-N-((4-((4-(hydroxymethyl)benzyl)sulfonyl)phenyl)carbamoyl)benzamide |
| H1256 | 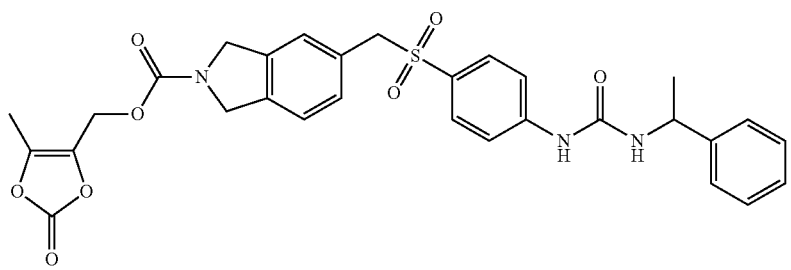 [SMILES: Cc1oc(=O)oc1COC(=O)N1Cc2ccc(CS(=O)(=O)c3ccc(NC(=O)NC(C)c4ccccc4)cc3)cc2C1] | (5-methyl-2-oxo-1,3-dioxol-4-yl)methyl 5-(((4-(3-(1-phenylethyl)ureido)phenyl)sulfonyl)methyl)isoindoline-2-carboxylate |
| H1259 | 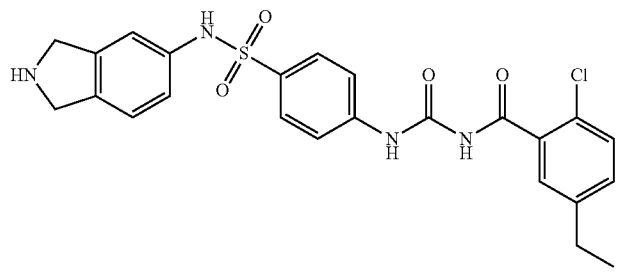 | 2-chloro-5-ethyl-N-((4-(N-(isoindolin-5-yl)sulfamoyl)phenyl)carbamoyl)benzamide |
| H1260 | 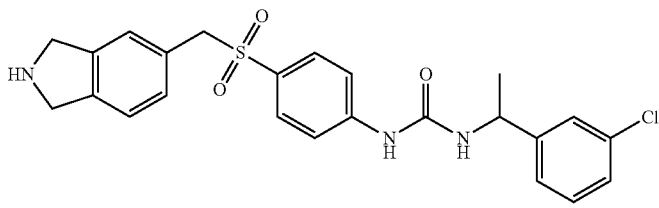 [SMILES: CC(NC(=O)Nc1ccc(S(=O)(=O)Cc2ccc3c(c2)CNC3)cc1)c1cccc(Cl)c1] | 1-(1-(3-chlorophenyl)ethyl)-3-(4-((isoindolin-5-ylmethyl)sulfonyl)phenyl)urea |
| H1261 | 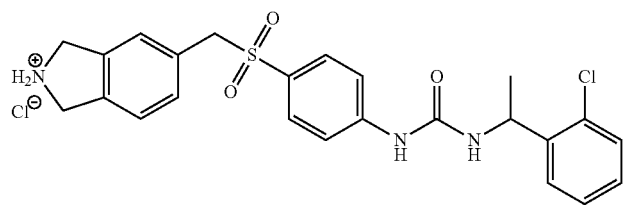 [SMILES: [Cl-] ; CC(NC(=O)Nc1ccc(S(=O)(=O)Cc2ccc3c(c2)C[NH2+]C3)cc1)c1ccccc1Cl] | 1-(1-(2-chlorophenyl)ethyl)-3-(4-((isoindolin-5-ylmethyl)sulfonyl)phenyl)urea |
| H1262 | 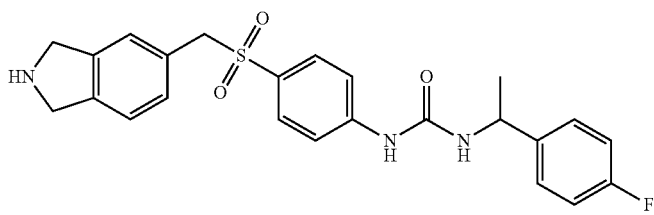 [SMILES: CC(NC(=O)Nc1ccc(S(=O)(=O)Cc2ccc3c(c2)CNC3)cc1)c1ccc(F)cc1] | 1-(1-(4-fluorophenyl)ethyl)-3-(4-((isoindolin-5-ylmethyl)sulfonyl)phenyl)urea |

-continued

| | Chemical Structure | Chemical Name |
|---|---|---|
| H1263 | 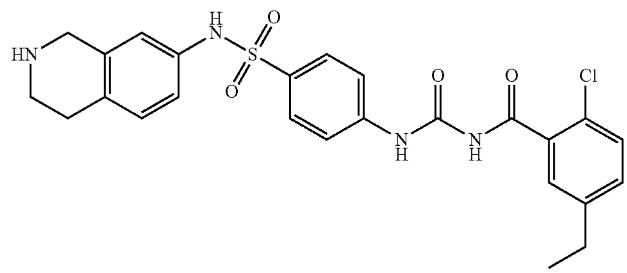 [SMILES: CCc1ccc(Cl)c(C(=O)NC(=O)Nc2ccc(S(=O)(=O)Nc3ccc4c(c3)CNCC4)cc2)c1] | 2-chloro-5-ethyl-N-((4-(N-(1,2,3,4-tetrahydroisoquinolin-7-yl)sulfamoyl)phenyl)carbamoyl)benzamide |
| H1264 | 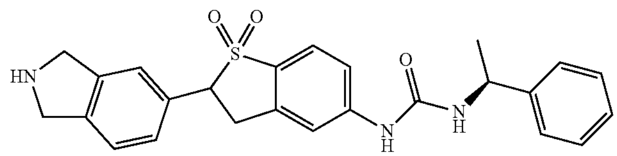 [SMILES: C[C@H](NC(=O)Nc1ccc2c(c1)CC(c1ccc3c(c1)CNC3)S2(=O)=O)c1ccccc1] | 1-(2-(isoindolin-5-yl)-1,1-dioxido-2,3-dihydrobenzo[b]thiophen-5-yl)-3-((S)-1-phenylethyl)urea |
| H1266 | 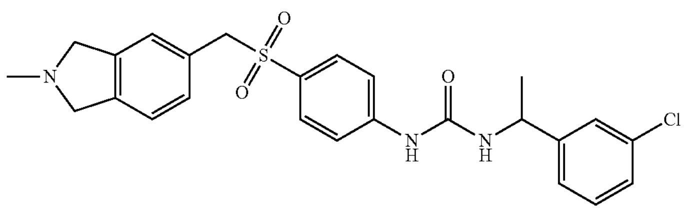 [SMILES: CC(NC(=O)Nc1ccc(S(=O)(=O)Cc2ccc3c(c2)CN(C)C3)cc1)c1cccc(Cl)c1] | 1-(1-(3-chlorophenyl)ethyl)-3-(4-(((2-methylisoindolin-5-yl)methyl)sulfonyl)phenyl)urea |
| H1267 | 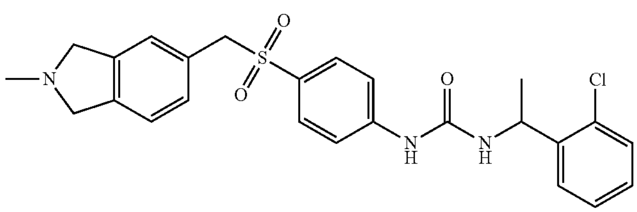 [SMILES: CC(NC(=O)Nc1ccc(S(=O)(=O)Cc2ccc3c(c2)CN(C)C3)cc1)c1ccccc1Cl] | 1-(1-(2-chlorophenyl)ethyl)-3-(4-(((2-methylisoindolin-5-yl)methyl)sulfonyl)phenyl)urea |
| H1268 | 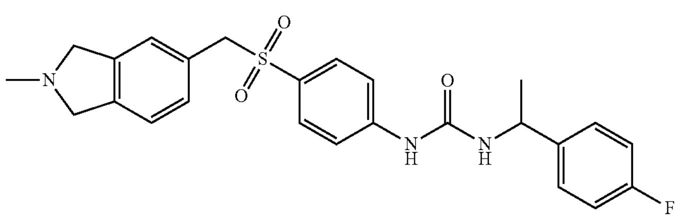 [SMILES: CC(NC(=O)Nc1ccc(S(=O)(=O)Cc2ccc3c(c2)CN(C)C3)cc1)c1ccc(F)cc1] | 1-(1-(4-fluorophenyl)ethyl)-3-(4-(((2-methylisoindolin-5-yl)methyl)sulfonyl)phenyl)urea |
| H1269 | 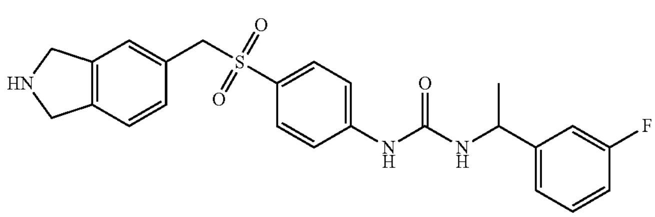 [SMILES: CC(NC(=O)Nc1ccc(S(=O)(=O)Cc2ccc3c(c2)CNC3)cc1)c1cccc(F)c1] | 1-(1-(3-fluorophenyl)ethyl)-3-(4-((isoindolin-5-ylmethyl)sulfonyl)phenyl)urea |
| H1270 | 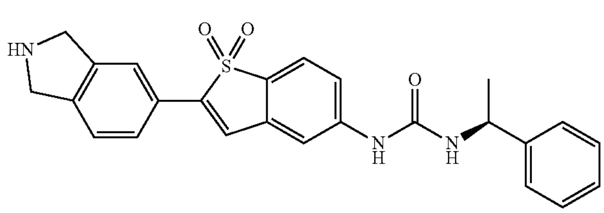 [SMILES: C[C@H](NC(=O)Nc1ccc2c(c1)C=C(c1ccc3c(c1)CNC3)S2(=O)=O)c1ccccc1] | (S)-1-(2-(isoindolin-5-yl)-1,1-dioxidobenzo[b]thiophen-5-yl)-3-(1-phenylethyl)urea |

| | Chemical Structure | Chemical Name |
|---|---|---|
| H1271 | 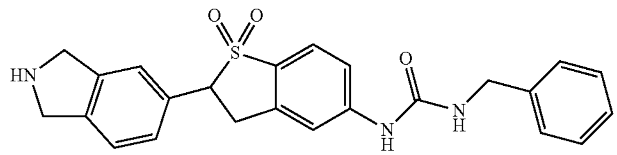 [SMILES: O=C(NCc1ccccc1)Nc1ccc2c(c1)CC(c1ccc3c(c1)CNC3)S2(=O)=O] | 1-benzyl-3-(2-(isoindolin-5-yl)-1,1-dioxido-2,3-dihydrobenzo[b]thiophen-5-yl)urea |
| H1272 | 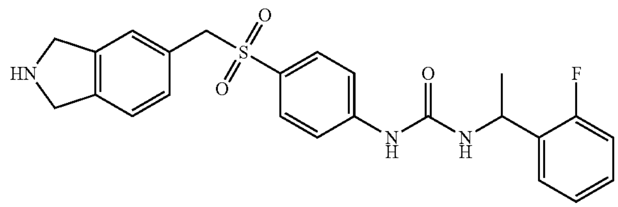 [SMILES: CC(NC(=O)Nc1ccc(S(=O)(=O)Cc2ccc3c(c2)CNC3)cc1)c1ccccc1F] | 1-(1-(2-fluorophenyl)ethyl)-3-(4-((isoindolin-5-ylmethyl)sulfonyl)phenyl)urea |
| H1273 | 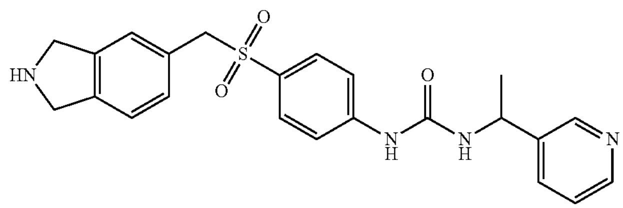 | 1-(4-((isoindolin-5-ylmethyl)sulfonyl)phenyl)-3-(1-(pyridin-3-yl)ethyl)urea |
| H1274 | 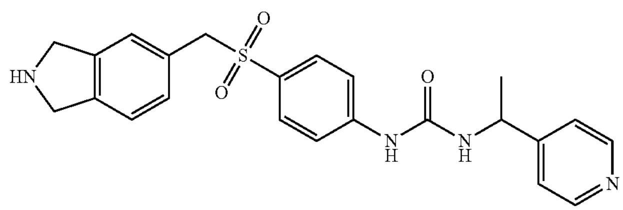 [SMILES: CC(NC(=O)Nc1ccc(S(=O)(=O)Cc2ccc3c(c2)CNC3)cc1)c1ccncc1] | 1-(4-((isoindolin-5-ylmethyl)sulfonyl)phenyl)-3-(1-(pyridin-4-yl)ethyl)urea |
| H1275 | 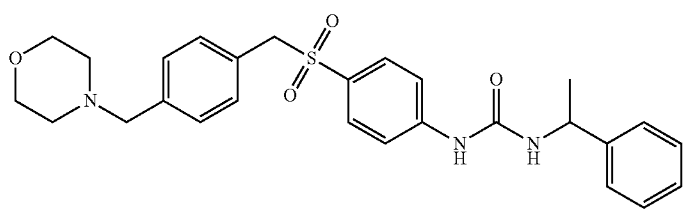 [SMILES: CC(NC(=O)Nc1ccc(S(=O)(=O)Cc2ccc(CN3CCOCC3)cc2)cc1)c1ccccc1] | 1-(4-((4-(morpholinomethyl)benzyl)sulfonyl)phenyl)-3-(1-phenylethyl)urea |
| H1276 | 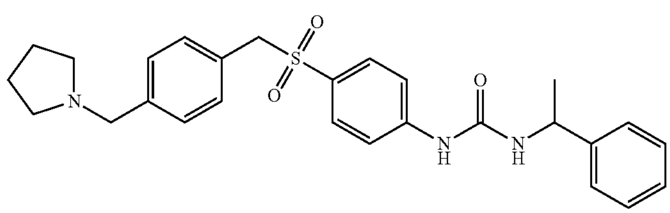 [SMILES: CC(NC(=O)Nc1ccc(S(=O)(=O)Cc2ccc(CN3CCCC3)cc2)cc1)c1ccccc1] | 1-(1-phenylethyl)-3-(4-((4-(pyrrolidin-1-ylmethyl)benzyl)sulfonyl)phenyl)urea |
| H1277 | 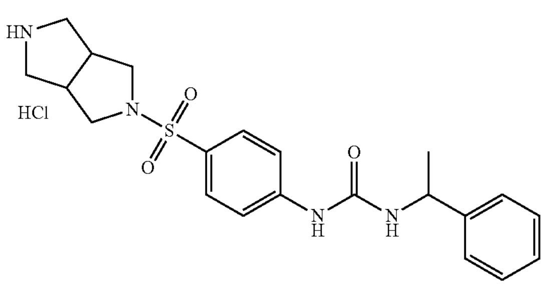 [SMILES: Cl ; CC(NC(=O)Nc1ccc(S(=O)(=O)N2CC3CNCC3C2)cc1)c1ccccc1] | 1-(4-((hexahydropyrrolo[3,4-c]pyrrol-2(1H)-yl)sulfonyl)phenyl)-3-(1-phenylethyl)urea |

| | Chemical Structure | Chemical Name |
|---|---|---|
| H1280 | 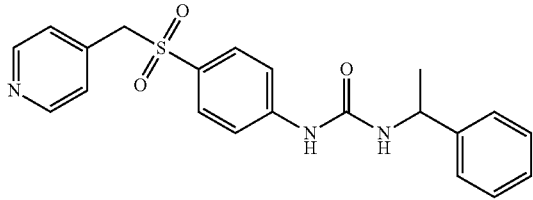 [SMILES: CC(NC(=O)Nc1ccc(S(=O)(=O)Cc2ccncc2)cc1)c1ccccc1] | 1-(1-phenylethyl)-3-(4-((pyridin-4-ylmethyl)sulfonyl)phenyl)urea |
| H1281 | 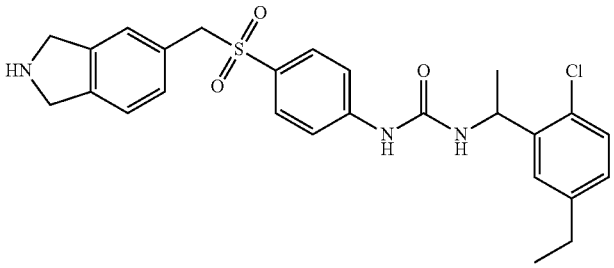 | 1-(1-(2-chloro-5-ethylphenyl)ethyl)-3-(4-((isoindolin-5-ylmethyl)sulfonyl)phenyl)urea |
| H1283 | 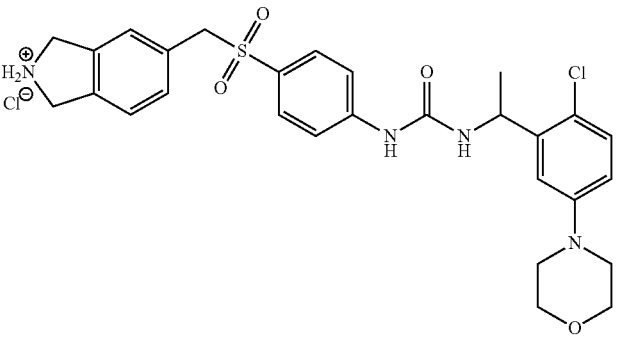 [SMILES: [Cl-] ; CC(NC(=O)Nc1ccc(S(=O)(=O)Cc2ccc3c(c2)C[NH2+]C3)cc1)c1cc(N2CCOCC2)ccc1Cl] | 1-(1-(2-chloro-5-morpholinophenyl)ethyl)-3-(4-((isoindolin-5-ylmethyl)sulfonyl)phenyl)urea |
| H1284 | 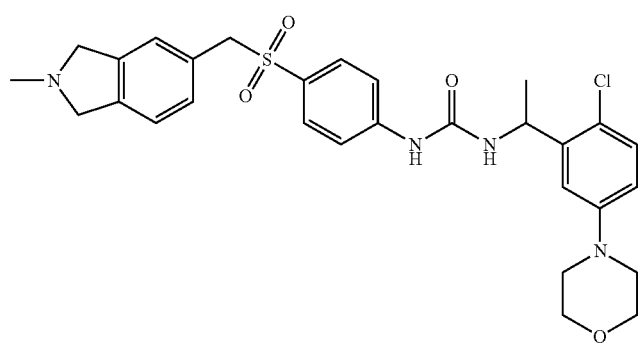 [SMILES: CC(NC(=O)Nc1ccc(S(=O)(=O)Cc2ccc3c(c2)CN(C)C3)cc1)c1cc(N2CCOCC2)ccc1Cl] | 1-(1-(2-chloro-5-morpholinophenyl)ethyl)-3-(4-(((2-methylisoindolin-5-yl)methyl)sulfonyl)phenyl)urea |
| H1285 | 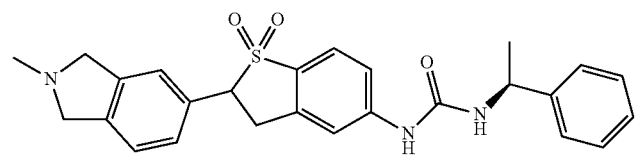 [SMILES: C[C@H](NC(=O)Nc1ccc2c(c1)CC(c1ccc3c(c1)CN(C)C3)S2(=O)=O)c1ccccc1] | 1-(2-(2-methylisoindolin-5-yl)-1,1-dioxido-2,3-dihydrobenzo[b]thiophen-5-yl)-3-((S)-1-phenylethyl)urea |
| H1286 | 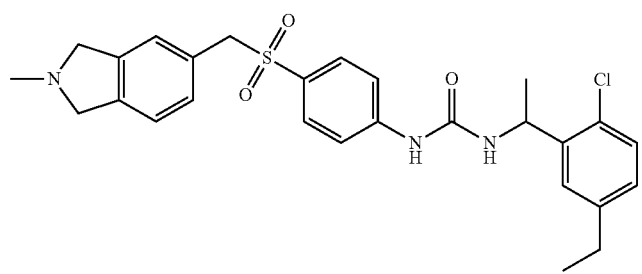 [SMILES: CCc1ccc(Cl)c(C(C)NC(=O)Nc2ccc(S(=O)(=O)Cc3ccc4c(c3)CN(C)C4)cc2)c1] | 1-(1-(2-chloro-5-ethylphenyl)ethyl)-3-(4-(((2-methylisoindolin-5-yl)methyl)sulfonyl)phenyl)urea |

| | Chemical Structure | Chemical Name |
|---|---|---|
| H1289 | 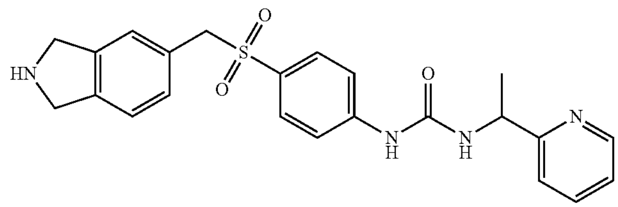 [SMILES: CC(NC(=O)Nc1ccc(S(=O)(=O)Cc2ccc3c(c2)CNC3)cc1)c1ccccn1] | 1-(4-((isoindolin-5-ylmethyl)sulfonyl)phenyl)-3-(1-(pyridin-2-yl)ethyl)urea |
| H1290 | 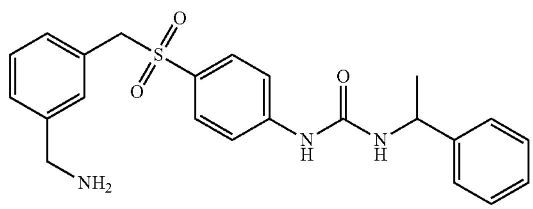 [SMILES: CC(NC(=O)Nc1ccc(S(=O)(=O)Cc2cccc(CN)c2)cc1)c1ccccc1] | 1-(4-((3-(aminomethyl)benzyl)sulfonyl)phenyl)-3-(1-phenylethyl)urea |
| H1291 | 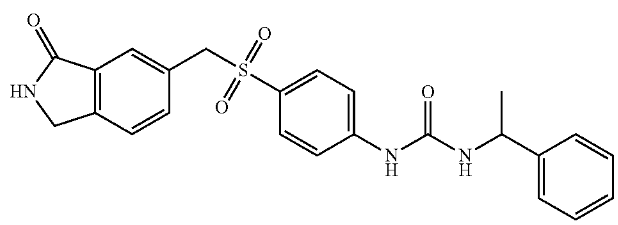 [SMILES: CC(NC(=O)Nc1ccc(S(=O)(=O)Cc2ccc3c(c2)C(=O)NC3)cc1)c1ccccc1] | 1-(4-(((3-oxoisoindolin-5-yl)methyl)sulfonyl)phenyl)-3-(1-phenylethyl)urea |
| H1292 | 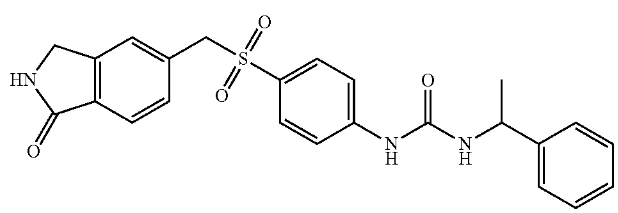 [SMILES: CC(NC(=O)Nc1ccc(S(=O)(=O)Cc2ccc3c(c2)CNC3=O)cc1)c1ccccc1] | 1-(4-(((1-oxoisoindolin-5-yl)methyl)sulfonyl)phenyl)-3-(1-phenylethyl)urea |
| H1293 | 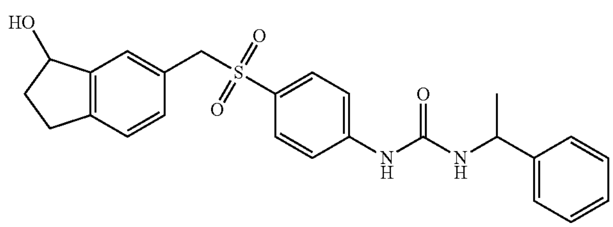 [SMILES: CC(NC(=O)Nc1ccc(S(=O)(=O)Cc2ccc3c(c2)C(O)CC3)cc1)c1ccccc1] | 1-(4-(((3-hydroxy-2,3-dihydro-1H-inden-5-yl)methyl)sulfonyl)phenyl)-3-(1-phenylethyl)urea |
| H1294 | 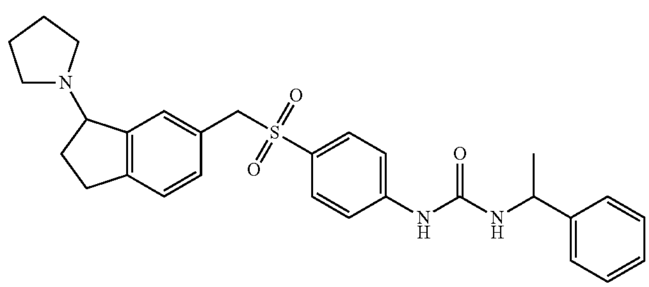 [SMILES: CC(NC(=O)Nc1ccc(S(=O)(=O)Cc2ccc3c(c2)C(N2CCCC2)CC3)cc1)c1ccccc1] | 1-(1-phenylethyl)-3-(4-(((3-(pyrrolidin-1-yl)-2,3-dihydro-1H-inden-5-yl)methyl)sulfonyl)phenyl)urea |

-continued

| | Chemical Structure | Chemical Name |
|---|---|---|
| H1296 | 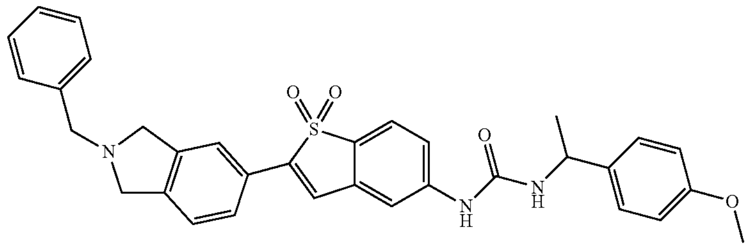 [SMILES: COc1ccc(C(C)NC(=O)Nc2ccc3c(c2)C=C(c2ccc4c(c2)CN(Cc2ccccc2)C4)S3(=O)=O)cc1] | 1-(2-(2-benzylisoindolin-5-yl)-1,1-dioxidobenzo[b]thiophen-5-yl)-3-(1-(4-methoxyphenyl)ethyl)urea |
| H1297 | 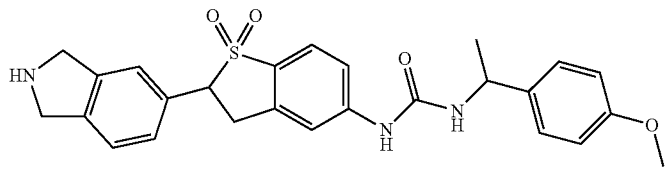 [SMILES: COc1ccc(C(C)NC(=O)Nc2ccc3c(c2)CC(c2ccc4c(c2)CNC4)S3(=O)=O)cc1] | 1-(2-(isoindolin-5-yl)-1,1-dioxido-2,3-dihydrobenzo[b]thiophen-5-yl)-3-(1-(4-methoxyphenyl)ethyl)urea |
| H1298 | 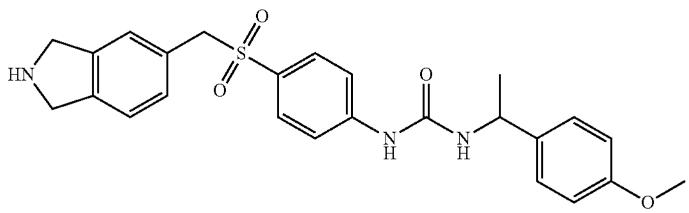 [SMILES: COc1ccc(C(C)NC(=O)Nc2ccc(S(=O)(=O)Cc3ccc4c(c3)CNC4)cc2)cc1] | 1-(4-((isoindolin-5-ylmethyl)sulfonyl)phenyl)-3-(1-(4-methoxyphenyl)ethyl)urea |
| H1299 | 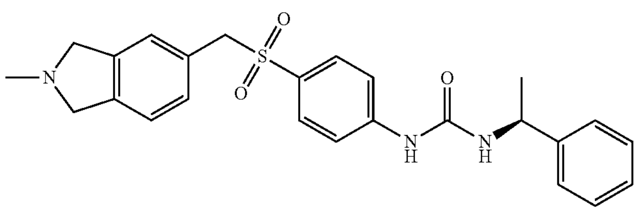 [SMILES: C[C@H](NC(=O)Nc1ccc(S(=O)(=O)Cc2ccc3c(c2)CN(C)C3)cc1)c1ccccc1] | (S)-1-(4-(((2-methylisoindolin-5-yl)methyl)sulfonyl)phenyl)-3-(1-phenylethyl)urea |
| H1300 | 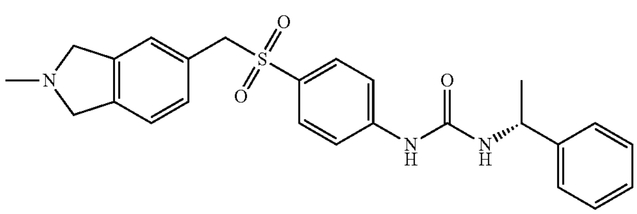 [SMILES: C[C@@H](NC(=O)Nc1ccc(S(=O)(=O)Cc2ccc3c(c2)CN(C)C3)cc1)c1ccccc1] | (R)-1-(4-(((2-methylisoindolin-5-yl)methyl)sulfonyl)phenyl)-3-(1-phenylethyl)urea |
| H1301 | 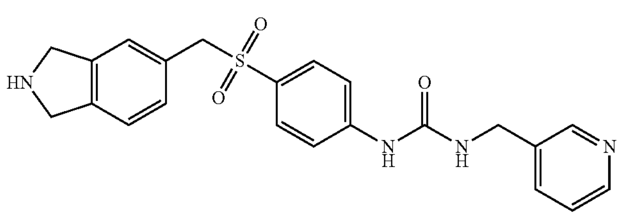 [SMILES: O=C(NCc1cccnc1)Nc1ccc(S(=O)(=O)Cc2ccc3c(c2)CNC3)cc1] | 1-(4-((isoindolin-5-ylmethyl)sulfonyl)phenyl)-3-(pyridin-3-ylmethyl)urea |
| H1302 | 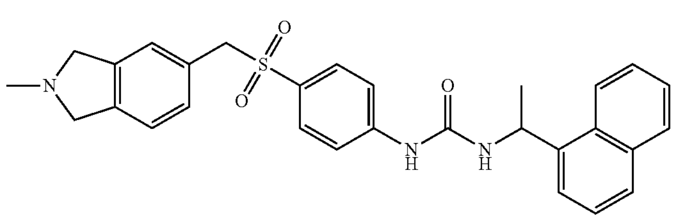 [SMILES: CC(NC(=O)Nc1ccc(S(=O)(=O)Cc2ccc3c(c2)CN(C)C3)cc1)c1cccc2ccccc12] | 1-(4-(((2-methylisoindolin-5-yl)methyl)sulfonyl)phenyl)-3-(1-(naphthalen-1-yl)ethyl)urea |

-continued

| | Chemical Structure | Chemical Name |
|---|---|---|
| H1303 | 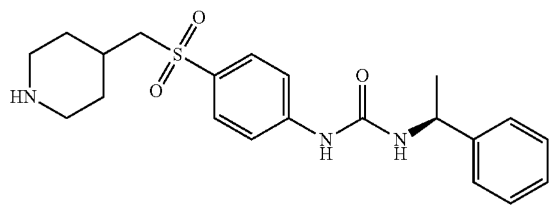 [SMILES: C[C@H](NC(=O)Nc1ccc(S(=O)(=O)CC2CCNCC2)cc1)c1ccccc1] | (S)-1-(1-phenylethyl)-3-(4-((piperidin-4-ylmethyl)sulfonyl)phenyl)urea |
| H1304 | 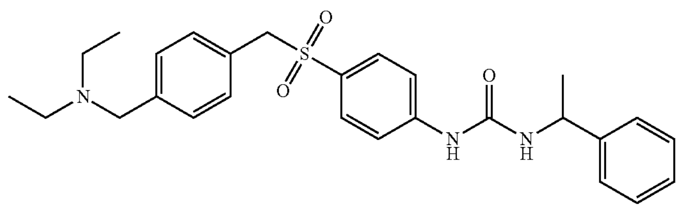 [SMILES: CCN(CC)Cc1ccc(CS(=O)(=O)c2ccc(NC(=O)NC(C)c3ccccc3)cc2)cc1] | 1-(4-((4-((diethylamino)methyl)benzyl)sulfonyl)phenyl)-3-(1-phenylethyl)urea |
| H1305 | 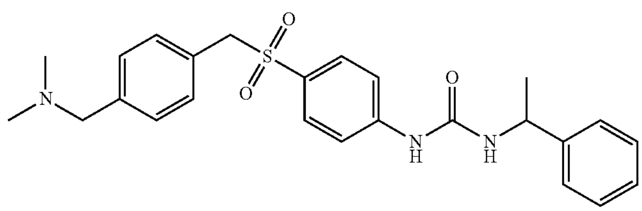 [SMILES: CC(NC(=O)Nc1ccc(S(=O)(=O)Cc2ccc(CN(C)C)cc2)cc1)c1ccccc1] | 1-(4-((4-((dimethylamino)methyl)benzyl)sulfonyl)phenyl)-3-(1-phenylethyl)urea |
| H1306 | 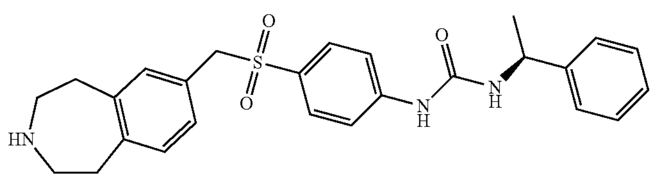 [SMILES: C[C@H](NC(=O)Nc1ccc(S(=O)(=O)Cc2ccc3c(c2)CCNCC3)cc1)c1ccccc1] | (S)-1-(1-phenylethyl)-3-(4-(((2,3,4,5-tetrahydro-1H-benzo[d]azepin-7-yl)methyl)sulfonyl)phenyl)urea |
| H1307 | 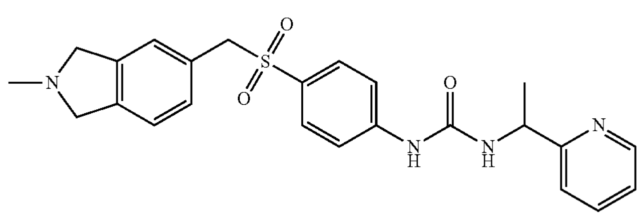 [SMILES: CC(NC(=O)Nc1ccc(S(=O)(=O)Cc2ccc3c(c2)CN(C)C3)cc1)c1ccccn1] | 1-(4-(((2-methylisoindolin-yl)methyl)sulfonyl)phenyl)-3-(1-(pyridin-2-yl)ethyl)urea |
| H1308 | 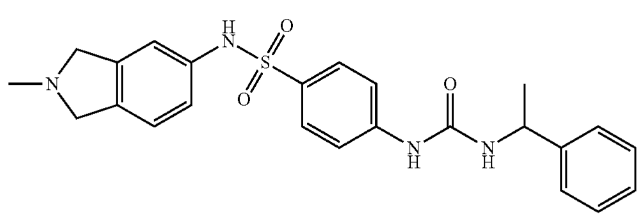 [SMILES: CC(NC(=O)Nc1ccc(S(=O)(=O)Nc2ccc3c(c2)CN(C)C3)cc1)c1ccccc1] | N-(2-methylisoindolin-5-yl)-4-(3-(1-phenylethyl)ureido)benzenesulfonamide |
| H1309 | 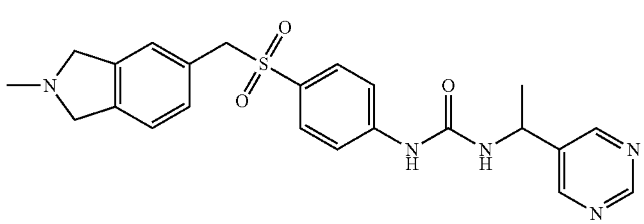 [SMILES: CC(NC(=O)Nc1ccc(S(=O)(=O)Cc2ccc3c(c2)CN(C)C3)cc1)c1cncnc1] | 1-(4-(((2-methylisoindolin-5-yl)methyl)sulfonyl)phenyl)-3-(1-(pyrimidin-5-yl)ethyl)urea |

-continued

| | Chemical Structure | Chemical Name |
|---|---|---|
| H1310 | 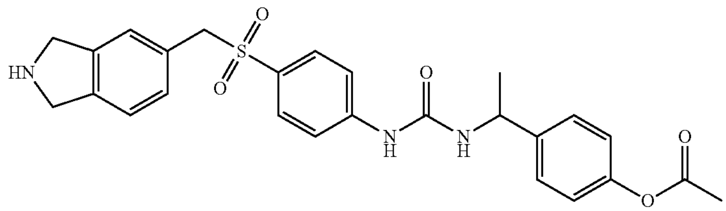 [SMILES: CC(=O)Oc1ccc(C(C)NC(=O)Nc2ccc(S(=O)(=O)Cc3ccc4c(c3)CNC4)cc2)cc1] | 4-(1-(3-(4-((isoindolin-5-ylmethyl)sulfonyl)phenyl)ureido)ethyl)phenylacetate |
| H1311 | 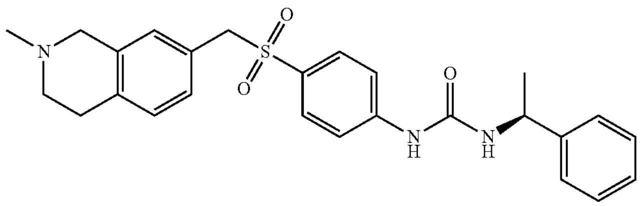 [SMILES: C[C@H](NC(=O)Nc1ccc(S(=O)(=O)Cc2ccc3c(c2)CN(C)CC3)cc1)c1ccccc1] | (S)-1-(4-(((2-methyl-1,2,3,4-tetrahydroisoquinolin-7-yl)methyl)sulfonyl)phenyl)-3-(1-phenylethyl)urea |
| H1312 | 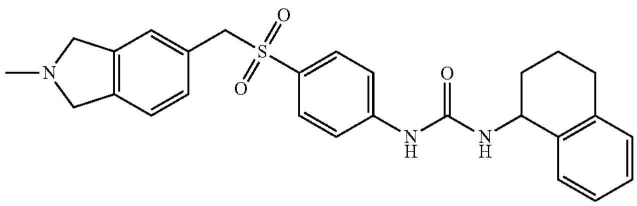 [SMILES: CN1Cc2ccc(CS(=O)(=O)c3ccc(NC(=O)NC4CCCc5ccccc54)cc3)cc2C1] | 1-(4-(((2-methylisoindolin-5-yl)methyl)sulfonyl)phenyl)-3-(1,2,3,4-tetrahydronaphthalen-1-yl)urea |
| H1313 | 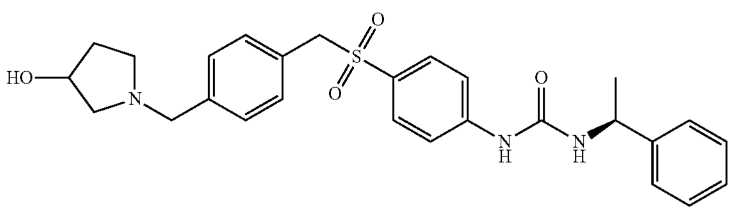 [SMILES: C[C@H](NC(=O)Nc1ccc(S(=O)(=O)Cc2ccc(CN3CCC(O)C3)cc2)cc1)c1ccccc1] | 1-(4-((4-((3-hydroxypyrrolidin-1-yl)methyl)benzyl)sulfonyl)phenyl)-3-((S)-1-phenylethyl)urea |
| H1314 | 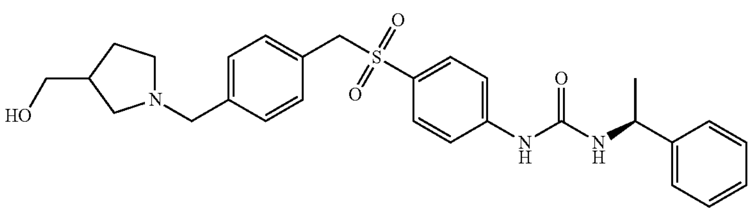 [SMILES: C[C@H](NC(=O)Nc1ccc(S(=O)(=O)Cc2ccc(CN3CCC(CO)C3)cc2)cc1)c1ccccc1] | 1-(4-((4-((3-(hydroxymethyl)pyrrolidin-1-yl)methyl)benzyl)sulfonyl)phenyl)-3-((S)-1-phenylethyl)urea |
| H1315 | 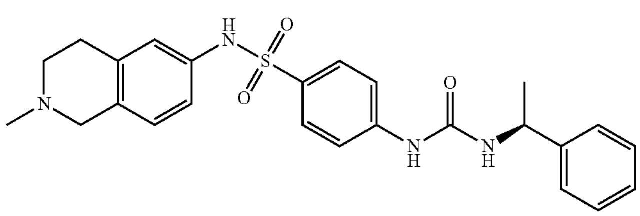 [SMILES: C[C@H](NC(=O)Nc1ccc(S(=O)(=O)Nc2ccc3c(c2)CCN(C)C3)cc1)c1ccccc1] | (S)-N-(2-methyl-1,2,3,4-tetrahydroisoquinolin-6-yl)-4-(3-(1-phenylethyl)ureido)benzenesulfonamide |
| H1316 | 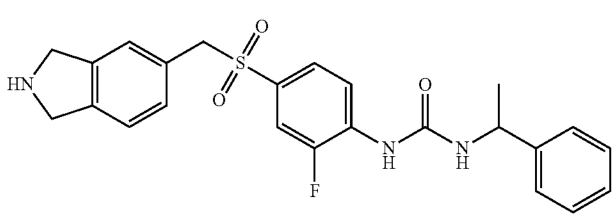 [SMILES: CC(NC(=O)Nc1ccc(S(=O)(=O)Cc2ccc3c(c2)CNC3)cc1F)c1ccccc1] | 1-(2-fluoro-4-((isoindolin-5-ylmethyl)sulfonyl)phenyl)-3-(1-phenylethyl)urea |

| | Chemical Structure | Chemical Name |
|---|---|---|
| H1317 | 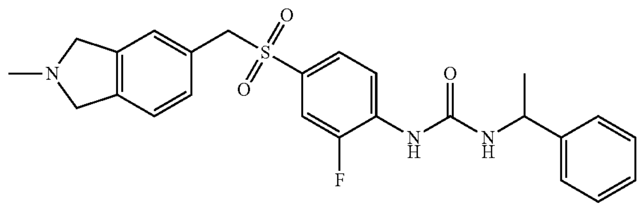 [SMILES: CC(NC(=O)Nc1ccc(S(=O)(=O)Cc2ccc3c(c2)CN(C)C3)cc1F)c1ccccc1] | 1-(2-fluoro-4-(((2-methylisoindolin-5-yl)methyl)sulfonyl)phenyl)-3-(1-phenylethyl)urea |
| H1318 | 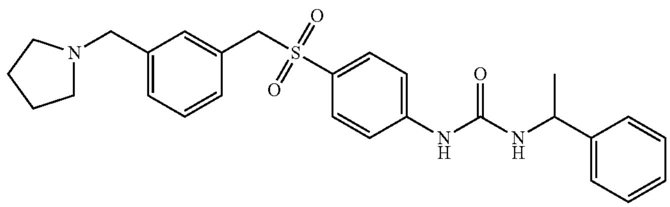 [SMILES: CC(NC(=O)Nc1ccc(S(=O)(=O)Cc2cccc(CN3CCCC3)c2)cc1)c1ccccc1] | 1-(1-phenylethyl)-3-(4-((3-(pyrrolidin-1-ylmethyl)benzyl)sulfonyl)phenyl)urea |
| H1319 | 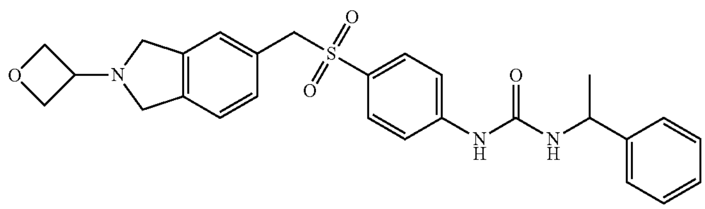 [SMILES: CC(NC(=O)Nc1ccc(S(=O)(=O)Cc2ccc3c(c2)CN(C2COC2)C3)cc1)c1ccccc1] | 1-(4-(((2-(oxetan-3-yl)isoindolin-5-yl)methyl)sulfonyl)phenyl)-3-(1-phenylethyl)urea |
| H1320 | 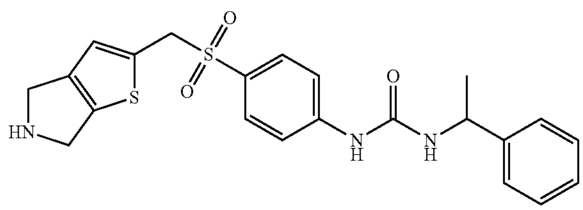 [SMILES: CC(NC(=O)Nc1ccc(S(=O)(=O)Cc2cc3c(s2)CNC3)cc1)c1ccccc1] | 1-(4-(((5,6-dihydro-4H-thieno[2,3-c]pyrrol-2-yl)methyl)sulfonyl)phenyl)-3-(1-phenylethyl)urea |
| H1321 | 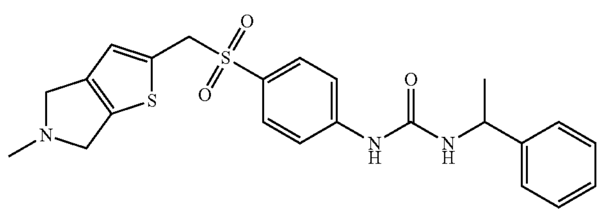 | 1-(4-(((5-methyl-5,6-dihydro-4H-thieno[2,3-c]pyrrol-2-yl)methyl)sulfonyl)phenyl)-3-(1-phenylethyl)urea |
| H1322 | 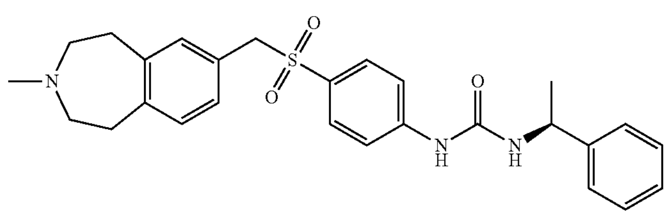 [SMILES: C[C@H](NC(=O)Nc1ccc(S(=O)(=O)Cc2ccc3c(c2)CCN(C)CC3)cc1)c1ccccc1] | (S)-1-(4-(((3-methyl-2,3,4,5-tetrahydro-1H-benzo[d]azepin-7-yl)methyl)sulfonyl)phenyl)-3-(1-phenylethyl)urea |
| H1323 | 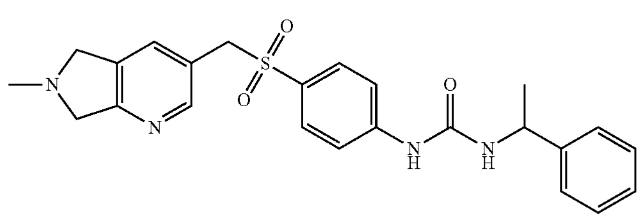 [SMILES: CC(NC(=O)Nc1ccc(S(=O)(=O)Cc2cnc3c(c2)CN(C)C3)cc1)c1ccccc1] | 1-(4-(((6-methyl-6,7-dihydro-5H-pyrrolo[3,4-b]pyridin-3-yl)methyl)sulfonyl)phenyl)-3-(1-phenylethyl)urea |

| | Chemical Structure | Chemical Name |
|---|---|---|
| H1324 | 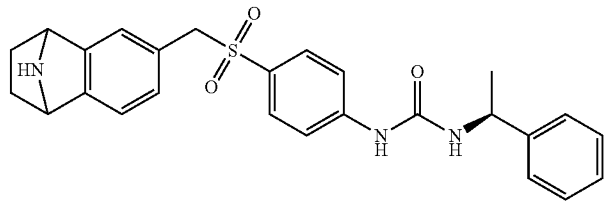 [SMILES: C[C@H](NC(=O)Nc1ccc(S(=O)(=O)Cc2ccc3c(c2)C2CCC3N2)cc1)c1ccccc1] | 1-((S)-1-phenylethyl)-3-(4-(((1,2,3,4-tetrahydro-1,4-epiminonaphthalen-6-yl)methyl)sulfonyl)phenyl)urea |
| H1325 | 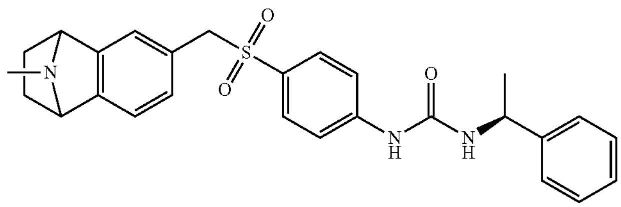 [SMILES: C[C@H](NC(=O)Nc1ccc(S(=O)(=O)Cc2ccc3c(c2)C2CCC3N2C)cc1)c1ccccc1] | 1-(4-(((9-methyl-1,2,3,4-tetrahydro-1,4-epiminonaphthalen-6-yl)methyl)sulfonyl)phenyl)-3-((S)-1-phenylethyl)urea |
| H1326 | 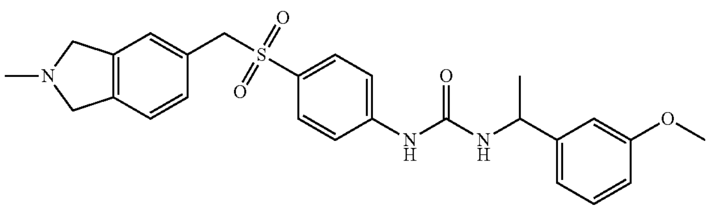 | 1-(1-(3-methoxyphenyl)ethyl)-3-(4-(((2-methylisoindolin-5-yl)methyl)sulfonyl)phenyl)urea |
| H1327 | 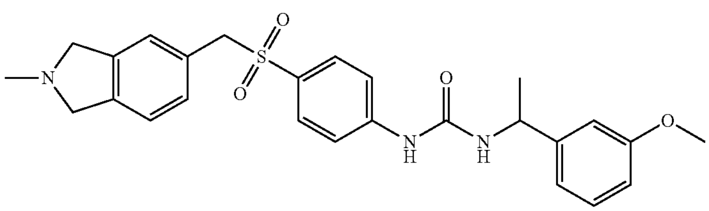 | 1-(1-(3-methoxyphenyl)ethyl)-3-(4-(((2-methylisoindolin-5-yl)methyl)sulfonyl)phenyl)urea |
| H1328 | 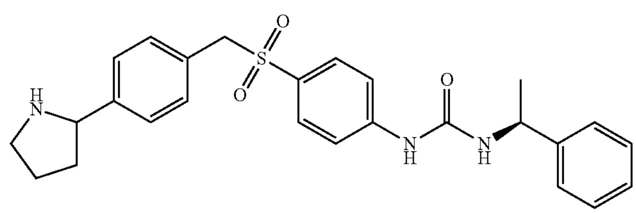 [SMILES: C[C@H](NC(=O)Nc1ccc(S(=O)(=O)Cc2ccc(C3CCCN3)cc2)cc1)c1ccccc1] | 1-((S)-1-phenylethyl)-3-(4-((4-(pyrrolidin-2-yl)benzyl)sulfonyl)phenyl)urea |
| H1329 | 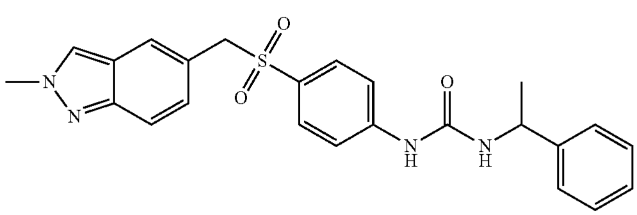 [SMILES: CC(NC(=O)Nc1ccc(S(=O)(=O)Cc2ccc3nn(C)cc3c2)cc1)c1ccccc1] | 1-(4-(((2-methyl-2H-indazol-5-yl)methyl)sulfonyl)phenyl)-3-(1-phenylethyl)urea |
| H1330 | 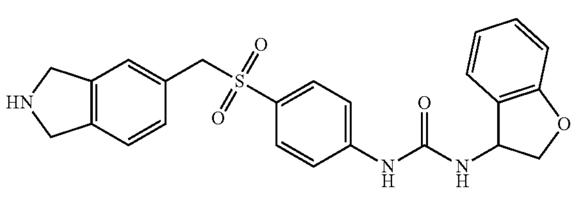 [SMILES: O=C(Nc1ccc(S(=O)(=O)Cc2ccc3c(c2)CNC3)cc1)NC1COc2ccccc21] | 1-(2,3-dihydrobenzofuran-3-yl)-3-(4-((isoindolin-5-ylmethyl)sulfonyl)phenyl)urea |

-continued

| | Chemical Structure | Chemical Name |
|---|---|---|
| H1331 | 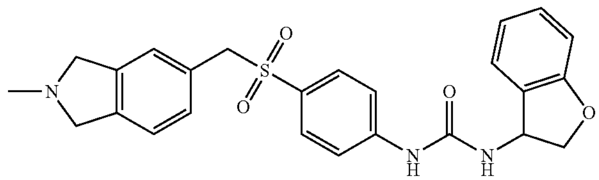 [SMILES: CN1Cc2ccc(CS(=O)(=O)c3ccc(NC(=O)NC4COc5ccccc54)cc3)cc2C1] | 1-(2,3-dihydrobenzofuran-3-yl)-3-(4-(((2-methylisoindolin-5-yl)methyl)sulfonyl)phenyl)urea |
| H1332 | 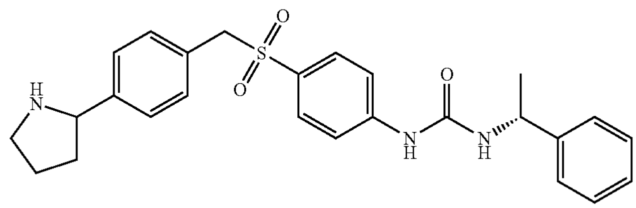 [SMILES: C[C@@H](NC(=O)Nc1ccc(S(=O)(=O)Cc2ccc(C3CCCN3)cc2)cc1)c1ccccc1] | 1-((R)-1-phenylethyl)-3-(4-((4-(pyrrolidin-2-yl)benzyl)sulfonyl)phenyl)urea |
| H1333 | 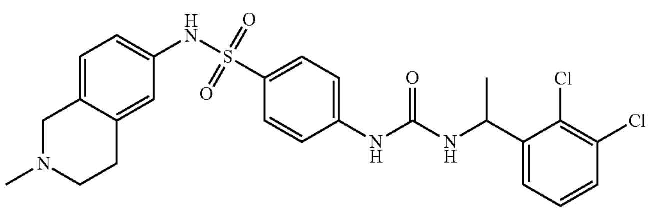 [SMILES: CC(NC(=O)Nc1ccc(S(=O)(=O)Nc2ccc3c(c2)CCN(C)C3)cc1)c1cccc(Cl)c1Cl] | 4-(3-(1-(2,3-dichlorophenyl)ethyl)ureido)-N-(2-methyl-1,2,3,4-tetrahydroisoquinolin-6-yl)benzenesulfonamide |
| H1334 | 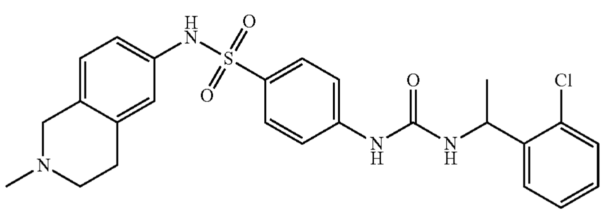 [SMILES: CC(NC(=O)Nc1ccc(S(=O)(=O)Nc2ccc3c(c2)CCN(C)C3)cc1)c1ccccc1Cl] | 4-(3-(1-(2-chlorophenyl)ethyl)ureido)-N-(2-methyl-1,2,3,4-tetrahydroisoquinolin-6-yl)benzenesulfonamide |
| H1335 | 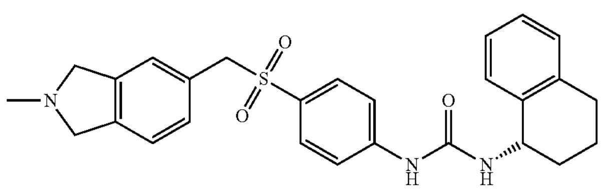 | (S)-1-(4-(((2-methylisoindolin-5-yl)methyl)sulfonyl)phenyl)-3-(1,2,3,4-tetrahydronaphthalen-1-yl)urea |
| H1336 | 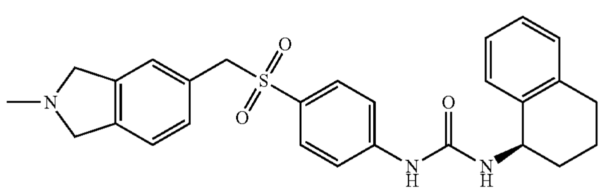 [SMILES: CN1Cc2ccc(CS(=O)(=O)c3ccc(NC(=O)N[C@@H]4CCCc5ccccc54)cc3)cc2C1] | (R)-1-(4-(((2-methylisoindolin-5-yl)methyl)sulfonyl)phenyl)-3-(1,2,3,4-tetrahydronaphthalen-1-yl)urea |
| H1337 | 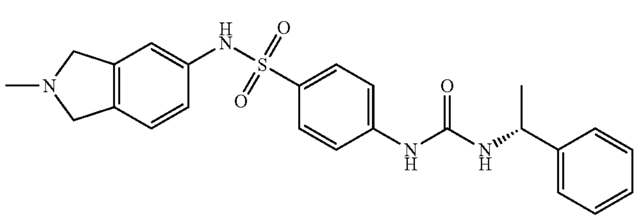 [SMILES: C[C@@H](NC(=O)Nc1ccc(S(=O)(=O)Nc2ccc3c(c2)CN(C)C3)cc1)c1ccccc1] | (R)-N-(2-methylisoindolin-5-yl)-4-(3-(1-phenylethyl)ureido)benzenesulfonamide |

| | Chemical Structure | Chemical Name |
|---|---|---|
| H1338 | 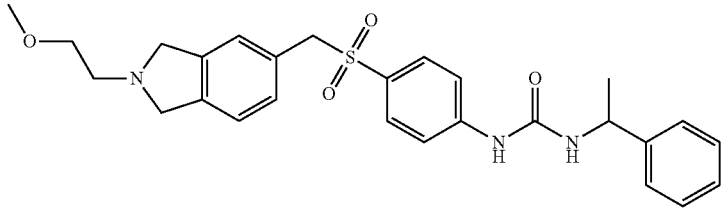 [SMILES: COCCN1Cc2ccc(CS(=O)(=O)c3ccc(NC(=O)NC(C)c4ccccc4)cc3)cc2C1] | 1-(4-(((2-(2-methoxyethyl)isoindolin-5-yl)methyl)sulfonyl)phenyl)-3-(1-phenylethyl)urea |
| H1339 | 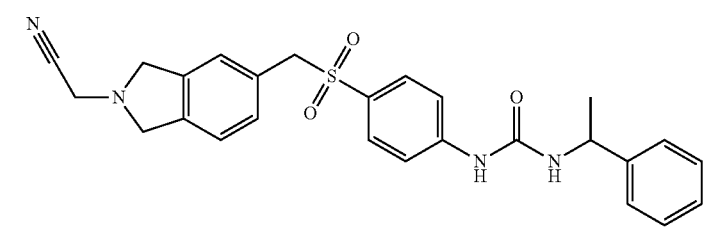 [SMILES: CC(NC(=O)Nc1ccc(S(=O)(=O)Cc2ccc3c(c2)CN(CC#N)C3)cc1)c1ccccc1] | 1-(4-(((2-(cyanomethyl)isoindolin-5-yl)methyl)sulfonyl)phenyl)-3-(1-phenylethyl)urea |
| H1340 | 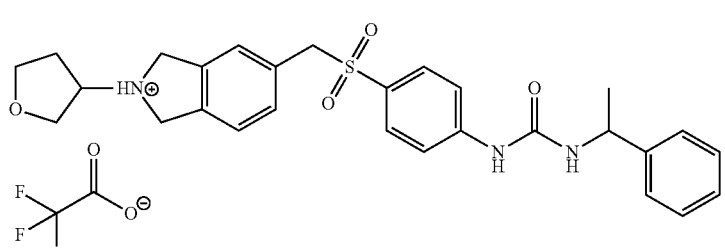 | 1-(1-phenylethyl)-3-(4-(((2-(tetrahydrofuran-3-yl)isoindolin-5-yl)methyl)sulfonyl)phenyl)urea |
| H1341 | 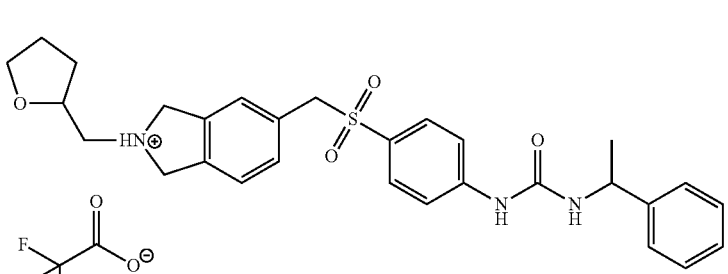 | 1-(1-phenylethyl)-3-(4-(((2-((tetrahydrofuran-2-yl)methyl)isoindolin-5-yl)methyl)sulfonyl)phenyl)urea |
| H1342 | 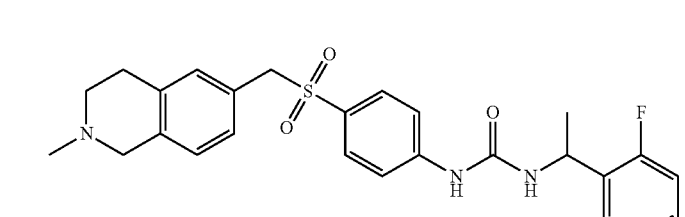 | 1-(1-(2-fluorophenyl)ethyl)-3-(4-(((2-methyl-1,2,3,4-tetrahydroisoquinolin-6-yl)methyl)sulfonyl)phenyl)urea |
| H1343 | 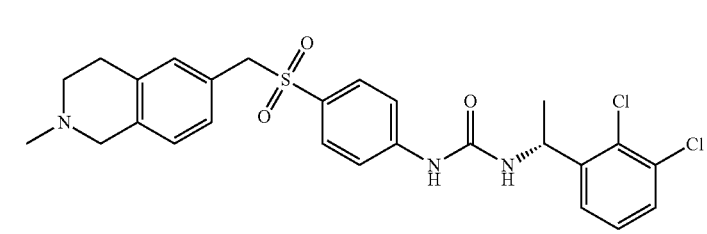 [SMILES: C[C@@H](NC(=O)Nc1ccc(S(=O)(=O)Cc2ccc3c(c2)CCN(C)C3)cc1)c1cccc(Cl)c1Cl] | (R)-1-(1-(2,3-dichlorophenyl)ethyl)-3-(4-(((2-methyl-1,2,3,4-tetrahydroisoquinolin-6-yl)methyl)sulfonyl)phenyl)urea |

| | Chemical Structure | Chemical Name |
|---|---|---|
| H1344 | 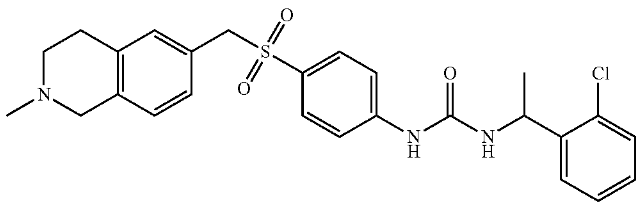 [SMILES: CC(NC(=O)Nc1ccc(S(=O)(=O)Cc2ccc3c(c2)CCN(C)C3)cc1)c1ccccc1Cl] | 1-(1-(2-chlorophenyl)ethyl)-3-(4-(((2-methyl-1,2,3,4-tetrahydroisoquinolin-6-yl)methyl)sulfonyl)phenyl)urea |
| H1345 | 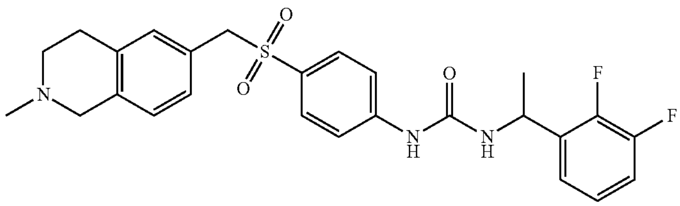 [SMILES: CC(NC(=O)Nc1ccc(S(=O)(=O)Cc2ccc3c(c2)CCN(C)C3)cc1)c1cccc(F)c1F] | 1-(1-(2,3-difluorophenyl)ethyl)-3-(4-(((2-methyl-1,2,3,4-tetrahydroisoquinolin-6-yl)methyl)sulfonyl)phenyl)urea |
| H1346 | 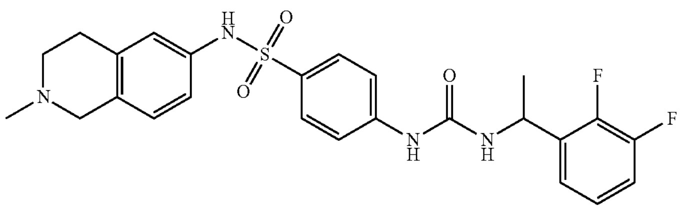 [SMILES: CC(NC(=O)Nc1ccc(S(=O)(=O)Nc2ccc3c(c2)CCN(C)C3)cc1)c1cccc(F)c1F] | 4-(3-(1-(2,3-difluorophenyl)ethyl)ureido)-N-(2-methyl-1,2,3,4-tetrahydroisoquinolin-6-yl)benzenesulfonamide |
| H1347 | 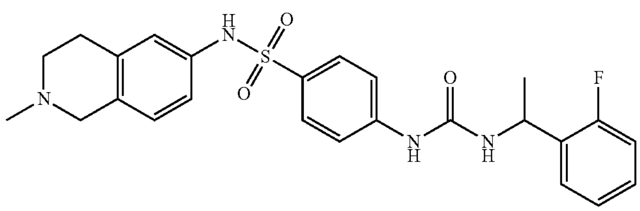 [SMILES: CC(NC(=O)Nc1ccc(S(=O)(=O)Nc2ccc3c(c2)CCN(C)C3)cc1)c1ccccc1F] | 4-(3-(1-(2-fluorophenyl)ethyl)ureido)-N-(2-methyl-1,2,3,4-tetrahydroisoquinolin-6-yl)benzenesulfonamide |
| H1348 | 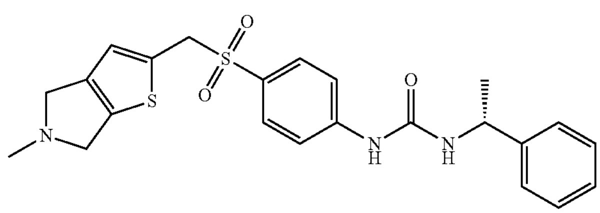 | (R)-1-(4-(((5-methyl-5,6-dihydro-4H-thieno[2,3-c]pyrrol-2-yl)methyl)sulfonyl)phenyl)-3-(1-phenylethyl)urea |
| H1349 | 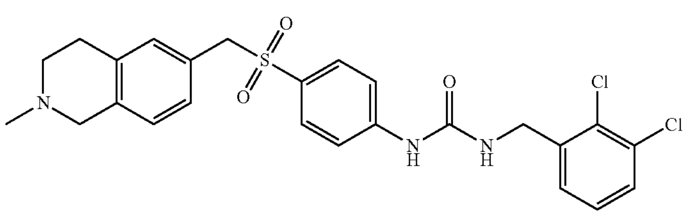 [SMILES: CN1CCc2cc(CS(=O)(=O)c3ccc(NC(=O)NCc4cccc(Cl)c4Cl)cc3)ccc2C1] | 1-(2,3-dichlorobenzyl)-3-(4-(((2-methyl-1,2,3,4-tetrahydroisoquinolin-6-yl)methyl)sulfonyl)phenyl)urea |
| H1350 | 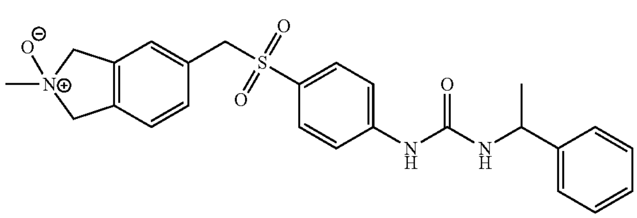 [SMILES: CC(NC(=O)Nc1ccc(S(=O)(=O)Cc2ccc3c(c2)C[N+](C)([O-])C3)cc1)c1ccccc1] | 2-methyl-5-(((4-(3-(1-phenylethyl)ureido)phenyl)sulfonyl)methyl)isoindoline 2-oxide |

-continued

| | Chemical Structure | Chemical Name |
|---|---|---|
| H1351 | 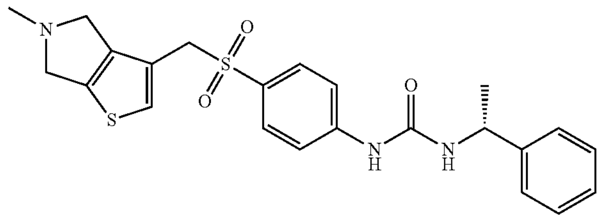 [SMILES: C[C@@H](NC(=O)Nc1ccc(S(=O)(=O)Cc2csc3c2CN(C)C3)cc1)c1ccccc1] | (R)-1-(4-(((5-methyl-5,6-dihydro-4H-thieno[2,3-c]pyrrol-3-yl)methyl)sulfonyl)phenyl)-3-(1-phenylethyl)urea |
| H1352 | 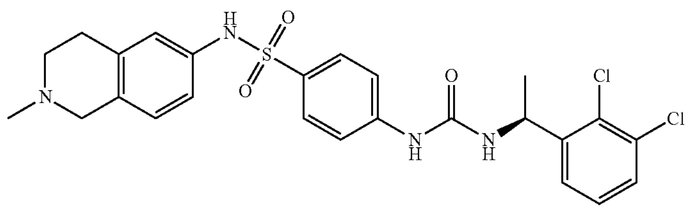 [SMILES: C[C@H](NC(=O)Nc1ccc(S(=O)(=O)Nc2ccc3c(c2)CCN(C)C3)cc1)c1cccc(Cl)c1Cl] | (S)-4-(3-(1-(2,3-dichlorophenyl)ethyl)ureido)-N-(2-methyl-1,2,3,4-tetrahydroisoquinolin-6-yl)benzenesulfonamide |
| H1353 | 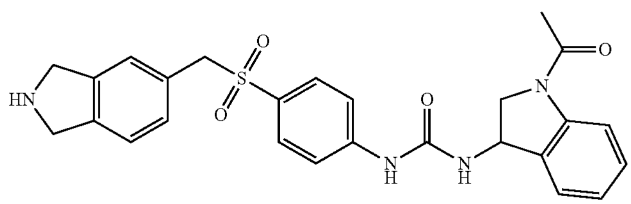 [SMILES: CC(=O)N1CC(NC(=O)Nc2ccc(S(=O)(=O)Cc3ccc4c(c3)CNC4)cc2)c2ccccc21] | 1-(1-acetylindolin-3-yl)-3-(4-((isoindolin-5-ylmethyl)sulfonyl)phenyl)urea |
| H1354 | 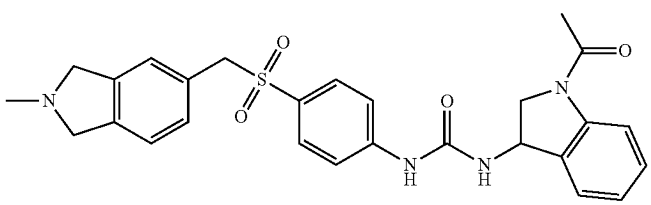 [SMILES: CC(=O)N1CC(NC(=O)Nc2ccc(S(=O)(=O)Cc3ccc4c(c3)CN(C)C4)cc2)c2ccccc21] | 1-(1-acetylindolin-3-yl)-3-(4-(((2-methylisoindolin-5-yl)methyl)sulfonyl)phenyl)urea |
| H1355 | 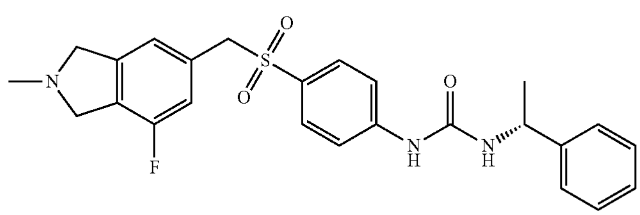 [SMILES: C[C@@H](NC(=O)Nc1ccc(S(=O)(=O)Cc2cc(F)c3c(c2)CN(C)C3)cc1)c1ccccc1] | (R)-1-(4-(((7-fluoro-2-methylisoindolin-5-yl)methyl)sulfonyl)phenyl)-3-(1-phenylethyl)urea |
| H1356 | 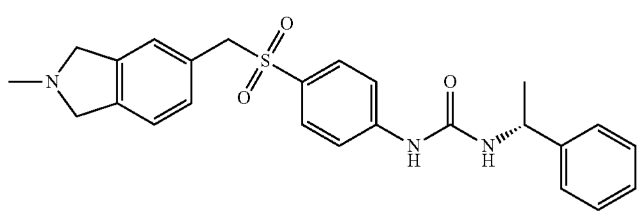 [SMILES: C[C@@H](NC(=O)Nc1ccc(S(=O)(=O)Cc2ccc3c(c2)CN(C)C3)cc1)c1ccccc1] | (R)-1-(4-(((2-methylisoindolin-5-yl)methyl)sulfonyl)phenyl)-3-(1-phenylethyl)urea |
| H1357 | 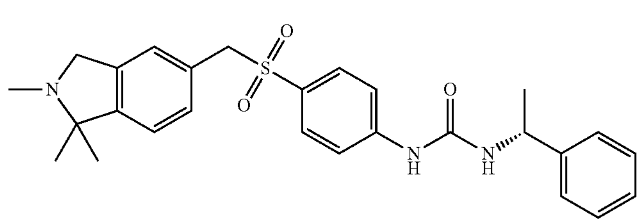 [SMILES: C[C@@H](NC(=O)Nc1ccc(S(=O)(=O)Cc2ccc3c(c2)CN(C)C3(C)C)cc1)c1ccccc1] | (R)-1-(1-phenylethyl)-3-(4-(((1,1,2-trimethylisoindolin-5-yl)methyl)sulfonyl)phenyl)urea |

| | Chemical Structure | Chemical Name |
|---|---|---|
| H1358 | 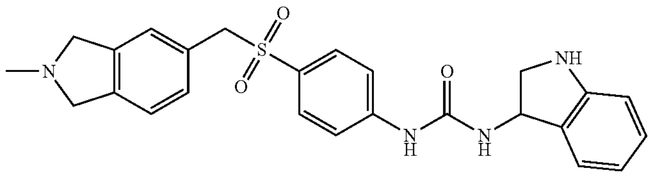 [SMILES: CN1Cc2ccc(CS(=O)(=O)c3ccc(NC(=O)NC4CNc5ccccc54)cc3)cc2C1] | 1-(indolin-3-yl)-3-(4-(((2-methylisoindolin-5-yl)methyl)sulfonyl)phenyl)urea |
| H1359 | 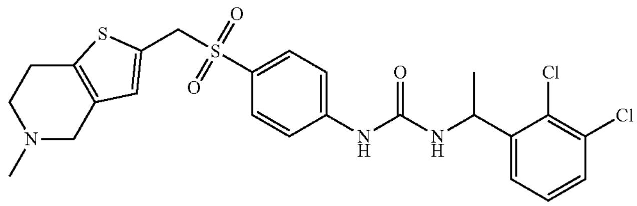 [SMILES: CC(NC(=O)Nc1ccc(S(=O)(=O)Cc2cc3c(s2)CCN(C)C3)cc1)c1cccc(Cl)c1Cl] | 1-(1-(2,3-dichlorophenyl)ethyl)-3-(4-(((5-methyl-4,5,6,7-tetrahydrothieno[3,2-c]pyridin-2-yl)methyl)sulfonyl)phenyl)urea |
| H1360 | 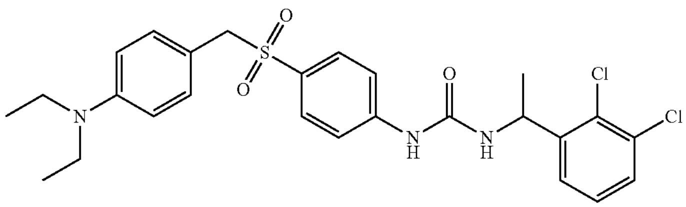 [SMILES: CCN(CC)c1ccc(CS(=O)(=O)c2ccc(NC(=O)NC(C)c3cccc(Cl)c3Cl)cc2)cc1] | 1-(1-(2,3-dichlorophenyl)ethyl)-3-(4-((4-(diethylamino)benzyl)sulfonyl)phenyl)urea |
| H1361 | 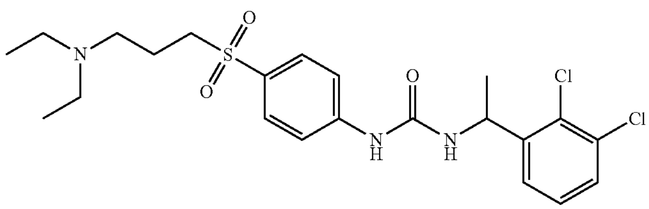 [SMILES: CCN(CC)CCCS(=O)(=O)c1ccc(NC(=O)NC(C)c2cccc(Cl)c2Cl)cc1] | 1-(1-(2,3-dichlorophenyl)ethyl)-3-(4-((3-(diethylamino)propyl)sulfonyl)phenyl)urea |
| H1362 | 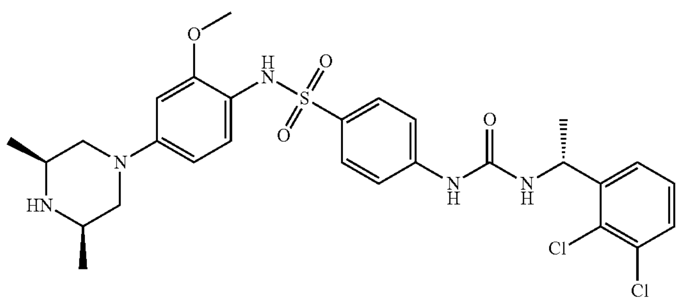 [SMILES: COc1cc(N2C[C@@H](C)N[C@@H](C)C2)ccc1NS(=O)(=O)c1ccc(NC(=O)N[C@H](C)c2cccc(Cl)c2Cl)cc1] | 4-(3-((R)-1-(2,3-dichlorophenyl)ethyl)ureido)-N-(4-((cis)-3,5-dimethylpiperazin-1-yl)-2-methoxyphenyl)benzenesulfonamide |
| H1363 | 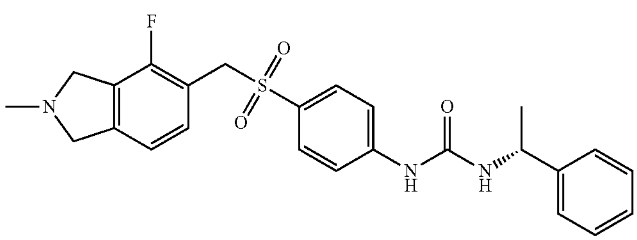 [SMILES: C[C@@H](NC(=O)Nc1ccc(S(=O)(=O)Cc2ccc3c(c2F)CN(C)C3)cc1)c1ccccc1] | (R)-1-(4-(((4-fluoro-2-methylisoindolin-5-yl)methyl)sulfonyl)phenyl)-3-(1-phenylethyl)urea |
| H1364 | 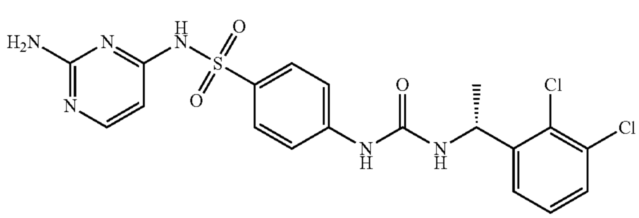 [SMILES: C[C@@H](NC(=O)Nc1ccc(S(=O)(=O)Nc2ccnc(N)n2)cc1)c1cccc(Cl)c1Cl] | (R)-N-(2-aminopyrimidin-4-yl)-4-(3-(1-(2,3-dichlorophenyl)ethyl)ureido)benzenesulfonamide |

-continued

| | Chemical Structure | Chemical Name |
|---|---|---|
| H1366 | 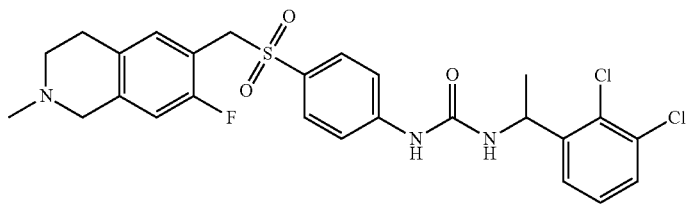 [SMILES: CC(NC(=O)Nc1ccc(S(=O)(=O)Cc2cc3c(cc2F)CN(C)CC3)cc1)c1cccc(Cl)c1Cl] | 1-(1-(2,3-dichlorophenyl)ethyl)-3-(4-(((7-fluoro-2-methyl-1,2,3,4-tetrahydroisoquinolin-6-yl)methyl)sulfonyl)phenyl)urea |
| H1367 | 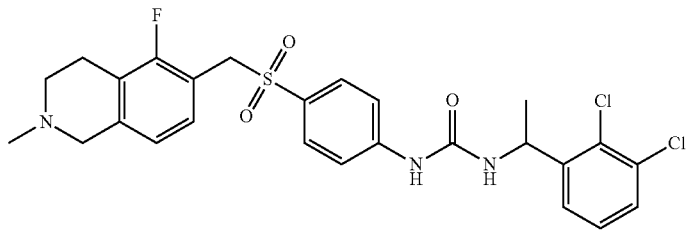 [SMILES: CC(NC(=O)Nc1ccc(S(=O)(=O)Cc2ccc3c(c2F)CCN(C)C3)cc1)c1cccc(Cl)c1Cl] | 1-(1-(2,3-dichlorophenyl)ethyl)-3-(4-(((5-fluoro-2-methyl-1,2,3,4-tetrahydroisoquinolin-6-yl)methyl)sulfonyl)phenyl)urea |
| H1368 | 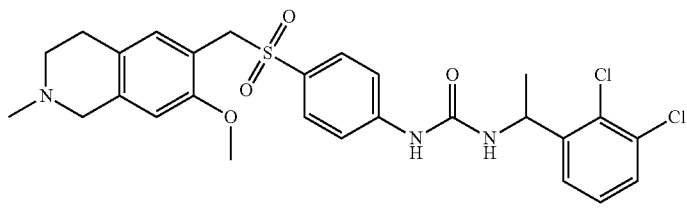 [SMILES: COc1cc2c(cc1CS(=O)(=O)c1ccc(NC(=O)NC(C)c3cccc(Cl)c3Cl)cc1)CCN(C)C2] | 1-(1-(2,3-dichlorophenyl)ethyl)-3-(4-(((7-methoxy-2-methyl-1,2,3,4-tetrahydroisoquinolin-6-yl)methyl)sulfonyl)phenyl)urea |
| H1369 | 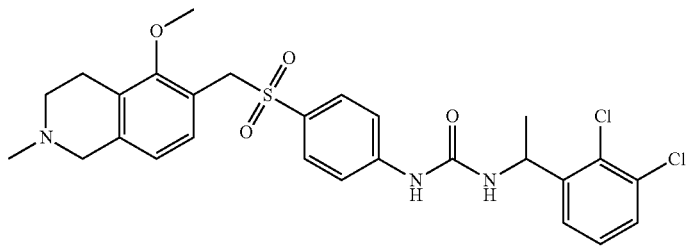 [SMILES: COc1c(CS(=O)(=O)c2ccc(NC(=O)NC(C)c3cccc(Cl)c3Cl)cc2)ccc2c1CCN(C)C2] | 1-(1-(2,3-dichlorophenyl)ethyl)-3-(4-(((5-methoxy-2-methyl-1,2,3,4-tetrahydroisoquinolin-6-yl)methyl)sulfonyl)phenyl)urea |
| H1371 | 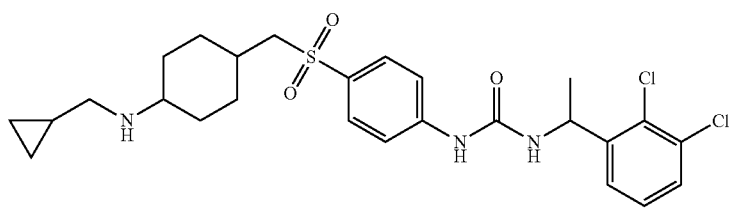 [SMILES: CC(NC(=O)Nc1ccc(S(=O)(=O)CC2CCC(NCC3CC3)CC2)cc1)c1cccc(Cl)c1Cl] | 1-(4-(((4-((cyclopropylmethyl)amino)cyclohexyl)methyl)sulfonyl)phenyl)-3-(1-(2,3-dichlorophenyl)ethyl)urea |
| H1372 | 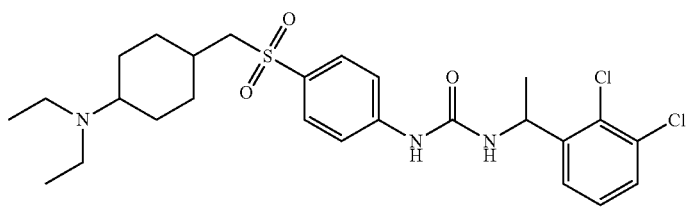 [SMILES: CCN(CC)C1CCC(CS(=O)(=O)c2ccc(NC(=O)NC(C)c3cccc(Cl)c3Cl)cc2)CC1] | 1-(1-(2,3-dichlorophenyl)ethyl)-3-(4-(((4-(diethylamino)cyclohexyl)methyl)sulfonyl)phenyl)urea |
| H1373 | 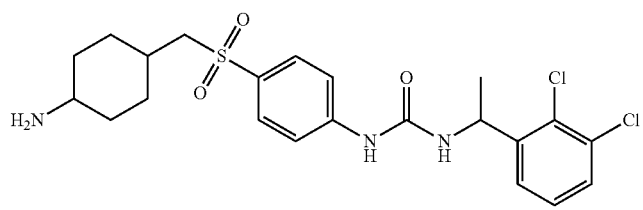 [SMILES: CC(NC(=O)Nc1ccc(S(=O)(=O)CC2CCC(N)CC2)cc1)c1cccc(Cl)c1Cl] | 1-(4-(((4-aminocyclohexyl)methyl)sulfonyl)phenyl)-3-(1-(2,3-dichlorophenyl)ethyl)urea |

| | Chemical Structure | Chemical Name |
|---|---|---|
| H1374 | 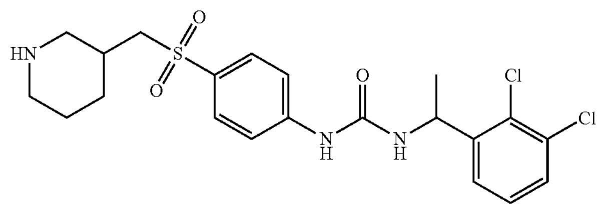 [SMILES: CC(NC(=O)Nc1ccc(S(=O)(=O)CC2CCCNC2)cc1)c1cccc(Cl)c1Cl] | 1-(1-(2,3-dichlorophenyl)ethyl)-3-(4-((piperidin-3-ylmethyl)sulfonyl)phenyl)urea |
| H1375 | 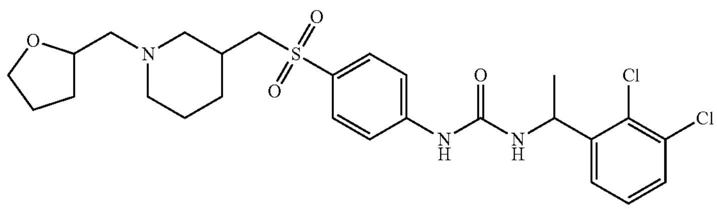 [SMILES: CC(NC(=O)Nc1ccc(S(=O)(=O)CC2CCCN(CC3CCCO3)C2)cc1)c1cccc(Cl)c1Cl] | 1-(1-(2,3-dichlorophenyl)ethyl)-3-(4-(((1-((tetrahydrofuran-2-yl)methyl)piperidin-3-yl)methyl)sulfonyl)phenyl)urea |
| H1376 | 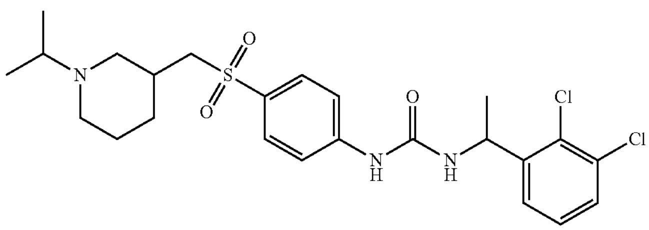 [SMILES: CC(NC(=O)Nc1ccc(S(=O)(=O)CC2CCCN(C(C)C)C2)cc1)c1cccc(Cl)c1Cl] | 1-(1-(2,3-dichlorophenyl)ethyl)-3-(4-(((1-isopropylpiperidin-3-yl)methyl)sulfonyl)phenyl)urea |
| H1377 | 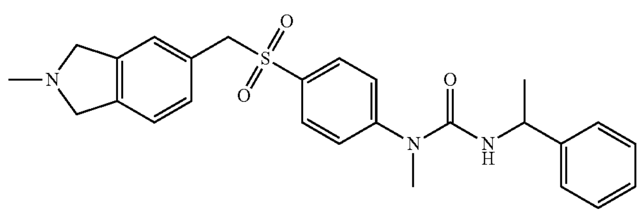 [SMILES: CC(NC(=O)N(C)c1ccc(S(=O)(=O)Cc2ccc3c(c2)CN(C)C3)cc1)c1ccccc1] | 1-methyl-1-(4-(((2-methylisoindolin-5-yl)methyl)sulfonyl)phenyl)-3-(1-phenylethyl)urea |
| H1378 | 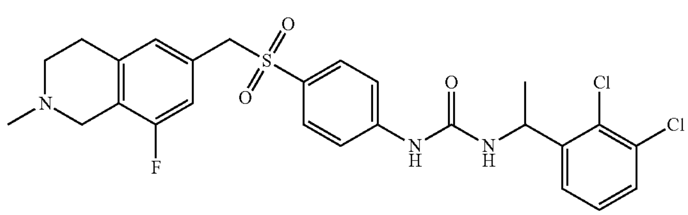 [SMILES: CC(NC(=O)Nc1ccc(S(=O)(=O)Cc2cc(F)c3c(c2)CCN(C)C3)cc1)c1cccc(Cl)c1Cl] | 1-(1-(2,3-dichlorophenyl)ethyl)-3-(4-(((8-fluoro-2-methyl-1,2,3,4-tetrahydroisoquinolin-6-yl)methyl)sulfonyl)phenyl)urea |
| H1379 | 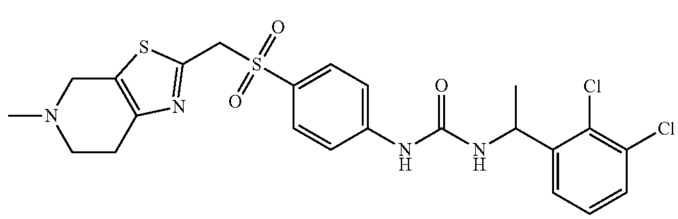 [SMILES: CC(NC(=O)Nc1ccc(S(=O)(=O)Cc2nc3c(s2)CN(C)CC3)cc1)c1cccc(Cl)c1Cl] | 1-(1-(2,3-dichlorophenyl)ethyl)-3-(4-(((5-methyl-4,5,6,7-tetrahydrothiazolo[5,4-c]pyridin-2-yl)methyl)sulfonyl)phenyl)urea |
| H1380 | 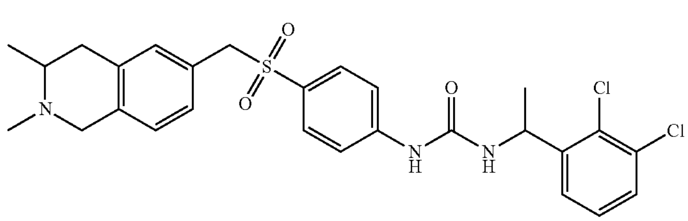 [SMILES: CC(NC(=O)Nc1ccc(S(=O)(=O)Cc2ccc3c(c2)CC(C)N(C)C3)cc1)c1cccc(Cl)c1Cl] | 1-(1-(2,3-dichlorophenyl)ethyl)-3-(4-(((2,3-dimethyl-1,2,3,4-tetrahydroisoquinolin-6-yl)methyl)sulfonyl)phenyl)urea |

-continued

| | Chemical Structure | Chemical Name |
|---|---|---|
| H1381 | 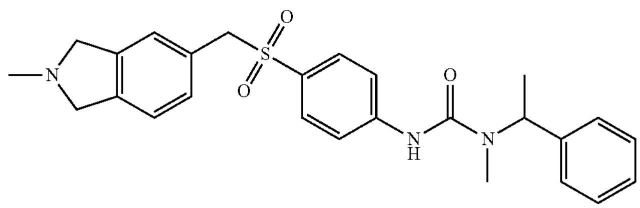 [SMILES: CC(c1ccccc1)N(C)C(=O)Nc1ccc(S(=O)(=O)Cc2ccc3c(c2)CN(C)C3)cc1] | 1-methyl-3-(4-(((2-methylisoindolin-5-yl)methyl)sulfonyl)phenyl)-1-(1-phenylethyl)urea |
| H1382 | 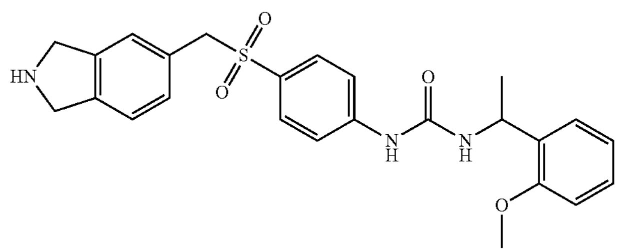 [SMILES: COc1ccccc1C(C)NC(=O)Nc1ccc(S(=O)(=O)Cc2ccc3c(c2)CNC3)cc1] | 1-(4-((isoindolin-5-ylmethyl)sulfonyl)phenyl)-3-(1-(2-methoxyphenyl)ethyl)urea |
| H1383 | 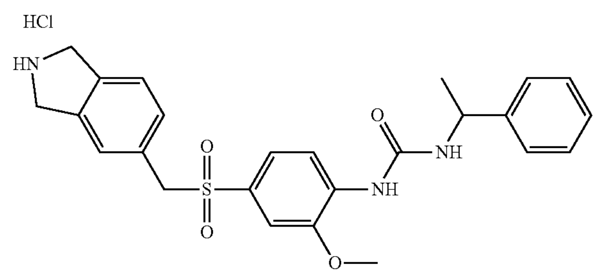 [SMILES: Cl ; COc1cc(S(=O)(=O)Cc2ccc3c(c2)CNC3)ccc1NC(=O)NC(C)c1ccccc1] | 1-(4-((isoindolin-5-ylmethyl)sulfonyl)-2-methoxyphenyl)-3-(1-phenylethyl)urea |
| H1384 | 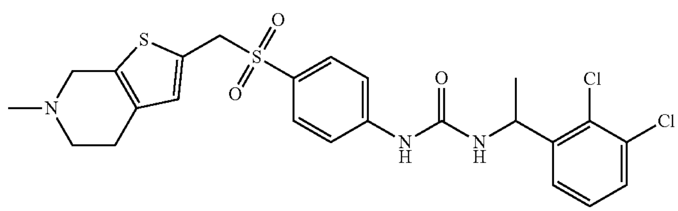 [SMILES: CC(NC(=O)Nc1ccc(S(=O)(=O)Cc2cc3c(s2)CN(C)CC3)cc1)c1cccc(Cl)c1Cl] | 1-(1-(2,3-dichlorophenyl)ethyl)-3-(4-(((6-methyl-4,5,6,7-tetrahydrothieno[2,3-c]pyridin-2-yl)methyl)sulfonyl)phenyl)urea |
| H1385 | 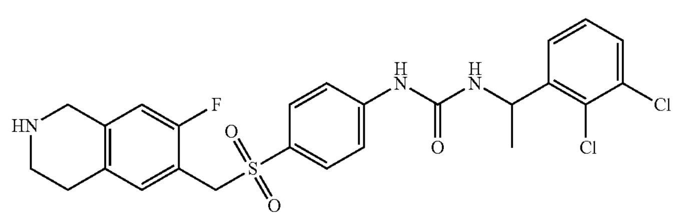 [SMILES: CC(NC(=O)Nc1ccc(S(=O)(=O)Cc2cc3c(cc2F)CNCC3)cc1)c1cccc(Cl)c1Cl] | 1-(1-(2,3-dichlorophenyl)ethyl)-3-(4-(((7-fluoro-1,2,3,4-tetrahydroisoquinolin-6-yl)methyl)sulfonyl)phenyl)urea |
| H1386 | 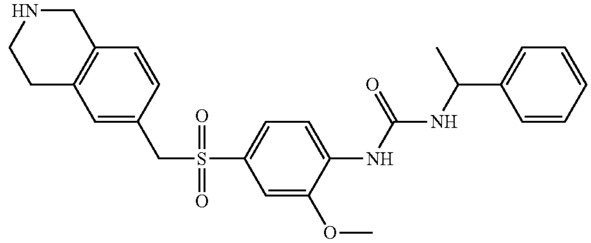 [SMILES: COc1cc(S(=O)(=O)Cc2ccc3c(c2)CCNC3)ccc1NC(=O)NC(C)c1ccccc1] | 1-(2-methoxy-4-(((1,2,3,4-tetrahydroisoquinolin-6-yl)methyl)sulfonyl)phenyl)-3-(1-phenylethyl)urea |

-continued

| | Chemical Structure | Chemical Name |
|---|---|---|
| H1387 | 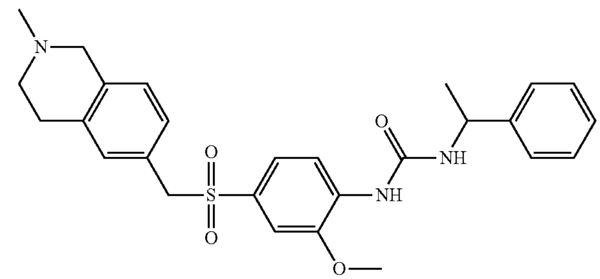 [SMILES: COc1cc(S(=O)(=O)Cc2ccc3c(c2)CCN(C)C3)ccc1NC(=O)NC(C)c1ccccc1] | 1-(2-methoxy-4-(((2-methyl-1,2,3,4-tetrahydroisoquinolin-6-yl)methyl)sulfonyl)phenyl)-3-(1-phenylethyl)urea |
| H1388 | 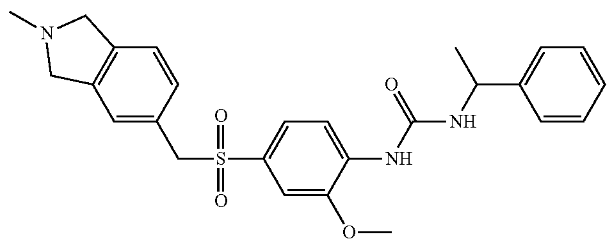 [SMILES: COc1cc(S(=O)(=O)Cc2ccc3c(c2)CN(C)C3)ccc1NC(=O)NC(C)c1ccccc1] | 1-(2-methoxy-4-(((2-methylisoindolin-5-yl)methyl)sulfonyl)phenyl)-3-(1-phenylethyl)urea |
| H1389 | 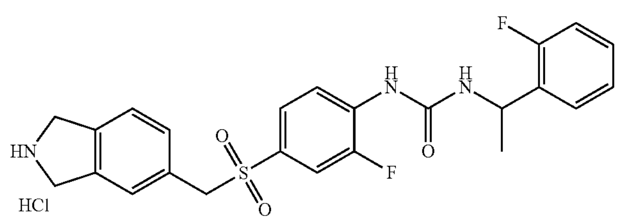 [SMILES: Cl ; CC(NC(=O)Nc1ccc(S(=O)(=O)Cc2ccc3c(c2)CNC3)cc1F)c1ccccc1F] | 1-(2-fluoro-4-((isoindolin-5-ylmethyl)sulfonyl)phenyl)-3-(1-(2-fluorophenyl)ethyl)urea |
| H1390 | 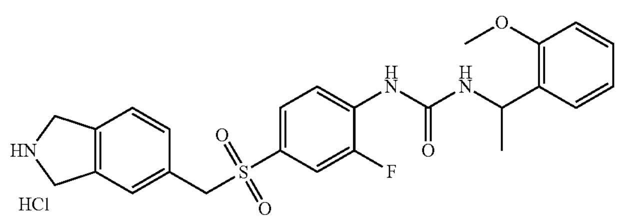 [SMILES: Cl ; COc1ccccc1C(C)NC(=O)Nc1ccc(S(=O)(=O)Cc2ccc3c(c2)CNC3)cc1F] | 1-(2-fluoro-4-((isoindolin-5-ylmethyl)sulfonyl)phenyl)-3-(1-(2-methoxyphenyl)ethyl)urea |
| H1391 | 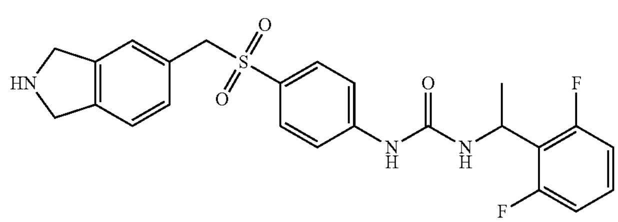 [SMILES: CC(NC(=O)Nc1ccc(S(=O)(=O)Cc2ccc3c(c2)CNC3)cc1)c1c(F)cccc1F] | 1-(1-(2,6-difluorophenyl)ethyl)-3-(4-((isoindolin-5-ylmethyl)sulfonyl)phenyl)urea |
| H1392 | 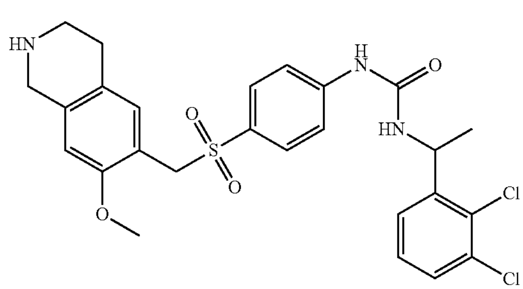 [SMILES: COc1cc2c(cc1CS(=O)(=O)c1ccc(NC(=O)NC(C)c3cccc(Cl)c3Cl)cc1)CCNC2] | 1-(1-(2,3-dichlorophenyl)ethyl)-3-(4-(((7-methoxy-1,2,3,4-tetrahydroisoquinolin-6-yl)methyl)sulfonyl)phenyl)urea |

-continued

| | Chemical Structure | Chemical Name |
|---|---|---|
| H1393 | 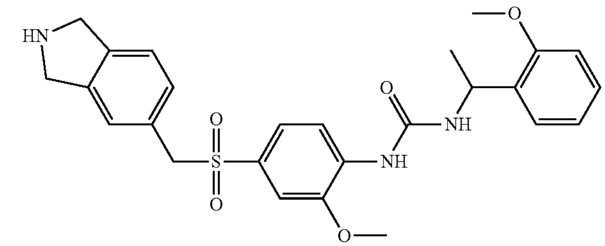 [SMILES: COc1cc(S(=O)(=O)Cc2ccc3c(c2)CNC3)ccc1NC(=O)NC(C)c1ccccc1OC] | 1-(4-((isoindolin-5-ylmethyl)sulfonyl)-2-methoxyphenyl)-3-(1-(2-methoxyphenyl)ethyl)urea |
| H1394 | 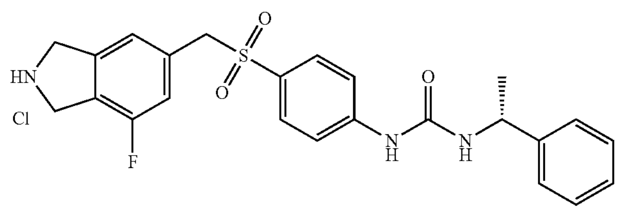 [SMILES: Cl ; C[C@@H](NC(=O)Nc1ccc(S(=O)(=O)Cc2cc(F)c3c(c2)CNC3)cc1)c1ccccc1] | (R)-1-(4-(((7-fluoroisoindolin-5-yl)methyl)sulfonyl)phenyl)-3-(1-phenylethyl)urea |
| H1395 | 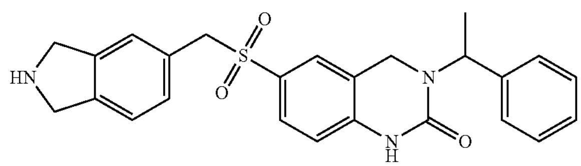 [SMILES: CC(c1ccccc1)N1Cc2cc(S(=O)(=O)Cc3ccc4c(c3)CNC4)ccc2NC1=O] | 6-((isoindolin-5-ylmethyl)sulfonyl)-3-(1-phenylethyl)-3,4-dihydroquinazolin-2(1H)-one |
| H1396 | 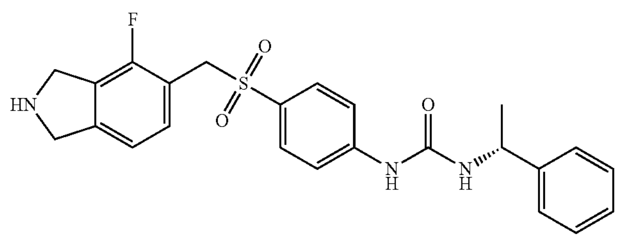 [SMILES: C[C@@H](NC(=O)Nc1ccc(S(=O)(=O)Cc2ccc3c(c2F)CNC3)cc1)c1ccccc1] | (R)-1-(4-(((4-fluoroisoindolin-5-yl)methyl)sulfonyl)phenyl)-3-(1-phenylethyl)urea |
| H1397 | 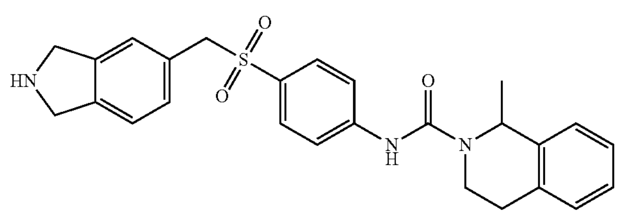 [SMILES: CC1c2ccccc2CCN1C(=O)Nc1ccc(S(=O)(=O)Cc2ccc3c(c2)CNC3)cc1] | N-(4-((isoindolin-5-ylmethyl)sulfonyl)phenyl)-1-methyl-3,4-dihydroisoquinoline-2(1H)-carboxamide |
| H1398 | 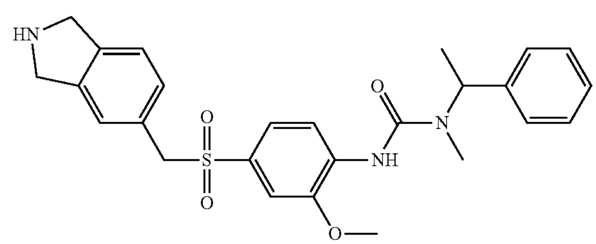 [SMILES: COc1cc(S(=O)(=O)Cc2ccc3c(c2)CNC3)ccc1NC(=O)N(C)C(C)c1ccccc1] | 3-(4-((isoindolin-5-ylmethyl)sulfonyl)-2-methoxyphenyl)-1-methyl-1-(1-phenylethyl)urea |
| H1399 | 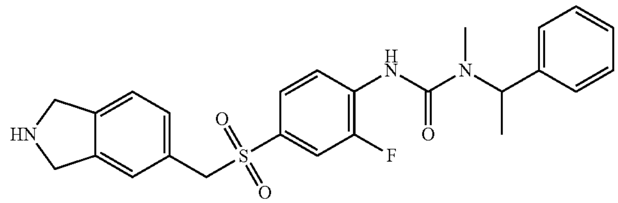 [SMILES: CC(c1ccccc1)N(C)C(=O)Nc1ccc(S(=O)(=O)Cc2ccc3c(c2)CNC3)cc1F] | 3-(2-fluoro-4-((isoindolin-5-ylmethyl)sulfonyl)phenyl)-1-methyl-1-(1-phenylethyl)urea |

| | Chemical Structure | Chemical Name |
|---|---|---|
| H1400 | 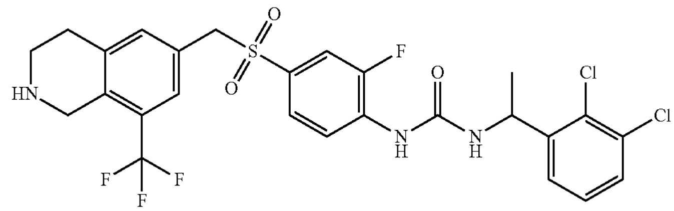 [SMILES: CC(NC(=O)Nc1ccc(S(=O)(=O)Cc2cc3c(c(C(F)(F)F)c2)CNCC3)cc1F)c1cccc(Cl)c1Cl] | 1-(1-(2,3-dichlorophenyl)ethyl)-3-(2-fluoro-4-(((8-(trifluoromethyl)-1,2,3,4-tetrahydroisoquinolin-6-yl)methyl)sulfonyl)phenyl)urea |
| H1401 | 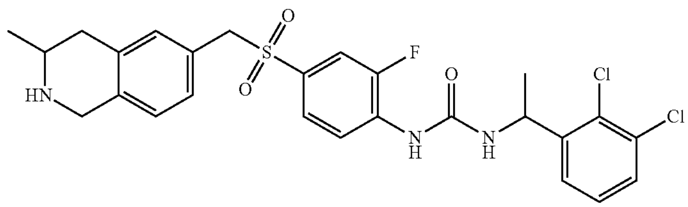 [SMILES: CC1Cc2cc(CS(=O)(=O)c3ccc(NC(=O)NC(C)c4cccc(Cl)c4Cl)c(F)c3)ccc2CN1] | 1-(1-(2,3-dichlorophenyl)ethyl)-3-(2-fluoro-4-(((3-methyl-1,2,3,4-tetrahydroisoquinolin-6-yl)methyl)sulfonyl)phenyl)urea |
| H1402 | 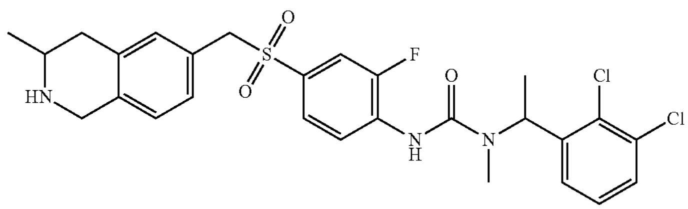 [SMILES: CC1Cc2cc(CS(=O)(=O)c3ccc(NC(=O)N(C)C(C)c4cccc(Cl)c4Cl)c(F)c3)ccc2CN1] | 1-(1-(2,3-dichlorophenyl)ethyl)-3-(2-fluoro-4-(((3-methyl-1,2,3,4-tetrahydroisoquinolin-6-yl)methyl)sulfonyl)phenyl)-1-methylurea |
| H1403 | 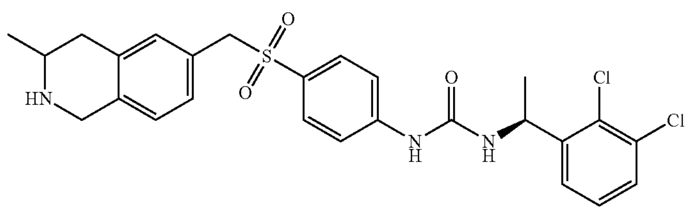 [SMILES: CC1Cc2cc(CS(=O)(=O)c3ccc(NC(=O)N[C@@H](C)c4cccc(Cl)c4Cl)cc3)ccc2CN1] | 1-((S)-1-(2,3-dichlorophenyl)ethyl)-3-(4-(((3-methyl-1,2,3,4-tetrahydroisoquinolin-6-yl)methyl)sulfonyl)phenyl)urea |
| H1404 | 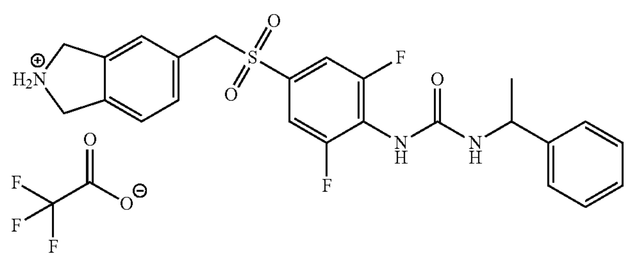 [SMILES: O=C([O-])C(F)(F)F ; CC(NC(=O)Nc1c(F)cc(S(=O)(=O)Cc2ccc3c(c2)C[NH2+]C3)cc1F)c1ccccc1] | 1-(2,6-difluoro-4-((isoindolin-5-ylmethyl)sulfonyl)phenyl)-3-(1-phenylethyl)urea |
| H1405 | 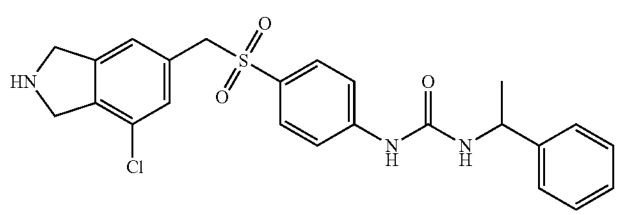 [SMILES: CC(NC(=O)Nc1ccc(S(=O)(=O)Cc2cc(Cl)c3c(c2)CNC3)cc1)c1ccccc1] | 1-(4-(((7-chloroisoindolin-5-yl)methyl)sulfonyl)phenyl)-3-(1-phenylethyl)urea |
| H1406 | 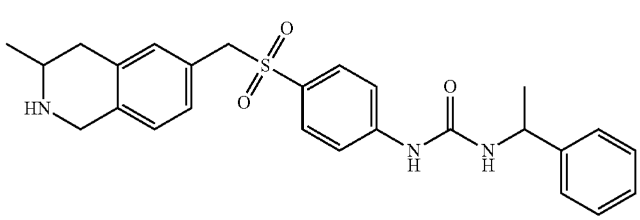 [SMILES: CC1Cc2cc(CS(=O)(=O)c3ccc(NC(=O)NC(C)c4ccccc4)cc3)ccc2CN1] | 1-(4-(((3-methyl-1,2,3,4-tetrahydroisoquinolin-6-yl)methyl)sulfonyl)phenyl)-3-(1-phenylethyl)urea |

| | Chemical Structure | Chemical Name |
|---|---|---|
| H1407 | 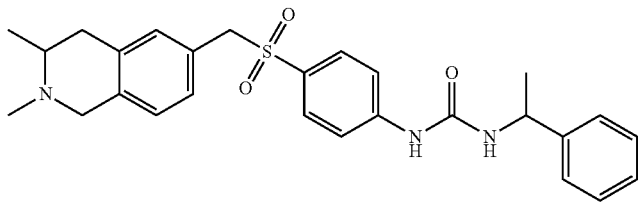 [SMILES: CC(NC(=O)Nc1ccc(S(=O)(=O)Cc2ccc3c(c2)CC(C)N(C)C3)cc1)c1ccccc1] | 1-(4-(((2,3-dimethyl-1,2,3,4-tetrahydroisoquinolin-6-yl)methyl)sulfonyl)phenyl)-3-(1-phenylethyl)urea |
| H1408 | 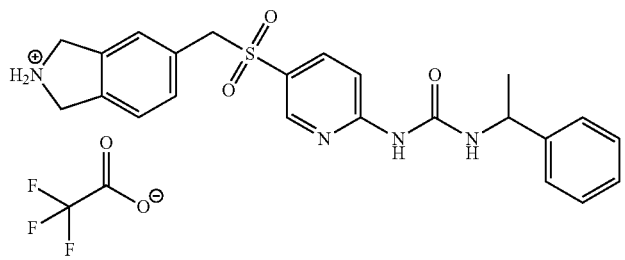 [SMILES: O=C([O-])C(F)(F)F ; CC(NC(=O)Nc1ccc(S(=O)(=O)Cc2ccc3c(c2)C[NH2+]C3)cn1)c1ccccc1] | 1-(5-((isoindolin-5-ylmethyl)sulfonyl)pyridin-2-yl)-3-(1-phenylethyl)urea |
| H1409 | 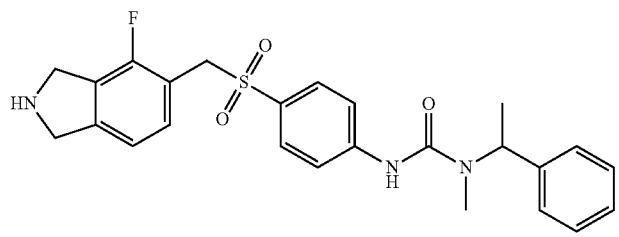 [SMILES: CC(c1ccccc1)N(C)C(=O)Nc1ccc(S(=O)(=O)Cc2ccc3c(c2F)CNC3)cc1] | 3-(4-(((4-fluoroisoindolin-5-yl)methyl)sulfonyl)phenyl)-1-methyl-1-(1-phenylethyl)urea |
| H1410 | 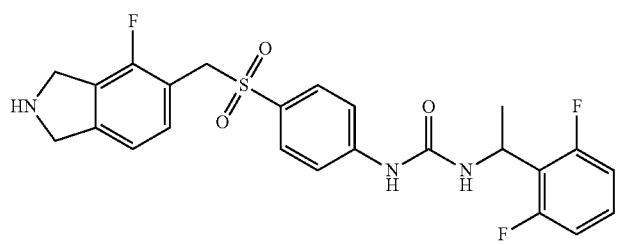 [SMILES: CC(NC(=O)Nc1ccc(S(=O)(=O)Cc2ccc3c(c2F)CNC3)cc1)c1c(F)cccc1F] | 1-(1-(2,6-difluorophenyl)ethyl-3-(4-(((4-fluoroisoindolin-5-yl)methyl)sulfonyl)phenyl)urea |
| H1411 | 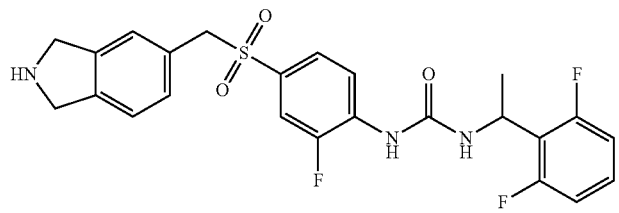 [SMILES: CC(NC(=O)Nc1ccc(S(=O)(=O)Cc2ccc3c(c2)CNC3)cc1F)c1c(F)cccc1F] | 1-(1-(2,6-difluorophenyl)ethyl)-3-(2-fluoro-4-((isoindolin-5-ylmethyl)sulfonyl)phenyl)urea |
| H1412 | 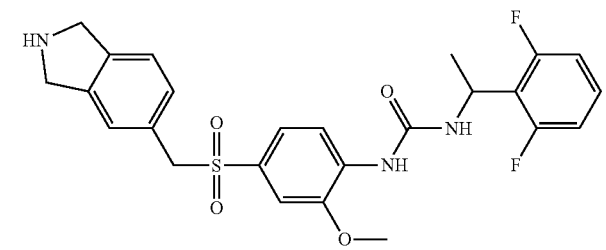 | 1-(1-(2,6-difluorophenyl)ethyl)-3-(4-((isoindolin-5-ylmethyl)sulfonyl)-2-methoxyphenyl)urea |

| | Chemical Structure | Chemical Name |
|---|---|---|
| H1413 | 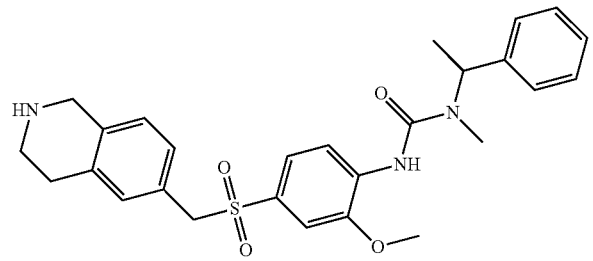 [SMILES: COc1cc(S(=O)(=O)Cc2ccc3c(c2)CCNC3)ccc1NC(=O)N(C)C(C)c1ccccc1] | 3-(2-methoxy-4-(((1,2,3,4-tetrahydroisoquinolin-6-yl)methyl)sulfonyl)phenyl)-1-methyl-1-(1-phenylethyl)urea |
| H1414 | 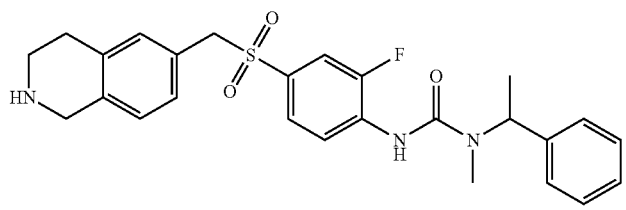 [SMILES: CC(c1ccccc1)N(C)C(=O)Nc1ccc(S(=O)(=O)Cc2ccc3c(c2)CCNC3)cc1F] | 3-(2-fluoro-4-(((1,2,3,4-tetrahydroisoquinolin-6-yl)methyl)sulfonyl)phenyl)-1-methyl-1-(1-phenylethyl)urea |
| H1415 | 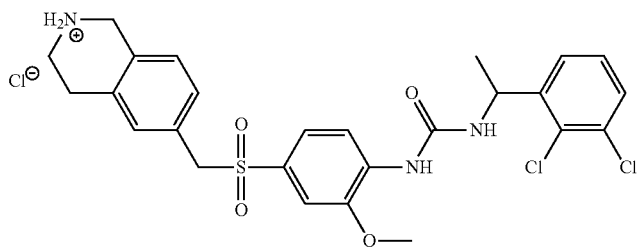 [SMILES: [Cl-] ; COc1cc(S(=O)(=O)Cc2ccc3c(c2)CC[NH2+]C3)ccc1NC(=O)NC(C)c1cccc(Cl)c1Cl] | 1-(1-(2,3-dichlorophenyl)ethyl)-3-(2-methoxy-4-(((1,2,3,4-tetrahydroisoquinolin-6-yl)methyl)sulfonyl)phenyl)urea |
| H1416 | 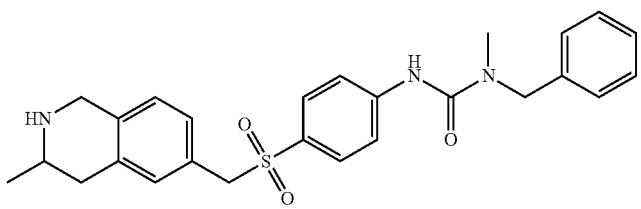 [SMILES: CC1Cc2cc(CS(=O)(=O)c3ccc(NC(=O)N(C)Cc4ccccc4)cc3)ccc2CN1] | 1-benzyl-1-methyl-3-(4-(((3-methyl-1,2,3,4-tetrahydroisoquinolin-6-yl)methyl)sulfonyl)phenyl)urea |
| H1417 | 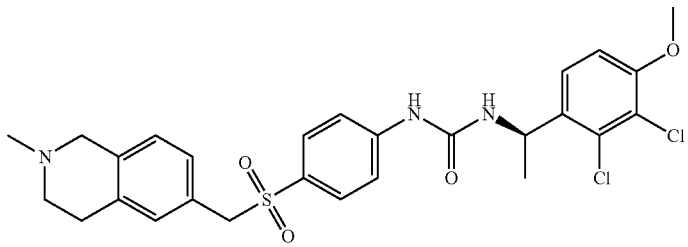 | (R)-1-(1-(2,3-dichloro-4-methoxyphenyl)ethyl)-3-(4-(((2-methyl-1,2,3,4-tetrahydroisoquinolin-6-yl)methyl)sulfonyl)phenyl)urea |
| H1418 | 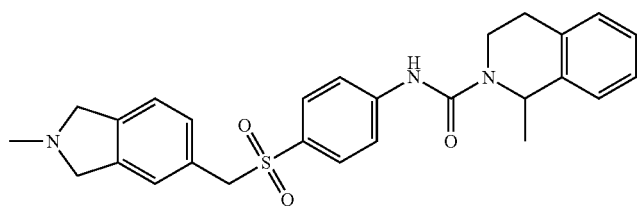 [SMILES: CC1c2ccccc2CCN1C(=O)Nc1ccc(S(=O)(=O)Cc2ccc3c(c2)CN(C)C3)cc1] | 1-methyl-N-(4-(((2-methylisoindolin-5-yl)methyl)sulfonyl)phenyl)-3,4-dihydroisoquinoline-2(1H)-carboxamide |

| | Chemical Structure | Chemical Name |
|---|---|---|
| H1419 | 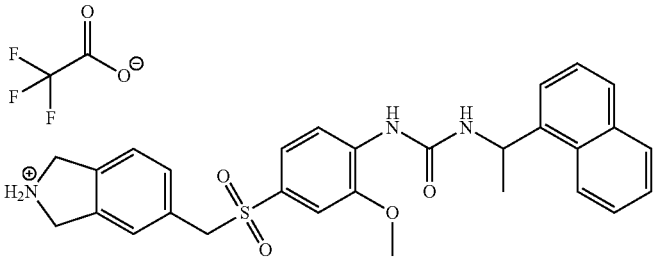 [SMILES: O=C([O-])C(F)(F)F ; COc1cc(S(=O)(=O)Cc2ccc3c(c2)C[NH2+]C3)ccc1NC(=O)NC(C)c1cccc2ccccc12] | 1-(4-((isoindolin-5-ylmethyl)sulfonyl)-2-methoxyphenyl)-3-(1-(naphthalen-1-yl)ethyl)urea |
| H1420 | 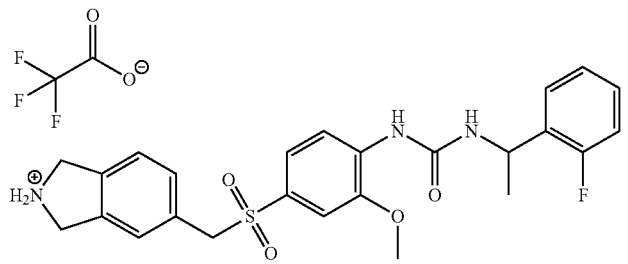 [SMILES: O=C([O-])C(F)(F)F ; COc1cc(S(=O)(=O)Cc2ccc3c(c2)C[NH2+]C3)ccc1NC(=O)NC(C)c1ccccc1F] | 1-(1-(2-fluorophenyl)ethyl)-3-(4-((isoindolin-5-ylmethyl)sulfonyl)-2-methoxyphenyl)urea |
| H1421 | 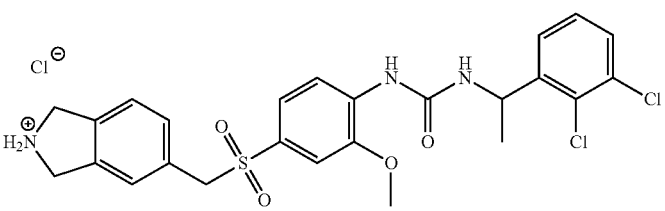 [SMILES: COc1cc(S(=O)(=O)Cc2ccc3c(c2)C[NH2+]C3)ccc1NC(=O)NC(C)c1cccc(Cl)c1Cl ; [Cl-]] | 1-(1-(2,3-dichlorophenyl)ethyl)-3-(4-((isoindolin-5-ylmethyl)sulfonyl)-2-methoxyphenyl)urea |
| H1422 | 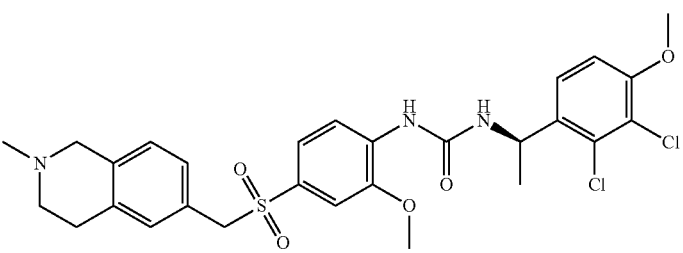 | (R)-1-(1-(2,3-dichloro-4-methoxyphenyl)ethyl)-3-(2-methoxy-4-(((2-methyl-1,2,3,4-tetrahydroisoquinolin-6-yl)methyl)sulfonyl)phenyl)urea |
| H1423 | 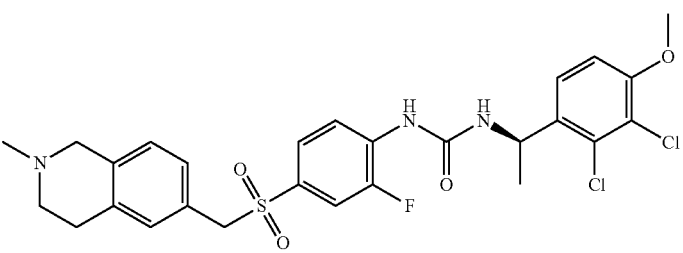 | (R)-1-(1-(2,3-dichloro-4-methoxyphenyl)ethyl)-3-(2-fluoro-4-(((2-methyl-1,2,3,4-tetrahydroisoquinolin-6-yl)methyl)sulfonyl)phenyl)urea |
| H1424 | 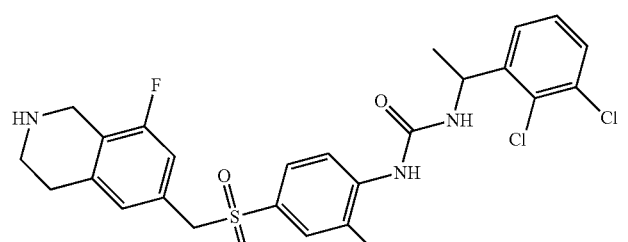 | 1-(1-(2,3-dichlorophenyl)ethyl)-3-(4-(((8-fluoro-1,2,3,4-tetrahydroisoquinolin-6-yl)methyl)sulfonyl)-2-methoxyphenyl)urea |

| | Chemical Structure | Chemical Name |
|---|---|---|
| H1425 | 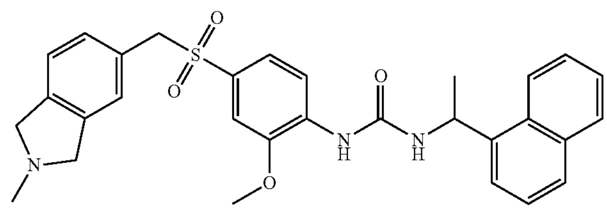 [SMILES: COc1cc(S(=O)(=O)Cc2ccc3c(c2)CN(C)C3)ccc1NC(=O)NC(C)c1cccc2ccccc12] | 1-(2-methoxy-4-(((2-methylisoindolin-5-yl)methyl)sulfonyl)phenyl)-3-(1-(naphthalen-1-yl)ethyl)urea |
| H1426 | 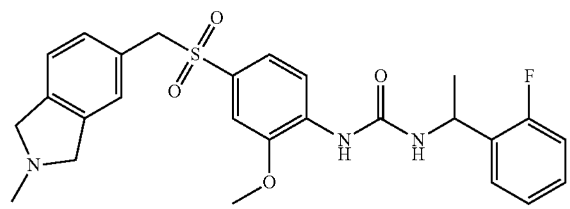 [SMILES: COc1cc(S(=O)(=O)Cc2ccc3c(c2)CN(C)C3)ccc1NC(=O)NC(C)c1ccccc1F] | 1-(1-(2-fluorophenyl)ethyl)-3-(2-methoxy-4-(((2-methylisoindolin-5-yl)methyl)sulfonyl)phenyl)urea |
| H1427 | 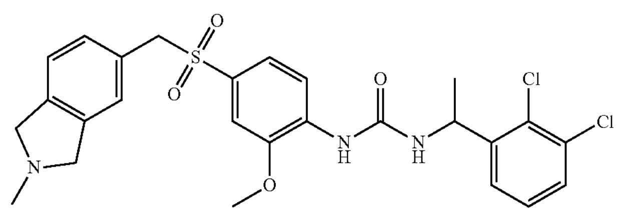 [SMILES: COc1cc(S(=O)(=O)Cc2ccc3c(c2)CN(C)C3)ccc1NC(=O)NC(C)c1cccc(Cl)c1Cl] | 1-(1-(2,3-dichlorophenyl)ethyl)-3-(2-methoxy-4-(((2-methylisoindolin-5-yl)methyl)sulfonyl)phenyl)urea |
| H1428 | 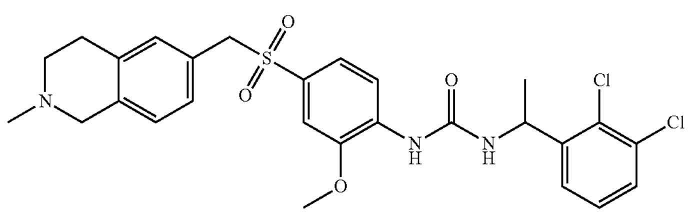 [SMILES: COc1cc(S(=O)(=O)Cc2ccc3c(c2)CCN(C)C3)ccc1NC(=O)NC(C)c1cccc(Cl)c1Cl] | 1-(1-(2,3-dichlorophenyl)ethyl)-3-(2-methoxy-4-(((2-methyl-1,2,3,4-tetrahydroisoquinolin-6-yl)methyl)sulfonyl)phenyl)urea |
| H1429 | 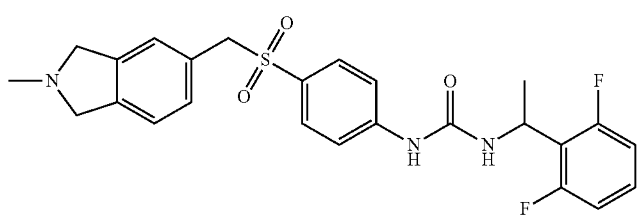 [SMILES: CC(NC(=O)Nc1ccc(S(=O)(=O)Cc2ccc3c(c2)CN(C)C3)cc1)c1c(F)cccc1F] | 1-(1-(2,6-difluorophenyl)ethyl)-3-(4-(((2-methylisoindolin-5-yl)methyl)sulfonyl)phenyl)urea |
| H1430 | 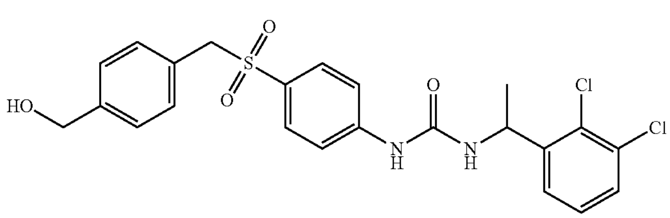 [SMILES: CC(NC(=O)Nc1ccc(S(=O)(=O)Cc2ccc(CO)cc2)cc1)c1cccc(Cl)c1Cl] | 1-(1-(2,3-dichlorophenyl)ethyl)-3-(4-((4-(hydroxymethyl)benzyl)sulfonyl)phenyl)urea |
| H1431 | 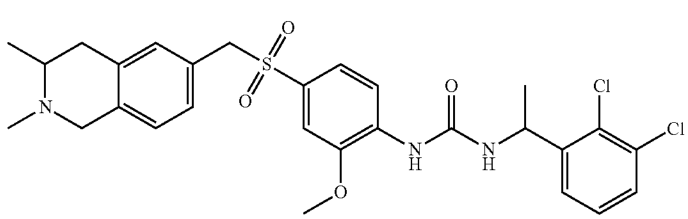 [SMILES: COc1cc(S(=O)(=O)Cc2ccc3c(c2)CC(C)N(C)C3)ccc1NC(=O)NC(C)c1cccc(Cl)c1Cl] | 1-(1-(2,3-dichlorophenyl)ethyl)-3-(4-(((2,3-dimethyl-1,2,3,4-tetrahydroisoquinolin-6-yl)methyl)sulfonyl)-2-methoxyphenyl)urea |

| | Chemical Structure | Chemical Name |
|---|---|---|
| H1432 | 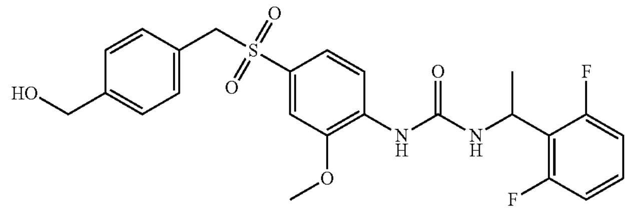 [SMILES: COc1cc(S(=O)(=O)Cc2ccc(CO)cc2)ccc1NC(=O)NC(C)c1c(F)cccc1F] | 1-(1-(2,6-difluorophenyl)ethyl)-3-(4-((4-(hydroxymethyl)benzyl)sulfonyl)-2-methoxyphenyl)urea |
| H1433 | 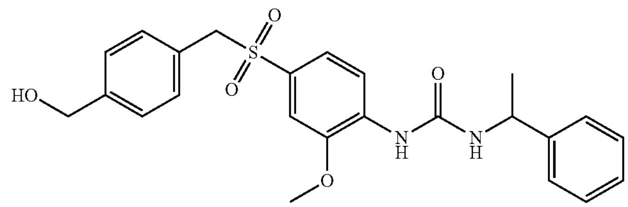 [SMILES: COc1cc(S(=O)(=O)Cc2ccc(CO)cc2)ccc1NC(=O)NC(C)c1ccccc1] | 1-(4-((4-(hydroxymethyl)benzyl)sulfonyl)-2-methoxyphenyl)-3-(1-phenylethyl)urea |
| H1434 | 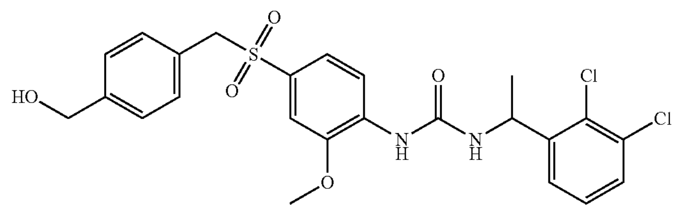 [SMILES: COc1cc(S(=O)(=O)Cc2ccc(CO)cc2)ccc1NC(=O)NC(C)c1cccc(Cl)c1Cl] | 1-(1-(2,3-dichlorophenyl)ethyl)-3-(4-((4-(hydroxymethyl)benzyl)sulfonyl)-2-methoxyphenyl)urea |
| H1435 | 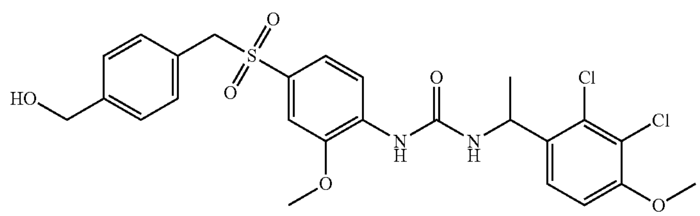 [SMILES: COc1cc(S(=O)(=O)Cc2ccc(CO)cc2)ccc1NC(=O)NC(C)c1ccc(OC)c(Cl)c1Cl] | 1-(1-(2,3-dichloro-4-methoxyphenyl)ethyl)-3-(4-((4-(hydroxymethyl)benzyl)sulfonyl)-2-methoxyphenyl)urea |
| H1436 | 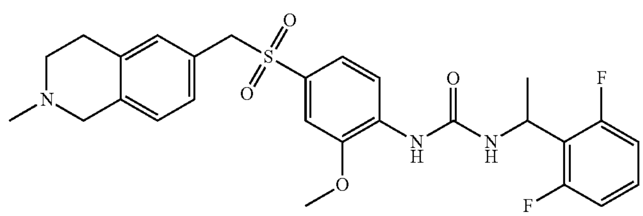 [SMILES: COc1cc(S(=O)(=O)Cc2ccc3c(c2)CCN(C)C3)ccc1NC(=O)NC(C)c1c(F)cccc1F] | 1-(1-(2,6-difluorophenyl)ethyl)-3-(2-methoxy-4-(((2-methyl-1,2,3,4-tetrahydroisoquinolin-6-yl)methyl)sulfonyl)phenyl)urea |
| H1437 | 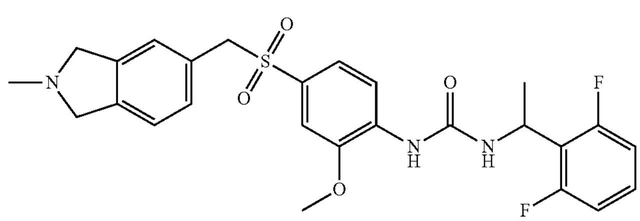 [SMILES: COc1cc(S(=O)(=O)Cc2ccc3c(c2)CN(C)C3)ccc1NC(=O)NC(C)c1c(F)cccc1F] | 1-(1-(2,6-difluorophenyl)ethyl)-3-(2-methoxy-4-(((2-methylisoindolin-5-yl)methyl)sulfonyl)phenyl)urea |
| H1438 | 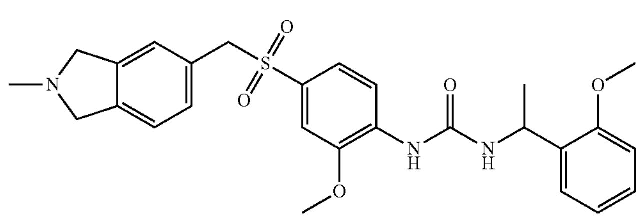 | 1-(2-methoxy-4-(((2-methylisoindolin-5-yl)methyl)sulfonyl)phenyl)-3-(1-(2-methoxyphenyl)ethyl)urea |

-continued

| | Chemical Structure | Chemical Name |
|---|---|---|
| H1439 | 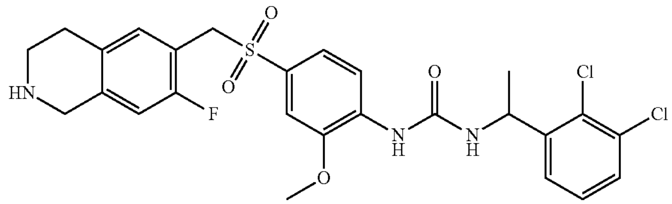 [SMILES: COc1cc(S(=O)(=O)Cc2cc3c(cc2F)CNCC3)ccc1NC(=O)NC(C)c1cccc(Cl)c1Cl] | 1-(1-(2,3-dichlorophenyl)ethyl)-3-(4-(((7-fluoro-1,2,3,4-tetrahydroisoquinolin-6-yl)methyl)sulfonyl)-2-methoxyphenyl)urea |
| H1440 | 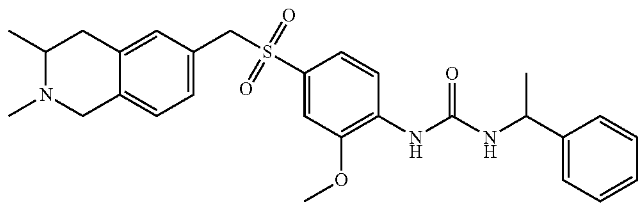 [SMILES: COc1cc(S(=O)(=O)Cc2ccc3c(c2)CC(C)N(C)C3)ccc1NC(=O)NC(C)c1ccccc1] | 1-(4-(((2,3-dimethyl-1,2,3,4-tetrahydroisoquinolin-6-yl)methyl)sulfonyl)-2-methoxyphenyl)-3-(1-phenylethyl)urea |
| H1441 | 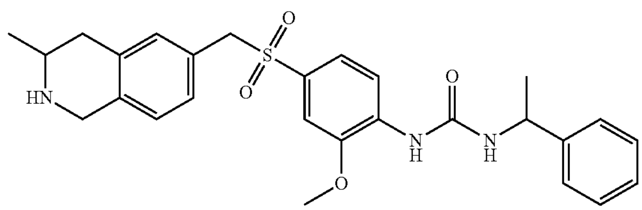 [SMILES: COc1cc(S(=O)(=O)Cc2ccc3c(c2)CC(C)NC3)ccc1NC(=O)NC(C)c1ccccc1] | 1-(2-methoxy-4-(((3-methyl-1,2,3,4-tetrahydroisoquinolin-6-yl)methyl)sulfonyl)phenyl)-3-(1-phenylethyl)urea |
| H1442 | 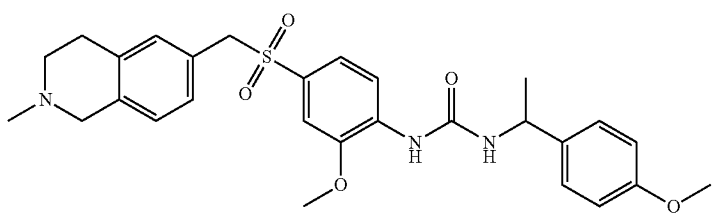 | 1-(2-methoxy-4-(((2-methyl-1,2,3,4-tetrahydroisoquinolin-6-yl)methyl)sulfonyl)phenyl)-3-(1-(4-methoxyphenyl)ethyl)urea |
| H1443 | 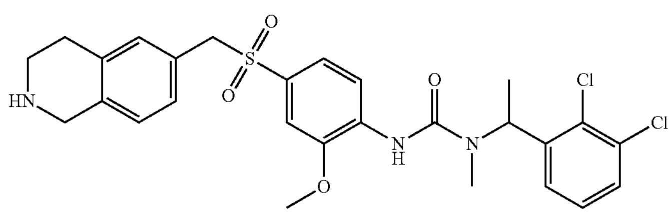 [SMILES: COc1cc(S(=O)(=O)Cc2ccc3c(c2)CCNC3)ccc1NC(=O)N(C)C(C)c1cccc(Cl)c1Cl] | 1-(1-(2,3-dichlorophenyl)ethyl)-3-(2-methoxy-4-(((1,2,3,4-tetrahydroisoquinolin-6-yl)methyl)sulfonyl)phenyl)-1-methylurea |
| H1444 | 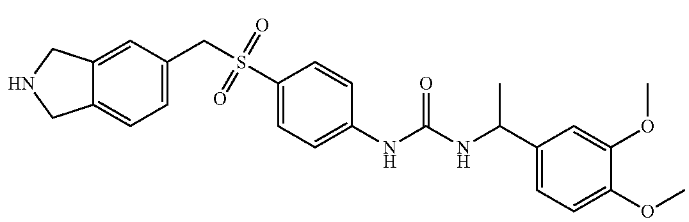 [SMILES: COc1ccc(C(C)NC(=O)Nc2ccc(S(=O)(=O)Cc3ccc4c(c3)CNC4)cc2)cc1OC] | 1-(1-(3,4-dimethoxyphenyl)ethyl)-3-(4-((isoindolin-5-ylmethyl)sulfonyl)phenyl)urea |
| H1445 | 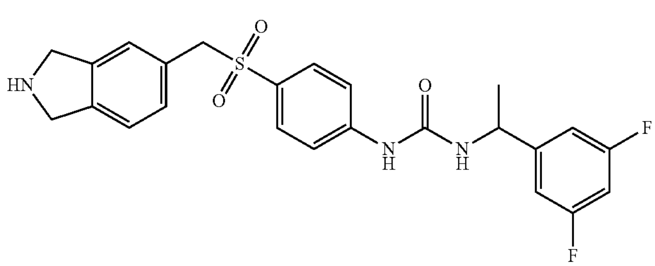 [SMILES: CC(NC(=O)Nc1ccc(S(=O)(=O)Cc2ccc3c(c2)CNC3)cc1)c1cc(F)cc(F)c1] | 1-(1-(3,5-difluorophenyl)ethyl)-3-(4-((isoindolin-5-ylmethyl)sulfonyl)phenyl)urea |

-continued

| | Chemical Structure | Chemical Name |
|---|---|---|
| H1446 | 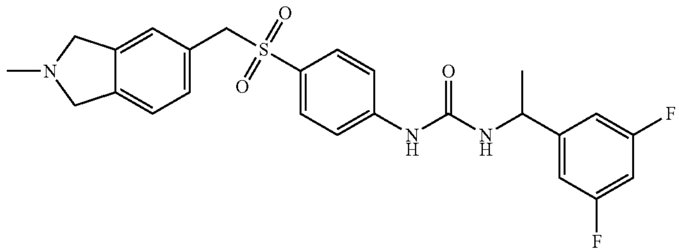 [SMILES: CC(NC(=O)Nc1ccc(S(=O)(=O)Cc2ccc3c(c2)CN(C)C3)cc1)c1cc(F)cc(F)c1] | 1-(1-(3,5-difluorophenyl)ethyl)-3-(4-(((2-methylisoindolin-5-yl)methyl)sulfonyl)phenyl)urea |
| H1447 | 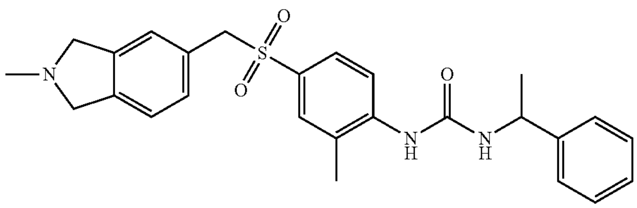 [SMILES: Cc1cc(S(=O)(=O)Cc2ccc3c(c2)CN(C)C3)ccc1NC(=O)NC(C)c1ccccc1] | 1-(2-methyl-4-(((2-methylisoindolin-5-yl)methyl)sulfonyl)phenyl)-3-(1-phenylethyl)urea |
| H1448 | 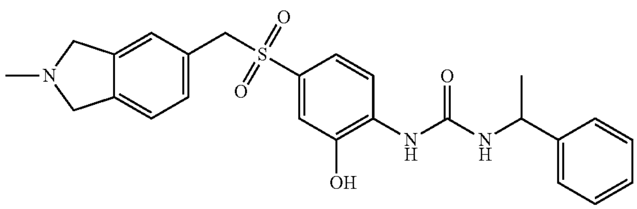 | 1-(2-hydroxy-4-(((2-methylisoindolin-5-yl)methyl)sulfonyl)phenyl)-3-(1-phenylethyl)urea |
| H1449 | 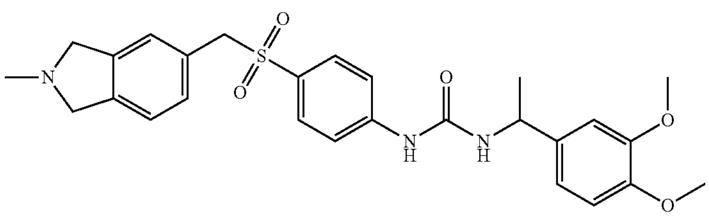 | 1-(1-(3,4-dimethoxyphenyl)ethyl)-3-(4-(((2-methylisoindolin-5-yl)methyl)sulfonyl)phenyl)urea |
| H1450 | 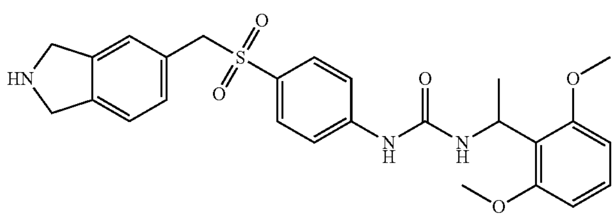 | 1-(1-(2,6-dimethoxyphenyl)ethyl)-3-(4-((isoindolin-5-ylmethyl)sulfonyl)phenyl)urea |
| H1451 | 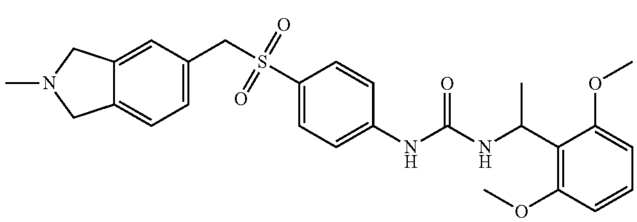 | 1-(1-(2,6-dimethoxyphenyl)ethyl)-3-(4-(((2-methylisoindolin-5-yl)methyl)sulfonyl)phenyl)urea |
| H1452 | 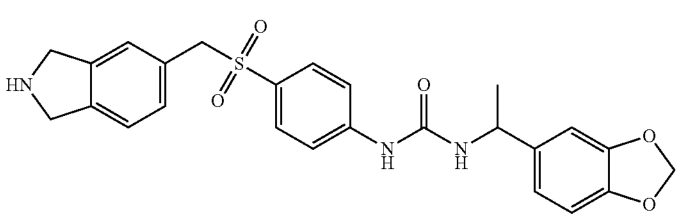 [SMILES: CC(NC(=O)Nc1ccc(S(=O)(=O)Cc2ccc3c(c2)CNC3)cc1)c1ccc2c(c1)OCO2] | 1-(1-(benzo[d][1,3]dioxol-5-yl)ethyl)-3-(4-((isoindolin-5-ylmethyl)sulfonyl)phenyl)urea |

-continued

| | Chemical Structure | Chemical Name |
|---|---|---|
| H1453 | 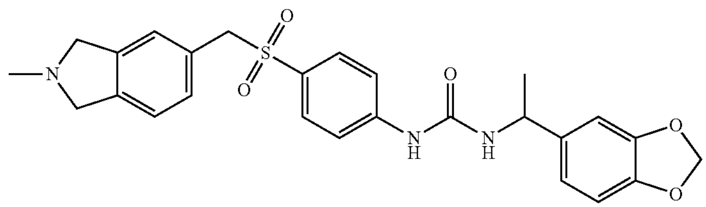 [SMILES: CC(NC(=O)Nc1ccc(S(=O)(=O)Cc2ccc3c(c2)CN(C)C3)cc1)c1ccc2c(c1)OCO2] | 1-(1-(benzo[d][1,3]dioxol-5-yl)ethyl)-3-(4-(((2-methylisoindolin-5-yl)methyl)sulfonyl)phenyl)urea |
| H1454 | 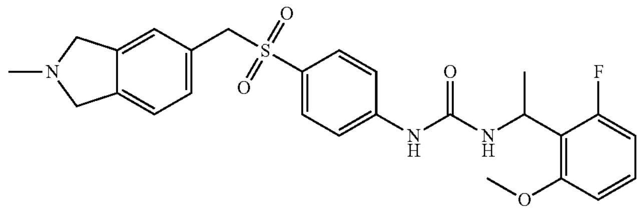 [SMILES: COc1cccc(F)c1C(C)NC(=O)Nc1ccc(S(=O)(=O)Cc2ccc3c(c2)CN(C)C3)cc1] | 1-(1-(2-fluoro-6-methoxyphenyl)ethyl)-3-(4-(((2-methylisoindolin-5-yl)methyl)sulfonyl)phenyl)urea |
| H1455 | 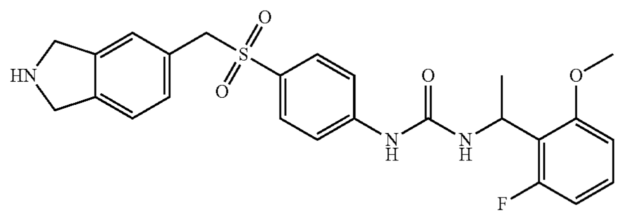 | 1-(1-(2-fluoro-6-methoxyphenyl)ethyl)-3-(4-((isoindolin-5-ylmethyl)sulfonyl)phenyl)urea |
| H1456 | 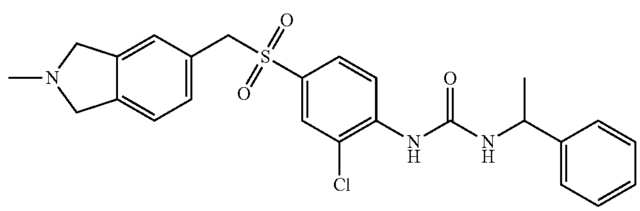 | 1-(2-chloro-4-(((2-methylisoindolin-5-yl)methyl)sulfonyl)phenyl)-3-(1-phenylethyl)urea |
| H1457 | 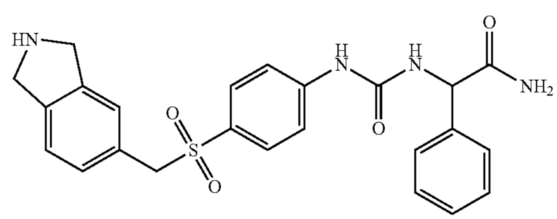 [SMILES: NC(=O)C(NC(=O)Nc1ccc(S(=O)(=O)Cc2ccc3c(c2)CNC3)cc1)c1ccccc1] | 2-(3-(4-((isoindolin-5-ylmethyl)sulfonyl)phenyl)ureido)-2-phenylacetamide |
| H1458 | 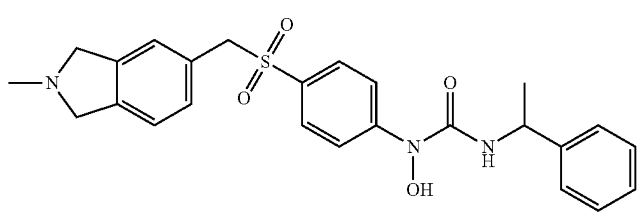 [SMILES: CC(NC(=O)N(O)c1ccc(S(=O)(=O)Cc2ccc3c(c2)CN(C)C3)cc1)c1ccccc1] | 1-hydroxy-1-(4-(((2-methylisoindolin-5-yl)methyl)sulfonyl)phenyl)-3-(1-phenylethyl)urea |
| H1459 | 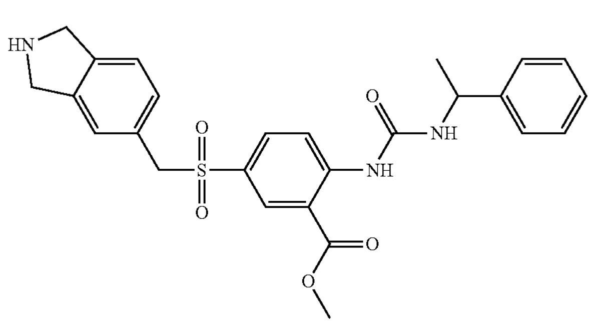 [SMILES: COC(=O)c1cc(S(=O)(=O)Cc2ccc3c(c2)CNC3)ccc1NC(=O)NC(C)c1ccccc1] | methyl 5-((isoindolin-5-ylmethyl)sulfonyl)-2-(3-(1-phenylethyl)ureido)benzoate |

-continued

| | Chemical Structure | Chemical Name |
|---|---|---|
| H1460 | 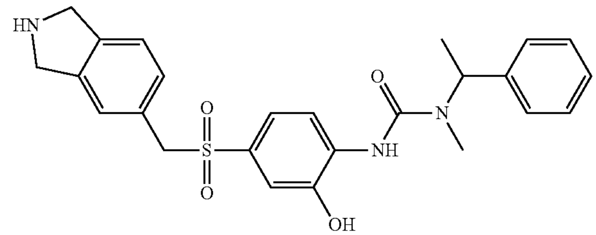 [SMILES: CC(c1ccccc1)N(C)C(=O)Nc1ccc(S(=O)(=O)Cc2ccc3c(c2)CNC3)cc1O] | 3-(2-hydroxy-4-((isoindolin-5-ylmethyl)sulfonyl)phenyl)-1-methyl-1-(1-phenylethyl)urea |
| H1461 | 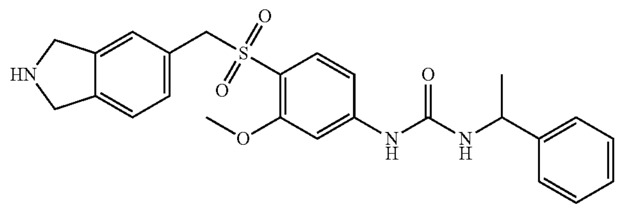 [SMILES: COc1cc(NC(=O)NC(C)c2ccccc2)ccc1S(=O)(=O)Cc1ccc2c(c1)CNC2] | 1-(4-((isoindolin-5-ylmethyl)sulfonyl)-3-methoxyphenyl)-3-(1-phenylethyl)urea |
| H1462 | 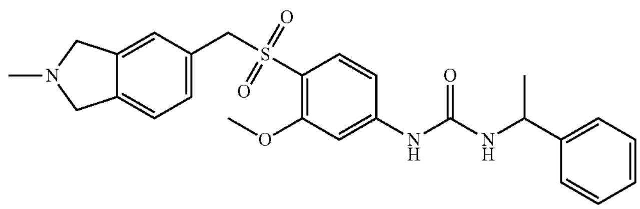 [SMILES: COc1cc(NC(=O)NC(C)c2ccccc2)ccc1S(=O)(=O)Cc1ccc2c(c1)CN(C)C2] | 1-(3-methoxy-4-(((2-methylisoindolin-5-yl)methyl)sulfonyl)phenyl)-3-(1-phenylethyl)urea |
| H1463 | 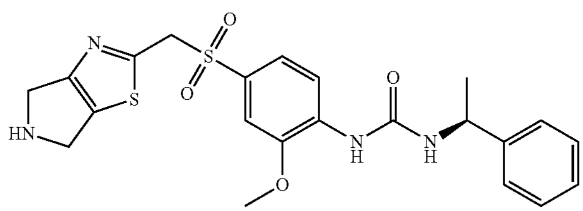 [SMILES: COc1cc(S(=O)(=O)Cc2nc3c(s2)CNC3)ccc1NC(=O)N[C@@H](C)c1ccccc1] | (S)-1-(4-(((5,6-dihydro-4H-pyrrolo[3,4-d]thiazol-2-yl)methyl)sulfonyl)-2-methoxyphenyl)-3-(1-phenylethyl)urea |
| H1464 | 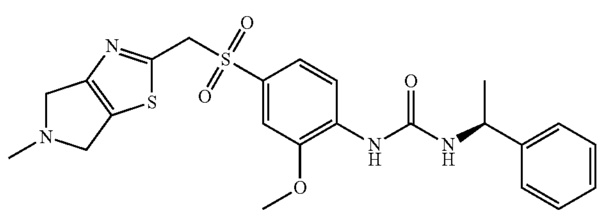 [SMILES: COc1cc(S(=O)(=O)Cc2nc3c(s2)CN(C)C3)ccc1NC(=O)N[C@@H](C)c1ccccc1] | (S)-1-(2-methoxy-4-(((5-methyl-5,6-dihydro-4H-pyrrolo[3,4-d]thiazol-2-yl)methyl)sulfonyl)phenyl)-3-(1-phenylethyl)urea |
| H1465 | 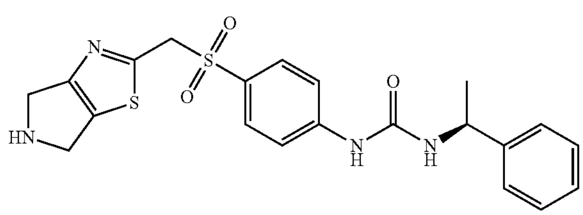 [SMILES: C[C@H](NC(=O)Nc1ccc(S(=O)(=O)Cc2nc3c(s2)CNC3)cc1)c1ccccc1] | (S)-1-(4-(((5,6-dihydro-4H-pyrrolo[3,4-d]thiazol-2-yl)methyl)sulfonyl)phenyl)-3-(1-phenylethyl)urea |
| H1466 | 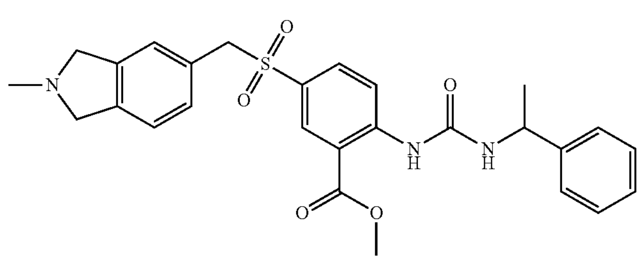 [SMILES: COC(=O)c1cc(S(=O)(=O)Cc2ccc3c(c2)CN(C)C3)ccc1NC(=O)NC(C)c1ccccc1] | methyl 5-(((2-methylisoindolin-5-yl)methyl)sulfonyl)-2-(3-(1-phenylethyl)ureido)benzoate |

-continued

| | Chemical Structure | Chemical Name |
|---|---|---|
| H1467 | 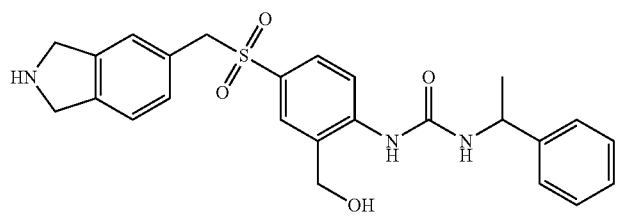 [SMILES: CC(NC(=O)Nc1ccc(S(=O)(=O)Cc2ccc3c(c2)CNC3)cc1CO)c1ccccc1] | 1-(2-(hydroxymethyl)-4-((isoindolin-5-ylmethyl)sulfonyl)phenyl)-3-(1-phenylethyl)urea |
| H1468 | 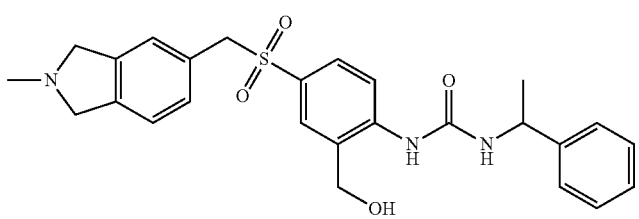 [SMILES: CC(NC(=O)Nc1ccc(S(=O)(=O)Cc2ccc3c(c2)CN(C)C3)cc1CO)c1ccccc1] | 1-(2-(hydroxymethyl)-4-(((2-methylisoindolin-5-yl)methyl)sulfonyl)phenyl)-3-(1-phenylethyl)urea |
| H1469 | 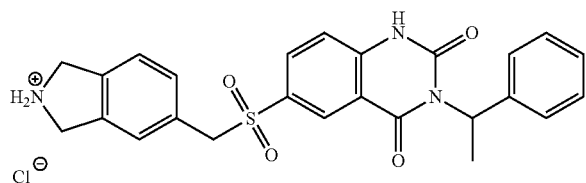 [SMILES: CC(c1ccccc1)n1c(=O)[nH]c2ccc(S(=O)(=O)Cc3ccc4c(c3)C[NH2+]C4)cc2c1=O ; [Cl-]] | 6-((isoindolin-5-ylmethyl)sulfonyl)-3-(1-phenylethyl)quinazoline-2,4(1H,3H)-dione |
| H1470 | 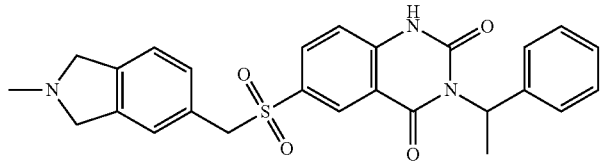 [SMILES: CC(c1ccccc1)n1c(=O)[nH]c2ccc(S(=O)(=O)Cc3ccc4c(c3)CN(C)C4)cc2c1=O] | 6-(((2-methylisoindolin-5-yl)methyl)sulfonyl)-3-(1-phenylethyl)quinazoline-2,4(1H,3H)-dione |
| H1471 | 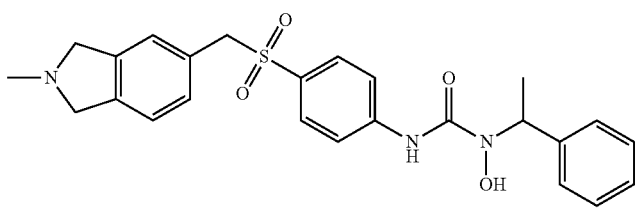 [SMILES: CC(c1ccccc1)N(O)C(=O)Nc1ccc(S(=O)(=O)Cc2ccc3c(c2)CN(C)C3)cc1] | 1-hydroxy-3-(4-(((2-methylisoindolin-5-yl)methyl)sulfonyl)phenyl)-1-(1-phenylethyl)urea |
| H1472 | 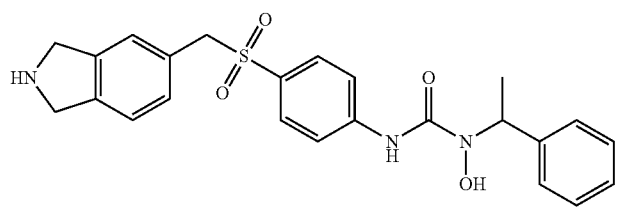 [SMILES: CC(c1ccccc1)N(O)C(=O)Nc1ccc(S(=O)(=O)Cc2ccc3c(c2)CNC3)cc1] | 1-hydroxy-3-(4-((isoindolin-5-ylmethyl)sulfonyl)phenyl)-1-(1-phenylethyl)urea |
| H1473 | 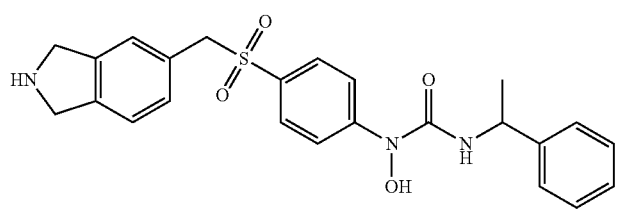 [SMILES: CC(NC(=O)N(O)c1ccc(S(=O)(=O)Cc2ccc3c(c2)CNC3)cc1)c1ccccc1] | 1-hydroxy-1-(4-((isoindolin-5-ylmethyl)sulfonyl)phenyl)-3-(1-phenylethyl)urea |

-continued

| | Chemical Structure | Chemical Name |
|---|---|---|
| H1474 | 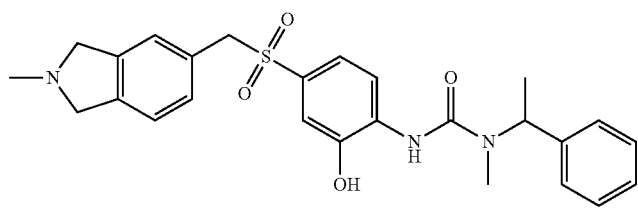 [SMILES: CC(c1ccccc1)N(C)C(=O)Nc1ccc(S(=O)(=O)Cc2ccc3c(c2)CN(C)C3)cc1O] | 3-(2-hydroxy-4-(((2-methylisoindolin-5-yl)methyl)sulfonyl)phenyl)-1-methyl-1-(1-phenylethyl)urea |
| H1475 | 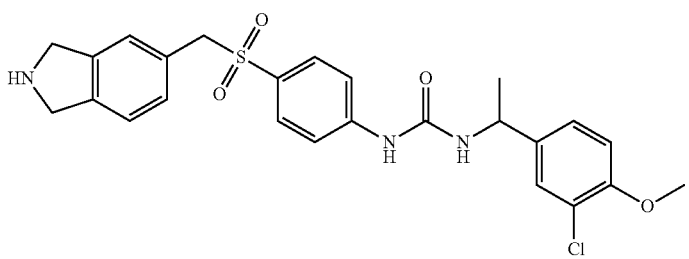 [SMILES: COc1ccc(C(C)NC(=O)Nc2ccc(S(=O)(=O)Cc3ccc4c(c3)CNC4)cc2)cc1Cl] | 1-(1-(3-chloro-4-methoxyphenyl)ethyl)-3-(4-((isoindolin-5-ylmethyl)sulfonyl)phenyl)urea |
| H1476 | 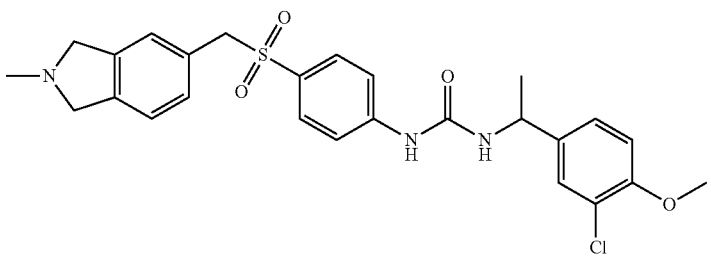 | 1-(1-(3-chloro-4-methoxyphenyl)ethyl)-3-(4-(((2-methylisoindolin-5-yl)methyl)sulfonyl)phenyl)urea |
| H1477 | 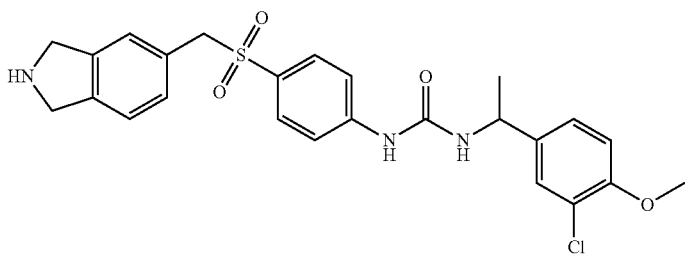 [SMILES: COc1ccc(C(C)NC(=O)Nc2ccc(S(=O)(=O)Cc3ccc4c(c3)CNC4)cc2)cc1Cl] | 1-(1-(3-chloro-4-methoxyphenyl)ethyl)-3-(4-((isoindolin-5-ylmethyl)sulfonyl)phenyl)urea |
| H1478 | 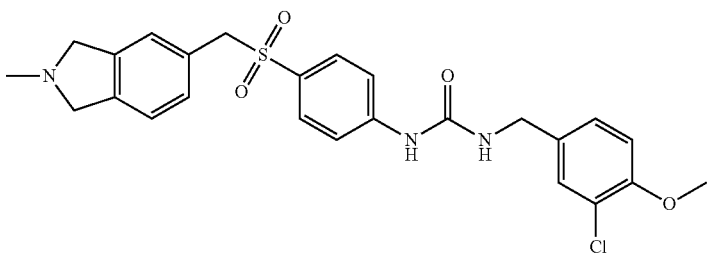 | 1-(3-chloro-4-methoxybenzyl)-3-(4-(((2-methylisoindolin-5-yl)methyl)sulfonyl)phenyl)urea |
| H1479 | 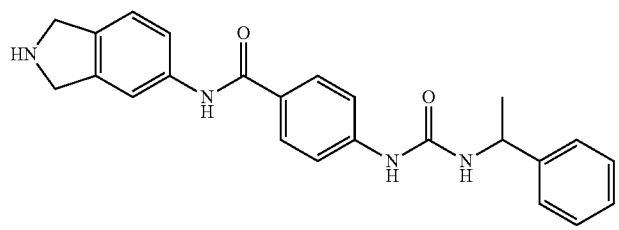 [SMILES: CC(NC(=O)Nc1ccc(C(=O)Nc2ccc3c(c2)CNC3)cc1)c1ccccc1] | N-(isoindolin-5-yl)-4-(3-(1-phenylethyl)ureido)benzamide |

-continued

| Chemical Structure | Chemical Name |
|---|---|
| H1480 | N-(2-methylisoindolin-5-yl)-4-(3-(1-phenylethyl)ureido)benzamide |
| H1481 | (R)-1-(1-(2,3-dichlorophenyl)ethyl)-3-(2-methoxy-4-(((1,2,3,4-tetrahydroisoquinolin-6-yl)methyl)sulfonyl)phenyl)urea |
| H1482 | (S)-1-(1-(2,3-dichlorophenyl)ethyl)-3-(2-methoxy-4-(((1,2,3,4-tetrahydroisoquinolin-6-yl)methyl)sulfonyl)phenyl)urea |
| H1483 | 1-((2,3-dihydrobenzo[b][1,4]dioxin-2-yl)methyl)-3-(4-((isoindolin-5-ylmethyl)sulfonyl)phenyl)urea |
| H1484 | 1-(2-cyclopropyl-4-((isoindolin-5-ylmethyl)sulfonyl)phenyl)-3-(1-phenylethyl)urea |
| H1485 | 1-(2-bromo-4-((isoindolin-5-ylmethyl)sulfonyl)phenyl)-3-(1-phenylethyl)urea |

-continued

| | Chemical Structure | Chemical Name |
|---|---|---|
| H1486 | 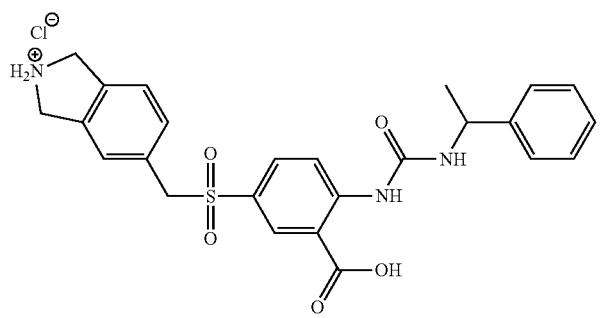 [SMILES: [Cl-] ; CC(NC(=O)Nc1ccc(S(=O)(=O)Cc2ccc3c(c2)C[NH2+]C3)cc1C(=O)O)c1ccccc1] | 5-((isoindolin-5-ylmethyl)sulfonyl)-2-(3-(1-phenylethyl)ureido)benzoic acid |
| H1487 | 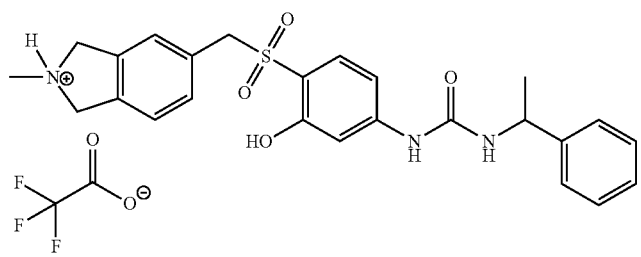 [SMILES: CC(NC(=O)Nc1ccc(S(=O)(=O)Cc2ccc3c(c2)C[NH+](C)C3)c(O)c1)c1ccccc1 ; O=C([O-])C(F)(F)F] | 1-(3-hydroxy-4-(((2-methylisoindolin-5-yl)methyl)sulfonyl)phenyl)-3-(1-phenylethyl)urea |
| H1488 | 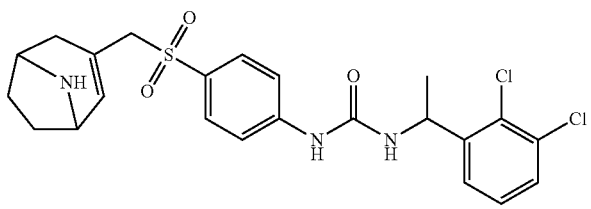 [SMILES: CC(NC(=O)Nc1ccc(S(=O)(=O)CC2=CC3CCC(C2)N3)cc1)c1cccc(Cl)c1Cl] | 1-(4-(((8-azabicyclo[3.2.1]oct-2-en-3-yl)methyl)sulfonyl)phenyl)-3-(1-(2,3-dichlorophenyl)ethyl)urea |
| H1489 | 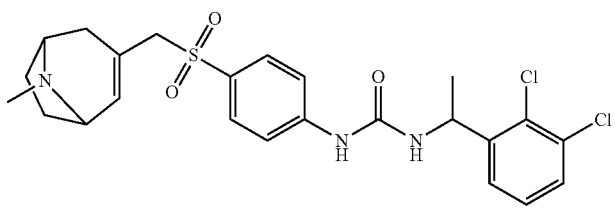 [SMILES: CC(NC(=O)Nc1ccc(S(=O)(=O)CC2=CC3CCC(C2)N3C)cc1)c1cccc(Cl)c1Cl] | 1-(1-(2,3-dichlorophenyl)ethyl)-3-(4-(((8-methyl-8-azabicyclo[3.2.1]oct-2-en-3-yl)methyl)sulfonyl)phenyl)urea |
| H1490 | 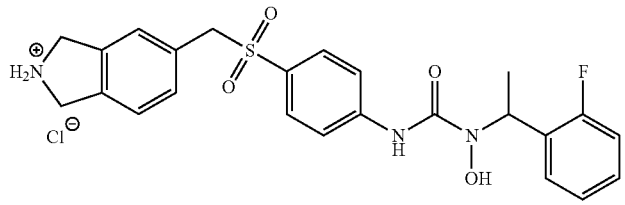 [SMILES: CC(c1ccccc1F)N(O)C(=O)Nc1ccc(S(=O)(=O)Cc2ccc3c(c2)C[NH2+]C3)cc1 ; [Cl-]] | 1-(1-(2-fluorophenyl)ethyl)-1-hydroxy-3-(4-((isoindolin-5-ylmethyl)sulfonyl)phenyl)urea |
| H1491 | 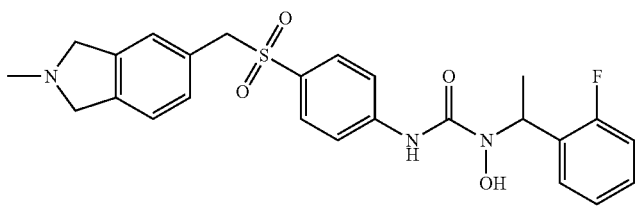 [SMILES: CC(c1ccccc1F)N(O)C(=O)Nc1ccc(S(=O)(=O)Cc2ccc3c(c2)CN(C)C3)cc1] | 1-(1-(2-fluorophenyl)ethyl)-1-hydroxy-3-(4-(((2-methylisoindolin-5-yl)methyl)sulfonyl)phenyl)urea |

| | Chemical Structure | Chemical Name |
|---|---|---|
| H1492 | 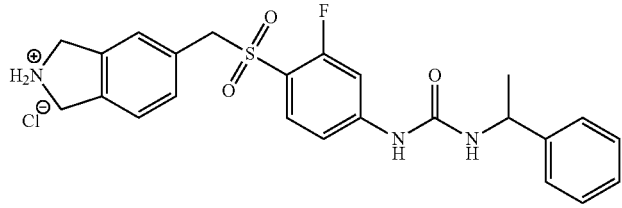 [SMILES: [Cl-] ; CC(NC(=O)Nc1ccc(S(=O)(=O)Cc2ccc3c(c2)C[NH2+]C3)c(F)c1)c1ccccc1] | 1-(3-fluoro-4-((isoindolin-5-ylmethyl)sulfonyl)phenyl)-3-(1-phenylethyl)urea |
| H1493 | 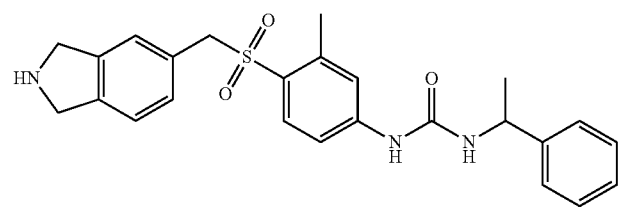 [SMILES: Cc1cc(NC(=O)NC(C)c2ccccc2)ccc1S(=O)(=O)Cc1ccc2c(c1)CNC2] | 1-(4-((isoindolin-5-ylmethyl)sulfonyl)-3-methylphenyl)-3-(1-phenylethyl)urea |
| H1494 | 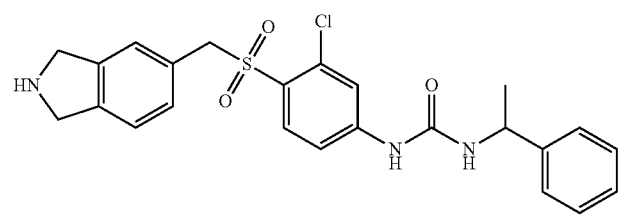 [SMILES: CC(NC(=O)Nc1ccc(S(=O)(=O)Cc2ccc3c(c2)CNC3)c(Cl)c1)c1ccccc1] | 1-(3-chloro-4-((isoindolin-5-ylmethyl)sulfonyl)phenyl)-3-(1-phenylethyl)urea |
| H1495 | 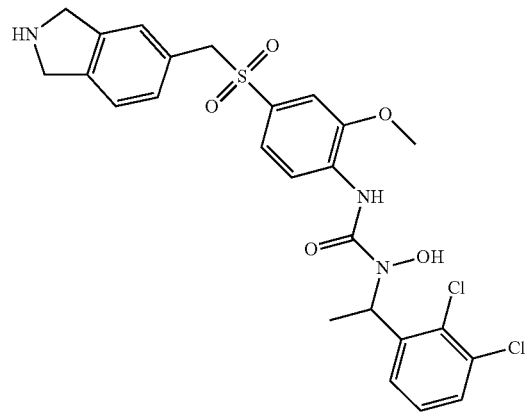 [SMILES: COc1cc(S(=O)(=O)Cc2ccc3c(c2)CNC3)ccc1NC(=O)N(O)C(C)c1cccc(Cl)c1Cl] | 1-(1-(2,3-dichlorophenyl)ethyl)-1-hydroxy-3-(4-((isoindolin-5-ylmethyl)sulfonyl)-2-methoxyphenyl)urea |
| H1496 | 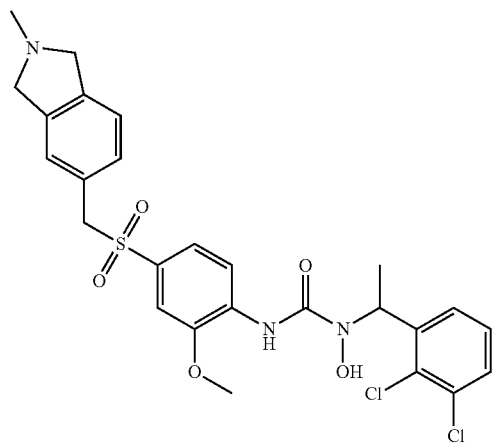 [SMILES: COc1cc(S(=O)(=O)Cc2ccc3c(c2)CN(C)C3)ccc1NC(=O)N(O)C(C)c1cccc(Cl)c1Cl] | 1-(1-(2,3-dichlorophenyl)ethyl)-1-hydroxy-3-(2-methoxy-4-(((2-methylisoindolin-5-yl)methyl)sulfonyl)phenyl)urea |

| Chemical Structure | Chemical Name |
|---|---|
| H1497 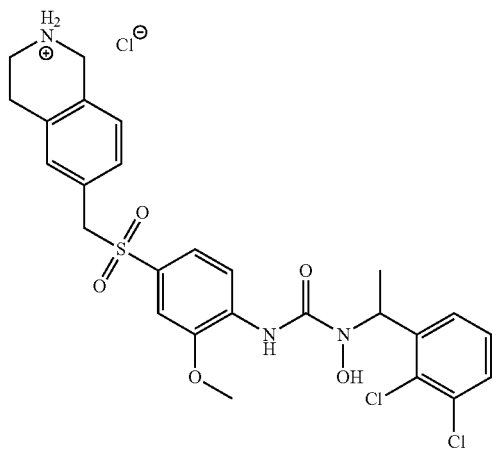 | 1-(1-(2,3-dichlorophenyl)ethyl)-1-hydroxy-3-(2-methoxy-4-(((1,2,3,4-tetrahydroisoquinolin-6-yl)methyl)sulfonyl)phenyl)urea |
| H1498 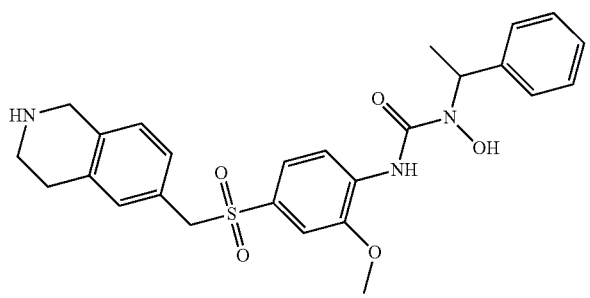 | 1-hydroxy-3-(2-methoxy-4-(((1,2,3,4-tetrahydroisoquinolin-6-yl)methyl)sulfonyl)phenyl)-1-(1-phenylethyl)urea |
| H1499 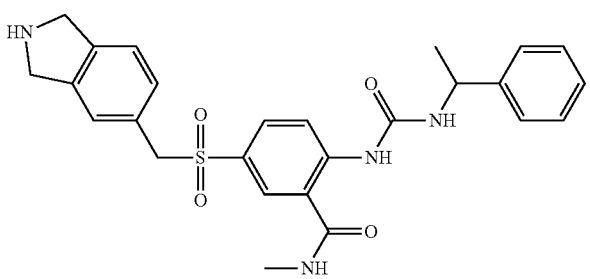 | 5-((isoindolin-5-ylmethyl)sulfonyl)-N-methyl-2-(3-(1-phenylethyl)ureido)benzamide |
| H1500 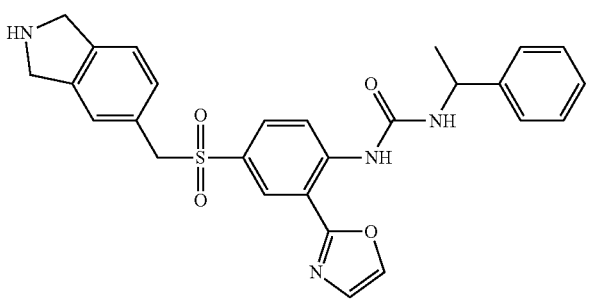 | 1-(4-((isoindolin-5-ylmethyl)sulfonyl)-2-(oxazol-2-yl)phenyl)-3-(1-phenylethyl)urea |

-continued

| | Chemical Structure | Chemical Name |
|---|---|---|
| H1501 | 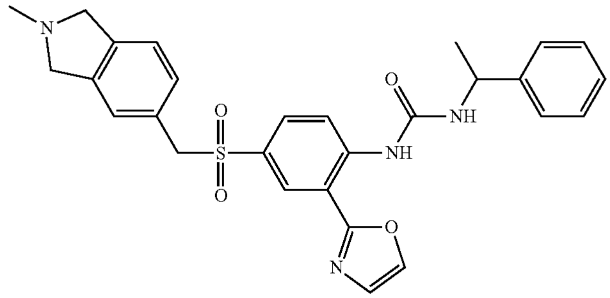 [SMILES: CC(NC(=O)Nc1ccc(S(=O)(=O)Cc2ccc3c(c2)CN(C)C3)cc1-c1ncco1)c1ccccc1] | 1-(4-(((2-methylisoindolin-5-yl)methyl)sulfonyl)-2-(oxazol-2-yl)phenyl)-3-(1-phenylethyl)urea |
| H1502 | 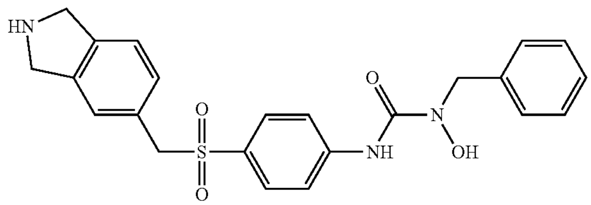 [SMILES: O=C(Nc1ccc(S(=O)(=O)Cc2ccc3c(c2)CNC3)cc1)N(O)Cc1ccccc1] | 1-benzyl-1-hydroxy-3-(4-((isoindolin-5-ylmethyl)sulfonyl)phenyl)urea |
| H1503 | 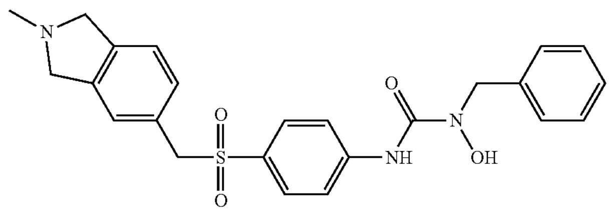 [SMILES: CN1Cc2ccc(CS(=O)(=O)c3ccc(NC(=O)N(O)Cc4ccccc4)cc3)cc2C1] | 1-benzyl-1-hydroxy-3-(4-(((2-methylisoindolin-5-yl)methyl)sulfonyl)phenyl)urea |
| H1504 | 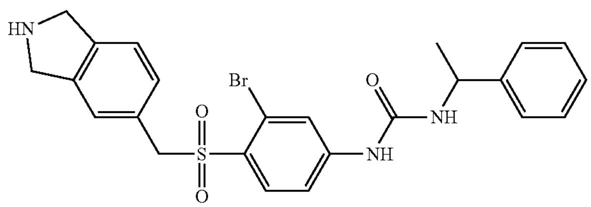 [SMILES: CC(NC(=O)Nc1ccc(S(=O)(=O)Cc2ccc3c(c2)CNC3)c(Br)c1)c1ccccc1] | 1-(3-bromo-4-((isoindolin-5-ylmethyl)sulfonyl)phenyl)-3-(1-phenylethyl)urea |
| H1505 | 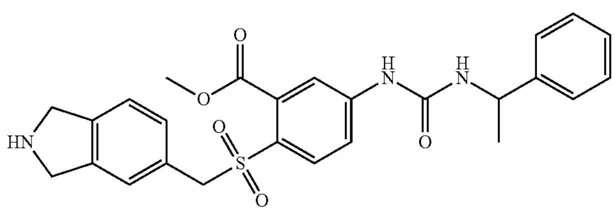 [SMILES: COC(=O)c1cc(NC(=O)NC(C)c2ccccc2)ccc1S(=O)(=O)Cc1ccc2c(c1)CNC2] | methyl 2-((isoindolin-5-ylmethyl)sulfonyl)-5-(3-(1-phenylethyl)ureido)benzoate |
| H1506 | 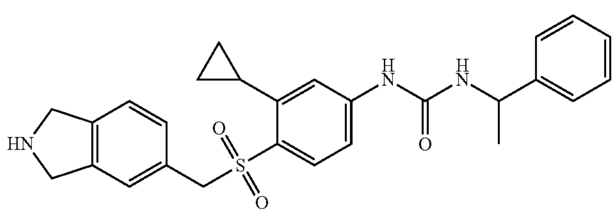 [SMILES: CC(NC(=O)Nc1ccc(S(=O)(=O)Cc2ccc3c(c2)CNC3)c(C2CC2)c1)c1ccccc1] | 1-(3-cyclopropyl-4-((isoindolin-5-ylmethyl)sulfonyl)phenyl)-3-(1-phenylethyl)urea |
| H1507 | 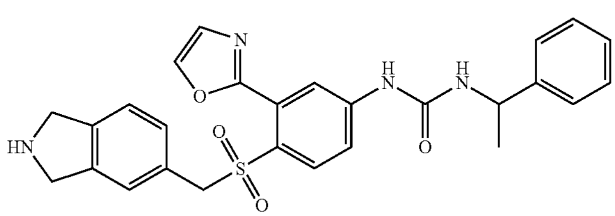 [SMILES: CC(NC(=O)Nc1ccc(S(=O)(=O)Cc2ccc3c(c2)CNC3)c(-c2ncco2)c1)c1ccccc1] | 1-(4-((isoindolin-5-ylmethyl)sulfonyl)-3-(oxazol-2-yl)phenyl)-3-(1-phenylethyl)urea |

| | Chemical Structure | Chemical Name |
|---|---|---|
| H1508 | 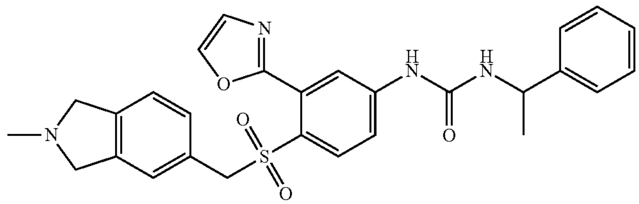 [SMILES: CC(NC(=O)Nc1ccc(S(=O)(=O)Cc2ccc3c(c2)CN(C)C3)c(-c2ncco2)c1)c1ccccc1] | 1-(4-(((2-methylisoindolin-5-yl)methyl)sulfonyl)-3-(oxazol-2-yl)phenyl)-3-(1-phenylethyl)urea |
| H1509 | 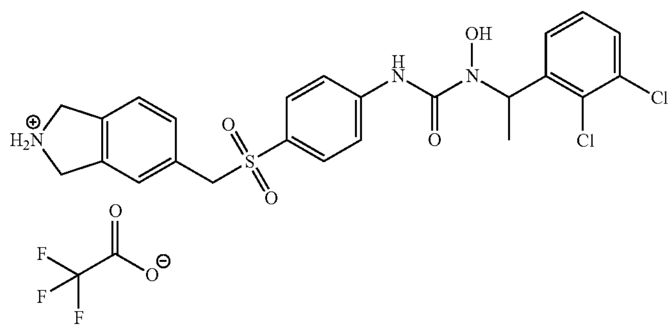 [SMILES: CC(c1cccc(Cl)c1Cl)N(O)C(=O)Nc1ccc(S(=O)(=O)Cc2ccc3c(c2)C[NH2+]C3)cc1 ; O=C([O-])C(F)(F)F] | 1-(1-(2,3-dichlorophenyl)ethyl)-1-hydroxy-3-(4-((isoindolin-5-ylmethyl)sulfonyl)phenyl)urea |
| H1510 | 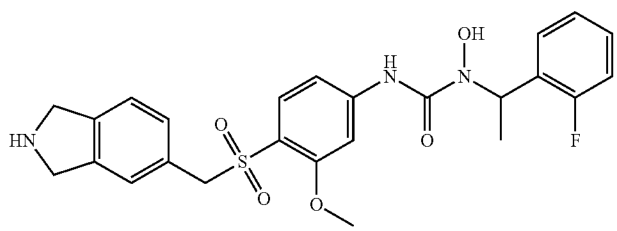 [SMILES: COc1cc(NC(=O)N(O)C(C)c2ccccc2F)ccc1S(=O)(=O)Cc1ccc2c(c1)CNC2] | 1-(1-(2-fluorophenyl)ethyl)-1-hydroxy-3-(4-((isoindolin-5-ylmethyl)sulfonyl)-3-methoxyphenyl)urea |
| H1511 | 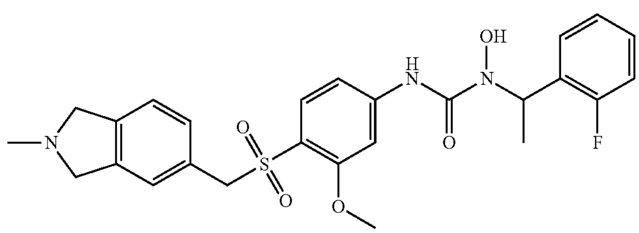 [SMILES: COc1cc(NC(=O)N(O)C(C)c2ccccc2F)ccc1S(=O)(=O)Cc1ccc2c(c1)CN(C)C2] | 1-(1-(2-fluorophenyl)ethyl)-1-hydroxy-3-(3-methoxy-4-(((2-methylisoindolin-5-yl)methyl)sulfonyl)phenyl)urea |
| H1512 | 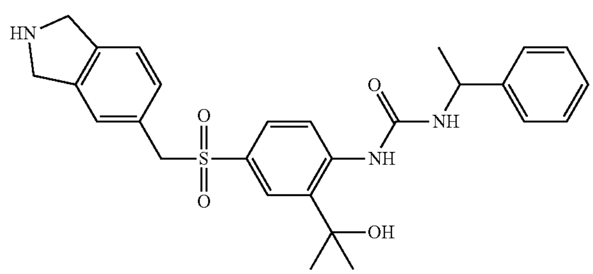 [SMILES: CC(NC(=O)Nc1ccc(S(=O)(=O)Cc2ccc3c(c2)CNC3)cc1C(C)(C)O)c1ccccc1] | 1-(2-(2-hydroxypropan-2-yl)-4-((isoindolin-5-ylmethyl)sulfonyl)phenyl)-3-(1-phenylethyl)urea |
| H1513 | 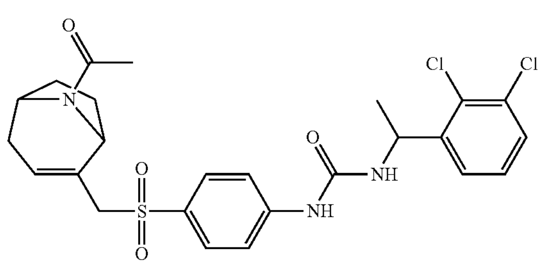 [SMILES: CC(=O)N1C2CC=C(CS(=O)(=O)c3ccc(NC(=O)NC(C)c4cccc(Cl)c4Cl)cc3)C1CC2] | 1-(4-(((8-acetyl-8-azabicyclo[3.2.1]oct-2-en-2-yl)methyl)sulfonyl)phenyl)-3-(1-(2,3-dichlorophenyl)ethyl)urea |

-continued

| | Chemical Structure | Chemical Name |
|---|---|---|
| H1514 | 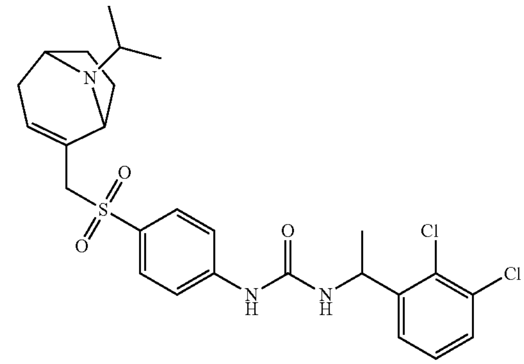 [SMILES: CC(NC(=O)Nc1ccc(S(=O)(=O)CC2=CCC3CCC2N3C(C)C)cc1)c1cccc(Cl)c1Cl] | 1-(1-(2,3-dichlorophenyl)ethyl)-3-(4-(((8-isopropyl-8-azabicyclo[3.2.1]oct-2-en-2-yl)methyl)sulfonyl)phenyl)urea |
| H1515 | 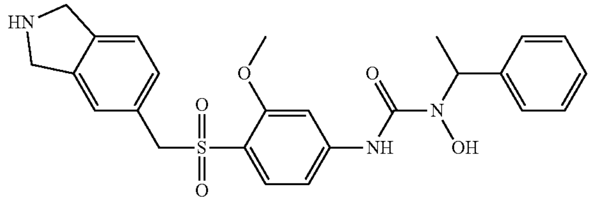 [SMILES: COc1cc(NC(=O)N(O)C(C)c2ccccc2)ccc1S(=O)(=O)Cc1ccc2c(c1)CNC2] | 1-hydroxy-3-(4-((isoindolin-5-ylmethyl)sulfonyl)-3-methoxyphenyl)-1-(1-phenylethyl)urea |
| H1516 | 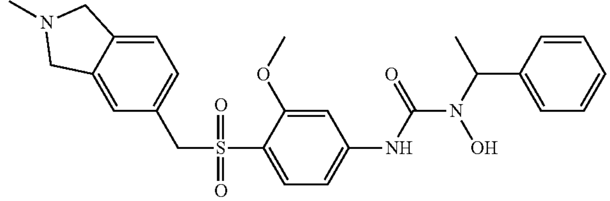 [SMILES: COc1cc(NC(=O)N(O)C(C)c2ccccc2)ccc1S(=O)(=O)Cc1ccc2c(c1)CN(C)C2] | 1-hydroxy-3-(3-methoxy-4-(((2-methylisoindolin-5-yl)methyl)sulfonyl)phenyl)-1-(1-phenylethyl)urea |
| H1517 | 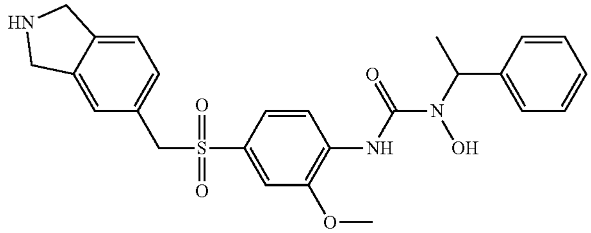 [SMILES: COc1cc(S(=O)(=O)Cc2ccc3c(c2)CNC3)ccc1NC(=O)N(O)C(C)c1ccccc1] | 1-hydroxy-3-(4-((isoindolin-5-ylmethyl)sulfonyl)-2-methoxyphenyl)-1-(1-phenylethyl)urea |
| H1518 | 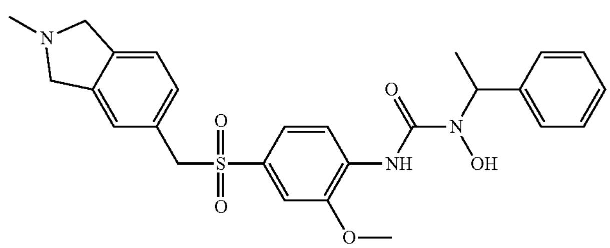 [SMILES: COc1cc(S(=O)(=O)Cc2ccc3c(c2)CN(C)C3)ccc1NC(=O)N(O)C(C)c1ccccc1] | 1-hydroxy-3-(2-methoxy-4-(((2-methylisoindolin-5-yl)methyl)sulfonyl)phenyl)-1-(1-phenylethyl)urea |
| H1519 | 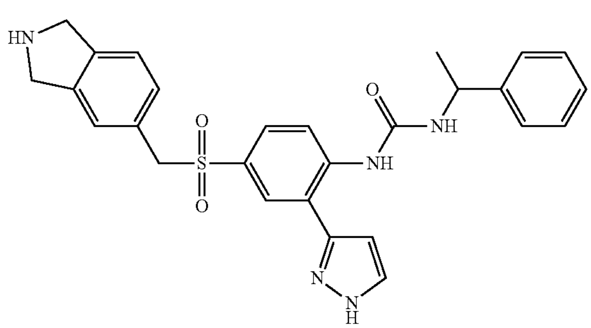 [SMILES: CC(NC(=O)Nc1ccc(S(=O)(=O)Cc2ccc3c(c2)CNC3)cc1-c1cc[nH]n1)c1ccccc1] | 1-(4-((isoindolin-5-ylmethyl)sulfonyl)-2-(1H-pyrazol-3-yl)phenyl)-3-(1-phenylethyl)urea |

-continued

| | Chemical Structure | Chemical Name |
|---|---|---|
| H1520 | 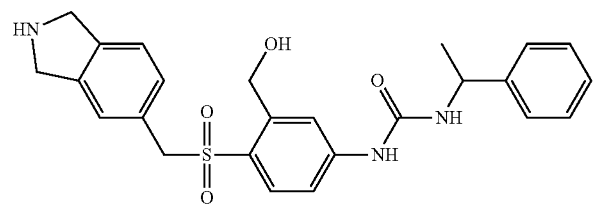 [SMILES: CC(NC(=O)Nc1ccc(S(=O)(=O)Cc2ccc3c(c2)CNC3)c(CO)c1)c1ccccc1] | 1-(3-(hydroxymethyl)-4-((isoindolin-5-ylmethyl)sulfonyl)phenyl)-3-(1-phenylethyl)urea |
| H1521 | 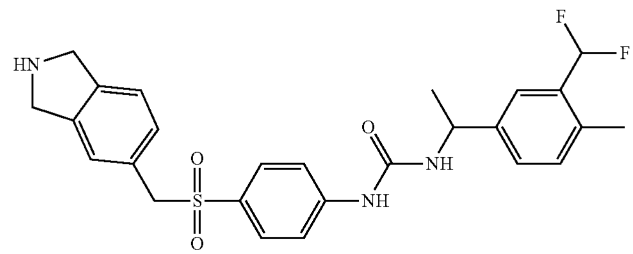 [SMILES: Cc1ccc(C(C)NC(=O)Nc2ccc(S(=O)(=O)Cc3ccc4c(c3)CNC4)cc2)cc1C(F)F] | 1-(1-(3-(difluoromethyl)-4-methylphenyl)ethyl)-3-(4-((isoindolin-5-ylmethyl)sulfonyl)phenyl)urea |
| H1522 | 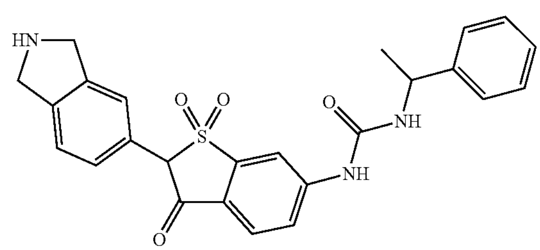 [SMILES: CC(NC(=O)Nc1ccc2c(c1)S(=O)(=O)C(c1ccc3c(c1)CNC3)C2=O)c1ccccc1] | 1-(2-(isoindolin-5-yl)-1,1-dioxido-3-oxo-2,3-dihydrobenzo[b]thiophen-6-yl)-3-(1-phenylethyl)urea |
| H1523 | 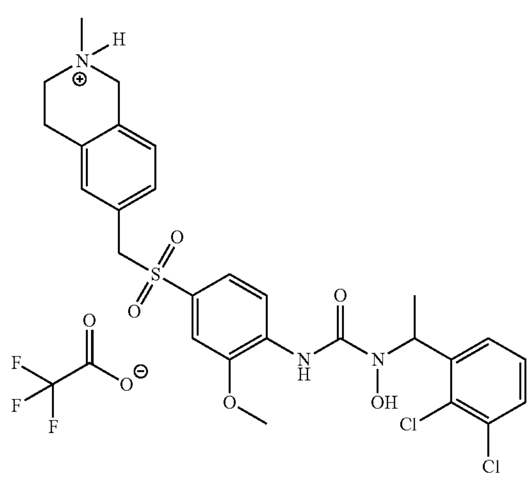 [SMILES: O=C([O-])C(F)(F)F ; COc1cc(S(=O)(=O)Cc2ccc3c(c2)CC[NH+](C)C3)ccc1NC(=O)N(O)C(C)c1cccc(Cl)c1Cl] | 1-(1-(2,3-dichlorophenyl)ethyl)-1-hydroxy-3-(2-methoxy-4-(((2-methyl-1,2,3,4-tetrahydroisoquinolin-6-yl)methyl)sulfonyl)phenyl)urea |
| H1524 | 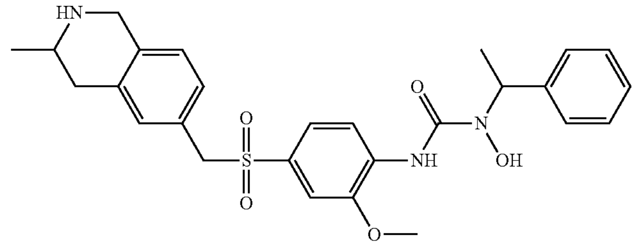 [SMILES: COc1cc(S(=O)(=O)Cc2ccc3c(c2)CC(C)NC3)ccc1NC(=O)N(O)C(C)c1ccccc1] | 1-hydroxy-3-(2-methoxy-4-(((3-methyl-1,2,3,4-tetrahydroisoquinolin-6-yl)methyl)sulfonyl)phenyl)-1-(1-phenylethyl)urea |

-continued

| | Chemical Structure | Chemical Name |
|---|---|---|
| H1525 | 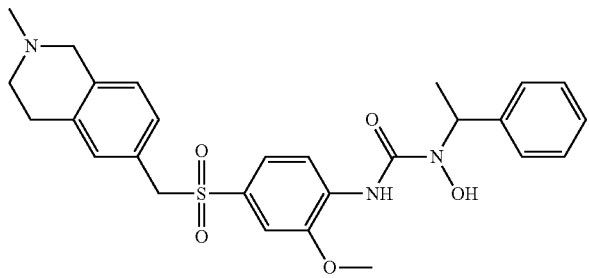 [SMILES: COc1cc(S(=O)(=O)Cc2ccc3c(c2)CCN(C)C3)ccc1NC(=O)N(O)C(C)c1ccccc1] | 1-hydroxy-3-(2-methoxy-4-(((2-methyl-1,2,3,4-tetrahydroisoquinolin-6-yl)methyl)sulfonyl)phenyl)-1-(1-phenylethyl)urea |
| H1526 | 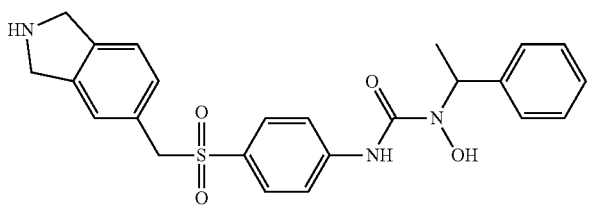 [SMILES: CC(c1ccccc1)N(O)C(=O)Nc1ccc(S(=O)(=O)Cc2ccc3c(c2)CNC3)cc1] | 1-hydroxy-3-(4-((isoindolin-5-ylmethyl)sulfonyl)phenyl)-1-(1-phenylethyl)urea |
| H1527 | 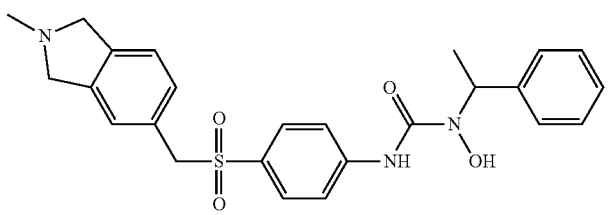 [SMILES: CC(c1ccccc1)N(O)C(=O)Nc1ccc(S(=O)(=O)Cc2ccc3c(c2)CN(C)C3)cc1] | 1-hydroxy-3-(4-(((2-methylisoindolin-5-yl)methyl)sulfonyl)phenyl)-1-(1-phenylethyl)urea |
| H1528 | 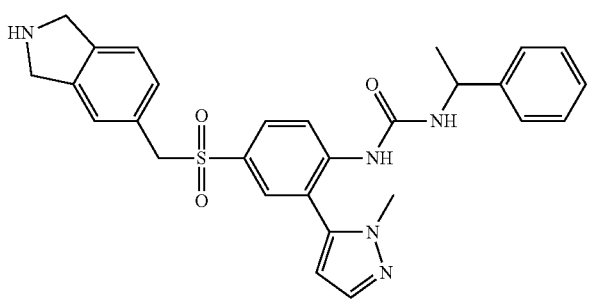 [SMILES: CC(NC(=O)Nc1ccc(S(=O)(=O)Cc2ccc3c(c2)CNC3)cc1-c1ccnn1C)c1ccccc1] | 1-(4-((isoindolin-5-ylmethyl)sulfonyl)-2-(1-methyl-1H-pyrazol-5-yl)phenyl)-3-(1-phenylethyl)urea |
| H1529 | 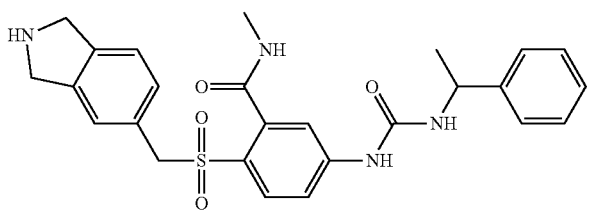 | 2-((isoindolin-5-ylmethyl)sulfonyl)-N-methyl-5-(3-(1-phenylethyl)ureido)benzamide |
| H1530 | 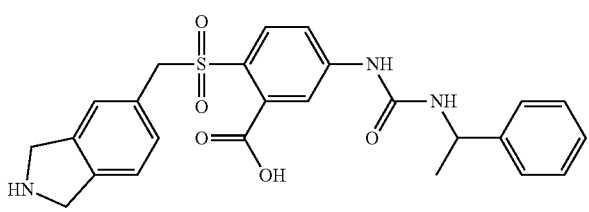 | 2-((isoindolin-5-ylmethyl)sulfonyl)-5-(3-(1-phenylethyl)ureido)benzoic acid |

-continued

| | Chemical Structure | Chemical Name |
|---|---|---|
| H1531 | 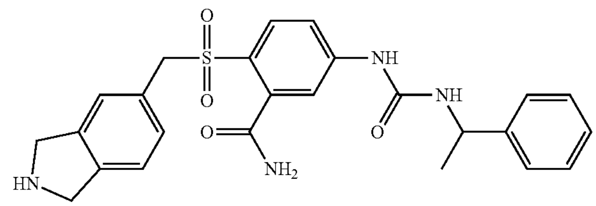 | 2-((isoindolin-5-ylmethyl)sulfonyl)-5-(3-(1-phenylethyl)ureido)benzamide |
| H1532 | 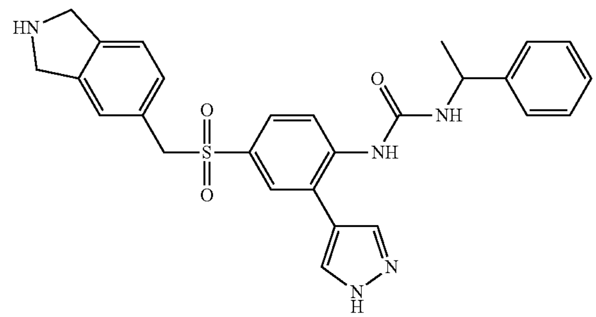 [SMILES: CC(NC(=O)Nc1ccc(S(=O)(=O)Cc2ccc3c(c2)CNC3)cc1-c1cn[nH]c1)c1ccccc1] | 1-(4-((isoindolin-5-ylmethyl)sulfonyl)-2-(1H-pyrazol-4-yl)phenyl)-3-(1-phenylethyl)urea |
| H1533 | 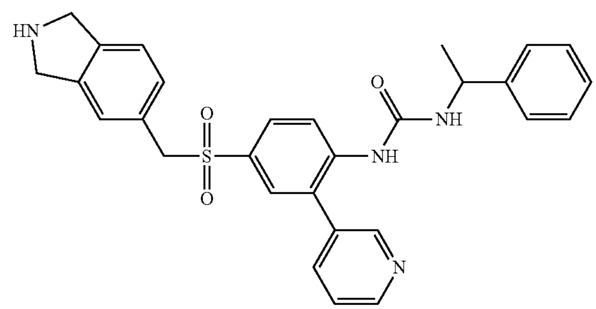 [SMILES: CC(NC(=O)Nc1ccc(S(=O)(=O)Cc2ccc3c(c2)CNC3)cc1-c1cccnc1)c1ccccc1] | 1-(4-((isoindolin-5-ylmethyl)sulfonyl)-2-(pyridin-3-yl)phenyl)-3-(1-phenylethyl)urea |
| H1534 | 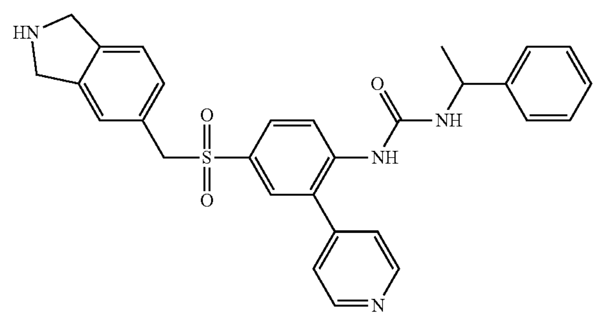 [SMILES: CC(NC(=O)Nc1ccc(S(=O)(=O)Cc2ccc3c(c2)CNC3)cc1-c1ccncc1)c1ccccc1] | 1-(4-((isoindolin-5-ylmethyl)sulfonyl)-2-(pyridin-4-yl)phenyl)-3-(1-phenylethyl)urea |
| H1535 | 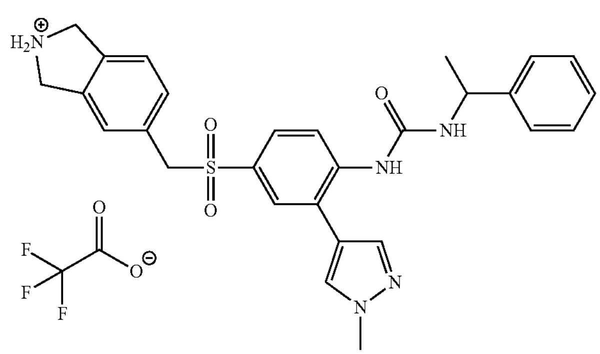 [SMILES: O=C([O-])C(F)(F)F ; CC(NC(=O)Nc1ccc(S(=O)(=O)Cc2ccc3c(c2)C[NH2+]C3)cc1-c1cnn(C)c1)c1ccccc1] | 1-(4-((isoindolin-5-ylmethyl)sulfonyl)-2-(1-methyl-1H-pyrazol-4-yl)phenyl)-3-(1-phenylethyl)urea |

-continued

| | Chemical Structure | Chemical Name |
|---|---|---|
| H1537 | 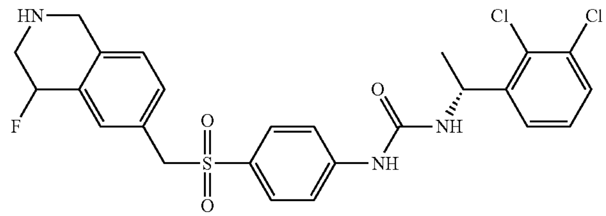 [SMILES: C[C@@H](NC(=O)Nc1ccc(S(=O)(=O)Cc2ccc3c(c2)C(F)CNC3)cc1)c1cccc(Cl)c1Cl] | 1-((R)-1-(2,3-dichlorophenyl)ethyl)-3-(4-(((4-fluoro-1,2,3,4-tetrahydroisoquinolin-6-yl)methyl)sulfonyl)phenyl)urea |
| H1538 | 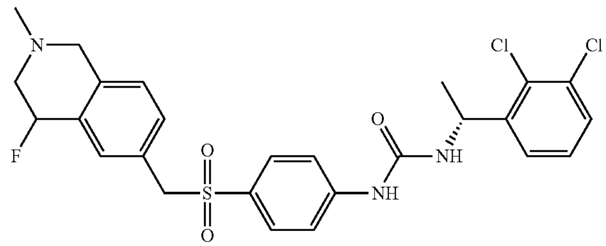 [SMILES: C[C@@H](NC(=O)Nc1ccc(S(=O)(=O)Cc2ccc3c(c2)C(F)CN(C)C3)cc1)c1cccc(Cl)c1Cl] | 1-((R)-1-(2,3-dichlorophenyl)ethyl)-3-(4-(((4-fluoro-2-methyl-1,2,3,4-tetrahydroisoquinolin-6-yl)methyl)sulfonyl)phenyl)urea |
| H1539 | 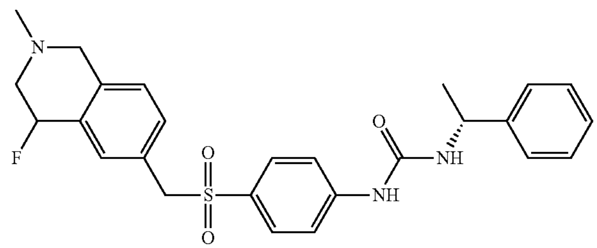 [SMILES: C[C@@H](NC(=O)Nc1ccc(S(=O)(=O)Cc2ccc3c(c2)C(F)CN(C)C3)cc1)c1ccccc1] | 1-(4-(((4-fluoro-2-methyl-1,2,3,4-tetrahydroisoquinolin-6-yl)methyl)sulfonyl)phenyl)-3-((R)-1-phenylethyl)urea |
| H1540 | 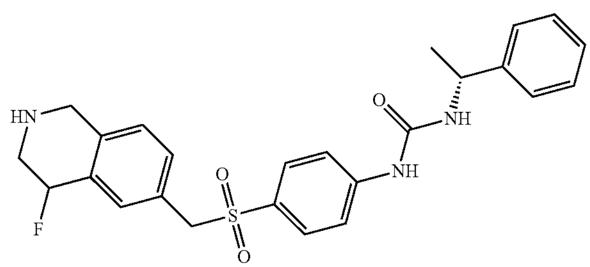 [SMILES: C[C@@H](NC(=O)Nc1ccc(S(=O)(=O)Cc2ccc3c(c2)C(F)CNC3)cc1)c1ccccc1] | 1-(4-(((4-fluoro-1,2,3,4-tetrahydroisoquinolin-6-yl)methyl)sulfonyl)phenyl)-3-((R)-1-phenylethyl)urea |
| H1541 | 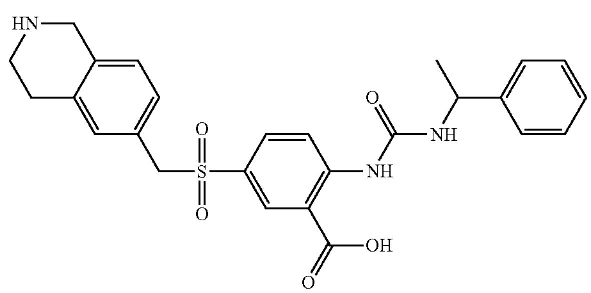 [SMILES: CC(NC(=O)Nc1ccc(S(=O)(=O)Cc2ccc3c(c2)CCNC3)cc1C(=O)O)c1ccccc1] | 2-(3-(1-phenylethyl)ureido)-5-(((1,2,3,4-tetrahydroisoquinolin-6-yl)methyl)sulfonyl)benzoic acid |
| H1542 | 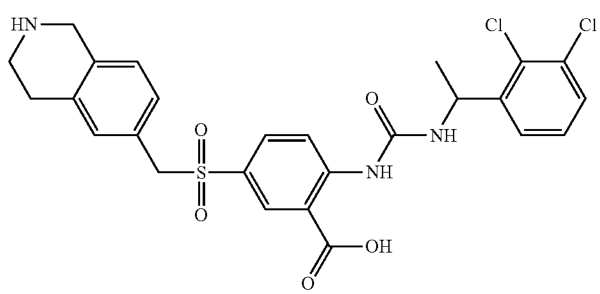 [SMILES: CC(NC(=O)Nc1ccc(S(=O)(=O)Cc2ccc3c(c2)CCNC3)cc1C(=O)O)c1cccc(Cl)c1Cl] | 2-(3-(1-(2,3-dichlorophenyl)ethyl)ureido)-5-(((1,2,3,4-tetrahydroisoquinolin-6-yl)methyl)sulfonyl)benzoic acid |

-continued

| | Chemical Structure | Chemical Name |
|---|---|---|
| H1543 | 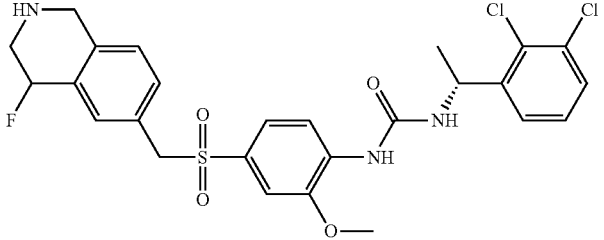 [SMILES: COc1cc(S(=O)(=O)Cc2ccc3c(c2)C(F)CNC3)ccc1NC(=O)N[C@H](C)c1cccc(Cl)c1Cl] | 1-((R)-1-(2,3-dichlorophenyl)ethyl)-3-(4-(((4-fluoro-1,2,3,4-tetrahydroisoquinolin-6-yl)methyl)sulfonyl)-2-methoxyphenyl)urea |
| H1544 | 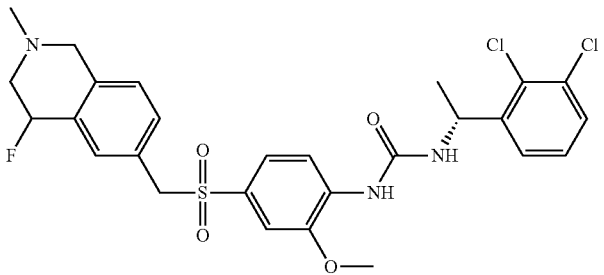 [SMILES: COc1cc(S(=O)(=O)Cc2ccc3c(c2)C(F)CN(C)C3)ccc1NC(=O)N[C@H](C)c1cccc(Cl)c1Cl] | 1-((R)-1-(2,3-dichlorophenyl)ethyl)-3-(4-(((4-fluoro-2-methyl-1,2,3,4-tetrahydroisoquinolin-6-yl)methyl)sulfonyl)-2-methoxyphenyl)urea |
| H1545 | 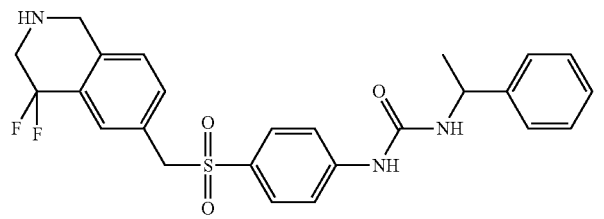 | 1-(4-(((4,4-difluoro-1,2,3,4-tetrahydroisoquinolin-6-yl)methyl)sulfonyl)phenyl)-3-(1-phenylethyl)urea |
| H1546 | 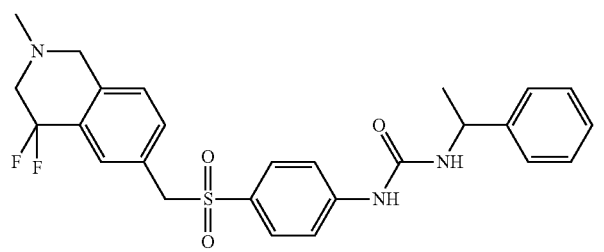 [SMILES: CC(NC(=O)Nc1ccc(S(=O)(=O)Cc2ccc3c(c2)C(F)(F)CN(C)C3)cc1)c1ccccc1] | 1-(4-(((4,4-difluoro-2-methyl-1,2,3,4-tetrahydroisoquinolin-6-yl)methyl)sulfonyl)phenyl)-3-(1-phenylethyl)urea |
| H1547 | 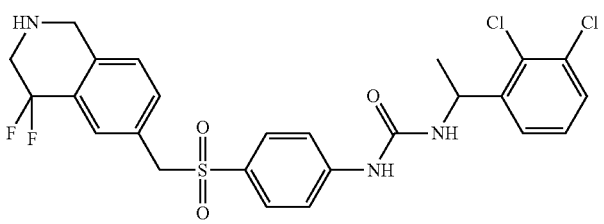 | 1-(1-(2,3-dichlorophenyl)ethyl)-3-(4-(((4,4-difluoro-1,2,3,4-tetrahydroisoquinolin-6-yl)methyl)sulfonyl)phenyl)urea |
| H1548 | 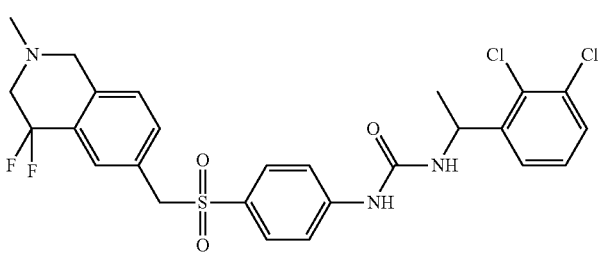 [SMILES: CC(NC(=O)Nc1ccc(S(=O)(=O)Cc2ccc3c(c2)C(F)(F)CN(C)C3)cc1)c1cccc(Cl)c1Cl] | 1-(1-(2,3-dichlorophenyl)ethyl)-3-(4-(((4,4-difluoro-2-methyl-1,2,3,4-tetrahydroisoquinolin-6-yl)methyl)sulfonyl)phenyl)urea |

| Chemical Structure | Chemical Name |
|---|---|
| H1549 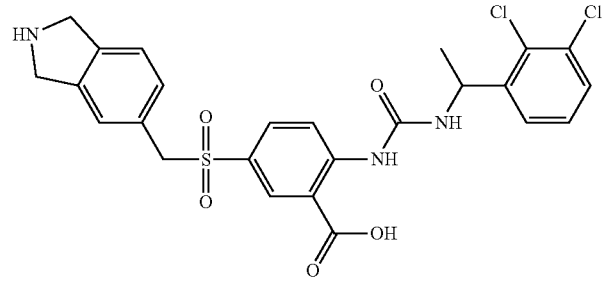 | 2-(3-(1-(2,3-dichlorophenyl)ethyl)ureido)-5-((isoindolin-5-ylmethyl)sulfonyl)benzoic acid |

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, cyclohexenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "hydroxylalkyl" refers to an alkyl group having one or more OH substituents. Example hydroxyalkyl groups include $CH_2OH$, $C_2H_4OH$, $C_3H_6OH$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems as well as spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, pentene, hexane, and the like. In some embodiments, cycloalkyl groups can have from about 3 to about 10, or about 3 to about 7 ring-forming carbon atoms.

As used herein, "heterocyclyl" or "heterocycle" refers to a saturated or unsaturated cyclic hydrocarbon wherein one or more of the ring-forming carbon atoms of the cyclic hydrocarbon is replaced by a heteroatom such as O, S, or N. Heterocyclyl groups can be aromatic (e.g., "heteroaryl") or non-aromatic (e.g., "heterocycloalkyl"). Heterocyclyl groups can also correspond to hydrogenated and partially hydrogenated heteroaryl groups. Heterocyclyl groups can include mono- or polycyclic (e.g., having 2, 3 or 4 fused rings) ring systems. Heterocyclyl groups can be characterized as having 3-14 or 3-7 ring-forming atoms. In some embodiments, heterocyclyl groups can contain, in addition to at least one heteroatom, from about 1 to about 13, about 2 to about 10, or about 2 to about 7 carbon atoms and can be attached through a carbon atom or heteroatom. In further embodiments, the heteroatom can be oxidized (e.g., have an oxo substituent) or a nitrogen atom can be quaternized. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like, as well as any of the groups listed below for "heteroaryl" and "heterocycloalkyl." Further example heterocycles include pyrimidinyl, phenanthridinyl, phenanthrolinyl, phenazinyl, phenothiazinyl, phenoxathiinyl, phenoxazinyl, phthalazinyl, piperazinyl, piperidinyl, 3,6-dihydropyridyl, 1,2,3,6-tetrahydropyridyl, 1,2,5,6-tetrahydropyridyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4- thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzo-thiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, deca-hydroquinolinyl, 2H,6H-1,5,2dithiazinyl, dihydrofuro[2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl and isoxazolyl. Further examples of heterocycles include azetidin-1-yl, 2,5-dihydro-1H-pyrrol-1-yl, piperindin-lyl, piperazin-1-yl, pyrrolidin-1-yl, isoquinol-2-yl, pyridin-1-yl, 3,6-dihydropyridin-1-yl, 2,3-dihydroindol-1-yl, 1,3,4,9-tetrahydrocarbolin-2-yl, thieno[2,3-c]pyridin-6-yl, 3,4,10,10a-tetrahydro-1H-pyrazino[1,2-a]indol-2-yl, 1,2,4,4a,5,6-hexahydro-pyrazino[1,2-a]quinolin-3-yl, pyrazino[1,2-c]quinolin-3-yl, diazepan-1-yl, 1,4,5,6-tetrahydro-2H-benzo[fJisoquinolin-3-yl, 1,4,4a,5,6,10b-hexahydro-2H-benzo[f]isoquinolin-3-yl, 3,3a,8,8a-tetrahydro-1H-2-aza-cyclopenta[a]inden-2-yl, and 2,3,4,7-tetrahydro-1H-azepin-1-yl, azepan-1-yl.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "thioalkoxy" refers to an —S-alkyl group.

As used here, "haloalkoxy" refers to an —O-haloalkyl group. An example haloalkoxy group is OCF.

As used herein, "cycloalkyloxy" refers to —O-cycloalkyl.

As used herein, "aralkyl" refers to an alkyl group substituted by an aryl group.

As used herein, "cycloalkylalkyl" refers to an alkyl group substituted by an cycloalkyl group.

As used herein, "heterocyclylalkyl" refers to an alkyl moiety substituted by a heterocarbocyclyl group. Example heterocyclylalkyl groups include "heteroarylalkyl" (alkyl substituted by heteroaryl) and "heterocycloalkylalkyl" (alkyl substituted by heterocycloalkyl). In some embodiments, heterocyclylalkyl groups have from 3 to 24 carbon atoms in addition to at least one ring-forming heteroatom.

As used herein "oxo" refers to =O.

The compounds described herein can be asymmetric (e.g., having one or more stereocenters). The description of a compound without specifying its stereochemistry is intended to capture mixtures of stereoisomers as well as each of the individual stereoisomer encompassed within the genus.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Synthesis

The compounds of the formulae (I), (II), (III) (IV) (and other disclosed compounds), or their pharmaceutically acceptable salts or adducts, can be prepared by the methods as illustrated by examples described in the "Examples" section, together with synthetic methods known in the art of organic chemistry, or modifications and derivatisations that are familiar to those of ordinary skill in the art.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Green and P. G. M. Wuts, Protective Groups in Organic Synthesis, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectrometry (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Pharmaceutical Compositions

Pharmaceutical compositions for preventing and/or treating a subject are further provided comprising a therapeutically effective amount of a compound of Formula I, or a pharmaceutically acceptable salt thereof, and one or more pharmaceutically acceptable excipients.

A "pharmaceutically acceptable" excipient is one that is not biologically or otherwise undesirable, i.e., the material can be administered to a subject without causing any undesirable biological effects or interacting in a deleterious manner with any of the other components of the pharmaceutical composition in which it is contained. The carrier can be selected to minimize any degradation of the active ingredient and to minimize any adverse side effects in the subject, as would be well known to one of skill in the art. The carrier can be a solid, a liquid, or both.

The disclosed compounds can be administered by any suitable route, preferably in the form of a pharmaceutical composition adapted to such a route, and in a dose effective for the treatment or prevention intended. The active compounds and compositions, for example, can be administered orally, rectally, parenterally, ocularly, inhalationaly, or topically. In particular, administration can be epicutaneous, inhalational, enema, conjunctival, eye drops, ear drops, alveolar, nasal, intranasal, vaginal, intravaginal, transvaginal, ocular, intraocular, transocular, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc.

Suitable carriers and their formulations are described in Remington: The Science and Practice of Pharmacy (19th ed.) ed. A.R. Gennaro, Mack Publishing Company, Easton, Pa., 1995. Oral administration of a solid dose form can be, for example, presented in discrete units, such as hard or soft capsules, pills, cachets, lozenges, or tablets, each containing a predetermined amount of at least one of the disclosed compound or compositions. In some forms, the oral administration can be in a powder or granule form. In some forms, the oral dose form is sub-lingual, such as, for example, a lozenge. In such solid dosage forms, the compounds of Formula I are ordinarily combined with one or more adjuvants. Such capsules or tablets can contain a controlled-release formulation. In the case of capsules, tablets, and pills, the dosage forms also can comprise buffering agents or can be prepared with enteric coatings.

In some forms, oral administration can be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also can comprise adjuvants, such as wetting, emulsifying, suspending, flavoring (e.g., sweetening), and/or perfuming agents.

In some forms, the disclosed compositions can comprise a parenteral dose form. "Parenteral administration" includes, for example, subcutaneous injections, intravenous injections, intraperitoneally, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Typically, an appropriate amount of a pharmaceutically acceptable carrier is used in the formulation to render the formulation isotonic. Examples of the pharmaceutically acceptable carrier include, but are not limited to, saline, Ringer's solution and dextrose solution. Other acceptable excipients include, but are not limited to, thickeners, diluents, buffers, preservatives, surface active agents and the like.

In some forms, the disclosed compositions can comprise a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation can include a compound which enhances absorption or penetration of the active ingredient through the skin or other affected areas. When the compounds and compositions are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes can also be used. Typical carriers include alcohol, water, mineral oil, liquid petrolatum, white petrolatum, glycerin, polyethylene glycol and propylene glycol. Penetration enhancers can be incorporated—see, for example, J Pharm Sci, 88 (10), 955-958, by Finnin and Morgan (October 1999).

Formulations suitable for topical administration to the eye include, for example, eye drops wherein the disclosed compound or composition is dissolved or suspended in suitable carrier. A typical formulation suitable for ocular or aural administration can be in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, can be incorporated together with a preservative, such as benzalkonium chloride. Such formulations can also be delivered by iontophoresis.

Other carrier materials and modes of administration known in the pharmaceutical art can also be used. The disclosed pharmaceutical compositions can be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients (3.sup.rd Ed.), American Pharmaceutical Association, Washington, 1999.

The disclosed compounds can be used, alone or in combination with other therapeutic agents, in the treatment or prevention of various conditions or disease states. The administration of two or more compounds "in combination" means that the two compounds are administered closely enough in time that the presence of one alters the biological effects of the other. The two or more compounds can be administered simultaneously, concurrently or sequentially.

Disclosed are pharmaceutical compositions comprising an effective amount of a compound of the invention or a pharmaceutically accepted salt thereof; and a pharmaceutically acceptable carrier or vehicle. These compositions may further comprise additional agents. These compositions are useful for modulating the activity of ghrelin receptor, thus to improve the prevention and treatment of ghrelin receptor associated human diseases such as obesity and/or metabolic disorders.

Methods

All of the methods of the invention may be practiced with a compound of the invention alone, or in combination with other agents.

The above-described compounds and compositions are useful for the inhibition, reduction, prevention, and/or treatment of diseases which are pathophysiologically modulated by the ghrelin receptor. Accordingly, in some forms, disclosed are methods of preventing and/or treating diseases which are pathophysiologically modulated by the ghrelin receptor, comprising administering to a subject a therapeutically effective amount of a compound of Formula I as disclosed above, or a pharmaceutically acceptable salt thereof.

Suitable subjects can include mammalian subjects. Mammals include, but are not limited to, canine, feline, bovine, caprine, equine, ovine, porcine, rodents, lagomorphs, primates, and the like, and encompass mammals in utero. In some forms, humans are the subjects. Human subjects can be of either gender and at any stage of development.

Diseases modulated by the ghrelin receptor, and potentially treatable by the methods disclosed herein, include obesity, diabetes and substance abuse. A therapeutically effective amount may vary widely depending on the severity of the disease, the age and relative health of the subject, the potency of the compound used and other factors. Therapeutically effective amounts of compounds of Formula I, II, III, and IV may range from approximately 0.01 microgram per Kg (µg/Kg) body weight per day to about 100 mg/Kg body weight per day.

Definitions of Terms

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

1. A, an, the

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

2. Abbreviations

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, "M" for molar, and like abbreviations).

3. About

The term "about," when used to modify the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. Whether modified by the term "about" the claims appended hereto include equivalents to these quantities.

4. Comprise

Throughout the description and claims of this specification, the word "comprise" and variations of the word, such as "comprising" and "comprises," means "including but not limited to," and is not intended to exclude, for example, other additives, components, integers or steps.

5. Ghrelin Receptor Agonist

A ghrelin receptor agonist is any molecule that binds to and activates the Ghrelin receptor in the cells.

6. Ghrelin Receptor Antagonist

A ghrelin receptor antagonist is any molecule that binds to and inhibits the activity of Ghrelin receptor.

7. Ghrelin Receptor Inverse Agonist

A ghrelin receptor inverse agonist is any molecule that binds to and decreases the activity of Ghrelin receptor to below the basal or constitutive level.

8. Pathophysiologically Mediated by Ghrelin Receptor

Something is "pathophysiologically mediated by the ghrelin receptor" if the ghrelin receptor is involved in the functional changes in body associated with or resulting from disease or injury.

9. Agonism Action

Agonism action refers to the binding of a molecule to a receptor that leads to the activation of the receptor, thus triggering a cellular response similar to the cellular response for a known agonist for the receptor.

10. Antagonism Action

Antagonism action refers to the binding of a molecule to a receptor that leads to the inhibition of the receptor.

11. Inverse Agonism Action

Inverse agonism action refers to the binding of a molecule to a receptor that leads to the decrease in the basal activity of the receptor.

12. Modulate

To modulate, or forms thereof, means either increasing, decreasing, or maintaining a cellular activity mediated through a cellular target. It is understood that wherever one of these words is used it is also disclosed that it could be 1%, 5%, 10%, 20%, 50%, 100%, 500%, or 1000% increased from a control, or it could be 1%, 5%, 10%, 20%, 50%, or 100% decreased from a control.

13. Optional

"Optional" or "optionally" means that the subsequently described event or circumstance may or may not occur, and that the description includes instances where said event or circumstance occurs and instances where it does not.

14. Or

The word "or" or like terms as used herein means any one member of a particular list and also includes any combination of members of that list.

15. Publications

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

16. Subject

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

17. Treating

By "treating" or "treatment" is meant the medical management of a patient with the intent to cure, ameliorate, stabilize, or prevent a disease, pathological condition, or disorder. These terms include active treatment, that is, treatment directed specifically toward the improvement of a disease, pathological condition, or disorder, and also includes causal treatment, that is, treatment directed toward removal of the cause of the associated disease, pathological condition, or disorder. These terms can mean that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease. In certain situations a treatment can inadvertently cause harm. In addition, these terms include palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. These terms mean both treatment having a curing or alleviating purpose and treatment having a preventive purpose. The treatment can be made either acutely or chronically. It is understood that treatment can mean a reduction or one or more symptoms or characteristics by at least 5% 10%, 20%, 30%, 40%, 50%, 60%, 70%, 80%, 90%, 95%, 99%, 99.9%, 99.99%, 100%, relative to a control. In the context of these terms, preventing refers to the ability of a compound or composition (such as the disclosed compounds and compositions) to prevent a disease identified herein in patients diagnosed as having the disease or who are at risk of developing such disease. In this context, preventing includes the delaying the onset of the disease relative to a control. These terms do not require that the treatment in fact be effective to produce any of the intended results. It is enough that the results are intended.

18. Therapeutically Effective

The term "therapeutically effective" means that the amount of the composition used is of sufficient quantity to treat a subject as defined herein.

19. Toxicity

Toxicity is the degree to which a substance, molecule, is able to damage something, such as a cell, a tissue, an organ, or a whole organism, that has been exposed to the substance or molecule. For example, the liver, or cells in the liver, hepatocytes, can be damaged by certain substances. The methods of the present invention are preferably non-toxic.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

The following are examples of preparation of compounds of formulae (I), (II), (III) and (IV). These examples are intended to be purely exemplary and are not intended to limit the disclosure.

General Synthetic Schemes

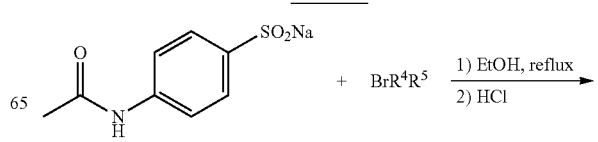

163

-continued

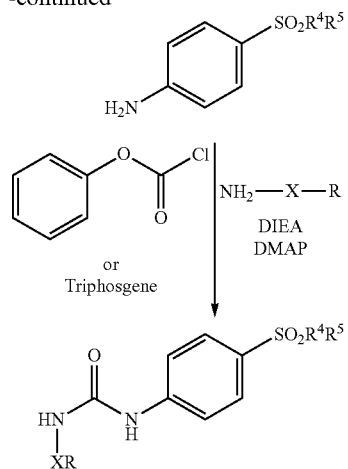

Scheme A constitutes a representative scheme for synthesizing the compounds of the present invention (where R, $R^4$ and $R^5$ are defined herein and where $R^4$ is $CH_2$) from the sodium 4-acetamidobenzenesulfinate intermediate.

Scheme B

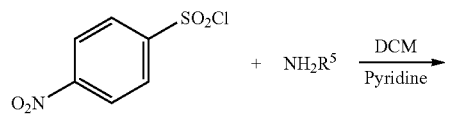

164

-continued

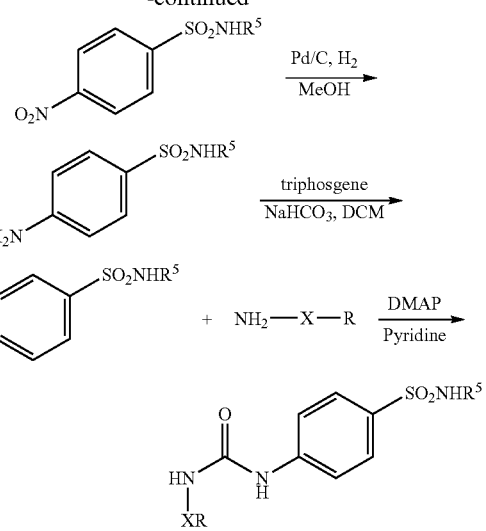

Scheme B constitutes a representative scheme for synthesizing the compounds of the present invention (where R, $R^4$ and $R^5$ are defined herein and where $R^4$ is NH) from the 4-nitrobenzenesulfonyl chloride intermediate.

Example 1

Synthesis of H0937

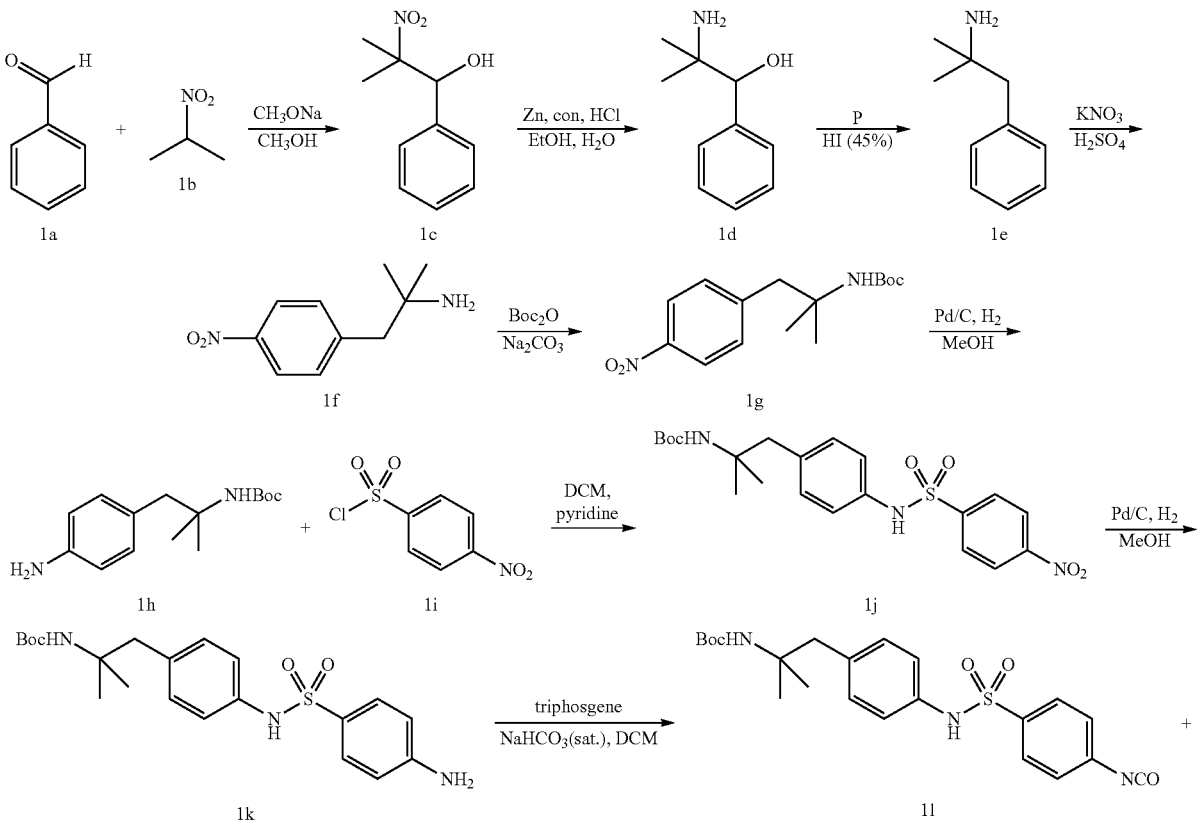

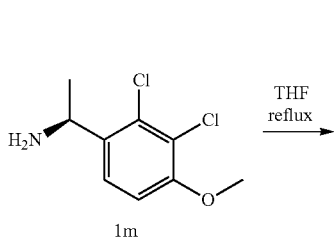
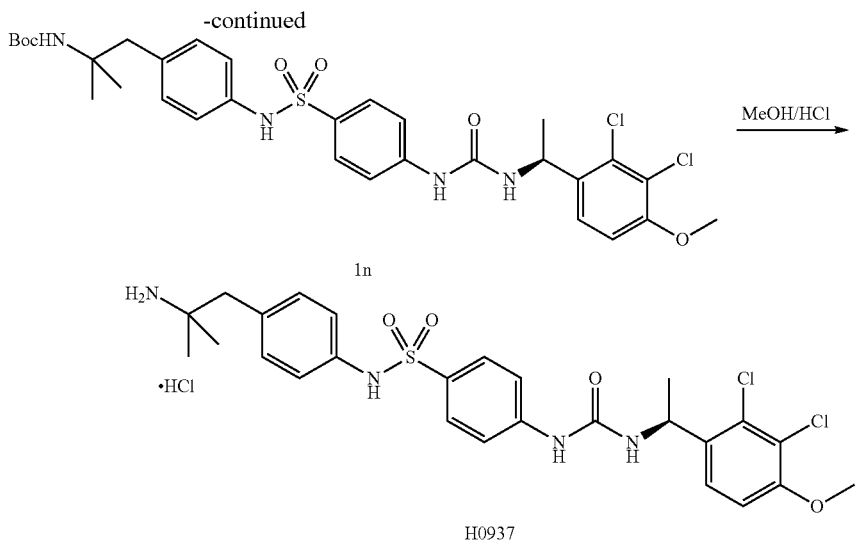

Synthesis of 1c: To a solution of sodium methanolate (2.16 g, 40 mmol) in MeOH (70 mL) were added 2-nitropropane (1b) (18.7 g, 210 mmol) and benzaldehyde (1a) (21.2 g, 200 mmol). The resulting mixture was stirred at room temperature overnight. The solvent was then evaporated under reduced pressure and the residue was dissolved in a mixture of water and ether (100 mL/100 mL). The ether layer was separated and washed with aqueous sodium hydrogen sulphite solution (100 mL×4), and then dried over anhydrous $Na_2SO_4$ and evaporated. The residue was purified by silica column chromatography (ethyl acetate: petroleum ether=1:5, v:v) to provide compound 1c (14.95 g, 38% yield).

Synthesis of 1d: To a solution of 1c (2.0 g, 10.25 mmol) in a mixture of EtOH (170 mL) and water (85 mL) was added 17 mL of con. HCl at room temperature, followed by Zinc powder (4.02 g, 61.15 mmol) in small portions. The resulting mixture was stirred at 70° C. for 4 hours, then cooled to room temperature and filtered. The filtrate was evaporated and the residue was purified by silica column chromatography (DCM:MeOH=20:1, v:v) to provide 1d (880 mg, 52% yield).

Synthesis of 1e: P (677 mg, 22 mmol) was slowly added to the solution of 1d (1.5 g, 9.1 mmol) in HI (22 mL 45% in water) at room temperature. The mixture was stirred at 135° C. overnight, and then cooled to room temperature. Water (100 mL) was added to the above mixture, which was filtered. Saturated aqueous $Na_2S_2O_3$ solution (100 mL) was added to the filtrate and was made basic with 40% NaOH (20 mL). The resulting mixture was extracted with ethyl acetate (100 mL×3). The combined ethyl acetate layer was washed with water and dried over anhydrous $Na_2SO_4$ and evaporated. The residue was purified by silica column chromatography (DCM: MeOH=30:1, v:v) to provide 1e (0.55 g, 41% yield).

Synthesis of 1f: 1e (7.0 g, 47 mmol) was added to con. $H_2SO_4$ (70 mL) and the mixture was cooled to −5° C. $KNO_3$ (4.7 g, 47 mmol) was added in small portions to the above mixture and stirred for 1 hour at −5° C. The mixture was then poured into ice-water and was adjusted to pH=10 with 40% NaOH aqueous solution. The resulting mixture was extracted with ethyl acetate (150 mL×3). The combined ethyl acetate layer was washed with brine, dried over anhydrous $Na_2SO_4$ and evaporated to provide 1f (6.5 g, 71% yield).

Synthesis of 1g: To a solution of 1f (6.4 g, 33 mmol) in THF (150 mL) was added aq. $Na_2CO_3$ solution (60 mL) and $Boc_2O$ (10.7 g, 49.5 mmol). The mixture was stirred at 50° C. overnight, and then cooled to room temperature. The solvent was evaporated under reduced pressure and the residue was partitioned between ethyl acetate and water (150 mL/150 mL). The organic layer was separated, dried over anhydrous $Na_2SO_4$ and evaporated. The residue was purified by silica column chromatography (ethyl acetate:petroleum ether=1:20, v:v) to provide 1g (9.5 g, 98% yield).

Synthesis of 1h: A mixture of 1g (2.0 g, 6.8 mmol) and 10% Pd/C (100 mg) in methanol (60 mL) was stirred under 1 atm hydrogen atmosphere at room temperature for 2 hours and then filtered. The filtrate was evaporated under reduced pressure and the residue was purified by silica column chromatography (ethyl acetate:petroleum ether=1:10, v:v) to provide 1h (1.0 g, 57% yield).

Synthesis of 1j: To a solution of 1h (250 mg, 0.95 mmol) in DCM (10 mL) was added pyridine (0.2 mL) and 1i (230 mg, 1.04 mmol). The mixture was stirred at room temperature overnight and evaporated under reduced pressure. The residue was purified by silica column chromatography (ethyl acetate:petroleum ether=1:5, v:v) to provide 1j (320 mg, 75% yield).

Synthesis of 1k: A mixture of 1j (320 mg, 0.71 mmol) and 10% Pd/C (50 mg) in methanol (20 mL) was stirred under 1 atm hydrogen atmosphere at room temperature for 2 hours and then filtered. The filtrate was evaporated under reduced pressure to provide crude 1k (298 mg, ca.100% yield).

Synthesis of 1l: To a solution of 1k (82 mg, 0.2 mmol) in DCM (10 mL) was added saturated aqueous $NaHCO_3$ solution (5 mL) at room temperature. Triphosgene (58 mg, 0.2 mmol) dissolved in DCM (1 mL) was added to the above mixture. The resulting mixture was stirred for 2 hours. DCM (20 ml) was then added to the mixture. The two layers were separated and the organic phase was washed by brine, dried over anhydrous $Na_2SO_4$ and evaporated under reduced pressure to give crude 1l (90 mg, ca.100% yield).

Synthesis of 1n: To a solution of 1l in THF (10 mL) was added 1m (36 mg, 0.16 mmol). The mixture was stirred at 70° C. overnight, then cooled and evaporated. The residue was purified by Prep-TLC (DCM:MeOH=10:1, v:v) to provide 1n (38 mg, 35% yield). LC-MS: 667.2 [M+1]+

Synthesis of H0937: To a solution of 1n (38 mg, 0.06 mmol) in MeOH (1 mL) was added HO/methanol solution (4 N, 1 mL). The mixture was stirred at room temperature overnight, then evaporated under reduced pressure to give H0937 (25 mg, 74% yield). $^1$H-NMR (CD$_3$OD, 400 MHz): 7.52 (d, 1H), 7.34 (d, 1H), 7.26 (d, 1H), 6.99-7.01 (m, 4H), 6.94 (d, 1H), 5.10-5.12 (m, 1H), 378 (s, 3H), 3.56 (t, 1H), 3.21 (s, 6H), 2.71 (s, 2H), 1.33 (d, 3H). LC-MS: 567.2[M+1]$^+$.

Example 2

Synthesis of H1027 & H1071

Synthesis of 2c: To a solution of 2b (1.96 g, 6.3 mmol) in dry DMF (40 mL) were added Pd(dppf)Cl$_2$ (1.03g, 1.26 mmol), TEA (3.18g, 31.5 mmol) and TES (2.92g, 25.2 mmol). The mixture was heated at 80° C. overnight under CO atmosphere, then cooled and added ethyl acetate (100 mL). The mixture was filtered and the filtrate was washed with water and brine, dried over anhydrous Na$_2$SO$_4$, and then evaporated under reduced pressure. The residue was purified by silica gel column chromatography (PE:EA=10:1, v:v) to provide 2c (1.1 g, 70% yield). LC-MS: 262 [M+1]$^+$.

Synthesis of 2d: To a solution of 2c (1.14 g, 4.4 mmol) in MeOH (20 mL) was added NaBH$_4$ (332 mg, 8.74 mmol) in portions at 0° C. After the addition was complete, the

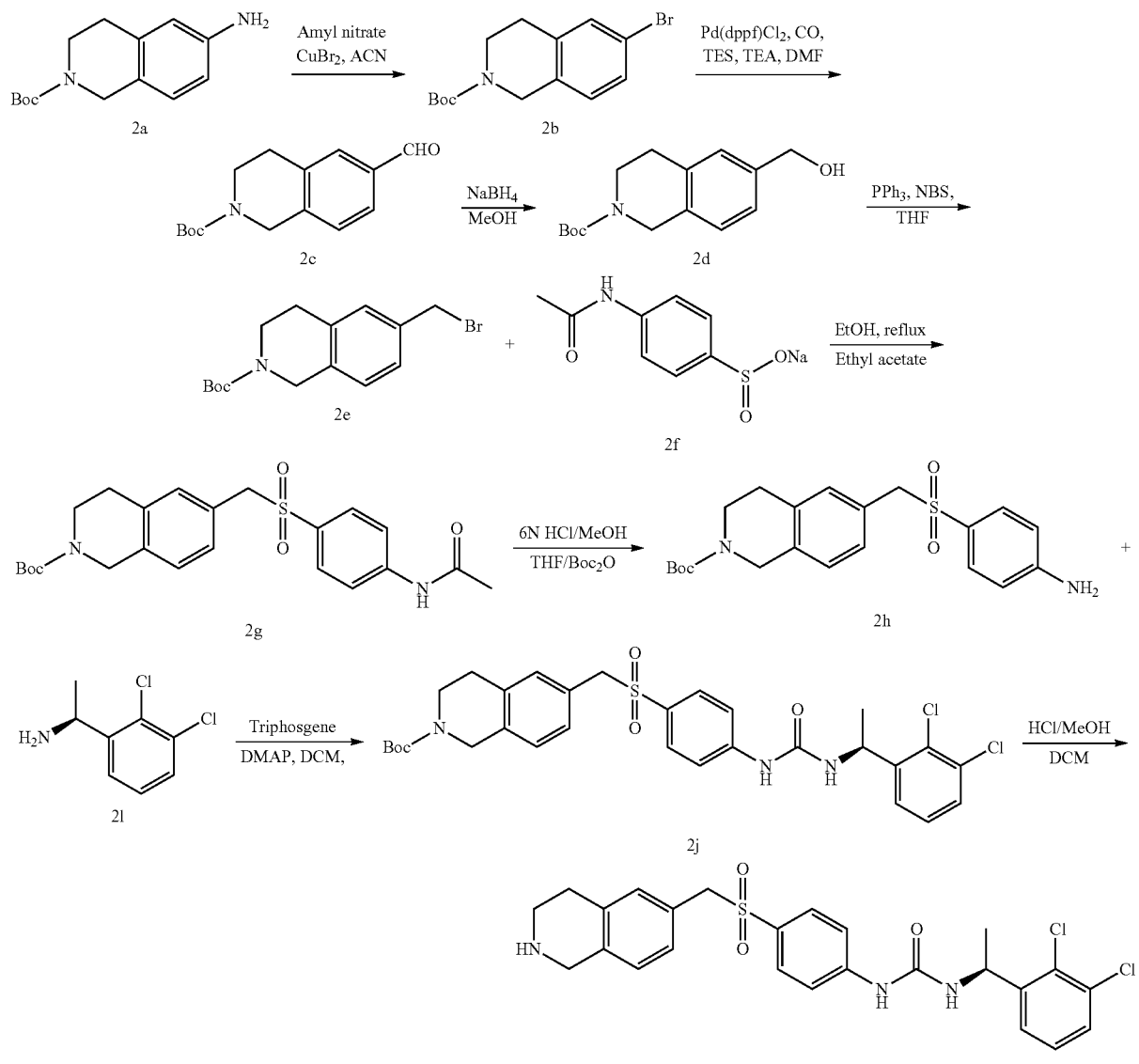

Synthesis of 2b: 2a (1.42 g, 5.7 mmol) was added to a mixture of amyl nitrate (1.42 g, 12.1 mmol) and CuBr$_2$ (2.16 g, 9.67 mmol) in CH$_3$CN (20 mL). The mixture was heated at 80° C. for 2 hours, then cooled and evaporated under reduced pressure. The residue was purified by silica gel column chromatography (PE:EA=10:1, v:v) to provide 2b (1.96 g, 78% yield) as a yellow oil. LC-MS: 312 [M+1]$^+$.

mixture was stirred for 1 hour at room temperature. Ethyl acetate (20 mL) was then added to the mixture. The mixture was washed with brine, dried over anhydrous Na$_2$SO$_4$ and evaporated to provide crude 2d (1.1 g, 96% yield). LC-MS: 264 [M+1]$^+$.

Synthesis of 2e: NBS (2.98 g, 16.7 mmol) was added in portions to a solution of 2d (1.1 g, 4.18 mmol) and PPh$_3$ (3.3 g, 12.6 mmol) in THF (20 mL) cooled to 0° C. After the addition was complete, the mixture was stirred for 1 hour at room temperature, and ethyl acetate (30 mL) was added to the mixture. The mixture was washed with water and brine, dried over anhydrous $Na_2SO_4$ and evaporated under reduced pressure. The residue was purified by silica gel column chromatography (PE:EA=10:1, v:v) to provide 2e (1.1 g, 83% yield). LC-MS: 326 [M+1]$^+$.

The DCM phase was separated and washed with water and brine and dried over anhydrous $Na_2SO_4$. The solvent was evaporated under reduced pressure, and the residue was re-dissolved in dry THF (5 ml). 2i (39.2 mg, 0.21 mmol) and DMAP (5 mg) were added to the above mixture and the resulting mixture was stirred for another 1 hour. The solution was evaporated under reduced pressure and the residue was purified by silica gel column chromatography (DCM: MeOH=20:1, v:v) to provide 2j (60 mg, 39% yield). LC-MS: 618 [M+1]$^+$.

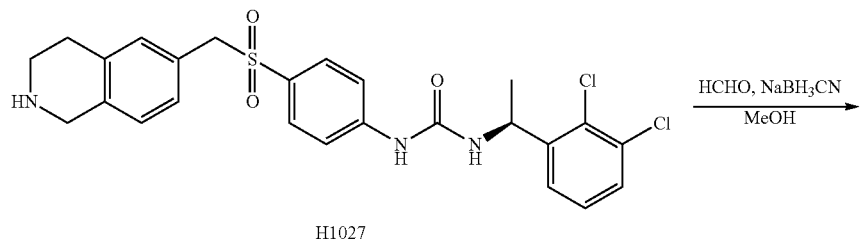

H1027

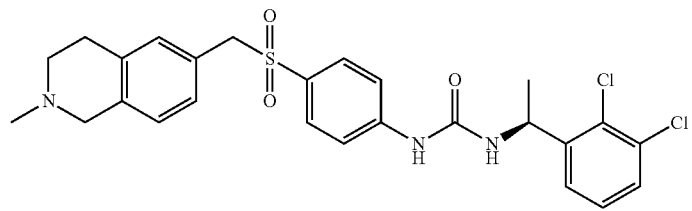

H1071

Synthesis of 2g: To a solution of 2e (1.1 g, 3.48 mmol) in EtOH (20 mL) was added 2f (1.0 g, 4.52 mmol) at room temperature. The mixture was then heated under reflux for 2 hours, cooled and evaporated under reduced pressure. Ethyl acetate (30 mL) was added to the residue. The mixture was washed with water and brine, dried over anhydrous $Na_2SO_4$ and evaporated under reduced pressure. The residue was purified by silica gel column chromatography (PE:EA=10:1, v:v) to provide 2g (1.5 g, 98% yield). LC-MS: 445 [M+1]$^+$.

Synthesis of 2h: A solution of 2g (1.51 g, 3.4 mmol) in a mixture of 6 N HCl (30 mL) and MeOH (30 mL) was heated at 80° C. for 2 hours, cooled and evaporated under reduced pressure. The residue was adjusted to pH=7 with saturated $Na_2CO_3$ solution. THF (30 mL) was added, followed by $Boc_2O$ (1.3 g, 4.1 mmol). The mixture was stirred at room temperature overnight. Ethyl acetate (30 mL) and water (30 mL) were added. The organic phase was separated and washed with water and brine and dried over anhydrous $Na_2SO_4$. The solvent was evaporated under reduced pressure, and the residue was purified by silica gel column chromatography (DCM:MeOH=20:1, v:v) to provide 2h (1.1 g, 80.3% yield). LC-MS: 403 [M+1]$^+$.

Synthesis of 2j: To a solution of compound 2h (100 mg, 0.25 mmol) in a mixture of sat. $NaHCO_3$ (2.5 ml) and DCM (10 mL) was added a solution of triphosgene (74 mg, 0.25 mmol) in DCM (2 mL) at 0° C. After the addition was complete, the mixture was stirred at room temperature for 2 hours, and then DCM (20 mL) was added to the mixture.

Synthesis of H1027: To a solution of 2j (60 mg, 0.1 mmol) in DCM (2 mL) was added HCl/MeOH (4 N, 5 mL) at room temperature. The mixture was stirred for 2 hours and then evaporated under reduced pressure. The residue was purified by Pre-HPLC to provide H1027 (28.4 mg, 57% yield). $^1$H-NMR (CDCl$_3$, 400 MHz): δ=7.39-7.41 (m, 2H), 7.27-7.31 (m, 4H), 7.07-7.11 (m, 1H), 6.79-6.95 (m, 1H), 6.72-6.81 (m, 1H), 5.59 (m, 1H), 5.22-5.26 (m, 1H), 4.23 (s, 1H), 4.15 (s, 1H), 3.87 (s, 2H), 3.67 (s, 1H), 2.92-3.00 (m, 2H), 2.52-2.62 (m, 2H), 1.41 (d, J=6.8 Hz, 3H). LC-MS: 518 [M+1]+.

Synthesis of H1071: To a solution of H1027 (25 mg, 0.05 mmol) in MeOH (5 mL) were added aqueous formaldehyde solution (40%, 0.1 mL), acetic acid (0.1 mL) and sodium acetate (20 mg), followed by NaBH$_3$CN (7 mg, 0.1 mmol). The mixture was stirred at room temperature for 2 hours and then evaporated. The residue was washed with aqueous NaHCO$_3$ solution and the mixture was extracted with CH$_2$Cl$_2$ (25 mL×3). The combined organic phase was dried over anhydrous Na$_2$SO$_4$ and concentrated under reduced pressure. The residue was purified by pre-HPLC to provide H1071 (20 mg, 75% yield) as light yellow solid. $^1$H-NMR (CD$_3$OD, 300 MHz): δ=7.41-7.59 (m, 6H), 7.29-7.32 (m, 1H), 7.17-7.20 (m, 1H), 6.98-7.09 (m, 2H), 5.30-5.33 (m, 1H), 4.54 (s, 1H), 4.42 (s, 1H), 4.27 (s, 2H), 3.59 (s, 1H), 3.02-3.08 (m, 3H), 2.87 (s, 3H), 1.48 (d, J=7.2 Hz, 3H) LC-MS: 532 [M+1]$^+$.

Example 3

Synthesis of H1060

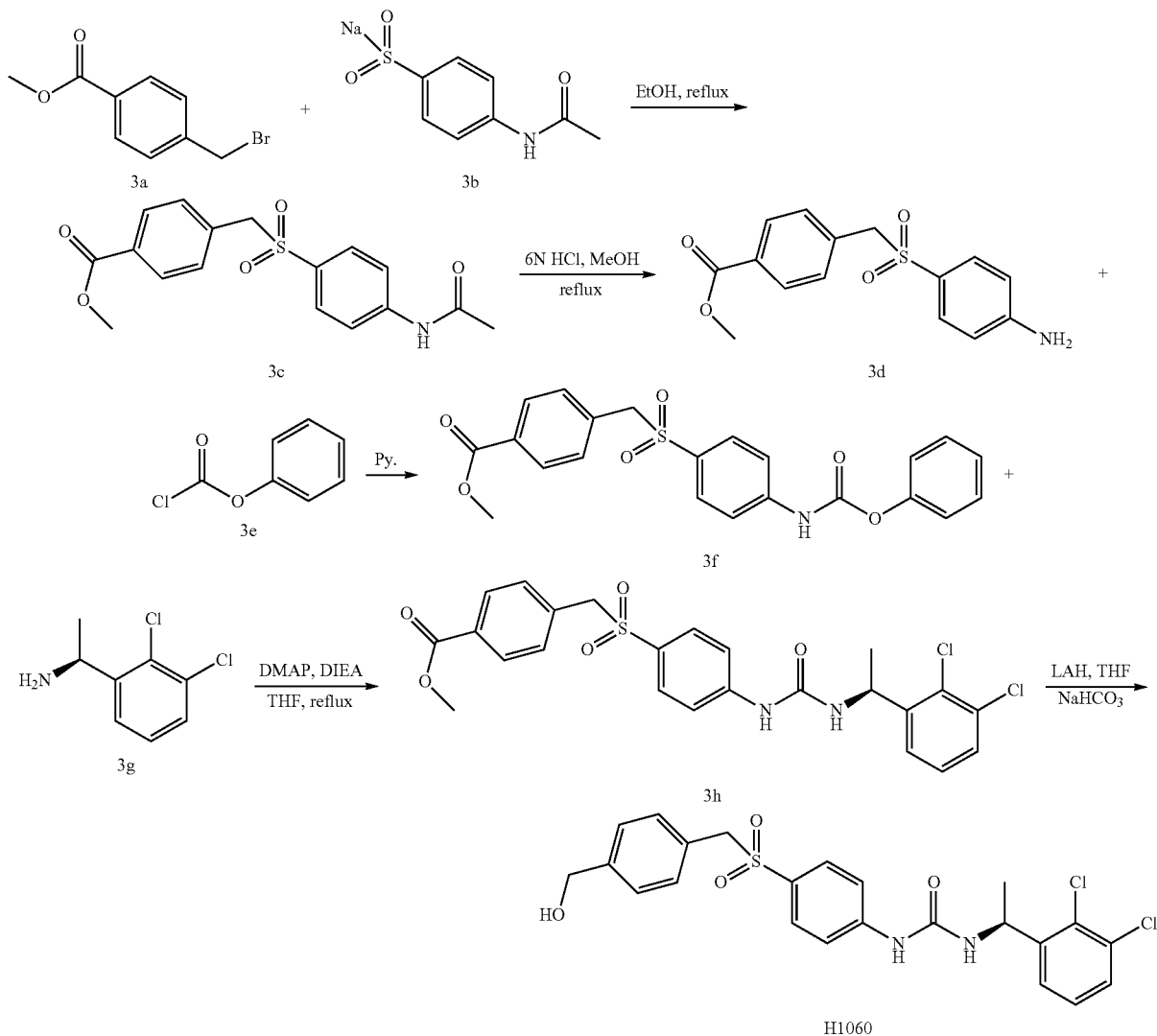

Synthesis of 3c: To a solution of 3a (1.5 g, 6.6 mmol) in EtOH (50 mL) was added 3b (1.74g, 7.9 mmol) at room temperature. The resulting mixture was heated under reflux for 2 hours, cooled and filtered to provide crude 3c (1.8 g, 81% yield) which was directly used in the next step. LC-MS: 348[M+1]$^+$.

Synthesis of 3d: To a suspension of 3c (1.8 g, 5.18 mmol) in MeOH (15 mL) was added HCl (6 N, 15 mL). The resulting mixture was heated under reflux for 16 hours, then cooled and filtered to provide 3d (1.2 g, 73% yield). LC-MS: 306 [M+1]$^+$.

Synthesis of 3f: To a solution of 3d (1.2 g, 3.71 mmol) in pyridine (15 mL) was added 3e (868 mg, 5.56 mmol) at room temperature. The resulting mixture was stirred for 3 hours and then evaporated under reduced pressure. The residue was partitioned between ethyl acetate and brine (50 mL/50 mL). The organic phase was separated, dried with anhydrous Na$_2$SO$_4$ and evaporated under reduced pressure. The residue was purified by silica column chromatography to provide 3f (1.1 g, 70% yield). LC-MS: 426 [M+1]$^+$.

Synthesis of 3h: To a solution of 3f (500 mg, 1.2 mmol) and 3g (265 mg, 1.4 mmol) in dry THF (15 mL) were added DMAP (15 mg, 0.12 mmol) and DIEA (301 mg, 2.3 mmol). The resulting mixture was heated under reflux for 16 hours, cooled to room temperature and evaporated under reduced pressure. The residue was partitioned between ethyl acetate and brine (50 mL/50 mL). The organic phase was separated, dried with anhydrous Na$_2$SO$_4$ and evaporated under reduced pressure. The residue was purified by silica column chromatography to provide 3h (414 mg, 68% yield). LC-MS: 521 [M+1]$^+$.

Synthesis of H1060: To a solution of 3h (414 mg, 0.80 mmol) in dry THF (15 mL) was added LAH (46 mg, 1.20 mmol) in portions at 0° C. After the addition was complete, the mixture was stirred for 2 hours and then quenched by aqueous NaHCO$_3$ solution (15 mL). The mixture was extracted with ethyl acetate (15 mL×3). The combined organic layer was washed with brine, dried over anhydrous Na$_2$SO$_4$ and evaporated under reduced pressure. The residue was purified by silica column chromatography to provide H1060 (278 mg, 71% yield). $^1$H-NMR (CD$_3$OD, 400 MHz): δ=7.39-7.47 (m, 6H), 7.29-7.31 (m, 1H), 7.24 (d, J=8 Hz, 2H), 7.08 (d, J=8 Hz, 2H), 5.29 (q, 1H), 4.56 (s, 2H), 4.42 (s, 2H), 1.46 (d, J=6.8 Hz, 3H). LC-MS: 493[M+1]+.

Example 4

Synthesis of H1148 & H1194

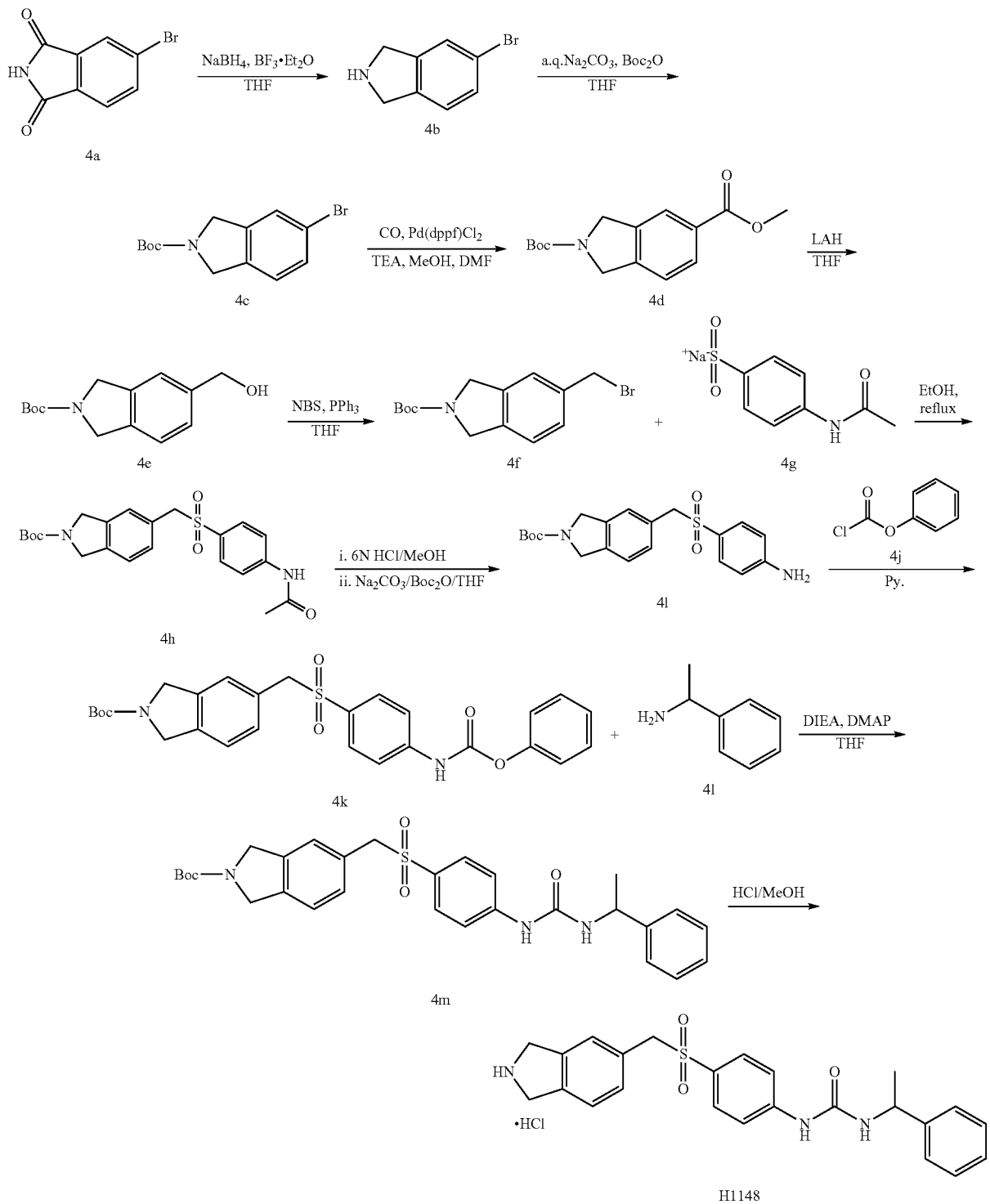

Synthesis of 4b: To a solution of 4a (10 g, 44.4 mmol) in THF (200 mL) was added NaBH$_4$ (17.6 g, 464.8 mmol), followed by BF$_3$·Et$_2$O (170 ml, 519.2 mmol) dropwise at room temperature. The mixture was then heated at 80° C. overnight, cooled to 0° C. and adjusted to pH 13 with aqueous NaOH solution. The mixture was extracted with ethyl acetate (100 mL×3). The combined organic phase was washed with water, brine and dried over anhydrous Na$_2$SO$_4$. The solvent was evaporated under reduced pressure and the residue was purified by silica gel column chromatography (DCM:MeOH=10:1, v:v) to provide 4b (7.3 g, 83% yield). LC-MS: 198 [M+1]$^+$.

Synthesis of 4c: To a solution of 4b (6 g, 30 mmol) in THF (100 mL) was added saturated Na$_2$CO$_3$ solution (25 mL), followed by Boc$_2$O (33 g, 151 mmol). The mixture was stirred at room temperature for 2 hours and evaporated under reduced pressure. The residue was extracted with ethyl acetate (50 mL×3). The combined organic phase was washed with brine, dried over anhydrous Na$_2$SO$_4$ and evaporated under reduced pressure. The residue was purified by silica gel column chromatography (PE:EA=10:1, v:v) to provide 4c (9 g, ca. 100% yield). LC-MS: 298 [M+1]$^+$.

Synthesis of 4d: To a solution of 4c (9 g, 30.3 mmol) in a mixture of MeOH (30 mL) and DMF (30 mL) were added Pd(dppf)Cl$_2$ (1.6 g, 2 mmol) and TEA (6.12 g, 60.6 mmol). The mixture was heated at 80° C. overnight under CO atmosphere, cooled and evaporated under reduced pressure. The residue was purified by silica gel column chromatography (PE:EA=10:1, v:v) to provide 4d (5.8 g, 69% yield). LC-MS: 278 [M+1]$^+$.

Synthesis of 4e: To a solution of 4d (5.8 g, 21 mmol) in THF (100 ml) was slowly added LAH (1.6 g, 42 mmol) at 0° C. After the addition was complete, the mixture was stirred for 2 hours at room temperature. Water (1.6 mL) and aqueous NaOH (10%, 1.6 mL) were slowly added, and the mixture was filtered. The filtrate was evaporated under reduced pressure and the residue was purified by silica gel column chromatography (PE:EA=3:1, v:v) to provide 4e (3.23 g, 62% yield). LC-MS: 250 [M+1]$^+$.

Synthesis of 4f: NBS (4.6 g, 26 mmol) was added in portions to a solution of 4e (3.23 g, 130 mmol) and PPh$_3$ (6.8 g, 26 mmol) in THF (150 mL) cooled to 0° C. After the addition was complete, the mixture was stirred for 3 hours at room temperature and then evaporated under reduced pressure. The residue was purified by silica gel column chromatography (PE:EA=3:1, v:v) to provide 4f (2 g, 50% yield). LC-MS: 312 [M+1]$^+$.

Synthesis of 4h: To a solution of 4f (2 g, 6.4 mmol) in EtOH (50 mL) was added 4g (2.8 g, 12.7 mmol) at room temperature. The mixture was heated at 80° C. overnight, cooled and evaporated under reduced pressure. The residue was dissolved in ethyl acetate (50 mL), washed with water and brine, dried over anhydrous Na$_2$SO$_4$, and evaporated under reduced pressure. The residue was purified by silica gel column chromatography (PE:EA=1:1, v:v) to provide 4h (1.9 g, 72% yield) as a white solid. LC-MS: 431 [M+1]$^+$.

Synthesis of 4i: A solution of 4h (1.9 g, 4.5 mmol) in 6 N HCl (20 mL) and MeOH (40 mL) was heated at 80° C. overnight, cooled and evaporated under reduced pressure. The residue was dissolved in a mixture of saturated Na$_2$CO$_3$ (20 ml) and THF (40 mL), and Boc$_2$O (1.45 g, 5.0 mmol) was then added. The mixture was stirred at room temperature overnight. Ethyl acetate (40 mL) and water (40 mL) were added to the above mixture. The organic phase was separated, washed with water and brine, dried over anhydrous Na$_2$SO$_4$ and evaporated under reduced pressure. The residue was purified by silica gel column chromatography (PE:EA=1:1, v:v) to provide 4i (1.36 g, 70% yield). LC-MS: 389 [M+1]$^+$.

Synthesis of 4k: To a solution of 4i (1.36 g, 3.50 mmol) in pyridine (20 mL) was added 4j (821 mg, 5.25 mmol) at room temperature. The mixture was stirred for 3 hours and then evaporated under reduced pressure. The residue was partitioned between ethyl acetate (20 mL) and brine (20 mL). The organic phase was separated, washed with brine, dried with anhydrous Na$_2$SO$_4$ and evaporated under pressure. The residue was purified by silica gel column chromatography (PE:EA=1:1, v:v) to provide 4k (1.24 g, 70% yield). LC-MS: 509 [M+1]$^+$.

Synthesis of 4m: To a solution of 4k (6.0 g, 11.8 mmol) and 4l (1.57 g, 13.0 mmol) in dry THF (150 mL) were added DMAP (100 mg, 0.008 mmol) and DIEA (10 mL, 60 mmol) at room temperature. The resulting mixture was heated at 80° C. overnight and evaporated under reduced pressure. The residue was partitioned between ethyl acetate (200 mL) and brine (200 mL). The organic phase was separated, dried with anhydrous Na$_2$SO$_4$ and evaporated under reduced pressure. The residue was purified by silica gel column chromatography (DCM:HCl=20:1, v:v) to provide 4m (4.0 g, 63.3% yield). LC-MS: 536 [M+1]$^+$.

Synthesis of H1148: To a solution of 4m (4.0 g, 7.5 mmol) in DCM (10 mL) was added HCl/MeOH (4 N, 50 mL) at room temperature. The solution was stirred for 2 hours and then filtered to provide H1148 (3.34 g, 94.4% yield). $^1$H NMR (CD$_3$OD, 400 MHz): δ=7.41 (s, 3H), 7.23-7.25 (m, 5H), 7.15 (s, 1H), 7.05 (d, J=7.6 Hz, 1H), 4.81 (q, 1H), 4.49 (s, 2H), 4.45 (s, 2H), 4.40 (s, 2H), 1.38 (d, J=6.8 Hz, 3H). LC-MS: 436 [M+1]$^+$.

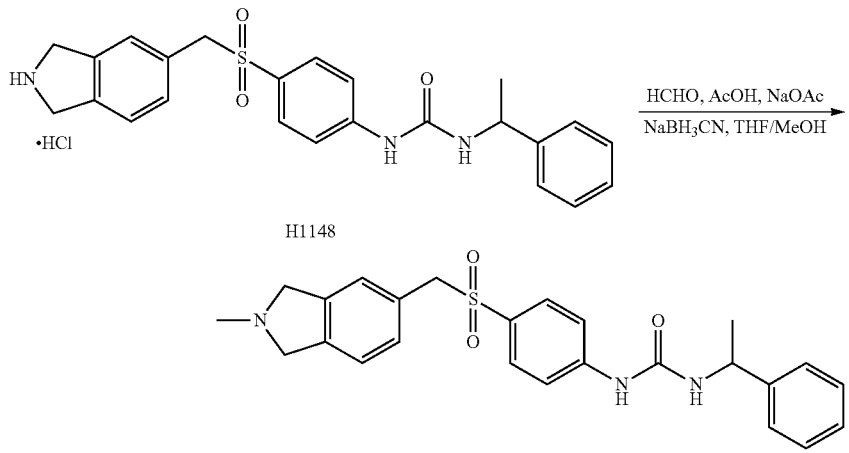

Synthesis of H1194: To a solution of H1148 (3.34 g, 7.1 mmol) in a mixture of THF (47 mL) and MeOH (47 mL) were added aqueous formaldehyde solution (40%, 9.5 mL), AcOH (1.0 mL) and NaOAc (1.0 g), followed by NaBH$_3$CN (895 mg, 14.2 mmol). The mixture was stirred for 3 hours at room temperature and evaporated under reduced pressure. Aqueous Na$_2$CO$_3$ solution (100 mL) was added and the mixture was extracted with DCM (100 mL×3). The combined organic phase was dried with anhydrous Na$_2$SO$_4$ and evaporated under reduced pressure. The residue was purified by silica gel column chromatography (DCM:HCl=20:1, v:v) to provide H1194 (2.3 g, 75% yield). $^1$H-NMR (CD$_3$OD, 400 MHz): δ=7.38-7.39 (m, 4H), 7.20-7.25 (m, 3H), 7.09-7.14 (m, 1H), 6.94-6.97 (m, 1H), 4.80 (q, 1H), 4.34 (s, 2H), 4.14 (s, 2H), 4.10 (s, 2H), 1.37 (d, J=7.2 Hz, 3H). LC-MS: 450[M+1]+.

Evaluation of Inverse Agonist on Food Intake Test in Mouse:

Male C57BL/6J mice, 18-22 g body weight, were fasted overnight (16 h before compound administration) and placed in a regular light dark cycle (6:00-18:00 light/18:00-6:00 dark). After 1 wk acclimation, animals were sorted into two groups (n=6 each, 2 per cage) based on body weight. Animals in group one were be treated with vehicle and animals in group 2 were treated with the test agent (n=6 for each group). The cumulative food intake was evaluated at 1, 2, 4, 8 and 24 hrs after drug or vehicle treatment. Food intake was measured by subtracting uneaten food from the initial premeasured food.

The following table presents representative compounds of Formula I with biological data including the ghrelin antagonist/agonist activity in vitro (Example A) and mouse food intake results (Example B). The data clearly demonstrates that compounds of Formula I are ghrelin receptor modulators and are useful in preventing and/or treating diseases associated with ghrelin receptor, for example, obesity.

Evaluation of Ghrelin Inverse Agonist Potency (EC$_{50}$) with IP-1 Assay:

HEK293 cells stably expressing recombinant human ghrelin receptor (HEK293/GRLN) were used in the IP-One HTRF assay. One day before the test, cells were seeded at a density of 1.5×10$^4$/well in a Matrigel® coated 384-well plate with 30 μL of complete Dulbecco's Modified Eagle's Medium and incubated at 37° C. in 5% CO$_2$ for 18-22 hours. On the test day, the medium was removed by centrifugation at 600 rpm for 30 seconds, and 20 μL of stimulation buffer containing 1x tested compound was added with Bravo (Agilent technologies). The plate was then incubated at 37° C. 5% CO$_2$ for 1 hour. After the incubation, 5 μL of IP1-d2 and 5 μL of Tb-Cryp were added to all wells using multidrop Combi(Thermo). After additional incubation at room temperature for 1 hour, the plates were read on Envision with 620 and 665 (Perkin Elmer).

Evaluation of Ghrelin Agonist (EC$_{50}$) and Antagonist Potency (IC$_{50}$) with Calcium FLIPR Assay:

The intracellular calcium assay was carried out in a 384-well format FLIPR™ (Molecular Device) HEK293/GHSR1a cell line. Cells were seeded 24 hr prior to the experiments at an optimal density per well. Preincubation with selected calcium dye lasted for 30-60 min at room temperature or 37° C. Test compounds, dissolved in DMSO, were added at the appropriate time and incubated for 15 min followed by the addition of ghrelin with FlexStation or FLIPR. Relative fluorescence was monitored by the FLIPR™ Molecular Device. EC$_{50}$ and IC$_{50}$ values were estimated from dose-response data using GraphPad Prism software. To check for GHSR-1a agonism, the compound was added at t=20 sec. and the calcium response was followed for 2 minutes. To check for GHSR-1a antagonism, the compound and Ghrelin (10 nM) were added to the cells at t=20 sec. and the calcium response was measured for 2 minutes. The potency of the antagonist was calculated by its ability to reduce the ghrelin response. Dose-response curves were made for relevant antagonists.

Metabolic Stability Study

The metabolic stability of compounds in human, dog, rat and mouse liver microsomes was performed according the experimental conditions reported below:

| Substrate (μM) | Protein (mg/ml) | Sample replicate | NADPH (mM) |
|---|---|---|---|
| 1 | 0.5 | N = 2 | 1.3 | a) Prepare the following 5 stock solutions:
  1. Test compound stock solutions: dilute 10 mM solution of dextromethorphan (Dtr) in DMSO, 10 mM solution of diphenhydramine (DPA) in DMSO, 10 mM solution of omeprazole (Ome) in DMSO, 10 mM solution of verapamil (Ver) in DMSO, and 10 mM of an inverse agonist compound in DMSO to 0.25 mM solution each with acetonitrile/water (70/30).
  2. Buffer: 100 mM potassium phosphate Buffer (PBS) at pH 7.4
  3. Liver microsomes (20 mg/ml): Thaw in 37° C. water bath quickly
  4. 2000 μL: of NADPH regenerating system (1.3 mM). Place this system on ice before use:

| | |
|---|---|
| 330 μl | 100 mM G6P |
| 1300 μl | 10 mM NADP |
| 5 μl | 1200 U/ml G6PD |
| 365 μl | PBS buffer |

5. Quench solution: acetonitrile with IS for LC-NIS/NIS analysis b) Dilute the 20 mg/mL stock liver microsomes to 0.628 mg/mL of protein with 100 mM PBS.

c) Aliquot 398 μL of microsomes protein mixture (0.628 mg/mL) into the incubation plate and place the plate on ice.

d) Spike 2 μL of a substrate stock solution into the incubation wells filled with 398 μL of the protein mixture in order to obtain a test compound concentration of 1.25 μM in each well.

e) Pipette 80 μL of the test compound and microsomes protein mixture into the wells of a stop plate pre-filled with 300 μL of cold quench solution and 20 μL of NADPH regenerating system. The test compound concentration in the wells, measured by LC-MS/MS, represents the concentration at time=0.

f) To determine the test compound concentration when t≠0, pre-incubate the NADPH regenerating system and the incubation plate containing the remaining 320 μL of incubation mixture (microsomes protein and test compound) for 5 minutes at 37° C.

g) Start the incubation reaction by adding 80 μL NADPH regenerating system to each well containing the remaining 320 μL incubation mixture.

h) After 10 min., 30 min., and 90 min. of incubation at 37° C., transfer 100 μL of the incubation mixture (microsomes protein, test compound, and NADPH) into the wells of a stop plate pre-filled with 300 μL of the cold quench solution. Shake well.

i) Centrifuge the stop plate at 5000×g for 10 minutes. Collect and dilute the supernatant 3 times with distilled water. Sample and analyze the test compound concentration for all the wells by LC-MS/MS.

Animal PK Studies via i.v. (intravenous), p.o. (orally) and s.c. (subcutaneous) administrations All treated animals received a single dose of a test compound (either through i.v., p.o., or s.c. administration) according to the regimen shown in the following table:

| Route of Dose | Number of Animals | Dose Level (mg/kg) | Dose volume (mL/kg) |
|---|---|---|---|
| i.v., s.c. | 3 male | 5 | 5 |
| p.o. | 3 male | 10 | 10 |

For oral dose groups, appropriate amount of test compound was prepared in the following formulation carrier: 1% DMSO (increase to 5% maximum if necessary) and 0.5% Methycellulose. Each mouse or rat received by oral gavage 10 mL/kg of the formulation mixture.

For i.v. and s.c dose groups, appropriate amount of test compound was dissolved in 1% DMSO (increase to 5% maximum if necessary), 99% of 20% HP-β-Cyclodextron (w/v). The pH was adjusted accordingly. Each mouse or rat received 5 mL/kg of the formulation mixture. i.v. dose was administered by tail vein injection. Subcutaneous injection was administered over the shoulders, into the loose skin over the neck. At designated time points (e.g., i.v. and s.c.: 0.083, 0.25, 0.5, 1, 2, 4, 8 and 24 hrs; p.o.: 0.25, 0.5, 1, 2, 4, 8 and 24 hrs), systemic samples of blood (50 μL in mouse or 500 μL in rat) were collected by puncture (submandibular vein in mouse or jugular vein in rat) into vacutainers containing EDTA-K2 as anti-coagulant. The blood was centrifuged at 6000 rpm for 8 min at 4° C. to obtain plasma. All plasma samples were stored at −20° C. All plasma samples were added to acetonitrile for protein precipitation and quantitatively analyzed by LC-MS/MS.

Food Intake Study—Evaluation of GHSR1a inverse agonists on Food Intake Test in Mouse:

Twelve male C57BL/6J mice, weighing 18-22 g each, were fasted overnight (16 h before compound administration) and placed in a regular light dark cycle (6:00-18:00 light/18:00-6:00 dark). After 1 week acclimation, animals were sorted into two groups (n=6 each, 2 per cage) based on body weight. Animals in group one were treated with carrier minus the test compound. (control group) and animals in group 2 were treated with carrier with the test compound (experimental group). The cumulative food intake was evaluated at 1, 2, 4, 8 and 24 hrs after experimental or control treatment. Food intake was measured by subtracting uneaten food from the initial premeasured food.

TABLE 1

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H0906 | (structure) | $IC_{50}$ = 0.0189<br>$EC_{50}/E_{Max}$ = 30<br>$EC_{50}$ = 0.0068<br>PPB = 99.84 (H)<br>PPB = 99.96 (M) | H = 19.9<br>M = 24.4<br>R = 13.6<br>D = 4904 | $CL_{iv}$ = 0.18<br>$CL_{po}$ = 239.47<br>$Vd_{iv}$ = 0.27<br>$Vd_{po}$ = 479.77<br>$t_{1/2\,iv}$ = 1.03<br>$t_{1/2po}$ = 1.39<br>F = 0.1 | Not performed |
| H0907 | (structure) | $IC_{50}$ = 0.0235<br>$EC_{50}/E_{Max}$ = 30<br>$EC_{50}$ = 1.61 | Not performed | Not performed | Not performed |
| H0937 | (structure) | $IC_{50}$ = 0.084<br>$EC_{50}/E_{Max}$ = 30<br>$EC_{50}$ = 0.0127 | H = <10<br>M = <10<br>R = <10<br>D = <10 | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) t$_{1/2}$ (h) F (%) | Food Intake Study |
|---|---|---|---|---|---|
| H0941 | 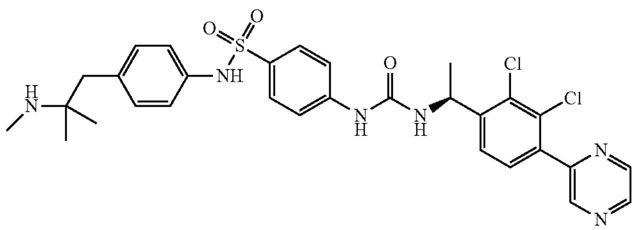 | IC$_{50}$ = 0.0077 EC$_{50}$/E$_{Max}$ = 30 EC$_{50}$ = 0.0028 PPB = 99.98 (H) PPB = 99.95 (M) | H = 47.7 M = 66.2 R = 36.2 D = 48.2 | Not performed | Not performed |
| H0942 | 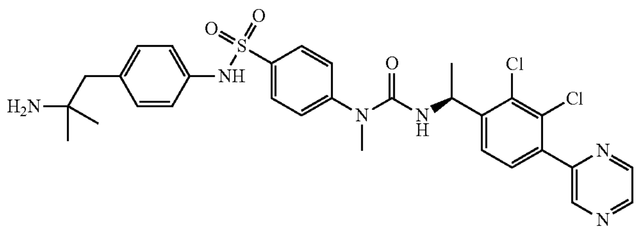 [SMILES: C[C@H](NC(=O)Nc1ccc(S(=O)(=O)Nc2ccc(CC(C)(C)N)cc2)cc1)c1ccc(-c2cnccn2)c(Cl)c1Cl] | IC$_{50}$ = 2.04 EC$_{50}$/E$_{Max}$ = 30 EC$_{50}$ = not reported | Not performed | Not performed | Not performed |
| H0943 | 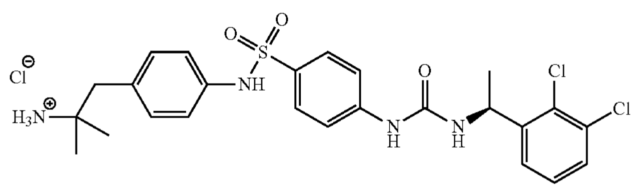 [SMILES: [Cl-] ; C[C@H](NC(=O)Nc1ccc(S(=O)(=O)Nc2ccc(CC(C)(C)[NH3+])cc2)cc1)c1cccc(Cl)c1Cl] | IC$_{50}$ = 0.0078 EC$_{50}$/E$_{Max}$ = 30 EC$_{50}$ = 0.0025 | H = 10.6 M = <10 R = 11.7 D = <10 | Not performed | Not performed |
| H0944 | 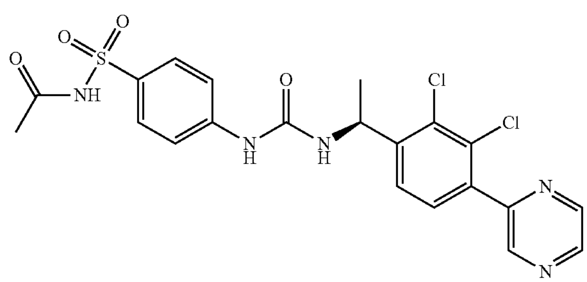 [SMILES: CC(=O)NS(=O)(=O)c1ccc(NC(=O)N[C@@H](C)c2ccc(-c3cnccn3)c(Cl)c2Cl)cc1] | IC$_{50}$ = 30 EC$_{50}$/E$_{Max}$ = 30 EC$_{50}$ = not reported | Not performed | Not performed | Not performed |
| H0950 | 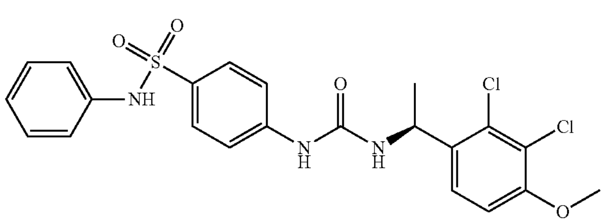 [SMILES: COc1ccc([C@H](C)NC(=O)Nc2ccc(S(=O)(=O)Nc3ccccc3)cc2)c(Cl)c1Cl] | IC$_{50}$ = 20.8 EC$_{50}$/E$_{Max}$ = 30 EC$_{50}$ = not reported | Not performed | Not performed | Not performed |
| H0951 | 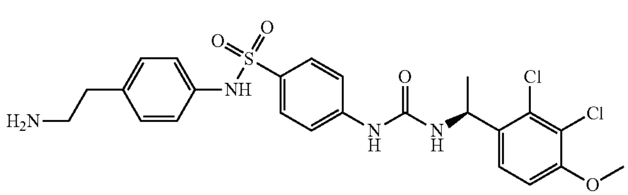 [SMILES: COc1ccc([C@H](C)NC(=O)Nc2ccc(S(=O)(=O)Nc3ccc(CCN)cc3)cc2)c(Cl)c1Cl] | IC$_{50}$ = 0.0838 EC$_{50}$/E$_{Max}$ = >30 EC$_{50}$ = 0.0327 | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H0953 | 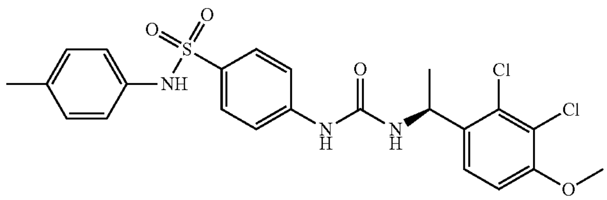 | $IC_{50}$ = >30 $EC_{50}$/$E_{Max}$ = >30 $EC_{50}$ = not reported | Not performed | Not performed | Not performed |
| H0954 | 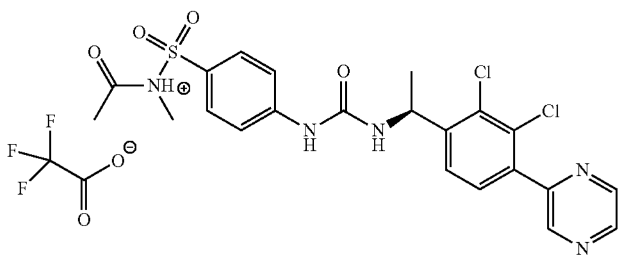 [SMILES: O=C([O-])C(F)(F)F ; CC(=O)[NH+](C)S(=O)(=O)c1ccc(NC(=O)N[C@@H](C)c2ccc(-c3cnccn3)c(Cl)c2Cl)cc1] | $IC_{50}$ = >30 $EC_{50}$/$E_{Max}$ = >30 $EC_{50}$ = not reported | Not performed | Not performed | Not performed |
| H0963 | 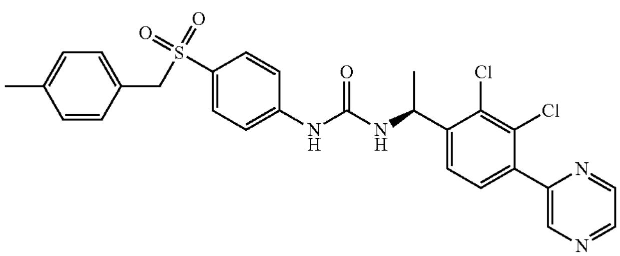 [SMILES: Cc1ccc(CS(=O)(=O)c2ccc(NC(=O)N[C@@H](C)c3ccc(-c4cnccn4)c(Cl)c3Cl)cc2)cc1] | $IC_{50}$ = >30 $EC_{50}$/$E_{Max}$ = >30 $EC_{50}$ = not reported | Not performed | Not performed | Not performed |
| H0964 | 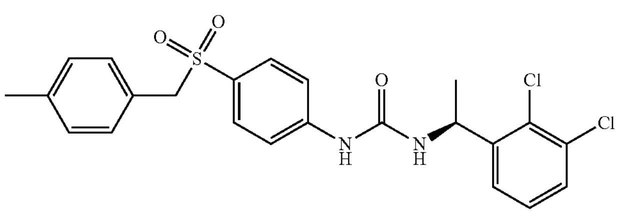 [SMILES: Cc1ccc(CS(=O)(=O)c2ccc(NC(=O)N[C@@H](C)c3cccc(Cl)c3Cl)cc2)cc1] | $IC_{50}$ = 4.17 $EC_{50}$/$E_{Max}$ = 13.05/1346 $EC_{50}$ = 2.477 | Not performed | Not performed | Not performed |
| H0965 | 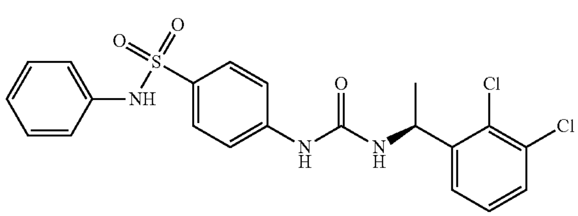 [SMILES: C[C@H](NC(=O)Nc1ccc(S(=O)(=O)Nc2ccccc2)cc1)c1cccc(Cl)c1Cl] | $IC_{50}$ = >30 $EC_{50}$/$E_{Max}$ = >30 $EC_{50}$ = not reported | Not performed | Not performed | Not performed |
| H0966 | 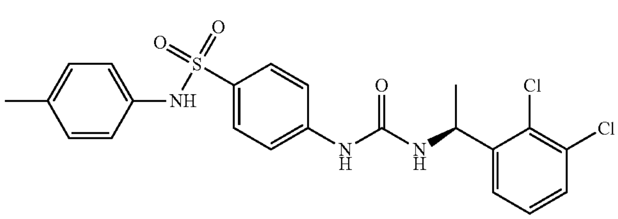 [SMILES: Cc1ccc(NS(=O)(=O)c2ccc(NC(=O)N[C@@H](C)c3cccc(Cl)c3Cl)cc2)cc1] | $IC_{50}$ = 6.58 $EC_{50}$/$E_{Max}$ = >30 $EC_{50}$ = not reported | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H0967 | 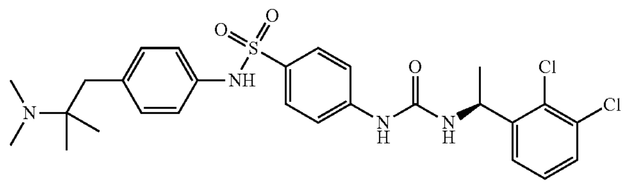 [SMILES: C[C@H](NC(=O)Nc1ccc(S(=O)(=O)Nc2ccc(CC(C)(C)N(C)C)cc2)cc1)c1cccc(Cl)c1Cl] | $IC_{50}$ = 0.016 $EC_{50}/E_{Max}$ = >30 $EC_{50}$ = 0.0047 | H = 38.2 M = 58 R = not reported D = not reported | $CL_{iv}$ = 2.34 $CL_{po}$ = 697.4 $Vd_{iv}$ = 8.62 $Vd_{po}$ = 2326.2 $t_{1/2iv}$ = 2.56 $t_{1/2po}$ = 2.31 F = 0.2 | 30 mg/kg po fasted - inh 5 mg/kg sc fasted - inh |
| H0968 | 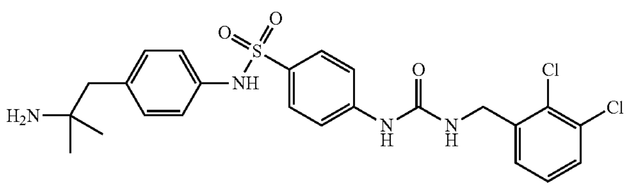 [SMILES: CC(C)(N)Cc1ccc(NS(=O)(=O)c2ccc(NC(=O)NCc3cccc(Cl)c3Cl)cc2)cc1] | $IC_{50}$ = 0.044 $EC_{50}/E_{Max}$ > 30 $EC_{50}$ = 0.0057 | H = 32.5 M = 27.4 R = not reported D = not reported | Not performed | 30 mg/kg po fasted - inh |
| H0969 | 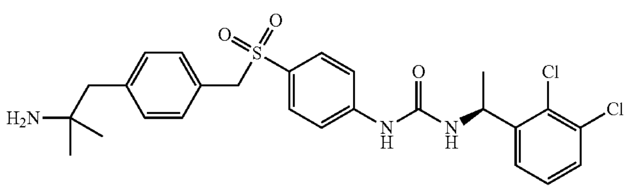 [SMILES: C[C@H](NC(=O)Nc1ccc(S(=O)(=O)Cc2ccc(CC(C)(C)N)cc2)cc1)c1cccc(Cl)c1Cl] | $IC_{50}$ = 0.053 $EC_{50}/E_{Max}$ = >30 $EC_{50}$ = 0.0189 | H = 19.5 M = 74.4 R = not reported D = not reported | $CL_{iv}$ = 0.46 $CL_{po}$ = 27.01 $Vd_{iv}$ = 1.97 $Vd_{po}$ = 168.2 $t_{1/2iv}$ = 2.96 $t_{1/2po}$ = 4.32 F = 1.3 | 30 mg/kg po fasted - inh |
| H0971 | 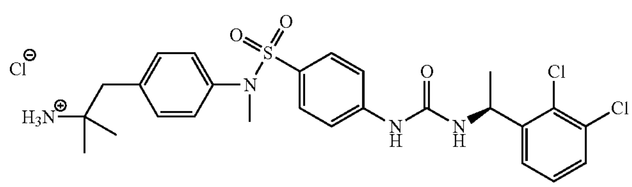 [SMILES: [Cl-] ; C[C@H](NC(=O)Nc1ccc(S(=O)(=O)N(C)c2ccc(CC(C)(C)[NH3+])cc2)cc1)c1cccc(Cl)c1Cl] | $IC_{50}$ = 0.417 $EC_{50}/E_{Max}$ > 30 $EC_{50}$ = 0.135 | H = 31.9 M = 24.8 R = not reported D = not reported | Not performed | Not performed |
| H0975 | 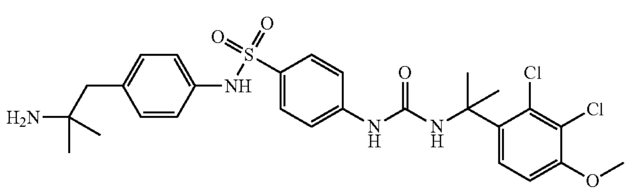 [SMILES: COc1ccc(C(C)(C)NC(=O)Nc2ccc(S(=O)(=O)Nc3ccc(CC(C)(C)N)cc3)cc2)c(Cl)c1Cl] | $IC_{50}$ = 0.0095 $EC_{50}/E_{Max}$ = 30 $EC_{50}$ = not reported | Not performed | Not performed | Not performed |
| H0981 | 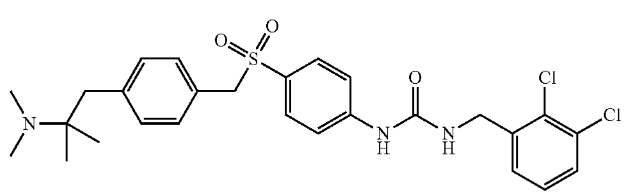 [SMILES: CN(C)C(C)(C)Cc1ccc(CS(=O)(=O)c2ccc(NC(=O)NCc3cccc(Cl)c3Cl)cc2)cc1] | $IC_{50}$ = 0.0095 $EC_{50}/E_{Max}$ = 30 $EC_{50}$ = not reported | Not performed | Not performed | Not performed |
| H0990 | 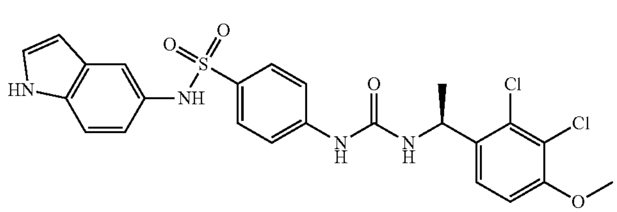 [SMILES: COc1ccc([C@H](C)NC(=O)Nc2ccc(S(=O)(=O)Nc3ccc4[nH]ccc4c3)cc2)c(Cl)c1Cl] | $IC_{50}$ = 0.823 $EC_{50}/E_{Max}$ = 30 $EC_{50}$ = not reported | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H0991 | 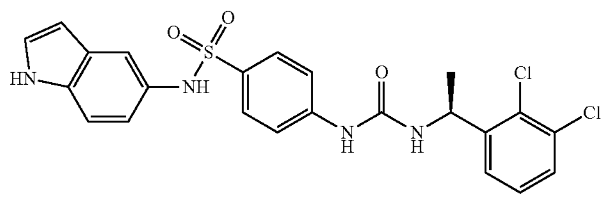 [SMILES: C[C@H](NC(=O)Nc1ccc(S(=O)(=O)Nc2ccc3[nH]ccc3c2)cc1)c1cccc(Cl)c1Cl] | $IC_{50}$ = 0.1455 $EC_{50}/E_{Max}$ = 30 $EC_{50}$ = 0.06677 | Not performed | Not performed | Not performed |
| H0993 | 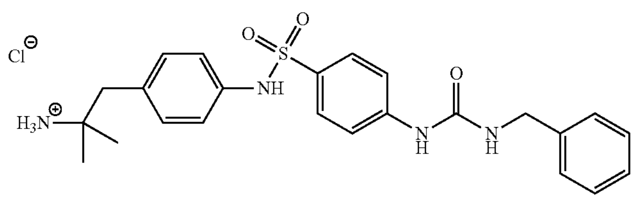 [SMILES: [Cl-] ; CC(C)([NH3+])Cc1ccc(NS(=O)(=O)c2ccc(NC(=O)NCc3ccccc3)cc2)cc1] | $IC_{50}$ = 0.2878 $EC_{50}/E_{Max}$ = 30 $EC_{50}$ = 0.021 | H = 18.5 M = 14.3 R = 15.1 D < 10 | $CL_{iv}$ = 2.15 $CL_{po}$ = 438.1 $Vd_{iv}$ = 4.31 $Vd_{po}$ = 2550 $t_{1/2iv}$ = 1.39 $t_{1/2po}$ = 4.03 F = 0.4 | Not performed |
| H0994 | 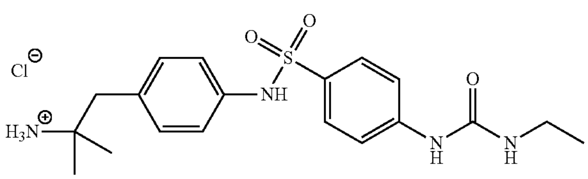 [SMILES: [Cl-] ; CCNC(=O)Nc1ccc(S(=O)(=O)Nc2ccc(CC(C)(C)[NH3+])cc2)cc1] | $IC_{50}$ = 30 $EC_{50}/E_{Max}$ = 30 $EC_{50}$ = 1.434 | Not performed | Not performed | Not performed |
| H0995 | 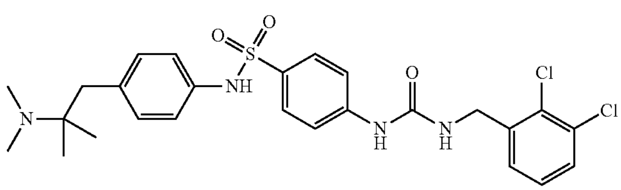 [SMILES: CN(C)C(C)(C)Cc1ccc(NS(=O)(=O)c2ccc(NC(=O)NCc3cccc(Cl)c3Cl)cc2)cc1] | $IC_{50}$ = 0.0321 $EC_{50}/E_{Max}$ = 30 $EC_{50}$ = 0.00252 | H = 54.5 M = 194.6 R = 92.4 D = 52.7 | Not performed | Not performed |
| H0996 | 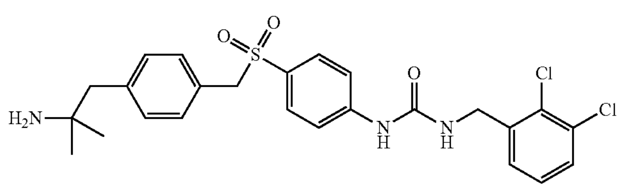 [SMILES: CC(C)(N)Cc1ccc(CS(=O)(=O)c2ccc(NC(=O)NCc3cccc(Cl)c3Cl)cc2)cc1] | $IC_{50}$ = 0.461 $EC_{50}/E_{Max}$ = 30 $EC_{50}$ = 0.064 | H = 27.5 M = 125.4 R = 77.8 D = <10 | Not performed | Not performed |
| H0997 | 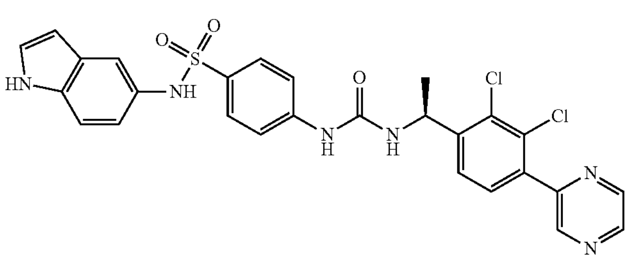 [SMILES: C[C@H](NC(=O)Nc1ccc(S(=O)(=O)Nc2ccc3[nH]ccc3c2)cc1)c1ccc(-c2cnccn2)c(Cl)c1Cl] | $IC_{50}$ = 30 $EC_{50}/E_{Max}$ = 30 $EC_{50}$ = not reported | Not performed | Not performed | Not performed |
| H1003 | 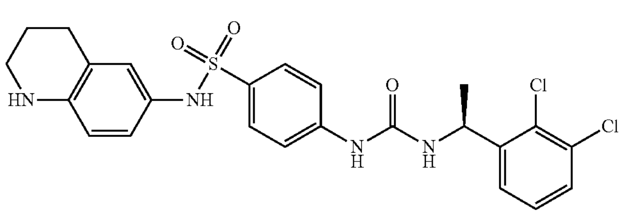 [SMILES: C[C@H](NC(=O)Nc1ccc(S(=O)(=O)Nc2ccc3c(c2)CCCN3)cc1)c1cccc(Cl)c1Cl] | $IC_{50}$ = 2.02 $EC_{50}/E_{Max}$ = 14.36/2228 $EC_{50}$ = not reported | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1004 | 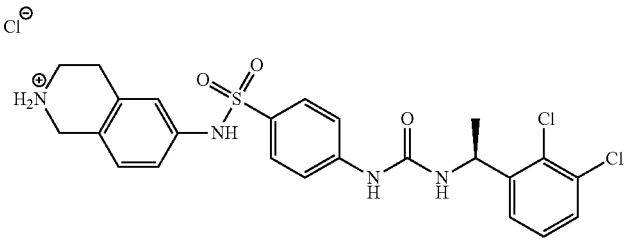 [SMILES: [Cl-] ; C[C@H](NC(=O)Nc1ccc(S(=O)(=O)Nc2ccc3c(c2)CC[NH2+]C3)cc1)c1cccc(Cl)c1Cl] | $IC_{50}$ = 0.0037 $EC_{50}/E_{Max}$ = >30 $EC_{50}$ = 0.00397 | Not performed | $CL_{iv}$ = 35.5 $CL_{po}$ = 223.9 $Vd_{iv}$ = 37.7 $Vd_{po}$ = 479.2 $t_{1/2iv}$ = 0.74 $t_{1/2po}$ = 1.48 F = 13 | Not performed |
| H1005 | 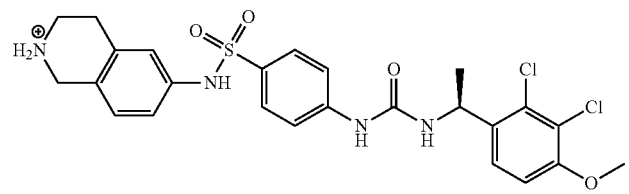 | $IC_{50}$ = 0.0198 $EC_{50}/E_{Max}$ = >30 $EC_{50}$ = 0.00888 | Not performed | $CL_{iv}$ = 0.44 $CL_{po}$ = 33.33 $Vd_{iv}$ = 1.46 $Vd_{po}$ = 112.3 $t_{1/2iv}$ = 2.3 $t_{1/2po}$ = 2.33 F = 1.3 | Not performed |
| H1006 | 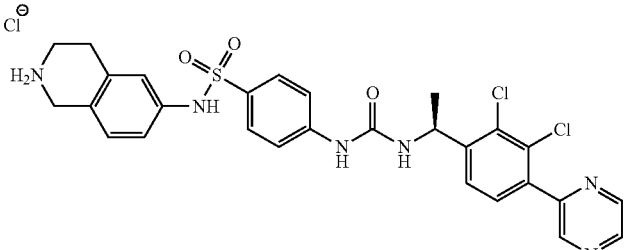 | $IC_{50}$ = 0.072 $EC_{50}/E_{Max}$ = >30 $EC_{50}$ = 0.0369 | Not performed | Not performed | Not performed |
| H1008 | 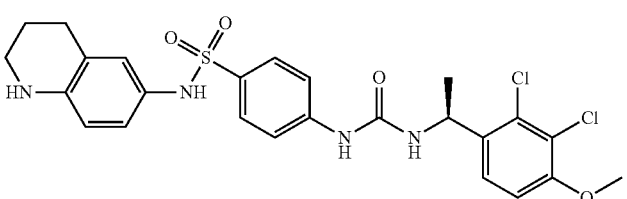 | $IC_{50}$ = 6.38 $EC_{50}/E_{Max}$ = 12.68/2021 $EC_{50}$ = not reported | Not performed | Not performed | Not performed |
| H1009 | 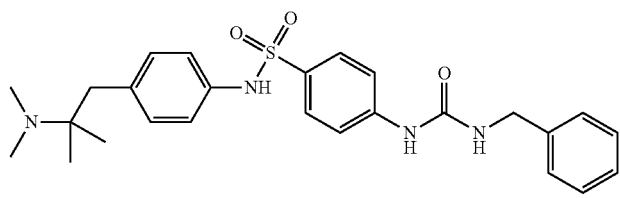 [SMILES: CN(C)C(C)(C)Cc1ccc(NS(=O)(=O)c2ccc(NC(=O)NCc3ccccc3)cc2)cc1] | $IC_{50}$ = 0.252 $EC_{50}/E_{Max}$ = 30 $EC_{50}$ = 0.0328 | H = 13.2 M = 33.8 R = not reported D = not reported | Not performed | Not performed |
| H1010 | 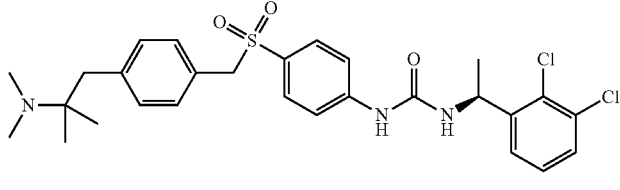 [SMILES: C[C@H](NC(=O)Nc1ccc(S(=O)(=O)Cc2ccc(CC(C)(C)N(C)C)cc2)cc1)c1cccc(Cl)c1Cl] | $IC_{50}$ = 0.042 $EC_{50}/E_{Max}$ = 30 $EC_{50}$ = 0.015 | H = 40.5 M = 40.5 R = not reported D = not reported | $CL_{iv}$ = 3.34 $CL_{po}$ = 108.2 $Vd_{iv}$ = 1.39 $Vd_{po}$ = 169 $t_{1/2iv}$ = 1.39 $t_{1/2po}$ = 1.08 F = 3.09 | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1017 | 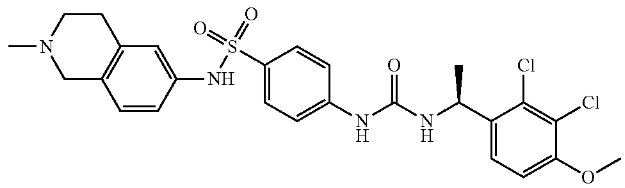 | $IC_{50}$ = 0.072 $EC_{50}/E_{Max}$ = 30 $EC_{50}$ = 0.0098 PPB (H) = 99.9 PPB (M) = 99.97 | H = 11.5 M = 30.5 R = not reported D = not reported | Not performed | Not performed |
| H1018 | 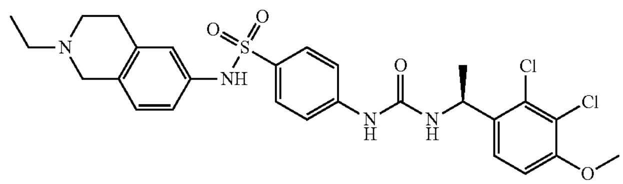 [SMILES: CCN1CCc2cc(NS(=O)(=O)c3ccc(NC(=O)N[C@@H](C)c4ccc(OC)c(Cl)c4Cl)cc3)ccc2C1] | $IC_{50}$ = 0.0998 $EC_{50}/E_{Max}$ = 30 $EC_{50}$ = 0.01367 | H = <10 M = 46.3 R = not reported D = not reported | Not performed | Not performed |
| H1024 | 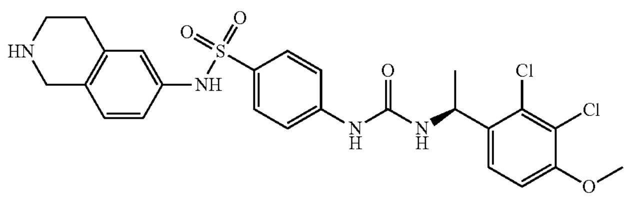 [SMILES: COc1ccc([C@H](C)NC(=O)Nc2ccc(S(=O)(=O)Nc3ccc4c(c3)CCNC4)cc2)c(Cl)c1Cl] | $IC_{50}$ = 0.0347 $EC_{50}/E_{Max}$ = >30 $EC_{50}$ = 0.0257 | H = <10 M = <10 R = not reported D = not reported | $CL_{iv}$ = 11.17 $CL_{po}$ = 132.3 $Vd_{iv}$ = 16.35 $Vd_{po}$ = 349.6 $t_{1/2iv}$ = 1.01 $t_{1/2po}$ = 1.83 F = 7.91 | Not performed |
| H1025 | 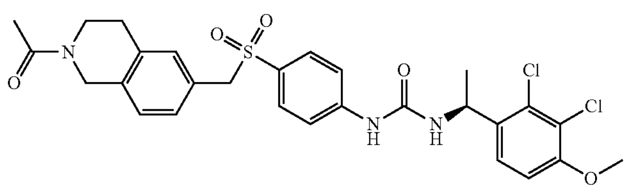 [SMILES: COc1ccc([C@H](C)NC(=O)Nc2ccc(S(=O)(=O)Cc3ccc4c(c3)CCN(C(C)=O)C4)cc2)c(Cl)c1Cl] | $IC_{50}$ = 21.45 $EC_{50}/E_{Max}$ = >30 $EC_{50}$ = not reported | H = 92.4 M = 159.5 R = not reported D = not reported | $CL_{iv}$ = 1.84 $CL_{po}$ = 30.89 $Vd_{iv}$ = 2.86 $Vd_{po}$ = 94.83 $t_{1/2iv}$ = 1.08 $t_{1/2po}$ = 1.45 F = 5.92 | Not performed |
| H1026 | 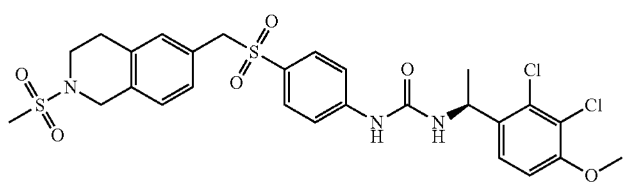 | $IC_{50}$ = 14.9 $EC_{50}/E_{Max}$ = >30 $EC_{50}$ = not reported | Not performed | Not performed | Not performed |
| H1027 | 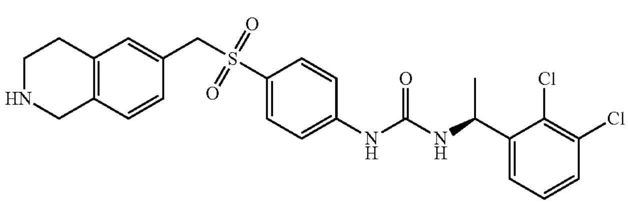 [SMILES: C[C@H](NC(=O)Nc1ccc(S(=O)(=O)Cc2ccc3c(c2)CCNC3)cc1)c1cccc(Cl)c1Cl] | $IC_{50}$ = 0.0025 $EC_{50}/E_{Max}$ = >30 $EC_{50}$ = 0.001616 | H = <10 M = <10 R = not reported D = not reported | $CL_{iv}$ = 0.71 (M); 12.34 (R) $CL_{po}$ = 85.67 (M); 24.98 (R) $Vd_{iv}$ = 1.64 (M); 168.2 (R) $Vd_{po}$ = 345 (M); 80.4 (R) $t_{1/2iv}$ = 1.61 (M); 10.2 (R) $t_{1/2po}$ = 2.79 (M); 2.21 (R) F = 0.72 (M); 57.14 (R) | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1028 | 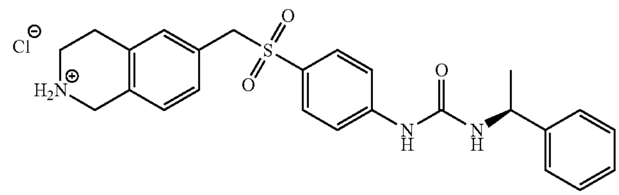 [SMILES: [Cl-] ; C[C@H](NC(=O)Nc1ccc(S(=O)(=O)Cc2ccc3c(c2)CC[NH2+]C3)cc1)c1ccccc1] | $IC_{50}$ = 0.414 $EC_{50}/E_{Max}$ = >30 $EC_{50}$ = 0.2335 | Not performed | Not performed | Not performed |
| H1029 | 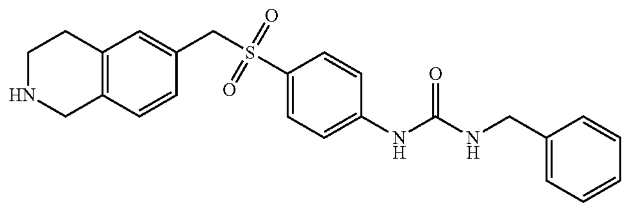 [SMILES: O=C(NCc1ccccc1)Nc1ccc(S(=O)(=O)Cc2ccc3c(c2)CCNC3)cc1] | $IC_{50}$ = 0.3323 $EC_{50}/E_{Max}$ = >30 $EC_{50}$ = 0.1878 | Not performed | Not performed | Not performed |
| H1033 | 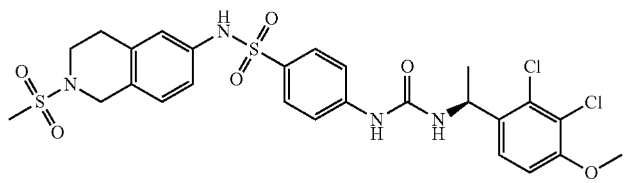 | $IC_{50}$ = 3.02 $EC_{50}/E_{Max}$ = >30 $EC_{50}$ = not reported | Not performed | Not performed | Not performed |
| H1034 | 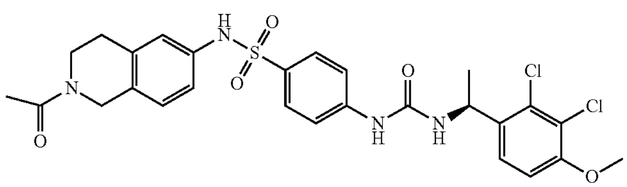 [SMILES: COc1ccc([C@H](C)NC(=O)Nc2ccc(S(=O)(=O)Nc3ccc4c(c3)CCN(C(C)=O)C4)cc2)c(Cl)c1Cl] | $IC_{50}$ = 1.258 $EC_{50}/E_{Max}$ = >30 $EC_{50}$ = 1.606 | Not performed | Not performed | Not performed |
| H1038 | 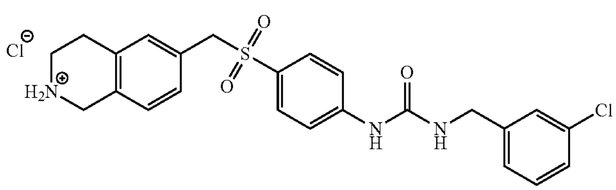 [SMILES: [Cl-] ; O=C(NCc1cccc(Cl)c1)Nc1ccc(S(=O)(=O)Cc2ccc3c(c2)CC[NH2+]C3)cc1] | $IC_{50}$ = 0.3761 $EC_{50}/E_{Max}$ = >30 $EC_{50}$ = 0.1234 | Not performed | Not performed | Not performed |
| H1039 | 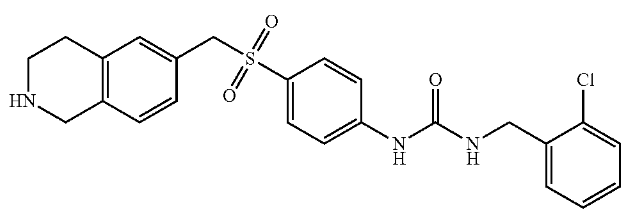 [SMILES: O=C(NCc1ccccc1Cl)Nc1ccc(S(=O)(=O)Cc2ccc3c(c2)CCNC3)cc1] | $IC_{50}$ = 0.1129 $EC_{50}/E_{Max}$ = >30 $EC_{50}$ = 0.0333 | H = <10 M = 13.5 R = not reported D = not reported | $CL_{iv}$ = 2.55 $CL_{po}$ = 334.4 $Vd_{iv}$ = 11.7 $Vd_{po}$ = 898 $t_{1/2iv}$ = 3.18 $t_{1/2po}$ = 1.86 F = 0.6 | Not performed |
| H1040 | 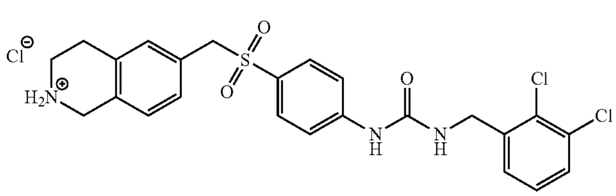 [SMILES: [Cl-] ; O=C(NCc1cccc(Cl)c1Cl)Nc1ccc(S(=O)(=O)Cc2ccc3c(c2)CC[NH2+]C3)cc1] | $IC_{50}$ = 0.0318 $EC_{50}/E_{Max}$ = >30 $EC_{50}$ = 0.1639 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1041 | 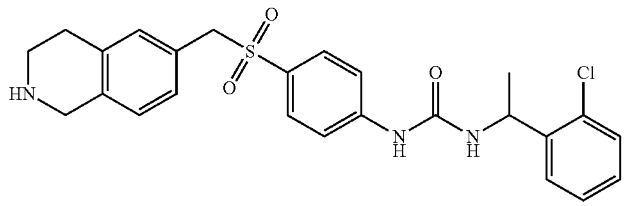 [SMILES: CC(NC(=O)Nc1ccc(S(=O)(=O)Cc2ccc3c(c2)CCNC3)cc1)c1ccccc1Cl] | $IC_{50}$ = 0.0174 $EC_{50}/E_{Max}$ = >30 $EC_{50}$ = 0.0555 | Not performed | Not performed | Not performed |
| H1042 | 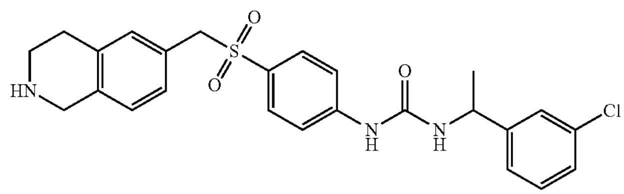 [SMILES: CC(NC(=O)Nc1ccc(S(=O)(=O)Cc2ccc3c(c2)CCNC3)cc1)c1cccc(Cl)c1] | $IC_{50}$ = 0.0366 $EC_{50}/E_{Max}$ = >30 $EC_{50}$ = 0.1222 | Not performed | Not performed | Not performed |
| H1043 | 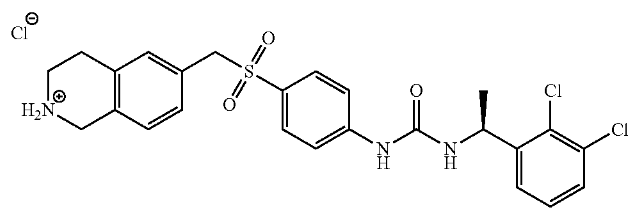 [SMILES: [Cl-] ; C[C@H](NC(=O)Nc1ccc(S(=O)(=O)Cc2ccc3c(c2)CC[NH2+]C3)cc1)c1cccc(Cl)c1Cl] | $IC_{50}$ = 0.0041 $EC_{50}/E_{Max}$ = >30 $EC_{50}$ = 0.0184 | Not performed | Not performed | Not performed |
| H1044 | 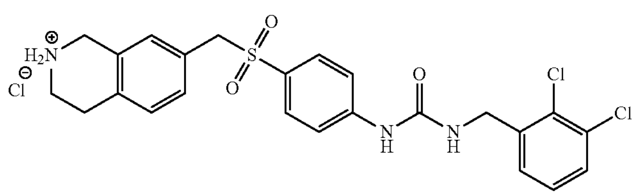 [SMILES: [Cl-] ; O=C(NCc1cccc(Cl)c1Cl)Nc1ccc(S(=O)(=O)Cc2ccc3c(c2)C[NH2+]CC3)cc1] | $IC_{50}$ = 0.0531 $EC_{50}/E_{Max}$ = >30 $EC_{50}$ = 0.1434 | Not performed | Not performed | Not performed |
| H1045 | 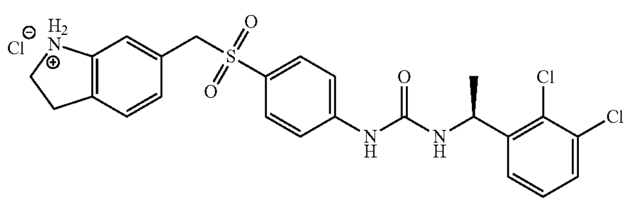 | $IC_{50}$ = 2.743 $EC_{50}/E_{Max}$ = >30 $EC_{50}$ = not reported | Not performed | Not performed | Not performed |
| H1046 | 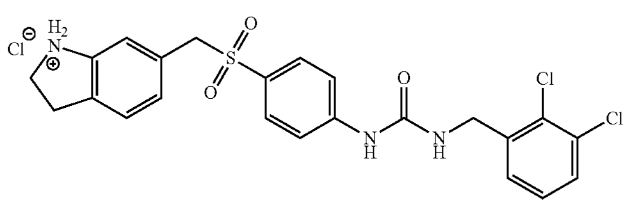 | $IC_{50}$ = 1.993 $EC_{50}/E_{Max}$ = >30 $EC_{50}$ = not reported | Not performed | Not performed | Not performed |
| H1047 | 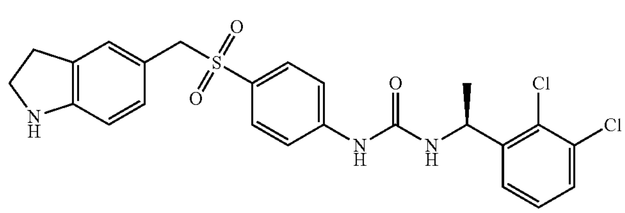 [SMILES: C[C@H](NC(=O)Nc1ccc(S(=O)(=O)Cc2ccc3c(c2)CCN3)cc1)c1cccc(Cl)c1Cl] | $IC_{50}$ = 0.865 $EC_{50}/E_{Max}$ = >30 $EC_{50}$ = 1.165 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1048 | 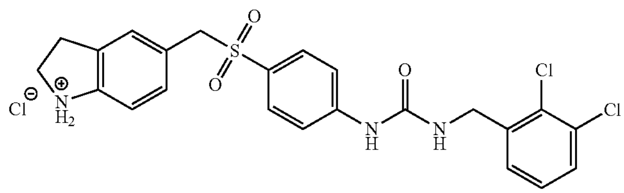 [SMILES: [Cl-] ; O=C(NCc1cccc(Cl)c1Cl)Nc1ccc(S(=O)(=O)Cc2ccc3c(c2)CC[NH2+]3)cc1] | $IC_{50}$ = 16.765 $EC_{50}$/ $E_{Max}$ = >30 $EC_{50}$ = not reported | Not performed | Not performed | Not performed |
| H1049 | 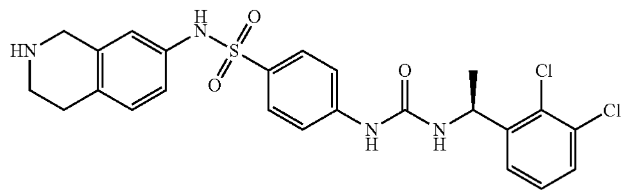 [SMILES: C[C@H](NC(=O)Nc1ccc(S(=O)(=O)Nc2ccc3c(c2)CNCC3)cc1)c1cccc(Cl)c1Cl] | $IC_{50}$ = 0.0163 $EC_{50}$/ $E_{Max}$ = >30 $EC_{50}$ = 0.0296 | Not performed | Not performed | Not performed |
| H1050 | 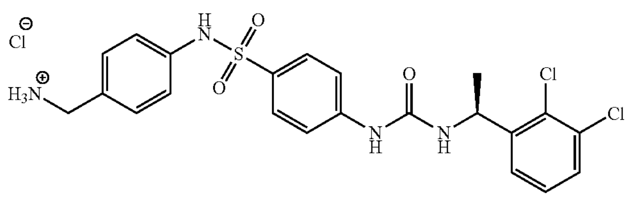 [SMILES: [Cl-] ; C[C@H](NC(=O)Nc1ccc(S(=O)(=O)Nc2ccc(C[NH3+])cc2)cc1)c1cccc(Cl)c1Cl] | $IC_{50}$ = 0.0574 $EC_{50}$/ $E_{Max}$ = >30 $EC_{50}$ = 0.1086 | Not performed | Not performed | Not performed |
| H1051 | 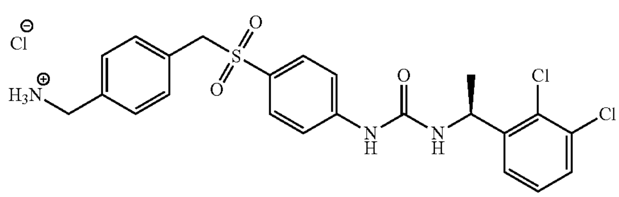 [SMILES: [Cl-] ; C[C@H](NC(=O)Nc1ccc(S(=O)(=O)Cc2ccc(C[NH3+])cc2)cc1)c1cccc(Cl)c1Cl] | $IC_{50}$ = 0.0537 $EC_{50}$/ $E_{Max}$ = >30 $EC_{50}$ = 0.116 | Not performed | Not performed | Not performed |
| H1052 | 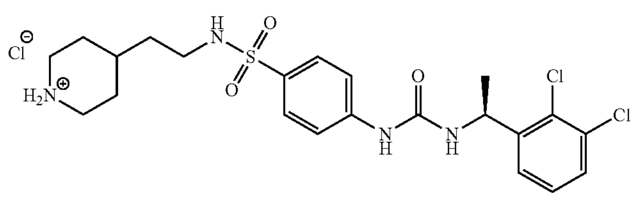 [SMILES: [Cl-] ; C[C@H](NC(=O)Nc1ccc(S(=O)(=O)NCCC2CC[NH2+]CC2)cc1)c1cccc(Cl)c1Cl] | $IC_{50}$ = 0.4675 $EC_{50}$/ $E_{Max}$ = >30 $EC_{50}$ = not reported | Not performed | Not performed | Not performed |
| H1054 | 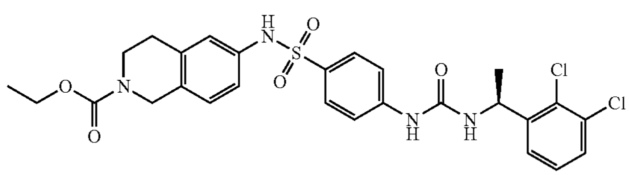 [SMILES: CCOC(=O)N1CCc2cc(NS(=O)(=O)c3ccc(NC(=O)N[C@@H](C)c4cccc(Cl)c4Cl)cc3)ccc2C1] | $IC_{50}$ = 10.09 $EC_{50}$/ $E_{Max}$ = >30 $EC_{50}$ = not reported | Not performed | $CL_{iv}$ = 1.62 $CL_{po}$ = 53.9 $Vd_{iv}$ = 4.32 $Vd_{po}$ = 96.2 $t_{1/2iv}$ = 1.85 $t_{1/2po}$ = 1.24 F = 3.0 | Not performed |
| H1055 | 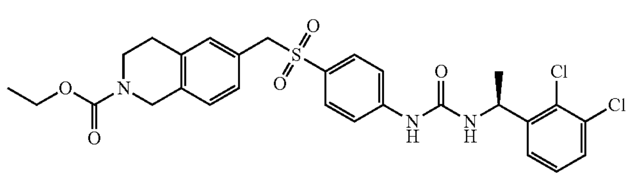 [SMILES: CCOC(=O)N1CCc2cc(CS(=O)(=O)c3ccc(NC(=O)N[C@@H](C)c4cccc(Cl)c4Cl)cc3)ccc2C1] | $IC_{50}$ = 4.47 $EC_{50}$/ $E_{Max}$ = >30 $EC_{50}$ = 0.516 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) t$_{1/2}$ (h) F (%) | Food Intake Study |
|---|---|---|---|---|---|
| H1056 | 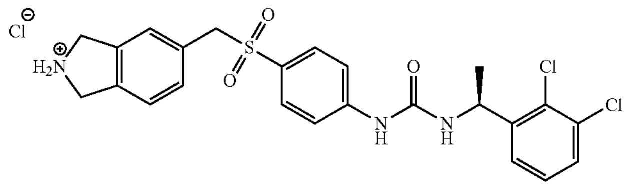 [SMILES: [Cl-] ; C[C@H](NC(=O)Nc1ccc(S(=O)(=O)Cc2ccc3c(c2)C[NH2+]C3)cc1)c1cccc(Cl)c1Cl] | IC$_{50}$ = 0.0058 EC$_{50}$/E$_{Max}$ = >30 EC$_{50}$ = 0.0026 | H = 16.4 M = 13.5 R = not reported D = not reported | Not performed | Not performed |
| H1057 | 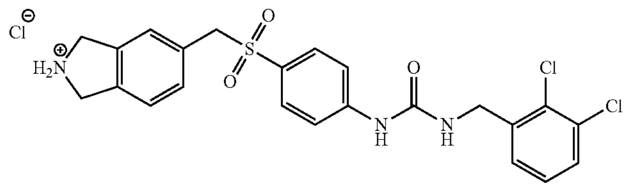 [SMILES: [Cl-] ; O=C(NCc1cccc(Cl)c1Cl)Nc1ccc(S(=O)(=O)Cc2ccc3c(c2)C[NH2+]C3)cc1] | IC$_{50}$ = 0.0193 EC$_{50}$/E$_{Max}$ = >30 EC$_{50}$ = 0.0069 PPB = 99.5 (H) PPB = 99.5 (M) | H = 12.6 M = 10.8 R = not reported D = not reported | CL$_{iv}$ = 1.57 CL$_{po}$ = 82.24 Vd$_{iv}$ = 2.18 Vd$_{po}$ = 368.9 t$_{1/2iv}$ = 0.96 t$_{1/2po}$ = 3.11 F = 1.6 | Not performed |
| H1058 | 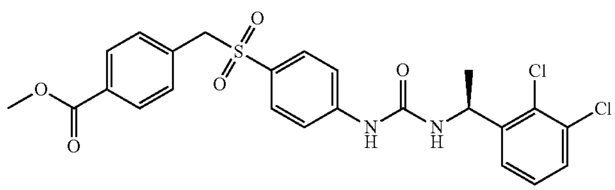 [SMILES: COC(=O)c1ccc(CS(=O)(=O)c2ccc(NC(=O)N[C@@H](C)c3cccc(Cl)c3Cl)cc2)cc1] | IC$_{50}$ = 20 EC$_{50}$/E$_{Max}$ = >30 EC$_{50}$ = not reported | Not performed | Not performed | Not performed |
| H1059 | 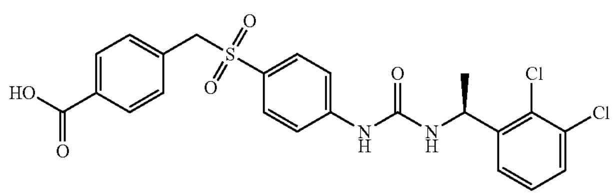 [SMILES: C[C@H](NC(=O)Nc1ccc(S(=O)(=O)Cc2ccc(C(=O)O)cc2)cc1)c1cccc(Cl)c1Cl] | IC$_{50}$ = >30 EC$_{50}$/E$_{Max}$ = >30 EC$_{50}$ = not reported | Not performed | Not performed | Not performed |
| H1060 | 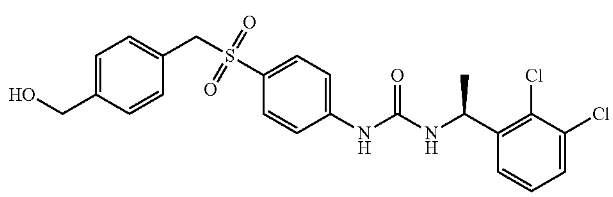 [SMILES: C[C@H](NC(=O)Nc1ccc(S(=O)(=O)Cc2ccc(CO)cc2)cc1)c1cccc(Cl)c1Cl] | IC$_{50}$ = 0.28 EC$_{50}$/E$_{Max}$ = >30 EC$_{50}$ = 0.0408 PPB = 99.87 (H) PPB = 99.81 (M) PPB = 99.82 (R) PPB = 99.88 (D) | H = 40 M = 108.7 R = not reported D = not reported | CL$_{iv}$ = 4.13 CL$_{po}$ = 22.1 Vd$_{iv}$ = 8.25 Vd$_{po}$ = 22.4 t$_{1/2iv}$ = 1.37 t$_{1/2po}$ = 0.7 F = 18.8 | Not performed |
| H1061 | 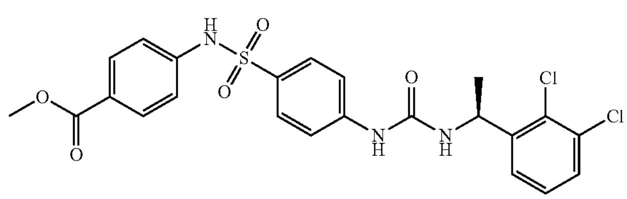 [SMILES: COC(=O)c1ccc(NS(=O)(=O)c2ccc(NC(=O)N[C@@H](C)c3cccc(Cl)c3Cl)cc2)cc1] | IC$_{50}$ = 2.87 EC$_{50}$/E$_{Max}$ = >30 EC$_{50}$ = not reported | Not performed | Not performed | Not performed |
| H1062 | 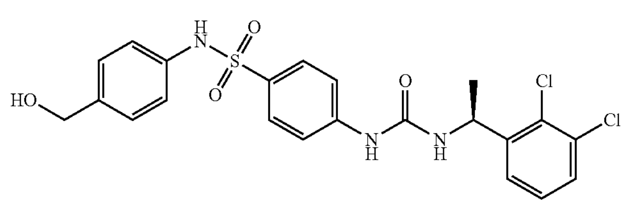 [SMILES: C[C@H](NC(=O)Nc1ccc(S(=O)(=O)Nc2ccc(CO)cc2)cc1)c1cccc(Cl)c1Cl] | IC$_{50}$ = 0.2225 EC$_{50}$/E$_{Max}$ = >30 EC$_{50}$ = 0.058 PPB = 99.88 (H) PPB = | H = 32.4 M = 67.2 R = not reported D = not reported | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| | | | | | |
| | | 99.81 (M) PPB = 99.88 (R) PPB = 99.83 (D) | | | |
| H1067 | 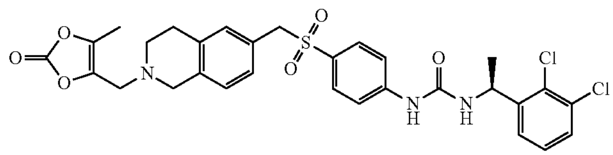 [SMILES: Cc1oc(=O)oc1CN1CCc2cc(CS(=O)(=O)c3ccc(NC(=O)N[C@@H](C)c4cccc(Cl)c4Cl)cc3)ccc2C1] | $IC_{50}$ = 0.014 $EC_{50}/$ $E_{Max}$ = >30 $EC_{50}$ = 0.0045 | H = 326.2 M = 289 R = not reported D = not reported | Not performed | Not performed |
| H1068 | 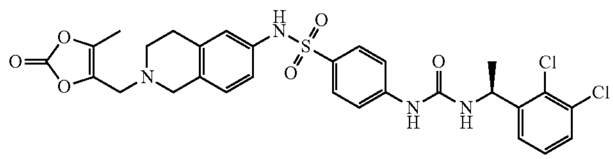 [SMILES: Cc1oc(=O)oc1CN1CCc2cc(NS(=O)(=O)c3ccc(NC(=O)N[C@@H](C)c4cccc(Cl)c4Cl)cc3)ccc2C1] | $IC_{50}$ = 0.0263 $EC_{50}/$ $E_{Max}$ = >30 $EC_{50}$ = 0.0084 | H = 199.7 M = 196.4 R = not reported D = not reported | Not performed | Not performed |
| H1070 | 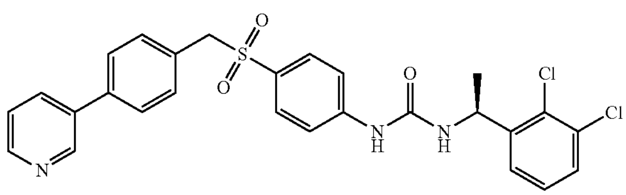 [SMILES: C[C@H](NC(=O)Nc1ccc(S(=O)(=O)Cc2ccc(-c3cccnc3)cc2)cc1)c1cccc(Cl)c1Cl] | $IC_{50}$ = 5.29 $EC_{50}/E_{Max}$ = 7.27 $EC_{50}$ = not reported | Not performed | Not performed | Not performed |
| H1071 | 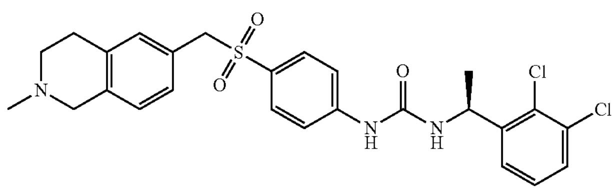 [SMILES: C[C@H](NC(=O)Nc1ccc(S(=O)(=O)Cc2ccc3c(c2)CCN(C)C3)cc1)c1cccc(Cl)c1Cl] | $IC_{50}$ = 0.005 $EC_{50}/$ $E_{Max}$ = >30 $EC_{50}$ = 0.0017 PPB = 99.11 (H) PPB = 99.02 (M) PPB = 99.13 (R) PPB = 99.18 (D) | H = 49.9/100.3 M = 80.7/152.5 R = 274/188 D = 172.6/160.7 | $CL_{iv}$ = 1.71 $CL_{po}$ = 8.28 $Vd_{iv}$ = 2.83 $Vd_{po}$ = 21.1 $t_{1/2iv}$ = 1.15 $t_{1/2po}$ = 1.77 F = 19.9 | Not performed |
| H1072 | 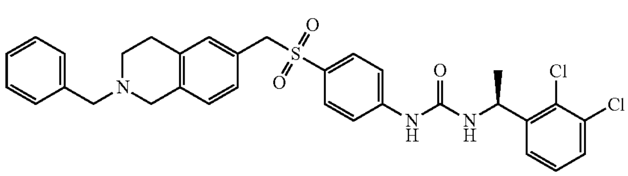 [SMILES: C[C@H](NC(=O)Nc1ccc(S(=O)(=O)Cc2ccc3c(c2)CCN(Cc2ccccc2)C3)cc1)c1cccc(Cl)c1Cl] | $IC_{50}$ = 0.1225 $EC_{50}/$ $E_{Max}$ = >30 $EC_{50}$ = 0.0219 | Not performed | Not performed | Not performed |
| H1073 | 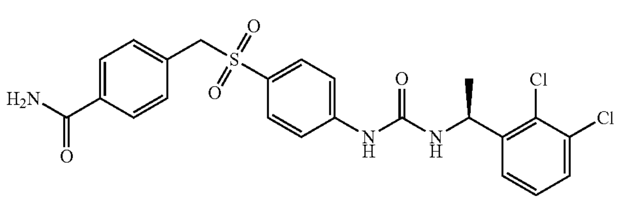 [SMILES: C[C@H](NC(=O)Nc1ccc(S(=O)(=O)Cc2ccc(C(N)=O)cc2)cc1)c1cccc(Cl)c1Cl] | $IC_{50}$ = >30 $EC_{50}/E_{Max}$ = 7.27 $EC_{50}$ = not reported | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1074 | 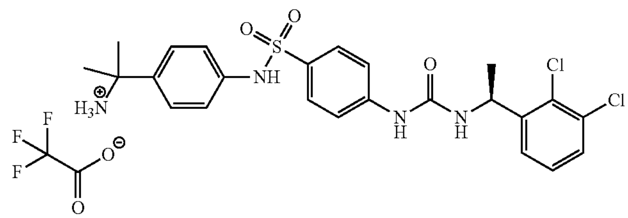 [SMILES: O=C([O-])C(F)(F)F ; C[C@H](NC(=O)Nc1ccc(S(=O)(=O)Nc2ccc(C(C)(C)[NH3+])cc2)cc1)c1cccc(Cl)c1Cl] | $IC_{50}$ = 3.25 $EC_{50}/E_{Max}$ = >30 $EC_{50}$ = 0.6568 | Not performed | Not performed | Not performed |
| H1075 | 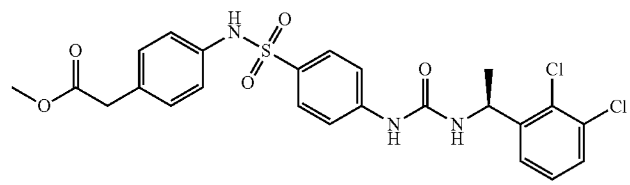 [SMILES: COC(=O)Cc1ccc(NS(=O)(=O)c2ccc(NC(=O)N[C@@H](C)c3cccc(Cl)c3Cl)cc2)cc1] | $IC_{50}$ = 3.018 $EC_{50}/E_{Max}$ > 30 $EC_{50}$ = not reported | Not performed | Not performed | Not performed |
| H1076 | 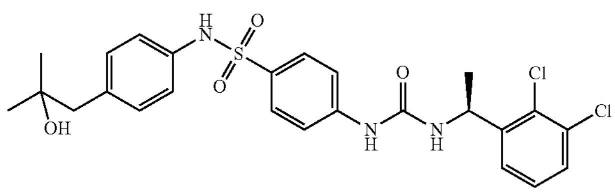 [SMILES: C[C@H](NC(=O)Nc1ccc(S(=O)(=O)Nc2ccc(CC(C)(C)O)cc2)cc1)c1cccc(Cl)c1Cl] | $IC_{50}$ = 0.515 $EC_{50}/E_{Max}$ = >30 $EC_{50}$ = 0.0577 | H = 91.4 M = 73.9 R = not reported D = not reported | Not performed | Not performed |
| H1078 | 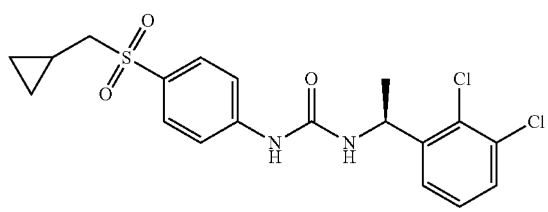 [SMILES: C[C@H](NC(=O)Nc1ccc(S(=O)(=O)CC2CC2)cc1)c1cccc(Cl)c1Cl] | $IC_{50}$ = 3.576 $EC_{50}/E_{Max}$ > 30 $EC_{50}$ = not reported | Not performed | Not performed | Not performed |
| H1080 | 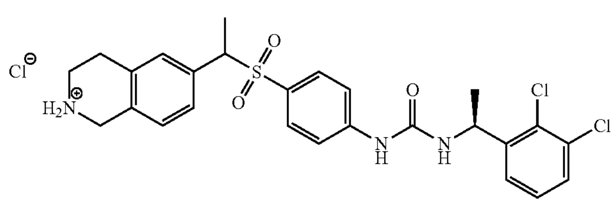 [SMILES: [Cl-] ; CC(c1ccc2c(c1)CC[NH2+]C2)S(=O)(=O)c1ccc(NC(=O)N[C@@H](C)c2cccc(Cl)c2Cl)cc1] | $IC_{50}$ = 0.0226 $EC_{50}/E_{Max}$ > 30 $EC_{50}$ = 0.0111/0.0412 hERG inh = 3.57 | H < 10 M < 10 R = not reported D = not reported | Not performed | Not performed |
| H1081 | 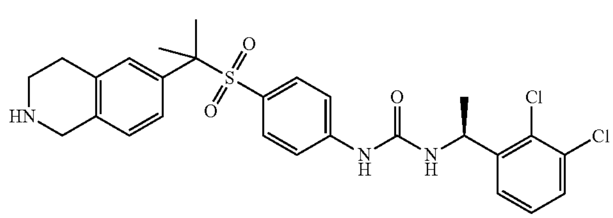 [SMILES: C[C@H](NC(=O)Nc1ccc(S(=O)(=O)C(C)(C)c2ccc3c(c2)CCNC3)cc1)c1cccc(Cl)c1Cl] | $IC_{50}$ = 1.238 $EC_{50}/E_{Max}$ > 30 $EC_{50}$ = not reported | Not performed | Not performed | Not performed |
| H1082 | 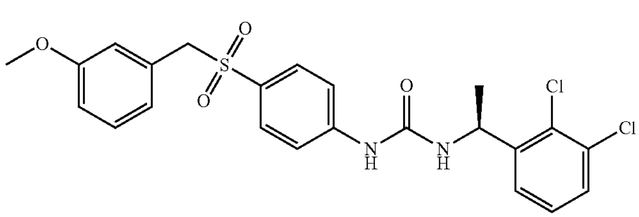 [SMILES: COc1cccc(CS(=O)(=O)c2ccc(NC(=O)N[C@@H](C)c3cccc(Cl)c3Cl)cc2)c1] | $IC_{50}$ > 30 $EC_{50}/E_{Max}$ > 30 $EC_{50}$ = not reported | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1083 | 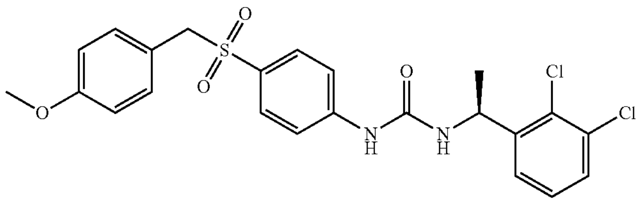 [SMILES: COc1ccc(CS(=O)(=O)c2ccc(NC(=O)N[C@@H](C)c3cccc(Cl)c3Cl)cc2)cc1] | $IC_{50} = 30$<br>$EC_{50}/$<br>$E_{Max} > 30$<br>$EC_{50} = 1.18$ | Not performed | Not performed | Not performed |
| H1084 | 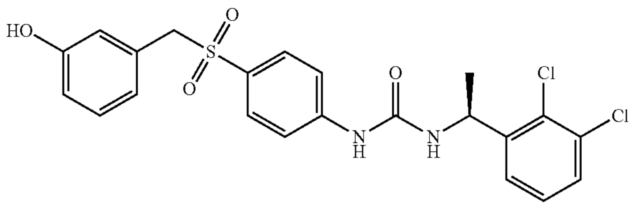 [SMILES: C[C@H](NC(=O)Nc1ccc(S(=O)(=O)Cc2cccc(O)c2)cc1)c1cccc(Cl)c1Cl] | $IC_{50} = 3.5$<br>$EC_{50}/E_{Max} = 10.8$<br>$EC_{50}$ = not reported | Not performed | Not performed | Not performed |
| H1087 | 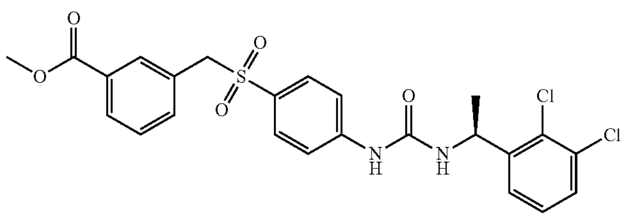 [SMILES: COC(=O)c1cccc(CS(=O)(=O)c2ccc(NC(=O)N[C@@H](C)c3cccc(Cl)c3Cl)cc2)c1] | $IC_{50} = 8.18$<br>$EC_{50}/$<br>$E_{Max} > 30$<br>$EC_{50}$ = not reported | Not performed | Not performed | Not performed |
| H1088 | 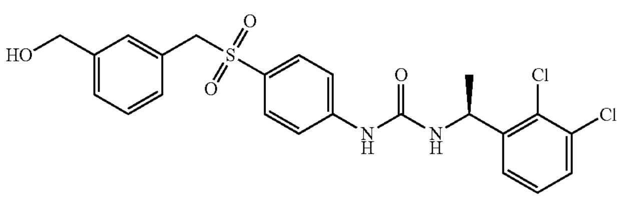 [SMILES: C[C@H](NC(=O)Nc1ccc(S(=O)(=O)Cc2cccc(CO)c2)cc1)c1cccc(Cl)c1Cl] | $IC_{50} = 7.97$<br>$EC_{50}/$<br>$E_{Max} > 30$<br>$EC_{50} = 0.367$ | Not performed | Not performed | Not performed |
| H1092 | 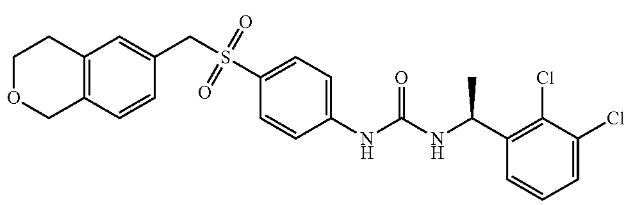 [SMILES: C[C@H](NC(=O)Nc1ccc(S(=O)(=O)Cc2ccc3c(c2)CCOC3)cc1)c1cccc(Cl)c1Cl] | $IC_{50} = 30$<br>$EC_{50}/$<br>$E_{Max} > 30$<br>$EC_{50} = 0.578$ | Not performed | Not performed | Not performed |
| H1093 | 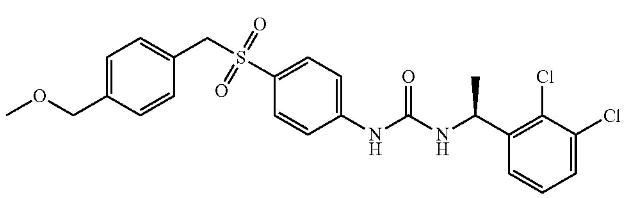 [SMILES: COCc1ccc(CS(=O)(=O)c2ccc(NC(=O)N[C@@H](C)c3cccc(Cl)c3Cl)cc2)cc1] | $IC_{50} = 2.382$<br>$EC_{50}/$<br>$E_{Max} > 30$<br>$EC_{50} = 0.327$ | Not performed | Not performed | Not performed |
| H1094 | 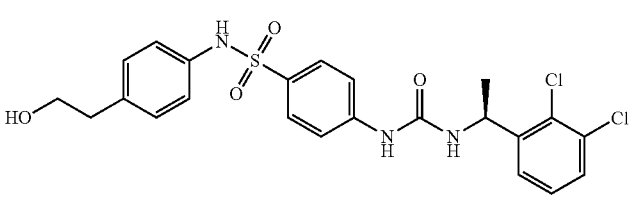 [SMILES: C[C@H](NC(=O)Nc1ccc(S(=O)(=O)Nc2ccc(CCO)cc2)cc1)c1cccc(Cl)c1Cl] | $IC_{50} = 0.488$<br>$EC_{50}/$<br>$E_{Max} > 30$<br>$EC_{50} = 0.118$ | H = 55.1<br>M = 100.8<br>R = not reported<br>D = not reported | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1095 | 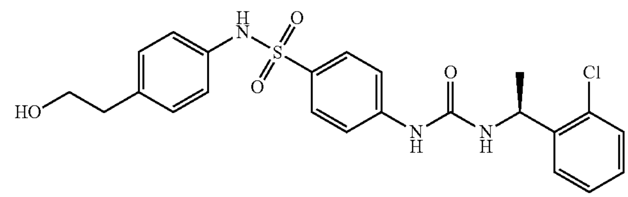 [SMILES: C[C@H](NC(=O)Nc1ccc(S(=O)(=O)Nc2ccc(CCO)cc2)cc1)c1ccccc1Cl] | $IC_{50}$ = 1.43 $EC_{50}$/$E_{Max}$ > 30 $EC_{50}$ = not reported | Not performed | Not performed | Not performed |
| H1096 | 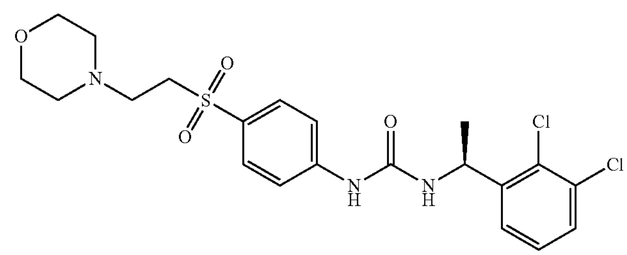 [SMILES: C[C@H](NC(=O)Nc1ccc(S(=O)(=O)CCN2CCOCC2)cc1)c1cccc(Cl)c1Cl] | $IC_{50}$ = 30 $EC_{50}$/$E_{Max}$ > 30 $EC_{50}$ = not reported | Not performed | Not performed | Not performed |
| H1097 | 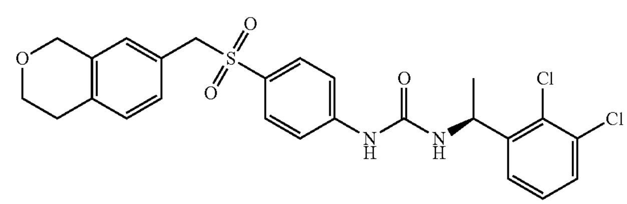 [SMILES: C[C@H](NC(=O)Nc1ccc(S(=O)(=O)Cc2ccc3c(c2)COCC3)cc1)c1cccc(Cl)c1Cl] | $IC_{50}$ = 1.969 $EC_{50}$/$E_{Max}$ > 30 $EC_{50}$ = 0.363 | Not performed | Not performed | Not performed |
| H1098 | 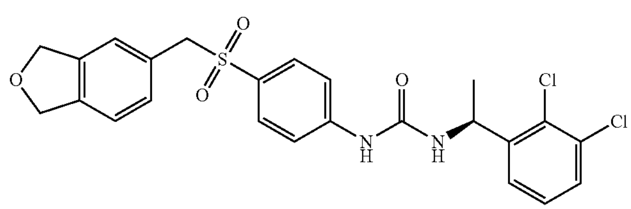 [SMILES: C[C@H](NC(=O)Nc1ccc(S(=O)(=O)Cc2ccc3c(c2)COC3)cc1)c1cccc(Cl)c1Cl] | $IC_{50}$ = 12.06 $EC_{50}$/$E_{Max}$ > 30 $EC_{50}$ = 0.649 | Not performed | Not performed | Not performed |
| H1099 | 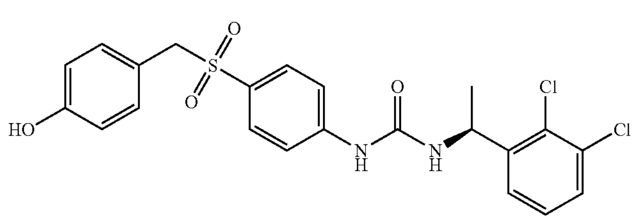 [SMILES: C[C@H](NC(=O)Nc1ccc(S(=O)(=O)Cc2ccc(O)cc2)cc1)c1cccc(Cl)c1Cl] | $IC_{50}$ = 8.673 $EC_{50}$/$E_{Max}$ > 30 $EC_{50}$ = 1.139 | Not performed | Not performed | Not performed |
| H1101 | 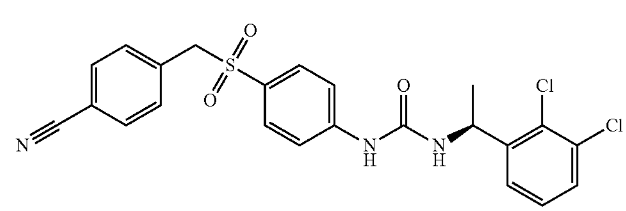 [SMILES: C[C@H](NC(=O)Nc1ccc(S(=O)(=O)Cc2ccc(C#N)cc2)cc1)c1cccc(Cl)c1Cl] | $IC_{50}$ = 30 $EC_{50}$/$E_{Max}$ > 30 $EC_{50}$ = not reported | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1102 | (R/S) structure | $IC_{50}$ = 0.0739 $EC_{50}/E_{Max} > 30$ $EC_{50}$ = 0.0583/0.036/0.0216 | Not performed | Not performed | Not performed |
| H1103 | (S/R) structure | $IC_{50}$ = 0.487 $EC_{50}/E_{Max} > 30$ $EC_{50}$ = 0.066/0.05572 | Not performed | Not performed | Not performed |
| H1106 | structure | $IC_{50}$ = 1.426 $EC_{50}/E_{Max} > 30$ $EC_{50}$ = 0.862 | Not performed | Not performed | Not performed |
| H1108 | structure | $IC_{50}$ = 0.422 $EC_{50}/E_{Max} > 30$ $EC_{50}$ = 0.1166 | H = 38.7 M = 47.5 R = not reported D = not reported | Not performed | Not performed |
| H1109 | structure | $IC_{50}$ = 0.427 $EC_{50}/E_{Max} > 30$ $EC_{50}$ = 0.136 | Not performed | Not performed | Not performed |
| H1110 | structure | $IC_{50}$ = 0.95 $EC_{50}/E_{Max} > 30$ $EC_{50}$ = not reported | Not performed | Not performed | Not performed |
| H1111 | structure | $IC_{50}$ = 2.251 $EC_{50}/E_{Max} > 30$ $EC_{50}$ = 1.233 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) t$_{1/2}$ (h) F (%) | Food Intake Study |
|---|---|---|---|---|---|
| H1125 | 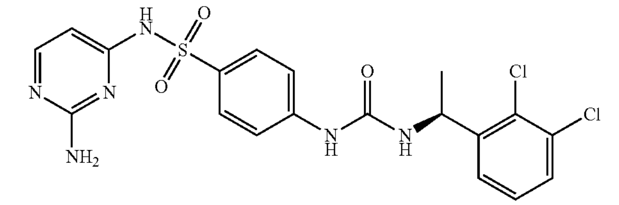 [SMILES: C[C@H](NC(=O)Nc1ccc(S(=O)(=O)Nc2ccnc(N)n2)cc1)c1cccc(Cl)c1Cl] | IC$_{50}$ = 0.893 EC$_{50}$/ E$_{Max}$ > 30 EC$_{50}$ = 0.0933 | H = 10.7 M = 14.9 R = not reported D = not reported | Not performed | Not performed |
| H1126 | 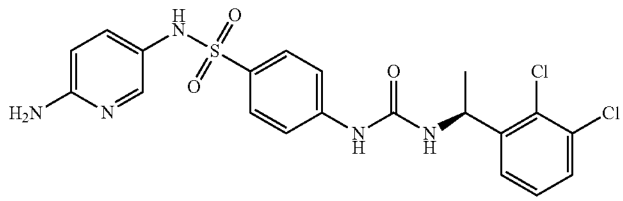 [SMILES: C[C@H](NC(=O)Nc1ccc(S(=O)(=O)Nc2ccc(N)nc2)cc1)c1cccc(Cl)c1Cl] | IC$_{50}$ = 0.183 EC$_{50}$/ E$_{Max}$ > 30 EC$_{50}$ = not reported | Not performed | Not performed | Not performed |
| H1127 | 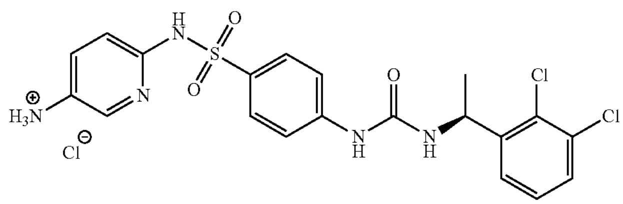 [SMILES: C[C@H](NC(=O)Nc1ccc(S(=O)(=O)Nc2ccc([NH3+])cn2)cc1)c1cccc(Cl)c1Cl ; [Cl-]] | IC$_{50}$ = 0.861 EC$_{50}$/ E$_{Max}$ > 30 EC$_{50}$ = 0.0947 | H = 41 M = 59.5 R = not reported D = not reported | Not performed | Not performed |
| H1129 | 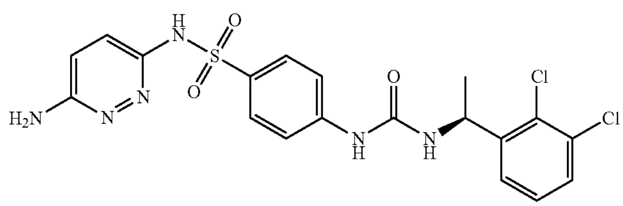 [SMILES: C[C@H](NC(=O)Nc1ccc(S(=O)(=O)Nc2ccc(N)nn2)cc1)c1cccc(Cl)c1Cl] | IC$_{50}$ = 3.33 EC$_{50}$/ E$_{Max}$ > 30 EC$_{50}$ = 2.461 | Not performed | Not performed | Not performed |
| H1130 | 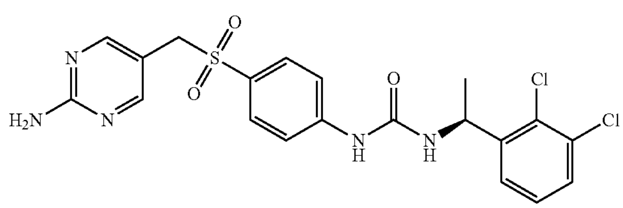 [SMILES: C[C@H](NC(=O)Nc1ccc(S(=O)(=O)Cc2cnc(N)nc2)cc1)c1cccc(Cl)c1Cl] | IC$_{50}$ = 3.38 EC$_{50}$/ E$_{Max}$ > 30 EC$_{50}$ = 1.28 | Not performed | Not performed | Not performed |
| H1131 | 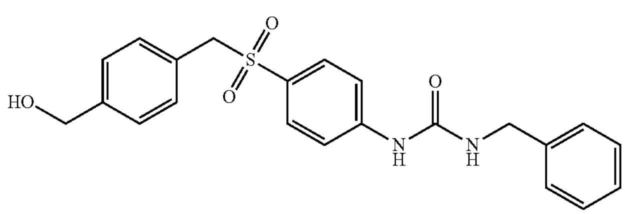 [SMILES: O=C(NCc1ccccc1)Nc1ccc(S(=O)(=O)Cc2ccc(CO)cc2)cc1] | IC$_{50}$ = 30 EC$_{50}$/ E$_{Max}$ > 30 EC$_{50}$ = not reported | Not performed | Not performed | Not performed |
| H1132 | 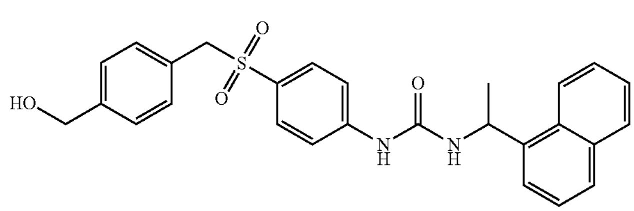 [SMILES: CC(NC(=O)Nc1ccc(S(=O)(=O)Cc2ccc(CO)cc2)cc1)c1cccc2ccccc12] | IC$_{50}$ = 0.574 EC$_{50}$/ E$_{Max}$ > 30 EC$_{50}$ = 0.219 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1133 | (structure) | $IC_{50}$ = 0.419<br>$EC_{50}$/<br>$E_{Max}$ > 30<br>$EC_{50}$ = 0.17 | Not performed | Not performed | Not performed |
| H1140 | (structure) | $IC_{50}$ = 30<br>$EC_{50}$/<br>$E_{Max}$ > 30<br>$EC_{50}$ = not reported | Not performed | Not performed | Not performed |
| H1141 | (structure) | $IC_{50}$ = 2.61<br>$EC_{50}$/<br>$E_{Max}$ > 30<br>$EC_{50}$ = 0.562 | Not performed | Not performed | Not performed |
| H1142 | (structure) | $IC_{50}$ = 30<br>$EC_{50}$/<br>$E_{Max}$ > 30<br>$EC_{50}$ = 0.44 | H = 114.9<br>M = 151.4<br>R = 209.6<br>D = not reported | Not performed | Not performed |
| H1145 | (structure) | $IC_{50}$ = 30<br>$EC_{50}$/<br>$E_{Max}$ > 30<br>$EC_{50}$ = not reported | Not performed | Not performed | Not performed |
| H1148 | (structure) | $IC_{50}$ = 0.01<br>$EC_{50}$/<br>$E_{Max}$ > 30<br>$EC_{50}$ = 0.0029 & 0.00313<br>PPB = 91.2 (H)<br>PPB = 94.5 (R)<br>PPB = 92.3 (M)<br>hERG inh = 12.52 | H = 22.2<br>M = 21.1<br>R = not reported<br>D = not reported | $CL_{iv}$ = 1.23/61.9 (M); 145.3 (R); 0.7 (D)<br>$CL_{po}$ = 96.7/164.5 (M); 4.82 (D)<br>$Vd_{iv}$ = 2.43/190.5 (M); 104.5 (R); 2.34 (D)<br>$Vd_{po}$ = 176.8/617.4 (M); 14.74 (D)<br>$t_{1/2iv}$ = 1.37/2.13 (M); 0.51 (R); | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| | | | | 2.32 (D) $t_{1/2po}$ = 1.27/2.6 (M); 2.34 (D) F = 1.3/36.23 (M); 15.7 (D) | |
| H1149 | 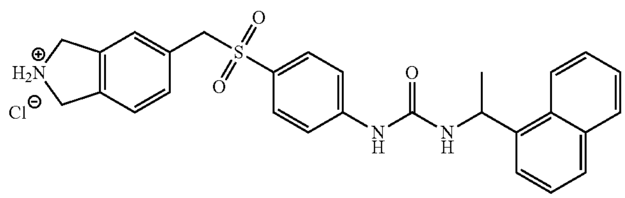 [SMILES: [Cl-] ; CC(NC(=O)Nc1ccc(S(=O)(=O)Cc2ccc3c(c2)C[NH2+]C3)cc1)c1cccc2ccccc12] | $IC_{50}$ = 0.0048 $EC_{50}$/ $E_{Max}$ > 30 $EC_{50}$ = 0.00169 & 0.00241 | H = 21.1 M = 24.3 R = not reported D = not reported | $CL_{iv}$ = 0.98 $CL_{po}$ = 107.5 $Vd_{iv}$ = 1.22 $Vd_{po}$ = 272 $t_{1/2iv}$ = 0.87 $t_{1/2po}$ = 1.75 F = 0.86 | Not performed |
| H1154 | 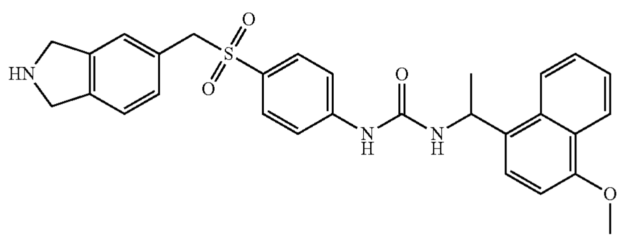 [SMILES: COc1ccc(C(C)NC(=O)Nc2ccc(S(=O)(=O)Cc3ccc4c(c3)CNC4)cc2)c2ccccc12] | $IC_{50}$ = 0.12648 $EC_{50}$/ $E_{Max}$ > 30 $EC_{50}$ = 0.0298 & 0.02677 | H = 19.2 M = 22.9 R = not reported D = not reported | Not performed | Not performed |
| H1155 | 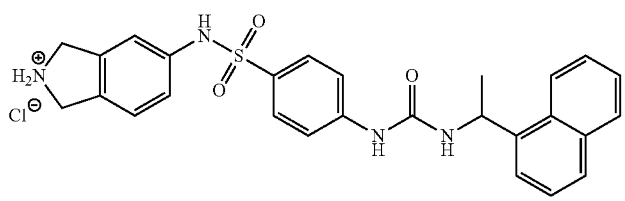 [SMILES: [Cl-] ; CC(NC(=O)Nc1ccc(S(=O)(=O)Nc2ccc3c(c2)C[NH2+]C3)cc1)c1cccc2ccccc12] | $IC_{50}$ = 0.0043 $EC_{50}$/ $E_{Max}$ > 30 $EC_{50}$ = 0.00503 (partial) | Not performed | Not performed | Not performed |
| H1156 | 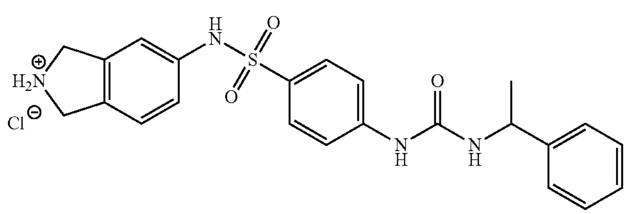 [SMILES: [Cl-] ; CC(NC(=O)Nc1ccc(S(=O)(=O)Nc2ccc3c(c2)C[NH2+]C3)cc1)c1ccccc1] | $IC_{50}$ = 0.0103 $EC_{50}$/ $E_{Max}$ > 30 $EC_{50}$ = 0.00426 | H = 18.1 M = 12.9 R = not reported D = not reported | Not performed | Not performed |
| H1166 | 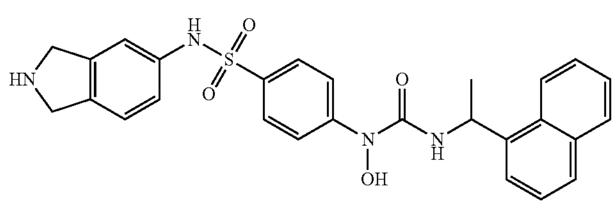 [SMILES: CC(NC(=O)N(O)c1ccc(S(=O)(=O)Nc2ccc3c(c2)CNC3)cc1)c1cccc2ccccc12] | $IC_{50}$ = 0.009 $EC_{50}$/ $E_{Max}$ > 30 $EC_{50}$ = 0.0071 | H = 19.9 M = 14.5 R = not reported D = not reported | Not performed | Not performed |
| H1178 | 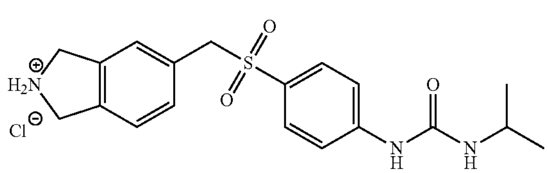 [SMILES: [Cl-] ; CC(C)NC(=O)Nc1ccc(S(=O)(=O)Cc2ccc3c(c2)C[NH2+]C3)cc1] | $IC_{50}$ = 4.89 $EC_{50}$/ $E_{Max}$ > 30 $EC_{50}$ = 1.017 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1179 | 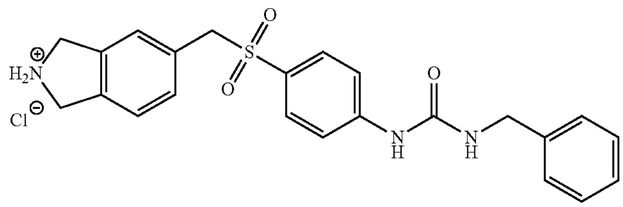 [SMILES: [Cl-] ; O=C(NCc1ccccc1)Nc1ccc(S(=O)(=O)Cc2ccc3c(c2)C[NH2+]C3)cc1] | $IC_{50}$ = 0.143 $EC_{50}$/ $E_{Max}$ > 30 $EC_{50}$ = 0.03743 | H = 14.9 M < 10 R = not reported D = not reported | Not performed | Not performed |
| H1180 | 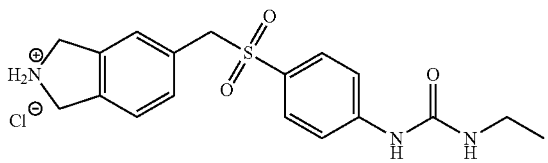 [SMILES: [Cl-] ; CCNC(=O)Nc1ccc(S(=O)(=O)Cc2ccc3c(c2)C[NH2+]C3)cc1] | $IC_{50}$ = 14.66 $EC_{50}$/ $E_{Max}$ > 30 $EC_{50}$ = 0.315 | Not performed | Not performed | Not performed |
| H1181 | 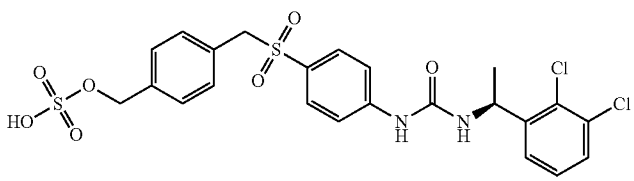 [SMILES: C[C@H](NC(=O)Nc1ccc(S(=O)(=O)Cc2ccc(COS(=O)(=O)O)cc2)cc1)c1cccc(Cl)c1Cl] | $IC_{50}$ = 3.31 $EC_{50}$/ $E_{Max}$ > 30 $EC_{50}$ = 0.957 | Not performed | Not performed | Not performed |
| H1188 | 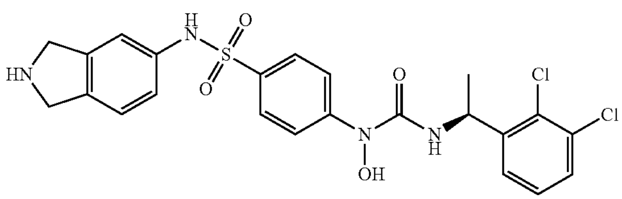 [SMILES: C[C@H](NC(=O)N(O)c1ccc(S(=O)(=O)Nc2ccc3c(c2)CNC3)cc1)c1cccc(Cl)c1Cl] | $IC_{50}$ = 0.539 $EC_{50}$/ $E_{Max}$ > 30 $EC_{50}$ = not reported | Not performed | Not performed | Not performed |
| H1190 | 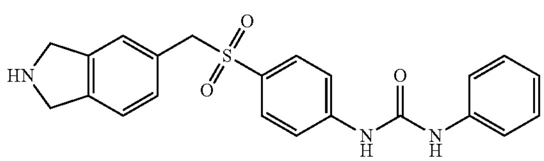 [SMILES: O=C(Nc1ccccc1)Nc1ccc(S(=O)(=O)Cc2ccc3c(c2)CNC3)cc1] | $IC_{50}$ = 0.264 $EC_{50}$/ $E_{Max}$ > 30 $EC_{50}$ = 0.317 | Not performed | Not performed | Not performed |
| H1193 | 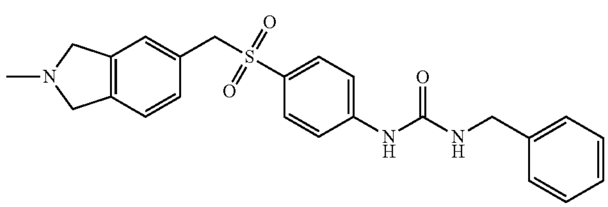 [SMILES: CN1Cc2ccc(CS(=O)(=O)c3ccc(NC(=O)NCc4ccccc4)cc3)cc2C1] | $IC_{50}$ = 0.324 $EC_{50}$/ $E_{Max}$ > 30 $EC_{50}$ = 0.064 | H = 49.8 M = 43.7 R = not reported D = not reported | Not performed | Not performed |
| H1194 | 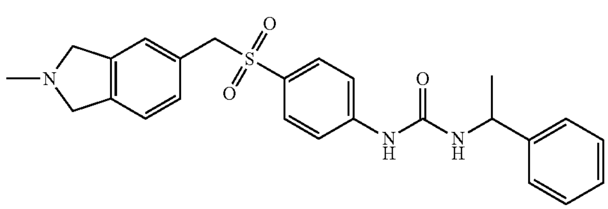 | $IC_{50}$ = 0.0383 $EC_{50}$/ $E_{Max}$ > 30 $EC_{50}$ = 0.0168 PPB = 92.4 (H) PPB = 94 (M) hERG inh = 22.6 | H = 111.6 M = 64.2 R = 56 D = 14 | $CL_{iv}$ = 3.61 (M); 5.68 (R); 1.00 (D) $CL_{po}$ = 22.8 (M); 50.9 (R); 1.84 (D) $Vd_{iv}$ = 6.33 (M); 8.86 (R); 2.11 (D) $Vd_{po}$ = 53.3 (M); 232.2 (R); 4.05 (D) | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| | | | | $t_{1/2iv}$ = 1.21 (M); 1.08 (R); 1.44 (D) $t_{1/2po}$ = 1.62 (M); 4.54 (R); 1.5 (D) F = 15.56 (M); 11.9 (R); 54.07 (D) | |
| H1199 | 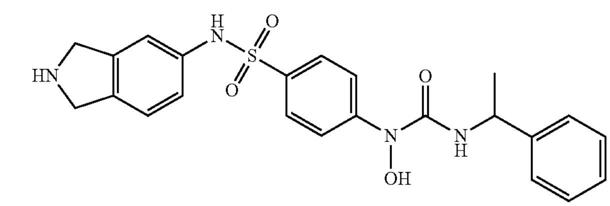 [SMILES: CC(NC(=O)N(O)c1ccc(S(=O)(=O)Nc2ccc3c(c2)CNC3)cc1)c1ccccc1] | $IC_{50}$ = 0.0757 $EC_{50}/E_{Max}$ > 30 $EC_{50}$ = not reported | Not performed | Not performed | Not performed |
| H1203 | 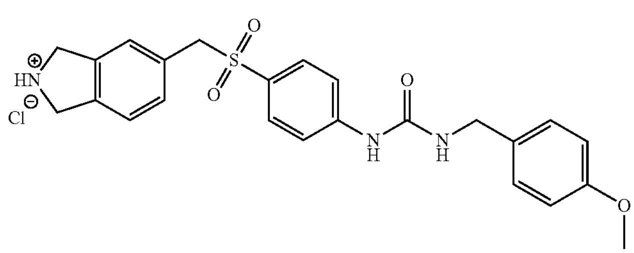 [SMILES: [Cl-] ; COc1ccc(CNC(=O)Nc2ccc(S(=O)(=O)Cc3ccc4c(c3)C[NH2+]C4)cc2)cc1] | $IC_{50}$ = 0.447 $EC_{50}/E_{Max}$ > 30 $EC_{50}$ = 0.161 | Not performed | Not performed | Not performed |
| H1204 | 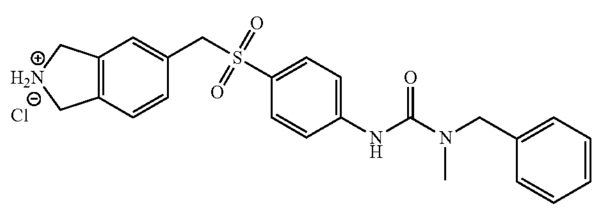 [SMILES: [Cl-] ; CN(Cc1ccccc1)C(=O)Nc1ccc(S(=O)(=O)Cc2ccc3c(c2)C[NH2+]C3)cc1] | $IC_{50}$ = 0.692 $EC_{50}/E_{Max}$ > 30 $EC_{50}$ = 0.624 | Not performed | Not performed | Not performed |
| H1205 | 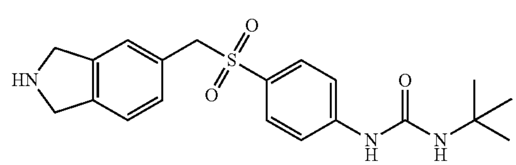 [SMILES: CC(C)(C)NC(=O)Nc1ccc(S(=O)(=O)Cc2ccc3c(c2)CNC3)cc1] | $IC_{50}$ = 9.87 $EC_{50}/E_{Max}$ > 30 $EC_{50}$ = 5.335 | Not performed | Not performed | Not performed |
| H1206 | 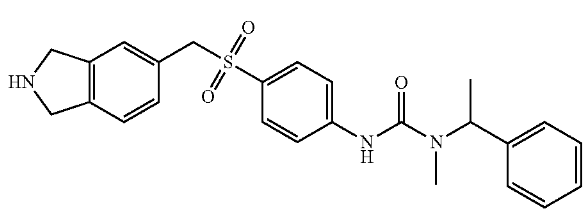 [SMILES: CC(c1ccccc1)N(C)C(=O)Nc1ccc(S(=O)(=O)Cc2ccc3c(c2)CNC3)cc1] | $IC_{50}$ = 0.262 $EC_{50}/E_{Max}$ > 30 $EC_{50}$ = 0.252 | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1208 | 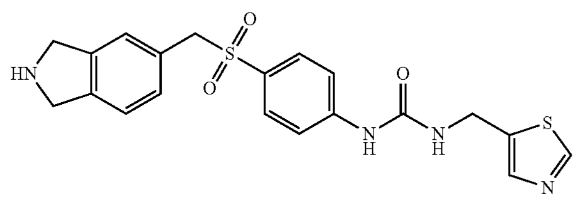 [SMILES: O=C(NCc1cncs1)Nc1ccc(S(=O)(=O)Cc2ccc3c(c2)CNC3)cc1] | $IC_{50}$ >30<br>$EC_{50}/E_{Max}$ > 30<br>$EC_{50}$ = not reported | Not performed | Not performed | Not performed |
| H1212 | 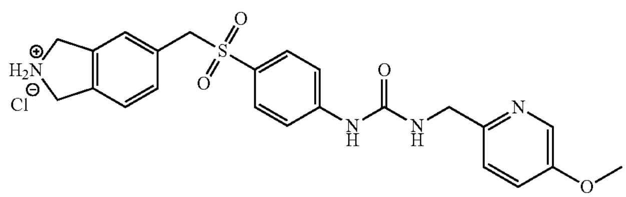 [SMILES: Cl ; COc1ccc(CNC(=O)Nc2ccc(S(=O)(=O)Cc3ccc4c(c3)CNC4)cc2)nc1] | $IC_{50}$ = 3.099<br>$EC_{50}/E_{Max}$ > 30<br>$EC_{50}$ = 1.775 | Not performed | Not performed | Not performed |
| H1213 | 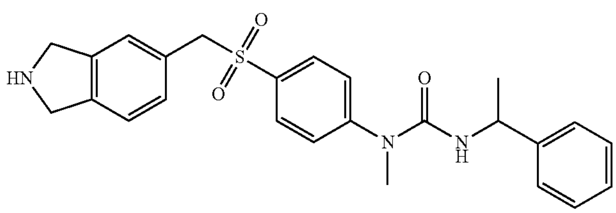 [SMILES: CC(NC(=O)N(C)c1ccc(S(=O)(=O)Cc2ccc3c(c2)CNC3)cc1)c1ccccc1] | $IC_{50}$ = 4.35<br>$EC_{50}/E_{Max}$ > 30<br>$EC_{50}$ = not reported | Not performed | Not performed | Not performed |
| H1214 | 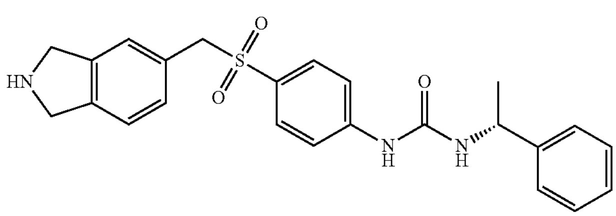 [SMILES: C[C@@H](NC(=O)Nc1ccc(S(=O)(=O)Cc2ccc3c(c2)CNC3)cc1)c1ccccc1] | $IC_{50}$ = 0.278<br>$EC_{50}/E_{Max}$ > 30<br>$EC_{50}$ = 0.147 | H = 16.6<br>M = 21.4<br>R = 18<br>D < 10 | Not performed | Not performed |
| H1215 | 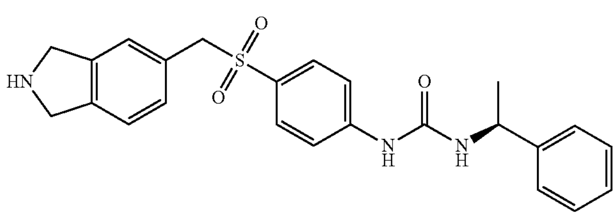 [SMILES: C[C@H](NC(=O)Nc1ccc(S(=O)(=O)Cc2ccc3c(c2)CNC3)cc1)c1ccccc1] | $IC_{50}$ = 0.0124<br>$EC_{50}/E_{Max}$ > 30<br>$EC_{50}$ = 0.0046<br>PPB = 90.3 (H)<br>PPB = 90.7 (M)<br>PPB = 93.5 (R) | H = 21<br>M = 13.7<br>R = 18.5<br>D = 16.6 | Not performed | Not performed |
| H1216 | 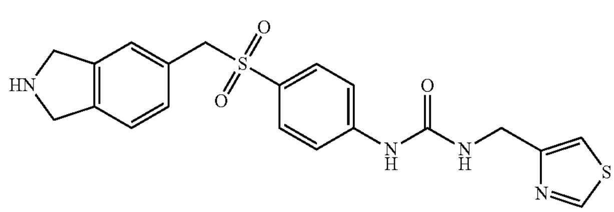 [SMILES: O=C(NCc1cscn1)Nc1ccc(S(=O)(=O)Cc2ccc3c(c2)CNC3)cc1] | $IC_{50}$ = 8.447<br>$EC_{50}/E_{Max}$ > 30<br>$EC_{50}$ = not reported | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) t$_{1/2}$ (h) F (%) | Food Intake Study |
|---|---|---|---|---|---|
| H1217 | 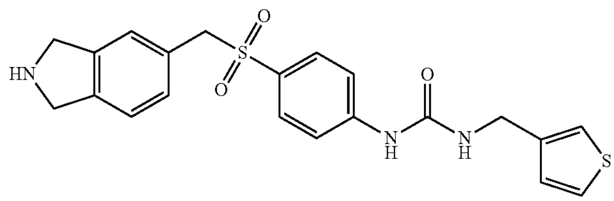 | IC$_{50}$ = 1.4475 EC$_{50}$/E$_{Max}$ > 30 EC$_{50}$ = 1.147 | Not performed | Not performed | Not performed |
| H1219 | 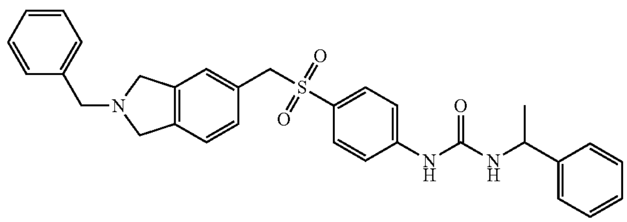 [SMILES: CC(NC(=O)Nc1ccc(S(=O)(=O)Cc2ccc3c(c2)CN(Cc2ccccc2)C3)cc1)c1ccccc1] | IC$_{50}$ = 0.00777 EC$_{50}$/E$_{Max}$ > 30 EC$_{50}$ = 0.163 | H > 500 M > 500 R = not reported D = not reported | Not performed | Not performed |
| H1220 | 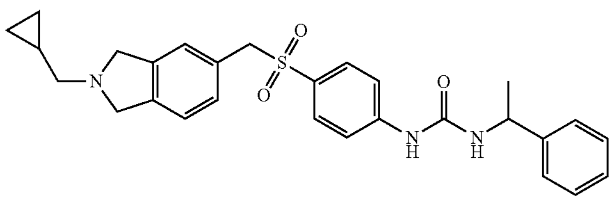 [SMILES: CC(NC(=O)Nc1ccc(S(=O)(=O)Cc2ccc3c(c2)CN(CC2CC2)C3)cc1)c1ccccc1] | IC$_{50}$ = 0.00361 EC$_{50}$/E$_{Max}$ > 30 EC$_{50}$ = 0.0304 | H = 183.8 M = 248 R = not reported D = not reported | CL$_{iv}$ = 3.05 CL$_{po}$ = 61.6 Vd$_{iv}$ = 3.08 Vd$_{po}$ = 78.7 t$_{1/2iv}$ = 0.7 t$_{1/2po}$ = 0.89 F = 4.71 | Not performed |
| H1221 | 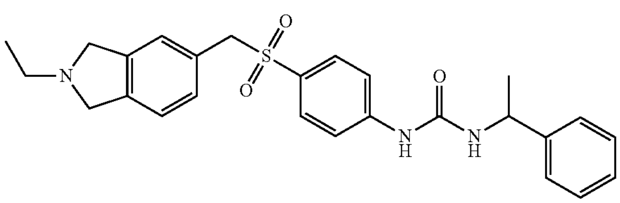 [SMILES: CCN1Cc2ccc(CS(=O)(=O)c3ccc(NC(=O)NC(C)c4ccccc4)cc3)cc2C1] | IC$_{50}$ = 0.0081 EC$_{50}$/E$_{Max}$ > 30 EC$_{50}$ = 0.0387 | H = 111.2 M = 107.7 R = not reported D = not reported | Not performed | Not performed |
| H1222 | 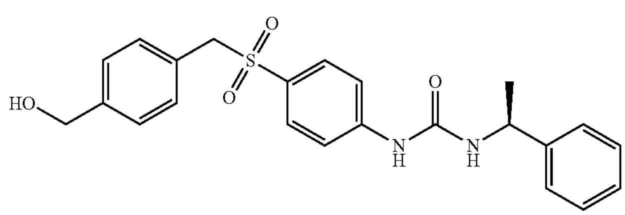 [SMILES: C[C@H](NC(=O)Nc1ccc(S(=O)(=O)Cc2ccc(CO)cc2)cc1)c1ccccc1] | IC$_{50}$ = 3.16 EC$_{50}$/E$_{Max}$ > 30 EC$_{50}$ = not reported | Not performed | Not performed | Not performed |
| H1225 | 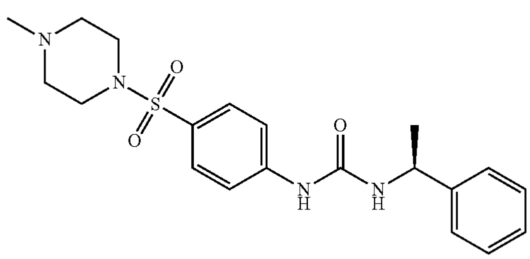 | IC$_{50}$ = 5.9 EC$_{50}$/E$_{Max}$ > 30 EC$_{50}$ = not reported | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1227 | 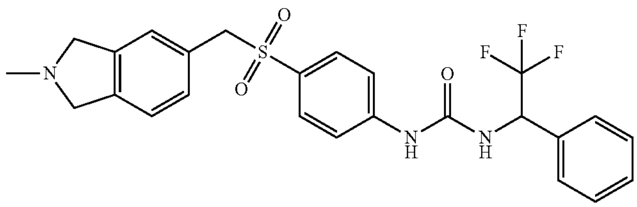 [SMILES: CN1Cc2ccc(CS(=O)(=O)c3ccc(NC(=O)NC(c4ccccc4)C(F)(F)F)cc3)cc2C1] | $IC_{50}$ = 0.0384 $EC_{50}/E_{Max}$ > 30 $EC_{50}$ = 0.175 | H = 99.4 M = 79.9 R = not reported D = not reported | Not performed | Not performed |
| H1228 | 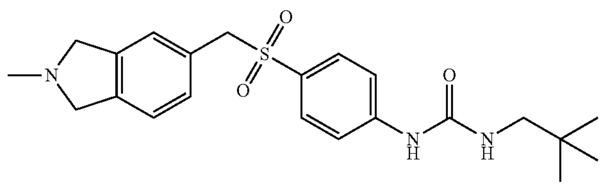 [SMILES: CN1Cc2ccc(CS(=O)(=O)c3ccc(NC(=O)NCC(C)(C)C)cc3)cc2C1] | $IC_{50}$ = 0.766 $EC_{50}/E_{Max}$ > 30 $EC_{50}$ = 1.263 | Not performed | Not performed | Not performed |
| H1229 | 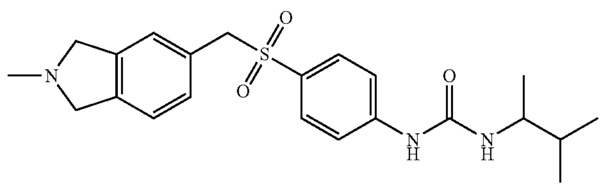 [SMILES: CC(C)C(C)NC(=O)Nc1ccc(S(=O)(=O)Cc2ccc3c(c2)CN(C)C3)cc1] | $IC_{50}$ = 0.291 $EC_{50}/E_{Max}$ > 30 $EC_{50}$ = 0.369 | Not performed | Not performed | Not performed |
| H1230 | 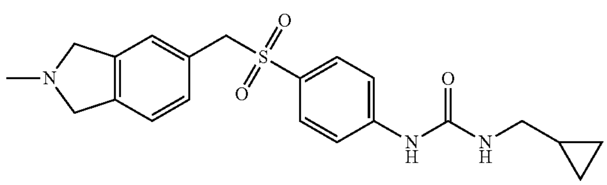 [SMILES: CN1Cc2ccc(CS(=O)(=O)c3ccc(NC(=O)NCC4CC4)cc3)cc2C1] | $IC_{50}$ = 6.4 $EC_{50}/E_{Max}$ > 30 $EC_{50}$ = not reported | Not performed | Not performed | Not performed |
| H1231 | 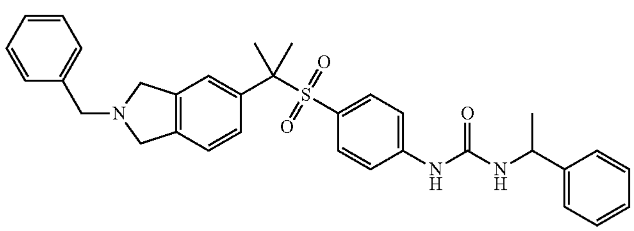 [SMILES: CC(NC(=O)Nc1ccc(S(=O)(=O)C(C)(C)c2ccc3c(c2)CN(Cc2ccccc2)C3)cc1)c1ccccc1] | $IC_{50}$ > 30 $EC_{50}/E_{Max}$ > 30 $EC_{50}$ = not reported | Not performed | Not performed | Not performed |
| H1232 | 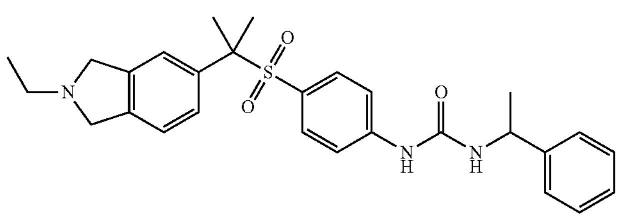 [SMILES: CCN1Cc2ccc(C(C)(C)S(=O)(=O)c3ccc(NC(=O)NC(C)c4ccccc4)cc3)cc2C1] | $IC_{50}$ > 30 $EC_{50}/E_{Max}$ > 30 $EC_{50}$ = 0.3095 | Not performed | Not performed | Not performed |
| H1233 | 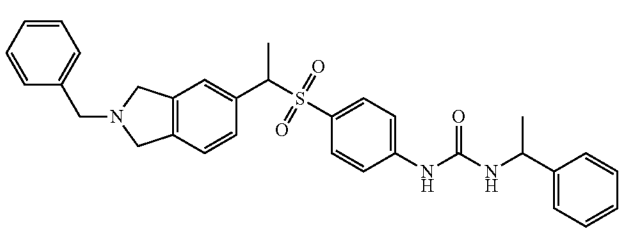 [SMILES: CC(NC(=O)Nc1ccc(S(=O)(=O)C(C)c2ccc3c(c2)CN(Cc2ccccc2)C3)cc1)c1ccccc1] | $IC_{50}$ = 0.2246 $EC_{50}/E_{Max}$ > 30 $EC_{50}$ = 0.1702 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1234 | 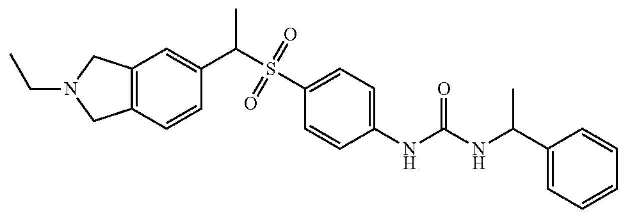 [SMILES: CCN1Cc2ccc(C(C)S(=O)(=O)c3ccc(NC(=O)NC(C)c4ccccc4)cc3)cc2C1] | $IC_{50}$ = 0.0426 $EC_{50}$/ $E_{Max}$ > 30 $EC_{50}$ = 0.0154 | H = 149.8 M = 122.7 R = not reported D = not reported | Not performed | Not performed |
| H1235 | 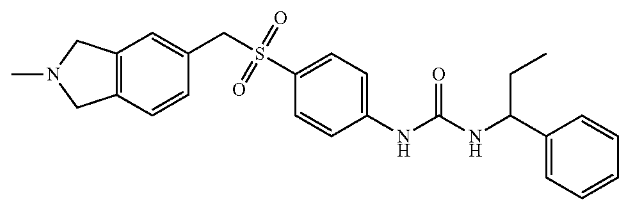 [SMILES: CCC(NC(=O)Nc1ccc(S(=O)(=O)Cc2ccc3c(c2)CN(C)C3)cc1)c1ccccc1] | $IC_{50}$ = 0.032 $EC_{50}$/ $E_{Max}$ > 30 $EC_{50}$ = 0.0061 | H = 102.4 M = 87.1 R = not reported D = not reported | Not performed | Not performed |
| H1236 | 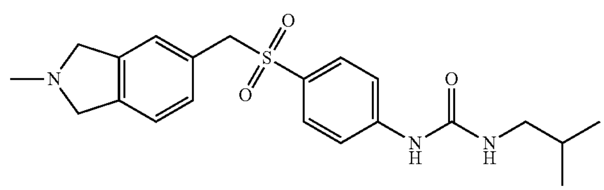 [SMILES: CC(C)CNC(=O)Nc1ccc(S(=O)(=O)Cc2ccc3c(c2)CN(C)C3)cc1] | $IC_{50}$ = 1.641 $EC_{50}$/ $E_{Max}$ > 30 $EC_{50}$ = 0.5066 | Not performed | Not performed | Not performed |
| H1237 | 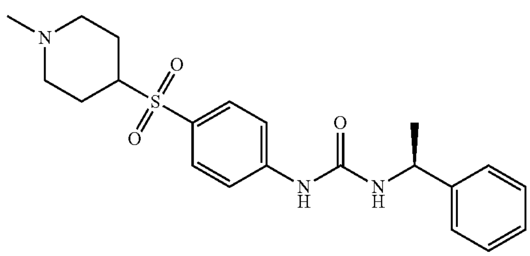 | $IC_{50}$ >30 $EC_{50}$/ $E_{Max}$ > 30 $EC_{50}$ = not reported | Not performed | Not performed | Not performed |
| H1238 | 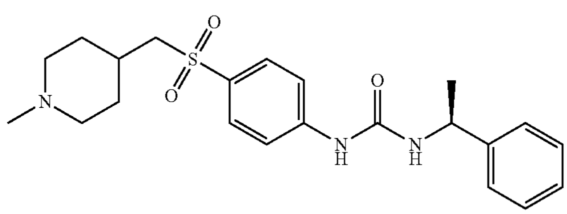 [SMILES: C[C@H](NC(=O)Nc1ccc(S(=O)(=O)CC2CCN(C)CC2)cc1)c1ccccc1] | $IC_{50}$ >30 $EC_{50}$/ $E_{Max}$ > 30 $EC_{50}$ = not reported | Not performed | Not performed | Not performed |
| H1239 | 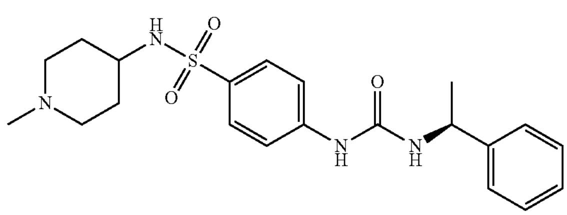 [SMILES: C[C@H](NC(=O)Nc1ccc(S(=O)(=O)NC2CCN(C)CC2)cc1)c1ccccc1] | $IC_{50}$ >30 $EC_{50}$/ $E_{Max}$ > 30 $EC_{50}$ = not reported | Not performed | Not performed | Not performed |
| H1244 | 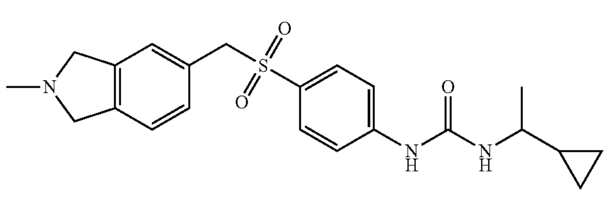 | $IC_{50}$ = 1.285 $EC_{50}$/ $E_{Max}$ > 30 $EC_{50}$ = 0.356 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1248 | 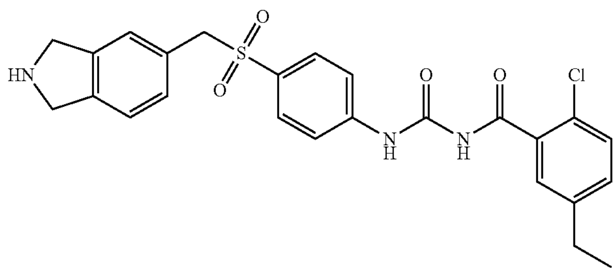 [SMILES: CCc1ccc(Cl)c(C(=O)NC(=O)Nc2ccc(S(=O)(=O)Cc3ccc4c(c3)CNC4)cc2)c1] | $IC_{50}$ = 0.283 $EC_{50}/$ $E_{Max}$ > 30 $EC_{50}$ = not reported | Not performed | Not performed | Not performed |
| H1249 | 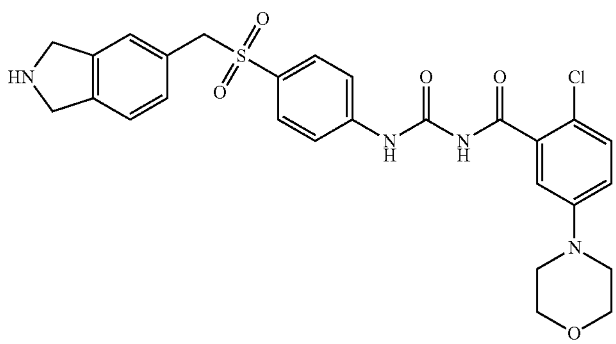 [SMILES: O=C(NC(=O)c1cc(N2CCOCC2)ccc1Cl)Nc1ccc(S(=O)(=O)Cc2ccc3c(c2)CNC3)cc1] | $IC_{50}$ = 3.29 $EC_{50}/$ $E_{Max}$ > 30 $EC_{50}$ = 1.63 | Not performed | Not performed | Not performed |
| H1250 | 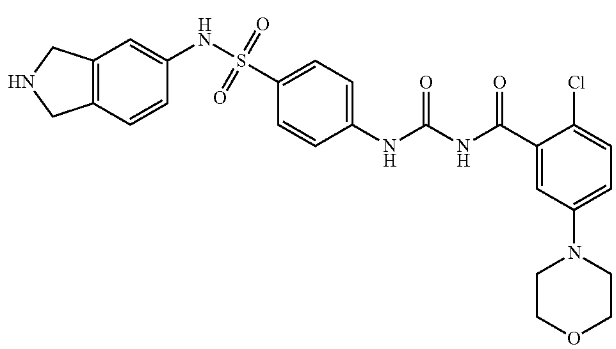 [SMILES: O=C(NC(=O)c1cc(N2CCOCC2)ccc1Cl)Nc1ccc(S(=O)(=O)Nc2ccc3c(c2)CNC3)cc1] | $IC_{50}$ = 1.373 $EC_{50}/$ $E_{Max}$ > 30 $EC_{50}$ = not reported | Not performed | Not performed | Not performed |
| H1251 | 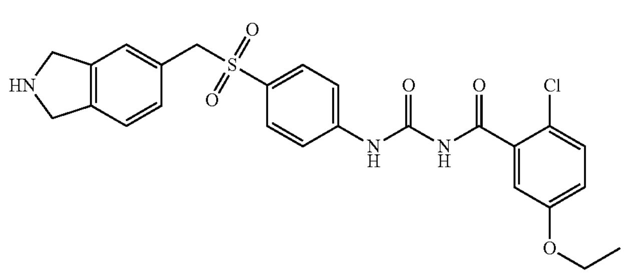 [SMILES: CCOc1ccc(Cl)c(C(=O)NC(=O)Nc2ccc(S(=O)(=O)Cc3ccc4c(c3)CNC4)cc2)c1] | $IC_{50}$ = 0.0896 $EC_{50}/$ $E_{Ma}$ > 30 $EC_{50}$ = not reported | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1252 | 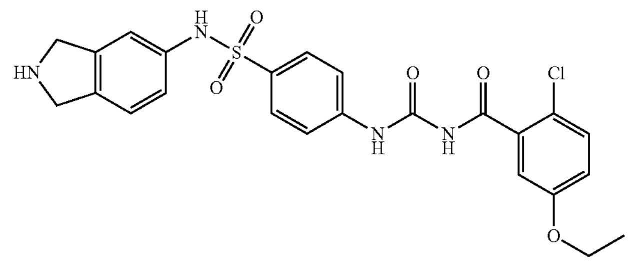 | $IC_{50}$ = 0.44 $EC_{50}/E_{Max}$ > 30 $EC_{50}$ = not reported | Not performed | Not performed | Not performed |
| H1253 | 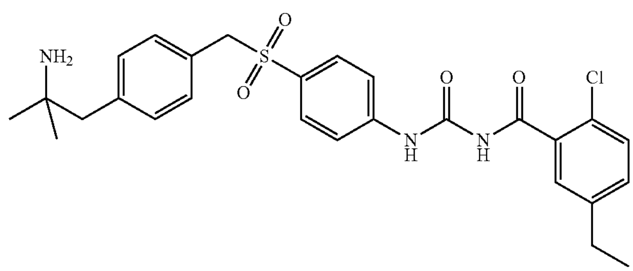 [SMILES: CCc1ccc(Cl)c(C(=O)NC(=O)Nc2ccc(S(=O)(=O)Cc3ccc(CC(C)(C)N)cc3)cc2)c1] | $IC_{50}$ = 0.0868 $EC_{50}/E_{Max}$ = 0.036/1485 $EC_{50}$ = not reported | Not performed | Not performed | Not performed |
| H1254 | 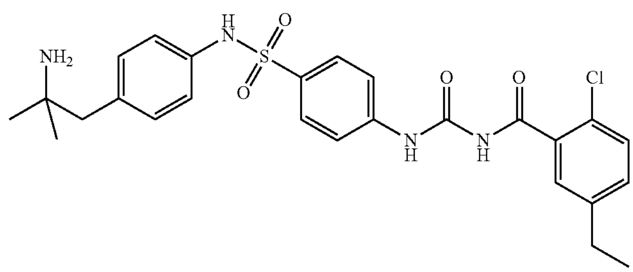 [SMILES: CCc1ccc(Cl)c(C(=O)NC(=O)Nc2ccc(S(=O)(=O)Nc3ccc(CC(C)(C)N)cc3)cc2)c1] | $IC_{50}$ = 0.0172 $EC_{50}/E_{Max}$ = 0.01754/ 3141 $EC_{50}$ = not reported | Not performed | Not performed | Not performed |
| H1255 | 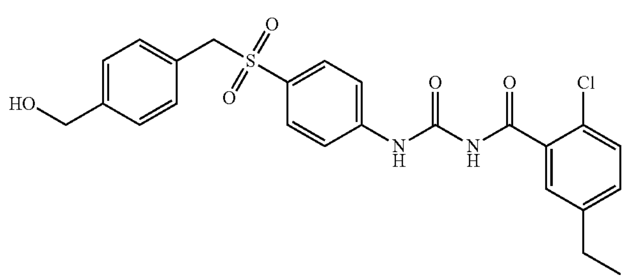 [SMILES: CCc1ccc(Cl)c(C(=O)NC(=O)Nc2ccc(S(=O)(=O)Cc3ccc(CO)cc3)cc2)c1] | $IC_{50}$ = 2.33 $EC_{50}/E_{Max}$ > 30 $EC_{50}$ = not reported | Not performed | Not performed | Not performed |
| H1256 | 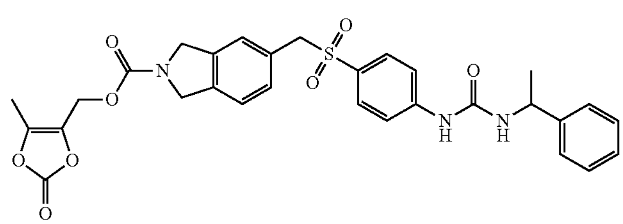 [SMILES: Cc1oc(=O)oc1COC(=O)N1Cc2ccc(CS(=O)(=O)c3ccc(NC(=O)NC(C)c4ccccc4)cc3)cc2C1] | $IC_{50}$ = 0.09 $EC_{50}/E_{Max}$ > 30 $EC_{50}$ = 0.1237 | H = 268.4 M = 272.6 | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1259 | 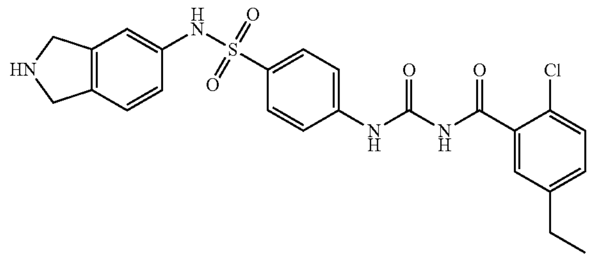 | $IC_{50}$ = 0.272 $EC_{50}$/ $E_{Max}$ > 30 $EC_{50}$ = not reported | Not performed | Not performed | Not performed |
| H1260 | 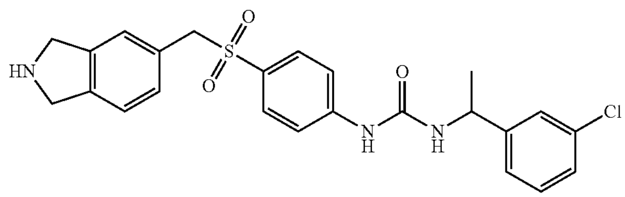 [SMILES: CC(NC(=O)Nc1ccc(S(=O)(=O)Cc2ccc3c(c2)CNC3)cc1)c1cccc(Cl)c1] | $IC_{50}$ = 0.0037 $EC_{50}$/ $E_{Max}$ > 30 $EC_{50}$ = 0.0044 | H = 38.9 M = 24.7 | Not performed | Not performed |
| H1261 | 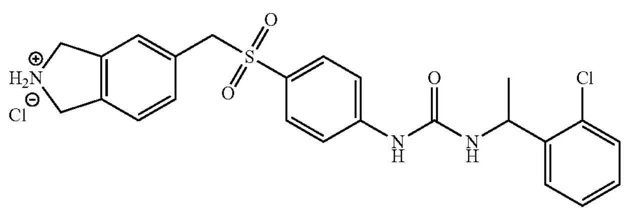 [SMILES: [Cl-] ; CC(NC(=O)Nc1ccc(S(=O)(=O)Cc2ccc3c(c2)C[NH2+]C3)cc1)c1ccccc1Cl] | $IC_{50}$ = 0.00157 $EC_{50}$/ $E_{Max}$ > 30 $EC_{50}$ = 0.0022 PPB = 95.5 (H) PPB = 98.1 (M) | H = 48.8 M = 23 | Not performed | Not performed |
| H1262 | 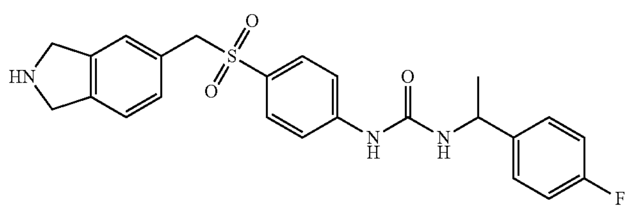 [SMILES: CC(NC(=O)Nc1ccc(S(=O)(=O)Cc2ccc3c(c2)CNC3)cc1)c1ccc(F)cc1] | $IC_{50}$ = 0.0106 $EC_{50}$/ $E_{Max}$ > 30 $EC_{50}$ = 0.0075 PPB = 90.1 (H) PPB = 95.0 (M) | H = 18.2 M = 11.2 R = not reported D = not reported | $CL_{iv}$ = 1.31 $CL_{po}$ = 110.8 $Vd_{iv}$ = 1.69 $Vd_{po}$ = 307 $t_{1/2iv}$ = 0.89 $t_{1/2po}$ = 1.92 F = 1.13 | Not performed |
| H1263 | 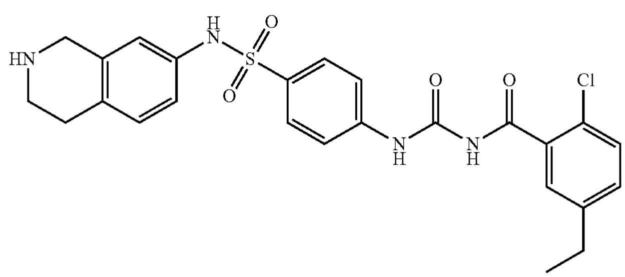 [SMILES: CCc1ccc(Cl)c(C(=O)NC(=O)Nc2ccc(S(=O)(=O)Nc3ccc4c(c3)CNCC4)cc2)c1] | $IC_{50}$ = 0.246 $EC_{50}/E_{Max}$ = 0.329/1540 $EC_{50}$ = not reported | Not performed | Not performed | Not performed |
| H1264 | 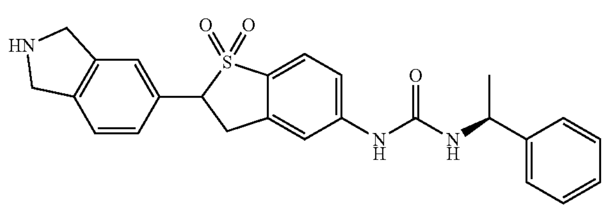 [SMILES: C[C@H](NC(=O)Nc1ccc2c(c1)CC(c1ccc3c(c1)CNC3)S2(=O)=O)c1ccccc1] | $IC_{50}$ = 0.0044 $EC_{50}/E_{Max}$ = 0.0047/4728 $EC_{50}$ = not reported PPB = 77.9 (H) PPB = 81.5 (M) | H < 10 M < 10 R = not reported D = not reported | $CL_{iv}$ = 2.89 $CL_{po}$ = 682.6 $Vd_{iv}$ = 4.83 $Vd_{po}$ = 627.9 $t_{1/2iv}$ = 1.16 $t_{1/2po}$ = 0.64 F = 0.36 | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1266 | 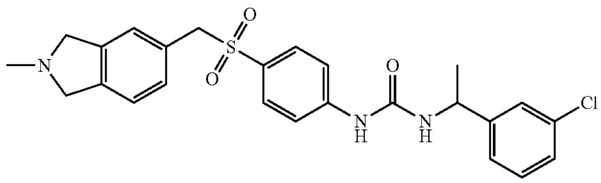 [SMILES: CC(NC(=O)Nc1ccc(S(=O)(=O)Cc2ccc3c(c2)CN(C)C3)cc1)c1cccc(Cl)c1] | $IC_{50}$ = 0.0242 $EC_{50}/E_{Max}$ > 30 $EC_{50}$ = 0.0191 | H = 169.4 M = 106.1 R = not reported D = not reported | Not performed | Not performed |
| H1267 | 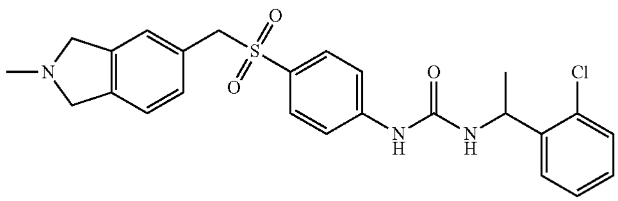 [SMILES: CC(NC(=O)Nc1ccc(S(=O)(=O)Cc2ccc3c(c2)CN(C)C3)cc1)c1ccccc1Cl] | $IC_{50}$ = 0.0092 $EC_{50}/E_{Max}$ > 30 $EC_{50}$ = 0.0047 | H = 109.8 M = 147.8 R = not reported D = not reported | Not performed | Not performed |
| H1268 | 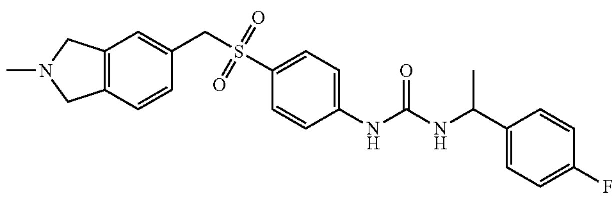 [SMILES: CC(NC(=O)Nc1ccc(S(=O)(=O)Cc2ccc3c(c2)CN(C)C3)cc1)c1ccc(F)cc1] | $IC_{50}$ = 0.0832 $EC_{50}/E_{Max}$ > 30 $EC_{50}$ = 0.0299 | H = 108.7 M = 60.5 R = not reported D = not reported | Not performed | Not performed |
| H1269 | 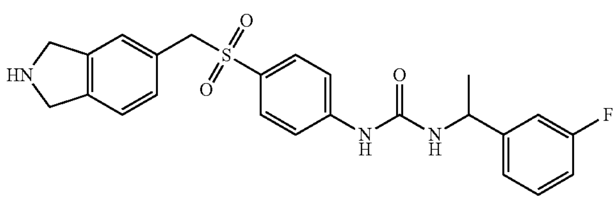 [SMILES: CC(NC(=O)Nc1ccc(S(=O)(=O)Cc2ccc3c(c2)CNC3)cc1)c1cccc(F)c1] | $IC_{50}$ = 0.024 $EC_{50}/E_{Max}$ > 30 $EC_{50}$ = 0.0088 | H = 25.7 M = 23.6 R = not reported D = not reported | Not performed | Not performed |
| H1270 | 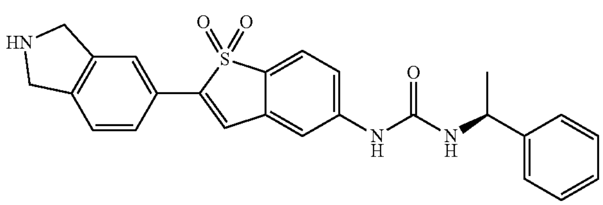 [SMILES: C[C@H](NC(=O)Nc1ccc2c(c1)C=C(c1ccc3c(c1)CNC3)S2(=O)=O)c1ccccc1] | $IC_{50}$ = 0.0251 $EC_{50}/E_{Max}$ = 0.0341/5442 $EC_{50}$ = not reported | Not performed | Not performed | Not performed |
| H1271 | 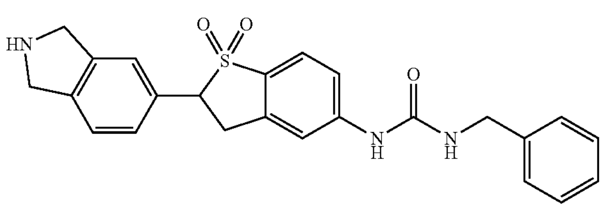 [SMILES: O=C(NCc1ccccc1)Nc1ccc2c(c1)CC(c1ccc3c(c1)CNC3)S2(=O)=O] | $IC_{50}$ = 0.005 $EC_{50}/E_{Max}$ = 0.0096/5006 $EC_{50}$ = not reported | H < 10 M < 10 R = not reported D = not reported | Not performed | Not performed |
| H1272 | 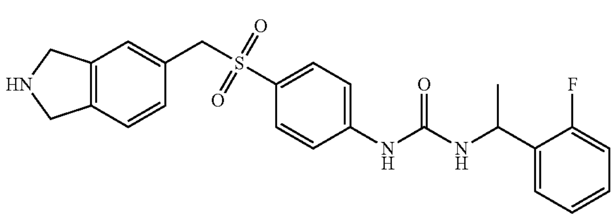 [SMILES: CC(NC(=O)Nc1ccc(S(=O)(=O)Cc2ccc3c(c2)CNC3)cc1)c1ccccc1F] | $IC_{50}$ = 0.0235 $EC_{50}/E_{Max}$ > 30 $EC_{50}$ = 0.0053 | H = 18.4 M = 18.6 R = not reported D = not reported | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1273 | 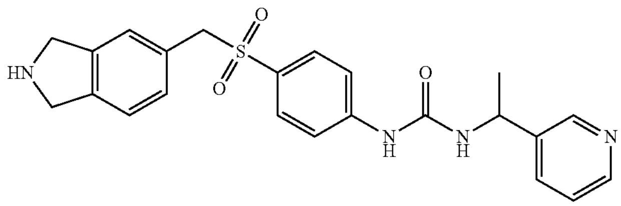 [SMILES: CC(NC(=O)Nc1ccc(S(=O)(=O)Cc2ccc3c(c2)CNC3)cc1)c1cccnc1] | $IC_{50}$ = 1.03 $EC_{50}/E_{Max}$ > 30 $EC_{50}$ = 0.192 | Not performed | Not performed | Not performed |
| H1274 | 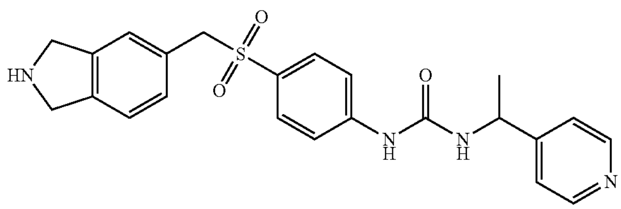 [SMILES: CC(NC(=O)Nc1ccc(S(=O)(=O)Cc2ccc3c(c2)CNC3)cc1)c1ccncc1] | $IC_{50}$ = 1.582 $EC_{50}/E_{Max}$ > 30 $EC_{50}$ = 0.685 | Not performed | Not performed | Not performed |
| H1275 | 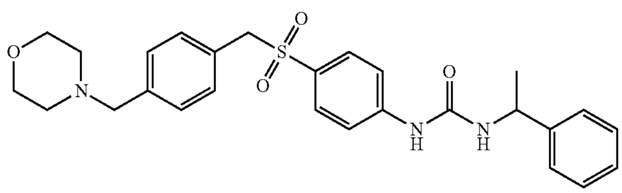 [SMILES: CC(NC(=O)Nc1ccc(S(=O)(=O)Cc2ccc(CN3CCOCC3)cc2)cc1)c1ccccc1] | $IC_{50}$ = 1.02 $EC_{50}/E_{Max}$ > 30 $EC_{50}$ = 0.31 | Not performed | Not performed | Not performed |
| H1276 | 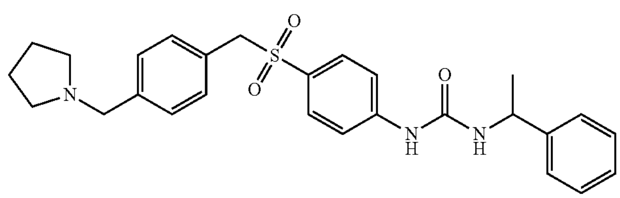 [SMILES: CC(NC(=O)Nc1ccc(S(=O)(=O)Cc2ccc(CN3CCCC3)cc2)cc1)c1ccccc1] | $IC_{50}$ = 0.076 $EC_{50}/E_{Max}$ > 30 $EC_{50}$ = 0.0234 | H = 109.7 M = 247 R = not reported D = not reported | Not performed | Not performed |
| H1277 | 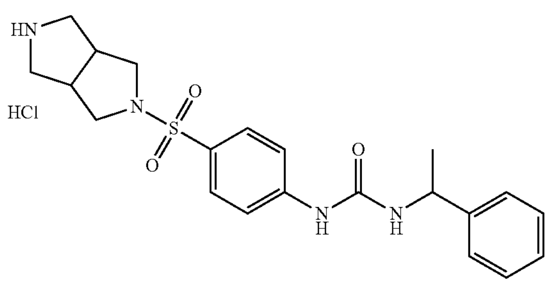 [SMILES: Cl ; CC(NC(=O)Nc1ccc(S(=O)(=O)N2CC3CNCC3C2)cc1)c1ccccc1] | $IC_{50}$ = 8.76 $EC_{50}/E_{Max}$ > 30 $EC_{50}$ = not reported | Not performed | Not performed | Not performed |
| H1280 | 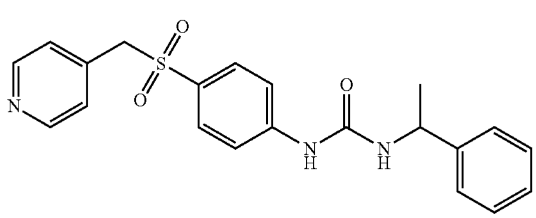 [SMILES: CC(NC(=O)Nc1ccc(S(=O)(=O)Cc2ccncc2)cc1)c1ccccc1] | $IC_{50}$ = 0.905 $EC_{50}/E_{Max}$ > 30 $EC_{50}$ = not reported | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1281 | 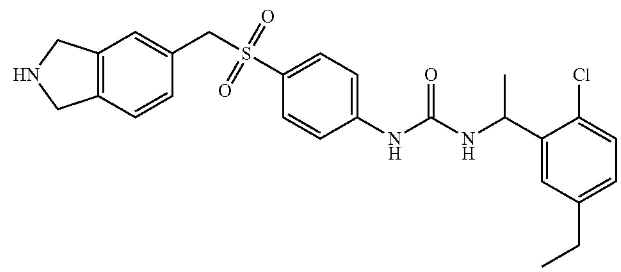 [SMILES: CCc1ccc(Cl)c(C(C)NC(=O)Nc2ccc(S(=O)(=O)Cc3ccc4c(c3)CNC4)cc2)c1] | $IC_{50} = 0.039$<br>$EC_{50}/E_{Max} > 30$<br>$EC_{50} = 0.0153$ | H = 63.8<br>M = 47.8<br>R = not reported<br>D = not reported | Not performed | Not performed |
| H1283 | 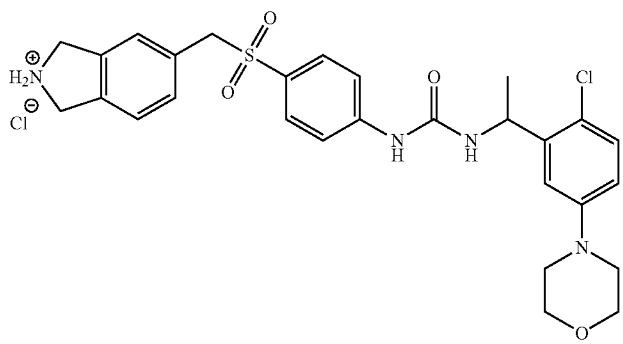 [SMILES: [Cl-] ; CC(NC(=O)Nc1ccc(S(=O)(=O)Cc2ccc3c(c2)C[NH2+]C3)cc1)c1cc(N2CCOCC2)ccc1Cl] | $IC_{50} = 0.379$<br>$EC_{50}/E_{Max} > 30$<br>$EC_{50} = 0.201$ | Not performed | Not performed | Not performed |
| H1284 | 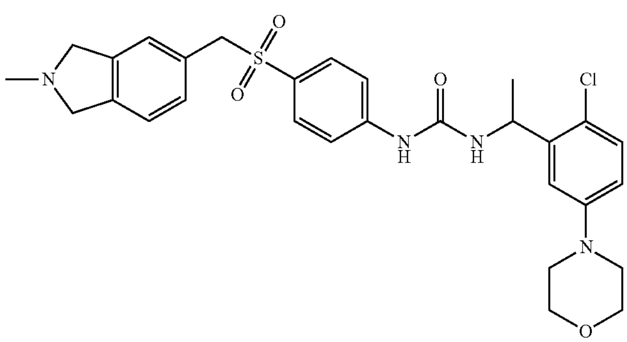 [SMILES: CC(NC(=O)Nc1ccc(S(=O)(=O)Cc2ccc3c(c2)CN(C)C3)cc1)c1cc(N2CCOCC2)ccc1Cl] | $IC_{50} = 1.896$<br>$EC_{50}/E_{Max} > 30$<br>$EC_{50} = 0.371$ | Not performed | Not performed | Not performed |
| H1285 | 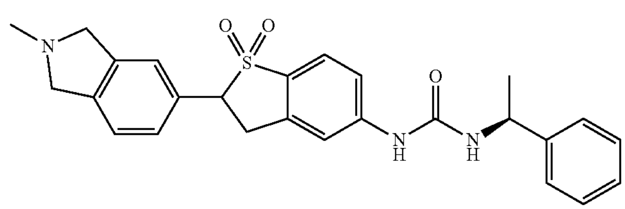 [SMILES: C[C@H](NC(=O)Nc1ccc2c(c1)CC(c1ccc3c(c1)CN(C)C3)S2(=O)=O)c1ccccc1] | $IC_{50} = 0.065$<br>$EC_{50}/E_{Max} = 0.147$<br>$EC_{50} = $ not reported | Not performed | Not performed | Not performed |
| H1286 | 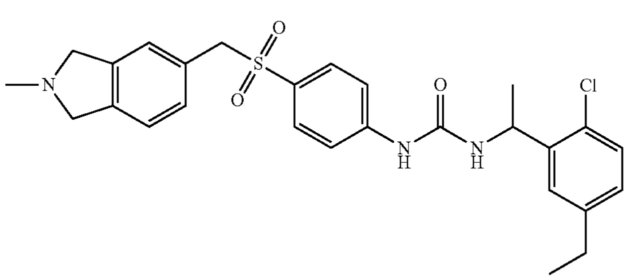 [SMILES: CCc1ccc(Cl)c(C(C)NC(=O)Nc2ccc(S(=O)(=O)Cc3ccc4c(c3)CN(C)C4)cc2)c1] | $IC_{50} = 0.0395$<br>$EC_{50}/E_{Max} > 30$<br>$EC_{50} = 0.0243$ | H = 251.8<br>M = 162.4<br>R = not reported<br>D = not reported | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1289 | 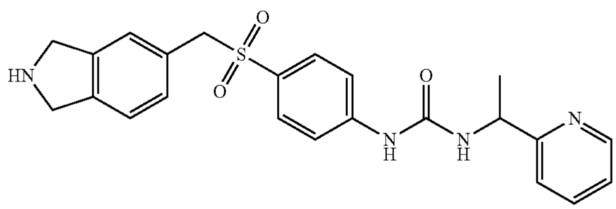 [SMILES: CC(NC(=O)Nc1ccc(S(=O)(=O)Cc2ccc3c(c2)CNC3)cc1)c1ccccn1] | $IC_{50}$ = 0.542<br>$EC_{50}/E_{Max}$ = 0.147<br>$EC_{50}$ = 0.161 | Not performed | Not performed | Not performed |
| H1290 | 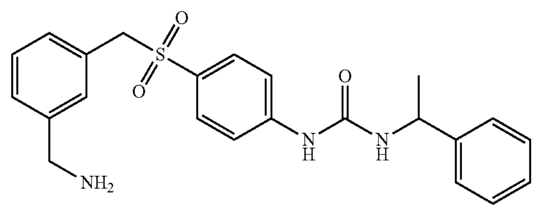 [SMILES: CC(NC(=O)Nc1ccc(S(=O)(=O)Cc2cccc(CN)c2)cc1)c1ccccc1] | $IC_{50}$ = 3.41<br>$EC_{50}/E_{Max}$ > 30<br>$EC_{50}$ = 0.722 | Not performed | Not performed | Not performed |
| H1291 | 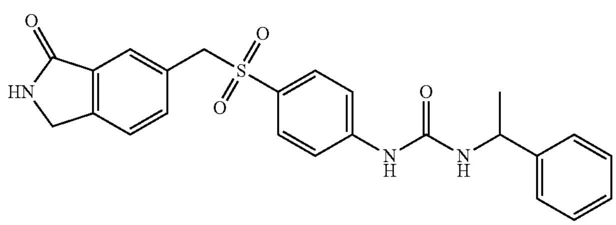 [SMILES: CC(NC(=O)Nc1ccc(S(=O)(=O)Cc2ccc3c(c2)C(=O)NC3)cc1)c1ccccc1] | $IC_{50}$ = 1.2<br>$EC_{50}/E_{Max}$ > 30<br>$EC_{50}$ = 0.468 | Not performed | Not performed | Not performed |
| H1292 | 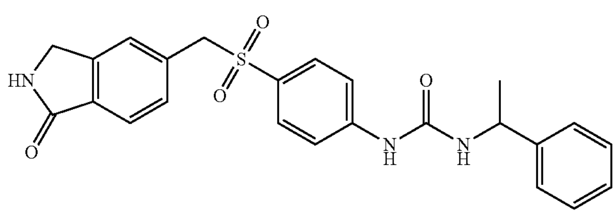 [SMILES: CC(NC(=O)Nc1ccc(S(=O)(=O)Cc2ccc3c(c2)CNC3=O)cc1)c1ccccc1] | $IC_{50}$ > 30<br>$EC_{50}/E_{Max}$ > 30<br>$EC_{50}$ = not reported | Not performed | Not performed | Not performed |
| H1293 | 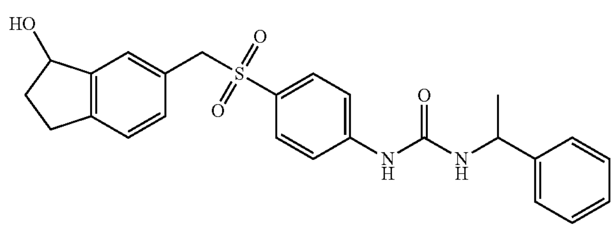 [SMILES: CC(NC(=O)Nc1ccc(S(=O)(=O)Cc2ccc3c(c2)C(O)CC3)cc1)c1ccccc1] | $IC_{50}$ = 5.68<br>$EC_{50}/E_{Max}$ > 30<br>$EC_{50}$ = 0.93 | Not performed | Not performed | Not performed |
| H1294 | 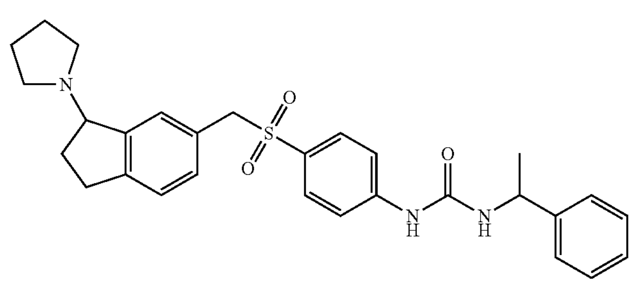 [SMILES: CC(NC(=O)Nc1ccc(S(=O)(=O)Cc2ccc3c(c2)C(N2CCCC2)CC3)cc1)c1ccccc1] | $IC_{50}$ = 3.32<br>$EC_{50}/E_{Max}$ = 12.87<br>$EC_{50}$ = not reported | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1296 | 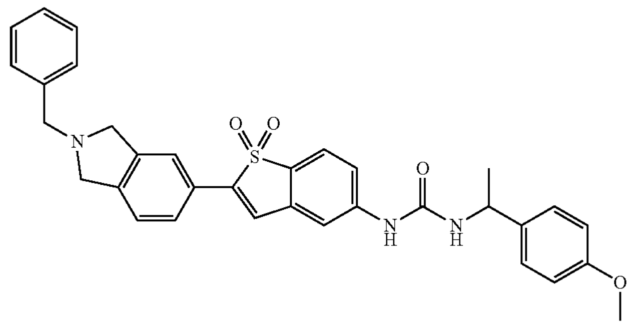 [SMILES: COc1ccc(C(C)NC(=O)Nc2ccc3c(c2)C=C(c2ccc4c(c2)CN(Cc2ccccc2)C4)S3(=O)=O)cc1] | $IC_{50} > 30$<br>$EC_{50}/E_{Max} = 13.24$<br>$EC_{50} = 4.92$ | Not performed | Not performed | Not performed |
| H1297 | 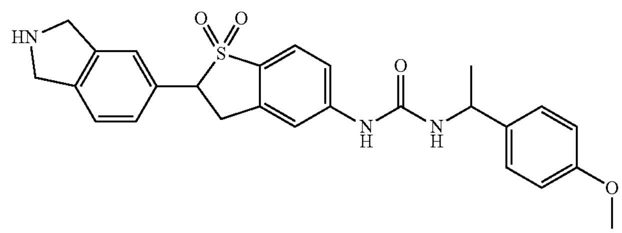 [SMILES: COc1ccc(C(C)NC(=O)Nc2ccc3c(c2)CC(c2ccc4c(c2)CNC4)S3(=O)=O)cc1] | $IC_{50} = 0.0231$<br>$EC_{50}/E_{Max} = 0.0158/4623$<br>$EC_{50}$ = not reported | Not performed | Not performed | Not performed |
| H1298 | 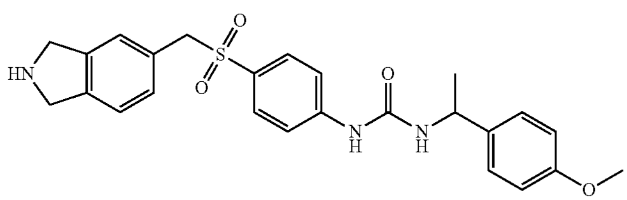 [SMILES: COc1ccc(C(C)NC(=O)Nc2ccc(S(=O)(=O)Cc3ccc4c(c3)CNC4)cc2)cc1] | $IC_{50} = 0.506$<br>$EC_{50}/E_{Max} > 30$<br>$EC_{50} = 0.1152$ | Not performed | Not performed | Not performed |
| H1299 | 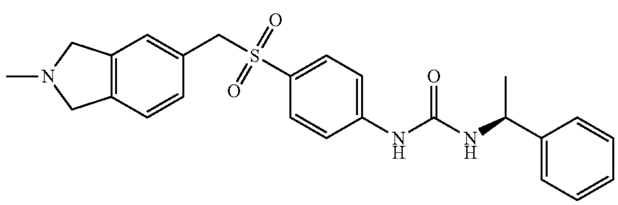 [SMILES: C[C@H](NC(=O)Nc1ccc(S(=O)(=O)Cc2ccc3c(c2)CN(C)C3)cc1)c1ccccc1] | $IC_{50} = 0.1925$<br>$EC_{50}/E_{Max} > 30$<br>$EC_{50} = 0.102$ | H = 71.5<br>M = 50.9<br>R = not reported<br>D = not reported | Not performed | Not performed |
| H1300 | 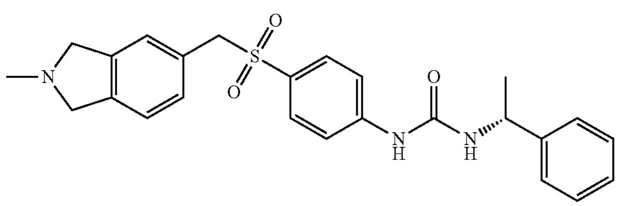 | $IC_{50} = 0.0083$<br>$EC_{50}/E_{Max} > 30$<br>$EC_{50} = 0.0047$ | H = 124.3<br>M = 42.1<br>R = not reported<br>D = not reported | Not performed | Not performed |
| H1301 | 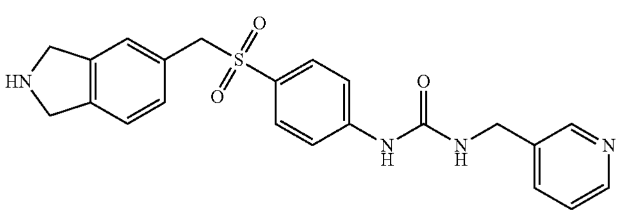 [SMILES: O=C(NCc1cccnc1)Nc1ccc(S(=O)(=O)Cc2ccc3c(c2)CNC3)cc1] | $IC_{50} = 4.45$<br>$EC_{50}/E_{Max} > 30$<br>$EC_{50} = 1.14$ | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1302 | 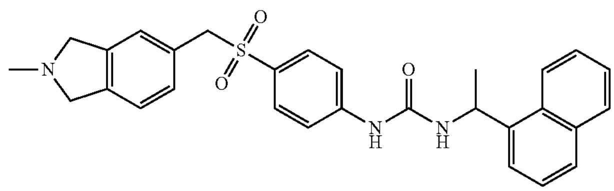 [SMILES: CC(NC(=O)Nc1ccc(S(=O)(=O)Cc2ccc3c(c2)CN(C)C3)cc1)c1cccc2ccccc12] | $IC_{50}$ = 0.0057 $EC_{50}/E_{Max}$ > 30 $EC_{50}$ = 0.0047 | H = 201.7 M = 164.1 R = not reported D = not reported | Not performed | Not performed |
| H1303 | 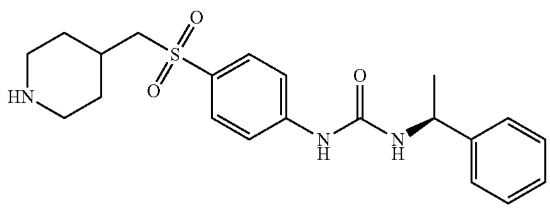 [SMILES: C[C@H](NC(=O)Nc1ccc(S(=O)(=O)CC2CCNCC2)cc1)c1ccccc1] | $IC_{50}$ > 30 $EC_{50}/E_{Max}$ > 30 $EC_{50}$ > 30 | Not performed | Not performed | Not performed |
| H1304 | 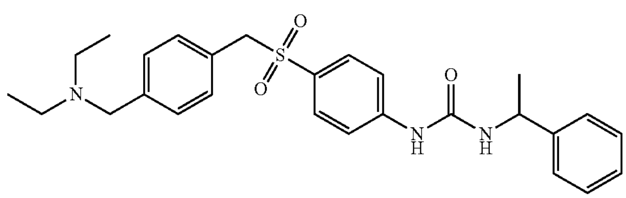 [SMILES: CCN(CC)Cc1ccc(CS(=O)(=O)c2ccc(NC(=O)NC(C)c3ccccc3)cc2)cc1] | $IC_{50}$ = 0.145 $EC_{50}/E_{Max}$ > 30 $EC_{50}$ = 0.1823 | Not performed | Not performed | Not performed |
| H1305 | 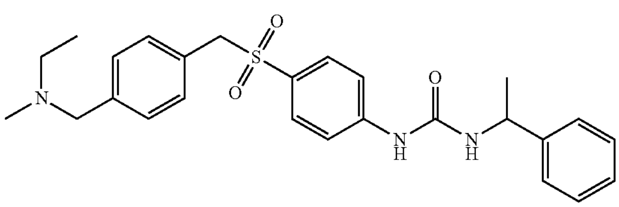 [SMILES: CCN(C)Cc1ccc(CS(=O)(=O)c2ccc(NC(=O)NC(C)c3ccccc3)cc2)cc1] | $IC_{50}$ = 0.298 $EC_{50}/E_{Max}$ > 30 $EC_{50}$ = 0.282 | Not performed | Not performed | Not performed |
| H1306 | 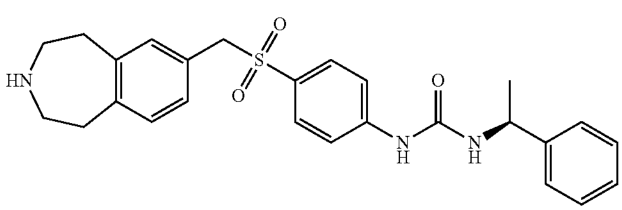 [SMILES: C[C@H](NC(=O)Nc1ccc(S(=O)(=O)Cc2ccc3c(c2)CCNCC3)cc1)c1ccccc1] | $IC_{50}$ = 0.062 $EC_{50}/E_{Max}$ > 30 $EC_{50}$ = 0.0746 | H = 31.2 M = 19.6 R = not reported D = not reported | Not performed | Not performed |
| H1307 | 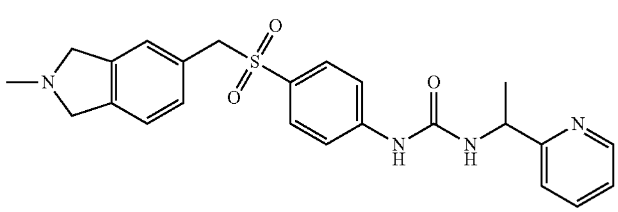 | $IC_{50}$ = 2.299 $EC_{50}/E_{Max}$ > 30 $EC_{50}$ = 0.935 | Not performed | Not performed | Not performed |
| H1308 | 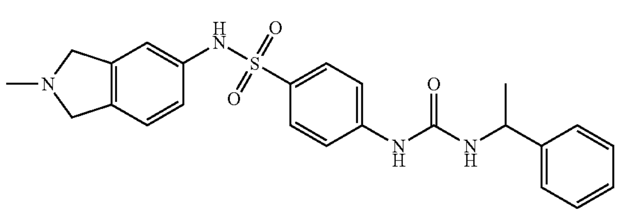 | $IC_{50}$ = 0.0235 $EC_{50}/E_{Max}$ > 30 $EC_{50}$ = 0.0312 | H = 49.4 M = 38.5 R = not reported D = not reported | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1309 | 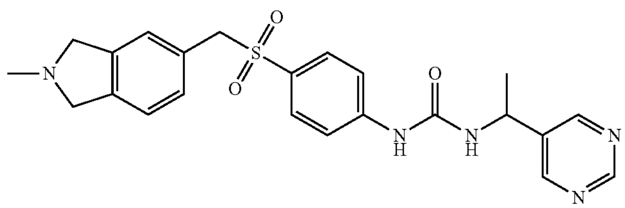 [SMILES: CC(NC(=O)Nc1ccc(S(=O)(=O)Cc2ccc3c(c2)CN(C)C3)cc1)c1cncnc1] | $IC_{50}$ = 4.497 $EC_{50}/E_{Max}$ > 30 $EC_{50}$ = 1.845 | Not performed | Not performed | Not performed |
| H1310 | 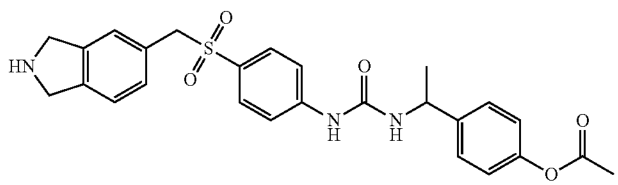 [SMILES: CC(=O)Oc1ccc(C(C)NC(=O)Nc2ccc(S(=O)(=O)Cc3ccc4c(c3)CNC4)cc2)cc1] | $IC_{50}$ = 0.262 $EC_{50}/E_{Max}$ > 30 $EC_{50}$ = 0.184 | Not performed | Not performed | Not performed |
| H1311 | 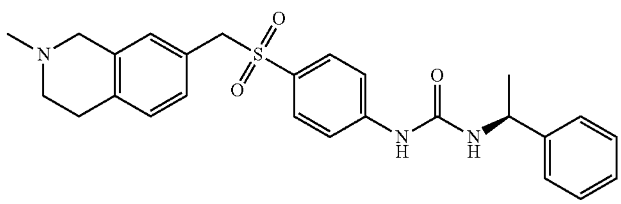 [SMILES: C[C@H](NC(=O)Nc1ccc(S(=O)(=O)Cc2ccc3c(c2)CN(C)CC3)cc1)c1ccccc1] | $IC_{50}$ = 0.108 $EC_{50}/E_{Max}$ > 30 $EC_{50}$ = 0.08464 | H = 95.9 M = 123.8 R = not reported D = not reported | Not performed | Not performed |
| H1312 | 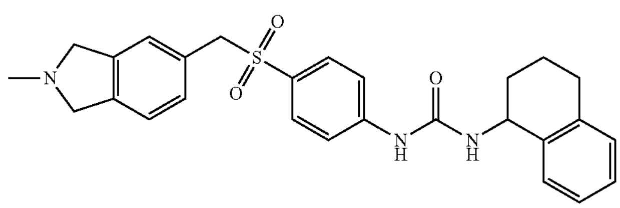 [SMILES: CN1Cc2ccc(CS(=O)(=O)c3ccc(NC(=O)NC4CCCc5ccccc54)cc3)cc2C1] | $IC_{50}$ = 0.069 $EC_{50}/E_{Max}$ > 30 $EC_{50}$ = 0.0858 | H = 93.5 M = 117.5 R = not reported D = not reported | Not performed | Not performed |
| H1313 | 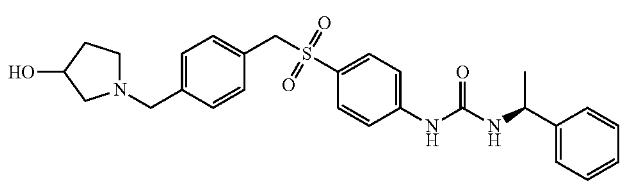 [SMILES: C[C@H](NC(=O)Nc1ccc(S(=O)(=O)Cc2ccc(CN3CCC(O)C3)cc2)cc1)c1ccccc1] | $IC_{50}$ = 1.459 $EC_{50}/E_{Max}$ > 30 $EC_{50}$ = not reported | Not performed | Not performed | Not performed |
| H1314 | 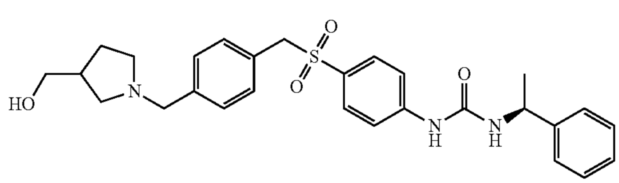 [SMILES: C[C@H](NC(=O)Nc1ccc(S(=O)(=O)Cc2ccc(CN3CCC(CO)C3)cc2)cc1)c1ccccc1] | $IC_{50}$ = 3.1 $EC_{50}/E_{Max}$ > 30 $EC_{50}$ = not reported | Not performed | Not performed | Not performed |
| H1315 | 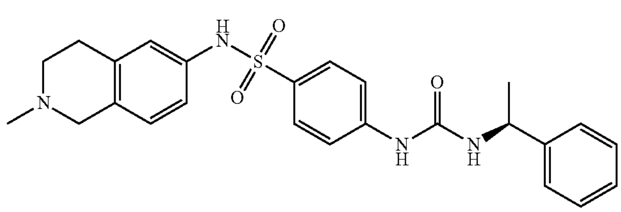 [SMILES: C[C@H](NC(=O)Nc1ccc(S(=O)(=O)Nc2ccc3c(c2)CCN(C)C3)cc1)c1ccccc1] | $IC_{50}$ = 0.301 $EC_{50}/E_{Max}$ > 30 $EC_{50}$ = not reported | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1316 | 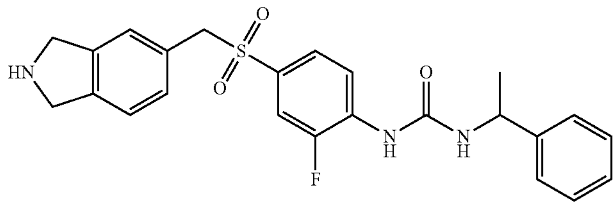 [SMILES: CC(NC(=O)Nc1ccc(S(=O)(=O)Cc2ccc3c(c2)CNC3)cc1F)c1ccccc1] | $IC_{50}$ = 0.0309 $EC_{50}/E_{Max}$ > 30 $EC_{50}$ = 0.0116 | Not performed | Not performed | Not performed |
| H1317 | 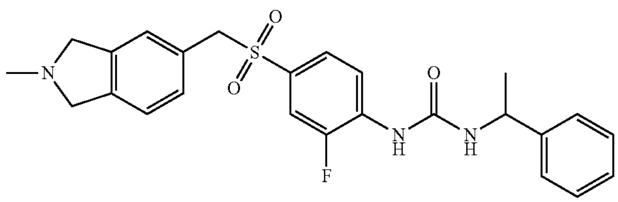 [SMILES: CC(NC(=O)Nc1ccc(S(=O)(=O)Cc2ccc3c(c2)CN(C)C3)cc1F)c1ccccc1] | $IC_{50}$ = 0.0484 $EC_{50}/E_{Max}$ > 30 $EC_{50}$ = 0.0182 | H = 96.7 M = 102.8 R = not reported D = not reported | Not performed | Not performed |
| H1318 | 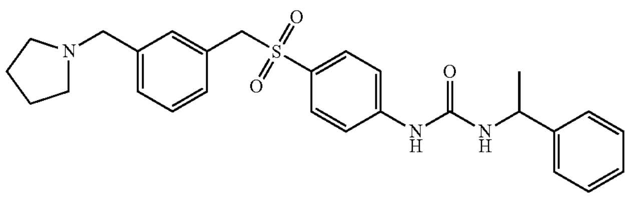 [SMILES: CC(NC(=O)Nc1ccc(S(=O)(=O)Cc2cccc(CN3CCCC3)c2)cc1)c1ccccc1] | $IC_{50}$ = 5.31 $EC_{50}/E_{Max}$ > 30 $EC_{50}$ = not reported | Not performed | Not performed | Not performed |
| H1319 | 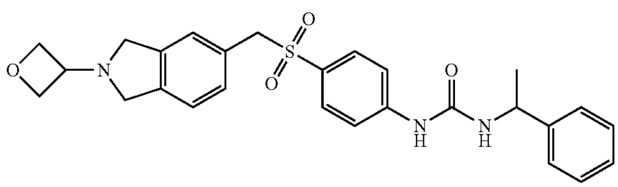 [SMILES: CC(NC(=O)Nc1ccc(S(=O)(=O)Cc2ccc3c(c2)CN(C2COC2)C3)cc1)c1ccccc1] | $IC_{50}$ = 0.041 $EC_{50}/E_{Max}$ > 30 $EC_{50}$ = 0.0125 | H = 195.6 M > 500 R = not reported D = not reported | Not performed | Not performed |
| H1320 | 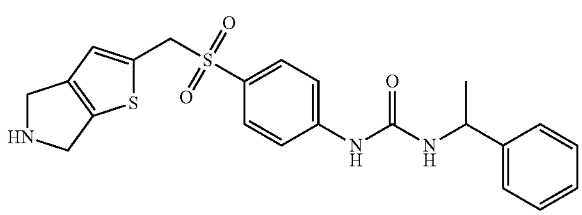 [SMILES: CC(NC(=O)Nc1ccc(S(=O)(=O)Cc2cc3c(s2)CNC3)cc1)c1ccccc1] | $IC_{50}$ = 0.0584 $EC_{50}/E_{Max}$ > 30 $EC_{50}$ = 0.0433 | Not performed | Not performed | Not performed |
| H1321 | 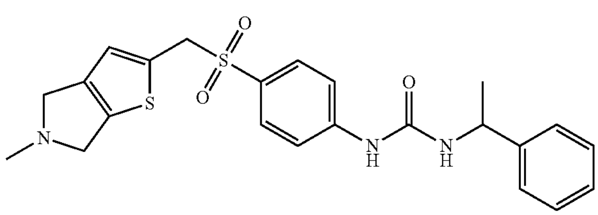 [SMILES: CC(NC(=O)Nc1ccc(S(=O)(=O)Cc2cc3c(s2)CN(C)C3)cc1)c1ccccc1] | $IC_{50}$ = 0.0475 $EC_{50}/E_{Max}$ > 30 $EC_{50}$ = 0.0232 | H = 85.3 M = 81.9 R = not reported D = not reported | Not performed | Not performed |
| H1322 | 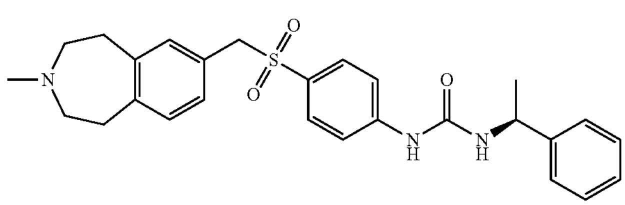 [SMILES: C[C@H](NC(=O)Nc1ccc(S(=O)(=O)Cc2ccc3c(c2)CCN(C)CC3)cc1)c1ccccc1] | $IC_{50}$ = 0.1117 $EC_{50}/E_{Max}$ > 30 $EC_{50}$ = 0.0815 | H = 129 M = 171.1 R = not reported D = not reported | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1323 | 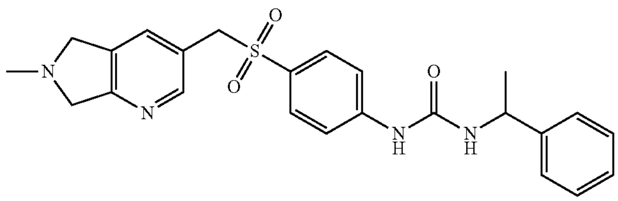 [SMILES: CC(NC(=O)Nc1ccc(S(=O)(=O)Cc2cnc3c(c2)CN(C)C3)cc1)c1ccccc1] | $IC_{50}$ = 0.2432 $EC_{50}$/ $E_{Max}$ > 30 $EC_{50}$ = 0.102 | H = 84.1 M = 58.5 R = not reported D = not reported | Not performed | Not performed |
| H1324 | 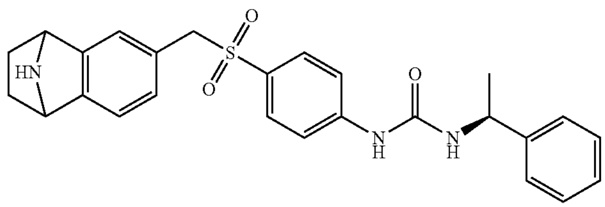 [SMILES: C[C@H](NC(=O)Nc1ccc(S(=O)(=O)Cc2ccc3c(c2)C2CCC3N2)cc1)c1ccccc1] | $IC_{50}$ = 10.5 $EC_{50}$/ $E_{Max}$ > 30 $EC_{50}$ = not reported | Not performed | Not performed | Not performed |
| H1325 | 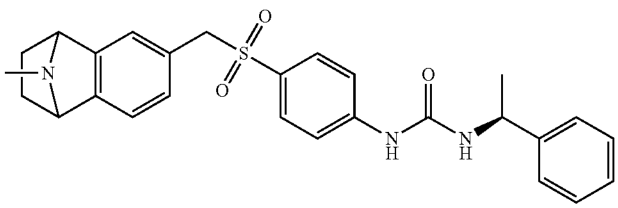 [SMILES: C[C@H](NC(=O)Nc1ccc(S(=O)(=O)Cc2ccc3c(c2)C2CCC3N2C)cc1)c1ccccc1] | $IC_{50}$ = 3.83 $EC_{50}$/ $E_{Max}$ > 30 $EC_{50}$ = not reported | Not performed | Not performed | Not performed |
| H1326 | 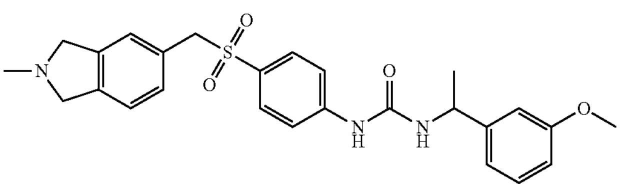 | $IC_{50}$ = 0.0098 $EC_{50}$/ $E_{Max}$ > 30 $EC_{50}$ = 0.0069 | H = 129.5 M = 60.5 R = not reported D = not reported | Not performed | Not performed |
| H1327 | 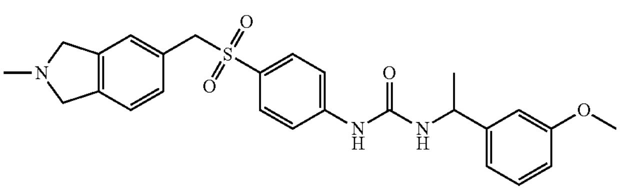 | $IC_{50}$ = 0.0056 $EC_{50}$/ $E_{Max}$ > 30 $EC_{50}$ = 0.0055 | H = 165.3 M = 144.8 R = not reported D = not reported | Not performed | Not performed |
| H1328 | 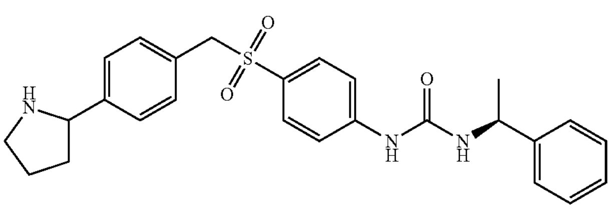 [SMILES: C[C@H](NC(=O)Nc1ccc(S(=O)(=O)Cc2ccc(C3CCCN3)cc2)cc1)c1ccccc1] | $IC_{50}$ = 0.546 $EC_{50}$/ $E_{Max}$ > 30 $EC_{50}$ = not reported | Not performed | Not performed | Not performed |
| H1329 | 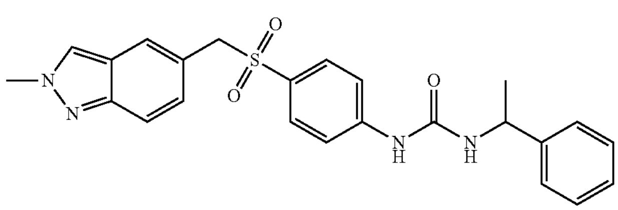 [SMILES: CC(NC(=O)Nc1ccc(S(=O)(=O)Cc2ccc3nn(C)cc3c2)cc1)c1ccccc1] | $IC_{50}$ > 30 $EC_{50}$/ $E_{Max}$ > 30 $EC_{50}$ = not reported | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) t$_{1/2}$ (h) F (%) | Food Intake Study |
|---|---|---|---|---|---|
| H1330 | 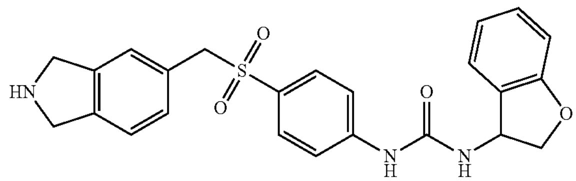 [SMILES: O=C(Nc1ccc(S(=O)(=O)Cc2ccc3c(c2)CNC3)cc1)NC1COc2ccccc21] | IC$_{50}$ = 0.147<br>EC$_{50}$/E$_{Max}$ > 30<br>EC$_{50}$ = 0.142 | Not performed | Not performed | Not performed |
| H1331 | 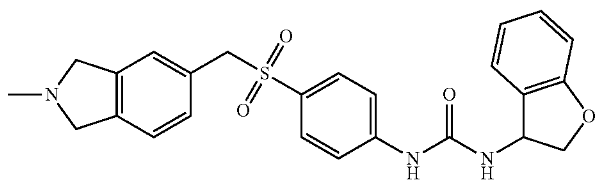 [SMILES: CN1Cc2ccc(CS(=O)(=O)c3ccc(NC(=O)NC4COc5ccccc54)cc3)cc2C1] | IC$_{50}$ = 0.213<br>EC$_{50}$/E$_{Max}$ > 30<br>EC$_{50}$ = 0.13 | Not performed | Not performed | Not performed |
| H1332 | 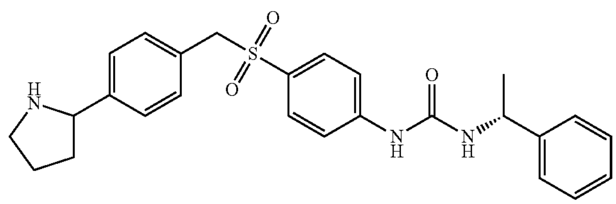 [SMILES: C[C@@H](NC(=O)Nc1ccc(S(=O)(=O)Cc2ccc(C3CCCN3)cc2)cc1)c1ccccc1] | IC$_{50}$ = 0.0732<br>EC$_{50}$/E$_{Max}$ > 30<br>EC$_{50}$ = 0.0421 | Not performed | Not performed | Not performed |
| H1333 | 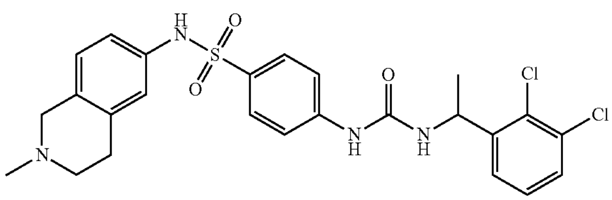 [SMILES: CC(NC(=O)Nc1ccc(S(=O)(=O)Nc2ccc3c(c2)CCN(C)C3)cc1)c1cccc(Cl)c1Cl] | IC$_{50}$ = 0.00224<br>EC$_{50}$/E$_{Max}$ > 30<br>EC$_{50}$ = 0.0013<br>PPB = 99.89 (H)<br>PPB = 99.94 (M)<br>PPB = 99.9 (R)<br>PPB = 99.85 (D) | H = 47.2<br>M = 54<br>R = not reported<br>D = not reported | CL$_{iv}$ = 1.78<br>CL$_{po}$ = 84.3<br>Vd$_{iv}$ = 3.26<br>Vd$_{po}$ = 170<br>t$_{1/2iv}$ = 1.27<br>t$_{1/2po}$ = 1.4<br>F = 2.08 | |
| H1334 | 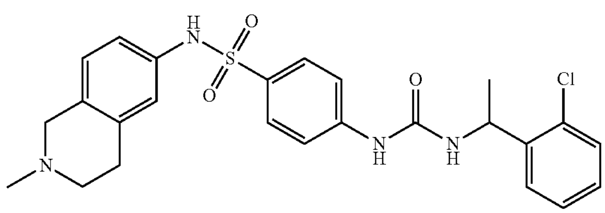 [SMILES: CC(NC(=O)Nc1ccc(S(=O)(=O)Nc2ccc3c(c2)CCN(C)C3)cc1)c1ccccc1Cl] | IC$_{50}$ = 0.00918<br>EC$_{50}$/E$_{Max}$ > 30<br>EC$_{50}$ = 0.0082 | H = 109.8<br>M = 97.9<br>R = not reported<br>D = not reported | Not performed | Not performed |
| H1335 | 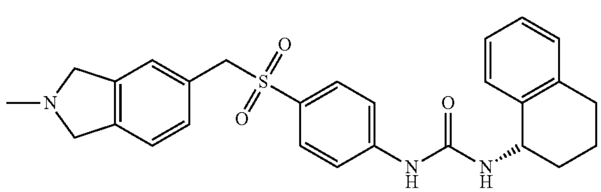 | IC$_{50}$ = 0.133<br>EC$_{50}$/E$_{Max}$ > 30<br>EC$_{50}$ = 0.0699 | Not performed | Not performed | Not performed |
| H1336 | 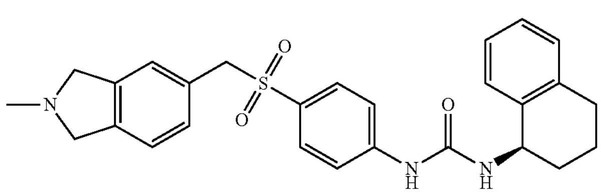 [SMILES: CN1Cc2ccc(CS(=O)(=O)c3ccc(NC(=O)N[C@@H]4CCCc5ccccc54)cc3)cc2C1] | IC$_{50}$ = 0.381<br>EC$_{50}$/E$_{Max}$ > 30<br>EC$_{50}$ = 0.2626 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1337 | 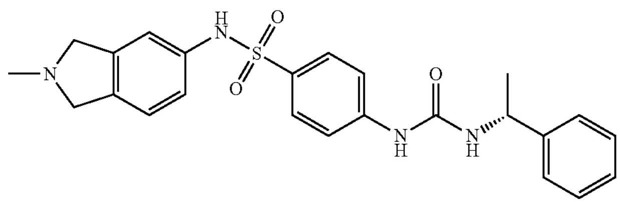 | $IC_{50}$ = 0.0241 $EC_{50}/E_{Max}$ > 30 $EC_{50}$ = 0.0105 | H = 58.6 M = 39.2 R = not reported D = not reported | Not performed | Not performed |
| H1338 | 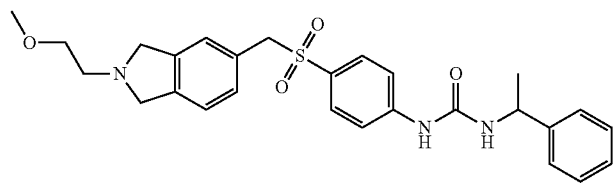 [SMILES: COCCN1Cc2ccc(CS(=O)(=O)c3ccc(NC(=O)NC(C)c4ccccc4)cc3)cc2C1] | $IC_{50}$ = 0.0076 $EC_{50}/E_{Max}$ > 30 $EC_{50}$ = 0.0065 | H = 106.9 M = 242.1 R = not reported D = not reported | Not performed | Not performed |
| H1339 | 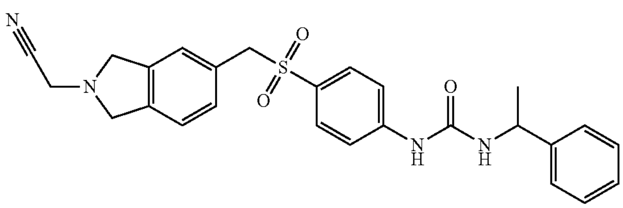 [SMILES: CC(NC(=O)Nc1ccc(S(=O)(=O)Cc2ccc3c(c2)CN(CC#N)C3)cc1)c1ccccc1] | $IC_{50}$ = 0.309 $EC_{50}/E_{Max}$ > 30 $EC_{50}$ = 0.176 | Not performed | Not performed | Not performed |
| H1340 | 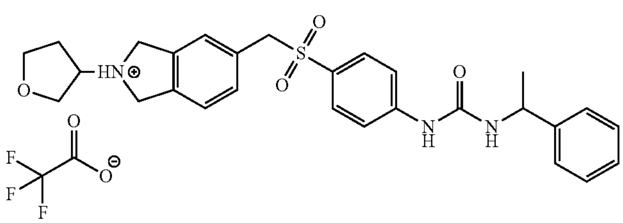 [SMILES: O=C([O-])C(F)(F)F ; CC(NC(=O)Nc1ccc(S(=O)(=O)Cc2ccc3c(c2)C[NH+](C2CCOC2)C3)cc1)c1ccccc1] | $IC_{50}$ = 0.0047 $EC_{50}/E_{Max}$ > 30 $EC_{50}$ = 0.0033 | H = 282.4 M > 500 R = not reported D = not reported | Not performed | Not performed |
| H1341 | 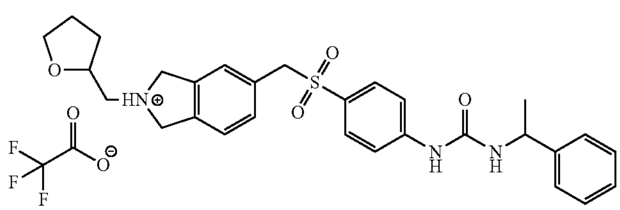 [SMILES: O=C([O-])C(F)(F)F ; CC(NC(=O)Nc1ccc(S(=O)(=O)Cc2ccc3c(c2)C[NH+](CC2CCCO2)C3)cc1)c1ccccc1] | $IC_{50}$ = 0.0697 $EC_{50}/E_{Max}$ > 30 $EC_{50}$ = 0.0209 | Not performed | Not performed | Not performed |
| H1342 | 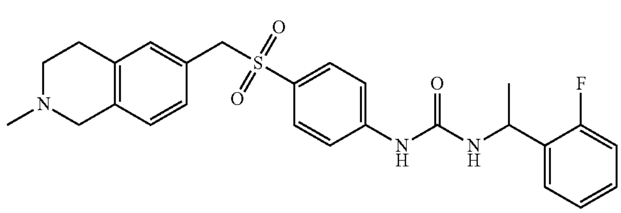 | $IC_{50}$ = 0.0174 $EC_{50}/E_{Max}$ > 30 $EC_{50}$ = 0.0079 | H = 80.1 M = 118.4 R = not reported D = not reported | Not performed | Not performed |
| H1343 | 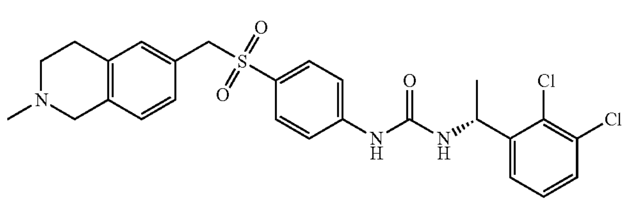 [SMILES: C[C@@H](NC(=O)Nc1ccc(S(=O)(=O)Cc2ccc3c(c2)CCN(C)C3)cc1)c1cccc(Cl)c1Cl] | $IC_{50}$ = 0.0052 $EC_{50}/E_{Max}$ > 30 $EC_{50}$ = 0.0021 | H = 71.9 M = 252.4 R = not reported D = not reported | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1344 | 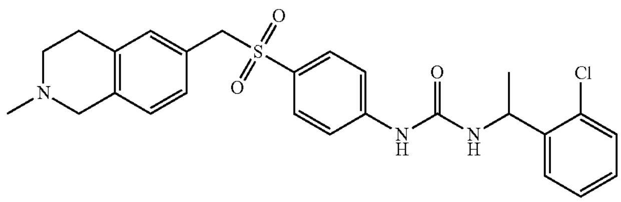 | $IC_{50}$ = 0.0044 $EC_{50}/E_{Max}$ > 30 $EC_{50}$ = 0.0041 | H = 53.5 M = 115.7 R = not reported D = not reported | Not performed | Not performed |
| H1345 | 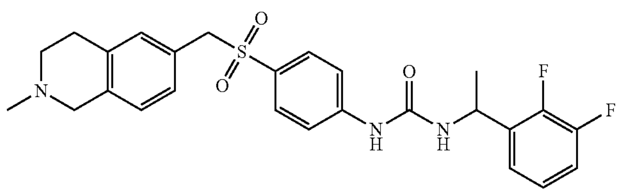 [SMILES: CC(NC(=O)Nc1ccc(S(=O)(=O)Cc2ccc3c(c2)CCN(C)C3)cc1)c1cccc(F)c1F] | $IC_{50}$ = 0.0052 $EC_{50}/E_{Max}$ > 30 $EC_{50}$ = 0.0042 | H = 86.5 M = 166.2 R = not reported D = not reported | Not performed | Not performed |
| H1346 | 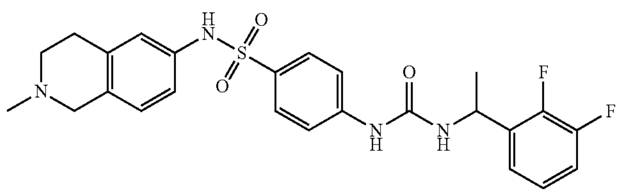 [SMILES: CC(NC(=O)Nc1ccc(S(=O)(=O)Nc2ccc3c(c2)CCN(C)C3)cc1)c1cccc(F)c1F] | $IC_{50}$ = 0.0191 $EC_{50}/E_{Max}$ > 30 $EC_{50}$ = 0.00698 | H = 72.9 M = 69.3 R = not reported D = not reported | Not performed | Not performed |
| H1347 | 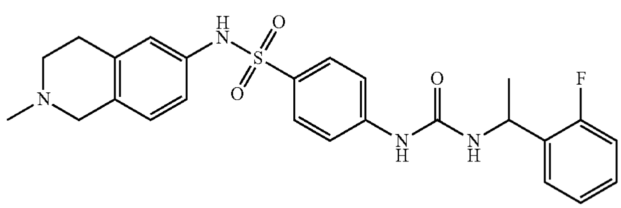 [SMILES: CC(NC(=O)Nc1ccc(S(=O)(=O)Nc2ccc3c(c2)CCN(C)C3)cc1)c1ccccc1F] | $IC_{50}$ = 0.0262 $EC_{50}/E_{Max}$ > 30 $EC_{50}$ = 0.00795 | H = 59.9 M = 58.1 R = not reported D = not reported | Not performed | Not performed |
| H1348 | 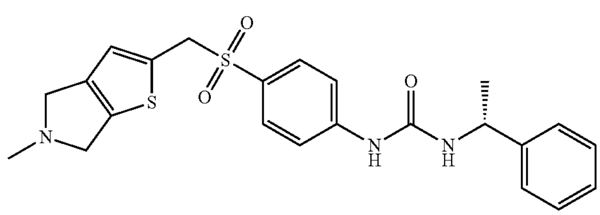 [SMILES: C[C@@H](NC(=O)Nc1ccc(S(=O)(=O)Cc2cc3c(s2)CN(C)C3)cc1)c1ccccc1] | $IC_{50}$ = 0.0650 $EC_{50}/E_{Max}$ > 30 $EC_{50}$ = 0.0199 | Not performed | Not performed | Not performed |
| H1349 | 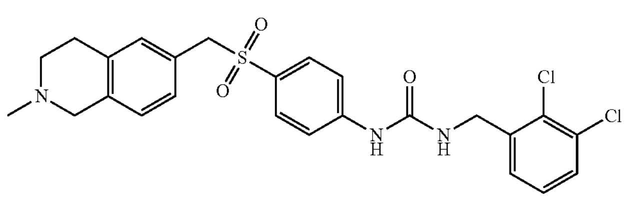 [SMILES: CN1CCc2cc(CS(=O)(=O)c3ccc(NC(=O)NCc4cccc(Cl)c4Cl)cc3)ccc2C1] | $IC_{50}$ = 0.0153 $EC_{50}/E_{Max}$ > 30 $EC_{50}$ = 0.029 | Not performed | Not performed | Not performed |
| H1350 | 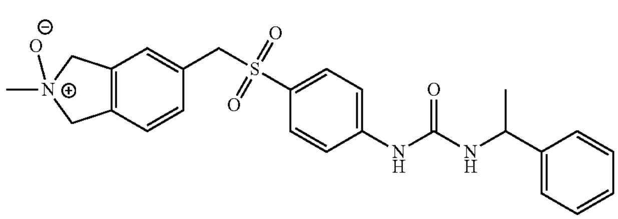 [SMILES: CC(NC(=O)Nc1ccc(S(=O)(=O)Cc2ccc3c(c2)C[N+](C)([O-])C3)cc1)c1ccccc1] | $IC_{50}$ = 18.2 $EC_{50}/E_{Max}$ > 30 $EC_{50}$ = 7.46 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) t$_{1/2}$ (h) F (%) | Food Intake Study |
|---|---|---|---|---|---|
| H1351 | 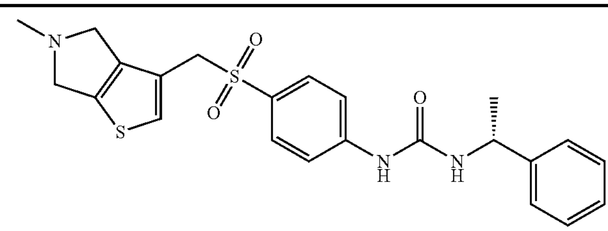 | IC$_{50}$ = 3.45 EC$_{50}$/E$_{Max}$ > 30 EC$_{50}$ = 6.96 | Not performed | Not performed | Not performed |
| H1352 | 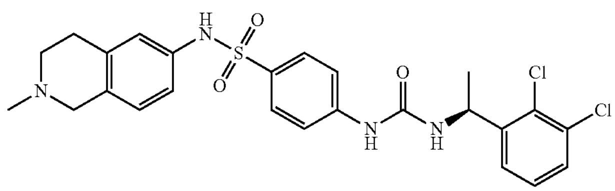 [SMILES: C[C@H](NC(=O)Nc1ccc(S(=O)(=O)Nc2ccc3c(c2)CCN(C)C3)cc1)c1cccc(Cl)c1Cl] | IC$_{50}$ = 0.0046 EC$_{50}$/E$_{Max}$ > 30 EC$_{50}$ = 0.0077 | Not performed | Not performed | Not performed |
| H1353 | 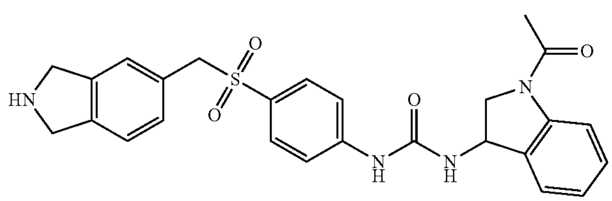 [SMILES: CC(=O)N1CC(NC(=O)Nc2ccc(S(=O)(=O)Cc3ccc4c(c3)CNC4)cc2)c2ccccc21] | IC$_{50}$ = 5.1 EC$_{50}$/E$_{Max}$ > 30 EC$_{50}$ = 8.23 | Not performed | Not performed | Not performed |
| H1354 | 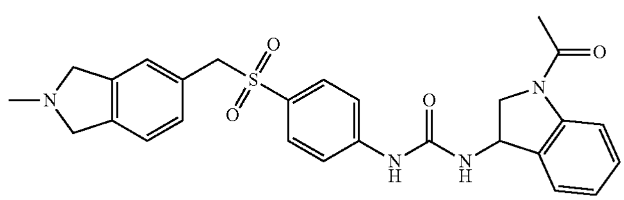 [SMILES: CC(=O)N1CC(NC(=O)Nc2ccc(S(=O)(=O)Cc3ccc4c(c3)CN(C)C4)cc2)c2ccccc21] | IC$_{50}$ = 8.899 EC$_{50}$/E$_{Max}$ > 30 EC$_{50}$ = 8.61 | Not performed | Not performed | Not performed |
| H1355 | 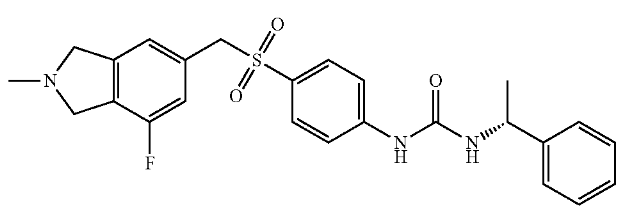 [SMILES: C[C@@H](NC(=O)Nc1ccc(S(=O)(=O)Cc2cc(F)c3c(c2)CN(C)C3)cc1)c1ccccc1] | IC$_{50}$ = 0.041 EC$_{50}$/E$_{Max}$ > 30 EC$_{50}$ = 0.0129 | H = 153.5 M = 304.3 R = not reported D = not reported | Not performed | Not performed |
| H1356 | 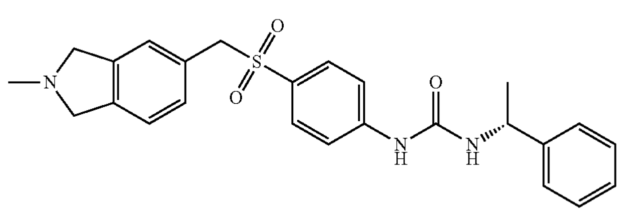 [SMILES: C[C@@H](NC(=O)Nc1ccc(S(=O)(=O)Cc2ccc3c(c2)CN(C)C3)cc1)c1ccccc1] | IC$_{50}$ = 0.0739 EC$_{50}$/E$_{Max}$ > 30 EC$_{50}$ = 0.029 | H = 382.5 M = 126 R = not reported D = not reported | Not performed | Not performed |
| H1357 | 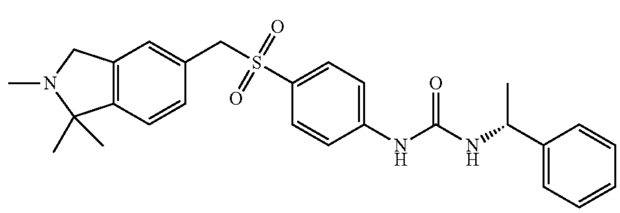 [SMILES: C[C@@H](NC(=O)Nc1ccc(S(=O)(=O)Cc2ccc3c(c2)CN(C)C3(C)C)cc1)c1ccccc1] | IC$_{50}$ = 0.057 EC$_{50}$/E$_{Max}$ > 30 EC$_{50}$ = 0.036 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) t$_{1/2}$ (h) F (%) | Food Intake Study |
|---|---|---|---|---|---|
| H1358 | 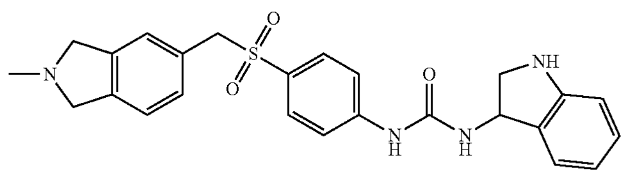 [SMILES: CN1Cc2ccc(CS(=O)(=O)c3ccc(NC(=O)NC4CNc5ccccc54)cc3)cc2C1] | IC$_{50}$ = 1.876 EC$_{50}$/E$_{Max}$ > 30 EC$_{50}$ = 1.821 | Not performed | Not performed | Not performed |
| H1359 | 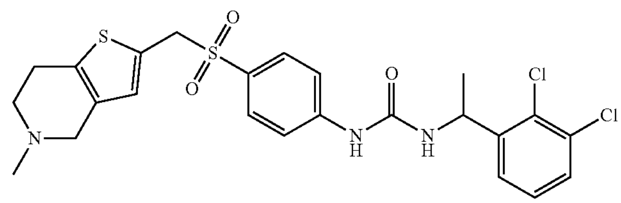 [SMILES: CC(NC(=O)Nc1ccc(S(=O)(=O)Cc2cc3c(s2)CCN(C)C3)cc1)c1cccc(Cl)c1Cl] | IC$_{50}$ = 0.0015 EC$_{50}$/E$_{Max}$ > 30 EC$_{50}$ = 0.004 | H = 108.6 M = 108.6 R = not reported D = not reported | Not performed | Not performed |
| H1360 | 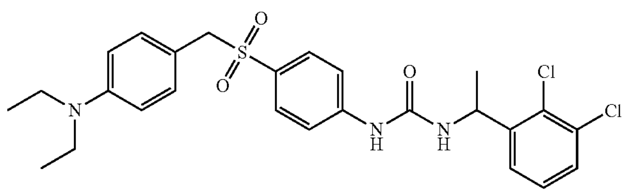 [SMILES: CCN(CC)c1ccc(CS(=O)(=O)c2ccc(NC(=O)NC(C)c3cccc(Cl)c3Cl)cc2)cc1] | IC$_{50}$ > 30 EC$_{50}$/E$_{Max}$ > 30 EC$_{50}$ = not reported | Not performed | Not performed | Not performed |
| H1361 | 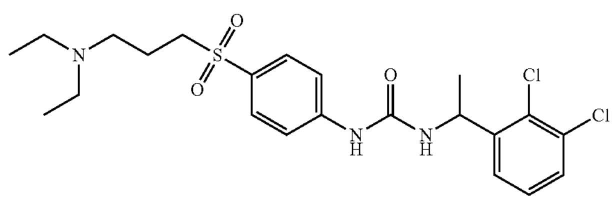 [SMILES: CCN(CC)CCCS(=O)(=O)c1ccc(NC(=O)NC(C)c2cccc(Cl)c2Cl)cc1] | IC$_{50}$ = 1.614 EC$_{50}$/E$_{Max}$ > 30 EC$_{50}$ = not reported | Not performed | Not performed | Not performed |
| H1362 | 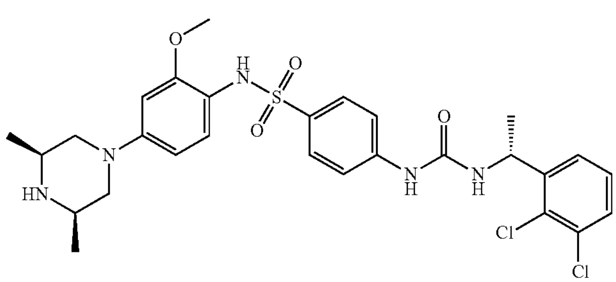 [SMILES: COc1cc(N2C[C@@H](C)N[C@@H](C)C2)ccc1NS(=O)(=O)c1ccc(NC(=O)N[C@H](C)c2cccc(Cl)c2Cl)cc1] | IC$_{50}$ = 1.553 EC$_{50}$/E$_{Max}$ > 30 EC$_{50}$ = not reported | Not performed | Not performed | Not performed |
| H1363 | 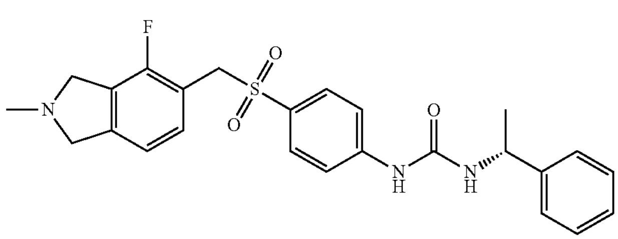 [SMILES: C[C@@H](NC(=O)Nc1ccc(S(=O)(=O)Cc2ccc3c(c2F)CN(C)C3)cc1)c1ccccc1] | IC$_{50}$ = 0.0084 EC$_{50}$/E$_{Max}$ > 30 EC$_{50}$ = 0.00315 | H = 140.1 M = 335.3 R = not reported D = not reported | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1364 | 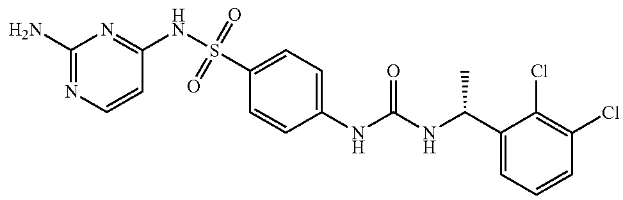 [SMILES: C[C@@H](NC(=O)Nc1ccc(S(=O)(=O)Nc2ccnc(N)n2)cc1)c1cccc(Cl)c1Cl] | $IC_{50}$ = 0.0296 $EC_{50}/$ $E_{Max}$ > 30 $EC_{50}$ = 0.13 | H < 10 M = 36 R = not reported D = not reported | Not performed | Not performed |
| H1366 | 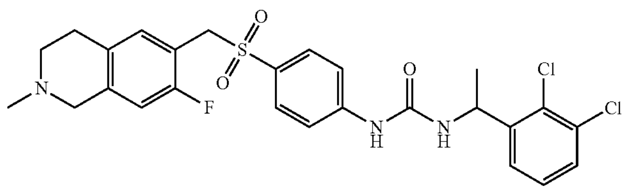 [SMILES: CC(NC(=O)Nc1ccc(S(=O)(=O)Cc2cc3c(cc2F)CN(C)CC3)cc1)c1cccc(Cl)c1Cl] | $IC_{50}$ = 0.0215 $EC_{50}/$ $E_{Max}$ > 30 $EC_{50}$ = 0.0025 | Not performed | Not performed | Not performed |
| H1367 | 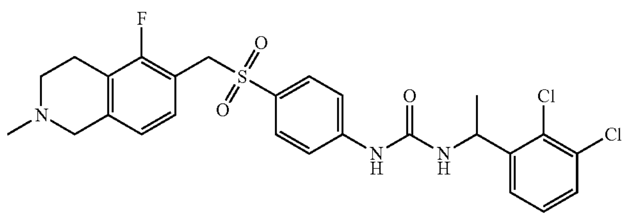 [SMILES: CC(NC(=O)Nc1ccc(S(=O)(=O)Cc2ccc3c(c2F)CCN(C)C3)cc1)c1cccc(Cl)c1Cl] | $IC_{50}$ = 0.0212 $EC_{50}/$ $E_{Max}$ > 30 $EC_{50}$ = 0.0033 | Not performed | Not performed | Not performed |
| H1368 | 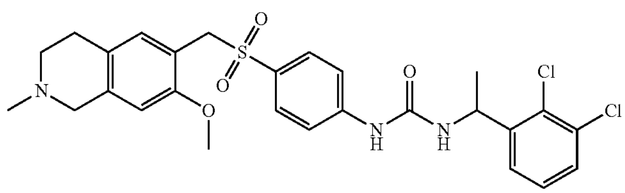 [SMILES: COc1cc2c(cc1CS(=O)(=O)c1ccc(NC(=O)NC(C)c3cccc(Cl)c3Cl)cc1)CCN(C)C2] | $IC_{50}$ = 0.0203 $EC_{50}/$ $E_{Max}$ > 30 $EC_{50}$ = 0.0028 | Not performed | Not performed | Not performed |
| H1369 | 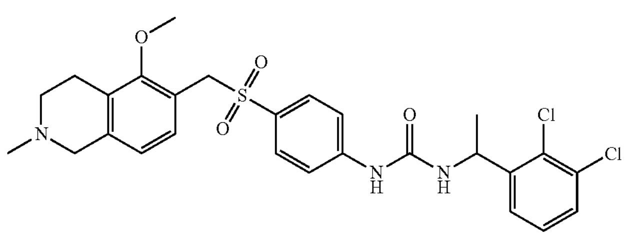 [SMILES: COc1c(CS(=O)(=O)c2ccc(NC(=O)NC(C)c3cccc(Cl)c3Cl)cc2)ccc2c1CCN(C)C2] | $IC_{50}$ = 0.00366 $EC_{50}/$ $E_{Max}$ > 30 $EC_{50}$ = 0.0011 | Not performed | Not performed | Not performed |
| H1371 | 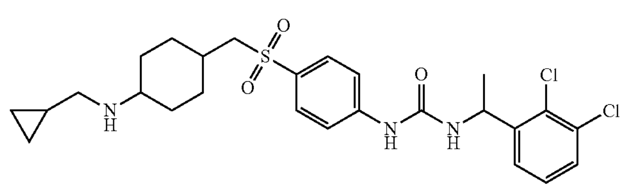 [SMILES: CC(NC(=O)Nc1ccc(S(=O)(=O)CC2CCC(NCC3CC3)CC2)cc1)c1cccc(Cl)c1Cl] | $IC_{50}$ = 2.44 $EC_{50}/$ $E_{Max}$ > 30 $EC_{50}$ = 0.231 | Not performed | Not performed | Not performed |
| H1372 | 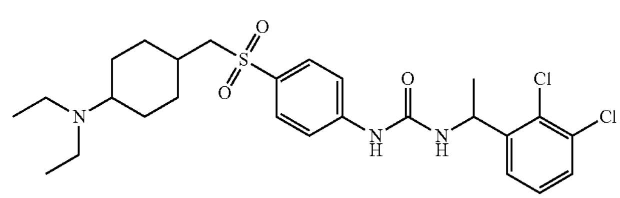 [SMILES: CCN(CC)C1CCC(CS(=O)(=O)c2ccc(NC(=O)NC(C)c3cccc(Cl)c3Cl)cc2)CC1] | $IC_{50}$ = 18.2 $EC_{50}/$ $E_{Max}$ > 30 $EC_{50}$ = 0.936 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1373 | 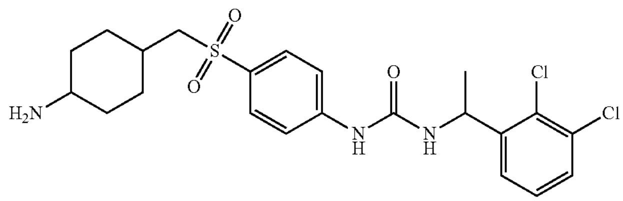 [SMILES: CC(NC(=O)Nc1ccc(S(=O)(=O)CC2CCC(N)CC2)cc1)c1cccc(Cl)c1Cl] | Not performed | Not performed | Not performed | Not performed |
| H1374 | 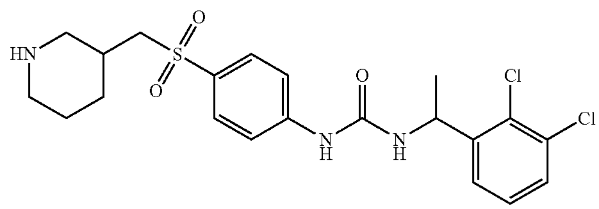 [SMILES: CC(NC(=O)Nc1ccc(S(=O)(=O)CC2CCCNC2)cc1)c1cccc(Cl)c1Cl] | Not performed | Not performed | Not performed | Not performed |
| H1375 | 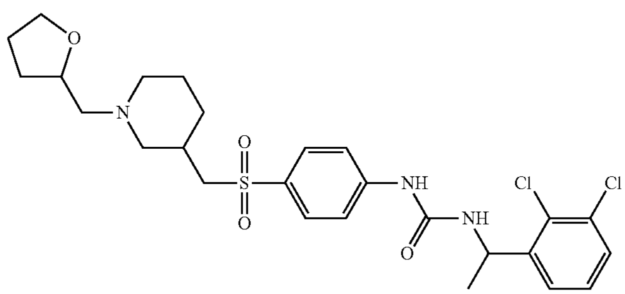 [SMILES: CC(NC(=O)Nc1ccc(S(=O)(=O)CC2CCCN(CC3CCCO3)C2)cc1)c1cccc(Cl)c1Cl] | $IC_{50}$ = >30 $EC_{50}$/ $E_{Max}$ = >30 | Not performed | Not performed | Not performed |
| H1376 | 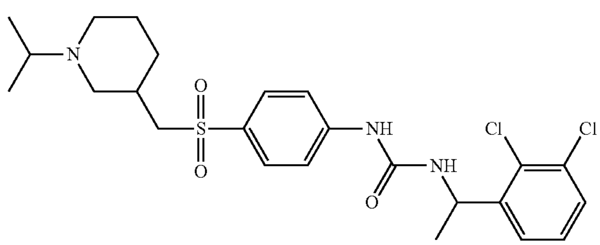 [SMILES: CC(NC(=O)Nc1ccc(S(=O)(=O)CC2CCCN(C(C)C)C2)cc1)c1cccc(Cl)c1Cl] | $IC_{50}$ = 6.89 $EC_{50}$/ $E_{Max}$ > 30 $EC_{50}$ = 0.631 | Not performed | Not performed | Not performed |
| H1377 | 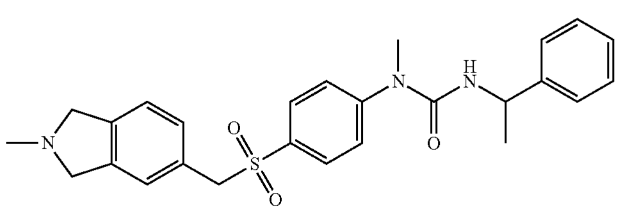 [SMILES: CC(NC(=O)N(C)c1ccc(S(=O)(=O)Cc2ccc3c(c2)CN(C)C3)cc1)c1ccccc1] | $IC_{50}$ = 5.52 $EC_{50}$/ $E_{Max}$ > 30 $EC_{50}$ = 0.384 | Not performed | Not performed | Not performed |
| H1378 | 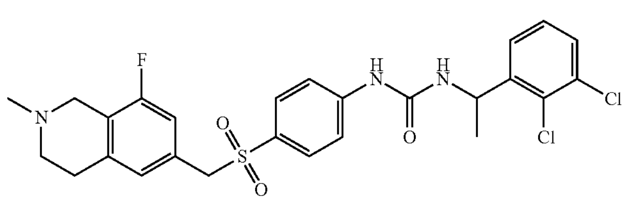 [SMILES: CC(NC(=O)Nc1ccc(S(=O)(=O)Cc2cc(F)c3c(c2)CCN(C)C3)cc1)c1cccc(Cl)c1Cl] | $IC_{50}$ = 0.019 $EC_{50}$/ $E_{Max}$ = >30 $EC_{50}$ = 0.0013 | H = 151.7 M = 245.9 D = 227.9 | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1379 | 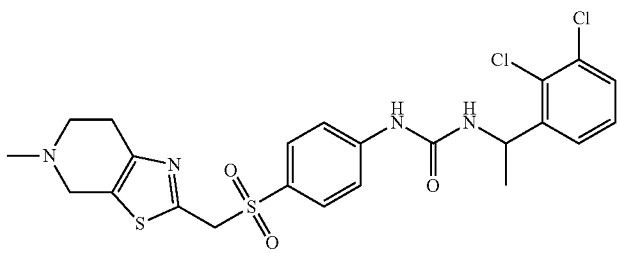 [SMILES: CC(NC(=O)Nc1ccc(S(=O)(=O)Cc2nc3c(s2)CN(C)CC3)cc1)c1cccc(Cl)c1Cl] | $IC_{50}$ = 0.0443 $EC_{50}/E_{Max}$ = >30 $EC_{50}$ = 0.00143 | H = 261.6 M = >500 D = >500 | Not performed | Not performed |
| H1380 | 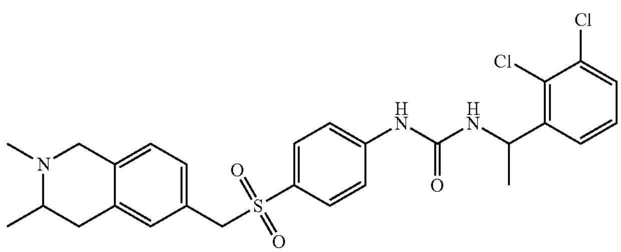 [SMILES: CC(NC(=O)Nc1ccc(S(=O)(=O)Cc2ccc3c(c2)CC(C)N(C)C3)cc1)c1cccc(Cl)c1Cl] | $IC_{50}$ = 0.0023 $EC_{50}/E_{Max}$ $_{Max}EC_{50}$ = 0.000367 | H = 137 M = 66.5 D = 169.9 | Not performed | Not performed |
| H1381 | 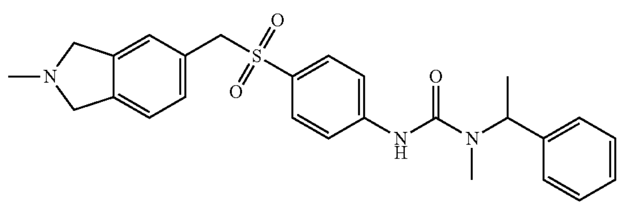 [SMILES: CC(c1ccccc1)N(C)C(=O)Nc1ccc(S(=O)(=O)Cc2ccc3c(c2)CN(C)C3)cc1] | $IC_{50}$ = 0.48/0.257 $EC_{50}/E_{Max}$ = >30 $EC_{50}$ = 0.0221/ 0.0331 PPB = 90.94 (H) PPB = 91.46 (M) | H = 60 M = 68.1 D = 88.7 | $CL_{i.v.}$ = 3.83 $CL_{p.o.}$ = 17.7 $Vd_{i.v.}$ = 3.1 $Vd_{p.o.}$ = 42.87 $T_{1/2\ i.v.}$ = 0/56 $T_{1/2\ p.o.}$ = 1.68 F (%) = 20.64 | Not performed |
| H1382 | 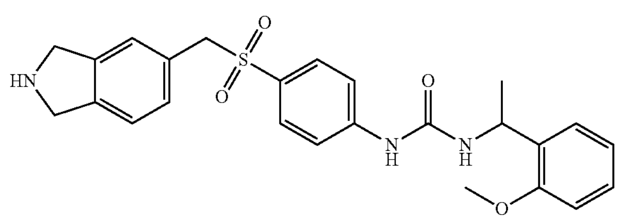 [SMILES: COc1ccccc1C(C)NC(=O)Nc1ccc(S(=O)(=O)Cc2ccc3c(c2)CNC3)cc1] | $IC_{50}$ = 0.0343 $EC_{50}/E_{Max}$ = >30 $EC_{50}$ = 0.00268 | H = 42.4 M = 43.4 D = 41.9 | Not performed | Not performed |
| H1383 | 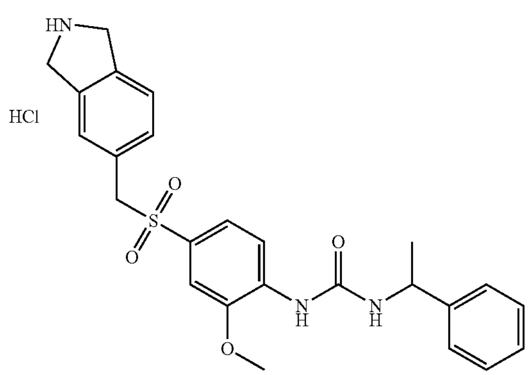 [SMILES: Cl ; COc1cc(S(=O)(=O)Cc2ccc3c(c2)CNC3)ccc1NC(=O)NC(C)c1ccccc1] | $IC_{50}$ = 0.0119 $EC_{50}/E_{Max}$ = >30 $EC_{50}$ = 0.00201 | H = 21 M = 91.9 R = 48.2 D = 27.8 | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) t$_{1/2}$ (h) F (%) | Food Intake Study |
|---|---|---|---|---|---|
| H1384 | 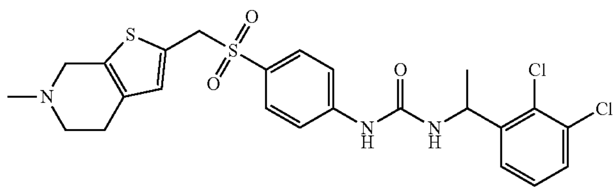 [SMILES: CC(NC(=O)Nc1ccc(S(=O)(=O)Cc2cc3c(s2)CN(C)CC3)cc1)c1cccc(Cl)c1Cl] | IC$_{50}$ = 0.00595 EC$_{50}$/ E$_{Max}$ = >30 EC$_{50}$ = 0.0024 | H = 95.1 M = 165.1 | Not performed | Not performed |
| H1385 | 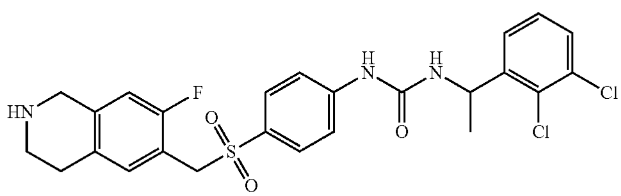 [SMILES: CC(NC(=O)Nc1ccc(S(=O)(=O)Cc2cc3c(cc2F)CNCC3)cc1)c1cccc(Cl)c1Cl] | IC$_{50}$ = 0.00398 EC$_{50}$/ E$_{Max}$ = >30 EC$_{50}$ = 0.0065 | H = <10 M = <10 | Not performed | Not performed |
| H1386 | 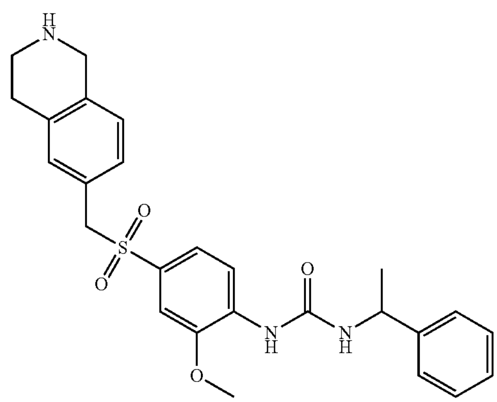 [SMILES: COc1cc(S(=O)(=O)Cc2ccc3c(c2)CCNC3)ccc1NC(=O)NC(C)c1ccccc1] | IC$_{50}$ = 0.0212 EC$_{50}$/ E$_{Max}$ = >30 EC$_{50}$ = 0.0117 | H = <10 M = 11 | Not performed | Not performed |
| H1387 | 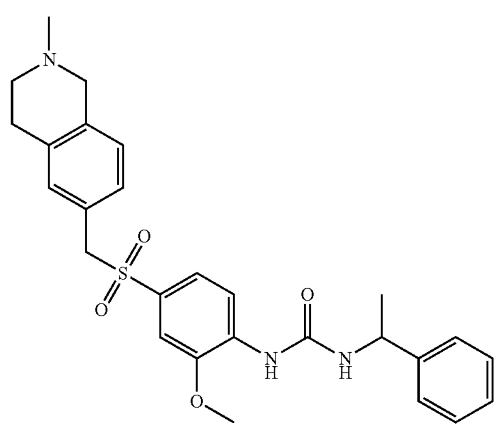 [SMILES: COc1cc(S(=O)(=O)Cc2ccc3c(c2)CCN(C)C3)ccc1NC(=O)NC(C)c1ccccc1] | IC$_{50}$ = 0.0074 EC$_{50}$/ E$_{Max}$ = >30 EC$_{50}$ = 0.0037 | H = 86.7 M = 167.5 | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1388 | 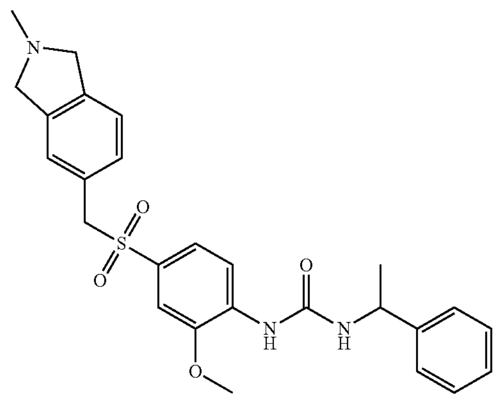 [SMILES: COc1cc(S(=O)(=O)Cc2ccc3c(c2)CN(C)C3)ccc1NC(=O)NC(C)c1ccccc1] | $IC_{50}$ = 0.0102 $EC_{50}/E_{Max}$ = >30 $EC_{50}$ = 0.0046 PPB = 96.9 (H) PPB = 92.1 (M) | H = 58.1 M = 42.4 | $CL_{i.v.}$ = 4.66 $CL_{p.o.}$ = 40.5 $Vd_{i.v.}$ = 6.3 $Vd_{p.o.}$ = 86.8 $T_{1/2\ i.v.}$ = 0.93 $T_{1/2\ p.o.}$ = 1.49 F (%) = 11.3 | Not performed |
| H1389 | 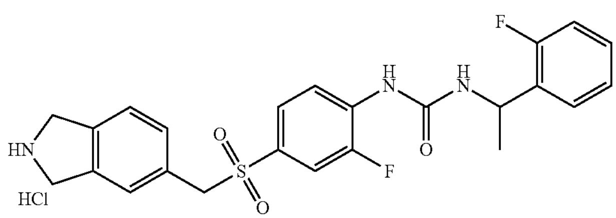 [SMILES: Cl ; CC(NC(=O)Nc1ccc(S(=O)(=O)Cc2ccc3c(c2)CNC3)cc1F)c1ccccc1F] | $IC_{50}$ = 0.0276 $EC_{50}/E_{Max}$ = >30 $EC_{50}$ = 0.0151 | H = 21.3 M = 21.2 | Not performed | Not performed |
| H1390 | 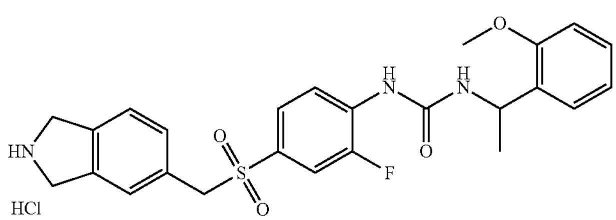 [SMILES: Cl ; COc1ccccc1C(C)NC(=O)Nc1ccc(S(=O)(=O)Cc2ccc3c(c2)CNC3)cc1F] | $IC_{50}$ = 0.0364 $EC_{50}/E_{Max}$ = >30 $EC_{50}$ = 0.0107 | H = 34.6 M = 55.9 | Not performed | Not performed |
| H1391 | 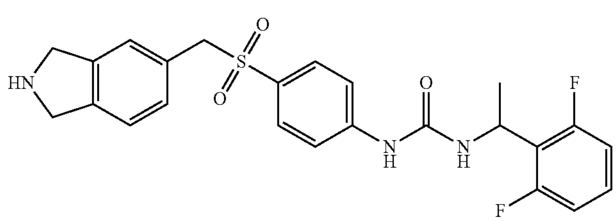 [SMILES: CC(NC(=O)Nc1ccc(S(=O)(=O)Cc2ccc3c(c2)CNC3)cc1)c1c(F)cccc1F] | $IC_{50}$ = 0.0105 $EC_{50}/E_{Max}$ = >30 $EC_{50}$ = 0.0072 | H = 14.8 M = 11.8 | Not performed | Not performed |
| H1392 | 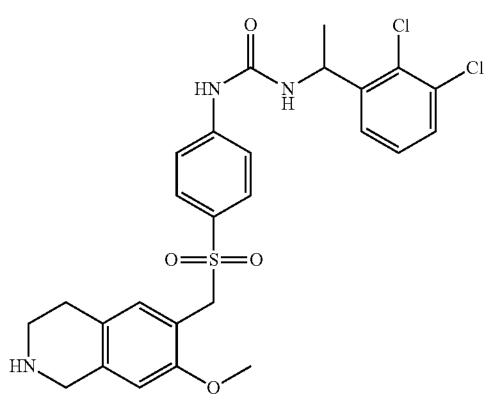 [SMILES: COc1cc2c(cc1CS(=O)(=O)c1ccc(NC(=O)NC(C)c3cccc(Cl)c3Cl)cc1)CCNC2] | $IC_{50}$ = 0.0988 $EC_{50}/E_{Max}$ = >30 $EC_{50}$ = 0.0526 | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1393 | 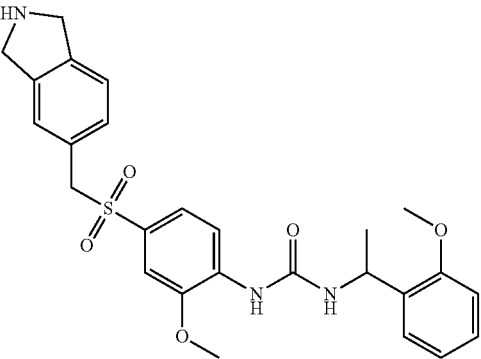 [SMILES: COc1cc(S(=O)(=O)Cc2ccc3c(c2)CNC3)ccc1NC(=O)NC(C)c1ccccc1OC] | $IC_{50}$ = 0.0092 $EC_{50}/E_{Max}$ = >30 $EC_{50}$ = 0.00373 | H = 55.5 M = 55.1 | Not performed | Not performed |
| H1394 | 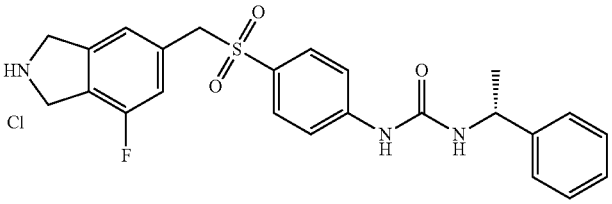 [SMILES: Cl ; C[C@@H](NC(=O)Nc1ccc(S(=O)(=O)Cc2cc(F)c3c(c2)CNC3)cc1)c1ccccc1] | $IC_{50}$ = 0.0519 $EC_{50}/E_{Max}$ = >30 $EC_{50}$ = 0.0078 | H = 67.4 M = 182.5 | Not performed | Not performed |
| H1395 | 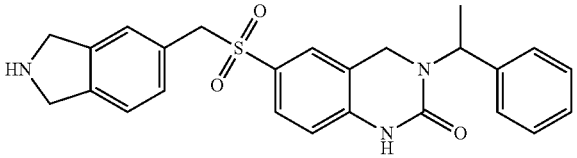 [SMILES: CC(c1ccccc1)N1Cc2cc(S(=O)(=O)Cc3ccc4c(c3)CNC4)ccc2NC1=O] | $IC_{50}$ = 0.0689 $EC_{50}/E_{Max}$ = 0.0461/1904 | Not performed | Not performed | Not performed |
| H1396 | 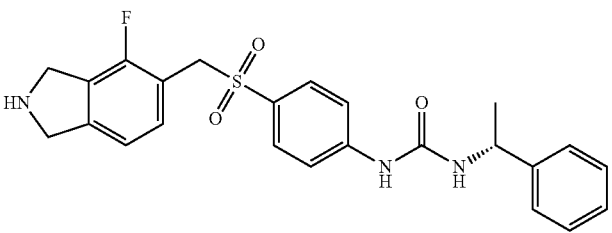 [SMILES: C[C@@H](NC(=O)Nc1ccc(S(=O)(=O)Cc2ccc3c(c2F)CNC3)cc1)c1ccccc1] | $IC_{50}$ = 0.0108 $EC_{50}/E_{Max}$ = >30 $EC_{50}$ = 0.0013 | H = 62.5 M = 330.4 | not performed | Not performed |
| H1397 | 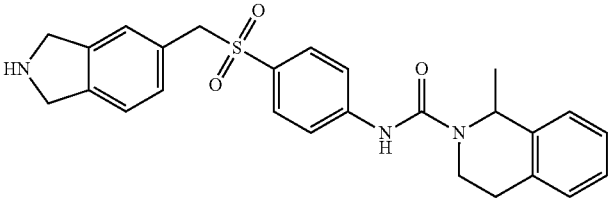 [SMILES: CC1c2ccccc2CCN1C(=O)Nc1ccc(S(=O)(=O)Cc2ccc3c(c2)CNC3)cc1] | $IC_{50}$ = 1.1 $EC_{50}/E_{Max}$ = >30 $EC_{50}$ = 0.0678 | H = 35.1 M = 32 | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1398 | 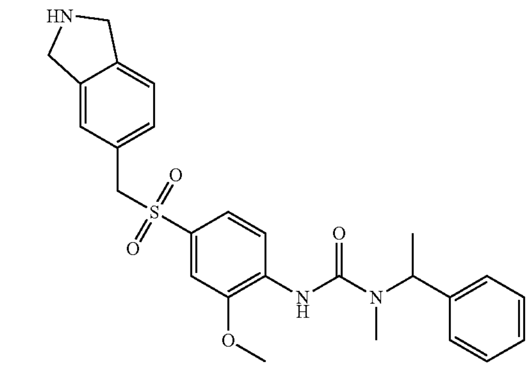 [SMILES: COc1cc(S(=O)(=O)Cc2ccc3c(c2)CNC3)ccc1NC(=O)N(C)C(C)c1ccccc1] | $IC_{50}$ = 0.629 $EC_{50}/E_{Max}$ = >30 $EC_{50}$ = 0.0626 | H = 52.9 M = 80.5 | Not performed | Not performed |
| H1399 | 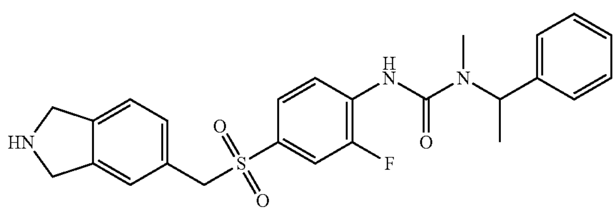 [SMILES: CC(c1ccccc1)N(C)C(=O)Nc1ccc(S(=O)(=O)Cc2ccc3c(c2)CNC3)cc1F] | $IC_{50}$ = 2.06 $EC_{50}/E_{Max}$ = >30 | Not performed | Not performed | Not performed |
| H1400 | 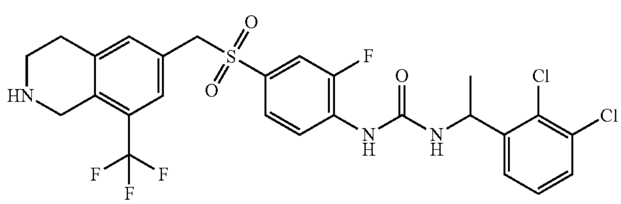 [SMILES: CC(NC(=O)Nc1ccc(S(=O)(=O)Cc2cc3c(c(C(F)(F)F)c2)CNCC3)cc1F)c1cccc(Cl)c1Cl] | $IC_{50}$ = 0.0705 $EC_{50}/E_{Max}$ = >30 $EC_{50}$ = 0.0154 | Not performed | Not performed | Not performed |
| H1401 | 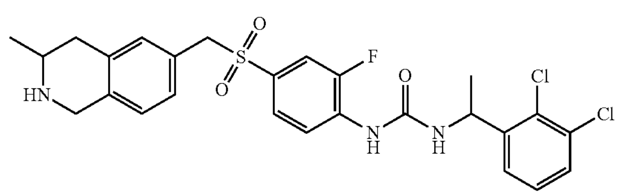 [SMILES: CC1Cc2cc(CS(=O)(=O)c3ccc(NC(=O)NC(C)c4cccc(Cl)c4Cl)c(F)c3)ccc2CN1] | $IC_{50}$ = 0.0034 $EC_{50}/E_{Max}$ = >30 | Not performed | Not performed | Not performed |
| H1402 | 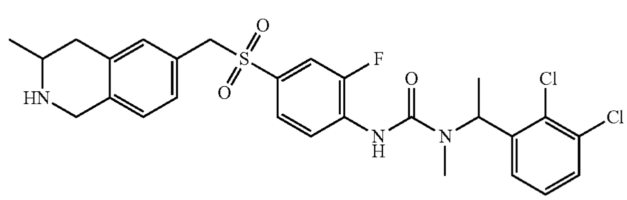 [SMILES: CC1Cc2cc(CS(=O)(=O)c3ccc(NC(=O)N(C)C(C)c4cccc(Cl)c4Cl)c(F)c3)ccc2CN1] | $IC_{50}$ = 0.075 $EC_{50}/E_{Max}$ = >30 | Not performed | Not performed | Not performed |
| H1403 | 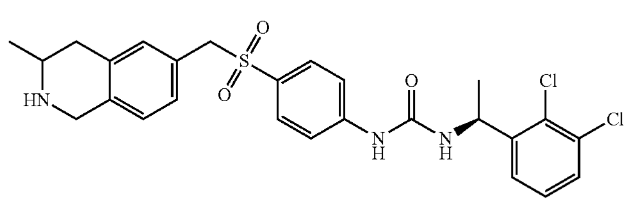 [SMILES: CC1Cc2cc(CS(=O)(=O)c3ccc(NC(=O)N[C@@H](C)c4cccc(Cl)c4Cl)cc3)ccc2CN1] | $IC_{50}$ = 0.0015 $EC_{50}/E_{Max}$ = >30 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1404 | 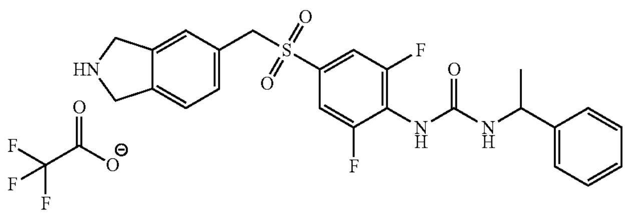 [SMILES: O=C([O-])C(F)(F)F ; CC(NC(=O)Nc1c(F)cc(S(=O)(=O)Cc2ccc3c(c2)CNC3)cc1F)c1ccccc1] | $IC_{50}$ = 1.62 $EC_{50}/$ $E_{Max}$ = >30 | H = 10 M = 19 | Not performed | Not performed |
| H1405 | 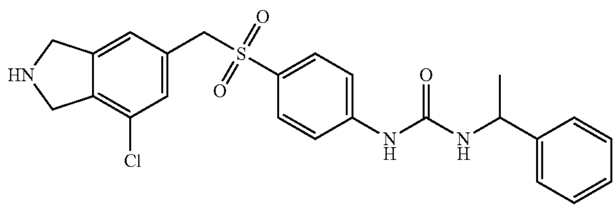 [SMILES: CC(NC(=O)Nc1ccc(S(=O)(=O)Cc2cc(Cl)c3c(c2)CNC3)cc1)c1ccccc1] | $IC_{50}$ = 1.86 $EC_{50}/$ $E_{Max}$ = >30 $EC_{50}$ = 0.09 | Not performed | Not performed | Not performed |
| H1406 | 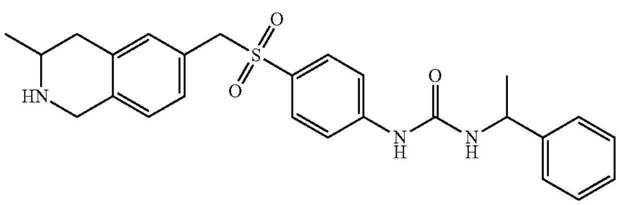 [SMILES: CC1Cc2cc(CS(=O)(=O)c3ccc(NC(=O)NC(C)c4ccccc4)cc3)ccc2CN1] | $IC_{50}$ = 0.0855 $EC_{50}/$ $E_{Max}$ = >30 $EC_{50}$ = 0.00792 | H = 15 M = 22.2 | Not performed | Not performed |
| H1407 | 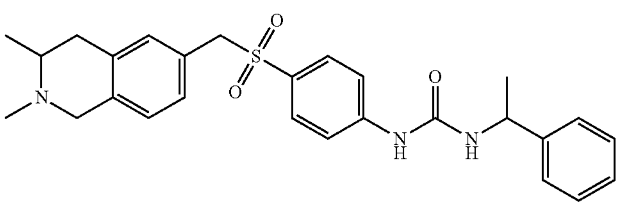 [SMILES: CC(NC(=O)Nc1ccc(S(=O)(=O)Cc2ccc3c(c2)CC(C)N(C)C3)cc1)c1ccccc1] | $IC_{50}$ = 0.0127 $EC_{50}/$ $E_{Max}$ = >30 $EC_{50}$ = 0.00145 | H = 144.4 M = 84.1 | Not performed | Not performed |
| H1408 | 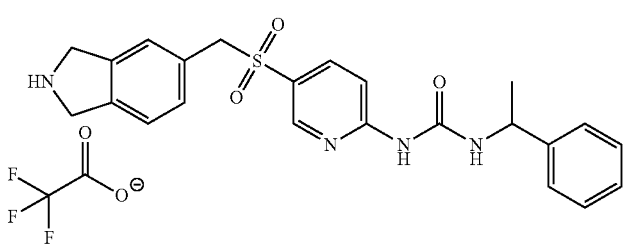 [SMILES: O=C([O-])C(F)(F)F ; CC(NC(=O)Nc1ccc(S(=O)(=O)Cc2ccc3c(c2)CNC3)cn1)c1ccccc1] | $IC_{50}$ = 0.162 $EC_{50}/$ $E_{Max}$ = >30 $EC_{50}$ = 0.036 | Not performed | Not performed | Not performed |
| H1409 | 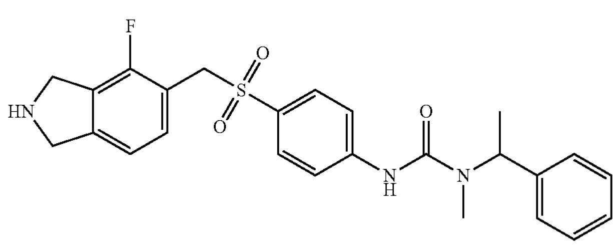 [SMILES: CC(c1ccccc1)N(C)C(=O)Nc1ccc(S(=O)(=O)Cc2ccc3c(c2F)CNC3)cc1] | $IC_{50}$ = 0.282 $EC_{50}/$ $E_{Max}$ = >30 $EC_{50}$ = 0.0745 | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1410 | 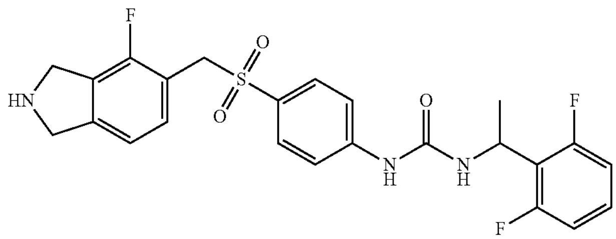 [SMILES: CC(NC(=O)Nc1ccc(S(=O)(=O)Cc2ccc3c(c2F)CNC3)cc1)c1c(F)cccc1F] | $IC_{50}$ = 0.032 $EC_{50}$/ $E_{Max}$ = >30 $EC_{50}$ = 0.0132 | H = 73.3 M = 358.6 | Not performed | Not performed |
| H1411 | 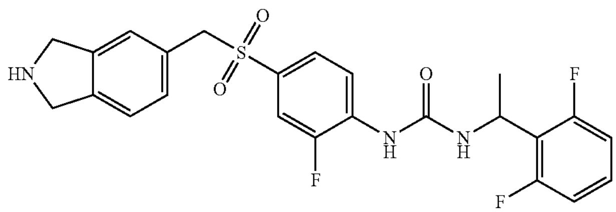 [SMILES: CC(NC(=O)Nc1ccc(S(=O)(=O)Cc2ccc3c(c2)CNC3)cc1F)c1c(F)cccc1F] | $IC_{50}$ = 0.124 $EC_{50}$/ $E_{Max}$ = >30 $EC_{50}$ = 0.0178 | Not performed | Not performed | Not performed |
| H1412 | 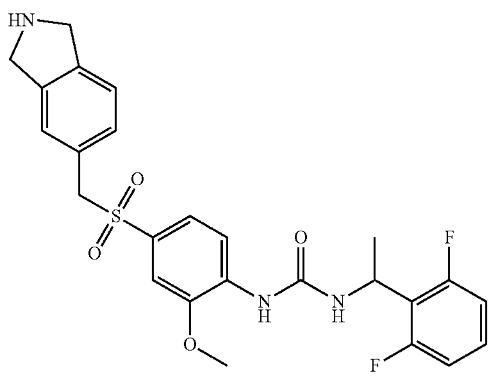 [SMILES: COc1cc(S(=O)(=O)Cc2ccc3c(c2)CNC3)ccc1NC(=O)NC(C)c1c(F)cccc1F] | $IC_{50}$ = 0.0157 $EC_{50}$/ $E_{Max}$ = >30 $EC_{50}$ = 0.0043 | H = 22.5 M = 122.4 | Not performed | Not performed |
| H1413 | 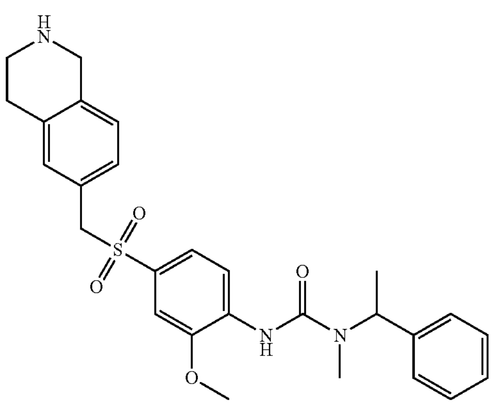 [SMILES: COc1cc(S(=O)(=O)Cc2ccc3c(c2)CCNC3)ccc1NC(=O)N(C)C(C)c1ccccc1] | $IC_{50}$ = 0.681 $EC_{50}$/ $E_{Max}$ = >30 $EC_{50}$ = 0.2254 | Not performed | Not performed | Not performed |
| H1414 | 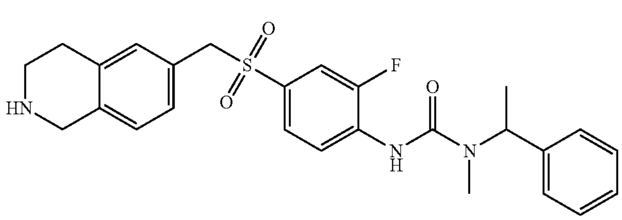 [SMILES: CC(c1ccccc1)N(C)C(=O)Nc1ccc(S(=O)(=O)Cc2ccc3c(c2)CCNC3)cc1F] | $IC_{50}$ = 2.09 $EC_{50}$/ $E_{Max}$ = >30 $EC_{50}$ = 0.589 | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1415 | 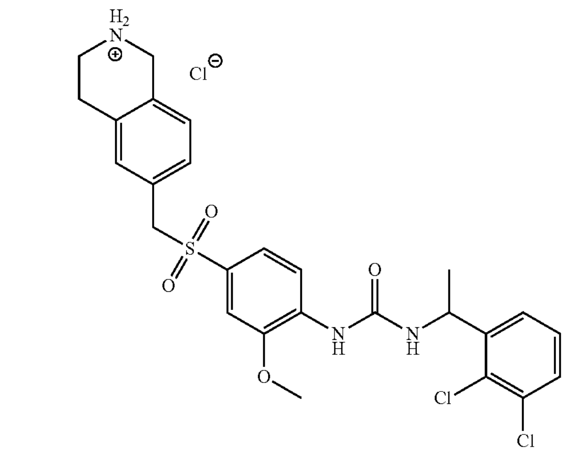 | $IC_{50}$ = 0.0011 (0.01593) $EC_{50}/E_{Max}$ = >30 $EC_{50}$ = 0.0005733 (0.0004) PPB = 99.85 (H) PPB = 99.77 (R) PPB = 99.93 (M) | H = <10 M = 12.8 R = 28.3 D = 10.5 | $CL_{i.v.}$ = 1.03 (M); 2.12 (R) $CL_{p.o.}$ = 74.5 (M) $CL_{i.p.}$ = 2.76 (R) $Vd_{i.v.}$ = 1.72 (M); 39.67 (R) $Vd_{p.o.}$ = 326.9 (M) $Vd_{i.p.}$ = 61.91 (R) $T_{1/2\ i.v.}$ = 1.16 (M); 12.96 (R) $T_{1/2\ p.o.}$ = 3.04 (M) $T_{1/2\ i.p.}$ = 17/23 (R) F (%) = 1.12 (M); 8.9 (R) | Not performed |
| H1416 | 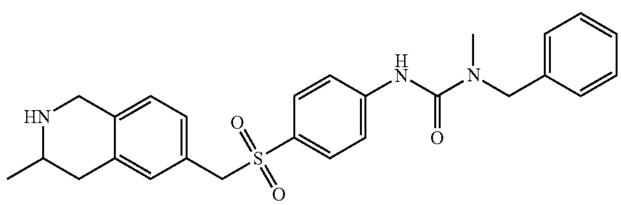 [SMILES: CC1Cc2cc(CS(=O)(=O)c3ccc(NC(=O)N(C)Cc4ccccc4)cc3)ccc2CN1] | $IC_{50}$ = 1.037 $EC_{50}/E_{Max}$ = >30 $EC_{50}$ = 0.0266 | Not performed | Not performed | Not performed |
| H1417 | 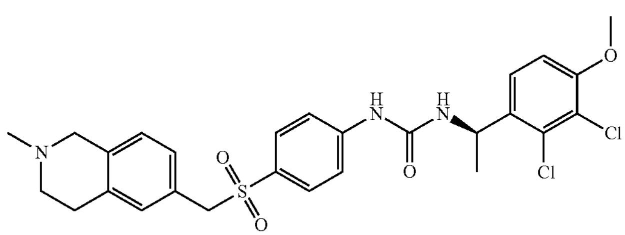 | $IC_{50}$ = 0.045 $EC_{50}/E_{Max}$ = >30 $EC_{50}$ = 0.00973 PPB = 99.85 (H) PPB = 99.88 (M) | H = 48.9 M = 53.4 | $CL_{i.v.}$ = 1.57 $CL_{p.o.}$ = 13.61 $Vd_{i.v.}$ = 4.74 $Vd_{p.o.}$ = 24.97 $T1/2_{i.v.}$ = 2.09 $T_{1/2\ p.o.}$ = 1.27 F (%) = 11.80 | Not performed |
| H1418 | 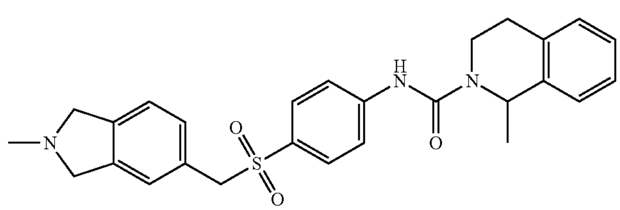 [SMILES: CC1c2ccccc2CCN1C(=O)Nc1ccc(S(=O)(=O)Cc2ccc3c(c2)CN(C)C3)cc1] | $IC_{50}$ = 2.7 $EC_{50}/E_{Max}$ = >30 $EC_{50}$ = 0.0695 | Not performed | Not performed | Not performed |
| H1419 | 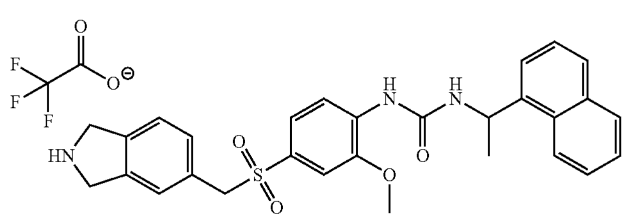 [SMILES: O=C([O-])C(F)(F)F ; COc1cc(S(=O)(=O)Cc2ccc3c(c2)CNC3)ccc1NC(=O)NC(C)c1cccc2ccccc12] | $IC_{50}$ = 0.0044 $EC_{50}/E_{Max}$ = >30 $EC_{50}$ = 0.0005 PPB = 99.59 (H) PPB = 99.69 (M) | H = 33.1 M = 45.1 | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1420 | 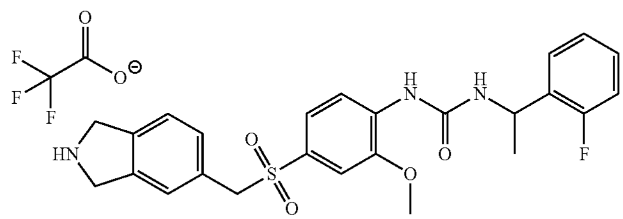 [SMILES: O=C([O-])C(F)(F)F ; COc1cc(S(=O)(=O)Cc2ccc3c(c2)CNC3)ccc1NC(=O)NC(C)c1ccccc1F] | $IC_{50}$ = 0.022 $EC_{50}/E_{Max}$ = >30 $EC_{50}$ = 0.001 PPB = 97.2 (H) PPB = 95.39 (M) | H = 17.4 M = 50.6 | Not performed | Not performed |
| H1421 | 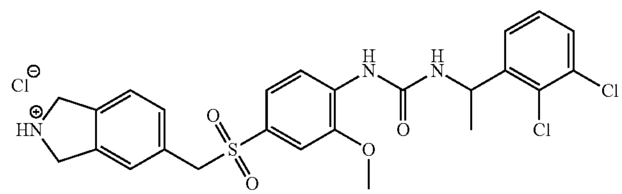 [SMILES: [Cl-] ; COc1cc(S(=O)(=O)Cc2ccc3c(c2)C[NH2+]C3)ccc1NC(=O)NC(C)c1cccc(Cl)c1Cl] | $IC_{50}$ = 0.0018 $EC_{50}/E_{Max}$ = >50 $EC_{50}$ = 0.0004 PPB = 99.63 (H) PPB = 99.66 (M) | H = 13.2 M = 38.8 | $CL_{i.p.}$ = 1.96 (R) $Vd_{i.p.}$ = 54.56 (R) $T_{1/2\ i.p.}$ = 19.01 (R) | Not performed |
| H1422 | 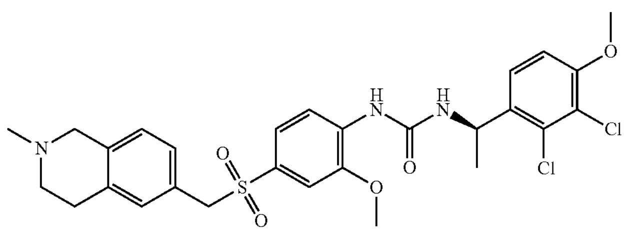 | $IC_{50}$ = 0.0294 $EC_{50}/E_{Max}$ = >30 $EC_{50}$ = 0.0007 | Not performed | Not performed | Not performed |
| H1423 | 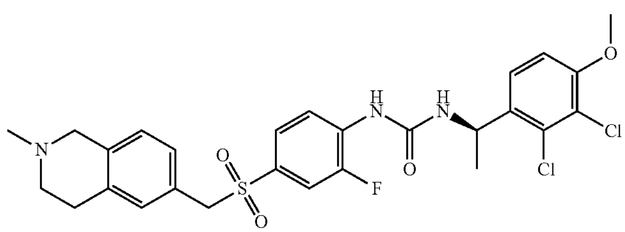 | $IC_{50}$ = 0.1144 $EC_{50}/E_{Max}$ = >30 $EC_{50}$ = 0.00377 | Not performed | Not performed | Not performed |
| H1424 | 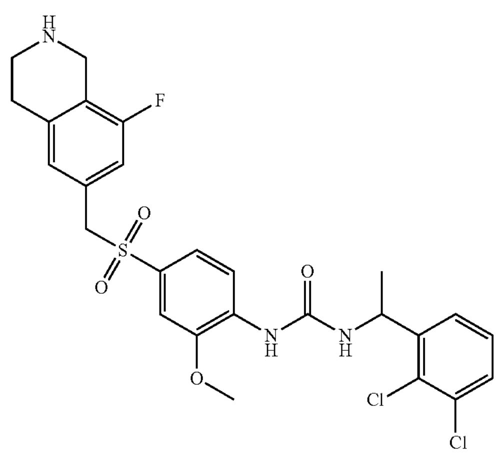 [SMILES: COc1cc(S(=O)(=O)Cc2cc(F)c3c(c2)CCNC3)ccc1NC(=O)NC(C)c1cccc(Cl)c1Cl] | $IC_{50}$ = 0.0154 $EC_{50}/E_{Max}$ = >30 $EC_{50}$ = 0.0089 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1425 | 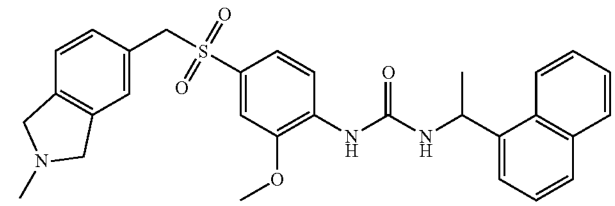 [SMILES: COc1cc(S(=O)(=O)Cc2ccc3c(c2)CN(C)C3)ccc1NC(=O)NC(C)c1cccc2ccccc12] | $IC_{50}$ = 0.0081 $EC_{50}/E_{Max}$ = >30 $EC_{50}$ = 0.0018 | H = 310.0 M = 141.5 | Not performed | Not performed |
| H1426 | 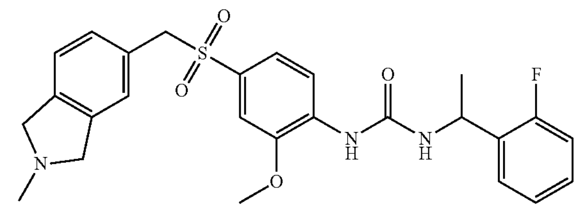 [SMILES: COc1cc(S(=O)(=O)Cc2ccc3c(c2)CN(C)C3)ccc1NC(=O)NC(C)c1ccccc1F] | $IC_{50}$ = 0.0529 $EC_{50}/E_{Max}$ = >30 $EC_{50}$ = 0.0034 | H = 77.3 M = 80.6 | Not performed | Not performed |
| H1427 | 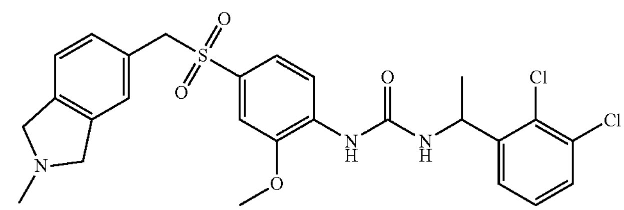 [SMILES: COc1cc(S(=O)(=O)Cc2ccc3c(c2)CN(C)C3)ccc1NC(=O)NC(C)c1cccc(Cl)c1Cl] | $IC_{50}$ = 0.0038 $EC_{50}/E_{Max}$ = >30 $EC_{50}$ = 0.0007 | H = 58.8 M = 82.1 | Not performed | Not performed |
| H1428 | 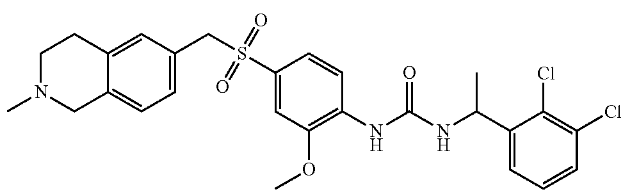 [SMILES: COc1cc(S(=O)(=O)Cc2ccc3c(c2)CCN(C)C3)ccc1NC(=O)NC(C)c1cccc(Cl)c1Cl] | $IC_{50}$ = 0.0033 $EC_{50}/E_{Max}$ = >30 $EC_{50}$ = 0.0005 | H = 69.3 M = 194.8 | Not performed | Not performed |
| H1429 | 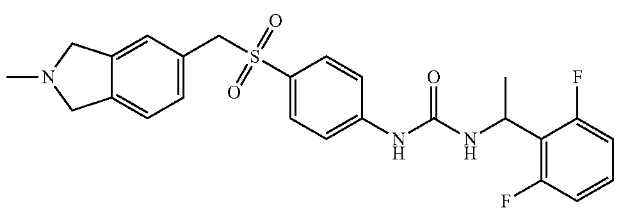 [SMILES: CC(NC(=O)Nc1ccc(S(=O)(=O)Cc2ccc3c(c2)CN(C)C3)cc1)c1c(F)cccc1F] | $IC_{50}$ = 0.16 $EC_{50}/E_{Max}$ = >30 $EC_{50}$ = 0.00731 | H = 65.2 M = 63.6 | Not performed | Not performed |
| H1430 | 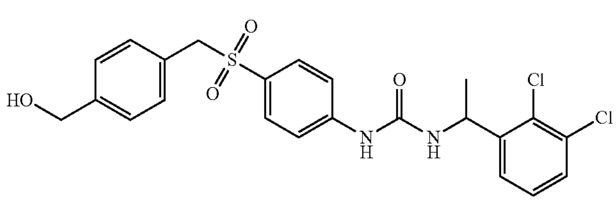 [SMILES: CC(NC(=O)Nc1ccc(S(=O)(=O)Cc2ccc(CO)cc2)cc1)c1cccc(Cl)c1Cl] | $IC_{50}$ = 2.473 $EC_{50}/E_{Max}$ = >30 $EC_{50}$ = 0.0564 | Not performed | Not performed | Not performed |
| H1431 | 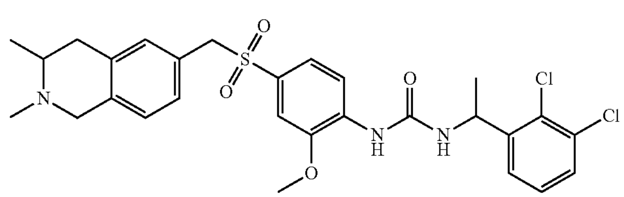 [SMILES: COc1cc(S(=O)(=O)Cc2ccc3c(c2)CC(C)N(C)C3)ccc1NC(=O)NC(C)c1cccc(Cl)c1Cl] | $IC_{50}$ = 0.00454 $EC_{50}/E_{Max}$ = >30 $EC_{50}$ = 0.000657 | H = 99.7 M = 135.7 | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1432 | 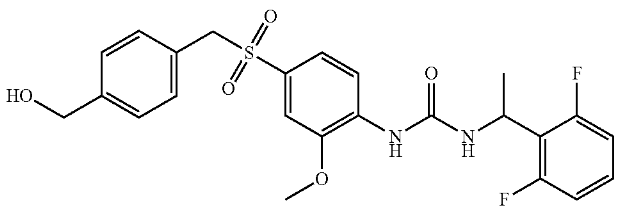 [SMILES: COc1cc(S(=O)(=O)Cc2ccc(CO)cc2)ccc1NC(=O)NC(C)c1c(F)cccc1F] | $IC_{50}$ = 5.5 $EC_{50}/E_{Max}$ = >30 $EC_{50}$ = 0.367 | Not performed | Not performed | Not performed |
| H1433 | 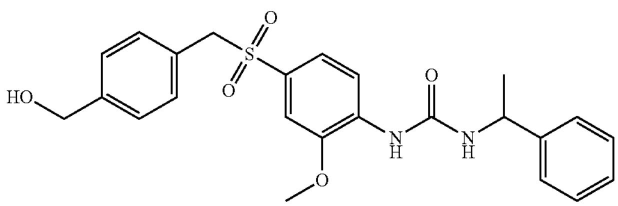 [SMILES: COc1cc(S(=O)(=O)Cc2ccc(CO)cc2)ccc1NC(=O)NC(C)c1ccccc1] | $IC_{50}$ = 3.1225 $EC_{50}/E_{Max}$ = >30 $EC_{50}$ = 0.4729 | Not performed | Not performed | Not performed |
| H1434 | 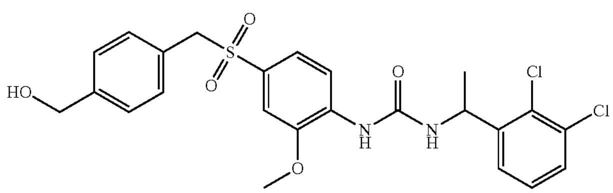 [SMILES: COc1cc(S(=O)(=O)Cc2ccc(CO)cc2)ccc1NC(=O)NC(C)c1cccc(Cl)c1Cl] | $IC_{50}$ = 0.8567 $EC_{50}/E_{Max}$ = >30 $EC_{50}$ = 0.0612 | Not performed | Not performed | Not performed |
| H1435 | 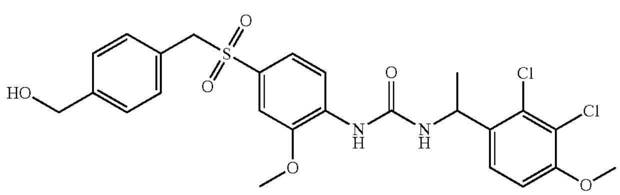 [SMILES: COc1cc(S(=O)(=O)Cc2ccc(CO)cc2)ccc1NC(=O)NC(C)c1ccc(OC)c(Cl)c1Cl] | $IC_{50}$ = >30 $EC_{50}/E_{Max}$ = >30 $EC_{50}$ = >10 | Not performed | Not performed | Not performed |
| H1436 | 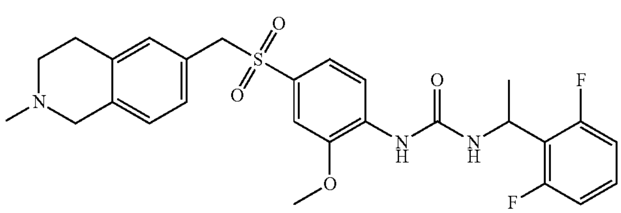 [SMILES: COc1cc(S(=O)(=O)Cc2ccc3c(c2)CCN(C)C3)ccc1NC(=O)NC(C)c1c(F)cccc1F] | $IC_{50}$ = 0.01954 $EC_{50}/E_{Max}$ = >30 $EC_{50}$ = 0.0043 | Not performed | Not performed | Not performed |
| H1437 | 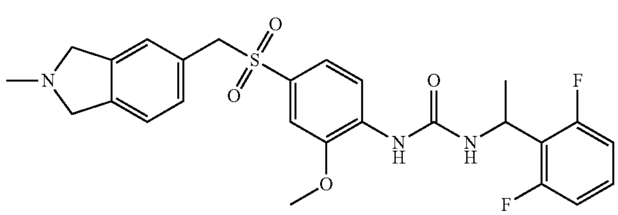 [SMILES: COc1cc(S(=O)(=O)Cc2ccc3c(c2)CN(C)C3)ccc1NC(=O)NC(C)c1c(F)cccc1F] | $IC_{50}$ = 0.02427 $EC_{50}/E_{Max}$ = >30 $EC_{50}$ = 0.01 | Not performed | Not performed | Not performed |
| H1438 | 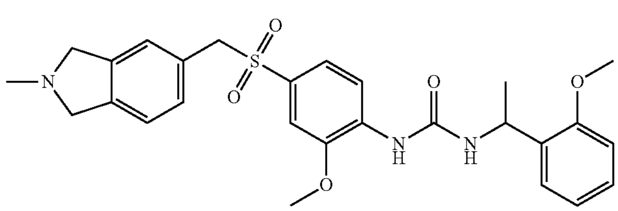 | $IC_{50}$ = 0.01261 $EC_{50}/E_{Max}$ = >30 $EC_{50}$ = 0.002758 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) t$_{1/2}$ (h) F (%) | Food Intake Study |
|---|---|---|---|---|---|
| H1439 | 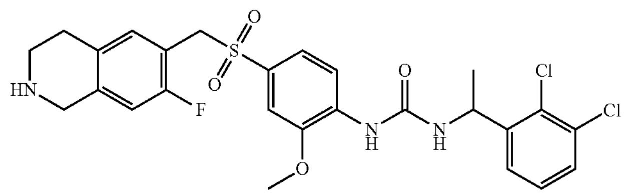 [SMILES: COc1cc(S(=O)(=O)Cc2cc3c(cc2F)CNCC3)ccc1NC(=O)NC(C)c1cccc(Cl)c1Cl] | IC$_{50}$ = 0.01245 EC$_{50}$/E$_{Max}$ = >30 EC$_{50}$ = 0.0141 | Not performed | Not performed | Not performed |
| H1440 | 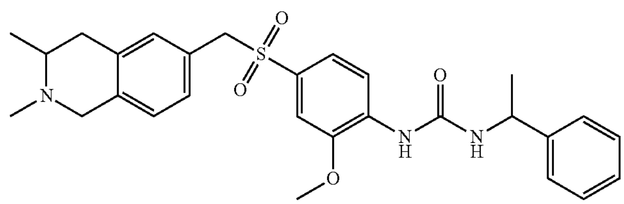 [SMILES: COc1cc(S(=O)(=O)Cc2ccc3c(c2)CC(C)N(C)C3)ccc1NC(=O)NC(C)c1ccccc1] | IC$_{50}$ = 0.004401 EC$_{50}$/E$_{Max}$ = >30 EC$_{50}$ = 0.0029 | Not performed | Not performed | Not performed |
| H1441 | 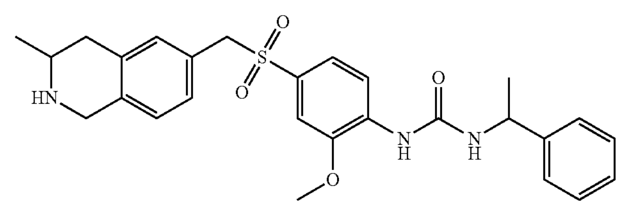 [SMILES: COc1cc(S(=O)(=O)Cc2ccc3c(c2)CC(C)NC3)ccc1NC(=O)NC(C)c1ccccc1] | IC$_{50}$ = 0.01494 (0.04043) EC$_{50}$/E$_{Max}$ = >30 EC$_{50}$ = 0.0043 (0.0033) PPB = 97.55 (H) PPB = 95.5 (M) | H = 17.3 M = 16.4 | Not performed | Not performed |
| H1442 | 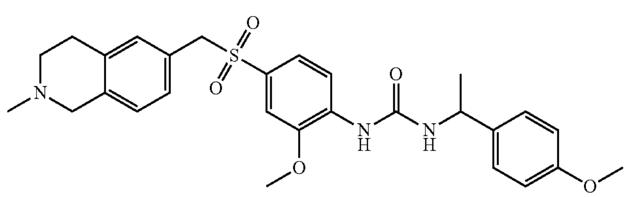 | IC$_{50}$ = 0.05809 EC$_{50}$/E$_{Max}$ = >30 EC$_{50}$ = 0.0164 | Not performed | Not performed | Not performed |
| H1443 | 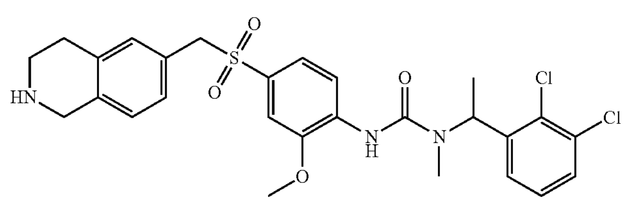 [SMILES: COc1cc(S(=O)(=O)Cc2ccc3c(c2)CCNC3)ccc1NC(=O)N(C)C(C)c1cccc(Cl)c1Cl] | IC$_{50}$ = 0.068 EC$_{50}$/E$_{Max}$ = >30 EC$_{50}$ = 0.0858 | Not performed | Not performed | Not performed |
| H1444 | 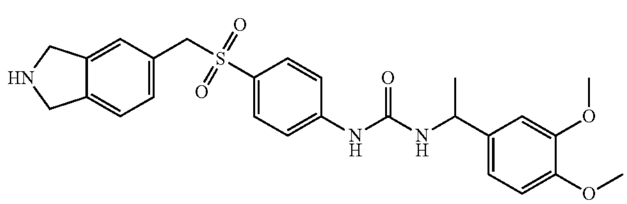 [SMILES: COc1ccc(C(C)NC(=O)Nc2ccc(S(=O)(=O)Cc3ccc4c(c3)CNC4)cc2)cc1OC] | IC$_{50}$ = 2.8605 EC$_{50}$/E$_{Max}$ = >30 EC$_{50}$ = 0.185 | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1445 | 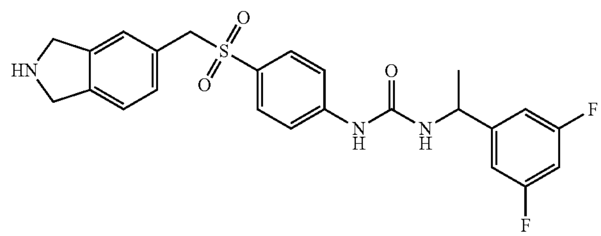 [SMILES: CC(NC(=O)Nc1ccc(S(=O)(=O)Cc2ccc3c(c2)CNC3)cc1)c1cc(F)cc(F)c1] | $IC_{50}$ = 0.02383 $EC_{50}/E_{Max}$ = >30 $EC_{50}$ = 0.0039 | H = 19.4 M = 17.3 | Not performed | Not performed |
| H1446 | 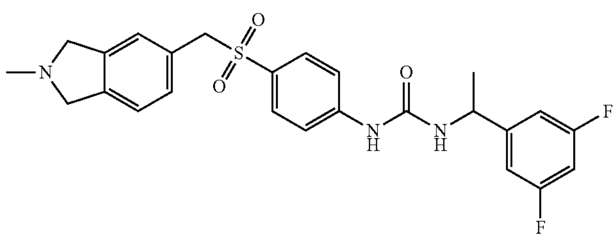 [SMILES: CC(NC(=O)Nc1ccc(S(=O)(=O)Cc2ccc3c(c2)CN(C)C3)cc1)c1cc(F)cc(F)c1] | $IC_{50}$ = 0.09655 $EC_{50}/E_{Max}$ = >30 $EC_{50}$ = 0.009 | H = 177.6 M = 58.5 | Not performed | Not performed |
| H1447 | 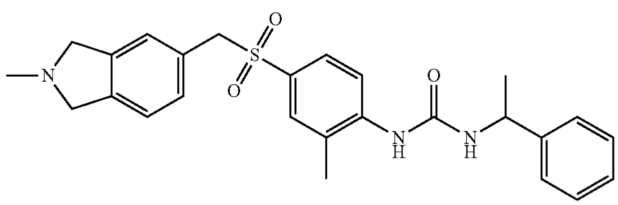 [SMILES: Cc1cc(S(=O)(=O)Cc2ccc3c(c2)CN(C)C3)ccc1NC(=O)NC(C)c1ccccc1] | $IC_{50}$ = 0.10002 $EC_{50}/E_{Max}$ = >30 $EC_{50}$ = 0.0065 | H = 72.5 M = 42.6 | Not performed | Not performed |
| H1448 | 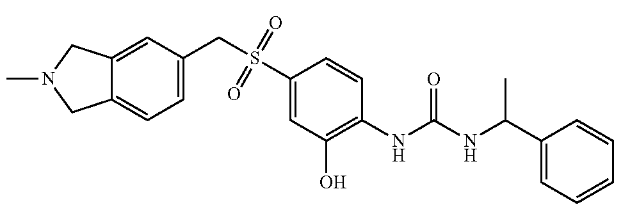 [SMILES: CC(NC(=O)Nc1ccc(S(=O)(=O)Cc2ccc3c(c2)CN(C)C3)cc1O)c1ccccc1] | $IC_{50}$ = 0.03029 $EC_{50}/E_{Max}$ = >30 $EC_{50}$ = 0.0033 | H = 28 M = 20.8 | $CL_{i.v.}$ = 4.83 $CL_{p.o.}$ = 254.6 $Vd_{i.v.}$ = 9.26 $Vd_{p.o.}$ = 242.2 $T_{1/2\ i.v.}$ = 1.33 $T_{1/2\ p.o.}$ = 0.66 F (%) = 1.90 | Not performed |
| H1449 | 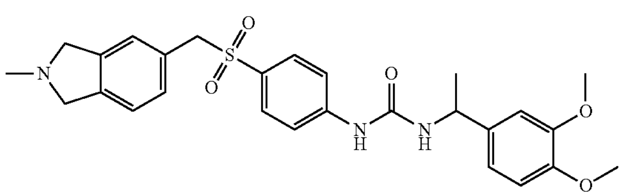 | $IC_{50}$ = 4.1695 $EC_{50}/E_{Max}$ = >30 $EC_{50}$ = 0.9276 | Not performed | Not performed | Not performed |
| H1450 | 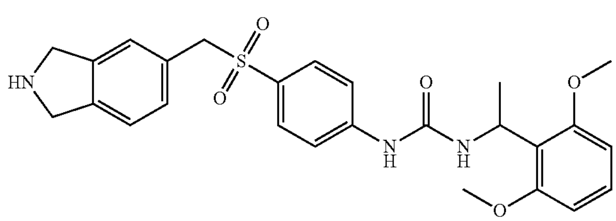 [SMILES: COc1cccc(OC)c1C(C)NC(=O)Nc1ccc(S(=O)(=O)Cc2ccc3c(c2)CNC3)cc1] | $IC_{50}$ = 0.2896 $EC_{50}/E_{Max}$ = >30 $EC_{50}$ = 0.1823 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1451 | 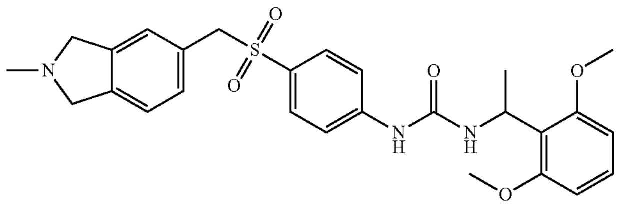 | $IC_{50}$ = 0.06852 $EC_{50}/E_{Max}$ = >30 $EC_{50}$ = 0.03329 | Not performed | Not performed | Not performed |
| H1452 | 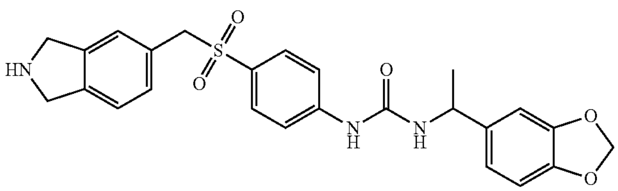 [SMILES: CC(NC(=O)Nc1ccc(S(=O)(=O)Cc2ccc3c(c2)CNC3)cc1)c1ccc2c(c1)OCO2] | $IC_{50}$ = 0.08695 $EC_{50}/E_{Max}$ = >30 $EC_{50}$ = 0.03475 | Not performed | Not performed | Not performed |
| H1453 | 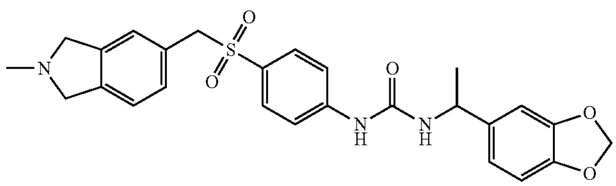 [SMILES: CC(NC(=O)Nc1ccc(S(=O)(=O)Cc2ccc3c(c2)CN(C)C3)cc1)c1ccc2c(c1)OCO2] | $IC_{50}$ = 0.1088 $EC_{50}/E_{Max}$ = >30 $EC_{50}$ = 0.04684 | Not performed | Not performed | Not performed |
| H1454 | 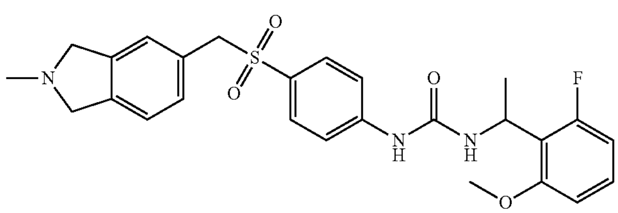 [SMILES: COc1cccc(F)c1C(C)NC(=O)Nc1ccc(S(=O)(=O)Cc2ccc3c(c2)CN(C)C3)cc1] | $IC_{50}$ = 0.03184 $EC_{50}/E_{Max}$ = >30 $EC_{50}$ = 0.0061 | H = 259.9 M = 193.3 | Not performed | Not performed |
| H1455 | 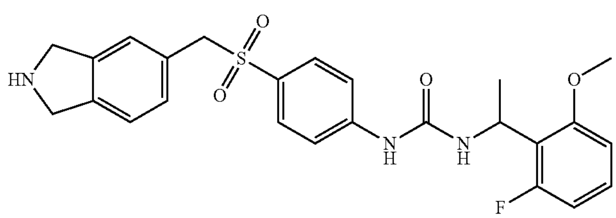 [SMILES: COc1cccc(F)c1C(C)NC(=O)Nc1ccc(S(=O)(=O)Cc2ccc3c(c2)CNC3)cc1] | $IC_{50}$ = 0.04255 $EC_{50}/E_{Max}$ = >30 $EC_{50}$ = 0.0052 | H = 55.5 M = 56.9 | Not performed | Not performed |
| H1456 | 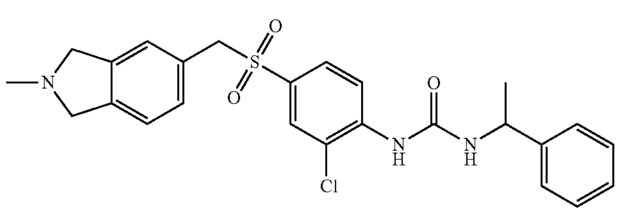 [SMILES: CC(NC(=O)Nc1ccc(S(=O)(=O)Cc2ccc3c(c2)CN(C)C3)cc1Cl)c1ccccc1] | $IC_{50}$ = 0.10898 $EC_{50}/E_{Max}$ = >30 $EC_{50}$ = 0.0062 | H = 160.6 M = 137.8 | Not performed | Not performed |
| H1457 | 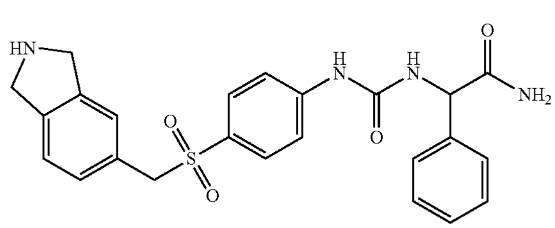 [SMILES: NC(=O)C(NC(=O)Nc1ccc(S(=O)(=O)Cc2ccc3c(c2)CNC3)cc1)c1ccccc1] | $IC_{50}$ = 16.6185 $EC_{50}/E_{Max}$ = >30 $EC_{50}$ = 0.1225 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) t$_{1/2}$ (h) F (%) | Food Intake Study |
|---|---|---|---|---|---|
| H1458 | 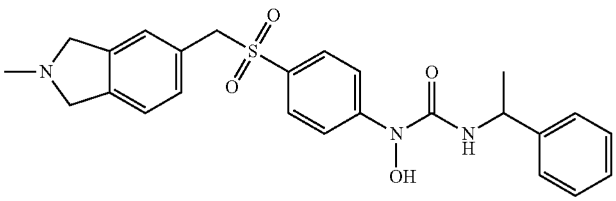 [SMILES: CC(NC(=O)N(O)c1ccc(S(=O)(=O)Cc2ccc3c(c2)CN(C)C3)cc1)c1ccccc1] | IC$_{50}$ = 1.1681 EC$_{50}$/E$_{Max}$ = >30 EC$_{50}$ = 0.2879 | Not performed | Not performed | Not performed |
| H1459 | 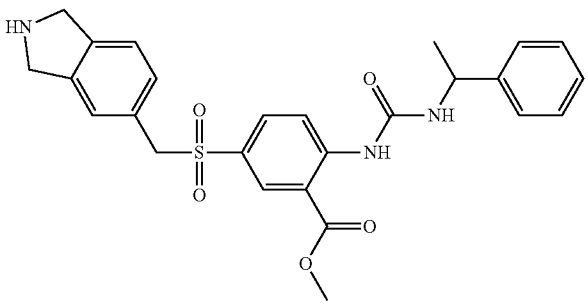 [SMILES: COC(=O)c1cc(S(=O)(=O)Cc2ccc3c(c2)CNC3)ccc1NC(=O)NC(C)c1ccccc1] | IC$_{50}$ = 0.011537 EC$_{50}$/E$_{Max}$ = >30 EC$_{50}$ = 0.0084 | H = 53.7 M = 49.3 | Not performed | Not performed |
| H1460 | 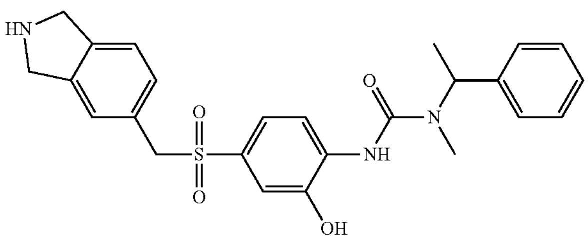 [SMILES: CC(c1ccccc1)N(C)C(=O)Nc1ccc(S(=O)(=O)Cc2ccc3c(c2)CNC3)cc1O] | IC$_{50}$ = 0.536 EC$_{50}$/E$_{Max}$ = >30 EC$_{50}$ = 0.1635 | Not performed | Not performed | Not performed |
| H1461 | 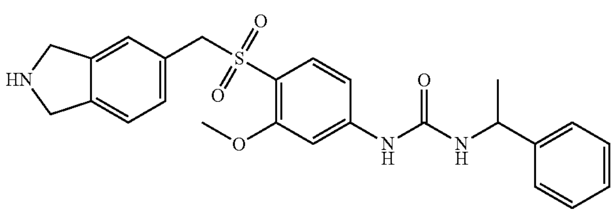 [SMILES: COc1cc(NC(=O)NC(C)c2ccccc2)ccc1S(=O)(=O)Cc1ccc2c(c1)CNC2] | IC$_{50}$ = 0.0078995 (1.721) EC$_{50}$/E$_{Max}$ = >30 EC$_{50}$ = 0.0035 (0.003) | H = 22.0 M = <10 | CL$_{i.p.}$ 2.30 (R) Vd$_{i.p.}$ 8.64 (R) T$_{1/2\ i.p.}$ 2.61 (R) | Not performed |
| H1462 | 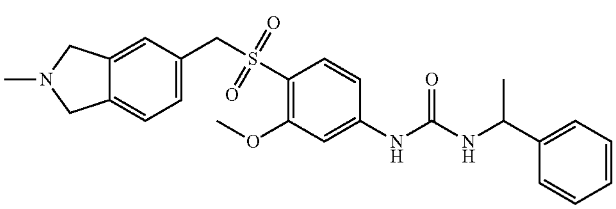 [SMILES: COc1cc(NC(=O)NC(C)c2ccccc2)ccc1S(=O)(=O)Cc1ccc2c(c1)CN(C)C2] | IC$_{50}$ = 0.0138 EC$_{50}$/E$_{Max}$ = >30 EC$_{50}$ = 0.006238 | H = 76.1 M = 15.8 | Not performed | Not performed |
| H1463 | 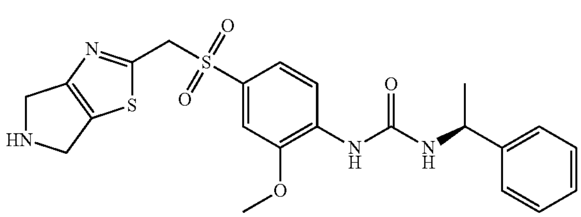 [SMILES: COc1cc(S(=O)(=O)Cc2nc3c(s2)CNC3)ccc1NC(=O)N[C@@H](C)c1ccccc1] | IC$_{50}$ = 1.1475 EC$_{50}$/E$_{Max}$ = >30 EC$_{50}$ = 0.2894 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1464 | 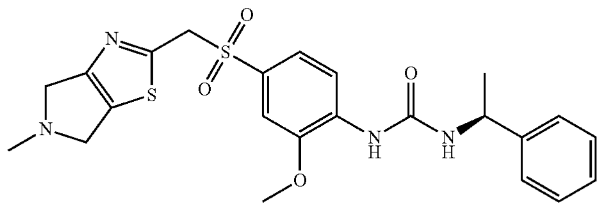 [SMILES: COc1cc(S(=O)(=O)Cc2nc3c(s2)CN(C)C3)ccc1NC(=O)N[C@@H](C)c1ccccc1] | $IC_{50}$ = 2.959 $EC_{50}/E_{Max}$ = >30 $EC_{50}$ = 0.2904 | Not performed | Not performed | Not performed |
| H1465 | 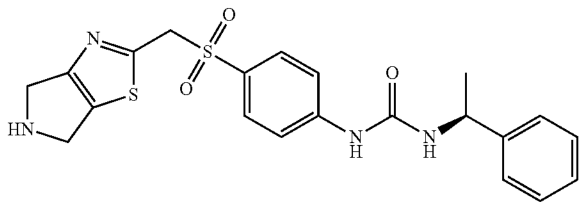 [SMILES: C[C@H](NC(=O)Nc1ccc(S(=O)(=O)Cc2nc3c(s2)CNC3)cc1)c1ccccc1] | $IC_{50}$ = 5.2895 $EC_{50}/E_{Max}$ = >30 $EC_{50}$ = 0.6776 | Not performed | Not performed | Not performed |
| H1466 | 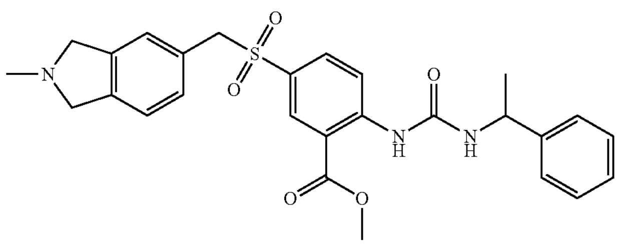 [SMILES: COC(=O)c1cc(S(=O)(=O)Cc2ccc3c(c2)CN(C)C3)ccc1NC(=O)NC(C)c1ccccc1] | $IC_{50}$ = 0.07241 $EC_{50}/E_{Max}$ = >30 $EC_{50}$ = 0.0168 | Not performed | Not performed | Not performed |
| H1467 | 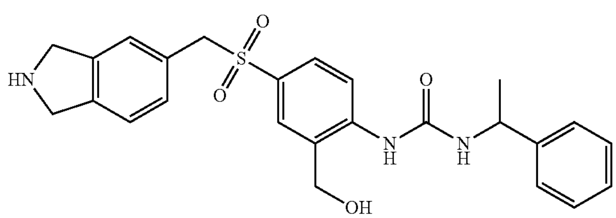 [SMILES: CC(NC(=O)Nc1ccc(S(=O)(=O)Cc2ccc3c(c2)CNC3)cc1CO)c1ccccc1] | $IC_{50}$ = 0.12124 $EC_{50}/E_{Max}$ = >30 $EC_{50}$ = 0.0197 | Not performed | Not performed | Not performed |
| H1468 | 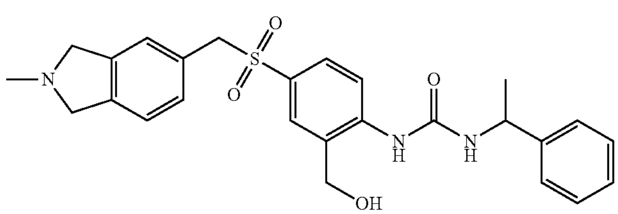 [SMILES: CC(NC(=O)Nc1ccc(S(=O)(=O)Cc2ccc3c(c2)CN(C)C3)cc1CO)c1ccccc1] | $IC_{50}$ = 0.0806 $EC_{50}/E_{Max}$ = >30 $EC_{50}$ = 0.01817 | Not performed | Not performed | Not performed |
| H1469 | 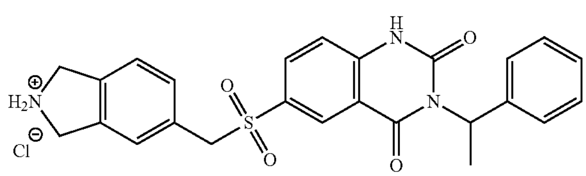 [SMILES: [Cl-] ; CC(c1ccccc1)n1c(=O)[nH]c2ccc(S(=O)(=O)Cc3ccc4c(c3)C[NH2+]C4)cc2c1=O] | $IC_{50}$ = 0.1104 $EC_{50}/E_{Max}$ = 01101 $EC_{50}$ = 0.026 | Not performed | Not performed | Not performed |
| H1470 | 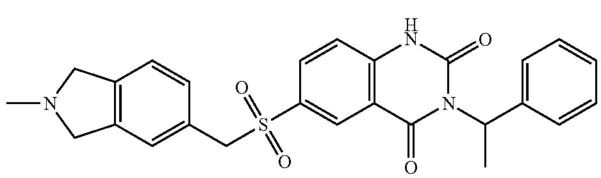 [SMILES: CC(c1ccccc1)n1c(=O)[nH]c2ccc(S(=O)(=O)Cc3ccc4c(c3)CN(C)C4)cc2c1=O] | $IC_{50}$ = 0.4833 $EC_{50}/E_{Max}$ = 02273 $EC_{50}$ = 0.02234 | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1471 | 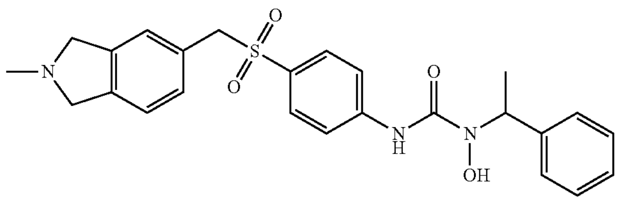 [SMILES: CC(c1ccccc1)N(O)C(=O)Nc1ccc(S(=O)(=O)Cc2ccc3c(c2)CN(C)C3)cc1] | $IC_{50}$ = 0.0118 $EC_{50}/E_{Max}$ = >30 $EC_{50}$ = 0.003887 | Not performed | Not performed | Not performed |
| H1472 | 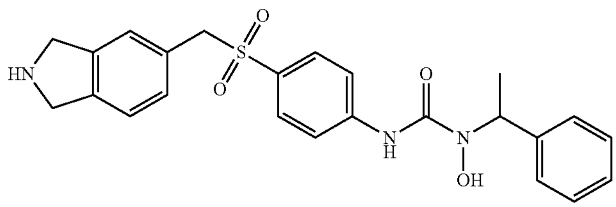 [SMILES: CC(c1ccccc1)N(O)C(=O)Nc1ccc(S(=O)(=O)Cc2ccc3c(c2)CNC3)cc1] | $IC_{50}$ = 0.006 $EC_{50}/E_{Max}$ = >30 $EC_{50}$ = 0.003252 | CL i.p. = 2.19 (R) Vd i.p. = 7.71 (R) T1/2 i.p. 2.43 (R) | Not performed | Not performed |
| H1473 | 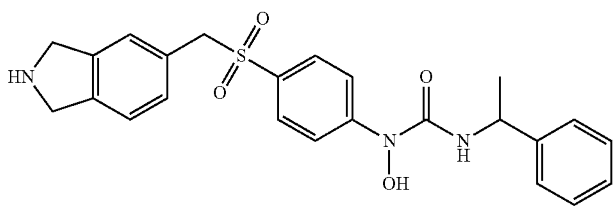 [SMILES: CC(NC(=O)N(O)c1ccc(S(=O)(=O)Cc2ccc3c(c2)CNC3)cc1)c1ccccc1] | $IC_{50}$ = 2.2385 $EC_{50}/E_{Max}$ = >30 $EC_{50}$ = 0.5146 | Not performed | Not performed | Not performed |
| H1474 | 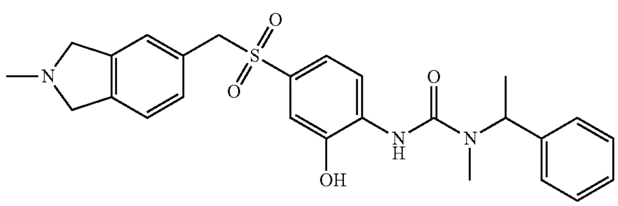 [SMILES: CC(c1ccccc1)N(C)C(=O)Nc1ccc(S(=O)(=O)Cc2ccc3c(c2)CN(C)C3)cc1O] | $IC_{50}$ = 0.7001 $EC_{50}/E_{Max}$ = >30 $EC_{50}$ = 0.1332 | Not performed | Not performed | Not performed |
| H1475 | 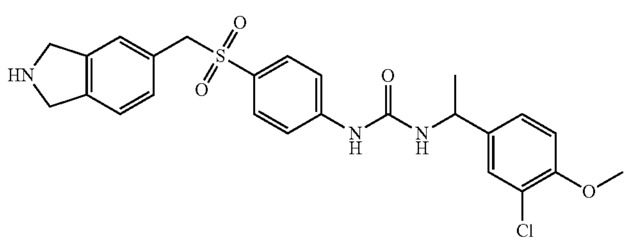 [SMILES: COc1ccc(C(C)NC(=O)Nc2ccc(S(=O)(=O)Cc3ccc4c(c3)CNC4)cc2)cc1Cl] | $IC_{50}$ = 0.03223 $EC_{50}/E_{Max}$ = >30 $EC_{50}$ = 0.0189 | Not performed | Not performed | Not performed |
| H1476 | 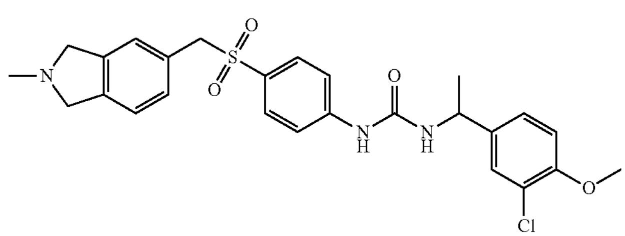 | $IC_{50}$ = 0.0426 $EC_{50}/E_{Max}$ = >30 $EC_{50}$ = 0.0241 | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) t$_{1/2}$ (h) F (%) | Food Intake Study |
|---|---|---|---|---|---|
| H1477 | 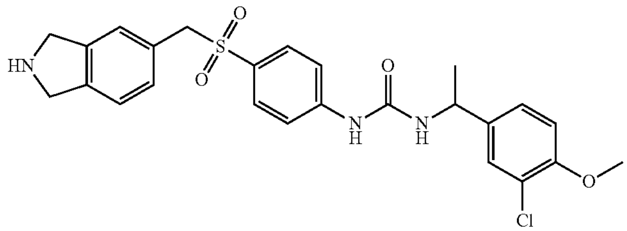 [SMILES: COc1ccc(C(C)NC(=O)Nc2ccc(S(=O)(=O)Cc3ccc4c(c3)CNC4)cc2)cc1Cl] | IC$_{50}$ = 0.03689 EC$_{50}$/ E$_{Max}$ = >30 EC$_{50}$ = 0.0174 | Not performed | Not performed | Not performed |
| H1478 | 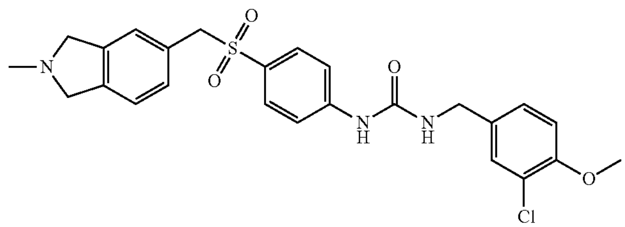 | IC$_{50}$ = 0.04028 EC$_{50}$/ E$_{Max}$ = >30 EC$_{50}$ = 0.0196 | Not performed | Not performed | Not performed |
| H1479 | 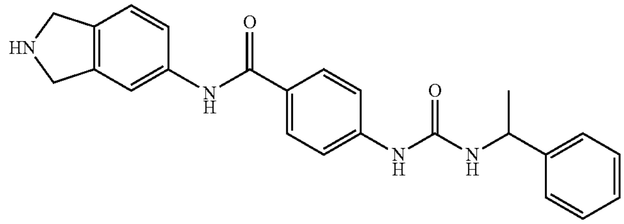 [SMILES: CC(NC(=O)Nc1ccc(C(=O)Nc2ccc3c(c2)CNC3)cc1)c1ccccc1] | IC$_{50}$ = 2.501 EC$_{50}$/ E$_{Max}$ = >30 EC$_{50}$ = 1.955 | Not performed | Not performed | Not performed |
| H1480 | 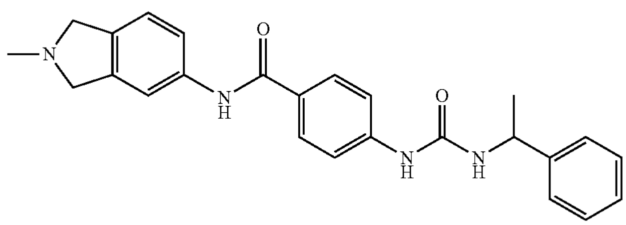 [SMILES: CC(NC(=O)Nc1ccc(C(=O)Nc2ccc3c(c2)CN(C)C3)cc1)c1ccccc1] | IC$_{50}$ = 24.15 EC$_{50}$/ E$_{Max}$ = >30 EC$_{50}$ = >10 | Not performed | Not performed | Not performed |
| H1481 | 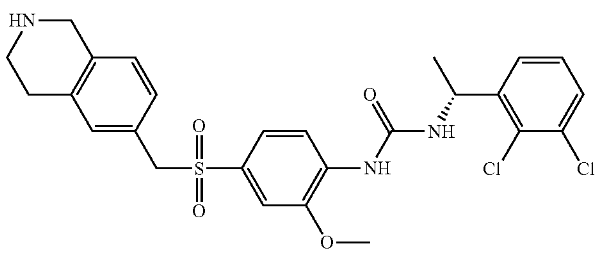 [SMILES: COc1cc(S(=O)(=O)Cc2ccc3c(c2)CCNC3)ccc1NC(=O)N[C@H](C)c1cccc(Cl)c1Cl] | IC$_{50}$ = <0.0003 (1.0765) EC$_{50}$/ E$_{Max}$ = >30 EC$_{50}$ = 0.0002 (0.0004) | H = <10 M = 13.2 | Not performed | Not performed |
| H1482 | 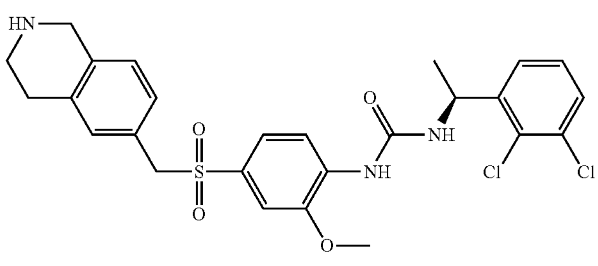 [SMILES: COc1cc(S(=O)(=O)Cc2ccc3c(c2)CCNC3)ccc1NC(=O)N[C@@H](C)c1cccc(Cl)c1Cl] | IC$_{50}$ = 0.00028195 EC$_{50}$/ E$_{Max}$ = >30 EC$_{50}$ = 0.0004 | H = <10 M = 12.5 | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1483 | 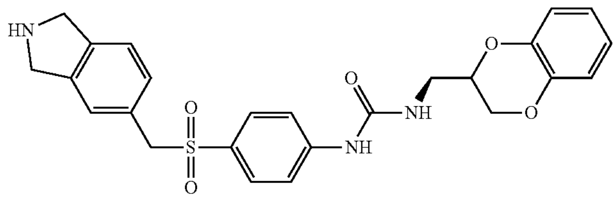 | $IC_{50}$ = 0.05382 $EC_{50}/E_{Max}$ = >30 $EC_{50}$ = 0.0241 | Not performed | Not performed | Not performed |
| H1484 | 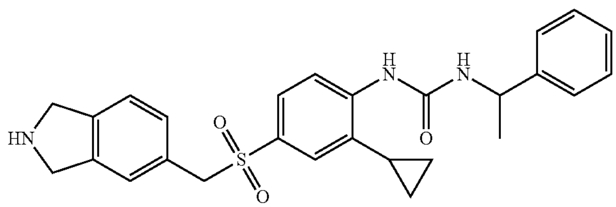 [SMILES: CC(NC(=O)Nc1ccc(S(=O)(=O)Cc2ccc3c(c2)CNC3)cc1C1CC1)c1ccccc1] | $IC_{50}$ = 0.02165 $EC_{50}/E_{Max}$ = >30 $EC_{50}$ = 0.0071 | H = 116.7 M = 149.3 | Not performed | Not performed |
| H1485 | 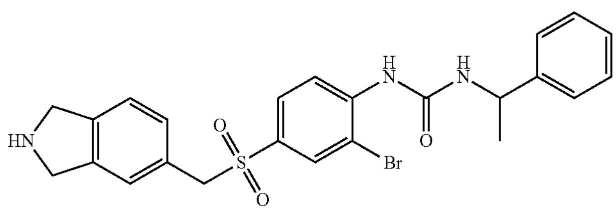 [SMILES: CC(NC(=O)Nc1ccc(S(=O)(=O)Cc2ccc3c(c2)CNC3)cc1Br)c1ccccc1] | $IC_{50}$ = 0.01906 $EC_{50}/E_{Max}$ = >30 $EC_{50}$ = 0.0102 | Not performed | Not performed | Not performed |
| H1486 | 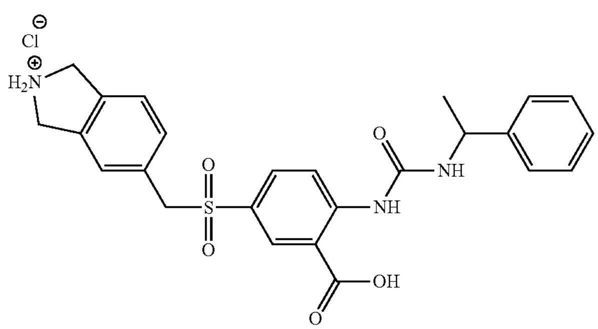 [SMILES: Cl ; CC(NC(=O)Nc1ccc(S(=O)(=O)Cc2ccc3c(c2)CNC3)cc1C(=O)O)c1ccccc1] | $IC_{50}$ = 0.009212 $EC_{50}/E_{Max}$ = >30 $EC_{50}$ = 0.0049 PPB = 94.81 (H) PPB = 97.35 (R) | H = <10 M = <10 | Not performed | Not performed |
| H1487 | 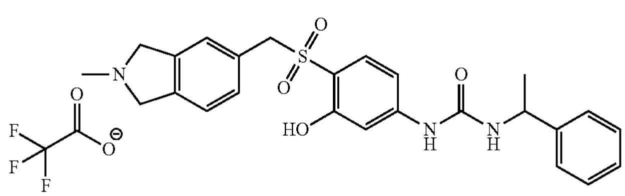 [SMILES: O=C([O-])C(F)(F)F ; CC(NC(=O)Nc1ccc(S(=O)(=O)Cc2ccc3c(c2)CN(C)C3)c(O)c1)c1ccccc1] | $IC_{50}$ = 0.018745 $EC_{50}/E_{Max}$ = >30 $EC_{50}$ = 0.0057 | H = 26.1 M = 16.9 | Not performed | Not performed |
| H1488 | 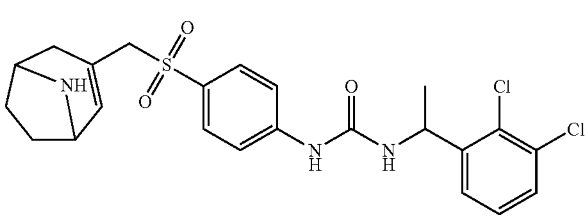 [SMILES: CC(NC(=O)Nc1ccc(S(=O)(=O)CC2=CC3CCC(C2)N3)cc1)c1cccc(Cl)c1Cl] | $IC_{50}$ = 2.0525 $EC_{50}/E_{Max}$ = >30 $EC_{50}$ = 0.6682 | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) t$_{1/2}$ (h) F (%) | Food Intake Study |
|---|---|---|---|---|---|
| H1489 | 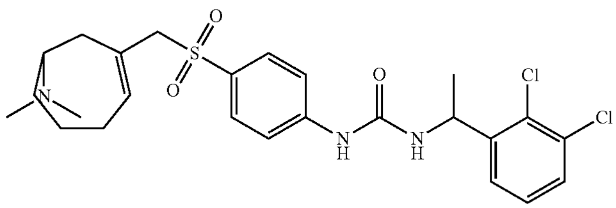 | IC$_{50}$ = 7.4695 EC$_{50}$/E$_{Max}$ = >30 EC$_{50}$ = 1.4110 | Not performed | Not performed | Not performed |
| H1490 | 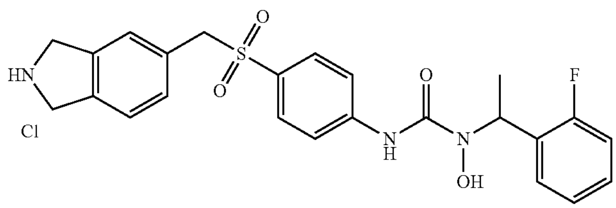 [SMILES: Cl ; CC(c1ccccc1F)N(O)C(=O)Nc1ccc(S(=O)(=O)Cc2ccc3c(c2)CNC3)cc1] | IC$_{50}$ = 0.005427 EC$_{50}$/E$_{Max}$ = >30 EC$_{50}$ = 0.0036 | H = 12.8 | Not performed | Not performed |
| H1491 | 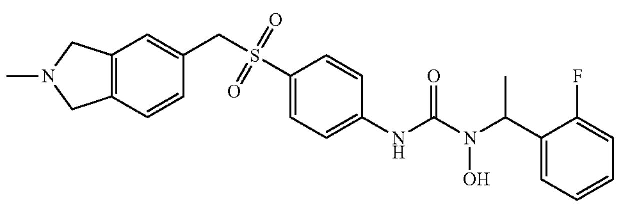 [SMILES: CC(c1ccccc1F)N(O)C(=O)Nc1ccc(S(=O)(=O)Cc2ccc3c(c2)CN(C)C3)cc1] | IC$_{50}$ = 0.029695 EC$_{50}$/E$_{Max}$ = >30 EC$_{50}$ = 0.0046 | H = 79.5 | Not performed | Not performed |
| H1492 | 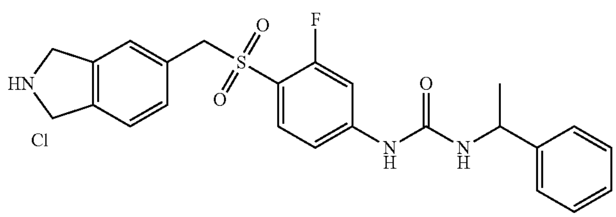 [SMILES: CC(NC(=O)Nc1ccc(S(=O)(=O)Cc2ccc3c(c2)CNC3)c(F)c1)c1ccccc1 ; Cl] | IC$_{50}$ = 0.03627 EC$_{50}$/E$_{Max}$ = >30 EC$_{50}$ = 0.0051 | H = 24.4 | Not performed | Not performed |
| H1493 | 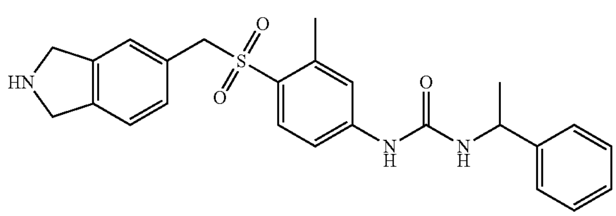 [SMILES: Cc1cc(NC(=O)NC(C)c2ccccc2)ccc1S(=O)(=O)Cc1ccc2c(c1)CNC2] | IC$_{50}$ = 0.01528 EC$_{50}$/E$_{Max}$ = >30 EC$_{50}$ = 0.0042 | H = 21.5 | Not performed | Not performed |
| H1494 | 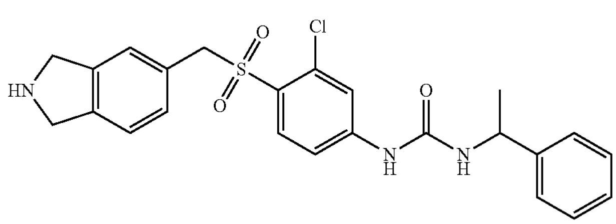 [SMILES: CC(NC(=O)Nc1ccc(S(=O)(=O)Cc2ccc3c(c2)CNC3)c(Cl)c1)c1ccccc1] | IC$_{50}$ = 0.01061 EC$_{50}$/E$_{Max}$ = >30 EC$_{50}$ = 0.0040 | H = 19.1 | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) t$_{1/2}$ (h) F (%) | Food Intake Study |
|---|---|---|---|---|---|
| H1495 | 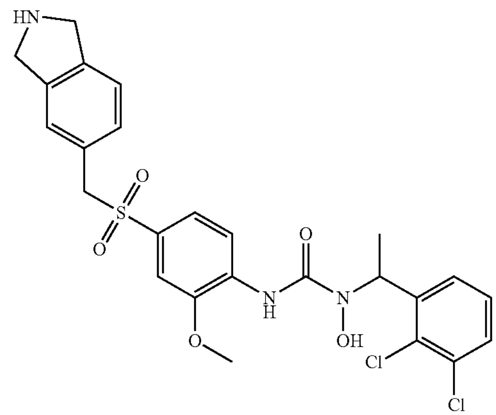 [SMILES: COc1cc(S(=O)(=O)Cc2ccc3c(c2)CNC3)ccc1NC(=O)N(O)C(C)c1cccc(Cl)c1Cl] | IC$_{50}$ = 0.002159<br>EC$_{50}$/E$_{Max}$ = >30<br>EC$_{50}$ = 0.0012 | H = 21.1 | Not performed | Not performed |
| H1496 | 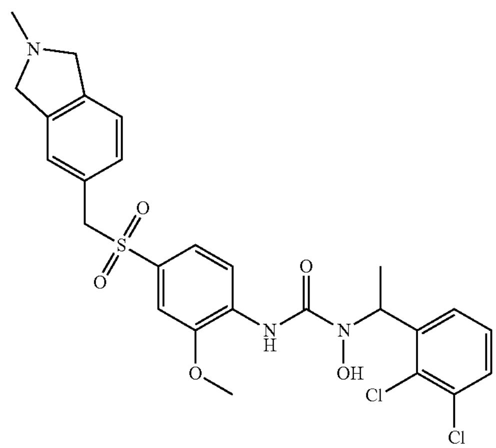 [SMILES: COc1cc(S(=O)(=O)Cc2ccc3c(c2)CN(C)C3)ccc1NC(=O)N(O)C(C)c1cccc(Cl)c1Cl] | IC$_{50}$ = 0.005906<br>EC$_{50}$/E$_{Max}$ = >30<br>EC$_{50}$ = 0.0025 | H = 178.3 | Not performed | Not performed |
| H1497 | 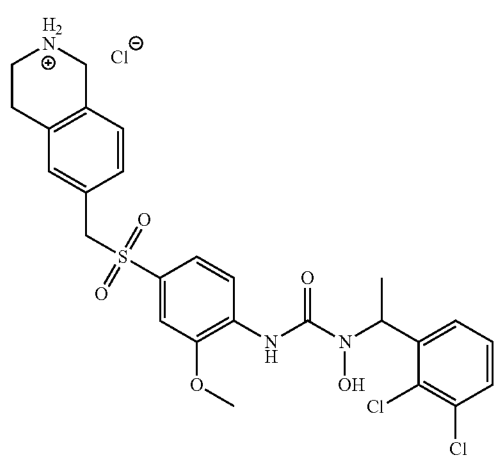 | IC$_{50}$ = 0.002814<br>EC$_{50}$/E$_{Max}$ = >30<br>EC$_{50}$ = 0.0033<br>PPB = 99.84 (H)<br>PPB = 99.8 (R) | H = <10 | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) t$_{1/2}$ (h) F (%) | Food Intake Study |
|---|---|---|---|---|---|
| H1498 | 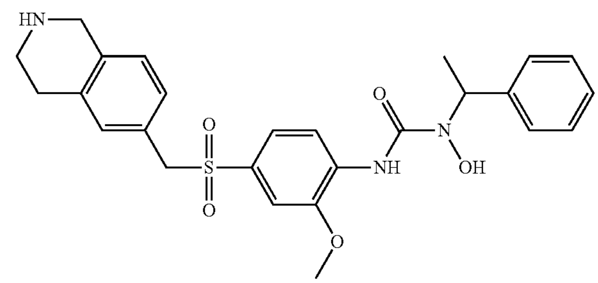 [SMILES: COc1cc(S(=O)(=O)Cc2ccc3c(c2)CCNC3)ccc1NC(=O)N(O)C(C)c1ccccc1] | IC$_{50}$ = 0.02476 EC$_{50}$/E$_{Max}$ = >30 EC$_{50}$ = 0.0072 PPB = 98.77 (H) PPB = 97.06 (R) | H = 9.9 | Not performed | Not performed |
| H1499 | 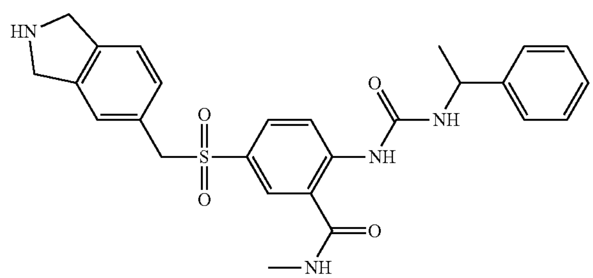 [SMILES: CNC(=O)c1cc(S(=O)(=O)Cc2ccc3c(c2)CNC3)ccc1NC(=O)NC(C)c1ccccc1] | IC$_{50}$ = 0.03798 EC$_{50}$/E$_{Max}$ = >30 EC$_{50}$ = 0.0071 | H = 27.1 | Not performed | Not performed |
| H1500 | 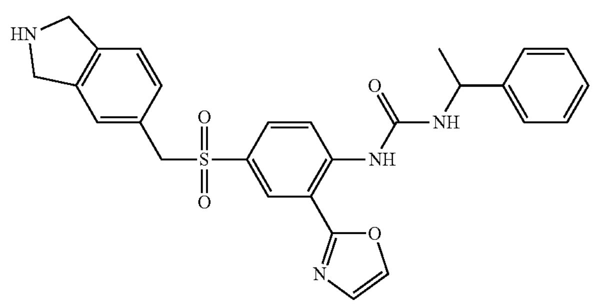 [SMILES: CC(NC(=O)Nc1ccc(S(=O)(=O)Cc2ccc3c(c2)CNC3)cc1-c1ncco1)c1ccccc1] | IC$_{50}$ = 0.01637 EC$_{50}$/E$_{Max}$ = >30 EC$_{50}$ = 0.0062 | H = 61.4 | Not performed | Not performed |
| H1501 | 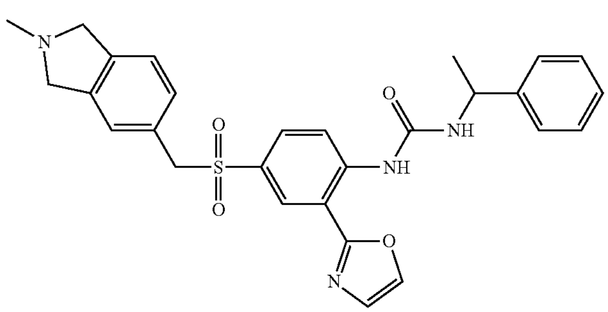 [SMILES: CC(NC(=O)Nc1ccc(S(=O)(=O)Cc2ccc3c(c2)CN(C)C3)cc1-c1ncco1)c1ccccc1] | IC$_{50}$ = 0.1188 EC$_{50}$/E$_{Max}$ = >30 EC$_{50}$ = 0.0181 | H = 319.6 | Not performed | Not performed |
| H1502 | 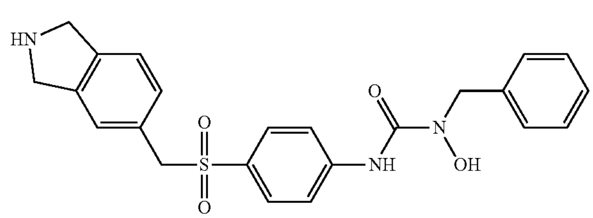 [SMILES: O=C(Nc1ccc(S(=O)(=O)Cc2ccc3c(c2)CNC3)cc1)N(O)Cc1ccccc1] | IC$_{50}$ = 0.1642 EC$_{50}$/E$_{Max}$ = >30 EC$_{50}$ = 0.03508 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1503 | 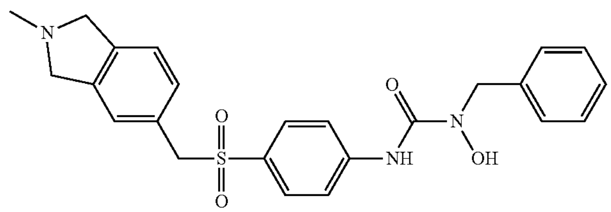 [SMILES: CN1Cc2ccc(CS(=O)(=O)c3ccc(NC(=O)N(O)Cc4ccccc4)cc3)cc2C1] | $IC_{50}$ = 0.5117 $EC_{50}/E_{Max}$ = >30 $EC_{50}$ = 0.101 | Not performed | Not performed | Not performed |
| H1504 | 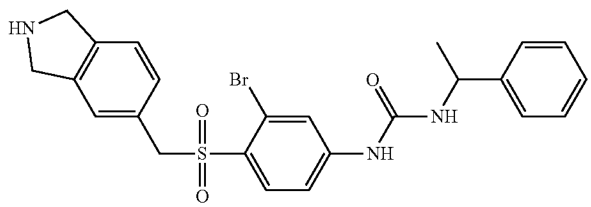 [SMILES: CC(NC(=O)Nc1ccc(S(=O)(=O)Cc2ccc3c(c2)CNC3)c(Br)c1)c1ccccc1] | $IC_{50}$ = 0.006473 $EC_{50}/E_{Max}$ = >30 $EC_{50}$ = 0.005554 | H = 19.3 | Not performed | Not performed |
| H1505 | 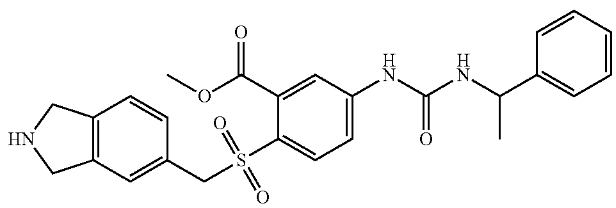 [SMILES: COC(=O)c1cc(NC(=O)NC(C)c2ccccc2)ccc1S(=O)(=O)Cc1ccc2c(c1)CNC2] | $IC_{50}$ = 0.008279 $EC_{50}/E_{Max}$ = >30 $EC_{50}$ = 0.0117 | H = 37.3 M = 135.5 | Not performed | Not performed |
| H1506 | 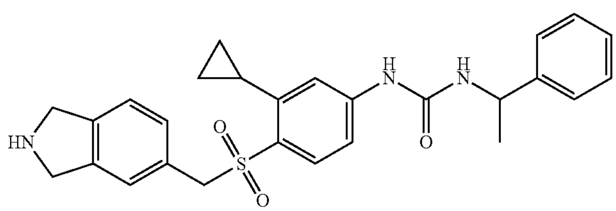 [SMILES: CC(NC(=O)Nc1ccc(S(=O)(=O)Cc2ccc3c(c2)CNC3)c(C2CC2)c1)c1ccccc1] | $IC_{50}$ = 0.002277 $EC_{50}/E_{Max}$ = >30 $EC_{50}$ = 0.0042 | H = 49.2 M = 132.5 | Not performed | Not performed |
| H1507 | 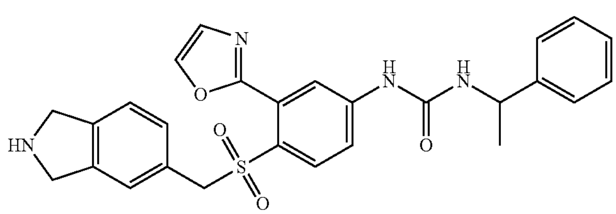 [SMILES: CC(NC(=O)Nc1ccc(S(=O)(=O)Cc2ccc3c(c2)CNC3)c(-c2ncco2)c1)c1ccccc1] | $IC_{50}$ = 0.01285 $EC_{50}/E_{Max}$ = >30 $EC_{50}$ = 0.0197 | Not performed | Not performed | Not performed |
| H1508 | 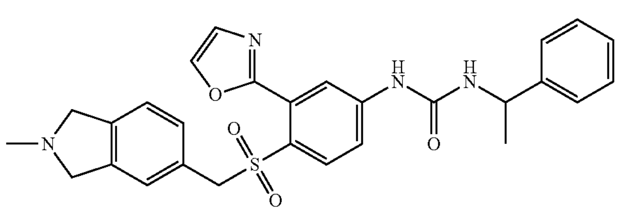 [SMILES: CC(NC(=O)Nc1ccc(S(=O)(=O)Cc2ccc3c(c2)CN(C)C3)c(-c2ncco2)c1)c1ccccc1] | $IC_{50}$ = 0.06176 $EC_{50}/E_{Max}$ = >30 $EC_{50}$ = 0.03 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1509 | 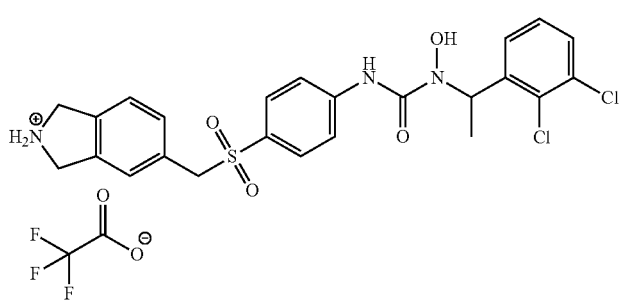 [SMILES: CC(c1cccc(Cl)c1Cl)N(O)C(=O)Nc1ccc(S(=O)(=O)Cc2ccc3c(c2)C[NH2+]C3)cc1 ; O=C([O-])C(F)(F)F] | $IC_{50}$ = 0.000336 (0.4564) $EC_{50}$/ $E_{Max}$ = >30 $EC_{50}$ = 0.001 (0.0008) | H = 15.9 M = 16.0 | Not performed | Not performed |
| H1510 | 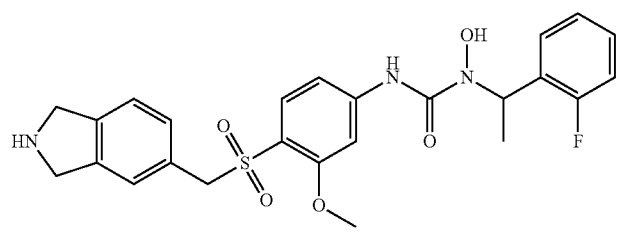 [SMILES: COc1cc(NC(=O)N(O)C(C)c2ccccc2F)ccc1S(=O)(=O)Cc1ccc2c(c1)CNC2] | $IC_{50}$ = 0.005363 $EC_{50}$/ $E_{Max}$ = >30 $EC_{50}$ = 0.0035 | H = 23.8 M = 18.4 | Not performed | Not performed |
| H1511 | 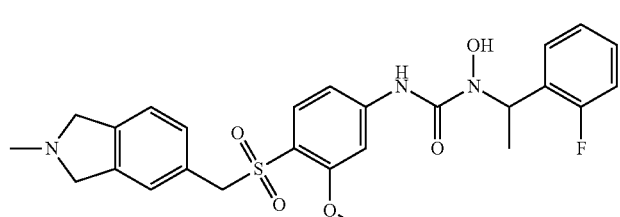 | $IC_{50}$ = 0.006043 $EC_{50}$/ $E_{Max}$ = >30 $EC_{50}$ = 0.0052 | H = 94.2 M = 44.5 | Not performed | Not performed |
| H1512 | 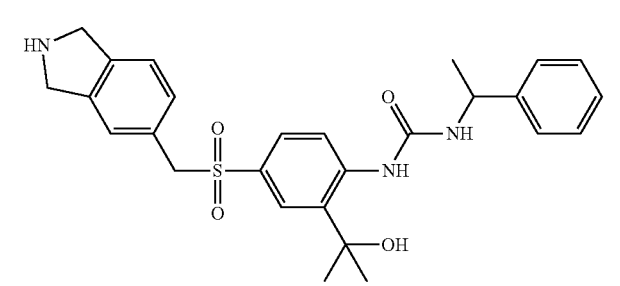 [SMILES: CC(NC(=O)Nc1ccc(S(=O)(=O)Cc2ccc3c(c2)CNC3)cc1C(C)(C)O)c1ccccc1] | $IC_{50}$ = 0.5824 $EC_{50}$/ $E_{Max}$ = >30 $EC_{50}$ = 0.2727 | Not performed | Not performed | Not performed |
| H1513 | 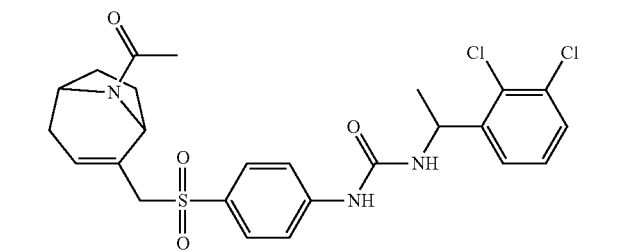 [SMILES: CC(=O)N1C2CC=C(CS(=O)(=O)c3ccc(NC(=O)NC(C)c4cccc(Cl)c4Cl)cc3)C1CC2] | $IC_{50}$ = 14.579 $EC_{50}$/ $E_{Max}$ = >30 $EC_{50}$ = 0.7073 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1514 | 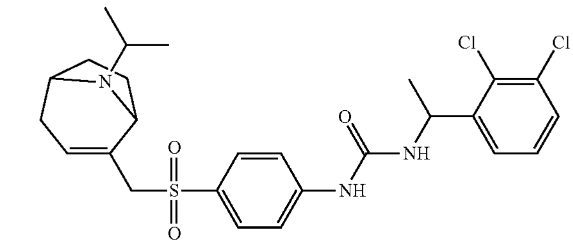 [SMILES: CC(NC(=O)Nc1ccc(S(=O)(=O)CC2=CCC3CCC2N3C(C)C)cc1)c1cccc(Cl)c1Cl] | $IC_{50}$ = 16.175 $EC_{50}/E_{Max}$ = >30 $EC_{50}$ = 0.0176 | Not performed | Not performed | Not performed |
| H1515 | 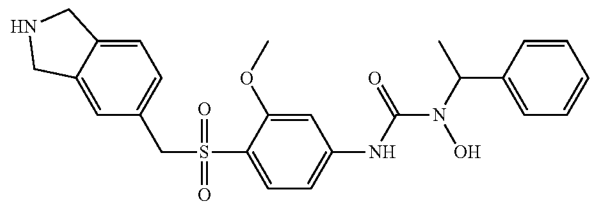 [SMILES: COc1cc(NC(=O)N(O)C(C)c2ccccc2)ccc1S(=O)(=O)Cc1ccc2c(c1)CNC2] | $IC_{50}$ = 0.01571 $EC_{50}/E_{Max}$ = >30 $EC_{50}$ = 0.0096 | H = 15.2 M = 18.4 | Not performed | Not performed |
| H1516 | 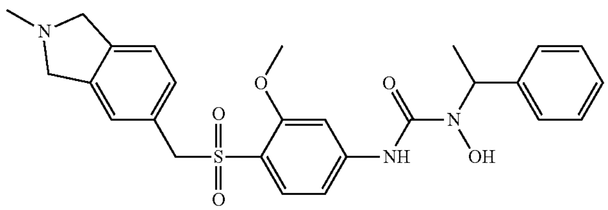 [SMILES: COc1cc(NC(=O)N(O)C(C)c2ccccc2)ccc1S(=O)(=O)Cc1ccc2c(c1)CN(C)C2] | $IC_{50}$ = 0.03352 $EC_{50}/E_{Max}$ = >30 $EC_{50}$ = 0.0113 | H = 65.2 M = 35.1 | Not performed | Not performed |
| H1517 | 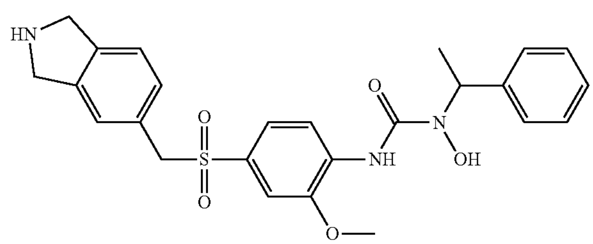 [SMILES: COc1cc(S(=O)(=O)Cc2ccc3c(c2)CNC3)ccc1NC(=O)N(O)C(C)c1ccccc1] | $IC_{50}$ = 0.01052 $EC_{50}/E_{Max}$ = >30 $EC_{50}$ = 0.0067 | H = 25.6 M = 56.6 | Not performed | Not performed |
| H1518 | 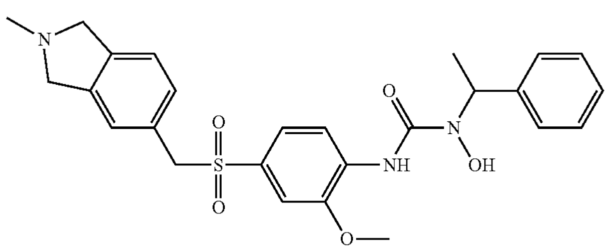 [SMILES: COc1cc(S(=O)(=O)Cc2ccc3c(c2)CN(C)C3)ccc1NC(=O)N(O)C(C)c1ccccc1] | $IC_{50}$ = 0.02739 $EC_{50}/E_{Max}$ = >30 $EC_{50}$ = 0.0078 | H = 151.1 M = 154.7 | Not performed | Not performed |
| H1519 | 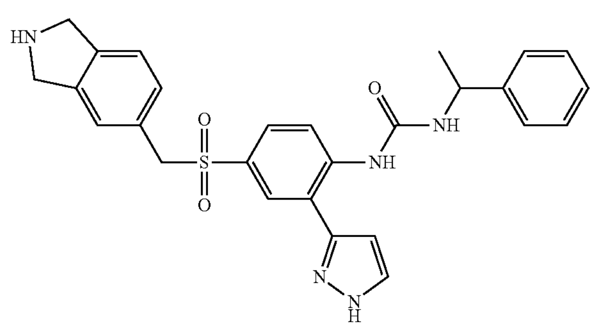 [SMILES: CC(NC(=O)Nc1ccc(S(=O)(=O)Cc2ccc3c(c2)CNC3)cc1-c1cc[nH]n1)c1ccccc1] | $IC_{50}$ = 0.01214 $EC_{50}/E_{Max}$ = >30 $EC_{50}$ = 0.0046 | H = 47.3 M = 169.8 | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1520 | 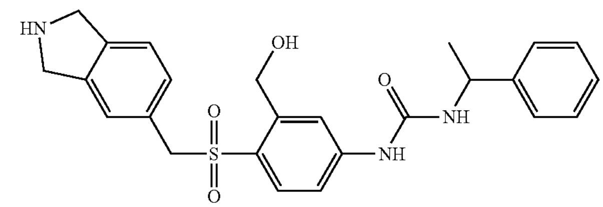 [SMILES: CC(NC(=O)Nc1ccc(S(=O)(=O)Cc2ccc3c(c2)CNC3)c(CO)c1)c1ccccc1] | $IC_{50}$ = 0.02617 $EC_{50}/E_{Max}$ = >30 $EC_{50}$ = 0.0127 | Not performed | Not performed | Not performed |
| H1521 | 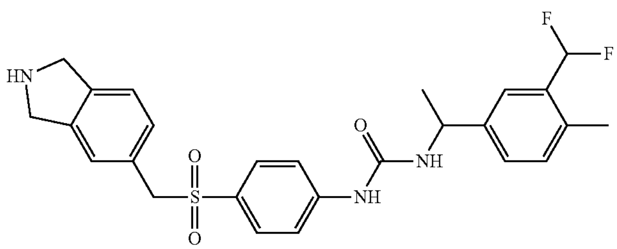 [SMILES: Cc1ccc(C(C)NC(=O)Nc2ccc(S(=O)(=O)Cc3ccc4c(c3)CNC4)cc2)cc1C(F)F] | $IC_{50}$ = 0.0523 $EC_{50}/E_{Max}$ = >30 $EC_{50}$ = 0.0178 | Not performed | Not performed | Not performed |
| H1522 | 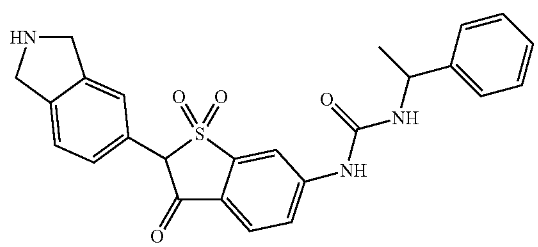 [SMILES: CC(NC(=O)Nc1ccc2c(c1)S(=O)(=O)C(c1ccc3c(c1)CNC3)C2=O)c1ccccc1] | $IC_{50}$ = 3.849 $EC_{50}/E_{Max}$ = >30 $EC_{50}$ = 1.889 | Not performed | Not performed | Not performed |
| H1523 | 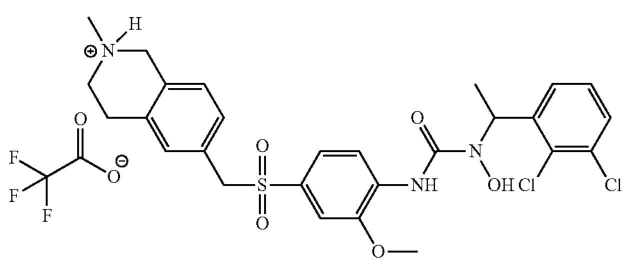 [SMILES: O=C([O-])C(F)(F)F ; COc1cc(S(=O)(=O)Cc2ccc3c(c2)CC[NH+](C)C3)ccc1NC(=O)N(O)C(C)c1cccc(Cl)c1Cl] | $IC_{50}$ = 0.004917 $EC_{50}/E_{Max}$ = >30 $EC_{50}$ = 0.0021 | H = 100.9 M = 155.5 | Not performed | Not performed |
| H1524 | 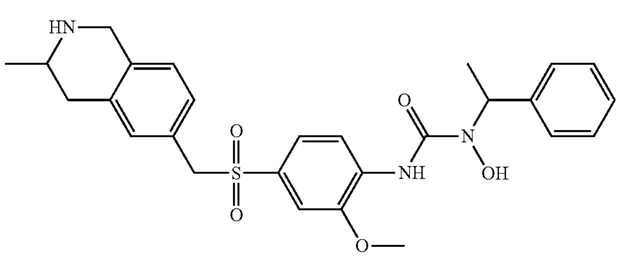 [SMILES: COc1cc(S(=O)(=O)Cc2ccc3c(c2)CC(C)NC3)ccc1NC(=O)N(O)C(C)c1ccccc1] | $IC_{50}$ = 0.009768 $EC_{50}/E_{Max}$ = >30 $EC_{50}$ = 0.0126 | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1525 | 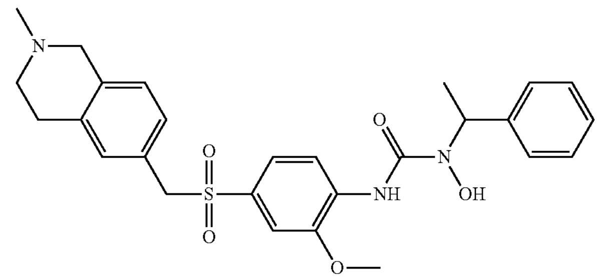 [SMILES: COc1cc(S(=O)(=O)Cc2ccc3c(c2)CCN(C)C3)ccc1NC(=O)N(O)C(C)c1ccccc1] | $IC_{50}$ = 0.03744 $EC_{50}/E_{Max}$ = >30 $EC_{50}$ = 0.02554 | Not performed | Not performed | Not performed |
| H1526 | 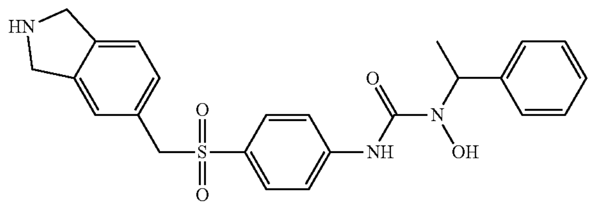 [SMILES: CC(c1ccccc1)N(O)C(=O)Nc1ccc(S(=O)(=O)Cc2ccc3c(c2)CNC3)cc1] | $IC_{50}$ = 0.03186 $EC_{50}/E_{Max}$ = >30 $EC_{50}$ = 0.02191 | Not performed | Not performed | Not performed |
| H1527 | 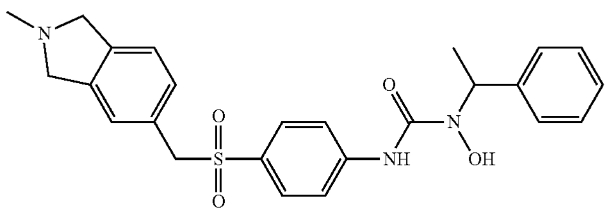 [SMILES: CC(c1ccccc1)N(O)C(=O)Nc1ccc(S(=O)(=O)Cc2ccc3c(c2)CN(C)C3)cc1] | $IC_{50}$ = 0.1298 $EC_{50}/E_{Max}$ = >30 $EC_{50}$ = 0.03403 | Not performed | Not performed | Not performed |
| H1528 | 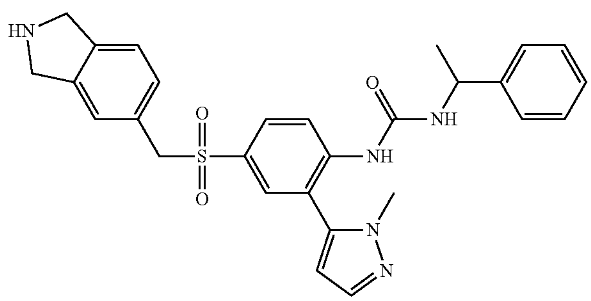 [SMILES: CC(NC(=O)Nc1ccc(S(=O)(=O)Cc2ccc3c(c2)CNC3)cc1-c1ccnn1C)c1ccccc1] | $IC_{50}$ = 0.5814 $EC_{50}/E_{Max}$ = >30 $EC_{50}$ = 0.08328 | Not performed | Not performed | Not performed |
| H1529 | 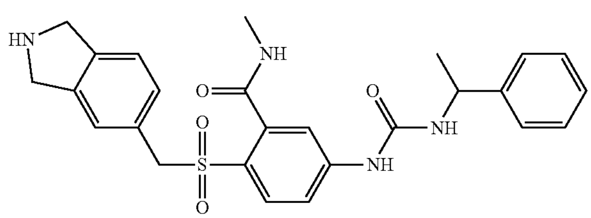 [SMILES: CNC(=O)c1cc(NC(=O)NC(C)c2ccccc2)ccc1S(=O)(=O)Cc1ccc2c(c1)CNC2] | $IC_{50}$ = 0.04738 $EC_{50}/E_{Max}$ = >30 $EC_{50}$ = 0.02781 | Not performed | Not performed | Not performed |
| H1530 | 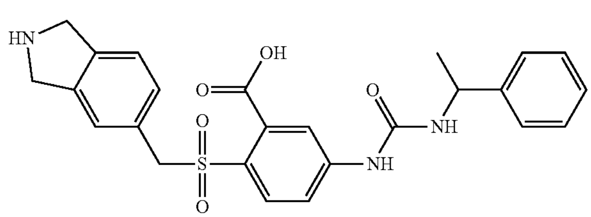 [SMILES: CC(NC(=O)Nc1ccc(S(=O)(=O)Cc2ccc3c(c2)CNC3)c(C(N)=O)c1)c1ccccc1] | $IC_{50}$ = 0.6142 $EC_{50}/E_{Max}$ = >30 $EC_{50}$ = 0.7839 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1531 | 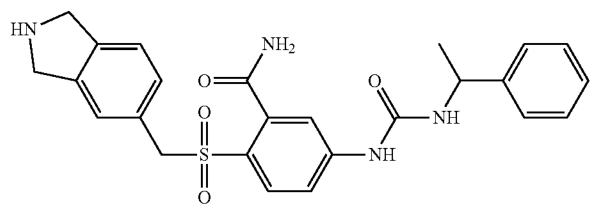 | $IC_{50}$ = 0.4179 $EC_{50}/E_{Max}$ = >30 $EC_{50}$ = 0.4444 | Not performed | Not performed | Not performed |
| H1532 | 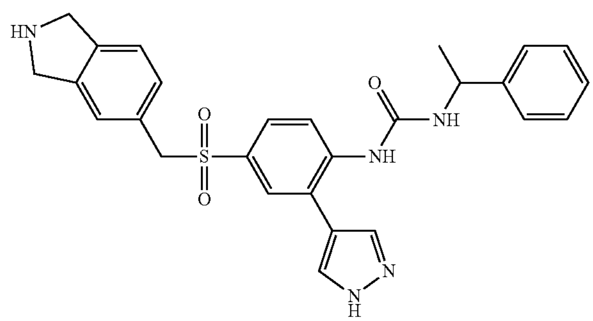 [SMILES: CC(NC(=O)Nc1ccc(S(=O)(=O)Cc2ccc3c(c2)CNC3)cc1-c1cn[nH]c1)c1ccccc1] | $IC_{50}$ = 1.6595 $EC_{50}/E_{Max}$ = >30 $EC_{50}$ = 0.0695 | Not performed | Not performed | Not performed |
| H1533 | 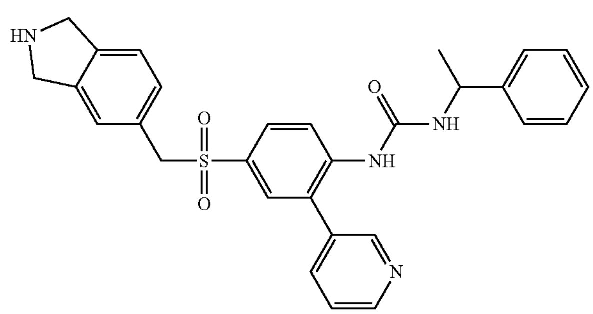 [SMILES: CC(NC(=O)Nc1ccc(S(=O)(=O)Cc2ccc3c(c2)CNC3)cc1-c1cccnc1)c1ccccc1] | $IC_{50}$ = 1.6955 $EC_{50}/E_{Max}$ = >30 $EC_{50}$ = 0.0762 | Not performed | Not performed | Not performed |
| H1534 | 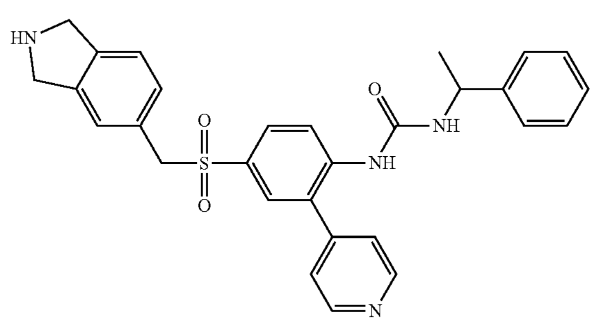 [SMILES: CC(NC(=O)Nc1ccc(S(=O)(=O)Cc2ccc3c(c2)CNC3)cc1-c1ccncc1)c1ccccc1] | $IC_{50}$ = 1.6635 $EC_{50}/E_{Max}$ = >30 $EC_{50}$ = 0.0895 | Not performed | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1535 | 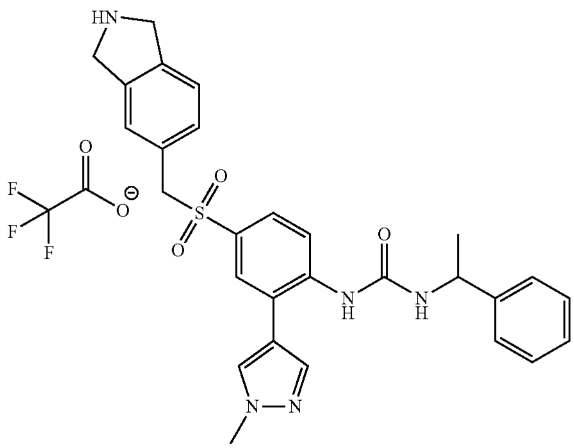 [SMILES: O=C([O-])C(F)(F)F ; CC(NC(=O)Nc1ccc(S(=O)(=O)Cc2ccc3c(c2)CNC3)cc1-c1cnn(C)c1)c1ccccc1] | $IC_{50}$ = 0.4926 $EC_{50}/E_{Max}$ = >30 $EC_{50}$ = 0.0214 | Not performed | Not performed | Not performed |
| H1537 | 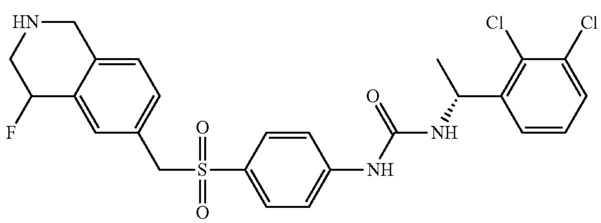 [SMILES: C[C@@H](NC(=O)Nc1ccc(S(=O)(=O)Cc2ccc3c(c2)C(F)CNC3)cc1)c1cccc(Cl)c1Cl] | $IC_{50}$ = 0.06895 $EC_{50}/E_{Max}$ = >30 $EC_{50}$ = 0.0184 | H = 43.2 M = 135.3 | Not performed | Not performed |
| H1538 | 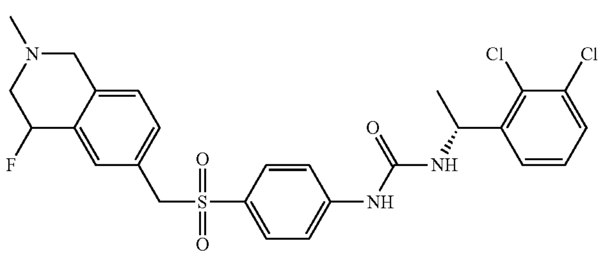 [SMILES: C[C@@H](NC(=O)Nc1ccc(S(=O)(=O)Cc2ccc3c(c2)C(F)CN(C)C3)cc1)c1cccc(Cl)c1Cl] | $IC_{50}$ = 0.1718 $EC_{50}/E_{Max}$ = >30 $EC_{50}$ = 0.0086 | H = 237.3 M = 354 | Not performed | Not performed |
| H1539 | 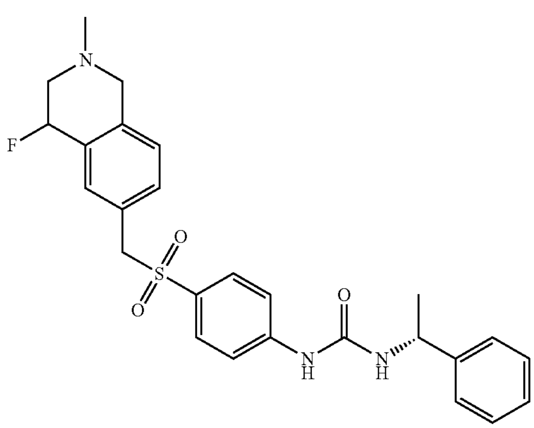 [SMILES: C[C@@H](NC(=O)Nc1ccc(S(=O)(=O)Cc2ccc3c(c2)C(F)CN(C)C3)cc1)c1ccccc1] | $IC_{50}$ = 8.0495 $EC_{50}/E_{Max}$ = >30 $EC_{50}$ = 0.2627 | Not performed | Not performed | Not performed |

TABLE 1-continued

| Compound No. | Chemical Structure | Activity (μM) | Metabolic Stability Study (H = human; M = mouse; R = rat; D = dog) [μL/min/mg] | PK[1] CL (L/h/kg) Vd (L/Kg) $t_{1/2}$ (h) F (%) | Food Intake Study |
|---|---|---|---|---|---|
| H1540 | 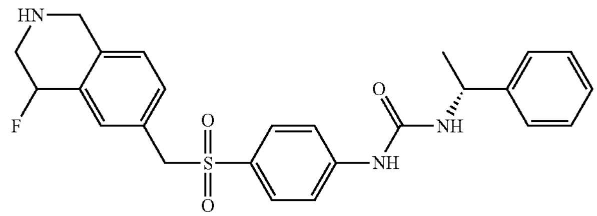 [SMILES: C[C@@H](NC(=O)Nc1ccc(S(=O)(=O)Cc2ccc3c(c2)C(F)CNC3)cc1)c1ccccc1] | $IC_{50}$ = 7.4405 $EC_{50}/E_{Max}$ = >30 $EC_{50}$ = 0.2063 | Not performed | Not performed | Not performed |
| H1541 | 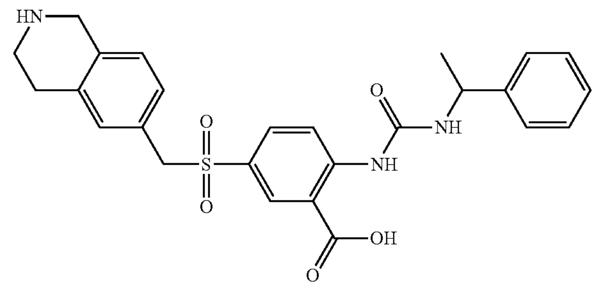 [SMILES: CC(NC(=O)Nc1ccc(S(=O)(=O)Cc2ccc3c(c2)CCNC3)cc1C(=O)O)c1ccccc1] | $IC_{50}$ = 0.07227 $EC_{50}/E_{Max}$ = >30 $EC_{50}$ = 0.0097 | H = <10 R = <10 | Not performed | Not performed |
| H1542 | 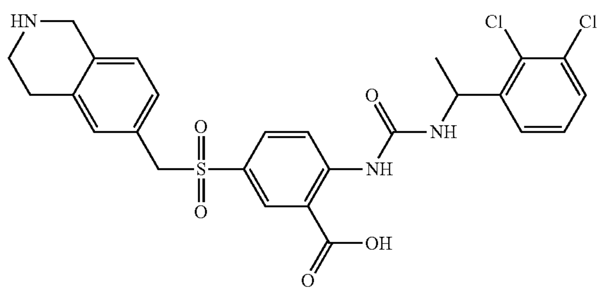 [SMILES: CC(NC(=O)Nc1ccc(S(=O)(=O)Cc2ccc3c(c2)CCNC3)cc1C(=O)O)c1cccc(Cl)c1Cl] | $IC_{50}$ = 0.001685 $EC_{50}/E_{Max}$ = >30 $EC_{50}$ = 0.0019 | H = <10 R = 13.3 | Not performed | Not performed |
| H1543 | 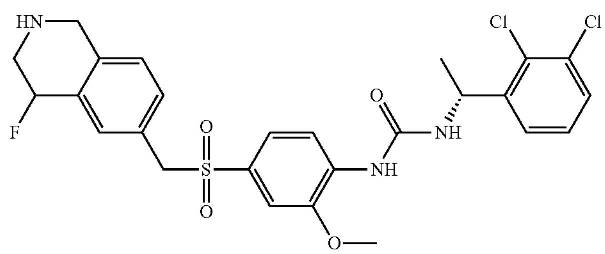 [SMILES: COc1cc(S(=O)(=O)Cc2ccc3c(c2)C(F)CNC3)ccc1NC(=O)N[C@H](C)c1cccc(Cl)c1Cl] | $IC_{50}$ = 0.01593 $EC_{50}/E_{Max}$ = >30 $EC_{50}$ = 0.0126 | H = 46.8 R = 204.6 | Not performed | Not performed |
| H1544 | 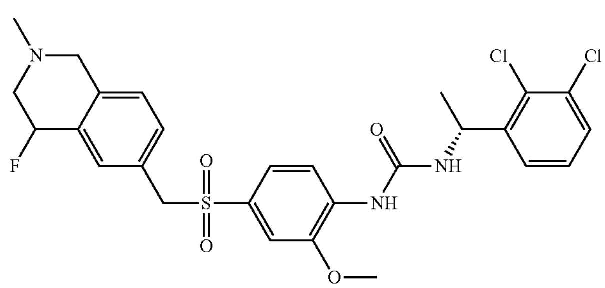 [SMILES: COc1cc(S(=O)(=O)Cc2ccc3c(c2)C(F)CN(C)C3)ccc1NC(=O)N[C@H](C)c1cccc(Cl)c1Cl] | $IC_{50}$ = 0.04043 $EC_{50}/E_{Max}$ = >30 $EC_{50}$ = 0.0097 | H = 323.3 R = 427.2 | Not performed | Not performed |

TABLE 1-continued

| Compound No. | Chemical Structure | Activity (µM) | Metabolic Stability Study (H = human; M = mouse; R = rat; D = dog) [µL/min/mg] | PK[1] CL (L/h/kg) Vd (L/Kg) $t_{1/2}$ (h) F (%) | Food Intake Study |
|---|---|---|---|---|---|
| H1545 | 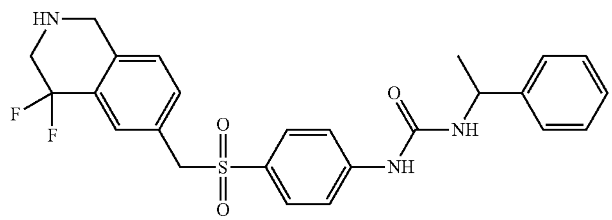 [SMILES: CC(NC(=O)Nc1ccc(S(=O)(=O)Cc2ccc3c(c2)C(F)(F)CNC3)cc1)c1ccccc1] | $IC_{50}$ = 1.721 $EC_{50}/E_{Max}$ = >30 $EC_{50}$ = 0.01912 | Not performed | Not performed | Not performed |
| H1546 | 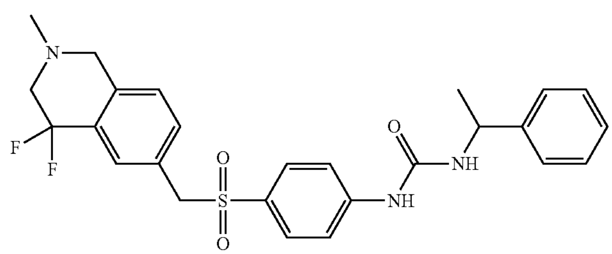 [SMILES: CC(NC(=O)Nc1ccc(S(=O)(=O)Cc2ccc3c(c2)C(F)(F)CN(C)C3)cc1)c1ccccc1] | $IC_{50}$ = 1.0765 $EC_{50}/E_{Max}$ = >30 $EC_{50}$ = 0.1265 | Not performed | Not performed | Not performed |
| H1547 | 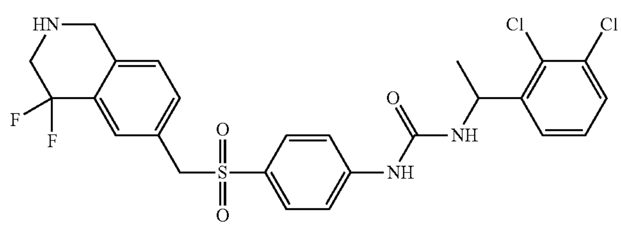 [SMILES: CC(NC(=O)Nc1ccc(S(=O)(=O)Cc2ccc3c(c2)C(F)(F)CNC3)cc1)c1cccc(Cl)c1Cl] | $IC_{50}$ = 0.4564 $EC_{50}/E_{Max}$ = >30 $EC_{50}$ = 0.035 | Not performed | Not performed | Not performed |
| H1548 | 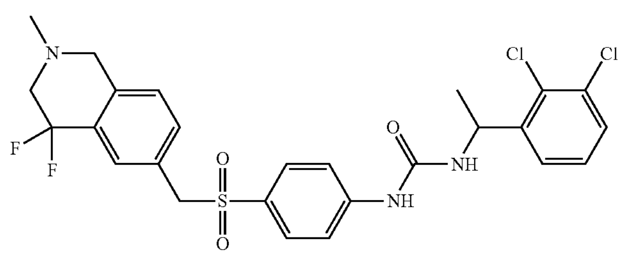 [SMILES: CC(NC(=O)Nc1ccc(S(=O)(=O)Cc2ccc3c(c2)C(F)(F)CN(C)C3)cc1)c1cccc(Cl)c1Cl] | $IC_{50}$ = 0.6553 $EC_{50}/E_{Max}$ = >30 $EC_{50}$ = 0.1324 | Not performed | Not performed | Not performed |
| H1549 | 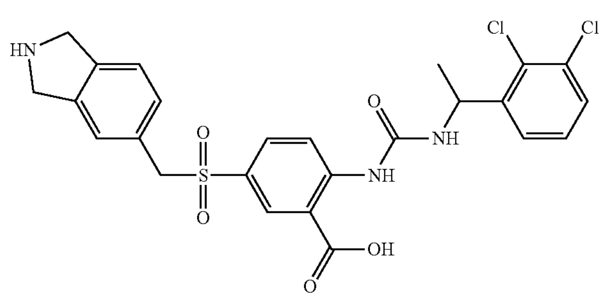 [SMILES: CC(NC(=O)Nc1ccc(S(=O)(=O)Cc2ccc3c(c2)CNC3)cc1C(=O)O)c1cccc(Cl)c1Cl] | $IC_{50}$ = 0.001685 $EC_{50}/E_{Max}$ = >30 $EC_{50}$ = 0.0012 | Not performed | Not performed | Not performed |

[1] Unless indicated otherwise, the PK values reported in this table are the PK's for mouse. If indicated, (R) = rat; (M) = mouse; and (D) = dog.

What is claimed is:

1. A compound of Formula IV:

*[Formula IV structure]* or a pharmaceutically acceptable salt thereof, wherein:
a dashed line indicates an optional bond;
X is a bond, CO, or $CR^7R^8$;
k is 0-2;
$R^1$ and $R^2$ are each independently, H, $C_{1-3}$ alkyl, methoxy, halo or OH;
or $R^1$ and $R^2$ taken together with the atoms to which they are attached form a 5-6 membered ring;
or $R^1$ and X taken together with the atoms to which they are attached form a 5-6 membered ring;
$R^3$ is H, $C_{1-3}$ alkyl, methoxy, halo, OH, $COOR^{12}$, $CR^{13}R^{14}OH$, $COHNR^{15}$, cycloalkyl, or heteroaryl;
$R^4$ is a bond, $NR^6$ or $CR^9R^{10}$;
or $R^3$ and $R^4$ taken together with the atoms to which they are attached form a 3-6-membered ring;
$R^6$ is a bond, H, or $CH_3$;
$R^7$ and $R^8$ are each, independently, H or $C_{1-3}$ alkyl, or $CONH_2$, wherein said $C_{1-3}$ alkyl is optionally substituted with halo;
$R^9$ and $R^{10}$ are each, independently, H or $C_{1-3}$ alkyl, wherein said $C_{1-3}$ alkyl is optionally substituted with halo;
$R^{12}$ is H or $C_{1-3}$ alkyl;
$R^{13}$ and $R^{14}$ are each independently H or $C_{1-3}$ alkyl;
$R^{15}$ is H or $C_{1-3}$ alkyl;
U is C, N, S, or 0;
Z is halo or methoxy;
R' is a halo, heteroaryl, $C_{1-6}$ alkoxy, $C_{1-6}$ alkyl, heterocycloalkyl, CN cycloalkyl, $CO_2(C_{1-6}$alkyl), or $CO(C_{1-6}$ alkyl);
or two R' taken together with the atoms to which they are attached form a 5-6-membered ring;
$R^{16}$ is H or $C_{1-3}$ alkyl;
$R^{17}$ is H, halo, or $C_{1-3}$ alkyl;
l is 0-3;
m is 0-3;
n is 0-3; and
p is 1-3.

2. The compound of claim 1, wherein X is CO.
3. The compound of claim 1, wherein X is a bond.
4. The compound of claim 1, wherein said X is $C_{1-3}$ alkyl.
5. The compound of claim 1, wherein X is $CH(CH_3)$.
6. The compound of claim 1, wherein X is $C(CH_3)_2$.
7. The compound of claim 1, wherein X is $CHCF_3$.
8. The compound of claim 1, wherein X is $CH(CH_2CH_3)$.
9. The compound of claim 1, wherein X is $C_{1-3}$ alkyl substituted with halo.

10. The compound of claim 1, wherein

*[phenyl-$(R')_n$ structure]* is selected from the group consisting of

*[list of substituent structures]*

-continued

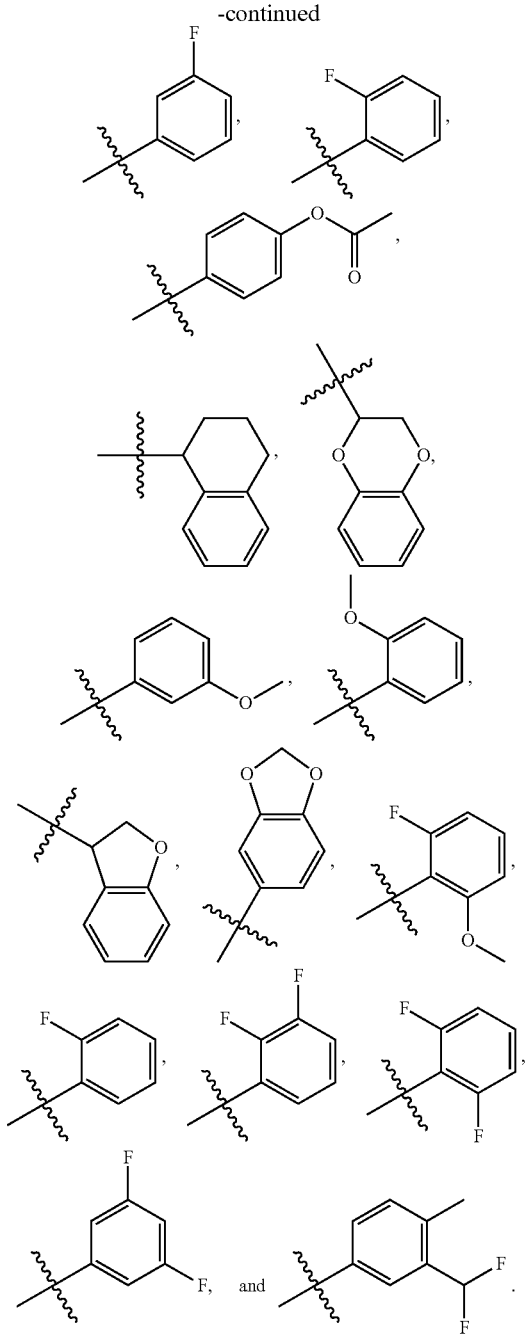

11. The compound of claim 1, wherein

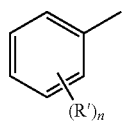

is phenyl.

12. The compound of claim 1, wherein $R^1$ is OH.
13. The compound of claim 1, wherein $R^1$ is $CH_3$.
14. The compound of claim 1, wherein $R^2$ is $CH_3$.
15. The compound of claim 1, wherein $R^3$ is F.
16. The compound of claim 1, wherein $R^3$ is Cl.
17. The compound of claim 1, wherein $R^3$ is methoxy.
18. The compound of claim 1, wherein $R^4$ is $CR^9R^{10}$.
19. The compound of claim 1, wherein $R^4$ is $CH_2$.
20. The compound of claim 1, wherein $R^4$ is $CHCH_3$.
21. The compound of claim 1, wherein $R^4$ is $C(CH_3)_2$.
22. The compound of claim 1, wherein $R^4$ is $NCH_3$.
23. The compound of claim 1, wherein $R^4$ and $R^3$ come together to form a 5-membered heterocyclic ring.
24. The compound of claim 1, wherein

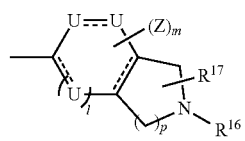

is selected from the group consisting of

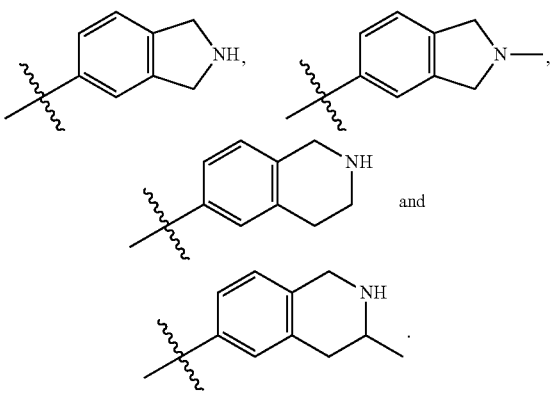

25. The compound of claim 1, wherein

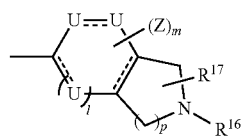

is

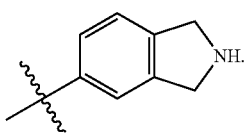 [SMILES: *c1ccc2c(c1)CNC2]

26. The compound of claim 1, wherein

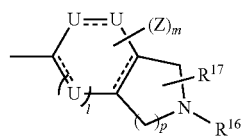

is

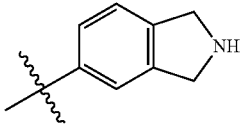 [SMILES: *c1ccc2c(c1)CNC2]

optionally substituted with 1-2 substituents from the group consisting of CH$_3$, CH$_2$CH$_3$, and F.

27. The compound of claim 1, wherein

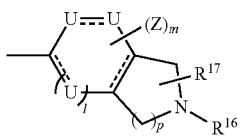

is tetrahydroisoquinoline.

28. The compound of claim 1, wherein

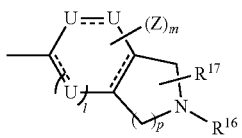

is tetrahydroisoquinoline substituted with 1-3 substituents from the group consisting of CH$_3$, CH$_2$CH$^3$, F, and methoxy.

29. The compound of claim 1, wherein

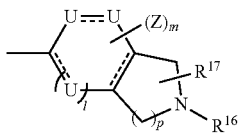

is selected from the group consisting of

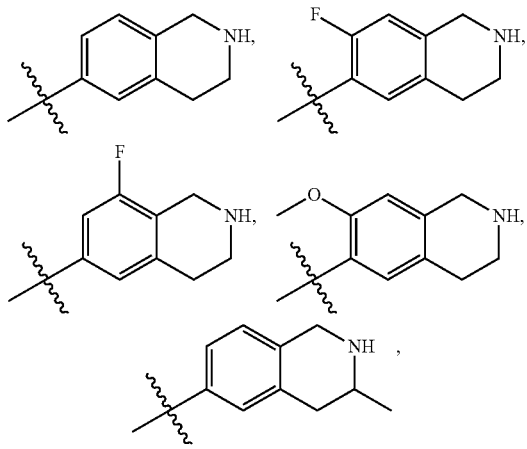

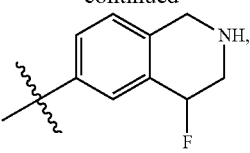

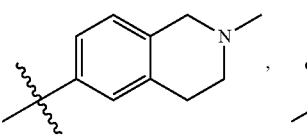

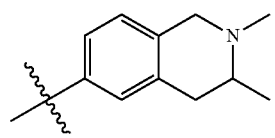

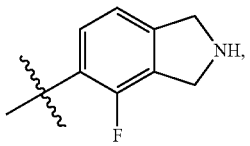

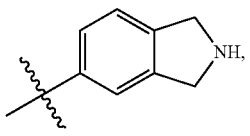

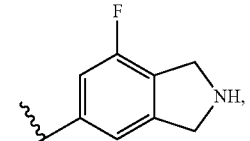

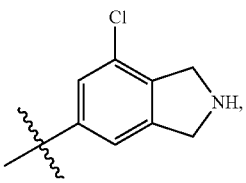 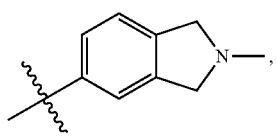

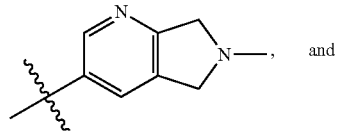 [SMILES: *c1cnc2c(c1)CN(C)C2]

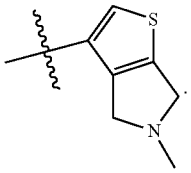 [SMILES: *c1csc2c1CN(C)C2]

30. The compound of claim 1, wherein p is 1.
31. The compound of claim 1, wherein p is 2.
32. The compound of claim 1, wherein n is 0.

33. A compound or a pharmaceutically acceptable salt thereof selected from the group consisting of:

| Compound No. | Chemical Structure | Chemical Name |
|---|---|---|
| H0990 | 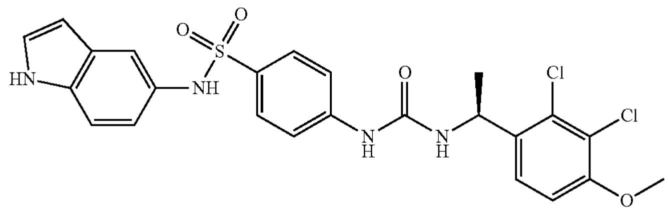 [SMILES: COc1ccc([C@H](C)NC(=O)Nc2ccc(S(=O)(=O)Nc3ccc4[nH]ccc4c3)cc2)c(Cl)c1Cl] | (S)-4-(3-(1-(2,3-dichloro-4-methoxyphenyl)ethyl)ureido)-N-(1H-indol-5-yl)benzenesulfonamide |
| H0991 | 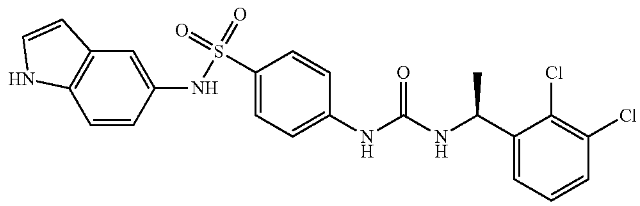 [SMILES: C[C@H](NC(=O)Nc1ccc(S(=O)(=O)Nc2ccc3[nH]ccc3c2)cc1)c1cccc(Cl)c1Cl] | (S)-4-(3-(1-(2,3-dichlorophenyl)ethyl)ureido)-N-(1H-indol-5-yl)benzenesulfonamide |
| H0997 | 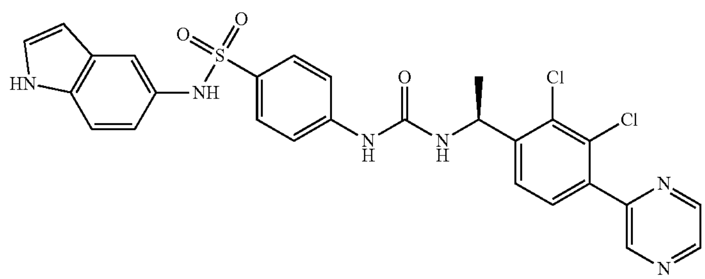 [SMILES: C[C@H](NC(=O)Nc1ccc(S(=O)(=O)Nc2ccc3[nH]ccc3c2)cc1)c1ccc(-c2cnccn2)c(Cl)c1Cl] | (S)-4-(3-(1-(2,3-dichloro-4-(pyrazin-2-yl)phenyl)ethyl)ureido)-N-(1H-indol-5-yl)benzenesulfonamide |
| H1003 | 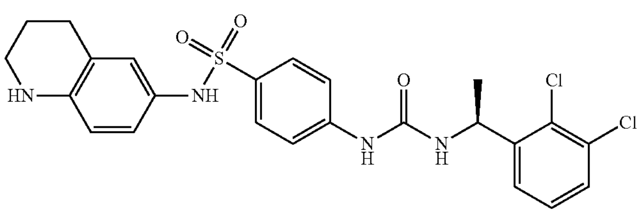 [SMILES: C[C@H](NC(=O)Nc1ccc(S(=O)(=O)Nc2ccc3c(c2)CCCN3)cc1)c1cccc(Cl)c1Cl] | (S)-4-(3-(1-(2,3-dichlorophenyl)ethyl)ureido)-N-(1,2,3,4-tetrahydroquinolin-6-yl)benzenesulfonamide |
| H1004 | 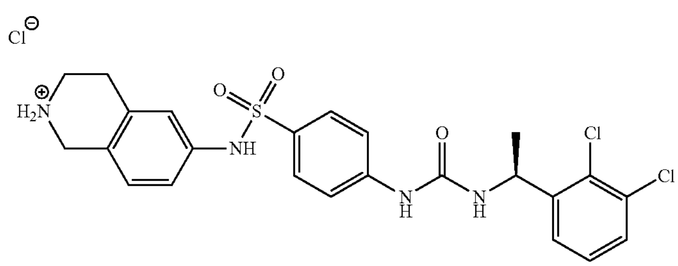 [SMILES: [Cl-] ; C[C@H](NC(=O)Nc1ccc(S(=O)(=O)Nc2ccc3c(c2)CC[NH2+]C3)cc1)c1cccc(Cl)c1Cl] | (S)-4-(3-(1-(2,3-dichlorophenyl)ethyl)ureido)-N-(1,2,3,4-tetrahydroisoquinolin-6-yl)benzenesulfonamide |
| H1005 | 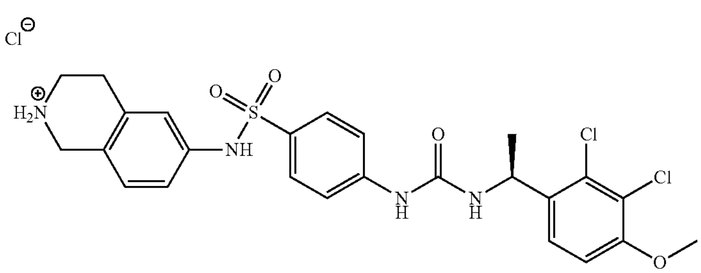 [SMILES: [Cl-] ; COc1ccc([C@H](C)NC(=O)Nc2ccc(S(=O)(=O)Nc3ccc4c(c3)CC[NH2+]C4)cc2)c(Cl)c1Cl] | (S)-4-(3-(1-(2,3-dichloro-4-methoxyphenyl)ethyl)ureido)-N-(1,2,3,4-tetrahydroisoquinolin-6-yl)benzenesulfonamide |

-continued

| Compound No. | Chemical Structure | Chemical Name |
|---|---|---|
| H1006 | 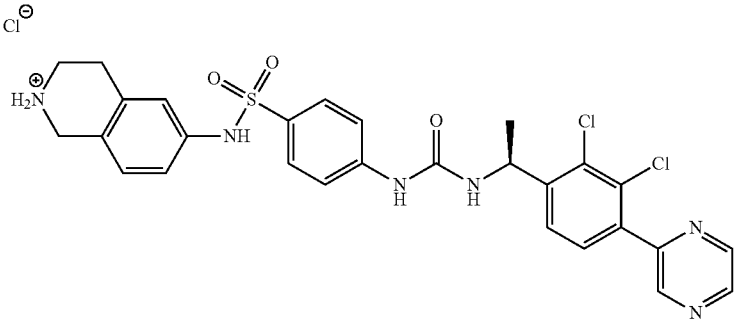 [SMILES: [Cl-] ; C[C@H](NC(=O)Nc1ccc(S(=O)(=O)Nc2ccc3c(c2)CC[NH2+]C3)cc1)c1ccc(-c2cnccn2)c(Cl)c1Cl] | (S)-4-(3-(1-(2,3-dichloro-4-(pyrazin-2-yl)phenyl)ethyl)ureido)-N-(1,2,3,4-tetrahydroisoquinolin-6-yl)benzenesulfonamide |
| H1008 | 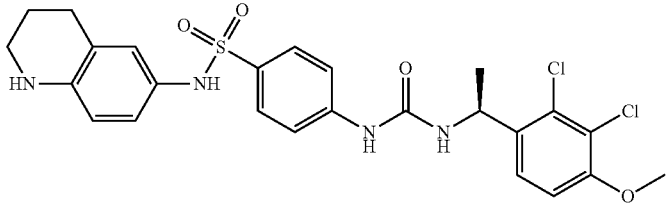 [SMILES: COc1ccc([C@H](C)NC(=O)Nc2ccc(S(=O)(=O)Nc3ccc4c(c3)CCCN4)cc2)c(Cl)c1Cl] | (S)-4-(3-(1-(2,3-dichloro-4-methoxyphenyl)ethyl)ureido)-N-(1,2,3,4-tetrahydroquinolin-6-yl)benzenesulfonamide |
| H1017 | 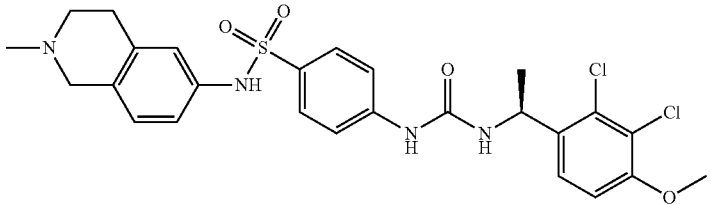 | (S)-4-(3-(1-(2,3-dichloro-4-methoxyphenyl)ethyl)ureido)-N-(2-methyl-1,2,3,4-tetrahydroisoquinolin-6-yl)benzenesulfonamide |
| H1018 | 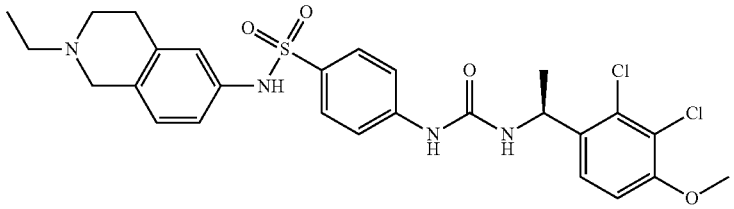 [SMILES: CCN1CCc2cc(NS(=O)(=O)c3ccc(NC(=O)N[C@@H](C)c4ccc(OC)c(Cl)c4Cl)cc3)ccc2C1] | (S)-4-(3-(1-(2,3-dichloro-4-methoxyphenyl)ethyl)ureido)-N-(2-ethyl-1,2,3,4-tetrahydroisoquinolin-6-yl)benzenesulfonamide |
| H1024 | 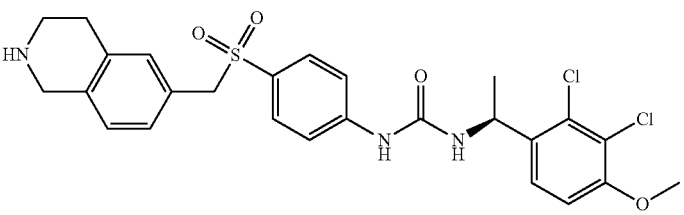 [SMILES: COc1ccc([C@H](C)NC(=O)Nc2ccc(S(=O)(=O)Cc3ccc4c(c3)CCNC4)cc2)c(Cl)c1Cl] | (S)-1-(1-(2,3-dichloro-4-methoxyphenyl)ethyl)-3-(4-(((1,2,3,4-tetrahydroisoquinolin-6-yl)methyl)sulfonyl)phenyl)urea |
| H1025 | 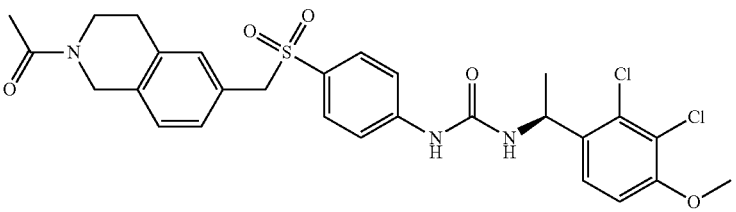 [SMILES: COc1ccc([C@H](C)NC(=O)Nc2ccc(S(=O)(=O)Cc3ccc4c(c3)CCN(C(C)=O)C4)cc2)c(Cl)c1Cl] | (S)-1-(4-(((2-acetyl-1,2,3,4-tetrahydroisoquinolin-6-yl)methyl)sulfonyl)phenyl)-3-(1-(2,3-dichloro-4-methoxyphenyl)ethyl)urea |

-continued

| Compound No. | Chemical Structure | Chemical Name |
|---|---|---|
| H1026 | 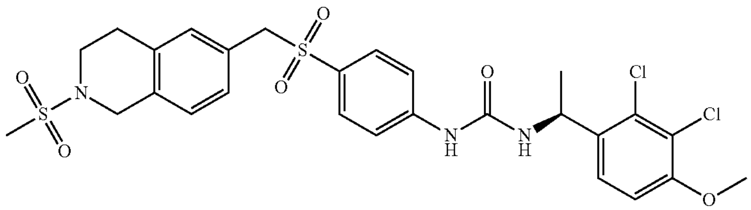 | (S)-1-(1-(2,3-dichloro-4-methoxyphenyl)ethyl)-3-(4-(((2-(methylsulfonyl)-1,2,3,4-tetrahydroisoquinolin-6-yl)methyl)sulfonyl)phenyl)urea |
| H1027 | 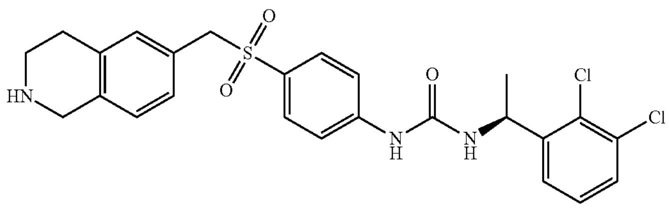 [SMILES: C[C@H](NC(=O)Nc1ccc(S(=O)(=O)Cc2ccc3c(c2)CCNC3)cc1)c1cccc(Cl)c1Cl] | (S)-1-(1-(2,3-dichlorophenyl)ethyl)-3-(4-(((1,2,3,4-tetrahydroisoquinolin-6-yl)methyl)sulfonyl)phenyl)urea |
| H1028 | 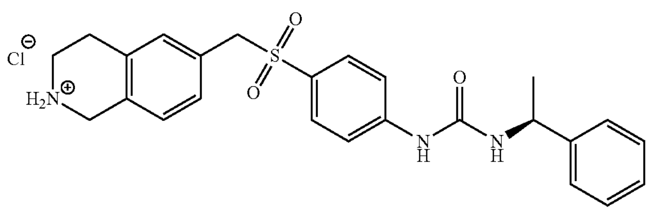 [SMILES: [Cl-] ; C[C@H](NC(=O)Nc1ccc(S(=O)(=O)Cc2ccc3c(c2)CC[NH2+]C3)cc1)c1ccccc1] | (S)-1-(1-phenylethyl)-3-(4-(((1,2,3,4-tetrahydroisoquinolin-6-yl)methyl)sulfonyl)phenyl)urea |
| H1029 | 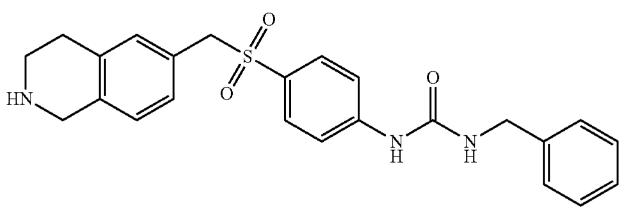 [SMILES: O=C(NCc1ccccc1)Nc1ccc(S(=O)(=O)Cc2ccc3c(c2)CCNC3)cc1] | 1-benzyl-3-(4-(((1,2,3,4-tetrahydroisoquinolin-6-yl)methyl)sulfonyl)phenyl)urea |
| H1033 | 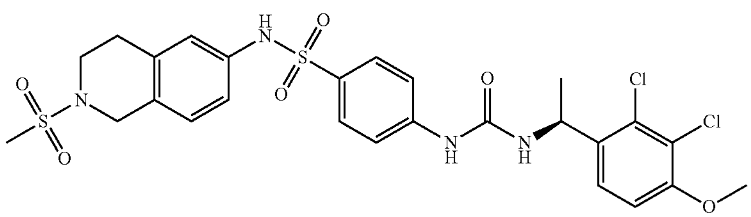 | (S)-4-(3-(1-(2,3-dichloro-4-methoxyphenyl)ethyl)ureido)-N-(2-(methylsulfonyl)-1,2,3,4-tetrahydroisoquinolin-6-yl)benzenesulfonamide |
| H1034 | 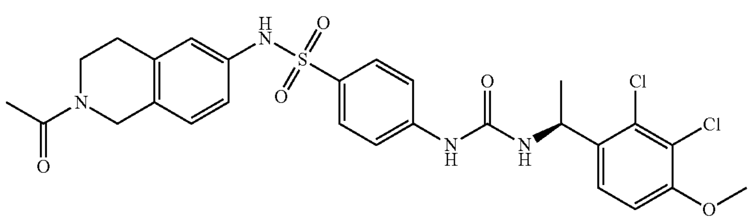 [SMILES: COc1ccc([C@H](C)NC(=O)Nc2ccc(S(=O)(=O)Nc3ccc4c(c3)CCN(C(C)=O)C4)cc2)c(Cl)c1Cl] | (S)-N-(2-acetyl-1,2,3,4-tetrahydroisoquinolin-6-yl)-4-(3-(1-(2,3-dichloro-4-methoxyphenyl)ethyl)ureido)benzenesulfonamide |
| H1038 | 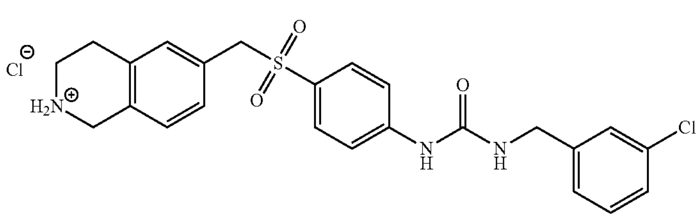 [SMILES: [Cl-] ; O=C(NCc1cccc(Cl)c1)Nc1ccc(S(=O)(=O)Cc2ccc3c(c2)CC[NH2+]C3)cc1] | 1-(3-chlorobenzyl)-3-(4-(((1,2,3,4-tetrahydroisoquinolin-6-yl)methyl)sulfonyl)phenyl)urea |

-continued

| Compound No. | Chemical Structure | Chemical Name |
| --- | --- | --- |
| H1039 | 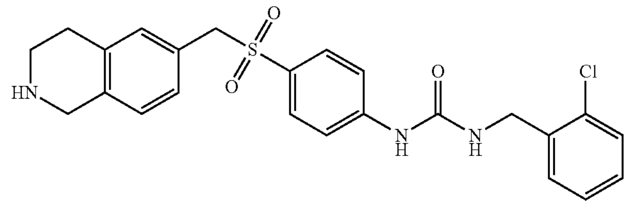 | 1-(2-chlorobenzyl)-3-(4-(((1,2,3,4-tetrahydroisoquinolin-6-yl)methyl)sulfonyl)phenyl)urea |
| H1040 | 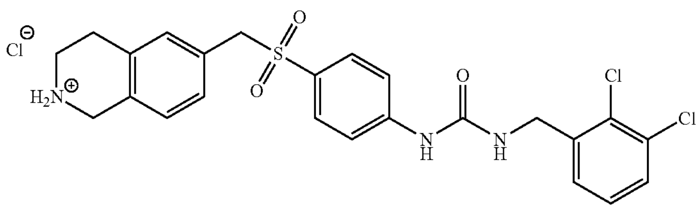 [SMILES: [Cl-] ; O=C(NCc1cccc(Cl)c1Cl)Nc1ccc(S(=O)(=O)Cc2ccc3c(c2)CC[NH2+]C3)cc1] | 1-(2,3-dichlorobenzyl)-3-(4-(((1,2,3,4-tetrahydroisoquinolin-6-yl)methyl)sulfonyl)phenyl)urea |
| H1041 | 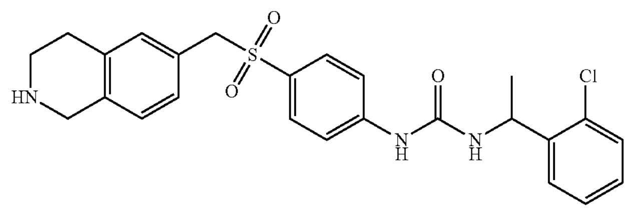 [SMILES: CC(NC(=O)Nc1ccc(S(=O)(=O)Cc2ccc3c(c2)CCNC3)cc1)c1ccccc1Cl] | 1-(1-(2-chlorophenyl)ethyl)-3-(4-(((1,2,3,4-tetrahydroisoquinolin-6-yl)methyl)sulfonyl)phenyl)urea |
| H1042 | 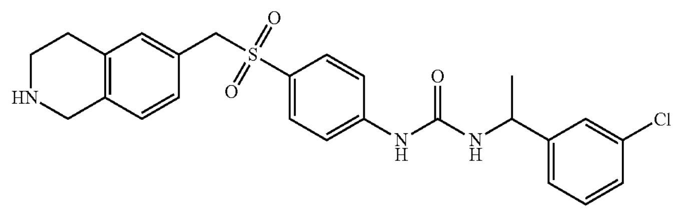 [SMILES: CC(NC(=O)Nc1ccc(S(=O)(=O)Cc2ccc3c(c2)CCNC3)cc1)c1cccc(Cl)c1] | 1-(1-(3-chlorophenyl)ethyl)-3-(4-(((1,2,3,4-tetrahydroisoquinolin-6-yl)methyl)sulfonyl)phenyl)urea |
| H1043 | 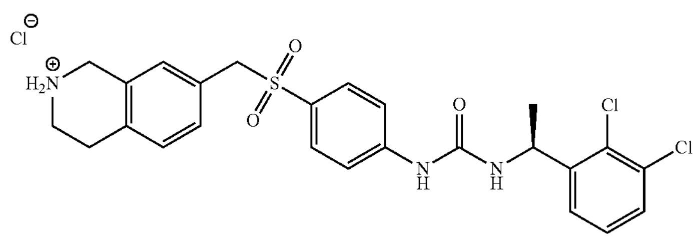 [SMILES: [Cl-] ; C[C@H](NC(=O)Nc1ccc(S(=O)(=O)Cc2ccc3c(c2)C[NH2+]CC3)cc1)c1cccc(Cl)c1Cl] | (S)-1-(1-(2,3-dichlorophenyl)ethyl)-3-(4-(((1,2,3,4-tetrahydroisoquinolin-7-yl)methyl)sulfonyl)phenyl)urea |
| H1044 | 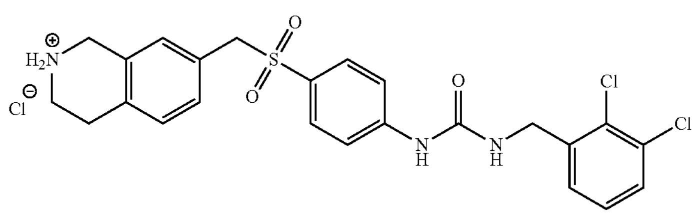 [SMILES: [Cl-] ; O=C(NCc1cccc(Cl)c1Cl)Nc1ccc(S(=O)(=O)Cc2ccc3c(c2)C[NH2+]CC3)cc1] | 1-(2,3-dichlorobenzyl)-3-(4-(((1,2,3,4-tetrahydroisoquinolin-7-yl)methyl)sulfonyl)phenyl)urea |
| H1045 | 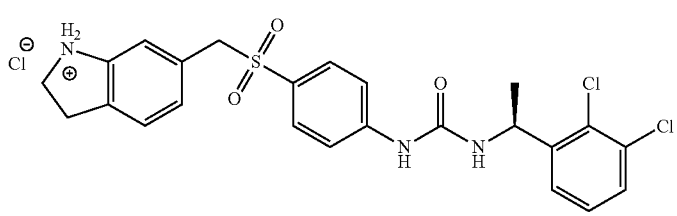 | (S)-1-(1-(2,3-dichlorophenyl)ethyl)-3-(4-((indolin-6-ylmethyl)sulfonyl)phenyl)urea |

-continued

| Compound No. | Chemical Structure | Chemical Name |
|---|---|---|
| H1046 | 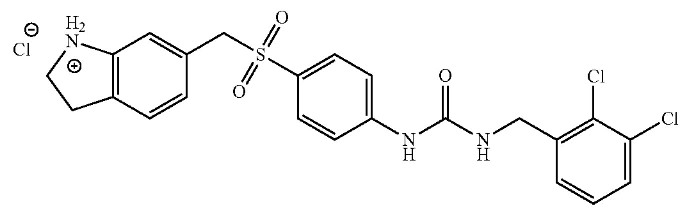 | 1-(2,3-dichlorobenzyl)-3-(4-((indolin-6-ylmethyl)sulfonyl)phenyl)urea |
| H1047 | 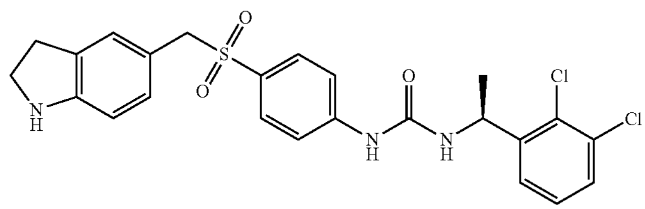 [SMILES: C[C@H](NC(=O)Nc1ccc(S(=O)(=O)Cc2ccc3c(c2)CCN3)cc1)c1cccc(Cl)c1Cl] | (S)-1-(1-(2,3-dichlorophenyl)ethyl)-3-(4-((indolin-5-ylmethyl)sulfonyl)phenyl)urea |
| H1048 | 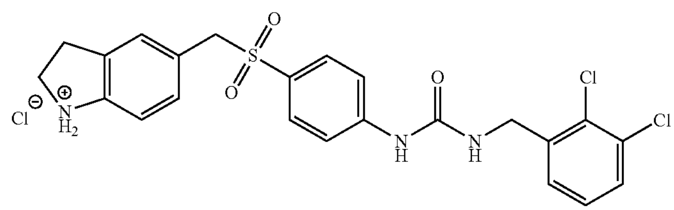 [SMILES: [Cl-] ; O=C(NCc1cccc(Cl)c1Cl)Nc1ccc(S(=O)(=O)Cc2ccc3c(c2)CC[NH2+]3)cc1] | 1-(2,3-dichlorobenzyl)-3-(4-((indolin-5-ylmethyl)sulfonyl)phenyl)urea |
| H1049 | 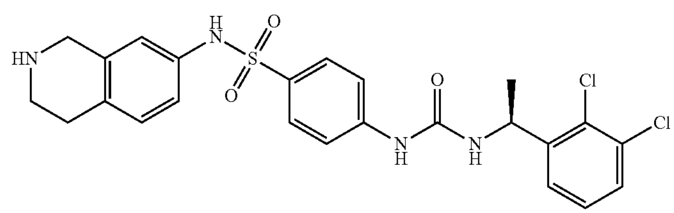 [SMILES: C[C@H](NC(=O)Nc1ccc(S(=O)(=O)Nc2ccc3c(c2)CNCC3)cc1)c1cccc(Cl)c1Cl] | (S)-4-(3-(1-(2,3-dichlorophenyl)ethyl)ureido)-N-(1,2,3,4-tetrahydroisoquinolin-7-yl)benzenesulfonamide |
| H1054 | 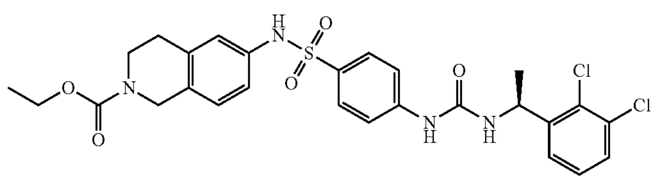 [SMILES: CCOC(=O)N1CCc2cc(NS(=O)(=O)c3ccc(NC(=O)N[C@@H](C)c4cccc(Cl)c4Cl)cc3)ccc2C1] | ethyl (S)-6-((4-(3-(1-(2,3-dichlorophenyl)ethyl)ureido)phenyl)sulfonamido)-3,4-dihydroisoquinoline-2(1H)-carboxylate |
| H1055 | 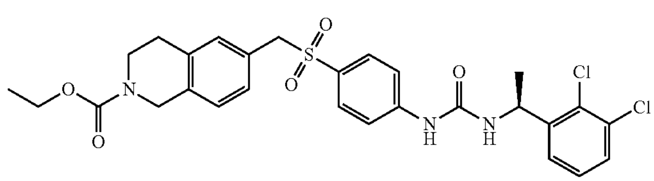 [SMILES: CCOC(=O)N1CCc2cc(CS(=O)(=O)c3ccc(NC(=O)N[C@@H](C)c4cccc(Cl)c4Cl)cc3)ccc2C1] | ethyl (S)-6-(((4-(3-(1-(2,3-dichlorophenyl)ethyl)ureido)phenyl)sulfonyl)methyl)-3,4-dihydroisoquinoline-2(1H)-carboxylate |
| H1056 | 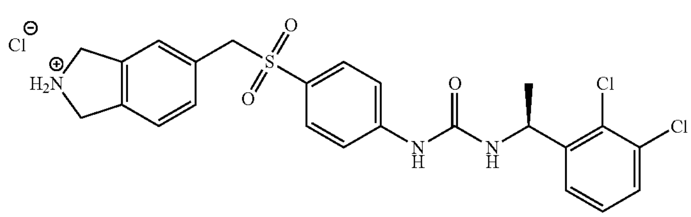 [SMILES: [Cl-] ; C[C@H](NC(=O)Nc1ccc(S(=O)(=O)Cc2ccc3c(c2)C[NH2+]C3)cc1)c1cccc(Cl)c1Cl] | (S)-1-(1-(2,3-dichlorophenyl)ethyl)-3-(4-((isoindolin-5-ylmethyl)sulfonyl)phenyl)urea |

-continued

| Compound No. | Chemical Structure | Chemical Name |
|---|---|---|
| H1057 | 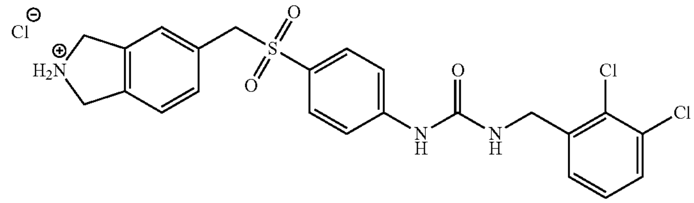 [SMILES: [Cl-] ; O=C(NCc1cccc(Cl)c1Cl)Nc1ccc(S(=O)(=O)Cc2ccc3c(c2)C[NH2+]C3)cc1] | 1-(2,3-dichlorobenzyl)-3-(4-((isoindolin-5-ylmethyl)sulfonyl)phenyl)urea |
| H1067 | 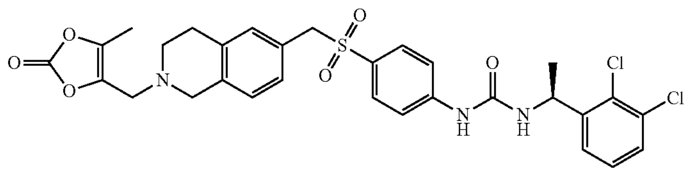 [SMILES: Cc1oc(=O)oc1CN1CCc2cc(CS(=O)(=O)c3ccc(NC(=O)N[C@@H](C)c4cccc(Cl)c4Cl)cc3)ccc2C1] | (S)-1-(1-(2,3-dichlorophenyl)ethyl)-3-(4-(((2-((5-methyl-2-oxo-1,3-dioxol-4-yl)methyl)-1,2,3,4-tetrahydroisoquinolin-6-yl)methyl)sulfonyl)phenyl)urea |
| H1068 | 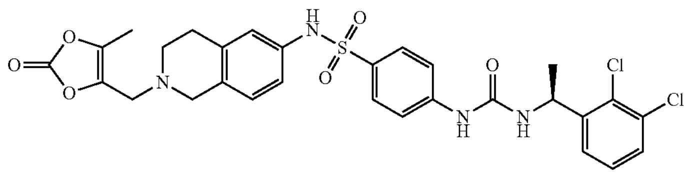 [SMILES: Cc1oc(=O)oc1CN1CCc2cc(NS(=O)(=O)c3ccc(NC(=O)N[C@@H](C)c4cccc(Cl)c4Cl)cc3)ccc2C1] | (S)-4-(3-(1-(2,3-dichlorophenyl)ethyl)ureido)-N-(2-((5-methyl-2-oxo-1,3-dioxol-4-yl)methyl)-1,2,3,4-tetrahydroisoquinolin-6-yl)benzenesulfonamide |
| H1071 | 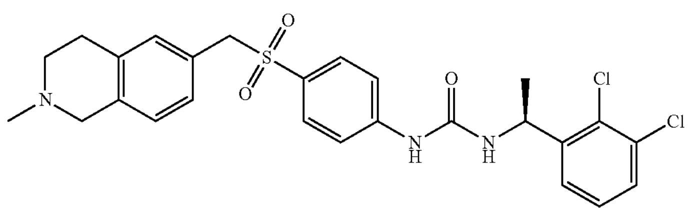 [SMILES: C[C@H](NC(=O)Nc1ccc(S(=O)(=O)Cc2ccc3c(c2)CCN(C)C3)cc1)c1cccc(Cl)c1Cl] | (S)-1-(1-(2,3-dichlorophenyl)ethyl)-3-(4-(((2-methyl-1,2,3,4-tetrahydroisoquinolin-6-yl)methyl)sulfonyl)phenyl)urea |
| H1072 | 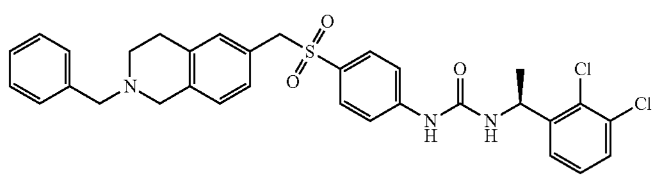 [SMILES: C[C@H](NC(=O)Nc1ccc(S(=O)(=O)Cc2ccc3c(c2)CCN(Cc2ccccc2)C3)cc1)c1cccc(Cl)c1Cl] | (S)-1-(4-(((2-benzyl-1,2,3,4-tetrahydroisoquinolin-6-yl)methyl)sulfonyl)phenyl)-3-(1-(2,3-dichlorophenyl)ethyl)urea |
| H1080 | 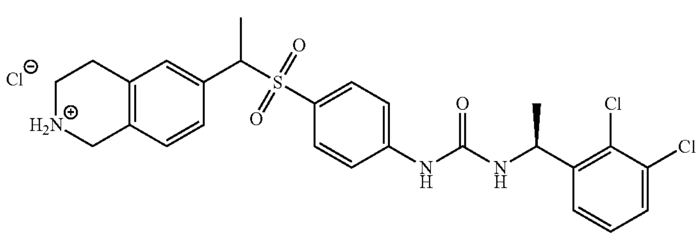 [SMILES: [Cl-] ; CC(c1ccc2c(c1)CC[NH2+]C2)S(=O)(=O)c1ccc(NC(=O)N[C@@H](C)c2cccc(Cl)c2Cl)cc1] | 1-((S)-1-(2,3-dichlorophenyl)ethyl)-3-(4-((1-(1,2,3,4-tetrahydroisoquinolin-6-yl)ethyl)sulfonyl)phenyl)urea |
| H1081 | 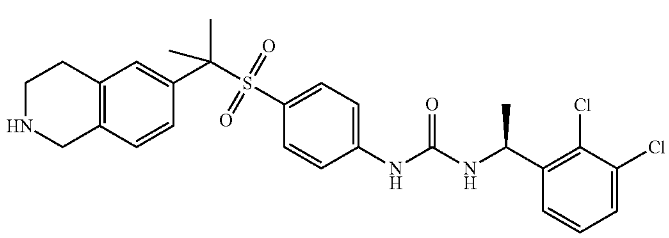 [SMILES: C[C@H](NC(=O)Nc1ccc(S(=O)(=O)C(C)(C)c2ccc3c(c2)CCNC3)cc1)c1cccc(Cl)c1Cl] | (S)-1-(1-(2,3-dichlorophenyl)ethyl)-3-(4-((2-(1,2,3,4-tetrahydroisoquinolin-6-yl)propan-2-yl)sulfonyl)phenyl)urea |

-continued

| Compound No. | Chemical Structure | Chemical Name |
|---|---|---|
| H1092 | 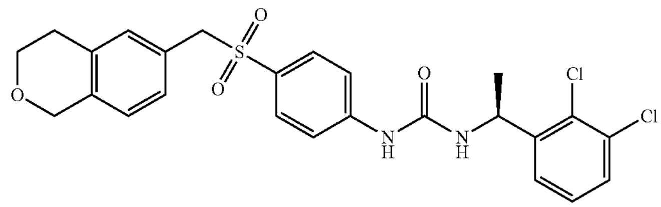 [SMILES: C[C@H](NC(=O)Nc1ccc(S(=O)(=O)Cc2ccc3c(c2)CCOC3)cc1)c1cccc(Cl)c1Cl] | (S)-1-(1-(2,3-dichlorophenyl)ethyl)-3-(4-((isochroman-6-ylmethyl)sulfonyl)phenyl)urea |
| H1097 | 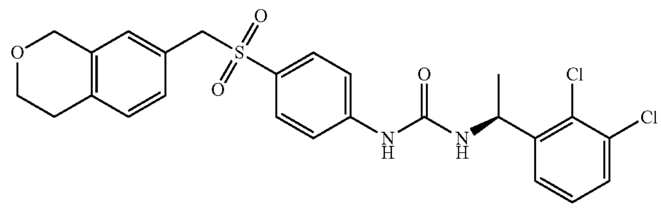 [SMILES: C[C@H](NC(=O)Nc1ccc(S(=O)(=O)Cc2ccc3c(c2)COCC3)cc1)c1cccc(Cl)c1Cl] | (S)-1-(1-(2,3-dichlorophenyl)ethyl)-3-(4-((isochroman-7-ylmethyl)sulfonyl)phenyl)urea |
| H1098 | 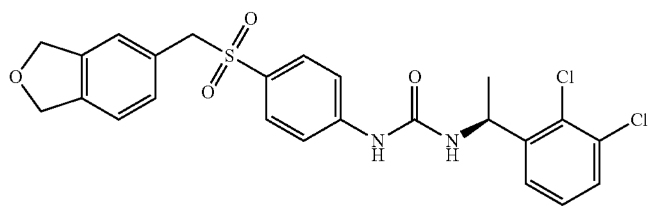 [SMILES: C[C@H](NC(=O)Nc1ccc(S(=O)(=O)Cc2ccc3c(c2)COC3)cc1)c1cccc(Cl)c1Cl] | (S)-1-(1-(2,3-dichlorophenyl)ethyl)-3-(4-(((1,3-dihydroisobenzofuran-5-yl)methyl)sulfonyl)phenyl)urea |
| H1102 | 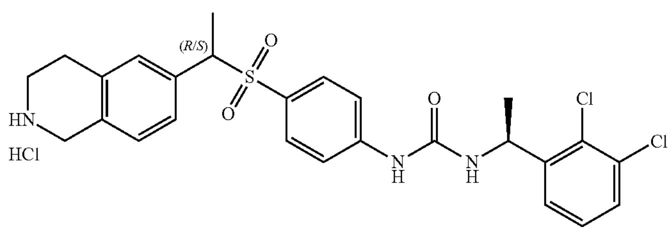 [SMILES: Cl ; CC(c1ccc2c(c1)CCNC2)S(=O)(=O)c1ccc(NC(=O)N[C@@H](C)c2cccc(Cl)c2Cl)cc1] | 1-((S)-1-(2,3-dichlorophenyl)ethyl)-3-(4-((1-(1,2,3,4-tetrahydroisoquinolin-6-yl)ethyl)sulfonyl)phenyl)urea hydrochloride |
| H1103 | 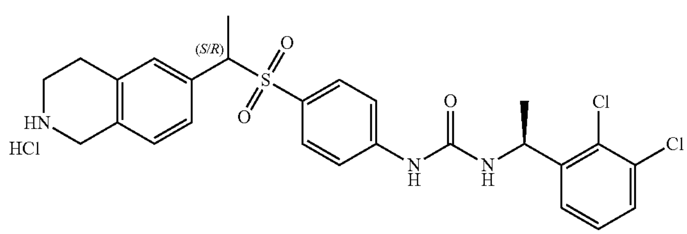 [SMILES: Cl ; CC(c1ccc2c(c1)CCNC2)S(=O)(=O)c1ccc(NC(=O)N[C@@H](C)c2cccc(Cl)c2Cl)cc1] | 1-((S)-1-(2,3-dichlorophenyl)ethyl)-3-(4-((1-(1,2,3,4-tetrahydroisoquinolin-6-yl)ethyl)sulfonyl)phenyl)urea hydrochloride |
| H1106 | 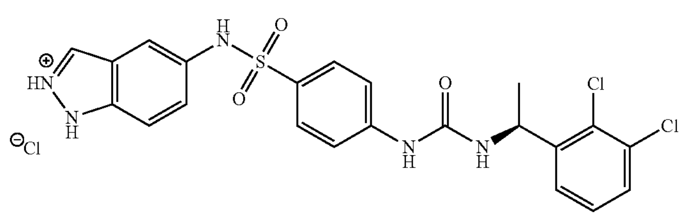 [SMILES: [Cl-] ; C[C@H](NC(=O)Nc1ccc(S(=O)(=O)Nc2ccc3[nH][nH+]cc3c2)cc1)c1cccc(Cl)c1Cl] | (S)-4-(3-(1-(2,3-dichlorophenyl)ethyl)ureido)-N-(1H-indazol-5-yl)benzenesulfonamide |
| H1111 | 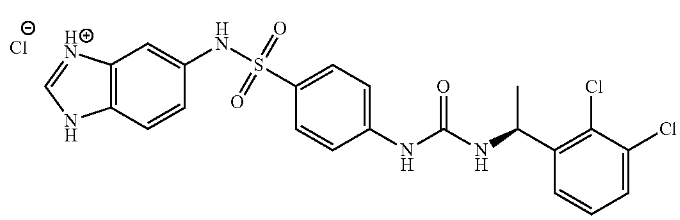 | (S)-N-(1H-benzo[d]imidazol-5-yl)-4-(3-(1-(2,3-dichlorophenyl)ethyl)ureido)benzenesulfonamide |

-continued

| Compound No. | Chemical Structure | Chemical Name |
|---|---|---|
| H1142 | 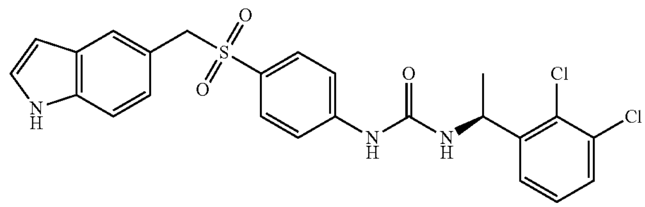 [SMILES: C[C@H](NC(=O)Nc1ccc(S(=O)(=O)Cc2ccc3[nH]ccc3c2)cc1)c1cccc(Cl)c1Cl] | (S)-1-(4-(((1H-indol-5-yl)methyl)sulfonyl)phenyl)-3-(1-(2,3-dichlorophenyl)ethyl)urea |
| H1148 | 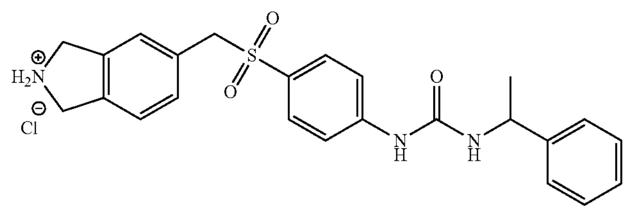 [SMILES: [Cl-] ; CC(NC(=O)Nc1ccc(S(=O)(=O)Cc2ccc3c(c2)C[NH2+]C3)cc1)c1ccccc1] | 1-(4-((isoindolin-5-ylmethyl)sulfonyl)phenyl)-3-(1-phenylethyl)urea |
| H1156 | 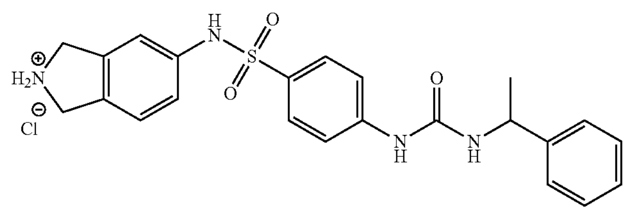 [SMILES: [Cl-] ; CC(NC(=O)Nc1ccc(S(=O)(=O)Nc2ccc3c(c2)C[NH2+]C3)cc1)c1ccccc1] | N-(isoindolin-5-yl)-4-(3-(1-phenylethyl)ureido)benzenesulfonamide |
| H1179 | 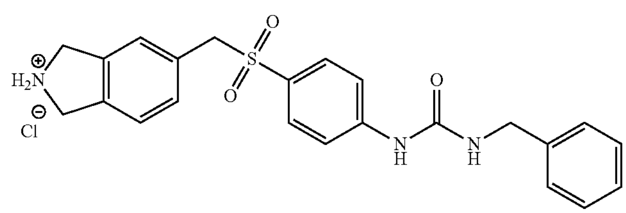 [SMILES: [Cl-] ; O=C(NCc1ccccc1)Nc1ccc(S(=O)(=O)Cc2ccc3c(c2)C[NH2+]C3)cc1] | 1-benzyl-3-(4-((isoindolin-5-ylmethyl)sulfonyl)phenyl)urea |
| H1188 | 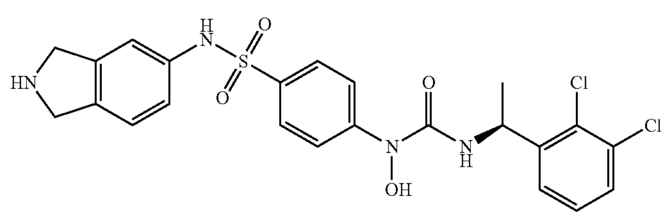 [SMILES: C[C@H](NC(=O)N(O)c1ccc(S(=O)(=O)Nc2ccc3c(c2)CNC3)cc1)c1cccc(Cl)c1Cl] | (S)-4-(3-(1-(2,3-dichlorophenyl)ethyl)-1-hydroxyureido)-N-(isoindolin-5-yl)benzenesulfonamide |
| H1190 | 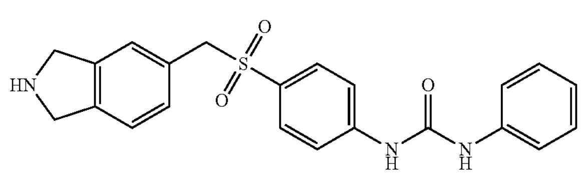 [SMILES: O=C(Nc1ccccc1)Nc1ccc(S(=O)(=O)Cc2ccc3c(c2)CNC3)cc1] | 1-(4-((isoindolin-5-ylmethyl)sulfonyl)phenyl)-3-phenylurea |
| H1193 | 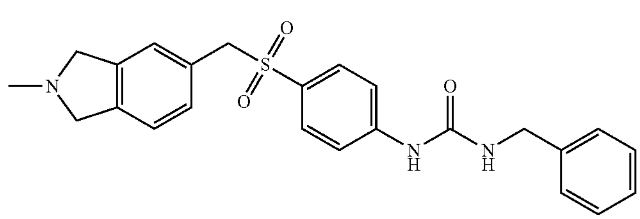 [SMILES: CN1Cc2ccc(CS(=O)(=O)c3ccc(NC(=O)NCc4ccccc4)cc3)cc2C1] | 1-benzyl-3-(4-(((2-methylisoindolin-5-yl)methyl)sulfonyl)phenyl)urea |

-continued

| Compound No. | Chemical Structure | Chemical Name |
|---|---|---|
| H1194 | 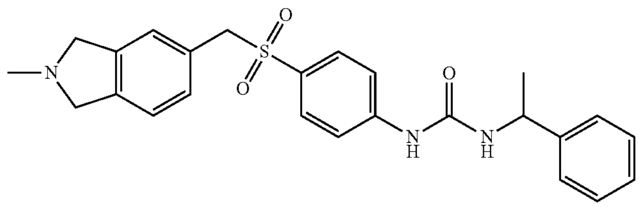 [SMILES: CC(NC(=O)Nc1ccc(S(=O)(=O)Cc2ccc3c(c2)CN(C)C3)cc1)c1ccccc1] | 1-(4-(((2-methylisoindolin-5-yl)methyl)sulfonyl)phenyl)-3-(1-phenylethyl)urea |
| H1199 | 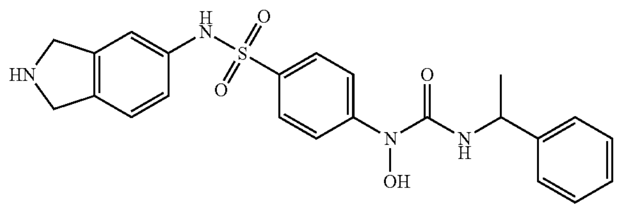 [SMILES: CC(NC(=O)N(O)c1ccc(S(=O)(=O)Nc2ccc3c(c2)CNC3)cc1)c1ccccc1] | 4-(1-hydroxy-3-(1-phenylethyl)ureido)-N-(isoindolin-5-yl)benzenesulfonamide |
| H1203 | 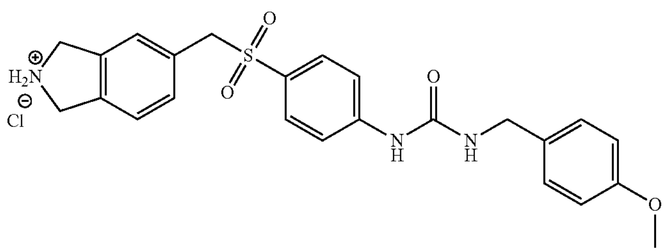 [SMILES: [Cl-] ; COc1ccc(CNC(=O)Nc2ccc(S(=O)(=O)Cc3ccc4c(c3)C[NH2+]C4)cc2)cc1] | 1-(4-((isoindolin-5-ylmethyl)sulfonyl)phenyl)-3-(4-methoxybenzyl)urea |
| H1204 | 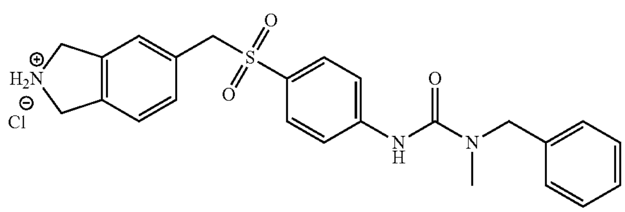 [SMILES: [Cl-] ; CN(Cc1ccccc1)C(=O)Nc1ccc(S(=O)(=O)Cc2ccc3c(c2)C[NH2+]C3)cc1] | 1-benzyl-3-(4-((isoindolin-5-ylmethyl)sulfonyl)phenyl)-1-methylurea |
| H1206 | 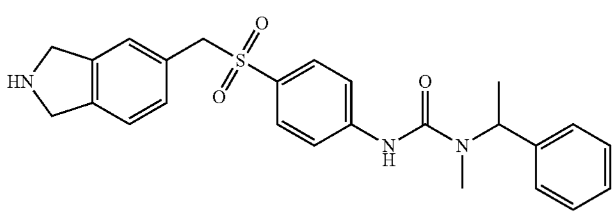 [SMILES: CC(c1ccccc1)N(C)C(=O)Nc1ccc(S(=O)(=O)Cc2ccc3c(c2)CNC3)cc1] | 3-(4-((isoindolin-5-ylmethyl)sulfonyl)phenyl)-1-methyl-1-(1-phenylethyl)urea |
| H1212 | 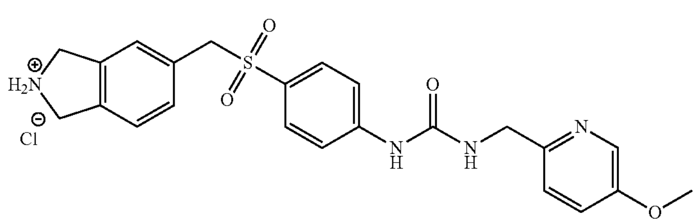 [SMILES: [Cl-] ; COc1ccc(CNC(=O)Nc2ccc(S(=O)(=O)Cc3ccc4c(c3)C[NH2+]C4)cc2)nc1] | 1-(4-((isoindolin-5-ylmethyl)sulfonyl)phenyl)-3-((5-methoxypyridin-2-yl)methyl)urea |
| H1213 | 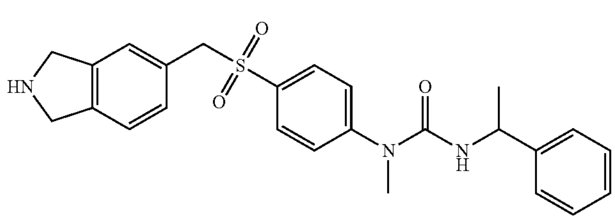 [SMILES: CC(NC(=O)N(C)c1ccc(S(=O)(=O)Cc2ccc3c(c2)CNC3)cc1)c1ccccc1] | 1-(4-((isoindolin-5-ylmethyl)sulfonyl)phenyl)-1-methyl-3-(1-phenylethyl)urea |

-continued

| Compound No. | Chemical Structure | Chemical Name |
|---|---|---|
| H1214 | 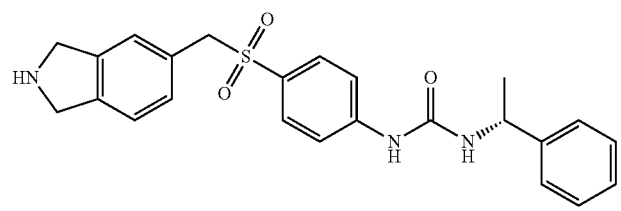 [SMILES: C[C@@H](NC(=O)Nc1ccc(S(=O)(=O)Cc2ccc3c(c2)CNC3)cc1)c1ccccc1] | (R)-1-(4-((isoindolin-5-ylmethyl)sulfonyl)phenyl)-3-(1-phenylethyl)urea |
| H1215 | 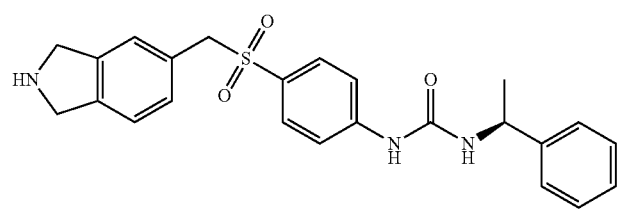 [SMILES: C[C@H](NC(=O)Nc1ccc(S(=O)(=O)Cc2ccc3c(c2)CNC3)cc1)c1ccccc1] | (S)-1-(4-((isoindolin-5-ylmethyl)sulfonyl)phenyl)-3-(1-phenylethyl)urea |
| H1219 | 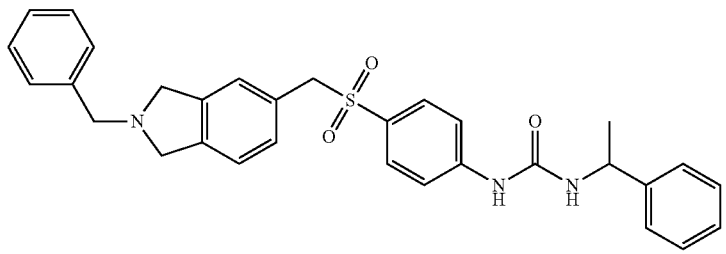 [SMILES: CC(NC(=O)Nc1ccc(S(=O)(=O)Cc2ccc3c(c2)CN(Cc2ccccc2)C3)cc1)c1ccccc1] | 1-(4-(((2-benzylisoindolin-5-yl)methyl)sulfonyl)phenyl)-3-(1-phenylethyl)urea |
| H1220 | 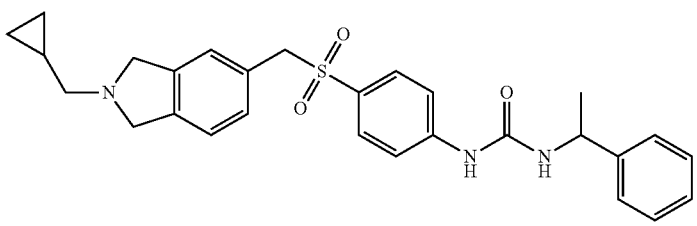 [SMILES: CC(NC(=O)Nc1ccc(S(=O)(=O)Cc2ccc3c(c2)CN(CC2CC2)C3)cc1)c1ccccc1] | 1-(4-(((2-(cyclopropylmethyl)isoindolin-5-yl)methyl)sulfonyl)phenyl)-3-(1-phenylethyl)urea |
| H1221 | 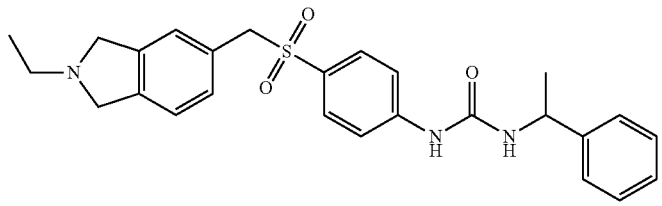 [SMILES: CCN1Cc2ccc(CS(=O)(=O)c3ccc(NC(=O)NC(C)c4ccccc4)cc3)cc2C1] | 1-(4-(((2-ethylisoindolin-5-yl)methyl)sulfonyl)phenyl)-3-(1-phenylethyl)urea |
| H1227 | 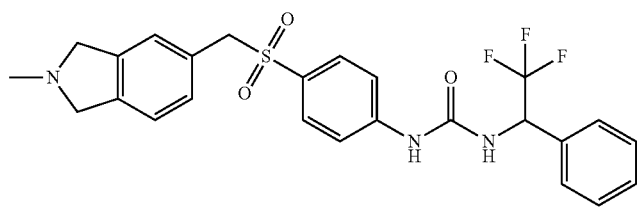 [SMILES: CN1Cc2ccc(CS(=O)(=O)c3ccc(NC(=O)NC(c4ccccc4)C(F)(F)F)cc3)cc2C1] | 1-(4-(((2-methylisoindolin-5-yl)methyl)sulfonyl)phenyl)-3-(2,2,2-trifluoro-1-phenylethyl)urea |

| Compound No. | Chemical Structure | Chemical Name |
|---|---|---|
| H1231 | 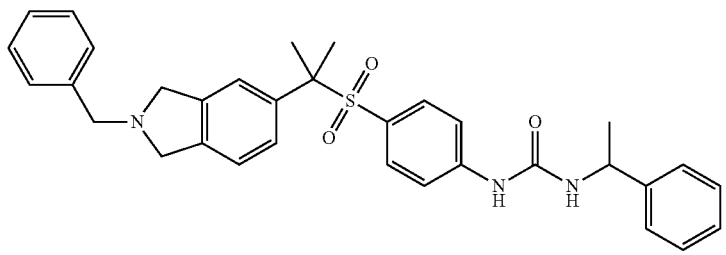 [SMILES: CC(NC(=O)Nc1ccc(S(=O)(=O)C(C)(C)c2ccc3c(c2)CN(Cc2ccccc2)C3)cc1)c1ccccc1] | 1-(4-((2-(2-benzylisoindolin-5-yl)propan-2-yl)sulfonyl)phenyl)-3-(1-phenylethyl)urea |
| H1232 | 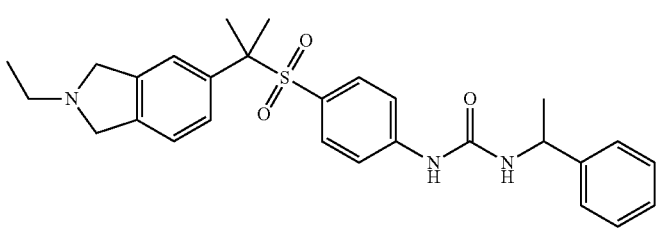 [SMILES: CCN1Cc2ccc(C(C)(C)S(=O)(=O)c3ccc(NC(=O)NC(C)c4ccccc4)cc3)cc2C1] | 1-(4-((2-(2-ethylisoindolin-5-yl)propan-2-yl)sulfonyl)phenyl)-3-(1-phenylethyl)urea |
| H1233 | 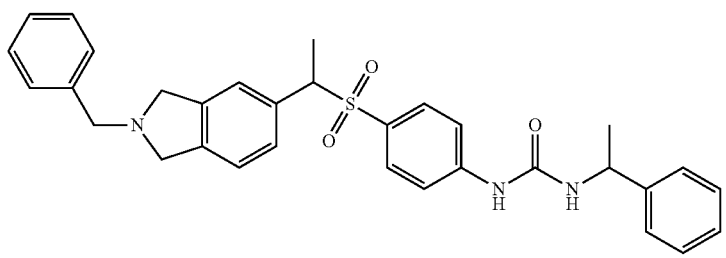 [SMILES: CC(NC(=O)Nc1ccc(S(=O)(=O)C(C)c2ccc3c(c2)CN(Cc2ccccc2)C3)cc1)c1ccccc1] | 1-(4-((1-(2-benzylisoindolin-5-yl)ethyl)sulfonyl)phenyl)-3-(1-phenylethyl)urea |
| H1234 | 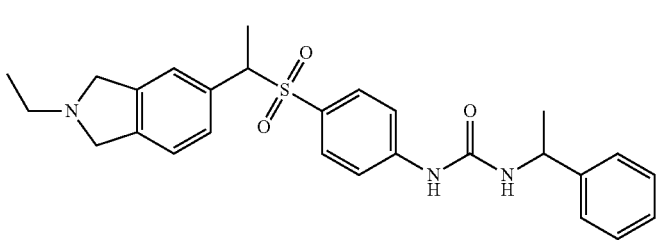 [SMILES: CCN1Cc2ccc(C(C)S(=O)(=O)c3ccc(NC(=O)NC(C)c4ccccc4)cc3)cc2C1] | 1-(4-((1-(2-ethylisoindolin-5-yl)ethyl)sulfonyl)phenyl)-3-(1-phenylethyl)urea |
| H1235 | 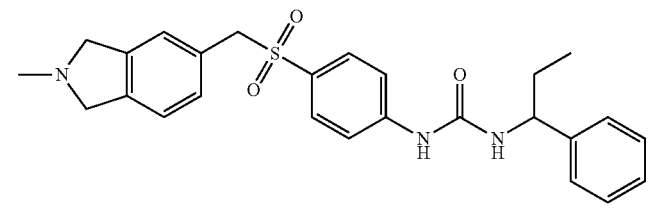 [SMILES: CCC(NC(=O)Nc1ccc(S(=O)(=O)Cc2ccc3c(c2)CN(C)C3)cc1)c1ccccc1] | 1-(4-(((2-methylisoindolin-5-yl)methyl)sulfonyl)phenyl)-3-(1-phenylpropyl)urea |
| H1248 | 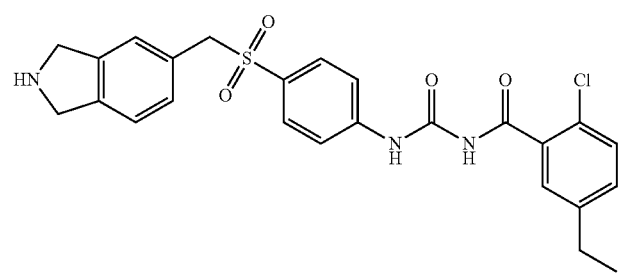 [SMILES: CCc1ccc(Cl)c(C(=O)NC(=O)Nc2ccc(S(=O)(=O)Cc3ccc4c(c3)CNC4)cc2)c1] | 2-chloro-5-ethyl-N-((4-((isoindolin-5-ylmethyl)sulfonyl)phenyl)carbamoyl)benzamide |

| Compound No. | Chemical Name |
|---|---|
| H1249 | 2-chloro-N-((4-((isoindolin-5-ylmethyl)sulfonyl)phenyl)carbamoyl)-5-morpholinobenzamide |
| H1250 | 2-chloro-N-((4-(N-(isoindolin-5-yl)sulfamoyl)phenyl)carbamoyl)-5-morpholinobenzamide |
| H1251 | 2-chloro-5-ethoxy-N-((4-((isoindolin-5-ylmethyl)sulfonyl)phenyl)carbamoyl)benzamide |
| H1252 | 2-chloro-5-ethoxy-N-((4-(N-(isoindolin-5-yl)sulfamoyl)phenyl)carbamoyl)benzamide |
| H1256 | (5-methyl-2-oxo-1,3-dioxol-4-yl)methyl 5-(((4-(3-(1-phenylethyl)ureido)phenyl)sulfonyl)methyl)isoindoline-2-carboxylate |

-continued

| Compound No. | Chemical Structure | Chemical Name |
|---|---|---|
| H1259 | 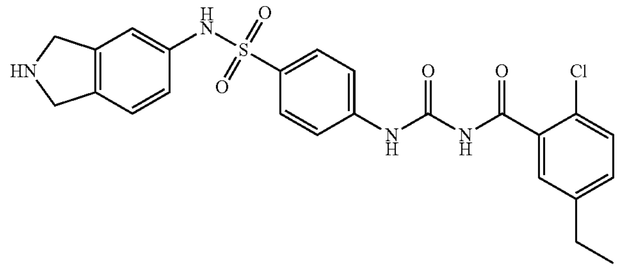 [SMILES: CCc1ccc(Cl)c(C(=O)NC(=O)Nc2ccc(S(=O)(=O)Nc3ccc4c(c3)CNC4)cc2)c1] | 2-chloro-5-ethyl-N-((4-(N-(isoindolin-5-yl)sulfamoyl)phenyl)carbamoyl)benzamide |
| H1260 | 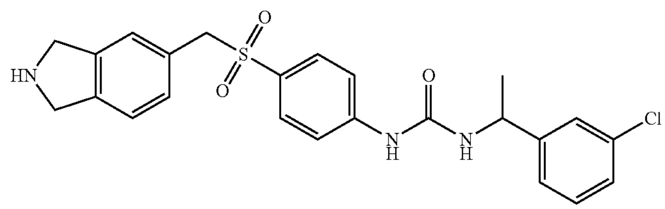 [SMILES: CC(NC(=O)Nc1ccc(S(=O)(=O)Cc2ccc3c(c2)CNC3)cc1)c1cccc(Cl)c1] | 1-(1-(3-chlorophenyl)ethyl)-3-(4-((isoindolin-5-ylmethyl)sulfonyl)phenyl)urea |
| H1261 | 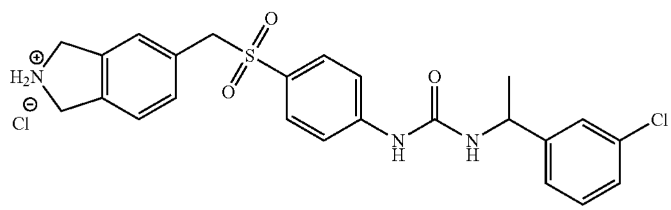 [SMILES: [Cl-] ; CC(NC(=O)Nc1ccc(S(=O)(=O)Cc2ccc3c(c2)C[NH2+]C3)cc1)c1cccc(Cl)c1] | 1-(1-(2-chlorophenyl)ethyl)-3-(4-((isoindolin-5-ylmethyl)sulfonyl)phenyl)urea |
| H1262 | 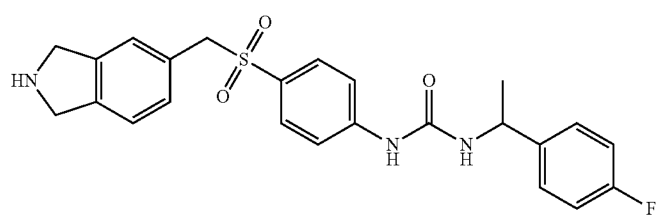 [SMILES: CC(NC(=O)Nc1ccc(S(=O)(=O)Cc2ccc3c(c2)CNC3)cc1)c1ccc(F)cc1] | 1-(1-(4-fluorophenyl)ethyl)-3-(4-((isoindolin-5-ylmethyl)sulfonyl)phenyl)urea |
| H1263 | 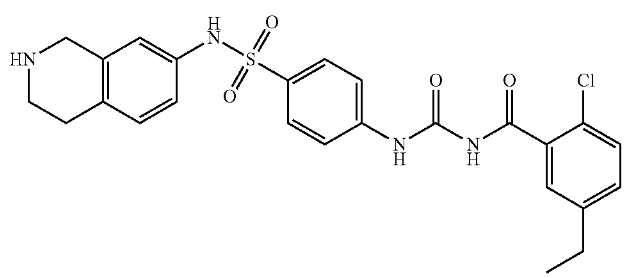 [SMILES: CCc1ccc(Cl)c(C(=O)NC(=O)Nc2ccc(S(=O)(=O)Nc3ccc4c(c3)CNCC4)cc2)c1] | 2-chloro-5-ethyl-N-((4-(N-(1,2,3,4-tetrahydroisoquinolin-7-yl)sulfamoyl)phenyl)carbamoyl)benzamide |
| H1266 | 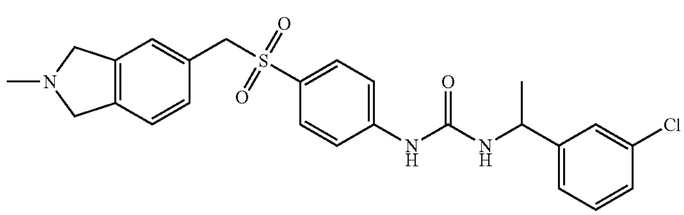 [SMILES: CC(NC(=O)Nc1ccc(S(=O)(=O)Cc2ccc3c(c2)CN(C)C3)cc1)c1cccc(Cl)c1] | 1-(1-(3-chlorophenyl)ethyl)-3-(4-(((2-methylisoindolin-5-yl)methyl)sulfonyl)phenyl)urea |

-continued

| Compound No. | Chemical Structure | Chemical Name |
|---|---|---|
| H1267 | 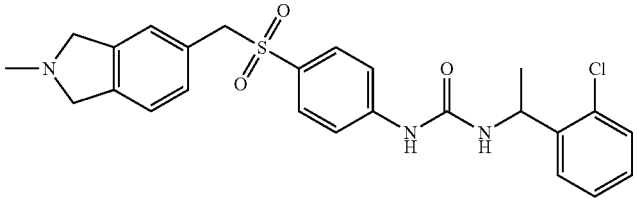 [SMILES: CC(NC(=O)Nc1ccc(S(=O)(=O)Cc2ccc3c(c2)CN(C)C3)cc1)c1ccccc1Cl] | 1-(1-(2-chlorophenyl)ethyl)-3-(4-(((2-methylisoindolin-5-yl)methyl)sulfonyl)phenyl)urea |
| H1268 | 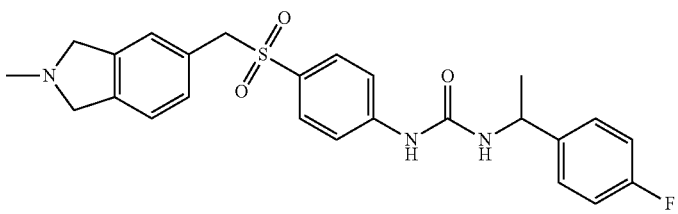 [SMILES: CC(NC(=O)Nc1ccc(S(=O)(=O)Cc2ccc3c(c2)CN(C)C3)cc1)c1ccc(F)cc1] | 1-(1-(4-fluorophenyl)ethyl)-3-(4-(((2-methylisoindolin-5-yl)methyl)sulfonyl)phenyl)urea |
| H1269 | 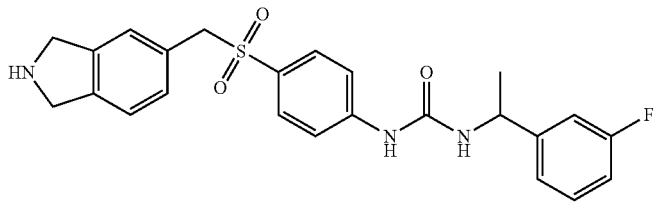 [SMILES: CC(NC(=O)Nc1ccc(S(=O)(=O)Cc2ccc3c(c2)CNC3)cc1)c1cccc(F)c1] | 1-(1-(3-fluorophenyl)ethyl)-3-(4-((isoindolin-5-ylmethyl)sulfonyl)phenyl)urea |
| H1272 | 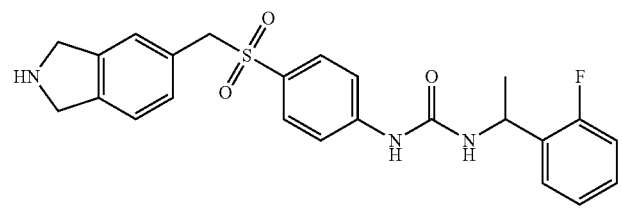 [SMILES: CC(NC(=O)Nc1ccc(S(=O)(=O)Cc2ccc3c(c2)CNC3)cc1)c1ccccc1F] | 1-(1-(2-fluorophenyl)ethyl)-3-(4-((isoindolin-5-ylmethyl)sulfonyl)phenyl)urea |
| H1281 | 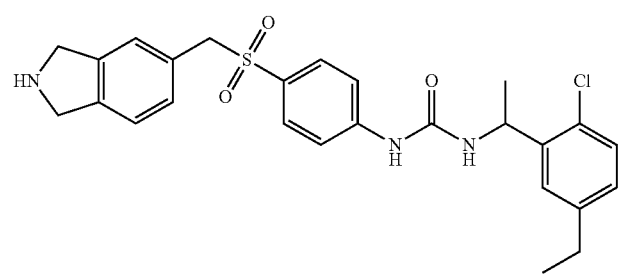 [SMILES: CCc1ccc(Cl)c(C(C)NC(=O)Nc2ccc(S(=O)(=O)Cc3ccc4c(c3)CNC4)cc2)c1] | 1-(1-(2-chloro-5-ethylphenyl)ethyl)-3-(4-((isoindolin-5-ylmethyl)sulfonyl)phenyl)urea |
| H1283 | 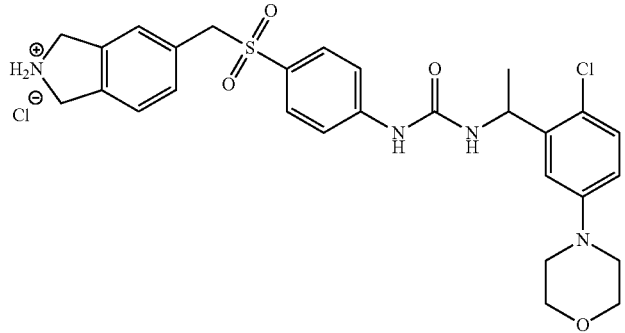 [SMILES: [Cl-] ; CC(NC(=O)Nc1ccc(S(=O)(=O)Cc2ccc3c(c2)C[NH2+]C3)cc1)c1cc(N2CCOCC2)ccc1Cl] | 1-(1-(2-chloro-5-morpholinophenyl)ethyl)-3-(4-((isoindolin-5-ylmethyl)sulfonyl)phenyl)urea |

-continued

| Compound No. | Chemical Structure | Chemical Name |
|---|---|---|
| H1284 | 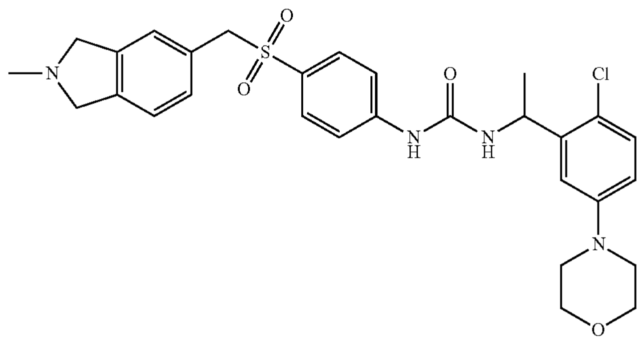 [SMILES: CC(NC(=O)Nc1ccc(S(=O)(=O)Cc2ccc3c(c2)CN(C)C3)cc1)c1cc(N2CCOCC2)ccc1Cl] | 1-(1-(2-chloro-5-morpholinophenyl)ethyl)-3-(4-(((2-methylisoindolin-5-yl)methyl)sulfonyl)phenyl)urea |
| H1286 | 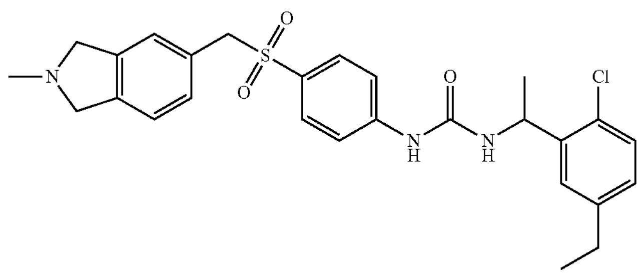 [SMILES: CCc1ccc(Cl)c(C(C)NC(=O)Nc2ccc(S(=O)(=O)Cc3ccc4c(c3)CN(C)C4)cc2)c1] | 1-1-(2-chloro-5-ethylphenyl)ethyl)-3-(4-(((2-methylisoindolin-5-yl)methyl)sulfonyl)phenyl)urea |
| H1291 | 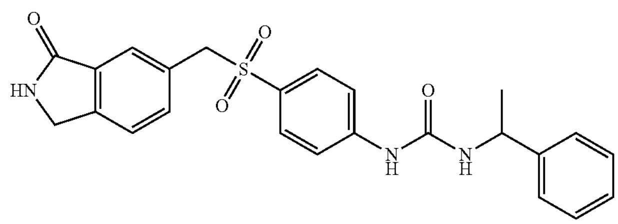 [SMILES: CC(NC(=O)Nc1ccc(S(=O)(=O)Cc2ccc3c(c2)C(=O)NC3)cc1)c1ccccc1] | 1-(4-(((3-oxoisoindolin-5-yl)methyl)sulfonyl)phenyl)-3-(1-phenylethyl)urea |
| H1292 | 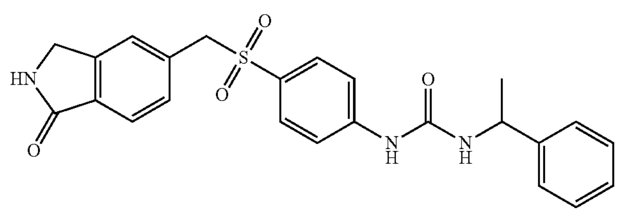 [SMILES: CC(NC(=O)Nc1ccc(S(=O)(=O)Cc2ccc3c(c2)CNC3=O)cc1)c1ccccc1] | 1-(4-(((1-oxoisoindolin-5-yl)methyl)sulfonyl)phenyl)-3-(1-phenylethyl)urea |
| H1293 | 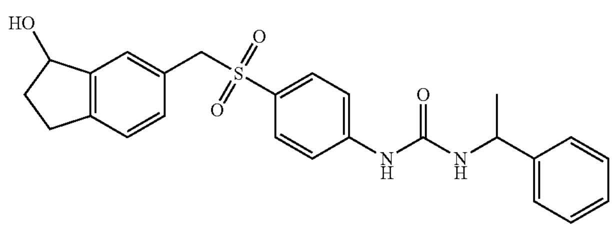 [SMILES: CC(NC(=O)Nc1ccc(S(=O)(=O)Cc2ccc3c(c2)C(O)CC3)cc1)c1ccccc1] | 1-(4-(((3-hydroxy-2,3-dihydro-1H-inden-5-yl)methyl)sulfonyl)phenyl)-3-(1-phenylethyl)urea |
| H1294 | 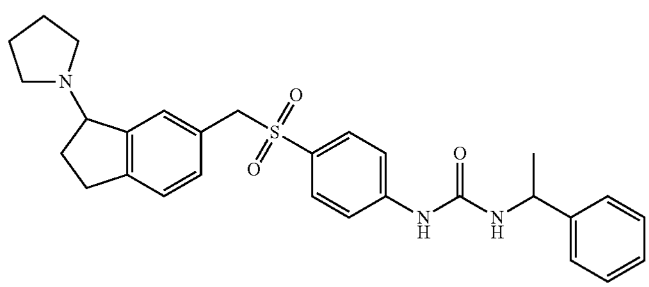 [SMILES: CC(NC(=O)Nc1ccc(S(=O)(=O)Cc2ccc3c(c2)C(N2CCCC2)CC3)cc1)c1ccccc1] | 1-(1-phenylethyl)-3-(4-(((3-(pyrrolidin-1-yl)-2,3-dihydro-1H-inden-5-yl)methyl)sulfonyl)phenyl)urea |

| Compound No. | Chemical Name |
|---|---|
| H1298 | 1-(4-((isoindolin-5-ylmethyl)sulfonyl)phenyl)-3-(1-(4-methoxyphenyl)ethyl)urea |
| H1299 | (S)-1-(4-(((2-methylisoindolin-5-yl)methyl)sulfonyl)phenyl)-3-(1-phenylethyl)urea |
| H1300 | (R)-1-(4-(((2-methylisoindolin-5-yl)methyl)sulfonyl)phenyl)-3-(1-phenylethyl)urea |
| H1306 | (S)-1-(1-phenylethyl)-3-(4-(((2,3,4,5-tetrahydro-1H-benzo[d]azepin-7-yl)methyl)sulfonyl)phenyl)urea |
| H1308 | N-(2-methylisoindolin-5-yl)-4-(3-(1-phenylethyl)ureido)benzenesulfonamide |
| H1310 | 4-(1-(3-(4-((isoindolin-5-ylmethyl)sulfonyl)phenyl)ureido)ethyl)phenyl acetate |
| H1311 | (S)-1-(4-(((2-methyl-1,2,3,4-tetrahydroisoquinolin-7-yl)methyl)sulfonyl)phenyl)-3-(1-phenylethyl)urea |

-continued

| Compound No. | Chemical Structure | Chemical Name |
|---|---|---|
| H1315 | 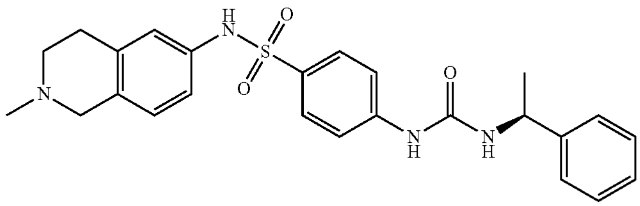 [SMILES: C[C@H](NC(=O)Nc1ccc(S(=O)(=O)Nc2ccc3c(c2)CCN(C)C3)cc1)c1ccccc1] | (S)-N-(2-methyl-1,2,3,4-tetrahydroisoquinolin-6-yl)-4-(3-(1-phenylethyl)ureido)benzenesulfonamide |
| H1316 | 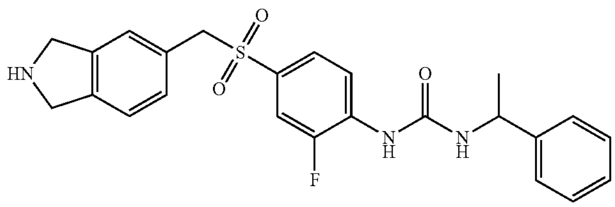 [SMILES: CC(NC(=O)Nc1ccc(S(=O)(=O)Cc2ccc3c(c2)CNC3)cc1F)c1ccccc1] | 1-(2-fluoro-4-((isoindolin-5-ylmethyl)sulfonyl)phenyl)-3-(1-phenylethyl)urea |
| H1317 | 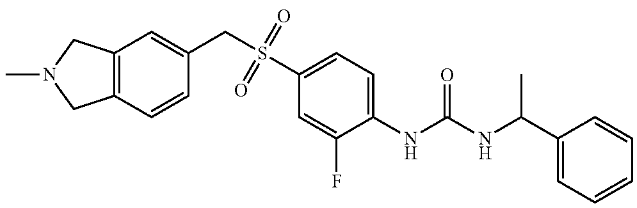 [SMILES: CC(NC(=O)Nc1ccc(S(=O)(=O)Cc2ccc3c(c2)CN(C)C3)cc1F)c1ccccc1] | 1-(2-fluoro-4-(((2-methylisoindolin-5-yl)methyl)sulfonyl)phenyl)-3-(1-phenylethyl)urea |
| H1319 | 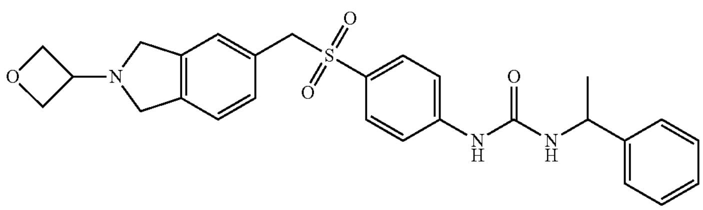 [SMILES: CC(NC(=O)Nc1ccc(S(=O)(=O)Cc2ccc3c(c2)CN(C2COC2)C3)cc1)c1ccccc1] | 1-(4-(((2-(oxetan-3-yl)isoindolin-5-yl)methyl)sulfonyl)phenyl)-3-(1-phenylethyl)urea |
| H1320 | 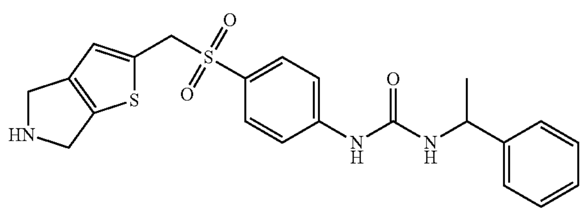 [SMILES: CC(NC(=O)Nc1ccc(S(=O)(=O)Cc2cc3c(s2)CNC3)cc1)c1ccccc1] | 1-(4-(((5,6-dihydro-4H-thieno[2,3-c]pyrrol-2-yl)methyl)sulfonyl)phenyl)-3-(1-phenylethyl)urea |
| H1321 | 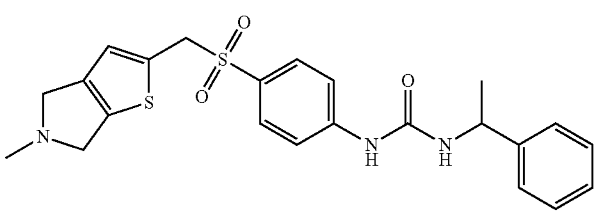 [SMILES: CC(NC(=O)Nc1ccc(S(=O)(=O)Cc2cc3c(s2)CN(C)C3)cc1)c1ccccc1] | 1-(4-(((5-methyl-5,6-dihydro-4H-thieno[2,3-c]pyrrol-2-yl)methyl)sulfonyl)phenyl)-3-(1-phenylethyl)urea |
| H1322 | 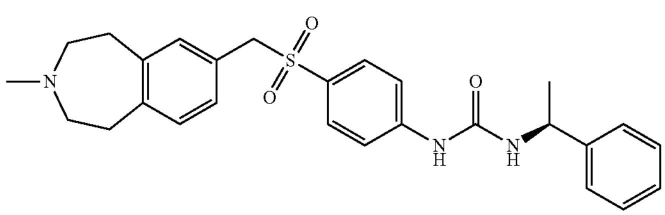 [SMILES: C[C@H](NC(=O)Nc1ccc(S(=O)(=O)Cc2ccc3c(c2)CCN(C)CC3)cc1)c1ccccc1] | (S)-1-(4-(((3-methyl-2,3,4,5-tetrahydro-1H-benzo[d]azepin-7-yl)methyl)sulfonyl)phenyl)-3-(1-phenylethyl)urea |

| Compound No. | Chemical Name |
|---|---|
| H1323 | 1-(4-(((6-methyl-6,7-dihydro-5H-pyrrolo[3,4-b]pyridin-3-yl)methyl)sulfonyl)phenyl)-3-(1-phenylethyl)urea |
| H1326 | 1-(1-(3-methoxyphenyl)ethyl)-3-(4-(((2-methylisoindolin-5-yl)methyl)sulfonyl)phenyl)urea |
| H1327 | 1-(1-(3-methoxyphenyl)ethyl)-3-(4-(((2-methylisoindolin-5-yl)methyl)sulfonyl)phenyl)urea |
| H1329 | 1-(4-(((2-methyl-2H-indazol-5-yl)methyl)sulfonyl)phenyl)-3-(1-phenylethyl)urea |
| H1333 | 4-(3-(1-(2,3-dichlorophenyl)ethyl)ureido)-N-(2-methyl-1,2,3,4-tetrahydroisoquinolin-6-yl)benzenesulfonamide |
| H1334 | 4-(3-(1-(2-chlorophenyl)ethyl)ureido)-N-(2-methyl-1,2,3,4-tetrahydroisoquinolin-6-yl)benzenesulfonamide |
| H1337 | (R)-N-(2-methylisoindolin-5-yl)-4-(3-(1-phenylethyl)ureido)benzenesulfonamide |

-continued

| Compound No. | Chemical Structure | Chemical Name |
|---|---|---|
| H1338 | 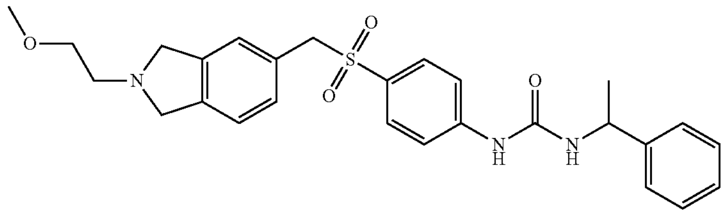 [SMILES: COCCN1Cc2ccc(CS(=O)(=O)c3ccc(NC(=O)NC(C)c4ccccc4)cc3)cc2C1] | 1-(4-(((2-(2-methoxyethyl)isoindolin-5-yl)methyl)sulfonyl)phenyl)-3-(1-phenylethyl)urea |
| H1339 | 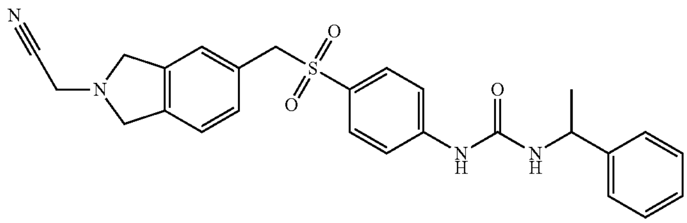 [SMILES: CC(NC(=O)Nc1ccc(S(=O)(=O)Cc2ccc3c(c2)CN(CC#N)C3)cc1)c1ccccc1] | 1-(4-(((2-(cyanomethyl)isoindolin-5-yl)methyl)sulfonyl)phenyl)-3-(1-phenylethyl)urea |
| H1340 | 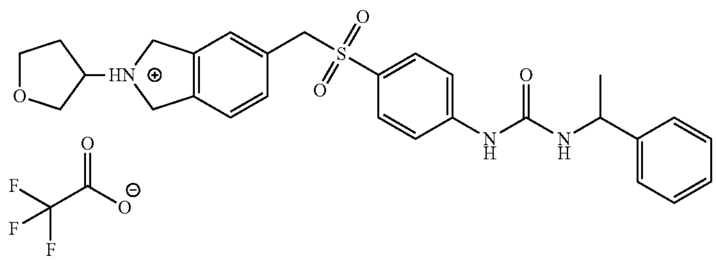 [SMILES: O=C([O-])C(F)(F)F ; CC(NC(=O)Nc1ccc(S(=O)(=O)Cc2ccc3c(c2)C[NH+](C2CCOC2)C3)cc1)c1ccccc1] | 1-(1-phenylethyl)-3-(4-(((2-(tetrahydrofuran-3-yl)isoindolin-5-yl)methyl)sulfonyl)phenyl)urea |
| H1341 | 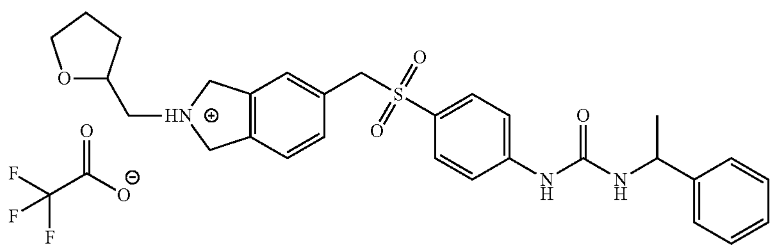 [SMILES: O=C([O-])C(F)(F)F ; CC(NC(=O)Nc1ccc(S(=O)(=O)Cc2ccc3c(c2)C[NH+](CC2CCCO2)C3)cc1)c1ccccc1] | 1-(1-phenylethyl)-3-(4-(((2-((tetrahydrofuran-2-yl)methyl)isoindolin-5-yl)methyl)sulfonyl)phenyl)urea |
| H1342 | 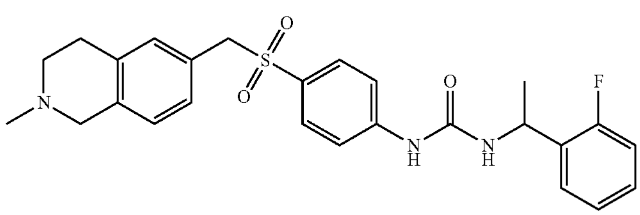 | 1-(1-(2-fluorophenyl)ethyl)-3-(4-(((2-methyl-1,2,3,4-tetrahydroisoquinolin-6-yl)methyl)sulfonyl)phenyl)urea |
| H1343 | 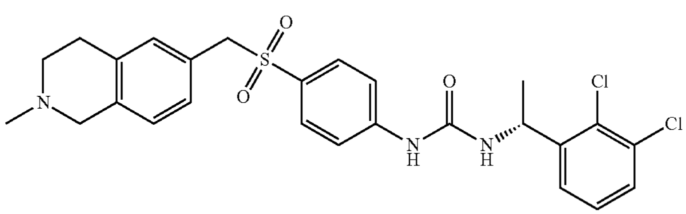 [SMILES: C[C@@H](NC(=O)Nc1ccc(S(=O)(=O)Cc2ccc3c(c2)CCN(C)C3)cc1)c1cccc(Cl)c1Cl] | (R)-1-(1-(2,3-dichlorophenyl)ethyl)-3-(4-(((2-methyl-1,2,3,4-tetrahydroisoquinolin-6-yl)methyl)sulfonyl)phenyl)urea |

-continued

| Compound No. | Chemical Structure | Chemical Name |
|---|---|---|
| H1344 | 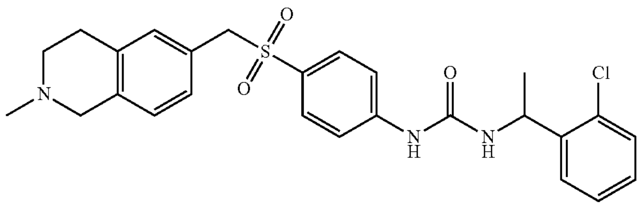 | 1-(1-(2-chlorophenyl)ethyl)-3-(4-(((2-methyl-1,2,3,4-tetrahydroisoquinolin-6-yl)methyl)sulfonyl)phenyl)urea |
| H1345 | 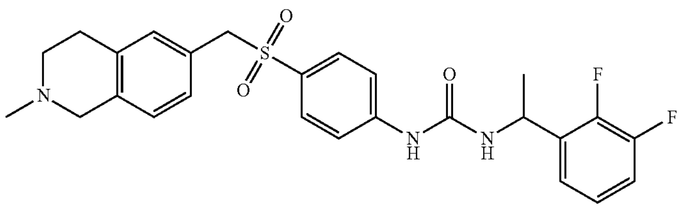 [SMILES: CC(NC(=O)Nc1ccc(S(=O)(=O)Cc2ccc3c(c2)CCN(C)C3)cc1)c1cccc(F)c1F] | 1-(1-(2,3-difluorophenyl)ethyl)-3-(4-(((2-methyl-1,2,3,4-tetrahydroisoquinolin-6-yl)methyl)sulfonyl)phenyl)urea |
| H1346 | 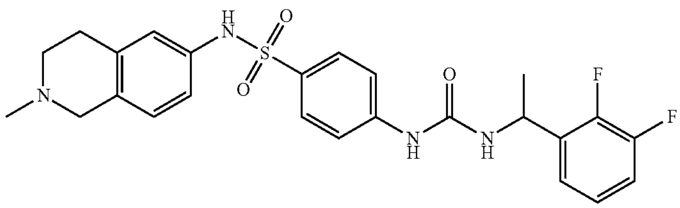 [SMILES: CC(NC(=O)Nc1ccc(S(=O)(=O)Nc2ccc3c(c2)CCN(C)C3)cc1)c1cccc(F)c1F] | 4-(3-(1-(2,3-difluorophenyl)ethyl)ureido)-N-(2-methyl-1,2,3,4-tetrahydroisoquinolin-6-yl)benzenesulfonamide |
| H1347 | 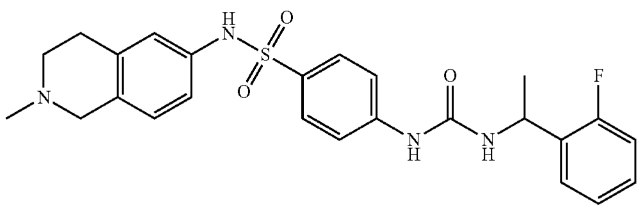 [SMILES: CC(NC(=O)Nc1ccc(S(=O)(=O)Nc2ccc3c(c2)CCN(C)C3)cc1)c1ccccc1F] | 4-(3-(1-(2-fluorophenyl)ethyl)ureido)-N-(2-methyl-1,2,3,4-tetrahydroisoquinolin-6-yl)benzenesulfonamide |
| H1348 | 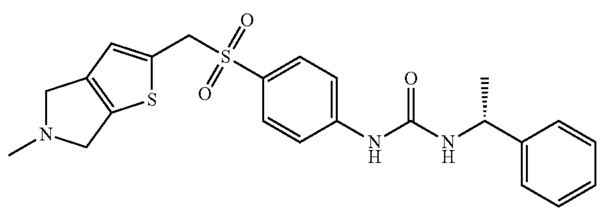 [SMILES: C[C@@H](NC(=O)Nc1ccc(S(=O)(=O)Cc2cc3c(s2)CN(C)C3)cc1)c1ccccc1] | (R)-1-(4-(((5-methyl-5,6-dihydro-4H-thieno[2,3-c]pyrrol-2-yl)methyl)sulfonyl)phenyl)-3-(1-phenylethyl)urea |
| H1349 | 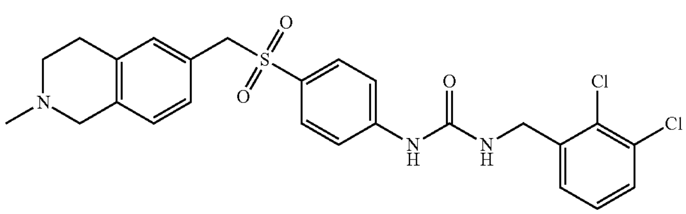 [SMILES: CN1CCc2cc(CS(=O)(=O)c3ccc(NC(=O)NCc4cccc(Cl)c4Cl)cc3)ccc2C1] | 1-(2,3-dichlorobenzyl)-3-(4-(((2-methyl-1,2,3,4-tetrahydroisoquinolin-6-yl)methyl)sulfonyl)phenyl)urea |
| H1350 | 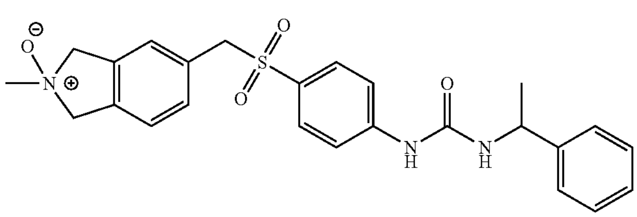 [SMILES: CC(NC(=O)Nc1ccc(S(=O)(=O)Cc2ccc3c(c2)C[N+](C)([O-])C3)cc1)c1ccccc1] | 2-methyl-5-(((4-(3-(1-phenylethyl)ureido)phenyl)sulfonyl)methyl)isoindoline 2-oxide |

-continued

| Compound No. | Chemical Structure | Chemical Name |
|---|---|---|
| H1351 | 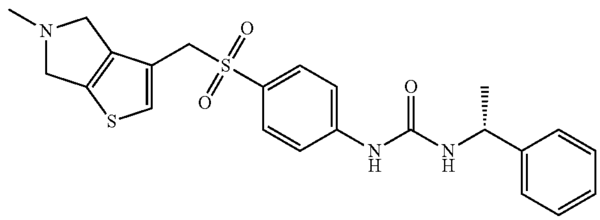 [SMILES: C[C@@H](NC(=O)Nc1ccc(S(=O)(=O)Cc2csc3c2CN(C)C3)cc1)c1ccccc1] | (R)-1-(4-(((5-methyl-5,6-dihydro-4H-thieno[2,3-c]pyrrol-3-yl)methyl)sulfonyl)phenyl)-3-(1-phenylethyl)urea |
| H1352 | 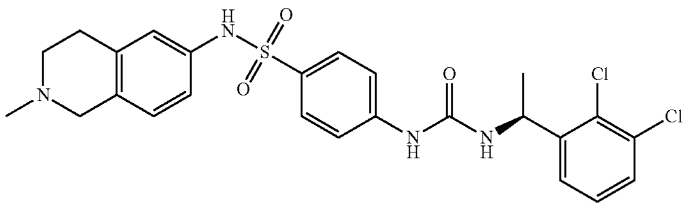 [SMILES: C[C@H](NC(=O)Nc1ccc(S(=O)(=O)Nc2ccc3c(c2)CCN(C)C3)cc1)c1cccc(Cl)c1Cl] | (S)-4-(3-(1-(2,3-dichlorophenyl)ethyl)ureido)-N-(2-methyl-1,2,3,4-tetrahydroisoquinolin-6-yl)benzenesulfonamide |
| H1355 | 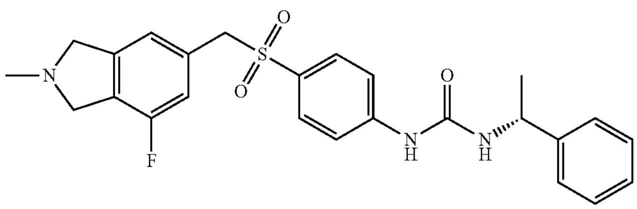 [SMILES: C[C@@H](NC(=O)Nc1ccc(S(=O)(=O)Cc2cc(F)c3c(c2)CN(C)C3)cc1)c1ccccc1] | (R)-1-(4-(((7-fluoro-2-methylisoindolin-5-yl)methyl)sulfonyl)phenyl)-3-(1-phenylethy)urea |
| H1356 | 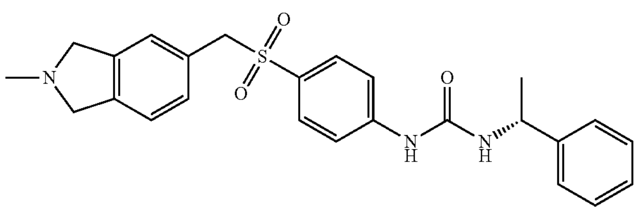 [SMILES: C[C@@H](NC(=O)Nc1ccc(S(=O)(=O)Cc2ccc3c(c2)CN(C)C3)cc1)c1ccccc1] | (R)-1-(4-(((2-methylisoindolin-5-yl)methyl)sulfonyl)phenyl)-3-(1-phenylethyl)urea |
| H1357 | 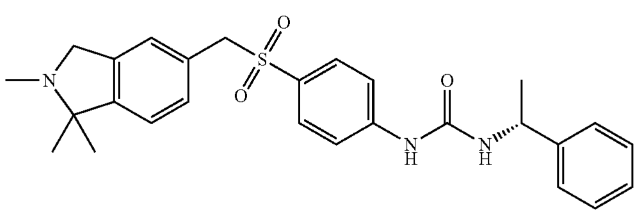 [SMILES: C[C@@H](NC(=O)Nc1ccc(S(=O)(=O)Cc2ccc3c(c2)CN(C)C3(C)C)cc1)c1ccccc1] | (R)-1-(1-phenylethyl)-3-(4-(((1,1,2-trimethylisoindolin-5-yl)methyl)sulfonyl)phenyl)urea |
| H1363 | 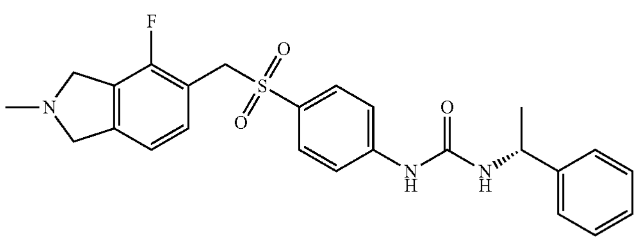 [SMILES: C[C@@H](NC(=O)Nc1ccc(S(=O)(=O)Cc2ccc3c(c2F)CN(C)C3)cc1)c1ccccc1] | (R)-1-(4-(((4-fluoro-2-methylisoindolin-5-yl)methyl)sulfonyl)phenyl)-3-(1-phenylethyl)urea |
| H1366 | 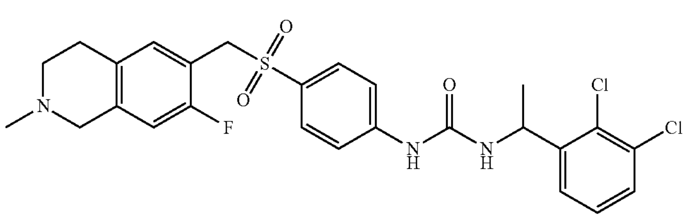 [SMILES: CC(NC(=O)Nc1ccc(S(=O)(=O)Cc2cc3c(cc2F)CN(C)CC3)cc1)c1cccc(Cl)c1Cl] | 1-(1-(2,3-dichlorophenyl)ethyl)-3-(4-(((7-fluoro-2-methyl-1,2,3,4-tetrahydroisoquinolin-6-yl)methyl)sulfonyl)phenyl)urea |

-continued

| Compound No. | Chemical Structure | Chemical Name |
|---|---|---|
| H1367 | 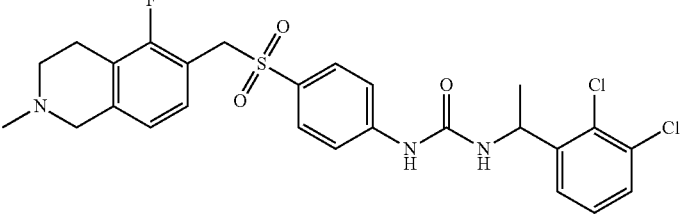 | 1-(1-(2,3-dichlorophenyl)ethyl)-3-(4-(((5-fluoro-2-methyl-1,2,3,4-tetrahydroisoquinolin-6-yl)methyl)sulfonyl)phenyl)urea |
| H1368 | 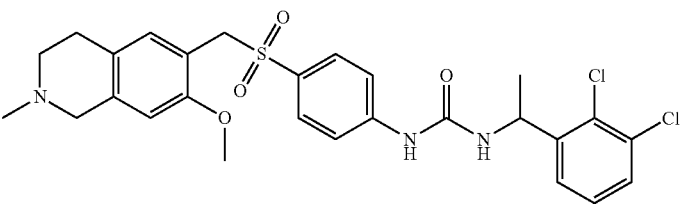 [SMILES: COc1cc2c(cc1CS(=O)(=O)c1ccc(NC(=O)NC(C)c3cccc(Cl)c3Cl)cc1)CCN(C)C2] | 1-(1-(2,3-dichlorophenyl)ethyl)-3-(4-(((7-methoxy-2-methyl-1,2,3,4-tetrahydroisoquinolin-6-yl)methyl)sulfonyl)phenyl)urea |
| H1369 | 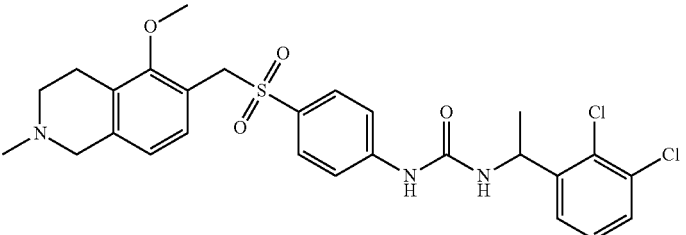 | 1-(1-(2,3-dichlorophenyl)ethyl)-3-(4-(((5-methoxy-2-methyl-1,2,3,4-tetrahydroisoquinolin-6-yl)methyl)sulfonyl)phenyl)urea |
| H1377 | 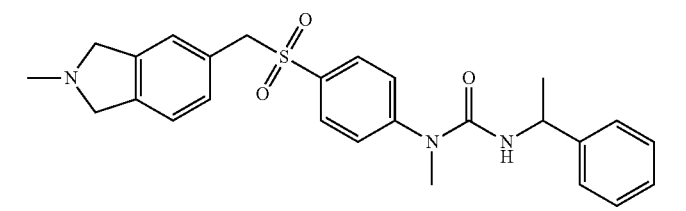 [SMILES: CC(NC(=O)N(C)c1ccc(S(=O)(=O)Cc2ccc3c(c2)CN(C)C3)cc1)c1ccccc1] | 1-methyl-1-(4-(((2-methylisoindolin-5-yl)methyl)sulfonyl)phenyl)-3-(1-phenylethyl)urea |
| H1378 | 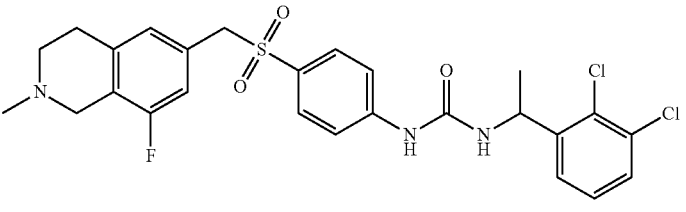 [SMILES: CC(NC(=O)Nc1ccc(S(=O)(=O)Cc2cc(F)c3c(c2)CCN(C)C3)cc1)c1cccc(Cl)c1Cl] | 1-(1-(2,3-dichlorophenyl)ethyl)-3-(4-(((8-fluoro-2-methyl-1,2,3,4-tetrahydroisoquinolin-6-yl)methyl)sulfonyl)phenyl)urea |
| H1379 | 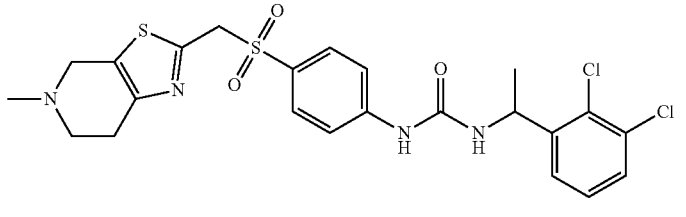 [SMILES: CC(NC(=O)Nc1ccc(S(=O)(=O)Cc2nc3c(s2)CN(C)CC3)cc1)c1cccc(Cl)c1Cl] | 1-(1-(2,3-dichlorophenyl)ethyl)-3-(4-(((5-methyl-4,5,6,7-tetrahydrothiazolo[5,4-c]pyridin-2-yl)methyl)sulfonyl)phenyl)urea |
| H1380 | 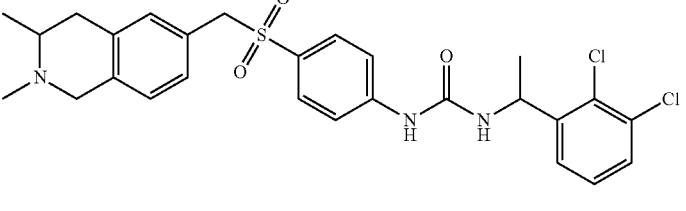 | 1-(1-(2,3-dichlorophenyl)ethyl)-3-(4-(((2,3-dimethyl-1,2,3,4-tetrahydroisoquinolin-6-yl)methyl)sulfonyl)phenyl)urea |

| Compound No. | Chemical Name |
|---|---|
| H1381 | 1-methyl-3-(4-(((2-methylisoindolin-5-yl)methyl)sulfonyl)phenyl)-1-(1-phenylethyl)urea |
| H1382 | 1-(4-((isoindolin-5-ylmethyl)sulfonyl)phenyl)-3-(1-(2-methoxyphenyl)ethyl)urea |
| H1383 | 1-(4-((isoindolin-5-ylmethyl)sulfonyl)-2-methoxyphenyl)-3-(1-phenylethyl)urea |
| H1384 | 1-(1-(2,3-dichlorophenyl)ethyl)-3-(4-(((6-methyl-4,5,6,7-tetrahydrothieno[2,3-c]pyridin-2-yl)methyl)sulfonyl)phenyl)urea |
| H1385 | 1-(1-(2,3-dichlorophenyl)ethyl)-3-(4-(((7-fluoro-1,2,3,4-tetrahydroisoquinolin-6-yl)methyl)sulfonyl)phenyl)urea |
| H1386 | 1-(2-methoxy-4-(((1,2,3,4-tetrahydroisoquinolin-6-yl)methyl)sulfonyl)phenyl)-3-(1-phenylethyl)urea |

-continued

| Compound No. | Chemical Structure | Chemical Name |
|---|---|---|
| H1387 | 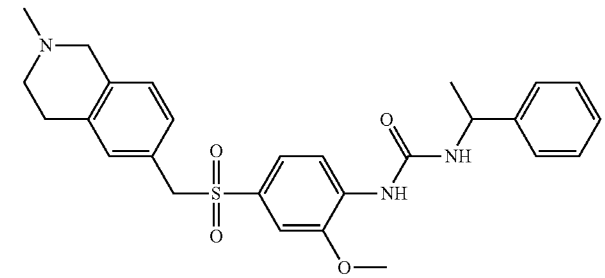 [SMILES: COc1cc(S(=O)(=O)Cc2ccc3c(c2)CCN(C)C3)ccc1NC(=O)NC(C)c1ccccc1] | 1-(2-methoxy-4-(((2-methyl-1,2,3,4-tetrahydroisoquinolin-6-yl)methyl)sulfonyl)phenyl)-3-(1-phenylethyl)urea |
| H1388 | 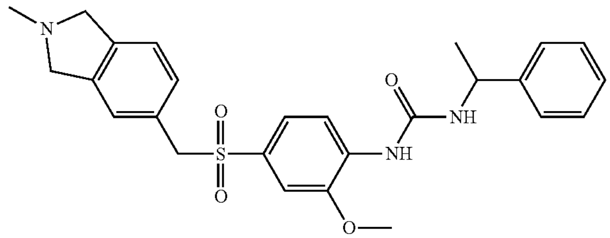 [SMILES: COc1cc(S(=O)(=O)Cc2ccc3c(c2)CN(C)C3)ccc1NC(=O)NC(C)c1ccccc1] | 1-(2-methoxy-4-(((2-methylisoindolin-5-yl)methyl)sulfonyl)phenyl)-3-(1-phenylethyl)urea |
| H1389 | 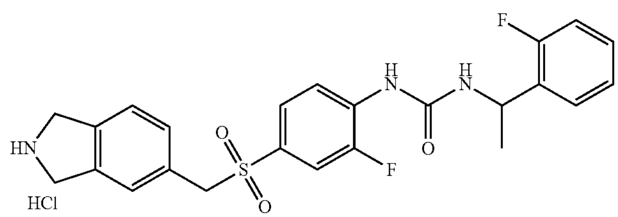 [SMILES: CC(NC(=O)Nc1ccc(S(=O)(=O)Cc2ccc3c(c2)CNC3)cc1F)c1ccccc1F ; Cl] | 1-(2-fluoro-4-((isoindolin-5-ylmethyl)sulfonyl)phenyl)-3-(1-(2-fluorophenyl)ethyl)urea |
| H1390 | 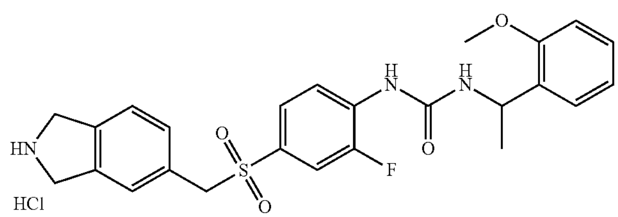 [SMILES: Cl ; COc1ccccc1C(C)NC(=O)Nc1ccc(S(=O)(=O)Cc2ccc3c(c2)CNC3)cc1F] | 1-(2-fluoro-4-((isoindolin-5-ylmethyl)sulfonyl)phenyl)-3-(1-(2-methoxyphenyl)ethyl)urea |
| H1391 | 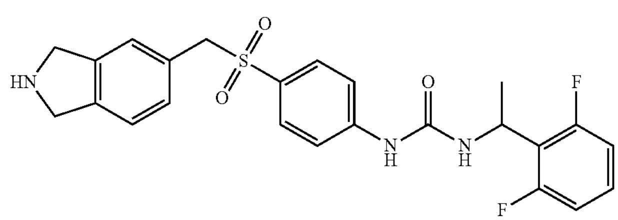 [SMILES: CC(NC(=O)Nc1ccc(S(=O)(=O)Cc2ccc3c(c2)CNC3)cc1)c1c(F)cccc1F] | 1-(1-(2,6-difluorophenyl)ethyl)-3-(4-((isoindolin-5-ylmethyl)sulfonyl)phenyl)urea |
| H1392 | 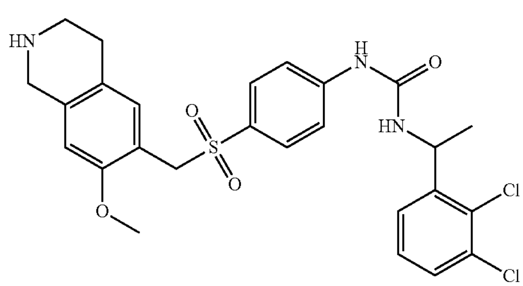 [SMILES: COc1cc2c(cc1CS(=O)(=O)c1ccc(NC(=O)NC(C)c3cccc(Cl)c3Cl)cc1)CCNC2] | 1-(1-(2,3-dichlorophenyl)ethyl)-3-(4-(((7-methoxy-1,2,3,4-tetrahydroisoquinolin-6-yl)methyl)sulfoyl)phenyl)urea |

-continued

| Compound No. | Chemical Structure | Chemical Name |
|---|---|---|
| H1393 | 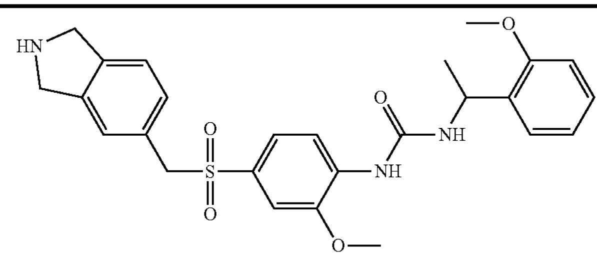 | 1-(4-((isoindolin-5-ylmethyl)sulfonyl)-2-methoxyphenyl)-3-(1-(2-methoxyphenyl)ethyl)urea |
| H1394 | 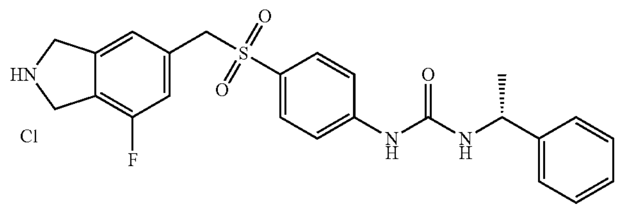 [SMILES: Cl ; C[C@@H](NC(=O)Nc1ccc(S(=O)(=O)Cc2cc(F)c3c(c2)CNC3)cc1)c1ccccc1] | (R)-1-(4-(((7-fluoroisoindolin-5-yl)methyl)sulfonyl)phenyl)-3-(1-phenylethyl)urea |
| H1396 | 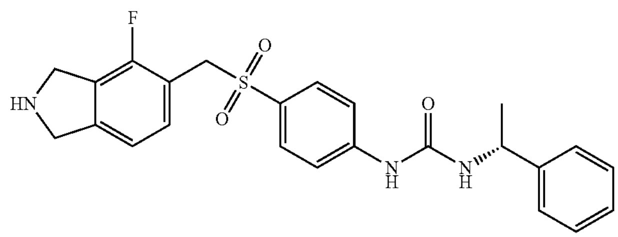 [SMILES: C[C@@H](NC(=O)Nc1ccc(S(=O)(=O)Cc2ccc3c(c2F)CNC3)cc1)c1ccccc1] | (R)-1-(4-(((4-fluoroisoindolin-5-yl)methyl)sulfonyl)phenyl)-3-(1-phenylethyl)urea |
| H1398 | 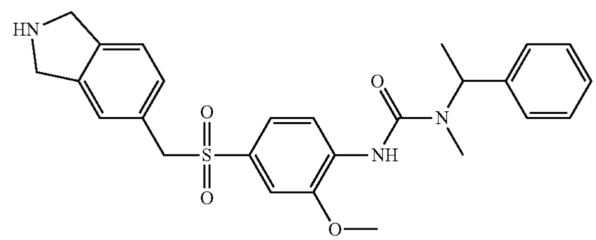 [SMILES: COc1cc(S(=O)(=O)Cc2ccc3c(c2)CNC3)ccc1NC(=O)N(C)C(C)c1ccccc1] | 3-(4-((isoindolin-5-ylmethyl)sulfonyl)-2-methoxyphenyl)-1-methyl-1-(1-phenylethyl)urea |
| H1399 | 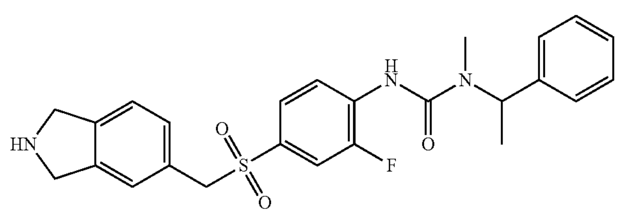 [SMILES: CC(c1ccccc1)N(C)C(=O)Nc1ccc(S(=O)(=O)Cc2ccc3c(c2)CNC3)cc1F] | 3-(2-fluoro-4-((isoindolin-5-ylmethyl)sulfonyl)phenyl)-1-methyl-1-(1-phenylethyl)urea |
| H1400 | 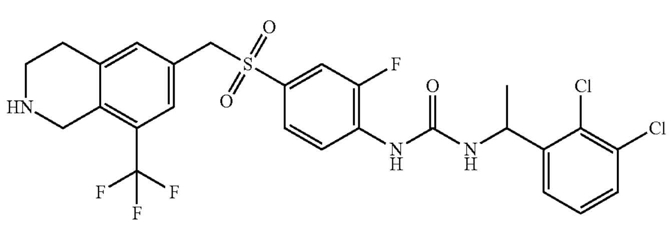 [SMILES: CC(NC(=O)Nc1ccc(S(=O)(=O)Cc2cc3c(c(C(F)(F)F)c2)CNCC3)cc1F)c1cccc(Cl)c1Cl] | 1-(1-(2,3-dichlorophenyl)ethyl)-3-(2-fluoro-4-(((8-(trifluoromethyl)-1,2,3,4-tetrahydroisoquinolin-6-yl)methyl)sulfonyl)phenyl)urea |
| H1401 | 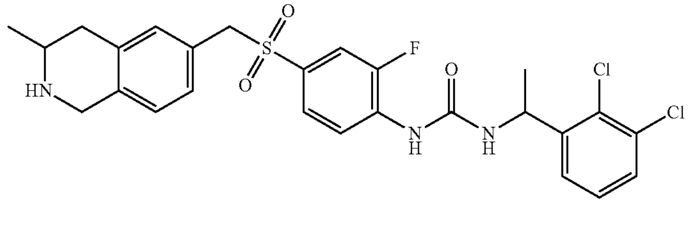 [SMILES: CC1Cc2cc(CS(=O)(=O)c3ccc(NC(=O)NC(C)c4cccc(Cl)c4Cl)c(F)c3)ccc2CN1] | 1-(1-(2,3-dichlorophenyl)ethyl)-3-(2-fluoro-4-(((3-methyl-1,2,3,4-tetrahydroisoquinolin-6-yl)methyl)sulfonyl)phenyl)urea |

-continued

| Compound No. | Chemical Structure | Chemical Name |
| --- | --- | --- |
| H1402 | 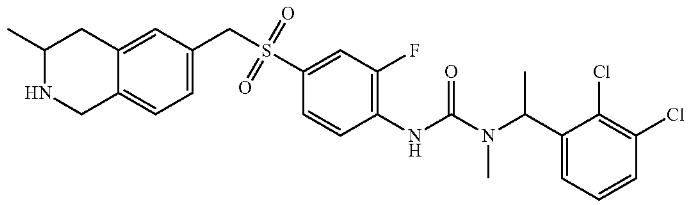 [SMILES: CC1Cc2cc(CS(=O)(=O)c3ccc(NC(=O)N(C)C(C)c4cccc(Cl)c4Cl)c(F)c3)ccc2CN1] | 1-(1-(2,3-dichlorophenyl)ethyl)-3-(2-fluoro-4-(((3-methyl-1,2,3,4-tetrahydroisoquinolin-6-yl)methyl)sulfonyl)phenyl)-1-methylurea |
| H1403 | 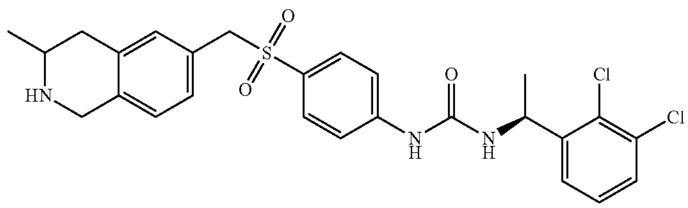 [SMILES: CC1Cc2cc(CS(=O)(=O)c3ccc(NC(=O)N[C@@H](C)c4cccc(Cl)c4Cl)cc3)ccc2CN1] | 1-((S)-1-(2,3-dichlorophenyl)ethyl)-3-(4-(((3-methyl-1,2,3,4-tetrahydroisoquinolin-6-yl)methyl)sulfonyl)phenyl)urea |
| H1404 | 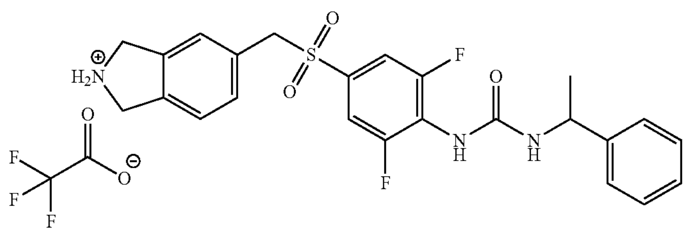 [SMILES: O=C([O-])C(F)(F)F ; CC(NC(=O)Nc1c(F)cc(S(=O)(=O)Cc2ccc3c(c2)C[NH2+]C3)cc1F)c1ccccc1] | 1-(2,6-difluoro-4-((isoindolin-5-ylmethyl)sulfonyl)phenyl)-3-(1-phenylethyl)urea |
| H1405 | 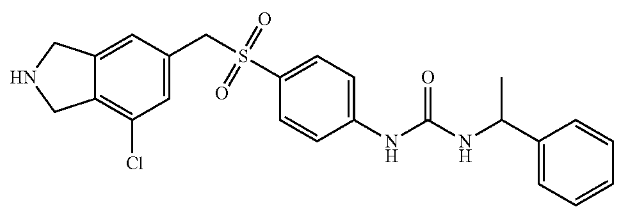 [SMILES: CC(NC(=O)Nc1ccc(S(=O)(=O)Cc2cc(Cl)c3c(c2)CNC3)cc1)c1ccccc1] | 1-(4-(((7-chloroisoindolin-5-yl)methyl)sulfonyl)phenyl)-3-(1-phenylethyl)urea |
| H1406 | 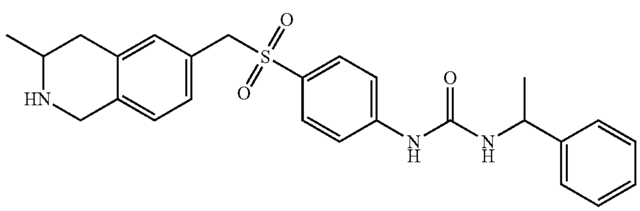 [SMILES: CC1Cc2cc(CS(=O)(=O)c3ccc(NC(=O)NC(C)c4ccccc4)cc3)ccc2CN1] | 1-(4-(((3-methyl-1,2,3,4-tetrahydroisoquinolin-6-yl)methyl)sulfonyl)phenyl)-3-(1-phenylethyl)urea |
| H1407 | 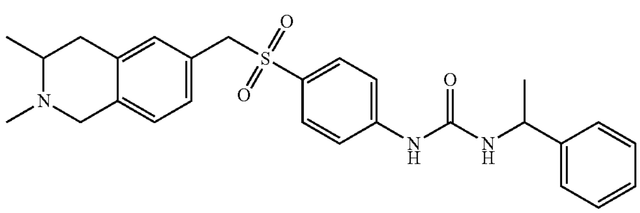 [SMILES: CC(NC(=O)Nc1ccc(S(=O)(=O)Cc2ccc3c(c2)CC(C)N(C)C3)cc1)c1ccccc1] | 1-(4-(((2,3-dimethyl-1,2,3,4-tetrahydroisoquinolin-6-yl)methyl)sulfonyl)phenyl)-3-(1-phenylethyl)urea |
| H1408 | 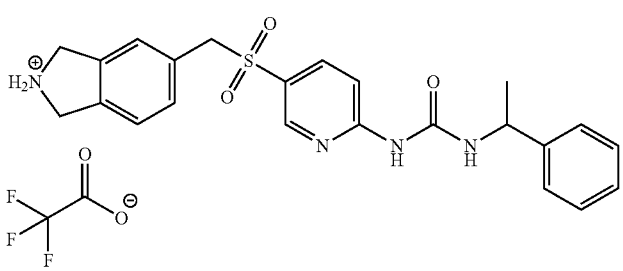 [SMILES: O=C([O-])C(F)(F)F ; CC(NC(=O)Nc1ccc(S(=O)(=O)Cc2ccc3c(c2)C[NH2+]C3)cn1)c1ccccc1] | 1-(5-((isoindolin-5-ylmethyl)sulfonyl)pyridin-2-yl)-3-(1-phenylethyl)urea |

| Compound No. | Chemical Structure | Chemical Name |
| --- | --- | --- |
| H1409 | 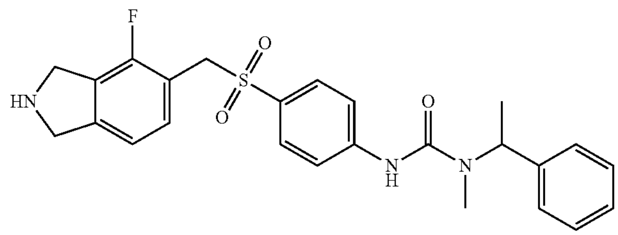 [SMILES: CC(c1ccccc1)N(C)C(=O)Nc1ccc(S(=O)(=O)Cc2ccc3c(c2F)CNC3)cc1] | 3-(4-(((4-fluoroisoindolin-5-yl)methyl)sulfonyl)phenyl)-1-methyl-1-(1-phenylethyl)urea |
| H1410 | 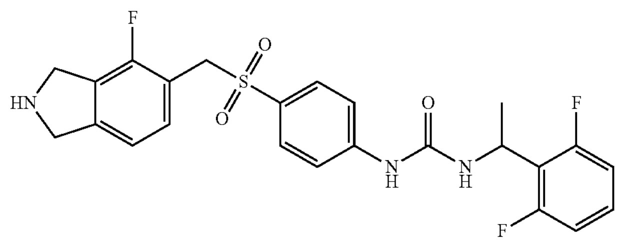 [SMILES: CC(NC(=O)Nc1ccc(S(=O)(=O)Cc2ccc3c(c2F)CNC3)cc1)c1c(F)cccc1F] | 1-(1-(2,6-difluorophenyl)ethyl)-3-(4-(((4-fluoroisoindolin-5-yl)methyl)sulfonyl)phenyl)urea |
| H1411 | 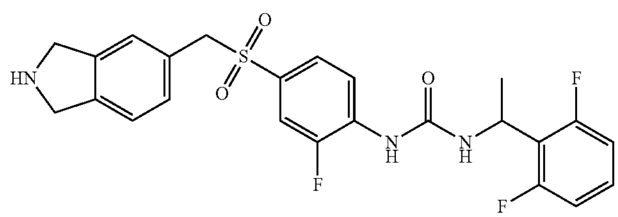 [SMILES: CC(NC(=O)Nc1ccc(S(=O)(=O)Cc2ccc3c(c2)CNC3)cc1F)c1c(F)cccc1F] | 1-(1-(2,6-difluorophenyl)ethyl)-3-(2-fluoro-4-((isoindolin-5-ylmethyl)sulfonyl)phenyl)urea |
| H1412 | 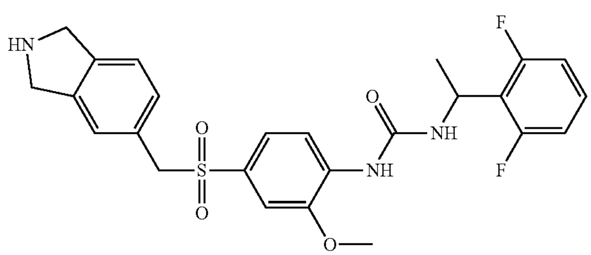 [SMILES: COc1cc(S(=O)(=O)Cc2ccc3c(c2)CNC3)ccc1NC(=O)NC(C)c1c(F)cccc1F] | 1-(1-(2,6-difluorophenyl)ethyl)-3-(4-((isoindolin-5-ylmethyl)sulfonyl)-2-methoxyphenyl)urea |
| H1413 | 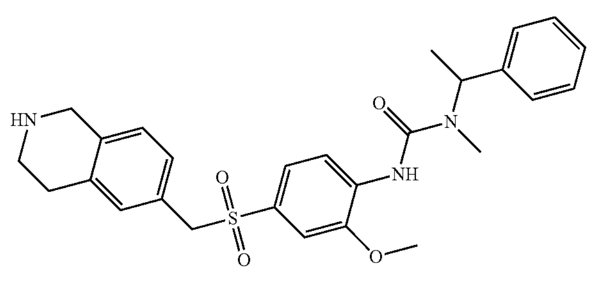 [SMILES: COc1cc(S(=O)(=O)Cc2ccc3c(c2)CCNC3)ccc1NC(=O)N(C)C(C)c1ccccc1] | 3-(2-methoxy-4-(((1,2,3,4-tetrahydroisoquinolin-6-yl)methyl)sulfonyl)phenyl)-1-methyl-1-(1-phenylethyl)urea |
| H1414 | 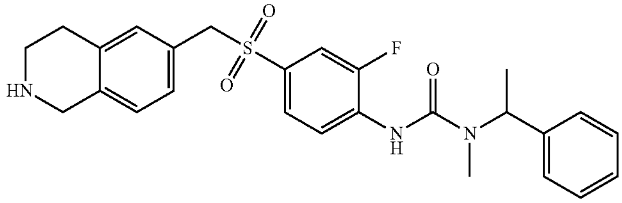 [SMILES: CC(c1ccccc1)N(C)C(=O)Nc1ccc(S(=O)(=O)Cc2ccc3c(c2)CCNC3)cc1F] | 3-(2-fluoro-4-(((1,2,3,4-tetrahydroisoquinolin-6-yl)methyl)sulfonyl)phenyl)-1-methyl-1-(1-phenylethyl)urea |

| Compound No. | Chemical Name |
|---|---|
| H1415 | 1-(1-(2,3-dichlorophenyl)ethyl)-3-(2-methoxy-4-(((1,2,3,4-tetrahydroisoquinolin-6-yl)methyl)sulfonyl)phenyl)urea |
| H1416 | 1-benzyl-1-methyl-3-(4-(((3-methyl-1,2,3,4-tetrahydroisoquinolin-6-yl)methyl)sulfonyl)phenyl)urea |
| H1417 | (R)-1-(1-(2,3-dichloro-4-methoxyphenyl)ethyl)-3-(4-(((2-methyl-1,2,3,4-tetrahydroisoquinolin-6-yl)methyl)sulfonyl)phenyl)urea |
| H1420 | 1-(1-(2-fluorophenyl)ethyl)-3-(4-((isoindolin-5-ylmethyl)sulfonyl)-2-methoxyphenyl)urea |
| H1421 | 1-(1-(2,3-dichlorophenyl)ethyl)-3-(4-((isoindolin-5-ylmethyl)sulfonyl)-2-methoxyphenyl)urea |
| H1422 | (R)-1-(1-(2,3-dichloro-4-methoxyphenyl)ethyl)-3-(2-methoxy-4-(((2-methyl-1,2,3,4-tetrahydroisoquinolin-6-yl)methyl)sulfonyl)phenyl)urea |

| Compound No. | Chemical Name |
|---|---|
| H1423 | (R)-1-(1-(2,3-dichloro-4-methoxyphenyl)ethyl)-3-(2-fluoro-4-(((2-methyl-1,2,3,4-tetrahydroisoquinolin-6-yl)methyl)sulfonyl)phenyl)urea |
| H1424 | 1-(1-(2,3-dichlorophenyl)ethyl)-3-(4-(((8-fluoro-1,2,3,4-tetrahydroisoquinolin-6-yl)methyl)sulfonyl)-2-methoxyphenyl)urea |
| H1426 | 1-(1-(2-fluorophenyl)ethyl)-3-(2-methoxy-4-(((2-methylisoindolin-5-yl)methyl)sulfonyl)phenyl)urea |
| H1427 | 1-(1-(2,3-dichlorophenyl)ethyl)-3-(2-methoxy-4-(((2-methylisoindolin-5-yl)methyl)sulfonyl)phenyl)urea |
| H1428 | 1-(1-(2,3-dichlorophenyl)ethyl)-3-(2-methoxy-4-(((2-methyl-1,2,3,4-tetrahydroisoquinolin-6-yl)methyl)sulfonyl)phenyl)urea |
| H1429 | 1-(1-(2,6-difluorophenyl)ethyl)-3-(4-(((2-methylisoindolin-5-yl)methyl)sulfonyl)phenyl)urea |
| H1431 | 1-(1-(2,3-dichlorophenyl)ethyl)-3-(4-(((2,3-dimethyl-1,2,3,4-tetrahydroisoquinolin-6-yl)methyl)sulfonyl)-2-methoxyphenyl)urea |

-continued

| Compound No. | Chemical Structure | Chemical Name |
|---|---|---|
| H1436 | 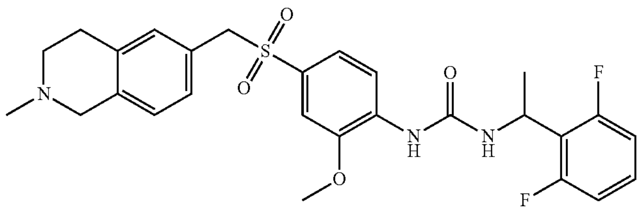 [SMILES: COc1cc(S(=O)(=O)Cc2ccc3c(c2)CCN(C)C3)ccc1NC(=O)NC(C)c1c(F)cccc1F] | 1-(1-(2,6-difluorophenyl)ethyl)-3-(2-methoxy-4-(((2-methyl-1,2,3,4-tetrahydroisoquinolin-6-yl)methyl)sulfonyl)phenyl)urea |
| H1437 | 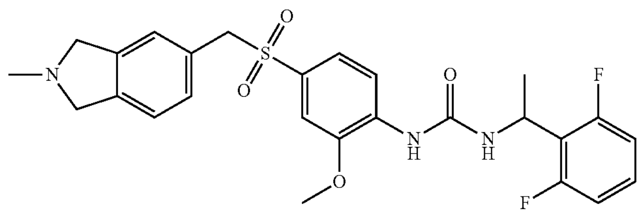 [SMILES: COc1cc(S(=O)(=O)Cc2ccc3c(c2)CN(C)C3)ccc1NC(=O)NC(C)c1c(F)cccc1F] | 1-(1-(2,6-difluorophenyl)ethyl)-3-(2-methoxy-4-(((2-methylisoindolin-5-yl)methyl)sulfonyl)phenyl)urea |
| H1438 | 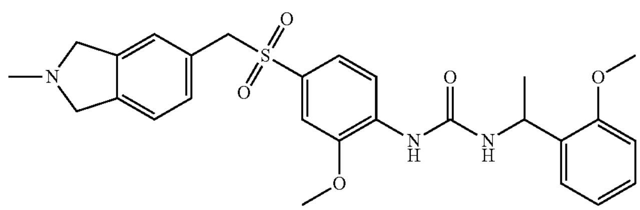 | 1-(2-methoxy-4-(((2-methylisoindolin-5-yl)methyl)sulfonyl)phenyl)-3-(1-(2-methoxyphenyl)ethyl)urea |
| H1439 | 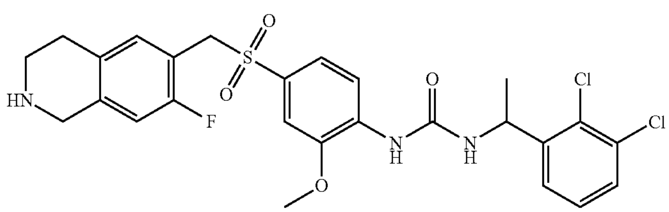 [SMILES: COc1cc(S(=O)(=O)Cc2cc3c(cc2F)CNCC3)ccc1NC(=O)NC(C)c1cccc(Cl)c1Cl] | 1-(1-(2,3-dichlorophenyl)ethyl)-3-(4-(((7-fluoro-1,2,3,4-tetrahydroisoquinolin-6-yl)methyl)sulfonyl)-2-methoxyphenyl)urea |
| H1440 | 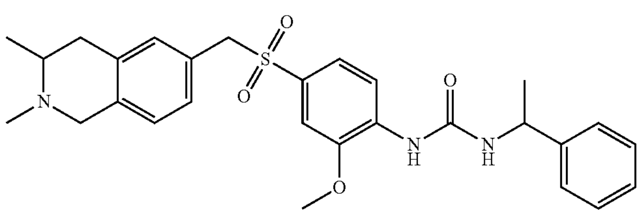 [SMILES: COc1cc(S(=O)(=O)Cc2ccc3c(c2)CC(C)N(C)C3)ccc1NC(=O)NC(C)c1ccccc1] | 1-(4-(((2,3-dimethyl-1,2,3,4-tetrahydroisoquinolin-6-yl)methyl)sulfonyl)-2-methoxyphenyl)-3-(1-phenylethyl)urea |
| H1441 | 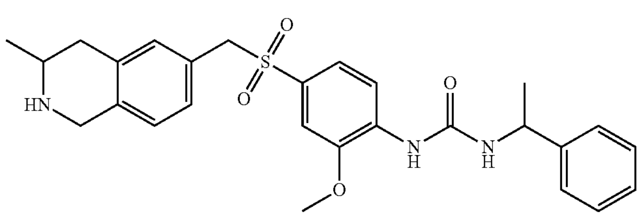 [SMILES: COc1cc(S(=O)(=O)Cc2ccc3c(c2)CC(C)NC3)ccc1NC(=O)NC(C)c1ccccc1] | 1-(2-methoxy-4-(((3-methyl-1,2,3,4-tetrahydroisoquinolin-6-yl)methyl)sulfonyl)phenyl)-3-(1-phenylethyl)urea |
| H1442 | 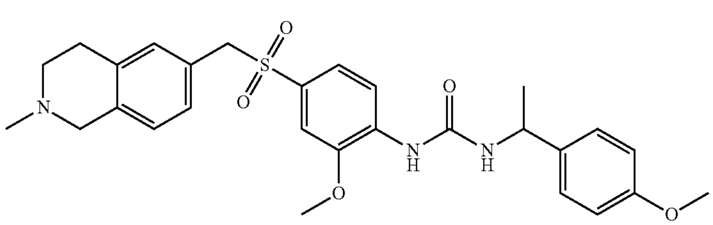 | 1-(2-methoxy-4-(((2-methyl-1,2,3,4-tetrahydroisoquinolin-6-yl)methyl)sulfonyl)phenyl)-3-(1-(4-methoxyphenyl)ethyl)urea |

-continued

| Compound No. | Chemical Structure | Chemical Name |
|---|---|---|
| H1443 | 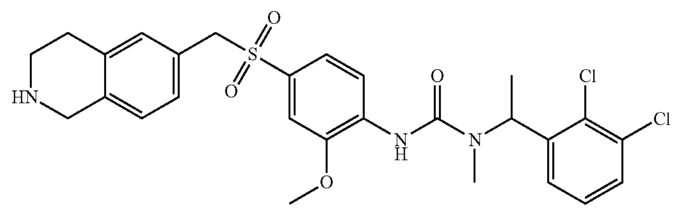 [SMILES: COc1cc(S(=O)(=O)Cc2ccc3c(c2)CCNC3)ccc1NC(=O)N(C)C(C)c1cccc(Cl)c1Cl] | 1-(1-(2,3-dichlorophenyl)ethyl)-3-(2-methoxy-4-(((1,2,3,4-tetrahydroisoquinolin-6-yl)methyl)sulfonyl)phenyl)-1-methylurea |
| H1444 | 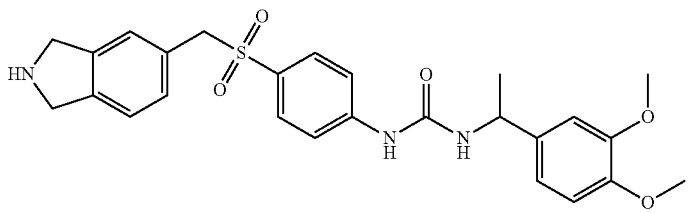 [SMILES: COc1ccc(C(C)NC(=O)Nc2ccc(S(=O)(=O)Cc3ccc4c(c3)CNC4)cc2)cc1OC] | 1-(1-(3,4-dimethoxyphenyl)ethyl)-3-(4-((isoindolin-5-ylmethyl)sulfonyl)phenyl)urea |
| H1445 | 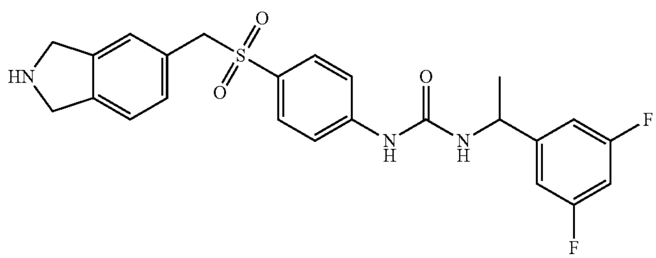 [SMILES: CC(NC(=O)Nc1ccc(S(=O)(=O)Cc2ccc3c(c2)CNC3)cc1)c1cc(F)cc(F)c1] | 1-(1-(3,5-difluorophenyl)ethyl)-3-(4-((isoindolin-5-ylmethyl)sulfonyl)phenyl)urea |
| H1446 | 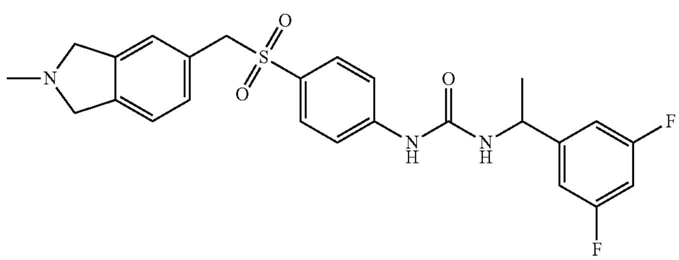 [SMILES: CC(NC(=O)Nc1ccc(S(=O)(=O)Cc2ccc3c(c2)CN(C)C3)cc1)c1cc(F)cc(F)c1] | 1-(1-(3,5-difluorophenyl)ethyl)-3-(4-(((2-methylisoindolin-5-yl)methyl)sulfonyl)phenyl)urea |
| H1447 | 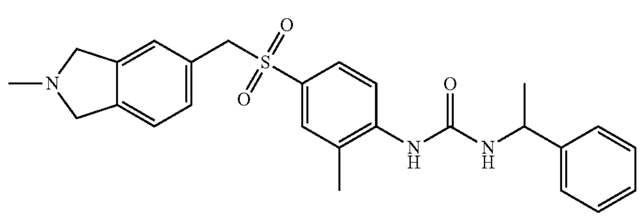 [SMILES: Cc1cc(S(=O)(=O)Cc2ccc3c(c2)CN(C)C3)ccc1NC(=O)NC(C)c1ccccc1] | 1-(2-methyl-4-(((2-methylisoindolin-5-yl)methyl)sulfonyl)phenyl)-3-(1-phenylethyl)urea |
| H1448 | 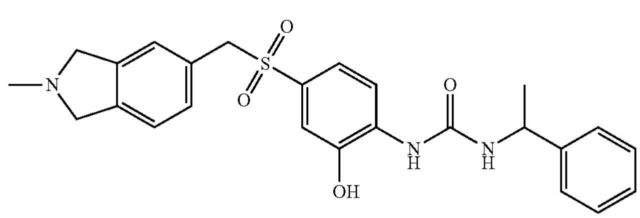 [SMILES: CC(NC(=O)Nc1ccc(S(=O)(=O)Cc2ccc3c(c2)CN(C)C3)cc1O)c1ccccc1] | 1-(2-hydroxy-4-(((2-methylisoindolin-5-yl)methyl)sulfonyl)phenyl)-3-(1-phenylethyl)urea |

-continued

| Compound No. | Chemical Structure | Chemical Name |
| --- | --- | --- |
| H1449 | 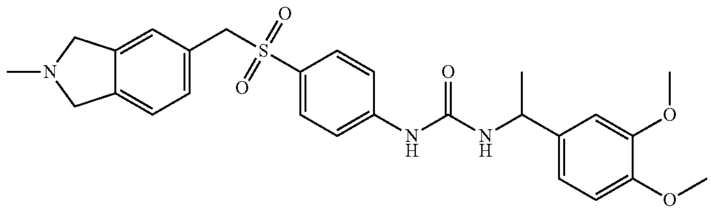 | 1-(1-(3,4-dimethoxyphenyl)ethyl)-3-(4-(((2-methylisoindolin-5-yl)methyl)sulfonyl)phenyl)urea |
| H1450 | 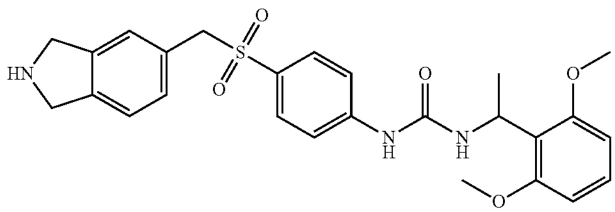 [SMILES: COc1cccc(OC)c1C(C)NC(=O)Nc1ccc(S(=O)(=O)Cc2ccc3c(c2)CNC3)cc1] | 1-(1-(2,6-dimethoxyphenyl)ethyl)-3-(4-((isoindolin-5-ylmethyl)sulfonyl)phenyl)urea |
| H1451 | 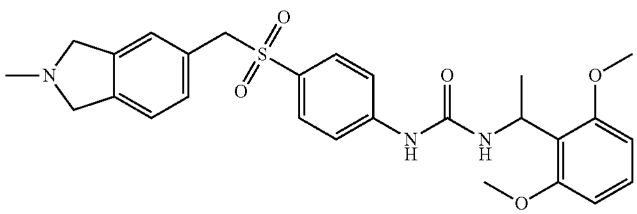 | 1-(1-(2,6-dimethoxyphenyl)ethyl)-3-(4-(((2-methylisoindolin-5-yl)methyl)sulfonyl)phenyl)urea |
| H1454 | 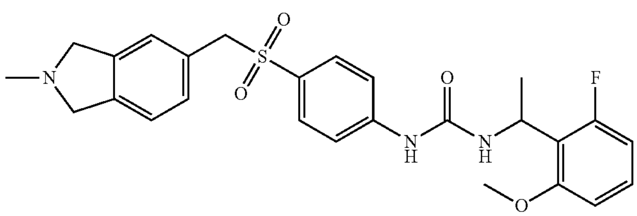 [SMILES: COc1cccc(F)c1C(C)NC(=O)Nc1ccc(S(=O)(=O)Cc2ccc3c(c2)CN(C)C3)cc1] | 1-(1-(2-fluoro-6-methoxyphenyl)ethyl)-3-(4-(((2-methylisoindolin-5-yl)methyl)sulfonyl)phenyl)urea |
| H1455 | 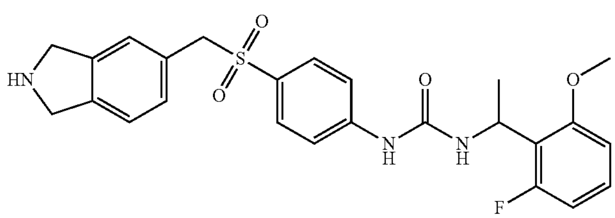 [SMILES: COc1cccc(F)c1C(C)NC(=O)Nc1ccc(S(=O)(=O)Cc2ccc3c(c2)CNC3)cc1] | 1-(1-(2-fluoro-6-methoxyphenyl)ethyl)-3-(4-((isoindolin-5-ylmethyl)sulfonyl)phenyl)urea |
| H1456 | 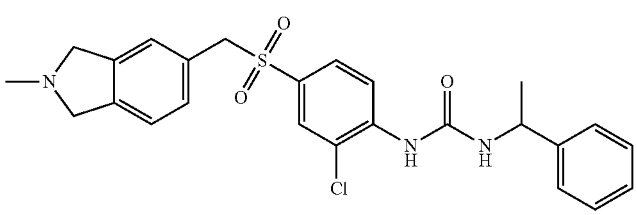 [SMILES: CC(NC(=O)Nc1ccc(S(=O)(=O)Cc2ccc3c(c2)CN(C)C3)cc1Cl)c1ccccc1] | 1-(2-chloro-4-(((2-methylisoindolin-5-yl)methyl)sulfonyl)phenyl)-3-(1-phenylethyl)urea |
| H1457 | 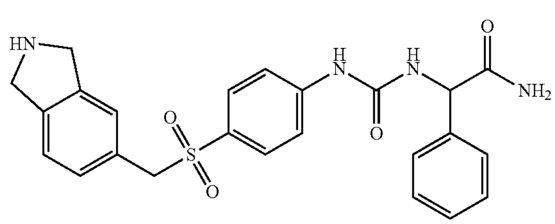 [SMILES: NC(=O)C(NC(=O)Nc1ccc(S(=O)(=O)Cc2ccc3c(c2)CNC3)cc1)c1ccccc1] | 2-(3-(4-((isoindolin-5-ylmethyl)sulfonyl)phenyl)ureido-2-phenylacetamide |

-continued

| Compound No. | Chemical Structure | Chemical Name |
|---|---|---|
| H1458 | 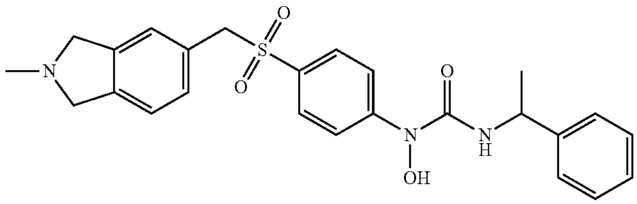 [SMILES: CC(NC(=O)N(O)c1ccc(S(=O)(=O)Cc2ccc3c(c2)CN(C)C3)cc1)c1ccccc1] | 1-hydroxy-1-(4-(((2-methylisoindolin-5-yl)methyl)sulfonyl)phenyl)-3-(1-phenylethyl)urea |
| H1459 | 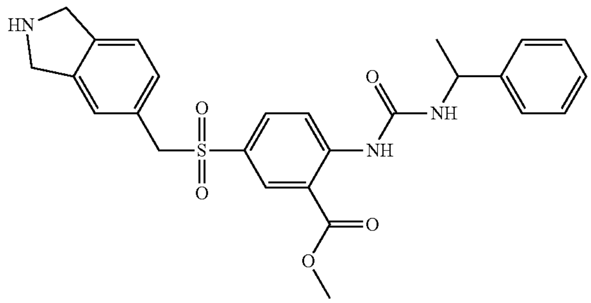 [SMILES: COC(=O)c1cc(S(=O)(=O)Cc2ccc3c(c2)CNC3)ccc1NC(=O)NC(C)c1ccccc1] | methyl 5-((isoindolin-5-ylmethyl)sulfonyl)-2-(3-(1-phenylethyl)ureido)benzoate |
| H1460 | 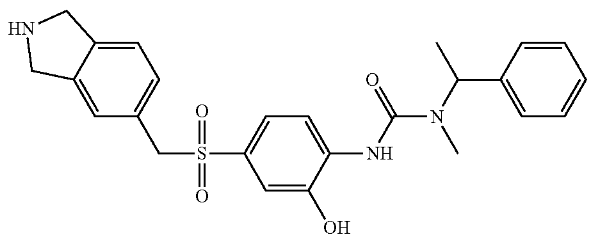 [SMILES: CC(c1ccccc1)N(C)C(=O)Nc1ccc(S(=O)(=O)Cc2ccc3c(c2)CNC3)cc1O] | 3-(2-hydroxy-4-((isoindolin-5-ylmethyl)sulfonyl)phenyl)-1-methyl-1-(1-phenylethyl)urea |
| H1461 | 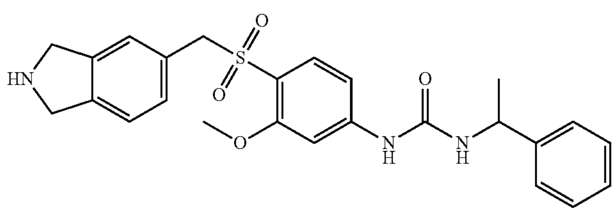 [SMILES: COc1cc(NC(=O)NC(C)c2ccccc2)ccc1S(=O)(=O)Cc1ccc2c(c1)CNC2] | 1-(4-((isoindolin-5-ylmethyl)sulfonyl)-3-methoxyphenyl)-3-(1-phenylethyl)urea |
| H1462 | 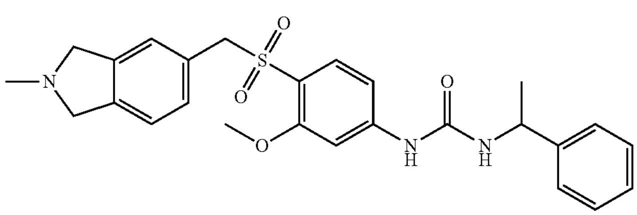 [SMILES: COc1cc(NC(=O)NC(C)c2ccccc2)ccc1S(=O)(=O)Cc1ccc2c(c1)CN(C)C2] | 1-(3-methoxy-4-(((2-methylisoindolin-5-yl)methyl)sulfonyl)phenyl)-3-(1-phenylethyl)urea |
| H1463 | 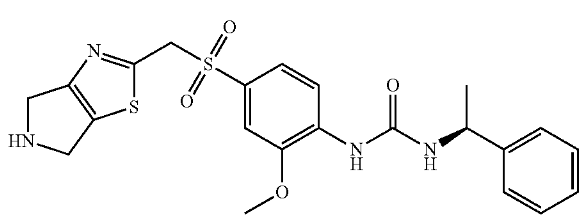 [SMILES: COc1cc(S(=O)(=O)Cc2nc3c(s2)CNC3)ccc1NC(=O)N[C@@H](C)c1ccccc1] | (S)-1-(4-(((5,6-dihydro-4H-pyrrolo[3,4-d]thiazol-2-yl)methyl)sulfonyl)-2-methoxyphenyl)-3-(1-phenylethyl)urea |

-continued

| Compound No. | Chemical Structure | Chemical Name |
|---|---|---|
| H1464 | 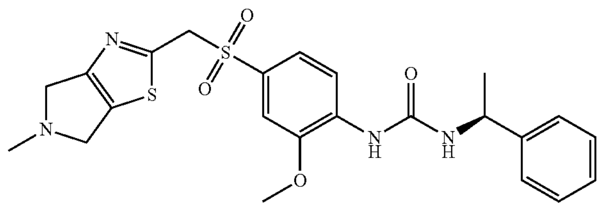 [SMILES: COc1cc(S(=O)(=O)Cc2nc3c(s2)CN(C)C3)ccc1NC(=O)N[C@@H](C)c1ccccc1] | (S)-1-(2-methoxy-4-(((5-methyl-5,6-dihydro-4H-pyrrolo[3,4-d]thiazol-2-yl)methyl)sulfonyl)phenyl)-3-(1-phenylethyl)urea |
| H1465 | 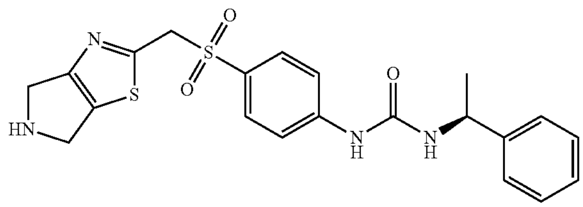 [SMILES: C[C@H](NC(=O)Nc1ccc(S(=O)(=O)Cc2nc3c(s2)CNC3)cc1)c1ccccc1] | (S)-1-(4-(((5,6-dihydro-4H-pyrrolo[3,4-d]thiazol-2-yl)methyl)sulfonyl)phenyl)-3-(1-phenylethyl)urea |
| H1466 | 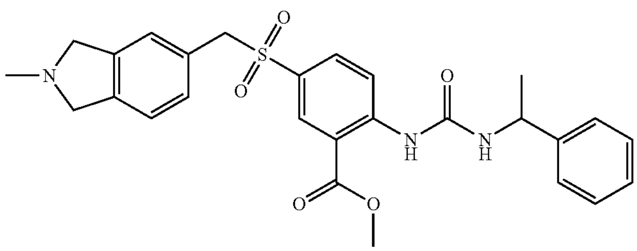 [SMILES: COC(=O)c1cc(S(=O)(=O)Cc2ccc3c(c2)CN(C)C3)ccc1NC(=O)NC(C)c1ccccc1] | methyl 5-(((2-methylisoindolin-5-yl)methyl)sulfonyl)-2-(3-(1-phenylethyl)ureido)benzoate |
| H1467 | 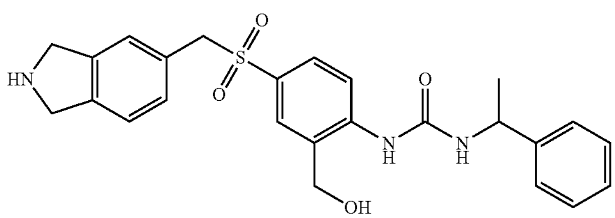 [SMILES: CC(NC(=O)Nc1ccc(S(=O)(=O)Cc2ccc3c(c2)CNC3)cc1CO)c1ccccc1] | 1-(2-(hydroxymethyl)-4-((isoindolin-5-ylmethyl)sulfonyl)phenyl)-3-(1-phenylethyl)urea |
| H1468 | 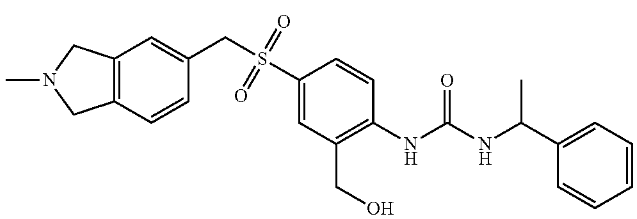 [SMILES: CC(NC(=O)Nc1ccc(S(=O)(=O)Cc2ccc3c(c2)CN(C)C3)cc1CO)c1ccccc1] | 1-(2-(hydroxymethyl)-4-(((2-methylisoindolin-5-yl)methyl)sulfonyl)phenyl)-3-(1-phenylethyl)urea |
| H1471 | 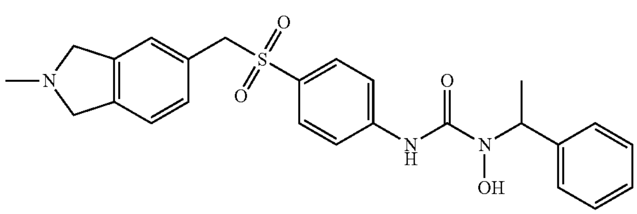 [SMILES: CC(c1ccccc1)N(O)C(=O)Nc1ccc(S(=O)(=O)Cc2ccc3c(c2)CN(C)C3)cc1] | 1-hydroxy-3-(4-(((2-methylisoindolin-5-yl)methyl)sulfonyl)phenyl)-1-(1-phenylethyl)urea |
| H1472 | 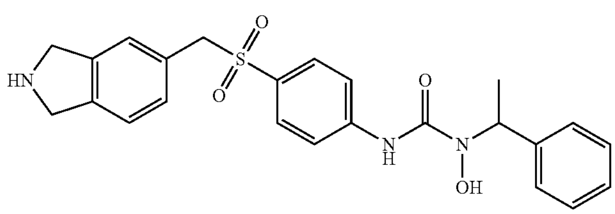 [SMILES: CC(c1ccccc1)N(O)C(=O)Nc1ccc(S(=O)(=O)Cc2ccc3c(c2)CNC3)cc1] | 1-hydroxy-3-(4-((isoindolin-5-ylmethyl)sulfonyl)phenyl)-1-(1-phenylethyl)urea |

-continued

| Compound No. | Chemical Structure | Chemical Name |
|---|---|---|
| H1473 | 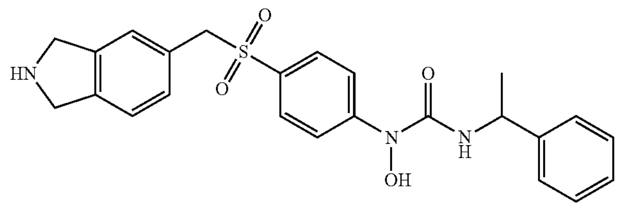 [SMILES: CC(NC(=O)N(O)c1ccc(S(=O)(=O)Cc2ccc3c(c2)CNC3)cc1)c1ccccc1] | 1-hydroxy-1-(4-((isoindolin-5-yl)methyl)sulfonyl)phenyl)-3-(1-phenylethyl)urea |
| H1474 | 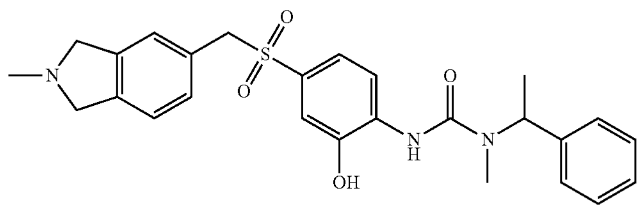 [SMILES: CC(c1ccccc1)N(C)C(=O)Nc1ccc(S(=O)(=O)Cc2ccc3c(c2)CN(C)C3)cc1O] | 3-(2-hydroxy-4-(((2-methylisoindolin-5-yl)methyl)sulfonyl)phenyl)-1-methyl-1-(1-phenylethyl)urea |
| H1475 | 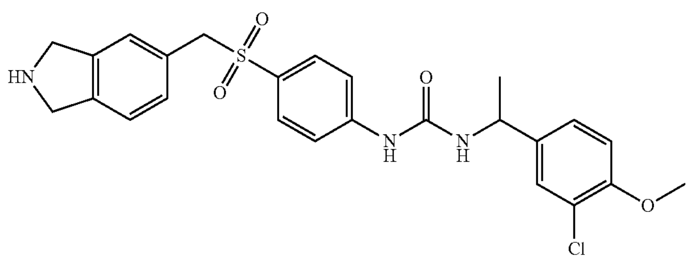 [SMILES: COc1ccc(C(C)NC(=O)Nc2ccc(S(=O)(=O)Cc3ccc4c(c3)CNC4)cc2)cc1Cl] | 1-(1-(3-chloro-4-methoxyphenyl)ethyl)-3-(4-((isoindolin-5-yl)methyl)sulfonyl)phenyl)urea |
| H1476 | 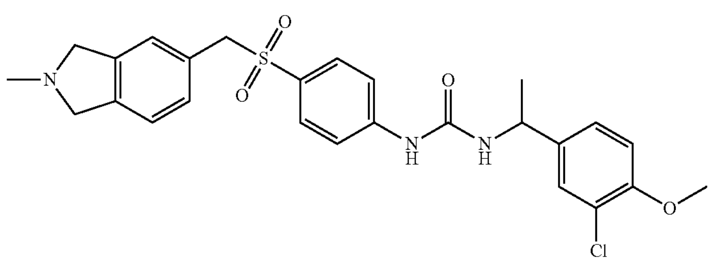 | 1-(1-(3-chloro-4-methoxyphenyl)ethyl)-3-(4-(((2-methylisoindolin-5-yl)methyl)sulfonyl)phenyl)urea |
| H1477 | 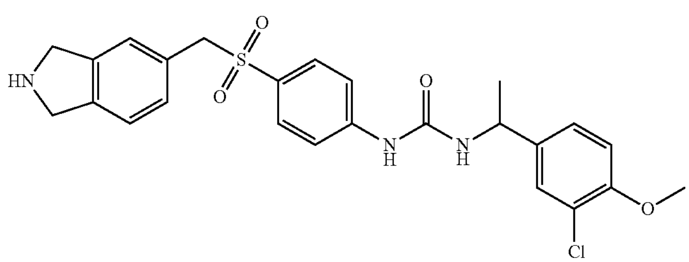 [SMILES: COc1ccc(C(C)NC(=O)Nc2ccc(S(=O)(=O)Cc3ccc4c(c3)CNC4)cc2)cc1Cl] | 1-(1-(3-chloro-4-methoxyphenyl)ethyl)-3-(4-((isoindolin-5-yl)methyl)sulfonyl)phenyl)urea |
| H1478 | 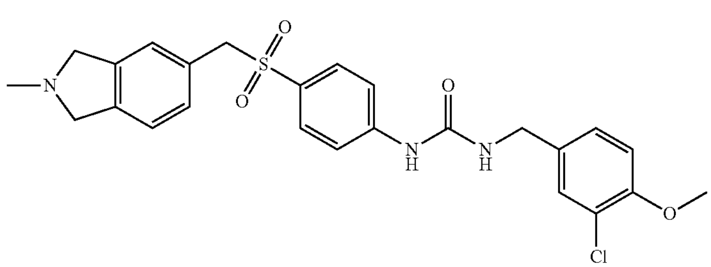 | 1-(3-chloro-4-methoxybenzyl)-3-(4-(((2-methylisoindolin-5-yl)methyl)sulfonyl)phenyl)urea |

-continued

| Compound No. | Chemical Structure | Chemical Name |
|---|---|---|
| H1479 | 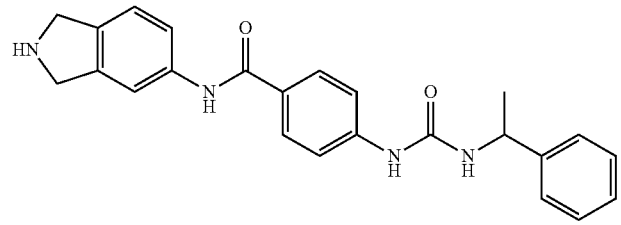 [SMILES: CC(NC(=O)Nc1ccc(C(=O)Nc2ccc3c(c2)CNC3)cc1)c1ccccc1] | N-(isoindolin-5-yl)-4-(3-(1-phenylethyl)ureido)benzamide |
| H1480 | 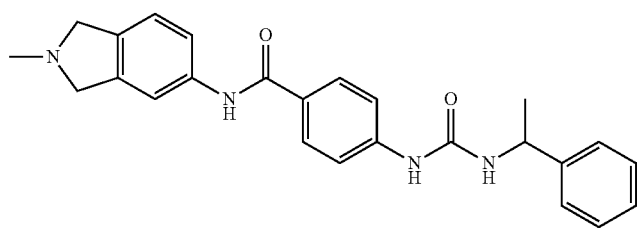 [SMILES: CC(NC(=O)Nc1ccc(C(=O)Nc2ccc3c(c2)CN(C)C3)cc1)c1ccccc1] | N-(2-methylisoindolin-5-yl)-4-(3-(1-phenylethyl)ureido)benzamide |
| H1481 | 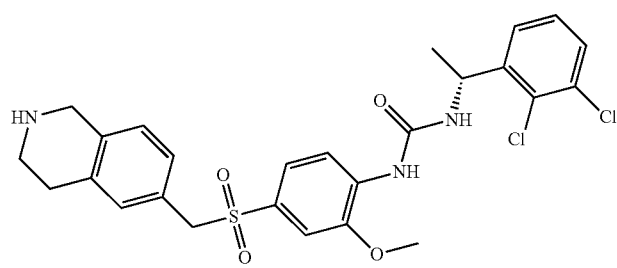 [SMILES: COc1cc(S(=O)(=O)Cc2ccc3c(c2)CCNC3)ccc1NC(=O)N[C@H](C)c1cccc(Cl)c1Cl] | (R)-1-(1-(2,3-dichlorophenyl)ethyl)-3-(2-methoxy-4-(((1,2,3,4-tetrahydroisoquinolin-6-yl)methyl)sulfonyl)phenyl)urea |
| H1482 | 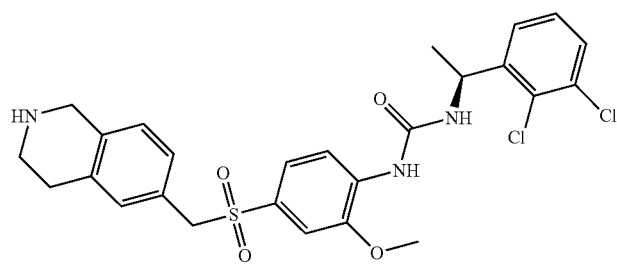 [SMILES: COc1cc(S(=O)(=O)Cc2ccc3c(c2)CCNC3)ccc1NC(=O)N[C@@H](C)c1cccc(Cl)c1Cl] | (S)-1-(1-(2,3-dichlorophenyl)ethyl)-3-(2-methoxy-4-(((1,2,3,4-tetrahydroisoquinolin-6-yl)methyl)sulfonyl)phenyl)urea |
| H1484 | 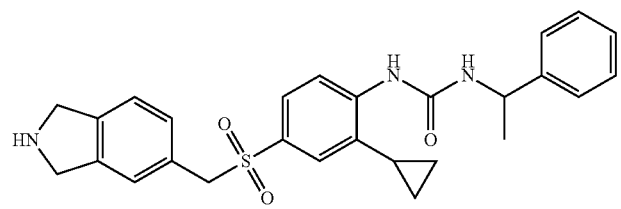 [SMILES: CC(NC(=O)Nc1ccc(S(=O)(=O)Cc2ccc3c(c2)CNC3)cc1C1CC1)c1ccccc1] | 1-(2-cyclopropyl-4-((isoindolin-5-ylmethyl)sulfonyl)phenyl)-3-(1-phenylethyl)urea |
| H1485 | 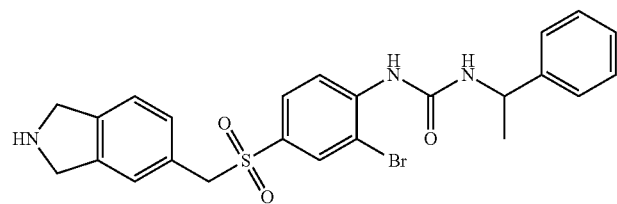 [SMILES: CC(NC(=O)Nc1ccc(S(=O)(=O)Cc2ccc3c(c2)CNC3)cc1Br)c1ccccc1] | 1-(2-bromo-4-((isoindolin-5-ylmethyl)sulfonyl)phenyl)-3-(1-phenylethyl)urea |

-continued

| Compound No. | Chemical Structure | Chemical Name |
|---|---|---|
| H1486 | 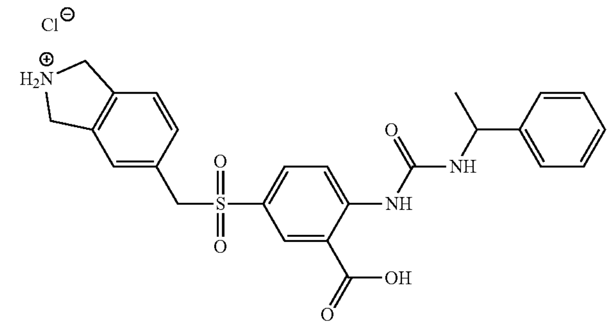 [SMILES: [Cl-] ; CC(NC(=O)Nc1ccc(S(=O)(=O)Cc2ccc3c(c2)C[NH2+]C3)cc1C(=O)O)c1ccccc1] | 5-((isoindolin-5-ylmethyl)sulfonyl)-2-(3-(1-phenylethyl)ureido)benzoic acid |
| H1487 | 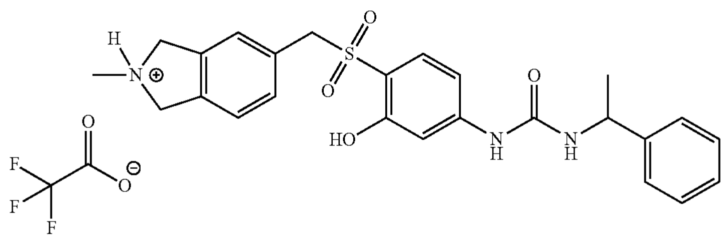 [SMILES: O=C([O-])C(F)(F)F ; CC(NC(=O)Nc1ccc(S(=O)(=O)Cc2ccc3c(c2)C[NH+](C)C3)c(O)c1)c1ccccc1] | 1-(3-hydroxy-4-(((2-methylisoindolin-5-yl)methyl)sulfonyl)phenyl)-3-(1-phenylethyl)urea |
| H1490 | 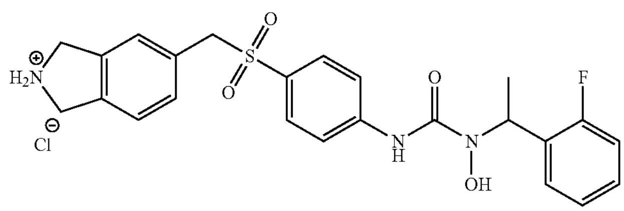 [SMILES: CC(c1ccccc1F)N(O)C(=O)Nc1ccc(S(=O)(=O)Cc2ccc3c(c2)C[NH2+]C3)cc1 ; [Cl-]] | 1-(1-(2-fluorophenyl)ethyl)-1-hydroxy-3-(4-((isoindolin-5-ylmethyl)sulfonyl)phenyl)urea |
| H1491 | 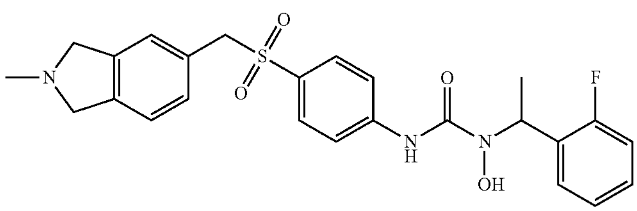 [SMILES: CC(c1ccccc1F)N(O)C(=O)Nc1ccc(S(=O)(=O)Cc2ccc3c(c2)CN(C)C3)cc1] | 1-(1-(2-fluorophenyl)ethyl)-1-hydroxy-3-(4-(((2-methylisoindolin-5-yl)methyl)sulfonyl)phenyl)urea |
| H1492 | 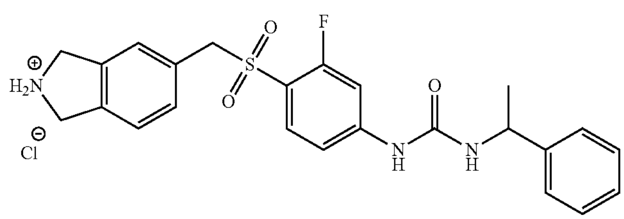 [SMILES: [Cl-] ; CC(NC(=O)Nc1ccc(S(=O)(=O)Cc2ccc3c(c2)C[NH2+]C3)c(F)c1)c1ccccc1] | 1-(3-fluoro-4-((isoindolin-5-ylmethyl)sulfonyl)phenyl)-3-(1-phenylethyl)urea |
| H1493 | 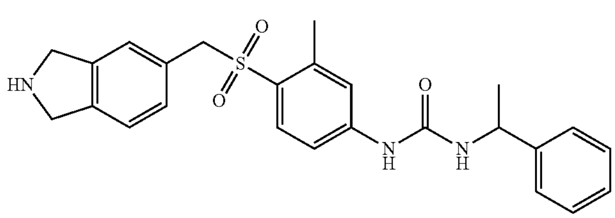 [SMILES: Cc1cc(NC(=O)NC(C)c2ccccc2)ccc1S(=O)(=O)Cc1ccc2c(c1)CNC2] | 1-(4-((isoindolin-5-ylmethyl)sulfonyl)-3-methylphenyl)-3-(1-phenylethyl)urea |

-continued

| Compound No. | Chemical Structure | Chemical Name |
|---|---|---|
| H1494 | 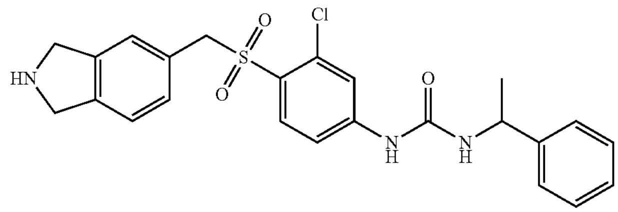 [SMILES: CC(NC(=O)Nc1ccc(S(=O)(=O)Cc2ccc3c(c2)CNC3)c(Cl)c1)c1ccccc1] | 1-(3-chloro-4-((isoindolin-5-ylmethyl)sulfonyl)phenyl)-3-(1-phenylethyl)urea |
| H1495 | 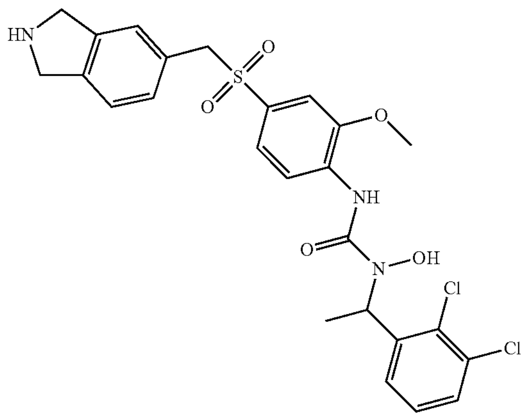 [SMILES: COc1cc(S(=O)(=O)Cc2ccc3c(c2)CNC3)ccc1NC(=O)N(O)C(C)c1cccc(Cl)c1Cl] | 1-(1-(2,3-dichlorophenyl)ethyl)-1-hydroxy-3-(4-((isoindolin-5-ylmethyl)sulfonyl)-2-methoxyphenyl)urea |
| H1496 | 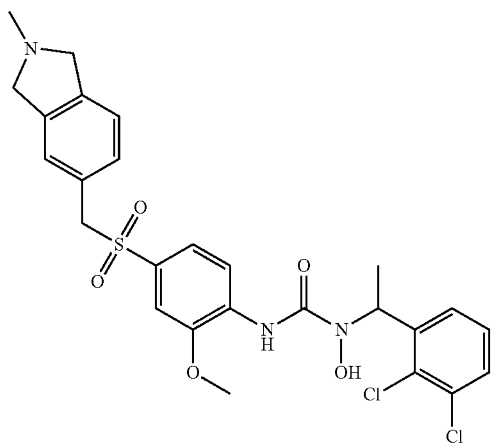 [SMILES: COc1cc(S(=O)(=O)Cc2ccc3c(c2)CN(C)C3)ccc1NC(=O)N(O)C(C)c1cccc(Cl)c1Cl] | 1-(1-(2,3-dichlorophenyl)ethyl)-1-hydroxy-3-(2-methoxy-4-(((2-methylisoindolin-5-yl)methyl)sulfonyl)phenyl)urea |
| H1497 | 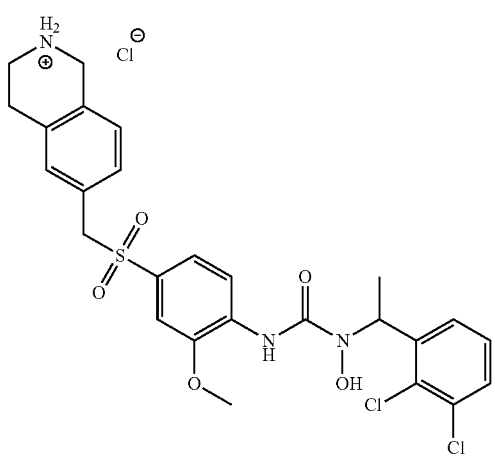 | 1-(1-(2,3-dichlorophenyl)ethyl)-1-hydroxy-3-(2-methoxy-4-(((1,2,3,4-tetrahydroisoquinolin-6-yl)methyl)sulfonyl)phenyl)urea |

-continued

| Compound No. | Chemical Structure | Chemical Name |
|---|---|---|
| H1498 | 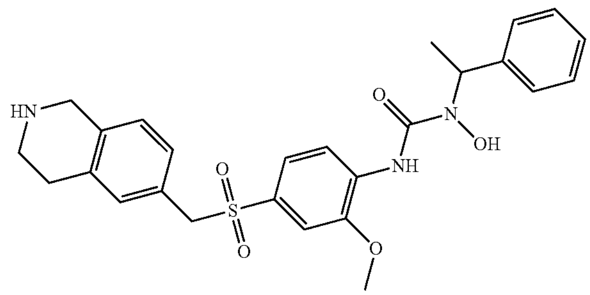 [SMILES: COc1cc(S(=O)(=O)Cc2ccc3c(c2)CCNC3)ccc1NC(=O)N(O)C(C)c1ccccc1] | 1-hydroxy-3-(2-methoxy-4-(((1,2,3,4-tetrahydroisoquinolin-6-yl)methyl)sulfonyl)phenyl)-1-(1-phenylethyl)urea |
| H1499 | 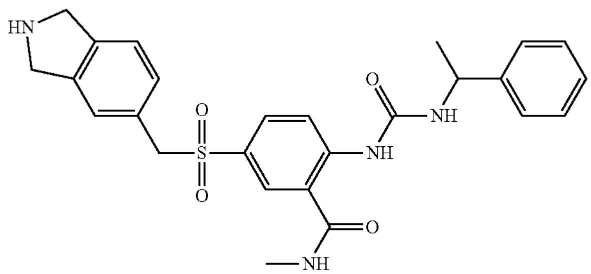 [SMILES: CNC(=O)c1cc(S(=O)(=O)Cc2ccc3c(c2)CNC3)ccc1NC(=O)NC(C)c1ccccc1] | 5-((isoindolin-5-ylmethyl)sulfonyl)-N-methyl-2-(3-(1-phenylethyl)ureido)benzamide |
| H1500 | 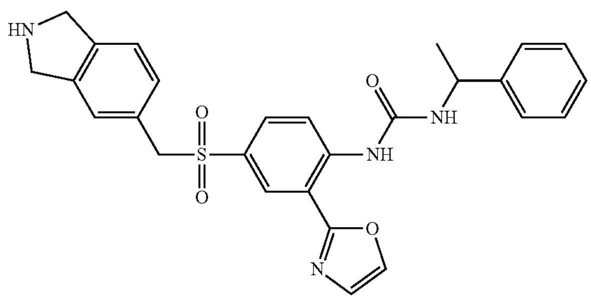 [SMILES: CC(NC(=O)Nc1ccc(S(=O)(=O)Cc2ccc3c(c2)CNC3)cc1-c1ncco1)c1ccccc1] | 1-(4-((isoindolin-5-ylmethyl)sulfonyl)-2-(oxazol-2-yl)phenyl)-3-(1-phenylethyl)urea |
| H1501 | 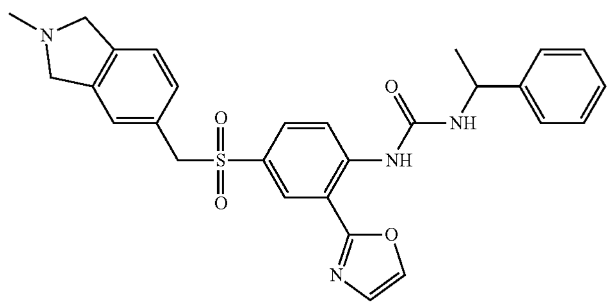 [SMILES: CC(NC(=O)Nc1ccc(S(=O)(=O)Cc2ccc3c(c2)CN(C)C3)cc1-c1ncco1)c1ccccc1] | 1-(4-(((2-methylisoindolin-5-yl)methyl)sulfonyl)-2-(oxazol-2-yl)phenyl)-3-(1-phenylethyl)urea |
| H1502 | 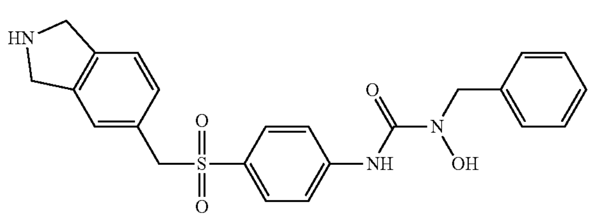 [SMILES: O=C(Nc1ccc(S(=O)(=O)Cc2ccc3c(c2)CNC3)cc1)N(O)Cc1ccccc1] | 1-benzyl-1-hydroxy-3-(4-((isoindolin-5-ylmethyl)sulfonyl)phenyl)urea |

-continued

| Compound No. | Chemical Structure | Chemical Name |
|---|---|---|
| H1503 | 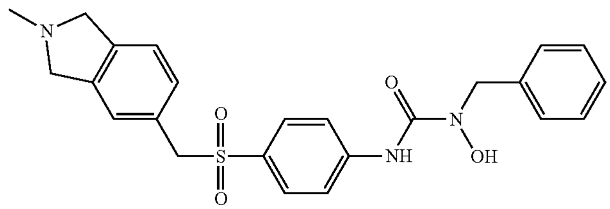 [SMILES: CN1Cc2ccc(CS(=O)(=O)c3ccc(NC(=O)N(O)Cc4ccccc4)cc3)cc2C1] | 1-benzyl-1-hydroxy-3-(4-(((2-methylisoindolin-5-yl)methyl)sulfonyl)phenyl)urea |
| H1504 | 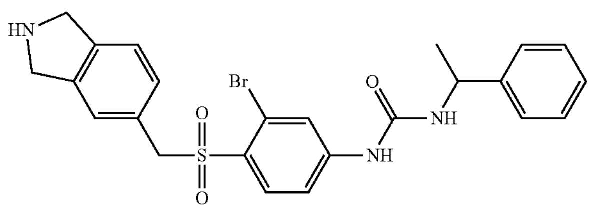 [SMILES: CC(NC(=O)Nc1ccc(S(=O)(=O)Cc2ccc3c(c2)CNC3)c(Br)c1)c1ccccc1] | 1-(3-bromo-4-((isoindolin-5-ylmethyl)sulfonyl)phenyl)-3-(1-phenylethyl)urea |
| H1505 | 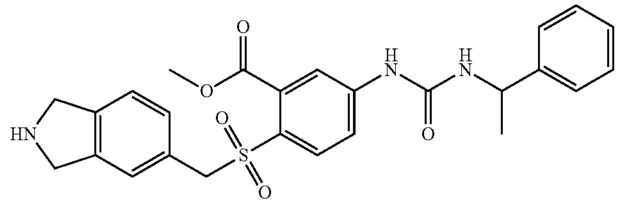 [SMILES: COC(=O)c1cc(NC(=O)NC(C)c2ccccc2)ccc1S(=O)(=O)Cc1ccc2c(c1)CNC2] | methyl 2-((isoindolin-5-ylmethyl)sulfonyl)-5-(3-(1-phenylethyl)ureido)benzoate |
| H1506 | 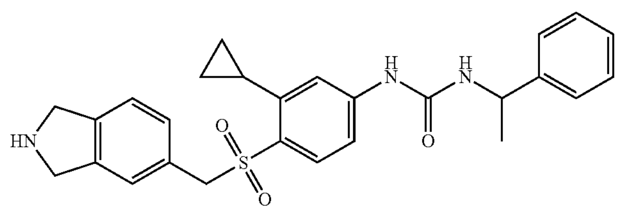 [SMILES: CC(NC(=O)Nc1ccc(S(=O)(=O)Cc2ccc3c(c2)CNC3)c(C2CC2)c1)c1ccccc1] | 1-(3-cyclopropyl-4-((isoindolin-5-ylmethyl)sulfonyl)phenyl)-3-(1-phenylethyl)urea |
| H1507 | 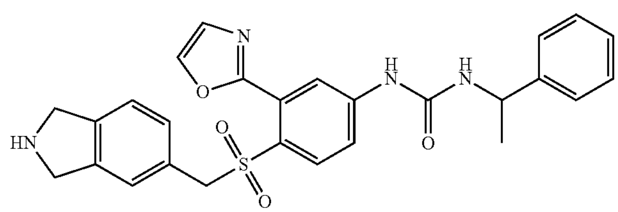 [SMILES: CC(NC(=O)Nc1ccc(S(=O)(=O)Cc2ccc3c(c2)CNC3)c(-c2ncco2)c1)c1ccccc1] | 1-(4-((isoindolin-5-ylmethyl)sulfonyl)-3-(oxazol-2-yl)phenyl)-3-(1-phenylethyl)urea |
| H1508 | 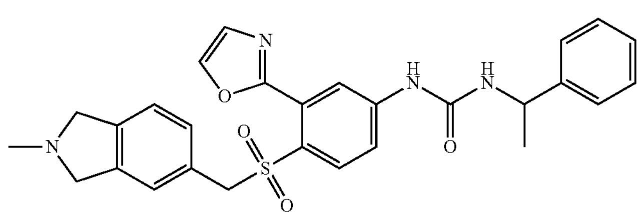 [SMILES: CC(NC(=O)Nc1ccc(S(=O)(=O)Cc2ccc3c(c2)CN(C)C3)c(-c2ncco2)c1)c1ccccc1] | 1-(4-(((2-methylisoindolin-5-yl)methyl)sulfonyl)-3-(oxazol-2-yl)phenyl)-3-(1-phenylethyl)urea |

| Compound No. | Chemical Structure | Chemical Name |
|---|---|---|
| H1509 | 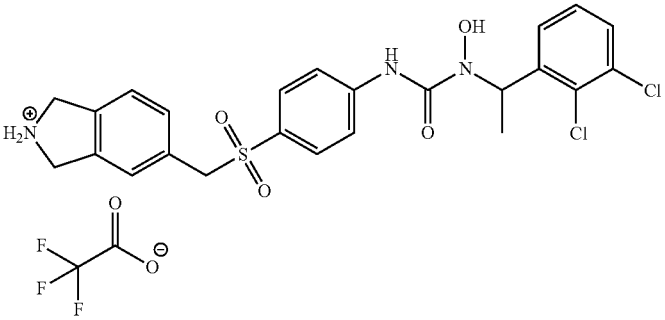 [SMILES: CC(c1cccc(Cl)c1Cl)N(O)C(=O)Nc1ccc(S(=O)(=O)Cc2ccc3c(c2)C[NH2+]C3)cc1 ; O=C([O-])C(F)(F)F] | 1-(1-(2,3-dichlorophenyl)ethyl)-1-hydroxy-3-(4-((isoindolin-5-ylmethyl)sulfonyl)phenyl)urea |
| H1510 | 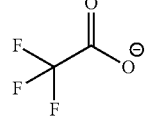 | 1-(1-(2-fluorophenyl)ethyl)-1-hydroxy-3-(4-((isoindolin-5-ylmethyl)sulfonyl)-3-methoxyphenyl)urea |
| H1511 | 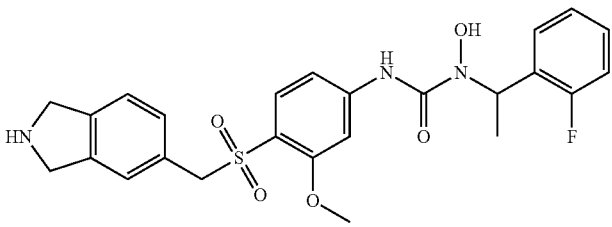 [SMILES: COc1cc(NC(=O)N(O)C(C)c2ccccc2F)ccc1S(=O)(=O)Cc1ccc2c(c1)CNC2] | 1-(1-(2-fluorophenyl)ethyl)-1-hydroxy-3-(3-methoxy-4-(((2-methylisoindolin-5-yl)methyl)sulfonyl)phenyl)urea |
| H1512 | 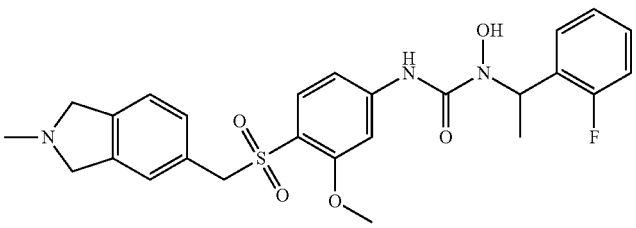 [SMILES: COc1cc(NC(=O)N(O)C(C)c2ccccc2F)ccc1S(=O)(=O)Cc1ccc2c(c1)CN(C)C2] | 1-(2-(2-hydroxypropan-2-yl)-4-((isoindolin-5-ylmethyl)sulfonyl)phenyl)-3-(1-phenylethyl)urea |
| H1515 | 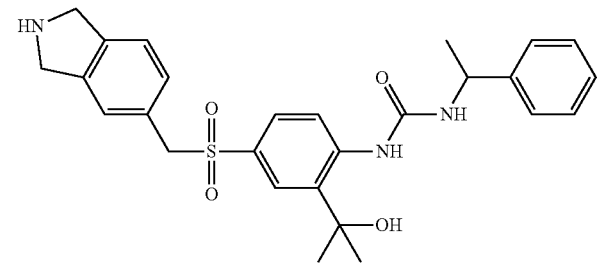 [SMILES: CC(NC(=O)Nc1ccc(S(=O)(=O)Cc2ccc3c(c2)CNC3)cc1C(C)(C)O)c1ccccc1] | 1-hydroxy-3-(4-((isoindolin-5-ylmethyl)sulfonyl)-3-methoxyphenyl)-1-(1-phenylethyl)urea |
| H1516 | 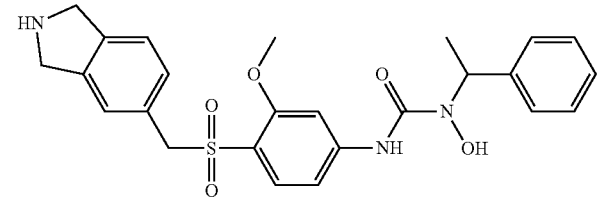 [SMILES: COc1cc(NC(=O)N(O)C(C)c2ccccc2)ccc1S(=O)(=O)Cc1ccc2c(c1)CNC2] | 1-hydroxy-3-(3-methoxy-4-(((2-methylisoindolin-5-yl)methyl)sulfonyl)phenyl)-1-(1-phenylethyl)urea |

-continued

| Compound No. | Chemical Structure | Chemical Name |
|---|---|---|
| H1517 | 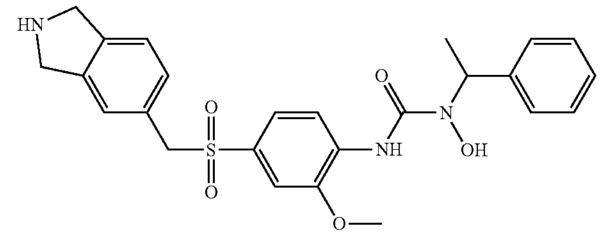 [SMILES: COc1cc(S(=O)(=O)Cc2ccc3c(c2)CNC3)ccc1NC(=O)N(O)C(C)c1ccccc1] | 1-hydroxy-3-(4-((isoindolin-5-ylmethyl)sulfonyl)-2-methoxyphenyl)-1-(1-phenylethyl)urea |
| H1518 | 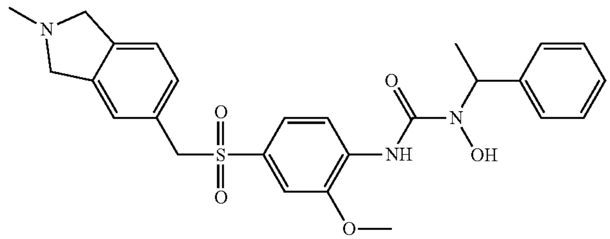 [SMILES: COc1cc(S(=O)(=O)Cc2ccc3c(c2)CN(C)C3)ccc1NC(=O)N(O)C(C)c1ccccc1] | 1-hydroxy-3-(2-methoxy-4-(((2-methylisoindolin-5-yl)methyl)sulfonyl)phenyl)-1-(1-phenylethyl)urea |
| H1519 | 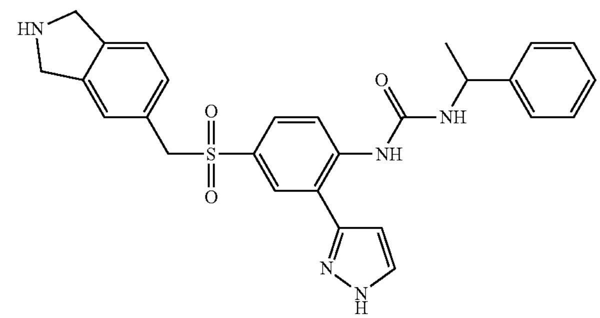 [SMILES: CC(NC(=O)Nc1ccc(S(=O)(=O)Cc2ccc3c(c2)CNC3)cc1-c1cc[nH]n1)c1ccccc1] | 1-(4-((isoindolin-5-ylmethyl)sulfonyl)-2-(1H-pyrazol-3-yl)phenyl)-3-(1-phenylethyl)urea |
| H1520 | 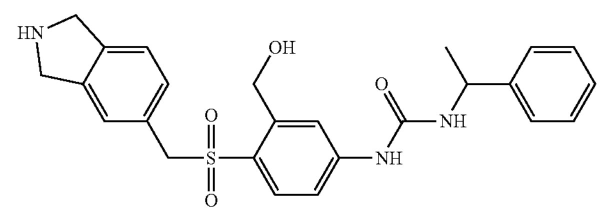 [SMILES: CC(NC(=O)Nc1ccc(S(=O)(=O)Cc2ccc3c(c2)CNC3)c(CO)c1)c1ccccc1] | 1-(3-(hydroxymethyl)-4-((isoindolin-5-ylmethyl)sulfonyl)phenyl)-3-(1-phenylethyl)urea |
| H1521 | 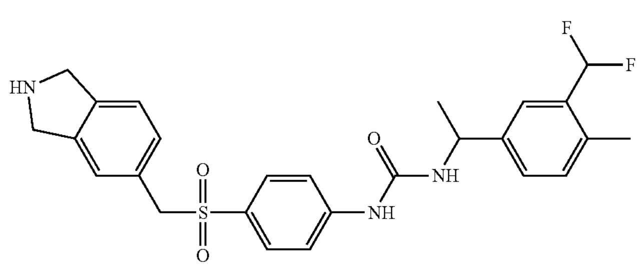 [SMILES: Cc1ccc(C(C)NC(=O)Nc2ccc(S(=O)(=O)Cc3ccc4c(c3)CNC4)cc2)cc1C(F)F] | 1-(1-(3-(difluoromethyl)-4-methylphenyl)ethyl)-3-(4-((isoindolin-5-ylmethyl)sulfonyl)phenyl)urea |

-continued

| Compound No. | Chemical Structure | Chemical Name |
|---|---|---|
| H1523 | 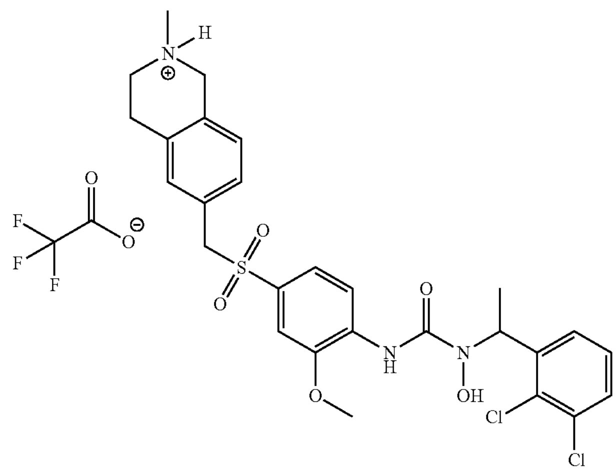 [SMILES: O=C([O-])C(F)(F)F ; COc1cc(S(=O)(=O)Cc2ccc3c(c2)CC[NH+](C)C3)ccc1NC(=O)N(O)C(C)c1cccc(Cl)c1Cl] | 1-(1-(2,3-dichlorophenyl)ethyl)-1-hydroxy-3-(2-methoxy-4-(((2-methyl-1,2,3,4-tetrahydroisoquinolin-6-yl)methyl)sulfonyl)phenyl)urea |
| H1524 | 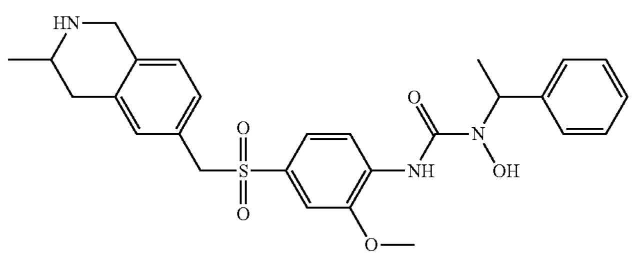 [SMILES: COc1cc(S(=O)(=O)Cc2ccc3c(c2)CC(C)NC3)ccc1NC(=O)N(O)C(C)c1ccccc1] | 1-hydroxy-3-(2-methoxy-4-(((3-methyl-1,2,3,4-tetrahydroisoquinolin-6-yl)methyl)sulfonyl)phenyl)-1-(1-phenylethyl)urea |
| H1525 | 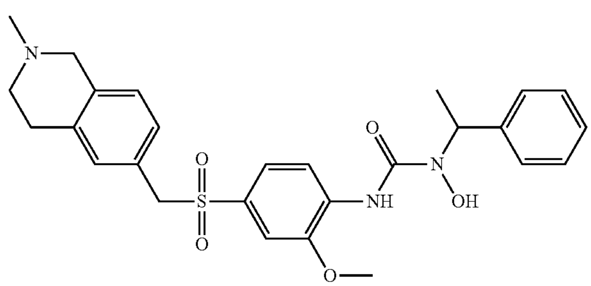 [SMILES: COc1cc(S(=O)(=O)Cc2ccc3c(c2)CCN(C)C3)ccc1NC(=O)N(O)C(C)c1ccccc1] | 1-hydroxy-3-(2-methoxy-4-(((2-methyl-1,2,3,4-tetrahydroisoquinolin-6-yl)methyl)sulfonyl)phenyl)-1-(1-phenylethyl)urea |
| H1526 | 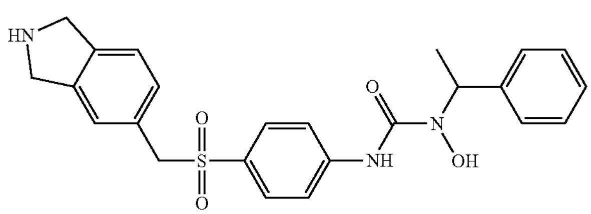 [SMILES: CC(c1ccccc1)N(O)C(=O)Nc1ccc(S(=O)(=O)Cc2ccc3c(c2)CNC3)cc1] | 1-hydroxy-3-(4-((isoindolin-5-ylmethyl)sulfonyl)phenyl)-1-(1-phenylethyl)urea |
| H1527 | 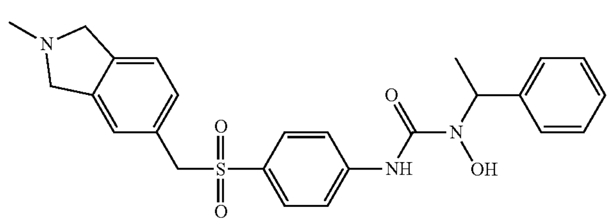 [SMILES: CC(c1ccccc1)N(O)C(=O)Nc1ccc(S(=O)(=O)Cc2ccc3c(c2)CN(C)C3)cc1] | 1-hydroxy-3-(4-(((2-methylisoindolin-5-yl)methyl)sulfonyl)phenyl)-1-(1-phenylethyl)urea |

-continued

| Compound No. | Chemical Structure | Chemical Name |
|---|---|---|
| H1528 | 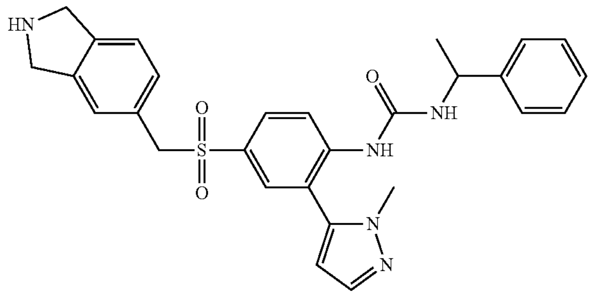 [SMILES: CC(NC(=O)Nc1ccc(S(=O)(=O)Cc2ccc3c(c2)CNC3)cc1-c1ccnn1C)c1ccccc1] | 1-(4-((isoindolin-5-ylmethyl)sulfonyl)-2-(1-methyl-1H-pyrazol-5-yl)phenyl)-3-(1-phenylethyl)urea |
| H1529 | 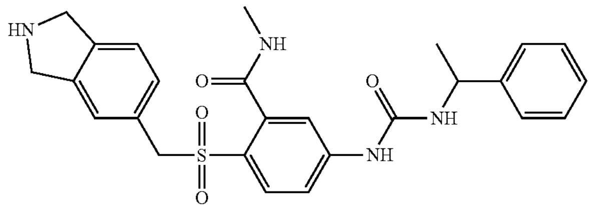 [SMILES: CNC(=O)c1cc(NC(=O)NC(C)c2ccccc2)ccc1S(=O)(=O)Cc1ccc2c(c1)CNC2] | 2-((isoindolin-5-ylmethyl)sulfonyl)-N-methyl-5-(3-1-phenylethyl)ureido)benzamide |
| H1530 | 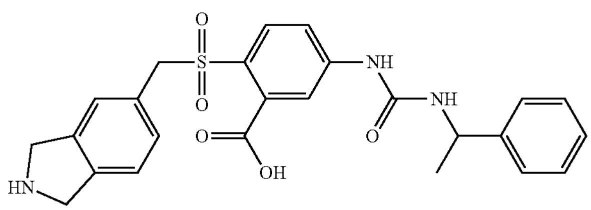 [SMILES: CC(NC(=O)Nc1ccc(S(=O)(=O)Cc2ccc3c(c2)CNC3)c(C(=O)O)c1)c1ccccc1] | 2-((isoindolin-5-ylmethyl)sulfonyl)-5-(3-(1-phenylethyl)ureido)benzoic acid |
| H1531 | 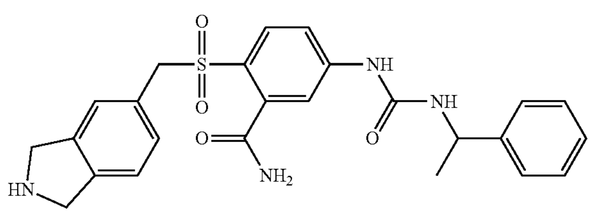 | 2-((isoindolin-5-ylmethyl)sulfonyl)-5-(3-(1-phenylethyl)ureido)benzamide |
| H1532 | 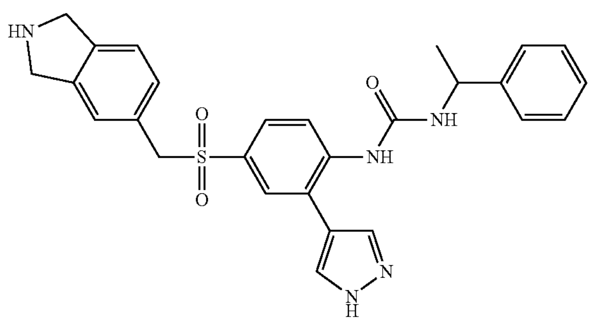 [SMILES: CC(NC(=O)Nc1ccc(S(=O)(=O)Cc2ccc3c(c2)CNC3)cc1-c1cn[nH]c1)c1ccccc1] | 1-(4-((isoindolin-5-ylmethyl)sulfonyl)-2-(1H-pyrazol-4-yl)phenyl)-3-(1-phenylethyl)urea |
| H1533 | 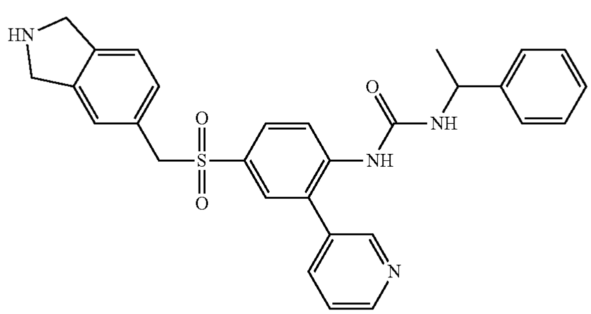 [SMILES: CC(NC(=O)Nc1ccc(S(=O)(=O)Cc2ccc3c(c2)CNC3)cc1-c1cccnc1)c1ccccc1] | 1-(4-((isoindolin-5-ylmethyl)sulfonyl)-2-(pyridin-3-yl)phenyl)-3-(1-phenylethyl)urea |

-continued

| Compound No. | Chemical Structure | Chemical Name |
|---|---|---|
| H1534 | 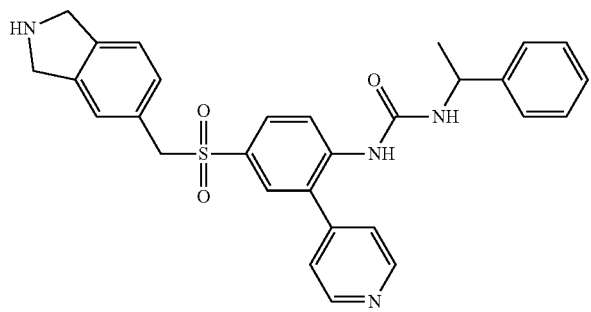 [SMILES: CC(NC(=O)Nc1ccc(S(=O)(=O)Cc2ccc3c(c2)CNC3)cc1-c1ccncc1)c1ccccc1] | 1-(4-((isoindolin-5-ylmethyl)sulfonyl)-2-(pyridin-4-yl)phenyl)-3-(1-phenylethyl)urea |
| H1535 | 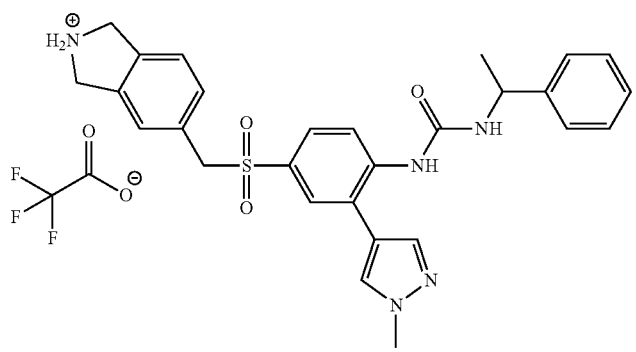 [SMILES: O=C([O-])C(F)(F)F ; CC(NC(=O)Nc1ccc(S(=O)(=O)Cc2ccc3c(c2)C[NH2+]C3)cc1-c1cnn(C)c1)c1ccccc1] | 1-(4-((isoindolin-5-ylmethyl)sulfonyl)-2-(1-methyl-1H-pyrazol-4-yl)phenyl)-3-(1-phenylethyl)urea |
| H1537 | 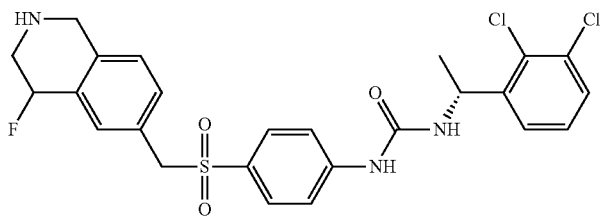 | 1-((R)-1-(2,3-dichlorophenyl)ethyl)-3-(4-(((4-fluoro-1,2,3,4-tetrahydroisoquinolin-6-yl)methyl)sulfonyl)phenyl)urea |
| H1538 | 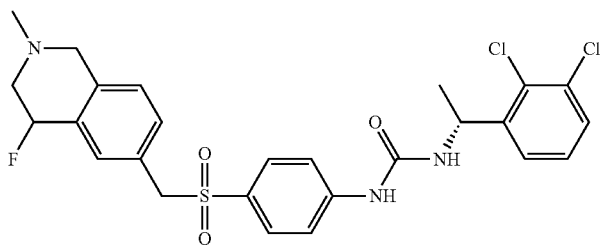 [SMILES: C[C@@H](NC(=O)Nc1ccc(S(=O)(=O)Cc2ccc3c(c2)C(F)CN(C)C3)cc1)c1cccc(Cl)c1Cl] | 1-((R)-1-(2,3-dichlorophenyl)ethyl)-3-(4-(((4-fluoro-2-methyl-1,2,3,4-tetrahydroisoquinolin-6-yl)methyl)sulfonyl)phenyl)urea |
| H1539 | 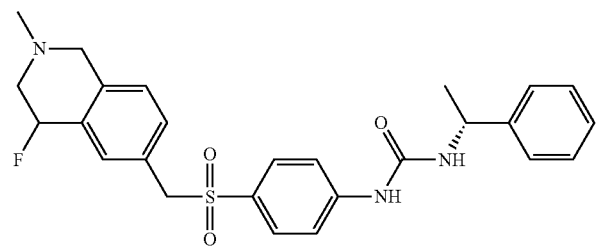 | 1-(4-(((4-fluoro-2-methyl-1,2,3,4-tetrahydroisoquinolin-6-yl)methyl)sulfonyl)phenyl)-3-((R)-1-phenylethyl)urea |

-continued

| Compound No. | Chemical Structure | Chemical Name |
|---|---|---|
| H1540 | 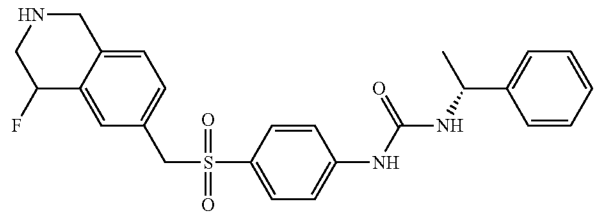 [SMILES: C[C@@H](NC(=O)Nc1ccc(S(=O)(=O)Cc2ccc3c(c2)C(F)CNC3)cc1)c1ccccc1] | 1-(4-(((4-fluoro-1,2,3,4-tetrahydroisoquinolin-6-yl)methyl)sulfonyl)phenyl)-3-((R)-1-phenylethyl)urea |
| H1541 | 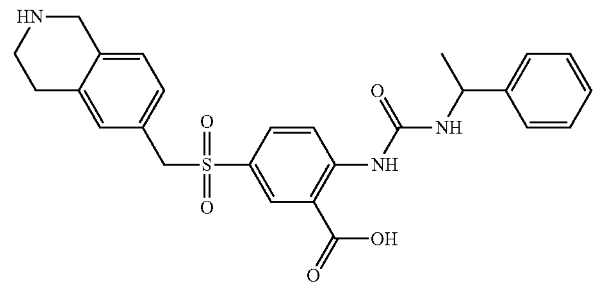 [SMILES: CC(NC(=O)Nc1ccc(S(=O)(=O)Cc2ccc3c(c2)CCNC3)cc1C(=O)O)c1ccccc1] | 2-(3-(1-phenylethyl)ureido)-5-((((1,2,3,4-tetrahydroisoquinolin-6-yl)methyl)sulfonyl)benzoic acid |
| H1542 | 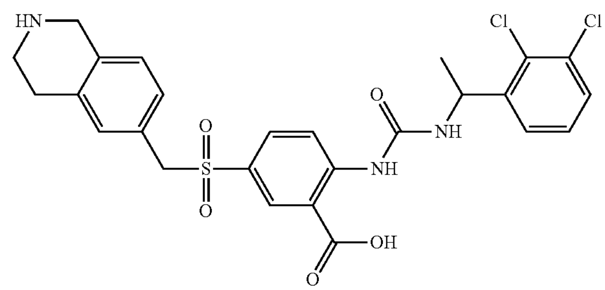 [SMILES: CC(NC(=O)Nc1ccc(S(=O)(=O)Cc2ccc3c(c2)CCNC3)cc1C(=O)O)c1cccc(Cl)c1Cl] | 2-(3-(1-(2,3-dichlorophenyl)ethyl)ureido)-5-((((1,2,3,4-tetrahydroisoquinolin-6-yl)methyl)sulfonyl)benzoic acid |
| H1543 | 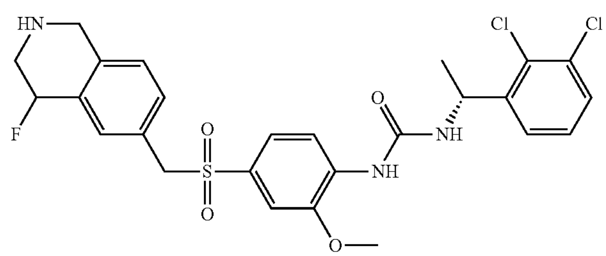 [SMILES: COc1cc(S(=O)(=O)Cc2ccc3c(c2)C(F)CNC3)ccc1NC(=O)N[C@H](C)c1cccc(Cl)c1Cl] | 1-((R)-1-(2,3-dichlorophenyl)ethyl)-3-(4-(((4-fluoro-1,2,3,4-tetrahydroisoquinolin-6-yl)methyl)sulfonyl)-2-methoxyphenyl)urea |
| H1544 | 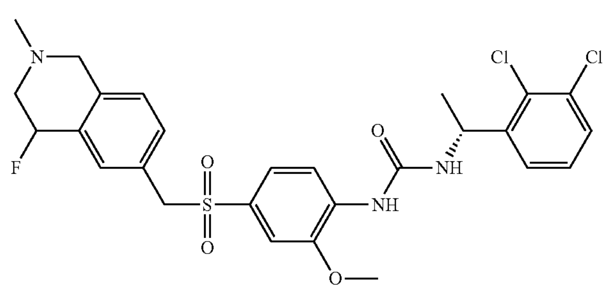 [SMILES: COc1cc(S(=O)(=O)Cc2ccc3c(c2)C(F)CN(C)C3)ccc1NC(=O)N[C@H](C)c1cccc(Cl)c1Cl] | 1-((R)-1-(2,3-dichlorophenyl)ethyl)-3-(4-(((4-fluoro-2-methyl-1,2,3,4-tetrahydroisoquinolin-6-yl)methyl)sulfonyl)-2-methoxyphenyl)urea |
| H1545 | 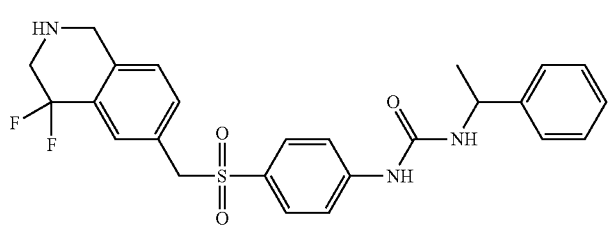 [SMILES: CC(NC(=O)Nc1ccc(S(=O)(=O)Cc2ccc3c(c2)C(F)(F)CNC3)cc1)c1ccccc1] | 1-(4-(((4,4-difluoro-1,2,3,4-tetrahydroisoquinolin-6-yl)methyl)sulfonyl)phenyl)-3-(1-phenylethyl)urea |

-continued

| Compound No. | Chemical Structure | Chemical Name |
|---|---|---|
| H1546 | 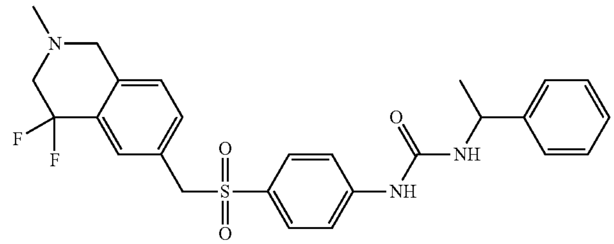 [SMILES: CC(NC(=O)Nc1ccc(S(=O)(=O)Cc2ccc3c(c2)C(F)(F)CN(C)C3)cc1)c1ccccc1] | 1-(4-(((4,4-difluoro-2-methyl-1,2,3,4-tetrahydroisoquinolin-6-yl)methyl)sulfonyl)phenyl)-3-(1-phenylethyl)urea |
| H1547 | 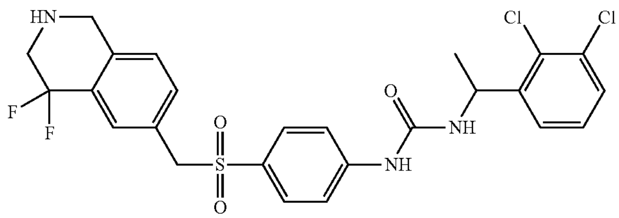 [SMILES: CC(NC(=O)Nc1ccc(S(=O)(=O)Cc2ccc3c(c2)C(F)(F)CNC3)cc1)c1cccc(Cl)c1Cl] | 1-(1-(2,3-dichlorophenyl)ethyl)-3-(4-(((4,4-difluoro-1,2,3,4-tetrahydroisoquinolin-6-yl)methyl)sulfonyl)phenyl)urea |
| H1548 | 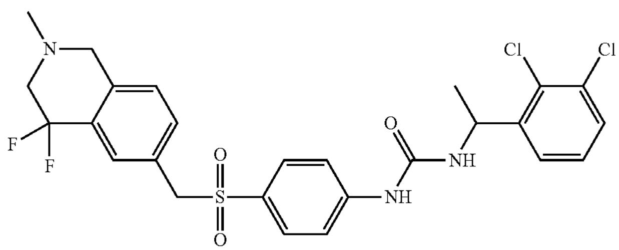 [SMILES: CC(NC(=O)Nc1ccc(S(=O)(=O)Cc2ccc3c(c2)C(F)(F)CN(C)C3)cc1)c1cccc(Cl)c1Cl] | 1-(1-(2,3-dichlorophenyl)ethyl)-3-(4-(((4,4-difluoro-2-methyl-1,2,3,4-tetrahydroisoquinolin-6-yl)methyl)sulfonyl)phenyl)urea |
| H1549 | 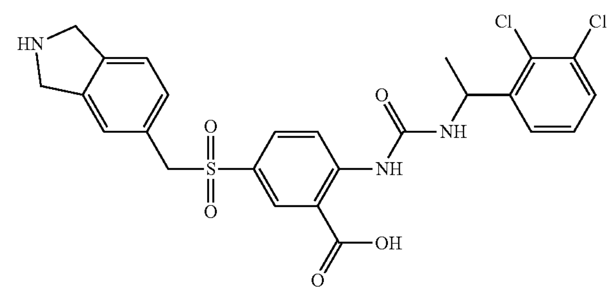 [SMILES: CC(NC(=O)Nc1ccc(S(=O)(=O)Cc2ccc3c(c2)CNC3)cc1C(=O)O)c1cccc(Cl)c1Cl] | 2-(3-(1-(2,3-dichlorophenyl)ethyl)ureido)-5-((isoindolin-5-ylmethyl)sulfonyl)benzoic acid. |

34. A compound selected from the group consisting of:

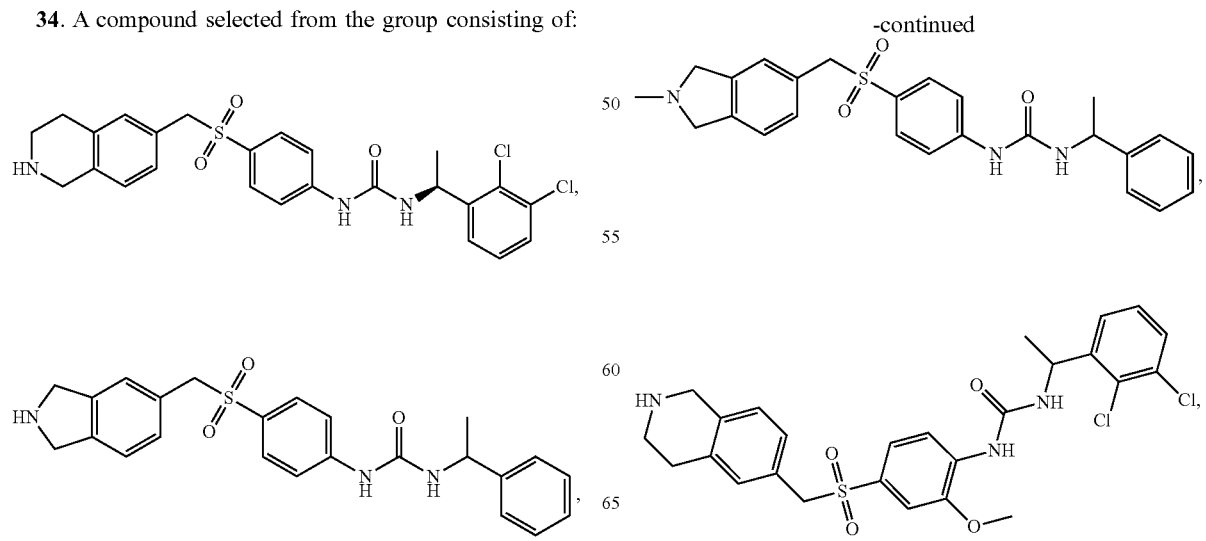

429
-continued
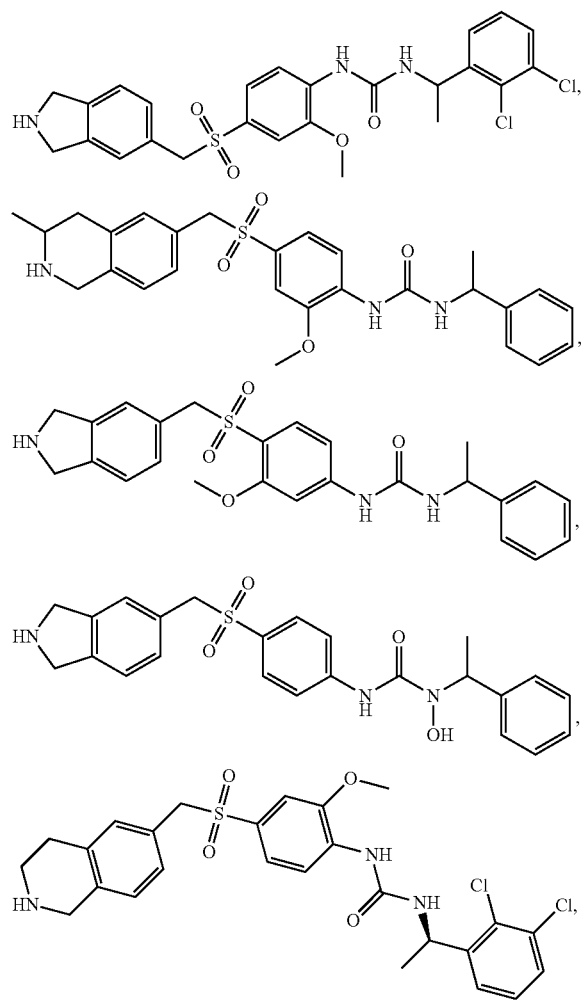
430
-continued
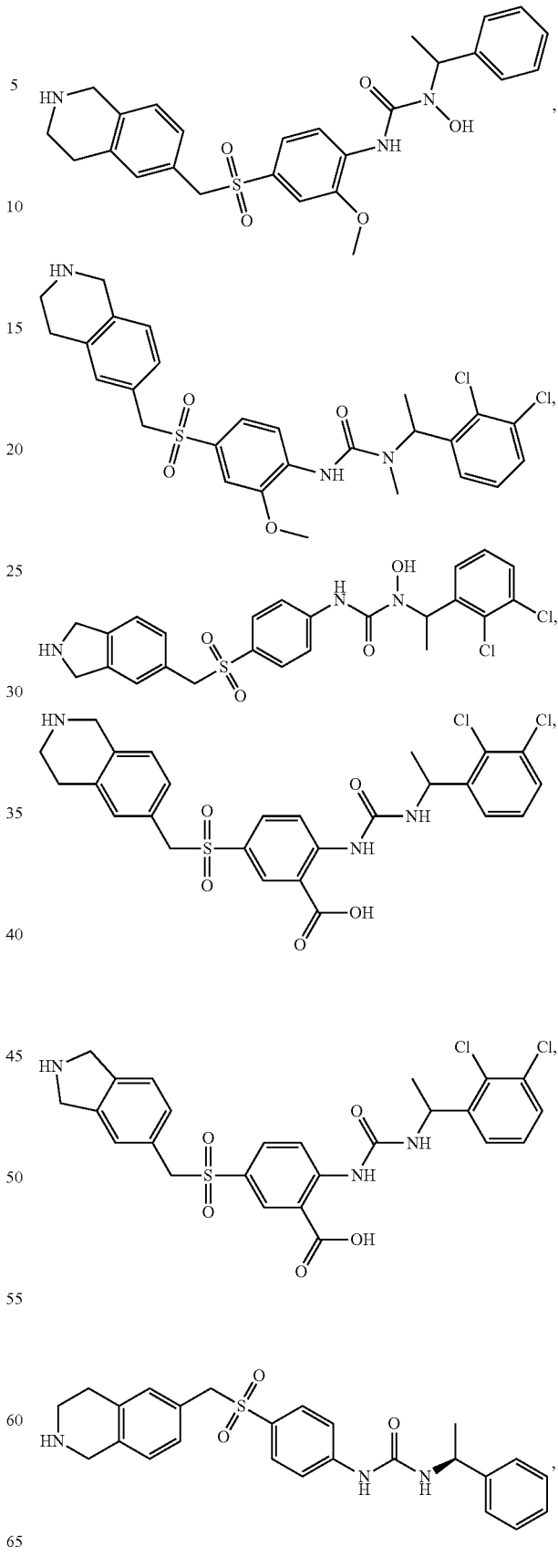
or a pharmaceutically acceptable salt thereof.

35. The compound of claim 34 having the structure:

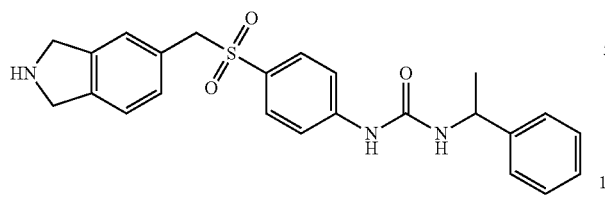

or a pharmaceutically acceptable salt thereof.

36. The compound of claim 34 having the structure:

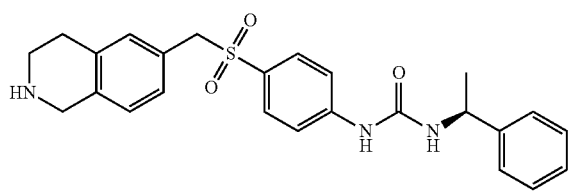 [SMILES: C[C@H](NC(=O)Nc1ccc(S(=O)(=O)Cc2ccc3c(c2)CCNC3)cc1)c1ccccc1]

or a pharmaceutically acceptable salt thereof.

37. The compound of claim 34 having the structure:

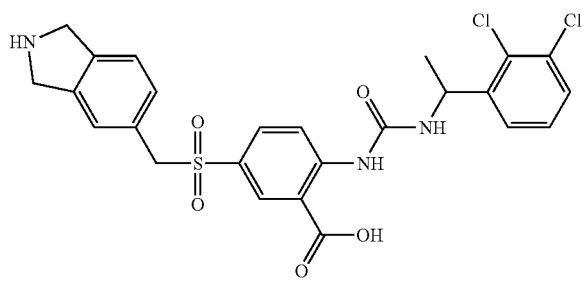 [SMILES: CC(NC(=O)Nc1ccc(S(=O)(=O)Cc2ccc3c(c2)CNC3)cc1C(=O)O)c1cccc(Cl)c1Cl]

or a pharmaceutically acceptable thereof.

38. The compound of claim 34 having the structure:

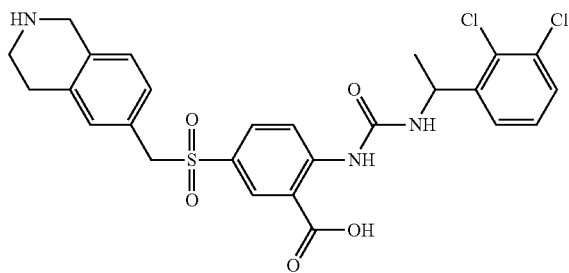 [SMILES: CC(NC(=O)Nc1ccc(S(=O)(=O)Cc2ccc3c(c2)CCNC3)cc1C(=O)O)c1cccc(Cl)c1Cl]

or a pharmaceutically acceptable salt thereof.

39. The compound of claim 34 having the structure:

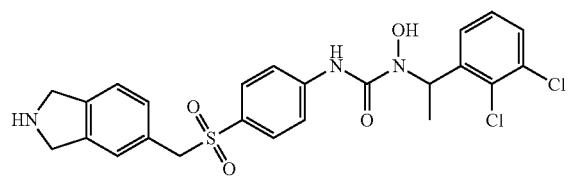 [SMILES: CC(c1cccc(Cl)c1Cl)N(O)C(=O)Nc1ccc(S(=O)(=O)Cc2ccc3c(c2)CNC3)cc1]

or a pharmaceutically acceptable salt thereof.

40. The compound of claim 34 having the structure:

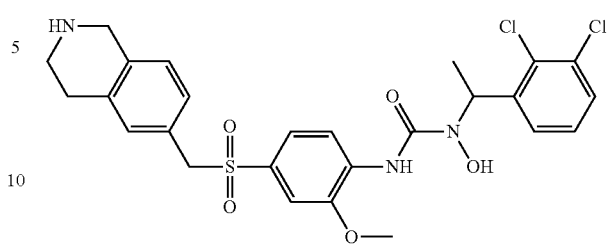

or a pharmaceutically acceptable salt thereof.

41. The compound of claim 34 having the structure:

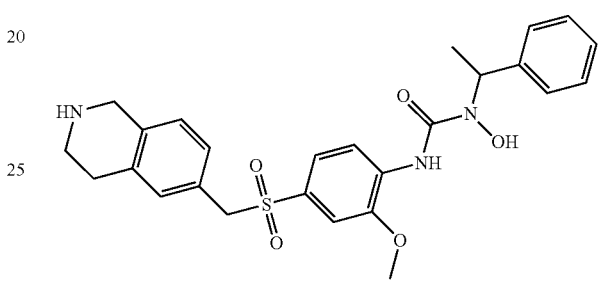

or a pharmaceutically acceptable salt thereof.

42. The compound of claim 34 having the structure:

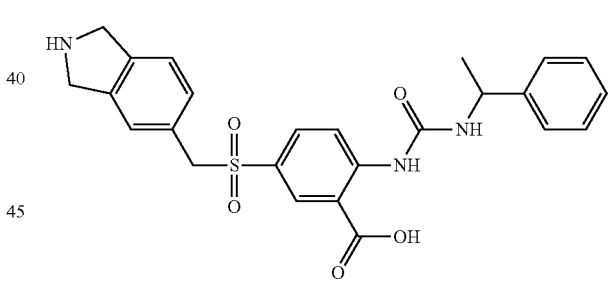

or a pharmaceutically acceptable salt thereof.

43. The compound of claim 34 having the structure:

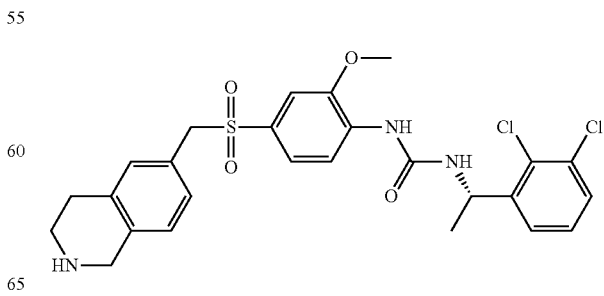

or a pharmaceutically acceptable salt thereof.

44. The compound of claim 34 having the structure:

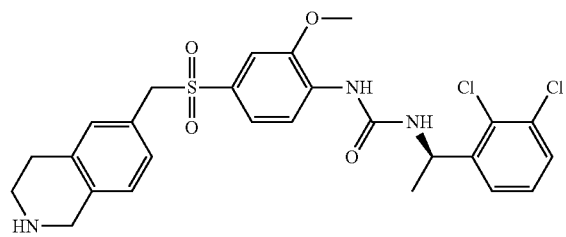 [SMILES: COc1cc(S(=O)(=O)Cc2ccc3c(c2)CCNC3)ccc1NC(=O)N[C@@H](C)c1cccc(Cl)c1Cl]

or a pharmaceutically acceptable salt thereof.

45. The compound of claim 34 having the structure:

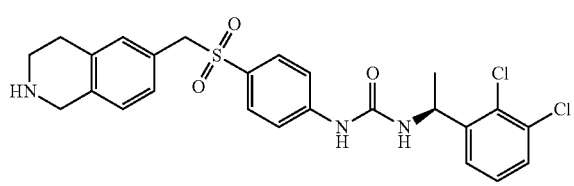 [SMILES: C[C@H](NC(=O)Nc1ccc(S(=O)(=O)Cc2ccc3c(c2)CCNC3)cc1)c1cccc(Cl)c1Cl]

or a pharmaceutically acceptable salt thereof.

46. The compound of claim 34 having the structure:

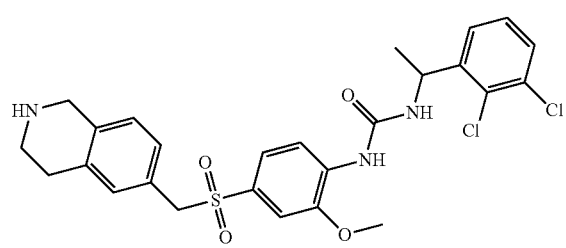 [SMILES: COc1cc(S(=O)(=O)Cc2ccc3c(c2)CCNC3)ccc1NC(=O)NC(C)c1cccc(Cl)c1Cl]

or a pharmaceutically acceptable salt thereof.

47. The compound of claim 34 having the structure:

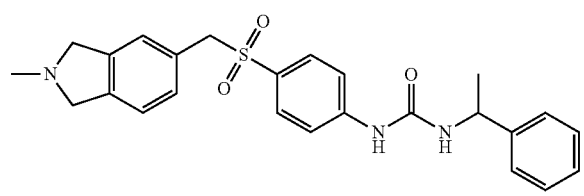 [SMILES: CC(NC(=O)Nc1ccc(S(=O)(=O)Cc2ccc3c(c2)CN(C)C3)cc1)c1ccccc1]

or a pharmaceutically acceptable salt thereof.

48. The compound of claim 34 having the structure:

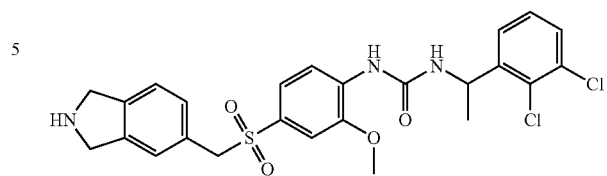

or a pharmaceutically acceptable salt thereof.

49. The compound of claim 34 having the structure:

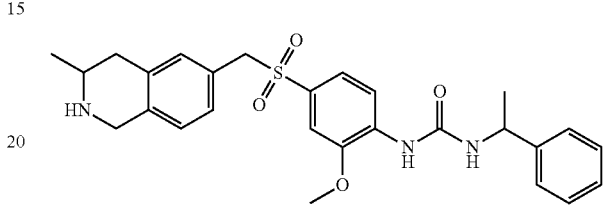

or a pharmaceutically acceptable salt thereof.

50. The compound of claim 34 having the structure:

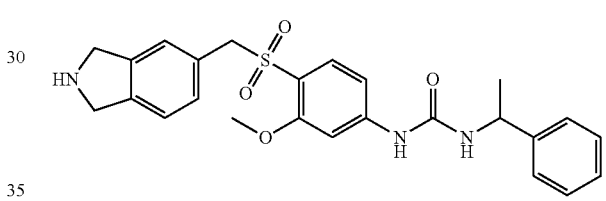

or a pharmaceutically acceptable salt thereof.

51. The compound of claim 34 having the structure:

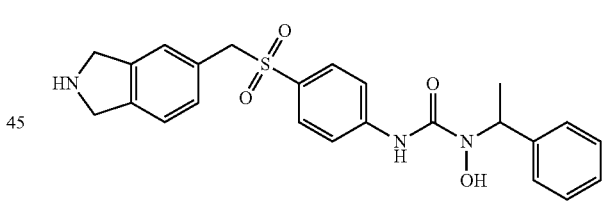

or a pharmaceutically acceptable salt thereof.

* * * * *